US010662200B2

(12) United States Patent
Tran et al.

(10) Patent No.: US 10,662,200 B2
(45) Date of Patent: *May 26, 2020

(54) MODULATORS OF THE BETA-3 ADRENERGIC RECEPTOR USEFUL FOR THE TREATMENT OR PREVENTION OF DISORDERS RELATED THERETO

(71) Applicant: Arena Pharmaceuticals, Inc., San Diego, CA (US)

(72) Inventors: Thuy-Anh Tran, San Diego, CA (US); Quyen-Quyen Do, San Diego, CA (US); Brett Ullman, San Diego, CA (US); Anthony C. Blackburn, San Diego, CA (US); Maiko Nagura, La Jolla, CA (US)

(73) Assignee: Arena Pharmaceuticals, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/563,353

(22) Filed: Sep. 6, 2019

(65) Prior Publication Data

US 2019/0389875 A1 Dec. 26, 2019

Related U.S. Application Data

(63) Continuation of application No. 16/431,209, filed on Jun. 4, 2019, now Pat. No. 10,479,797, which is a continuation of application No. 16/307,830, filed as application No. PCT/US2017/035867 on Jun. 5, 2017.

(60) Provisional application No. 62/346,293, filed on Jun. 6, 2016.

(51) Int. Cl.
| C07D 491/107 | (2006.01) |
| A61P 9/04 | (2006.01) |
| A61P 9/10 | (2006.01) |
| A61K 45/06 | (2006.01) |
| A61K 31/4525 | (2006.01) |

(52) U.S. Cl.
CPC ............ *C07D 491/107* (2013.01); *A61P 9/04* (2018.01); *A61P 9/10* (2018.01); *A61K 31/4525* (2013.01); *A61K 45/06* (2013.01)

(58) Field of Classification Search
CPC .......................... C07D 491/07; C07D 491/107
See application file for complete search history.

(56) References Cited

U.S. PATENT DOCUMENTS

| 5,254,595 | A | 10/1993 | Guzzi et al. | |
| 8,785,634 | B2 | 7/2014 | Ding | |
| 10,479,797 | B2 * | 9/2019 | Tran | C07D 491/107 |
| 2008/0293739 | A1 | 11/2008 | Trede | |
| 2019/0284200 | A1 * | 9/2019 | Tran | C07D 491/107 |

FOREIGN PATENT DOCUMENTS

| DE | 20204129 | 7/2002 |
| JP | 2012092038 | 5/2012 |
| WO | WO 98/03485 | 1/1998 |
| WO | WO9827080 | 6/1998 |
| WO | WO 9965895 | 12/1999 |
| WO | WO 0143744 | 6/2001 |
| WO | WO 2006/060122 | 6/2006 |
| WO | WO2006072000 | 7/2006 |
| WO | WO2008094507 | 8/2008 |
| WO | WO2009059225 | 5/2009 |
| WO | WO 2010/058318 | 5/2010 |
| WO | WO2010051374 | 5/2010 |
| WO | WO2010051476 | 5/2010 |
| WO | WO2010051497 | 5/2010 |
| WO | WO2014011917 | 1/2014 |
| WO | WO2014012054 | 1/2014 |
| WO | WO2015145143 | 10/2015 |
| WO | WO2019113359 | 6/2019 |

OTHER PUBLICATIONS

U.S. Appl. No. 16/307,830, filed Dec. 6, 2018, Tran et al.
U.S. Appl. No. 16/431,209, filed Jun. 4, 2019, Tran et al.
Berge, et. al., "Pharmaceutical Salts," Journal of Pharmaceutical Sciences,1977, 66:1-19.
Bioreversible Carriers in Drug Design, ed. Edward B. Roche, American Pharmaceutical Association and Pergamon Press, 1987 *too voluminous.
Collier et al., "Radiosynthesis and in-vivo evaluation of the pseudopeptide S-opioid antagonist," J. Labelled Compd. Radiopharmz., 1999, 42:S264-S266.

(Continued)

*Primary Examiner* — D Margaret M Seaman
(74) *Attorney, Agent, or Firm* — Fish & Richardson P.C.

(57) ABSTRACT

The present invention relates to compounds of Formula (Ia) and pharmaceutical compositions thereof that modulate the activity of the beta-3 adrenergic receptor. Compounds of the present invention and pharmaceutical compositions thereof are directed to methods useful in the treatment of a beta-3 adrenergic receptor-mediated disorder, such as, heart failure; cardiac performance in heart failure; mortality, reinfarction, and/or hospitalization in connection with heart failure; acute heart failure; acute decompensated heart failure; congestive heart failure; severe congestive heart failure; organ damage associated with heart failure (e.g., kidney damage or failure, heart valve problems, heart rhythm problems, and/or liver damage); heart failure due to left ventricular dysfunction; heart failure with normal ejection fraction; cardiovascular mortality following myocardial infarction; cardiovascular mortality in patients with left ventricular failure or left ventricular dysfunction; left ventricular failure; left ventricular dysfunction; class II heart failure using the New York Heart Association (NYHA) classification system; class III heart failure using the New York Heart Association (NYHA) classification system; class IV heart failure using the New York Heart Association (NYHA) classification system; LVEF<40% by radionuclide ventriculography; LVEF≤35% by echocardiography or ventricular contrast angiography; and conditions related thereto.

24 Claims, 35 Drawing Sheets

(56) References Cited

OTHER PUBLICATIONS

Francis et al., "Inotropes:" J Am College of Cardiology, 2014, 63(20):2069-2078.
G. P. Stably, "Diversity in Single- and Multiple-component Crystals. The Search for and Prevalence, of Polymorphs and Cocrystals," Crystal Growth & Design 2007, 7(6):1007-1026.
Gauthier et al., "Interspecies Differences in the Cardiac Negative Inotropic Effects of B3-Adrenoceptor Agonists," Journal of Pharmacology and Experimental Therapeutics, 1999, 290(2):687-693.
Gill et al., "Beta3-Adrenoceptor Antagonist SR59230A Attenuates the Imbalance of Systemic and Myocardial Oxygen Transport Induced Dopamine in Newborn Lambs," Clinical Medicine Insights: Cardiology, 2012, 6:45-51.
Greene, T. W. and Wuts, P. G. M., Protecting Groups in Organic Synthesis, 3rd Edition, 1999 [Wiley] *too voluminous.
International Search Report and Written Opinion, issued by European Patent Office dated Jul. 17, 2017, 3 pages.
International Search Report and Written Opinion in International Appln. No. PCT/US2017/035867 dated Jul. 17, 2017, 9 pages.
Katz AM and Konstam MA, Heart Failure: Pathophysiology, Molecular Biology and Clinical Management, Lippincott, Williams & Wilkins, 2nd edition, 199 *too voluminous.
Kulandavelu et al., "Alterations in Beta3-adrenergic cardiac innervation and nitric oxide signaling in heart failure," J Am College Cardiology, 2012, 59(22): 1988-90.
Le Bas, M.-D. and co-workers in J. Labelled Compd. Radiopharm. 2001, 44, S280-S282.
Masutani et al., "Beta3-Adrenergic receptor antagonist improves exercise in pacing-induced heart failure," Am. J. Physiol. Heart Circ. Physiol., 2013, 305:H923-930.
Morimoto et al., "Endogenous Beta3-adrenoreceptor activation contributes to left ventricular and cardiomyocyte dysfunction in heart failure," Am J Physiol Heart Circ Physiol, 2004 286: H2425-H2433.
Rastaldo et al., "Nitric oxide and cardiac function," Life Sciences, 2007, 81(10):779-793.
Remington, The Science and Practice of Pharmacy, 20th Edition, 2000, Lippincott Williams & Wilkins, (Editors: Gennaro et. al.) *too voluminous.
T. Higuchi and V. Stella, Pro-drugs as Novel Delivery Systems vol. 14 of the A.C.S. Symposium Series.
Zhu et al., "Synthesis and mode of action of (125)I- and (3)H-labeled thieno [2,3-c]pyridine antagonists of cell adhesion molecule expression," J. Org. Chem., 2002, 67:943-948.

* cited by examiner

Effect of Compound 88 on Hemodynamics and LV Contractility in Normal Dogs (n=4)

| Hemodynamic Parameters | Normal Control | After Compound 88 | | |
|---|---|---|---|---|
| | Baseline | 30 min | 60 min | 120 min |
| Heart rate (beats/min) | 108±8 | 109±7 | 105±8 | 108±7 |
| Maximum dP/dt (mmHg/sec) | 2320±213 | 2368±147 | 2240±139 | 2204±139 |
| Minimum dP/dt (mmHg/sec) | -1993±143 | -2053±109 | -1973±109 | -1944±98 |
| Stroke Volume (mL) | 16.1±2.3 | 16.8±3.1 | 17.5±3.3 | 16.7±2.7 |
| LV end-diastolic pressure (mmHg) | 6.4±2.7 | 6.0±1.4 | 7.2±1.6 | 6.9±2.3 |
| LV end-systolic pressure (mmHg) | 101±8.4 | 99±3.8 | 100±5.8 | 98±3.4 |
| Minimum LV pressure (mmHg) | 1.7±2.5 | -0.8±2.0 | 0.3±2.1 | -0.8±1.9 |
| LV end-diastolic volume (mL) | 50.3±9.3 | 50.7±5.1 | 51.2±4.2 | 51.6±5.0 |
| LV end-systolic volume (mL) | 34.2±4.8 | 33.9±3.5 | 33.7±3.1 | 34.9±4.0 |
| Time constant of relaxation (msec) | 27.9±2.0 | 25.8±2.6 | 26.7±2.0 | 26.7±1.9 |
| $E_{ES}$ (mmHg/mL) | 6.3±1.4 | 7.6±1.0 | 7.1±0.9 | 6.4±1.2 |
| $M_{SW}$ (mmHg) | 73.7±6.3 | 80.2±5.6 | 79.5±5.3 | 72.3±5.3 |

Values are means ± SD (n = 4)
$E_{ES}$: slope of linear $P_{ES}$–$V_{ES}$ relation
$M_{SW}$: slope of SW–$V_{ED}$ relation

FIGURE 34

MODULATORS OF THE BETA-3 ADRENERGIC RECEPTOR USEFUL FOR THE TREATMENT OR PREVENTION OF DISORDERS RELATED THERETO

FIELD OF THE INVENTION

The present invention relates to compounds of Formula (Ia) and pharmaceutical compositions thereof that modulate the activity of the beta-3 adrenergic receptor. Compounds of the present invention and pharmaceutical compositions thereof are directed to methods useful in the treatment of a beta-3 adrenergic receptor-mediated disorder, such as, heart failure; cardiac performance in heart failure; mortality, reinfarction, and/or hospitalization in connection with heart failure; acute heart failure; acute decompensated heart failure; congestive heart failure; severe congestive heart failure; organ damage associated with heart failure (e.g., kidney damage or failure, heart valve problems, heart rhythm problems, and/or liver damage); heart failure due to left ventricular dysfunction; heart failure with normal ejection fraction; cardiovascular mortality following myocardial infarction; cardiovascular mortality in patients with left ventricular failure or left ventricular dysfunction; left ventricular failure; left ventricular dysfunction; class II heart failure using the New York Heart Association (NYHA) classification system; class III heart failure using the New York Heart Association (NYHA) classification system; class IV heart failure using the New York Heart Association (NYHA) classification system; left ventricular ejection fraction (LVEF)<40% by radionuclide ventriculography; LVEF≤35% by echocardiography or ventricular contrast angiography; and conditions related thereto.

BACKGROUND OF THE INVENTION

Acute heart failure is a rapid decline in heart function that can cause anoxia of tissues (particularly the brain), leading to death. Acute heart failure can occur in previously asymptomatic individuals (e.g., individuals with pulmonary edema or cardiogenic shock), or in individuals with an acute exacerbation of chronic heart failure.

In the healthy heart, the actions of beta-1 and beta-2 adrenergic receptors are dominant and act through a Gs-coupled pathway to increase the force and frequency of myocardial contraction, while beta-3 adrengergic receptors act through a Gi-coupled eNOS pathway to exert weak negative inotropic effects. In the failing heart, beta-1 and beta-2 adrenergic receptors are downregulated or desensitized, while beta-3 adrenergic receptors are upregulated, thereby emphasizing the negative effects of beta-3 agonism on cardiac contractility. Morimoto, *Am J Physiol Heart Circ Physiol*, 286: H2425-H2433, 2004; Kulandavelu, *J Am College Cardiology* 59(22): 1988-90, 2012.

In individuals experiencing acute heart failure, the short-term goal is to increase contractility and improve hemodynamic status. The current standard of care for acute heart failure includes the administration of inotropes—agents that alter the force or energy of cardiac contractions. These agents are typically administered in an intensive care setting by continuous injection. Examples of such agents include adrenaline, dobutamine, dopamine, levosimendan, and noradrenaline. However, the initial improvement in contractility afforded by these agents can be followed by accelerated mortality. Katz A M and Konstam M A, *Heart Failure: Pathophysiology, Molecular Biology and Clinical Management*, Lippincott, Williams & Wilkins, 2nd edition, 1999.

The excessive mortality following administration of these agents has been linked to increased tachycardia and myocardial oxygen consumption that leads to arrhythmia and myocardial ischemia. Francis et al., *J Am College of Cardiology* 63(20): 2069-2078, 2014.

SUMMARY OF THE INVENTION

One aspect of the present invention encompasses certain 1-oxa-8-azaspiro[4.5]decan-3-yl-aminopropanyl-ether derivatives selected from compounds of Formula (Ia) and pharmaceutically acceptable salts, solvates, and hydrates thereof:

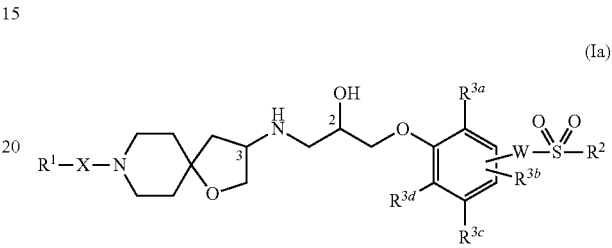

(Ia)

wherein:
X is —SO$_2$—, —C(═O)—, or —CH$_2$C(═O)—;
W is absent or C$_1$-C$_3$ alkylene;
R$^1$ is aryl or heteroaryl, wherein each is optionally substituted with one or more substituents selected from: C$_1$-C$_6$ alkoxy, C$_1$-C$_6$ alkyl, amino, cyano, C$_3$-C$_7$ cycloalkyl, C$_1$-C$_6$ haloalkyl, halogen, hydroxyl, oxo, and sulfamoyl; and wherein said C$_1$-C$_6$ alkyl and C$_3$-C$_7$ cycloalkyl are each optionally substituted with one or more substituents selected from: amino, C$_1$-C$_6$ alkoxy, C$_1$-C$_6$ alkylcarboxamide, —Y—C$_3$-C$_7$-cycloalkyl, —Y—C$_1$-C$_6$-alkylene-Z, C$_1$-C$_6$ alkylamino, C$_1$-C$_6$ haloalkylamino, and heterocyclyl;
Y is independently selected from: —O—, —NH—, and —N—(C$_1$-C$_4$ alkyl)-;
Z is independently selected from: hydroxyl, C$_1$-C$_6$ alkoxy, amino, C$_1$-C$_6$ alkylamino, and C$_2$-C$_6$ dialkylamino;
R$^2$ is selected from: C$_2$-C$_6$ alkenyl, C$_1$-C$_6$ alkyl, C$_3$-C$_7$ cycloalkyl, heterocyclyl, and C$_1$-C$_6$ haloalkyl; each optionally substituted with one or more substituents selected from: C$_1$-C$_6$ alkoxy, C$_1$-C$_6$ alkylenehydroxyl, amino, aryl, C$_3$-C$_7$ cycloalkyl, cyano, C$_3$-C$_7$ halocycloalkyl, hydroxyl, and oxo; and
R$^{3a}$, R$^{3b}$, R$^{3c}$, and R$^{3d}$ are each independently H or halogen.

One aspect of the present invention relates to pharmaceutical products selected from: a pharmaceutical composition, a formulation, a unit dosage form, and a kit; each comprising a compound of the present invention.

One aspect of the present invention relates to pharmaceutical compositions comprising a compound of the present invention, and a pharmaceutically acceptable carrier.

One aspect of the present invention relates to methods for preparing pharmaceutical compositions comprising the step of admixing a compound of the present invention and a pharmaceutically acceptable carrier.

One aspect of the present invention relates to methods for treating or preventing a beta-3 adrenergic receptor-mediated disorder in an individual, comprising administering to the individual in need thereof, a therapeutically effective amount of a compound of the present invention; a pharmaceutical product of the present invention; or a pharmaceutical composition of the present invention.

One aspect of the present invention relates to methods for treating or preventing heart failure in an individual, comprising administering to the individual in need thereof, a therapeutically effective amount of a compound of the present invention; a pharmaceutical product of the present invention; or a pharmaceutical composition of the present invention.

One aspect of the present invention relates to methods for treating a hypotensive patient, comprising administering to the patient in need thereof, a therapeutically effective amount of a compound of the present invention; a pharmaceutical product of the present invention; or a pharmaceutical composition of the present invention.

One aspect of the present invention relates to methods for treating a borderline hypotensive patient, comprising administering to the patient in need thereof, a therapeutically effective amount of a compound of the present invention; a pharmaceutical product of the present invention; or a pharmaceutical composition of the present invention.

One aspect of the present invention relates to methods for treating a normotensive patient, comprising administering to the patient in need thereof, a therapeutically effective amount of a compound of the present invention; a pharmaceutical product of the present invention; or a pharmaceutical composition of the present invention.

One aspect of the present invention relates to methods for treating a hypertensive patient, comprising administering to the patient in need thereof, a therapeutically effective amount of a compound of the present invention; a pharmaceutical product of the present invention; or a pharmaceutical composition of the present invention.

One aspect of the present invention relates to methods for treating a patient following myocardial infarction, comprising administering to the patient in need thereof, a therapeutically effective amount of a compound of the present invention; a pharmaceutical product of the present invention; or a pharmaceutical composition of the present invention.

One aspect of the present invention relates to uses of a compound of the present invention in the manufacture of a medicament for treating or preventing a beta-3 adrenergic receptor-mediated disorder in an individual.

One aspect of the present invention relates to uses of a compound of the present invention in the manufacture of a medicament for treating or preventing heart failure in an individual.

One aspect of the present invention relates to uses of a compound of the present invention in the manufacture of a medicament for treating a hypotensive patient.

One aspect of the present invention relates to uses of a compound of the present invention in the manufacture of a medicament for treating a borderline hypotensive patient.

One aspect of the present invention relates to uses of a compound of the present invention in the manufacture of a medicament for treating a normotensive patient.

One aspect of the present invention relates to uses of a compound of the present invention in the manufacture of a medicament for treating a hypertensive patient.

One aspect of the present invention relates to uses of a compound of the present invention in the manufacture of a medicament for treating a patient following myocardial infarction.

One aspect of the present invention relates to compounds of the present invention; a pharmaceutical product of the present invention; or a pharmaceutical composition of the present invention; for use in a method of treatment of the human or animal body by therapy.

One aspect of the present invention relates to compounds of the present invention; pharmaceutical products of the present invention; or pharmaceutical compositions of the present invention; for use in a method for treating or preventing a beta-3 adrenergic receptor-mediated disorder in an individual.

One aspect of the present invention relates to compounds of the present invention; pharmaceutical products of the present invention; or pharmaceutical compositions of the present invention; for use in a method for treating or preventing heart failure in an individual.

One aspect of the present invention relates to compounds of the present invention; pharmaceutical products of the present invention; or pharmaceutical compositions of the present invention; for use in a method for treating a hypotensive patient.

One aspect of the present invention relates to compounds of the present invention; pharmaceutical products of the present invention; or pharmaceutical compositions of the present invention; for use in a method for treating a borderline hypotensive patient.

One aspect of the present invention relates to compounds of the present invention; pharmaceutical products of the present invention; or pharmaceutical compositions of the present invention; for use in a method for treating a normotensive patient.

One aspect of the present invention relates to compounds of the present invention; pharmaceutical products of the present invention; or pharmaceutical compositions of the present invention; for use in a method for treating a hypertensive patient.

One aspect of the present invention relates to compounds of the present invention; pharmaceutical products of the present invention; or pharmaceutical compositions of the present invention; for use in a method for treating a patient following myocardial infarction.

In some embodiments, the beta-3 adrenergic receptor-mediated disorder is selected from the list consisting of: heart failure; cardiac performance in heart failure; mortality, reinfarction, and/or hospitalization in connection with heart failure; acute heart failure; acute decompensated heart failure; congestive heart failure; severe congestive heart failure; organ damage associated with heart failure (e.g., kidney damage or failure, heart valve problems, heart rhythm problems, and/or liver damage); heart failure due to left ventricular dysfunction; heart failure with normal ejection fraction; cardiovascular mortality following myocardial infarction; cardiovascular mortality in patients with left ventricular failure or left ventricular dysfunction; left ventricular failure; left ventricular dysfunction; class II heart failure using the New York Heart Association (NYHA) classification system; class III heart failure using the New York Heart Association (NYHA) classification system; class IV heart failure using the New York Heart Association (NYHA) classification system; LVEF<40% by radionuclide ventriculography; and LVEF≤35% by echocardiography or ventricular contrast angiography.

In some embodiments, the beta-3 adrenergic receptor-mediated disorder is heart failure.

In some embodiments, the beta-3 adrenergic receptor-mediated disorder is reduced cardiac performance in heart failure.

In some embodiments, the beta-3 adrenergic receptor-mediated disorder is mortality, reinfarction, and/or hospitalization in connection with heart failure.

In some embodiments, the beta-3 adrenergic receptor-mediated disorder is acute heart failure.

In some embodiments, the beta-3 adrenergic receptor-mediated disorder is acute decompensated heart failure.

In some embodiments, the beta-3 adrenergic receptor-mediated disorder is congestive heart failure.

In some embodiments, the beta-3 adrenergic receptor-mediated disorder is severe congestive heart failure.

In some embodiments, the beta-3 adrenergic receptor-mediated disorder is organ damage associated with heart failure (e.g., kidney damage or failure, heart valve problems, heart rhythm problems, and/or liver damage).

In some embodiments, the beta-3 adrenergic receptor-mediated disorder is heart failure due to left ventricular dysfunction.

In some embodiments, the beta-3 adrenergic receptor-mediated disorder is heart failure with normal ejection fraction.

In some embodiments, the beta-3 adrenergic receptor-mediated disorder is cardiovascular mortality following myocardial infarction.

In some embodiments, the beta-3 adrenergic receptor-mediated disorder is cardiovascular mortality in patients with left ventricular failure or left ventricular dysfunction.

In some embodiments, the beta-3 adrenergic receptor-mediated disorder is left ventricular failure.

In some embodiments, the beta-3 adrenergic receptor-mediated disorder is left ventricular dysfunction.

In some embodiments, the beta-3 adrenergic receptor-mediated disorder is class II heart failure using the New York Heart Association (NYHA) classification system.

In some embodiments, the beta-3 adrenergic receptor-mediated disorder is class III heart failure using the New York Heart Association (NYHA) classification system.

In some embodiments, the beta-3 adrenergic receptor-mediated disorder is class IV heart failure using the New York Heart Association (NYHA) classification system.

In some embodiments, the beta-3 adrenergic receptor-mediated disorder is left ventricular ejection fraction (LVEF)<40% by radionuclide ventriculography.

In some embodiments, the beta-3 adrenergic receptor-mediated disorder is left ventricular ejection fraction (LVEF)≤35% by echocardiography or ventricular contrast angiography.

Described herein are beta-3 adrenergic receptor antagonists that are useful for boosting contractility of the heart. These compounds are selective for the beta-3 adrenergic receptor and have a distinct mechanism of action that differs from currently prescribed inotropes with known cardiotoxic effects.

Because increased beta-3 adrenergic receptor activity is known to inhibit contractility in the failing heart, studies were conducted to evaluate the effect of beta-3 adrenergic receptor antagonists on contractile function. As described herein, these studies demonstrate that the inhibition of the beta-3 adrenergic receptor by beta-3 adrenergic receptor antagonists improves contractile function and hemodynamic status in the failing heart. There is a need for new agents that increase cardiac contractility while avoiding cardiotoxic effects.

These and other aspects of the invention disclosed herein will be set forth in greater detail as the patent disclosure proceeds.

BRIEF DESCRIPTION OF THE DRAWINGS

FIG. 4 shows a general synthetic scheme for the preparation of Compounds of Formula (Ia). It is understood that one or more chiral intermediates can be used in the scheme to provide chiral compounds of Formula (Ia). $PG^1$ and $PG^2$ are protecting groups such as, BOC (tert-butyloxycarbonyl), Cbz (carboxybenzyl or alternatively named benzyloxy carbamate) and the like.

FIG. 34 shows the effect of Compound 88 on hemodynamics and LV contractility in normal dogs (n=4).

DETAILED DESCRIPTION OF THE INVENTION

Definitions

Figure 1:
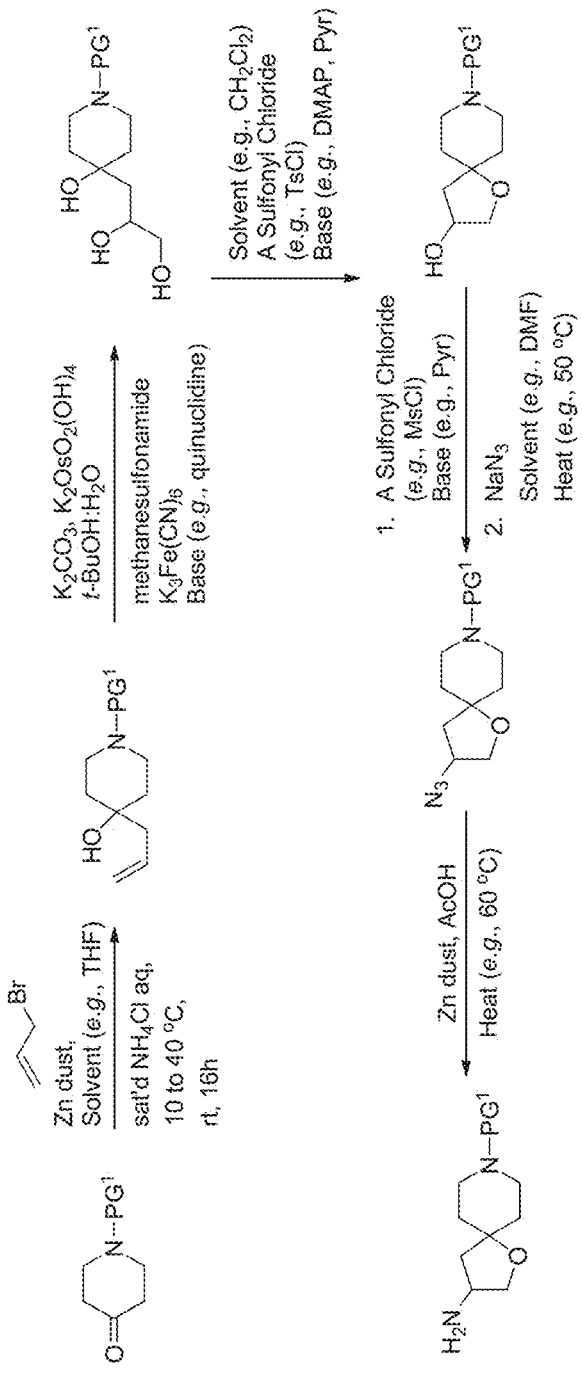
FIG. 1 shows a general synthetic scheme for the preparation of intermediates useful in preparing Compounds of Formula (Ia), wherein $PG^1$ (i.e., Protecting Group 1) can be a variety of protecting groups known to one skilled in the art, such as, a benzyloxy carbamate group.
Figure 2:
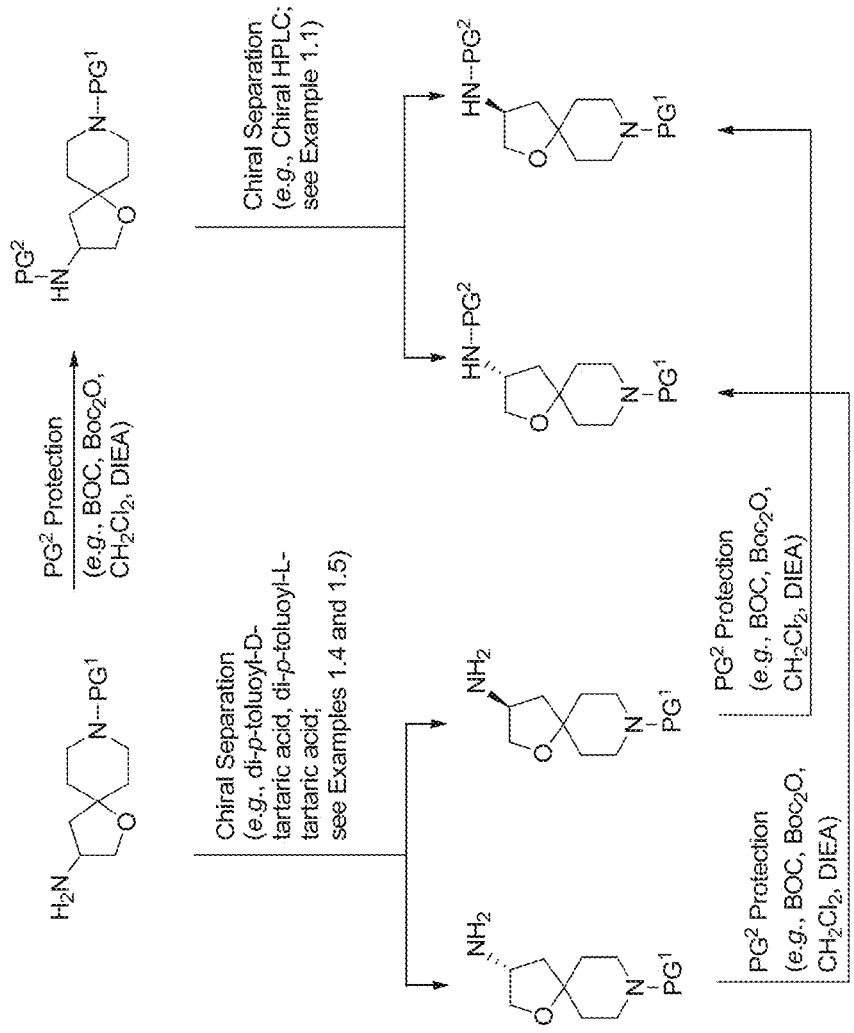
FIG. 2 shows a general synthetic scheme for the preparation of intermediates useful in preparing Compounds of Formula (Ia), wherein $PG^1$ (Protecting Group 1) and $PG^2$ (Protecting Group 2) can be a variety of protecting groups known to one skilled in the art, such as, a benzyloxy carbamate (Cbz) group and a tert-butoxycarbonyl (BOC) group. In certain instances, $PG^1$ and $PG^2$ are different and are orthogonal protecting groups, such as, $PG^1$ is Cbz and $PG^2$ is BOC.
Figure 3:
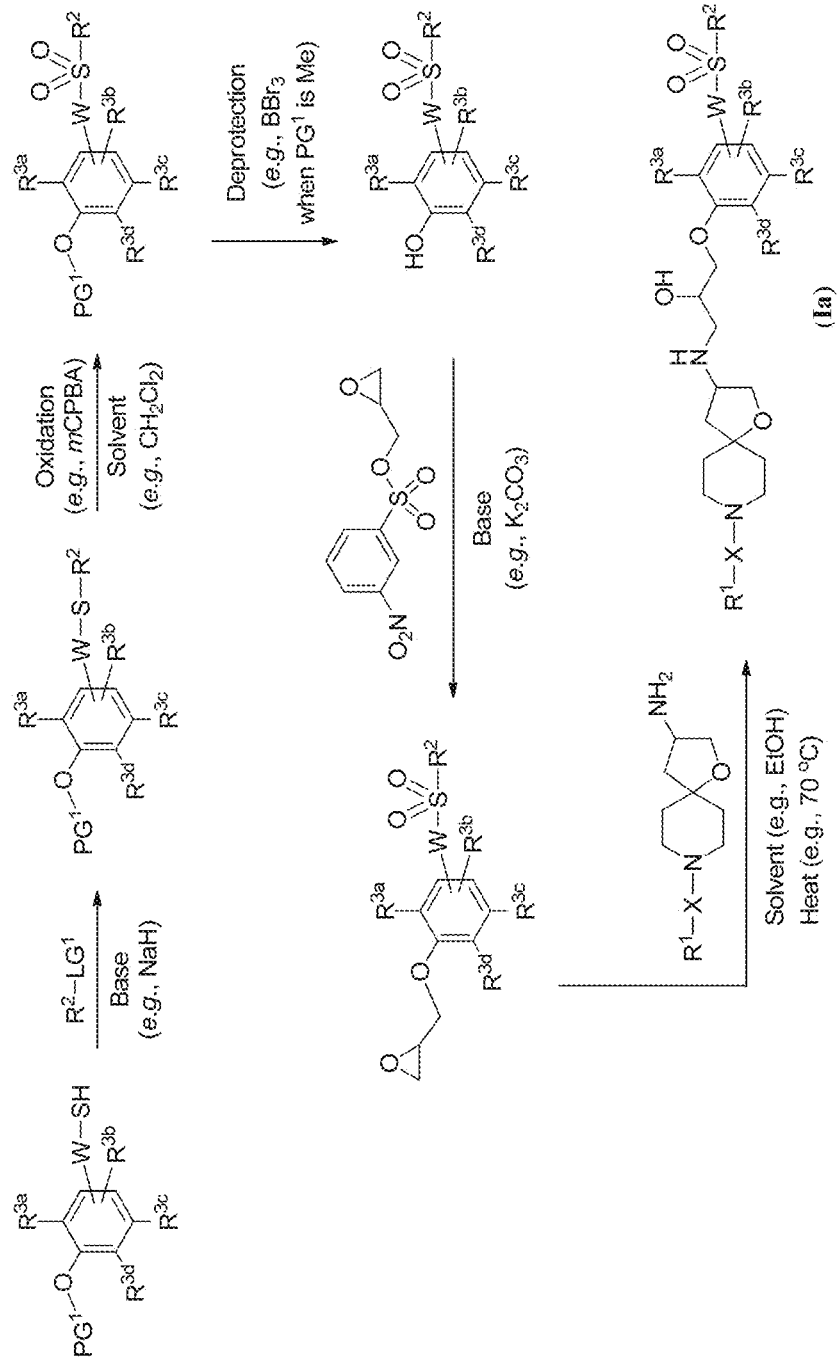
FIG. 3 shows a general synthetic scheme for the preparation of Compounds of Formula (Ia). It is understood that one or more chiral intermediates can be used in the scheme to provide chiral compounds of Formula (Ia).
Figure 4:
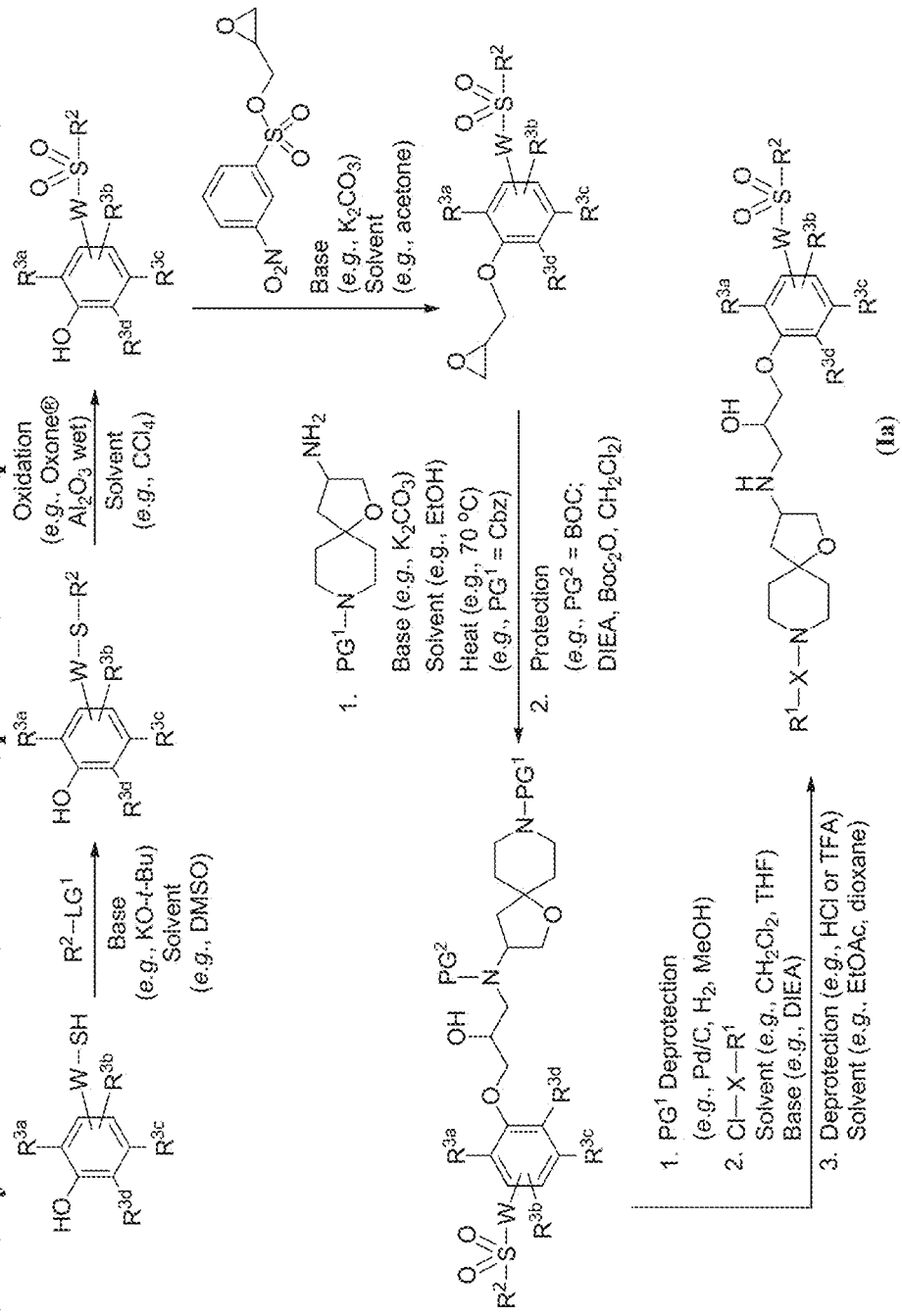
Figure 5:
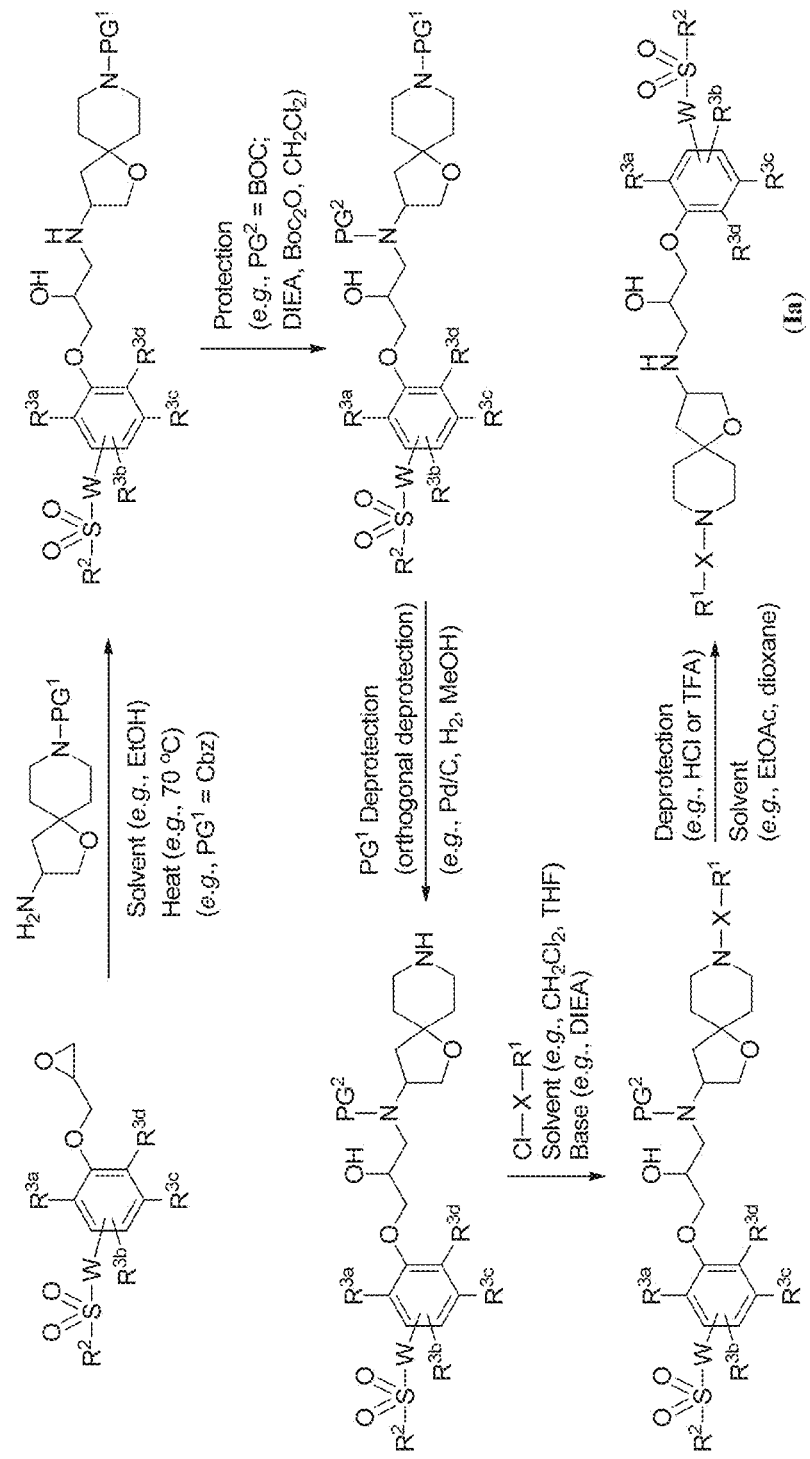
FIG. 5 shows a general synthetic scheme for the preparation of Compounds of Formula (Ia). It is understood that one or more chiral intermediates can be used in the scheme to provide chiral compounds of Formula (Ia).
Figure 6:
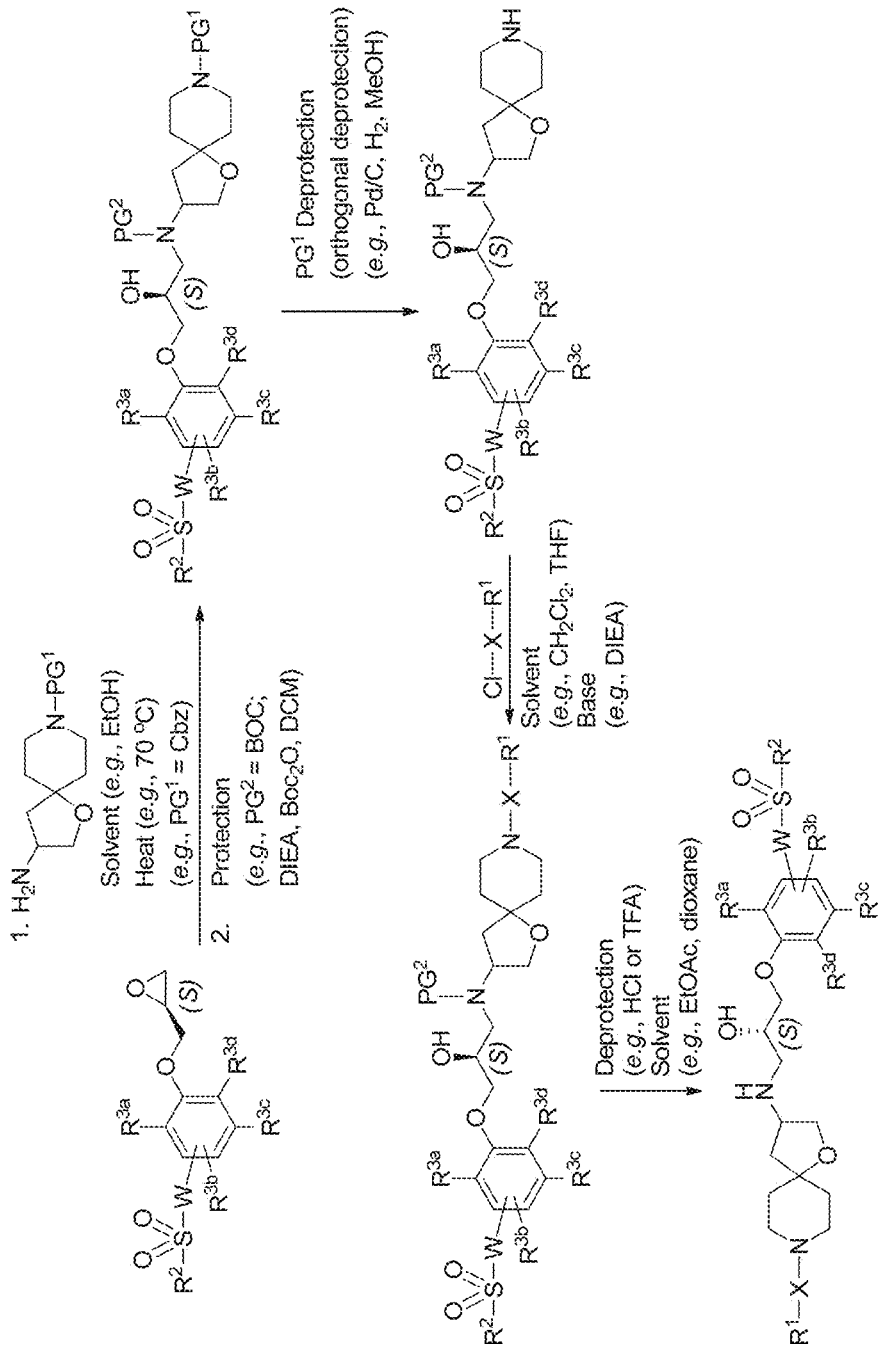
FIG. 6 shows a general synthetic scheme for the preparation of Compounds of Formula (Ia) utilizing a chiral oxirane.
Figure 7:
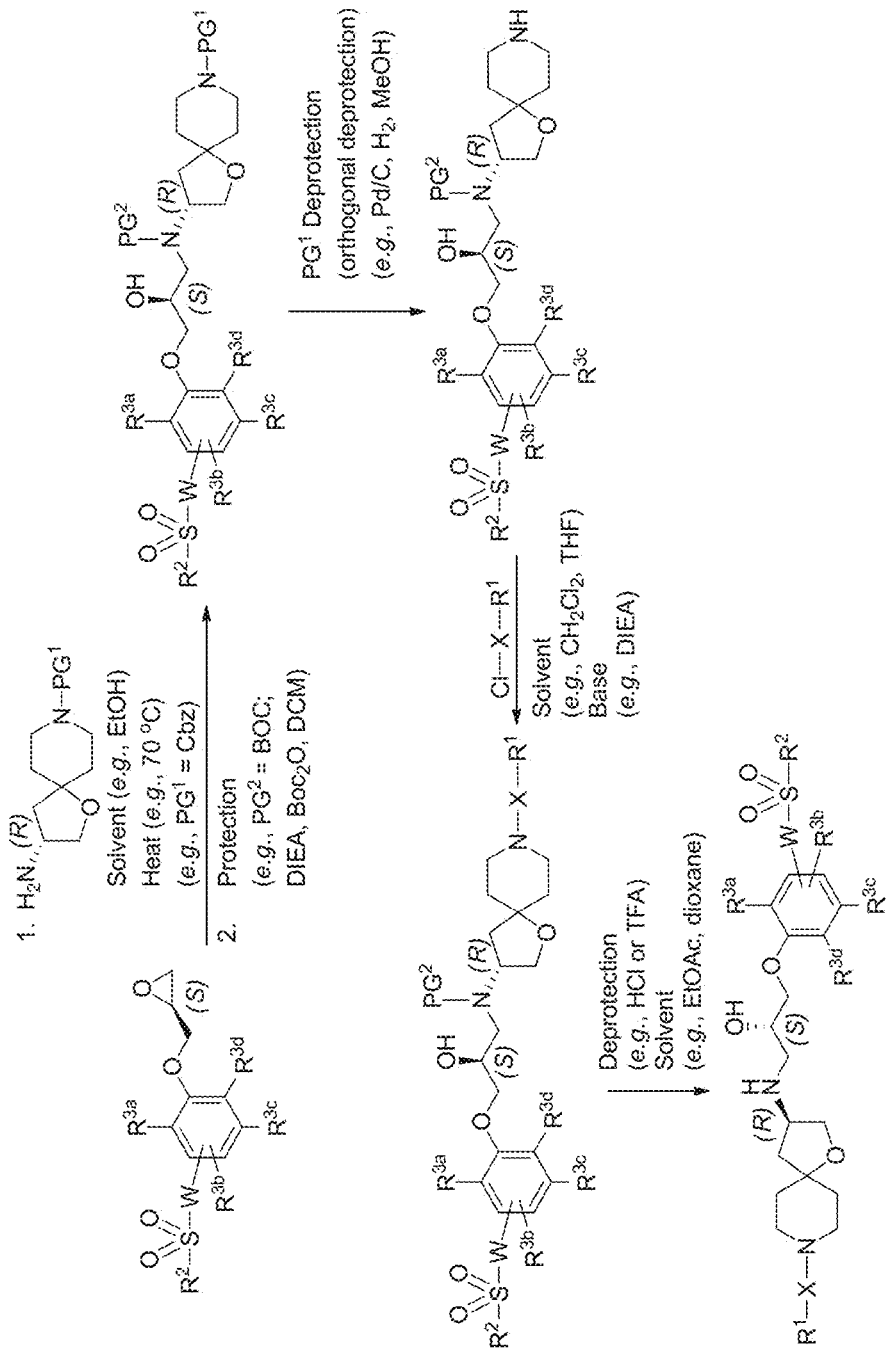
FIG. 7 shows a general synthetic scheme for the preparation of Compounds of Formula (Ia) utilizing a chiral oxirane and a chiral amine intermediate (see FIG. 2).
Figure 8:
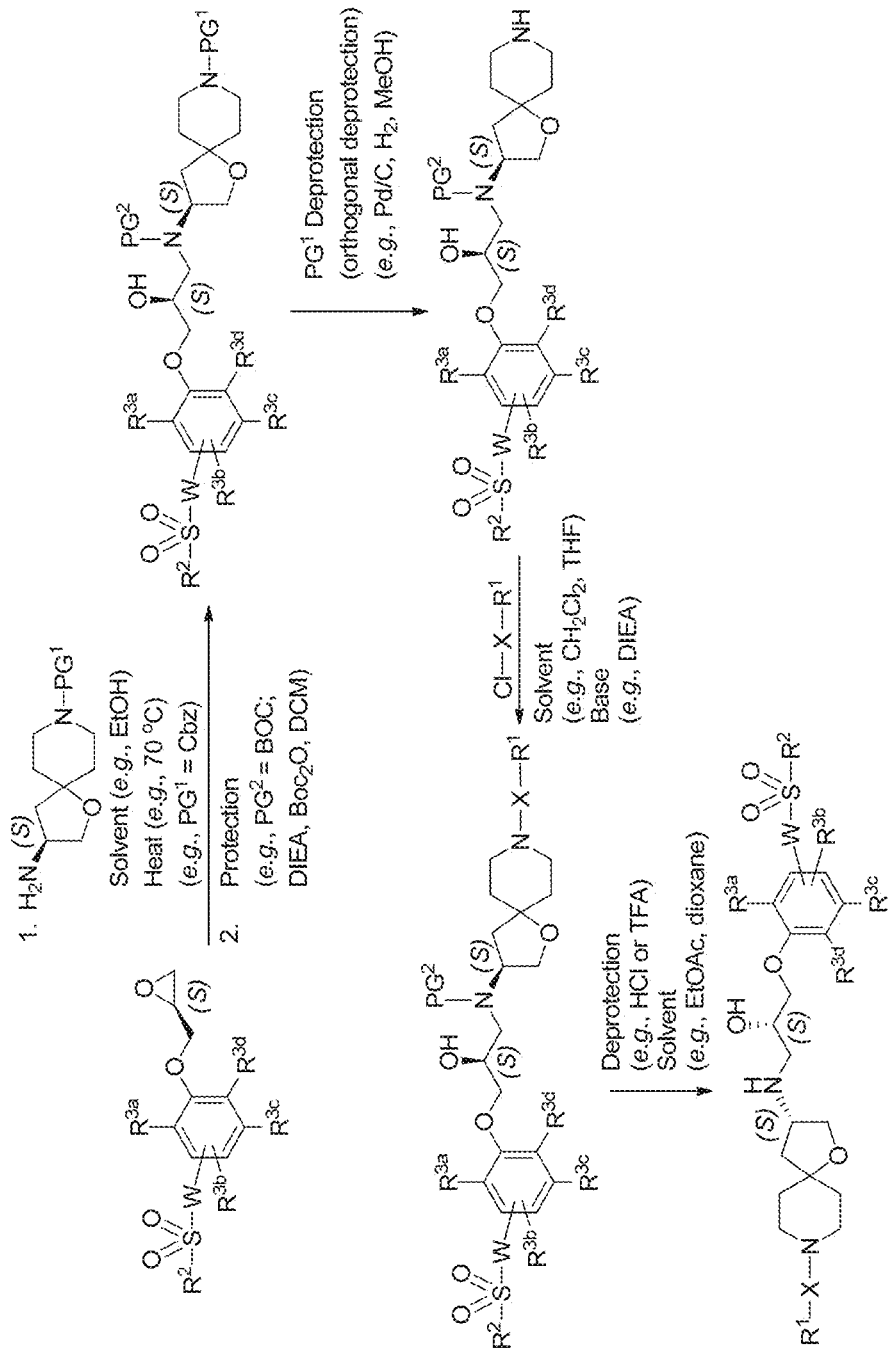
FIG. 8 shows a general synthetic scheme for the preparation of Compounds of Formula (Ia) utilizing a chiral oxirane and a chiral amine intermediate (see FIG. 2).
Figure 9:
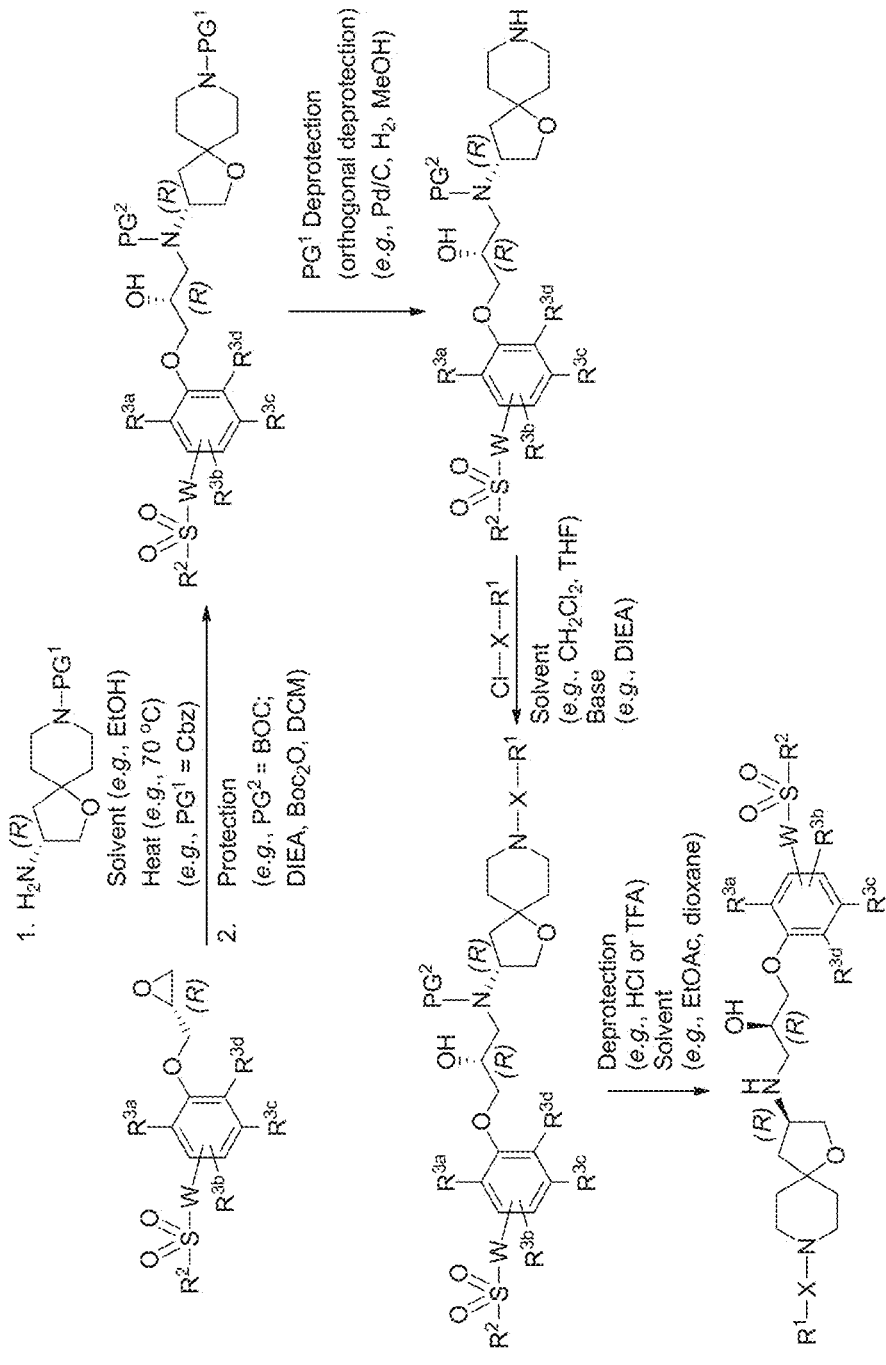
FIG. 9 shows a general synthetic scheme for the preparation of Compounds of Formula (Ia) utilizing a chiral oxirane and a chiral amine intermediate (see FIG. 2).
Figure 10:
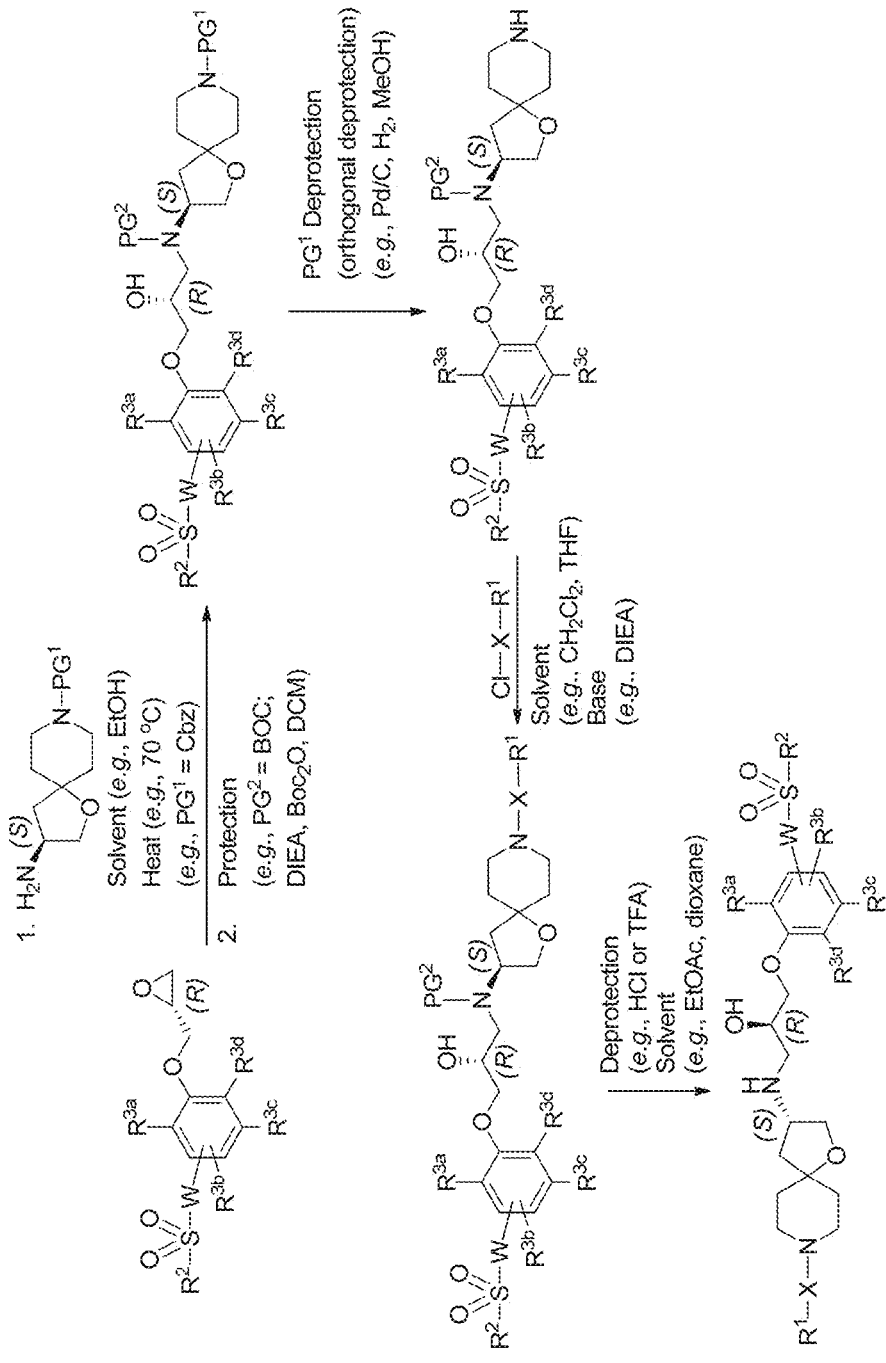
FIG. 10 shows a general synthetic scheme for the preparation of Compounds of Formula (Ia) utilizing a chiral oxirane and a chiral amine intermediate (see FIG. 2).
Figure 11:
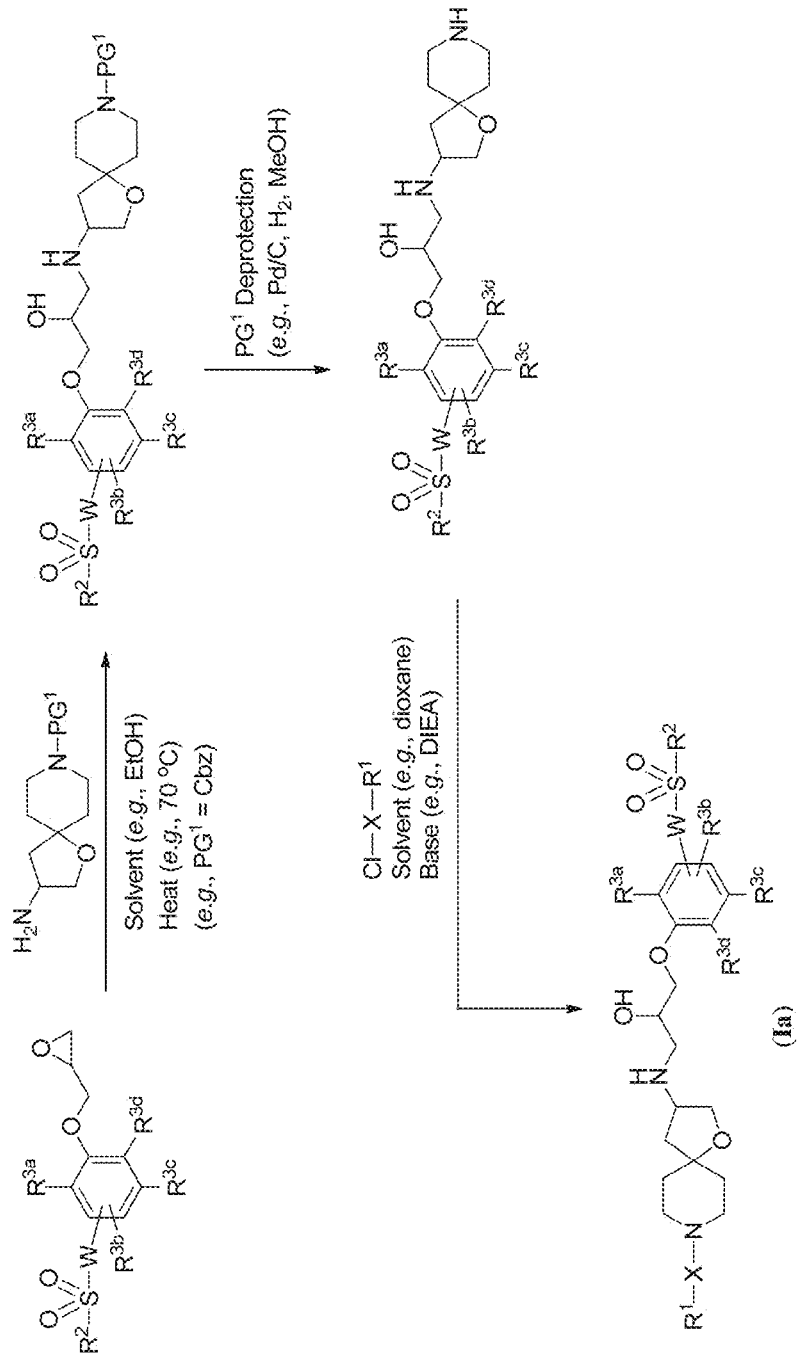
FIG. 11 shows a general synthetic scheme for the preparation of Compounds of Formula (Ia). It is understood that one or more chiral intermediates can be used in the scheme to provide chiral compounds of Formula (Ia).
Figure 12:
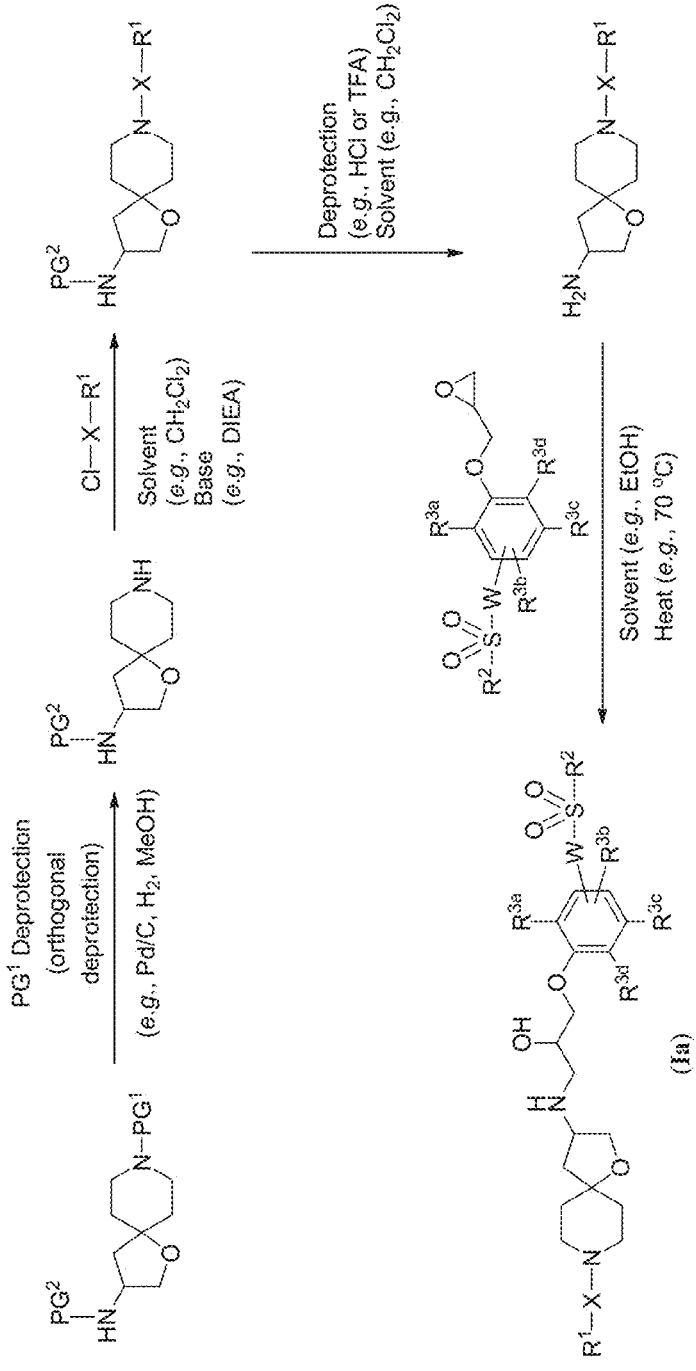
FIG. 12 shows a general synthetic scheme for the preparation of Compounds of Formula (Ia). It is understood that one or more chiral intermediates can be used in the scheme to provide chiral compounds of Formula (Ia).
Figure 13:
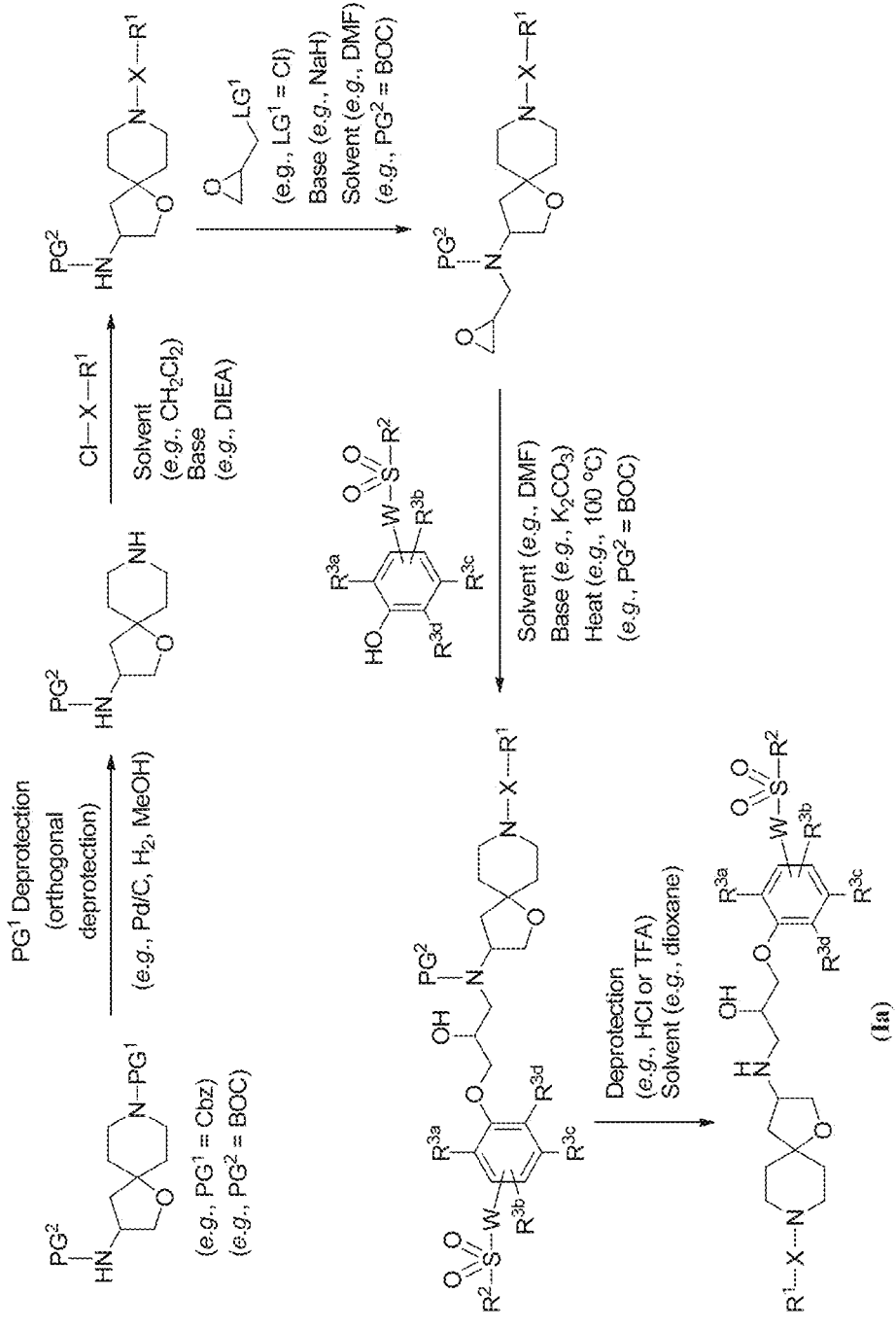
FIG. 13 shows a general synthetic scheme for the preparation of Compounds of Formula (Ia). It is understood that one or more chiral intermediates can be used in the scheme to provide chiral compounds of Formula (Ia).
Figure 14:
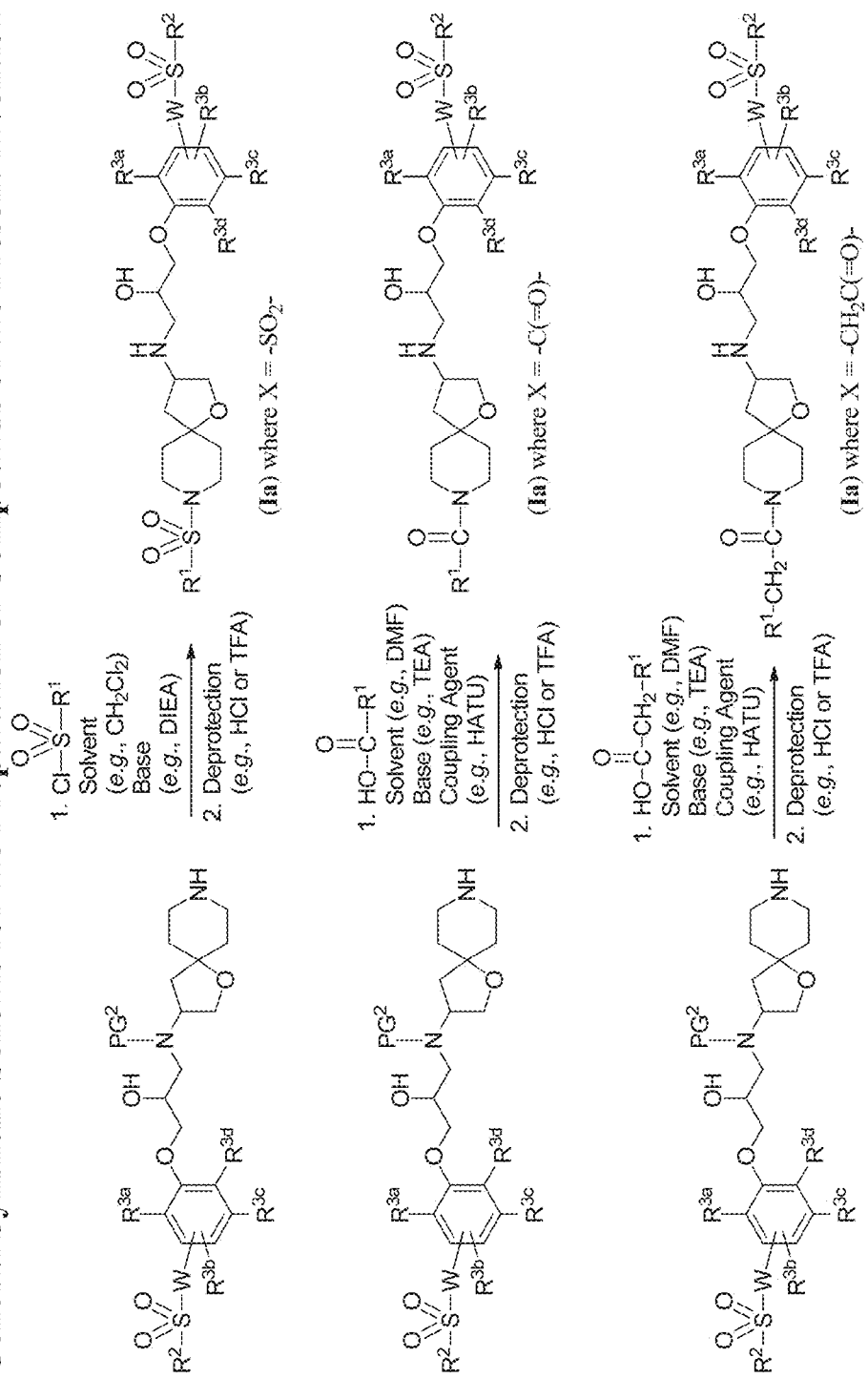
FIG. 14 shows three general synthetic schemes for the preparation of certain Compounds of Formula (Ia) wherein X is —$SO_2$—, —C(=O)—, and —$CH_2$C(=O)—. It is understood that the intermediates can be chiral providing chiral compounds of Formula (Ia).
Figure 15:
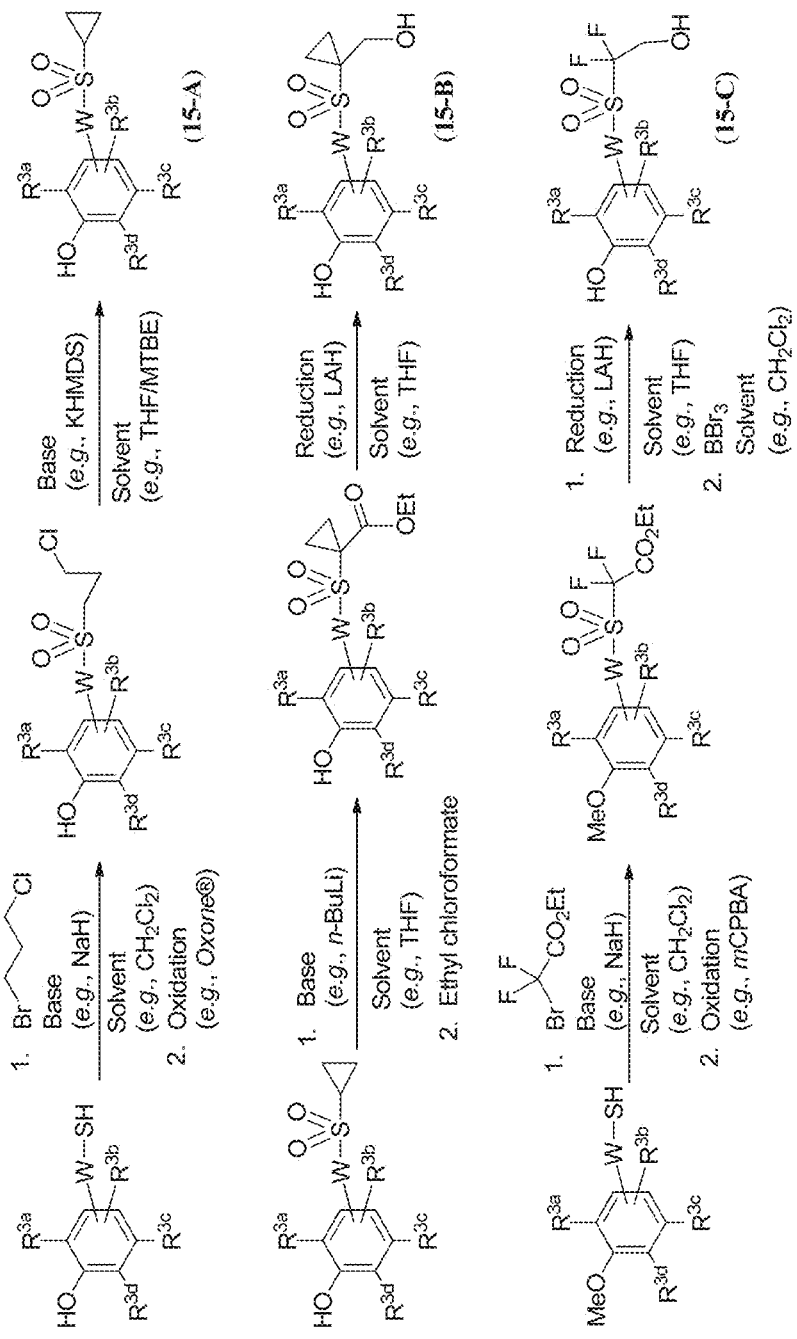
FIG. 15 shows a general synthetic scheme for the preparation of certain intermediates useful in preparing Compounds of Formula (Ia).
Figure 16:
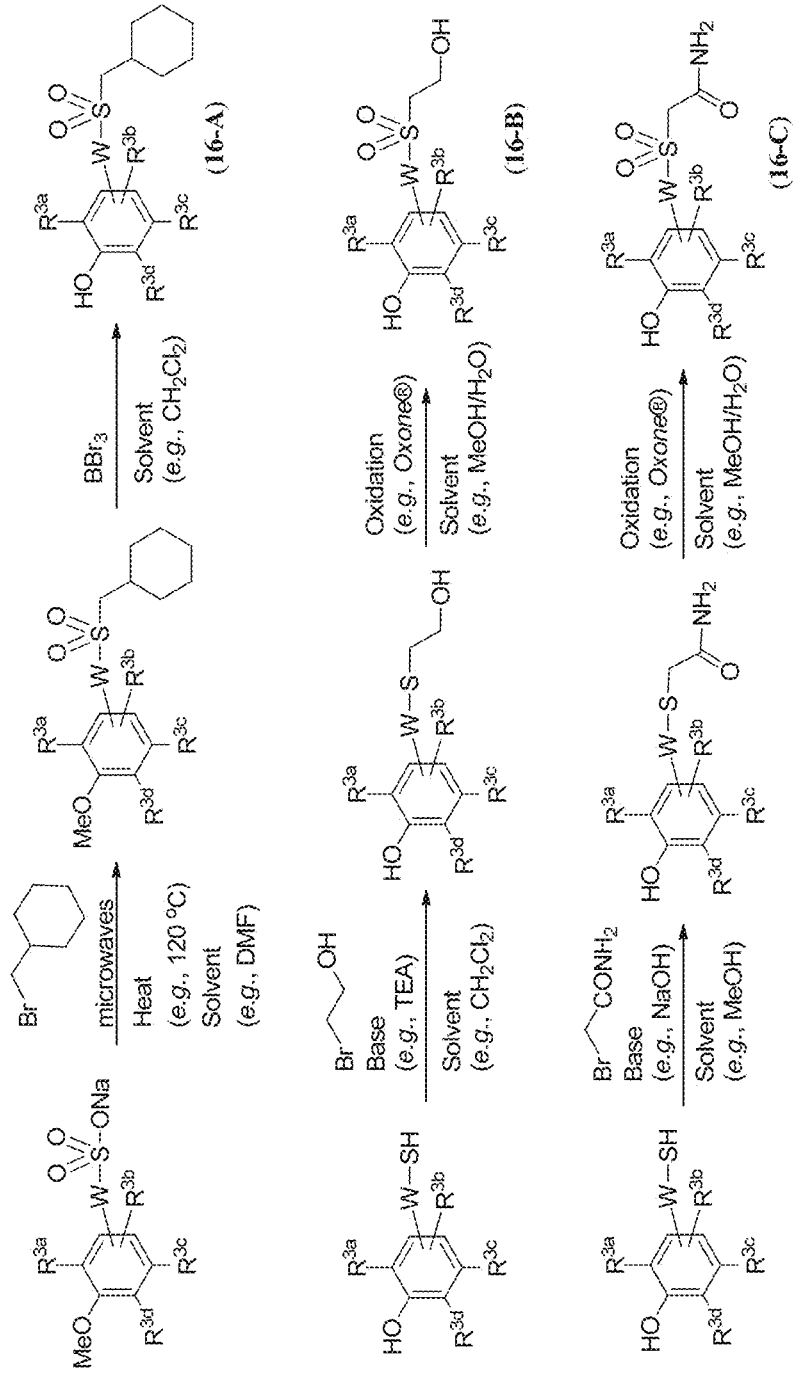
FIG. 16 shows a general synthetic scheme for the preparation of certain intermediates useful in preparing Compounds of Formula (Ia).
Figure 17:
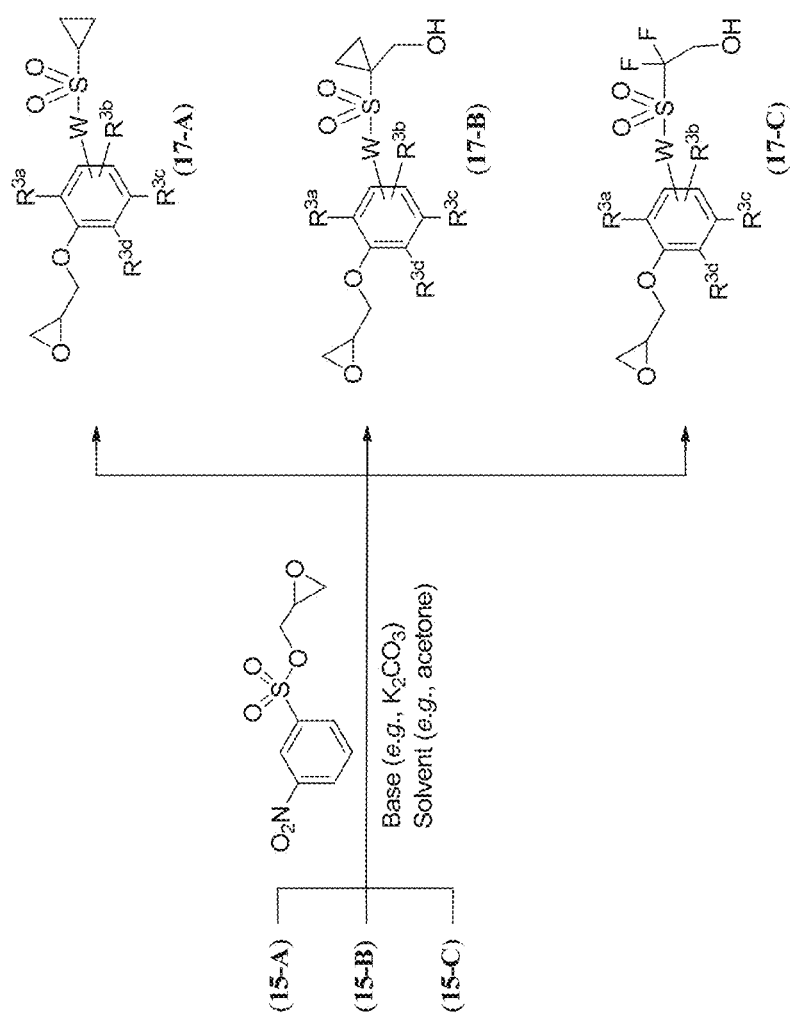
FIG. 17 shows a general synthetic scheme for the preparation of certain intermediates useful in preparing Compounds of Formula (Ia).
Figure 18:
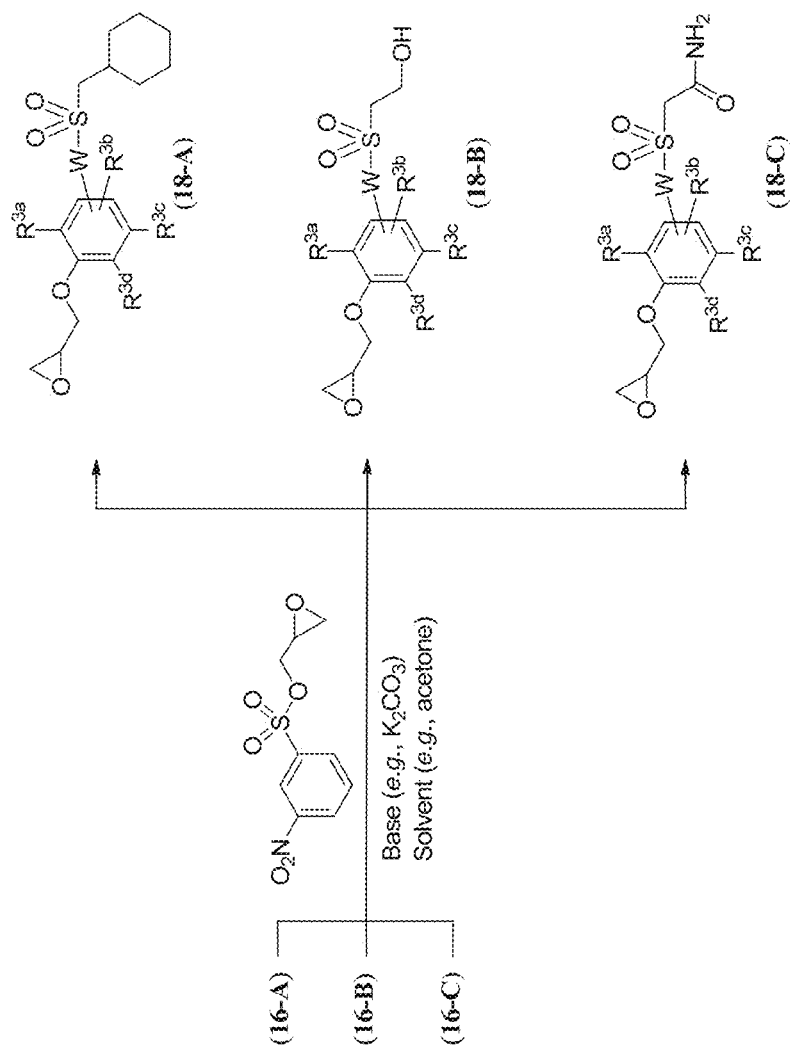
FIG. 18 shows a general synthetic scheme for the preparation of certain intermediates useful in preparing Compounds of Formula (Ia).
Figure 19:
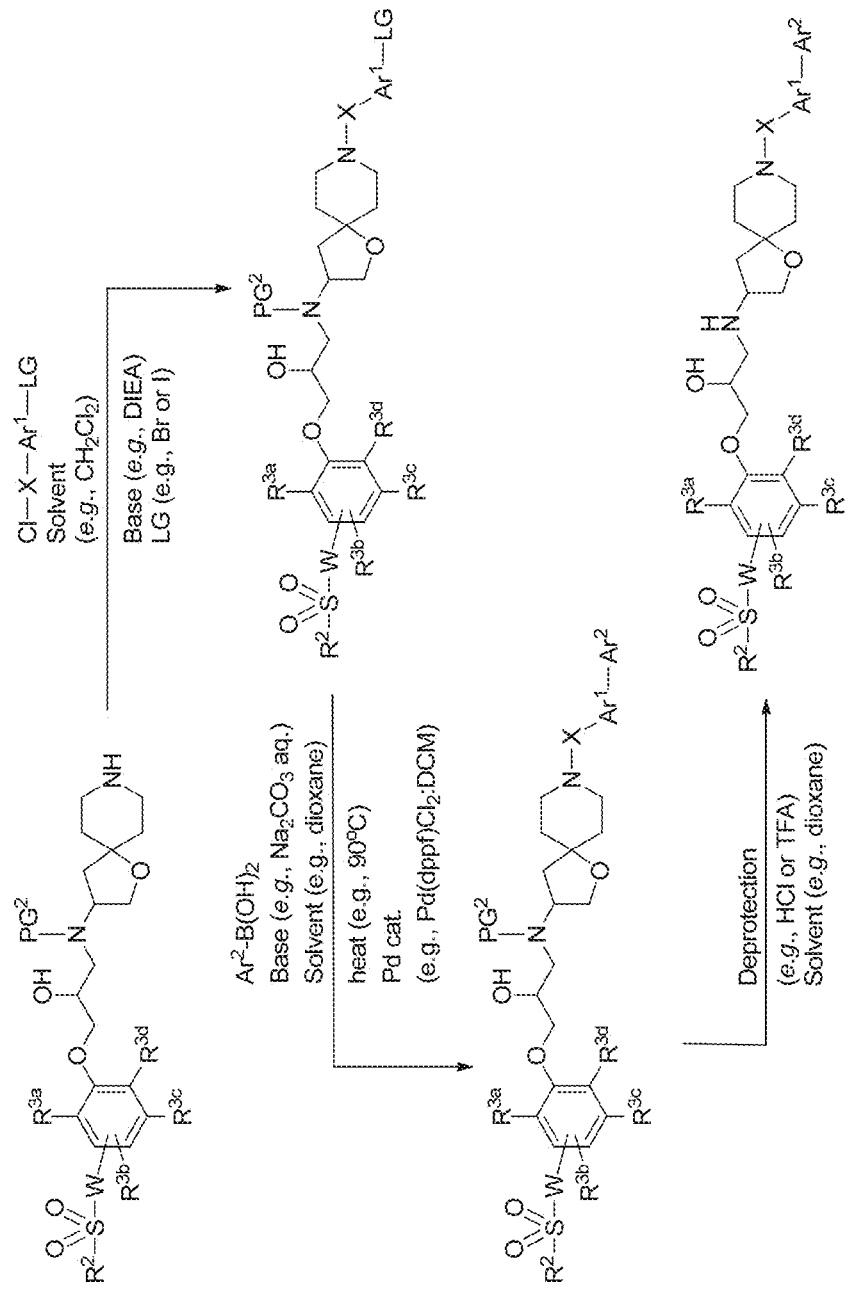
FIG. 19 shows a general synthetic scheme for the preparation of certain Compounds of Formula (Ia) wherein $R^1$ is —$Ar^1$—$Ar^2$. It is understood that $Ar^1$ and $Ar^2$ can be optionally substituted with one or more groups as described herein.
Figure 20:
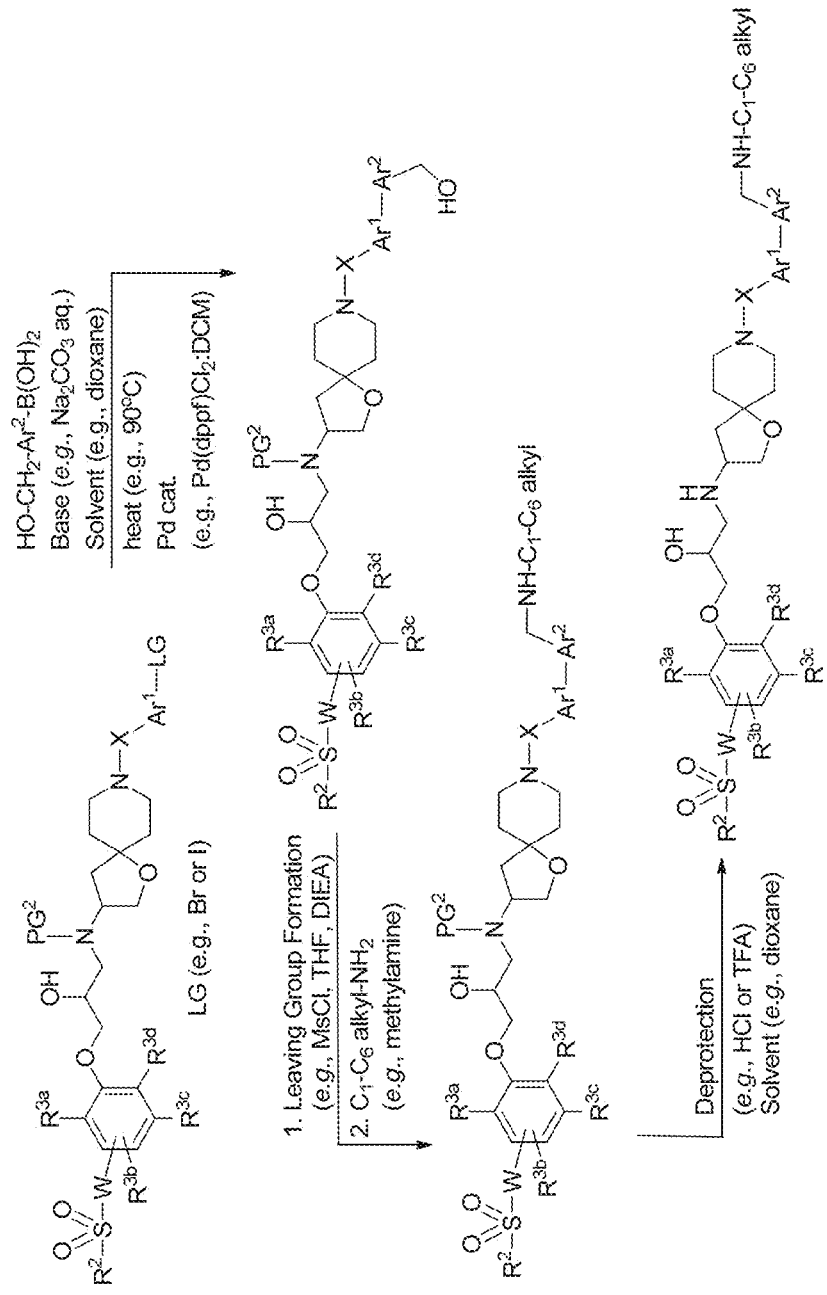
FIG. 20 shows a general synthetic scheme for the preparation of certain Compounds of Formula (Ia) wherein $R^1$ is —$Ar^1$—$Ar^2$. The scheme specifically shows $Ar^2$ substituted with at least —$CH_2OH$ or —$CH_2NH$—$C_1$-$C_6$ alkyl. It is understood that $Ar^1$ and $Ar^2$ (excluding the ring atom for $Ar^2$ that is bonded to either —$CH_2OH$ or —$CH_2NH$—$C_1$-$C_6$ alkyl) can be optionally substituted with one or more groups as described herein.
Figure 21:
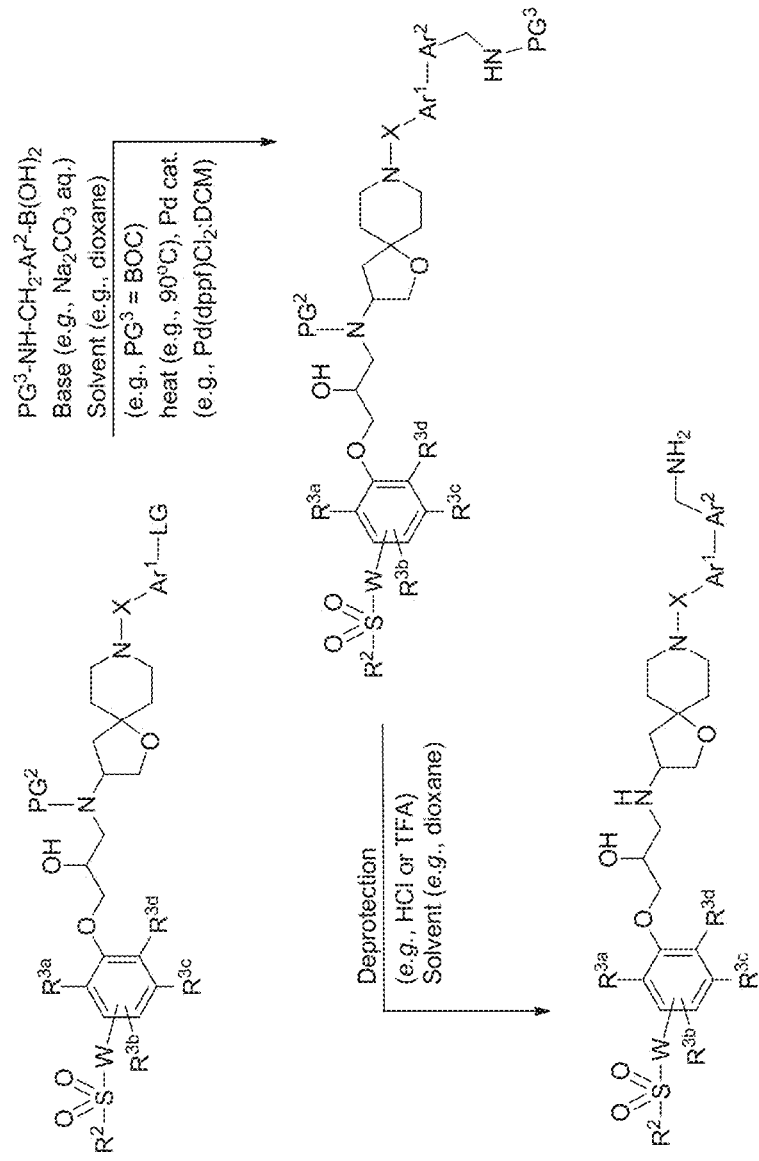
FIG. 21 shows a general synthetic scheme for the preparation of certain Compounds of Formula (Ia) wherein $R^1$ is —$Ar^1$—$Ar^2$. The scheme specifically shows $Ar^2$ substituted with at least —$CH_2NH_2$. It is understood that $Ar^1$ and $Ar^2$ (excluding the ring atom for $Ar^2$ that is bonded to —$CH_2NH_2$) can be optionally substituted with one or more groups as described herein.
Figure 22:
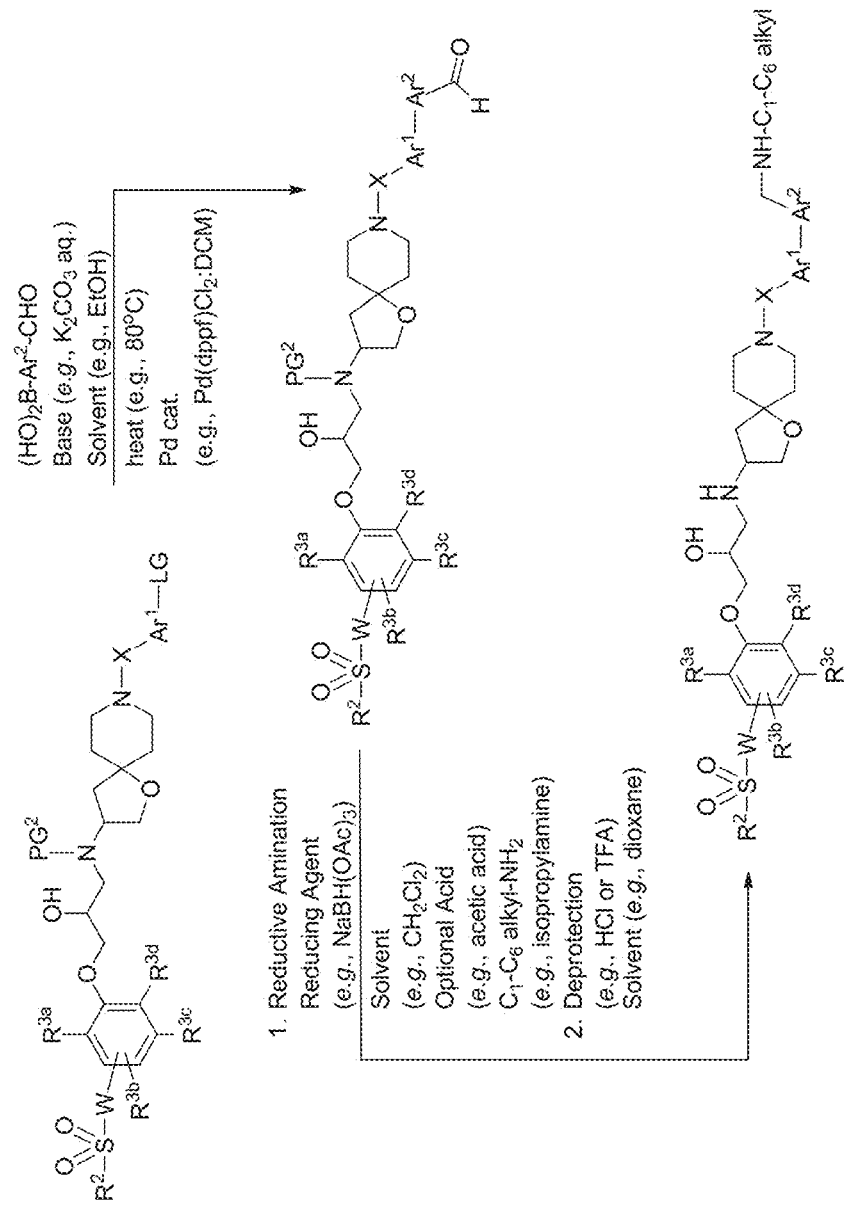
FIG. 22 shows a general synthetic scheme for the preparation of certain Compounds of Formula (Ia) wherein $R^1$ is —$Ar^1$—$Ar^2$. The scheme specifically shows $Ar^2$ substituted with at least —$C(=O)H$ or —$CH_2NH$—$C_1$-$C_6$ alkyl. It is understood that $Ar^1$ and $Ar^2$ (excluding the ring atom for $Ar^2$ that is bonded to either —$C(=O)H$ or —$CH_2NH$—$C_1$-$C_6$ alkyl) can be optionally substituted with one or more groups as described herein.
Figure 23:
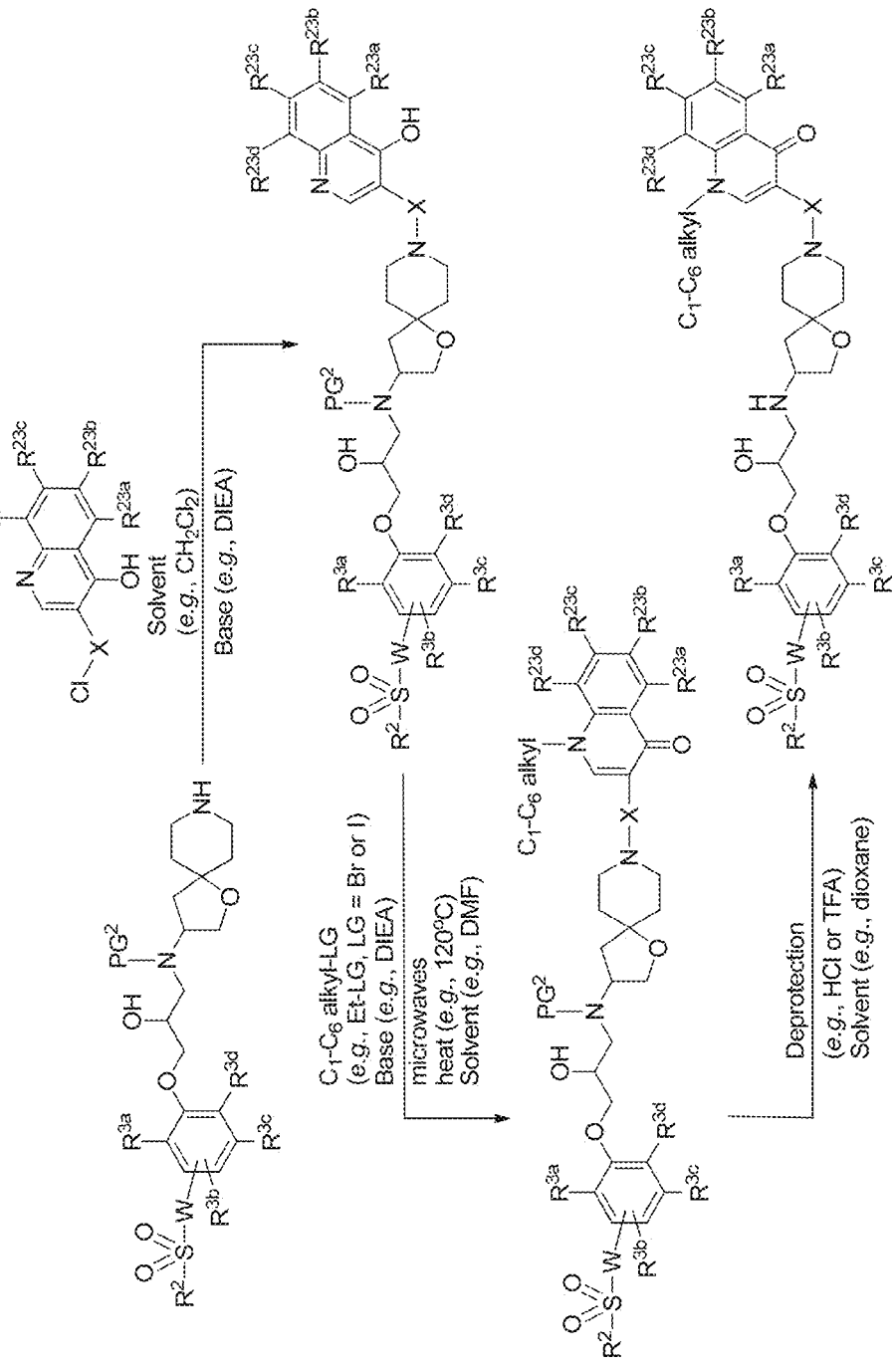
FIG. 23 shows a general synthetic scheme for the preparation of certain Compounds of Formula (Ia) wherein $R^1$ is 4-hydroxy-quinolin-3-yl (or a tautomer related thereto, such as, 4-oxo-1,4-dihydroquinolin-3-yl) or 1-($C_1$-$C_6$-alkyl)-4-oxo-1,4-dihydroquinolin-3-yl, such as, 1-ethyl-4-oxo-1,4-dihydroquinolin-3-yl. It is understood that $R^{23a}$, $R^{23b}$, $R^{23c}$, and $R^{23d}$ can be $C_1$-$C_6$ alkoxy, $C_1$-$C_6$ alkyl, amino, cyano, $C_3$-$C_7$ cycloalkyl, $C_1$-$C_6$ haloalkyl, halogen, hydroxyl, oxo, and sulfamoyl, and the $C_1$-$C_6$ alkyl and $C_3$-$C_7$ cycloalkyl each can be optionally substituted with one or more substituents selected from: amino, $C_1$-$C_6$ alkoxy, $C_1$-$C_6$ alkylcarboxamide, —Y—$C_3$-$C_7$-cycloalkyl, —Y—$C_1$-$C_6$-alkylene-Z, $C_1$-$C_6$ alkylamino, $C_1$-$C_6$ haloalkylamino, and heterocyclyl, wherein Y and Z are as defined herein.
Figure 24:
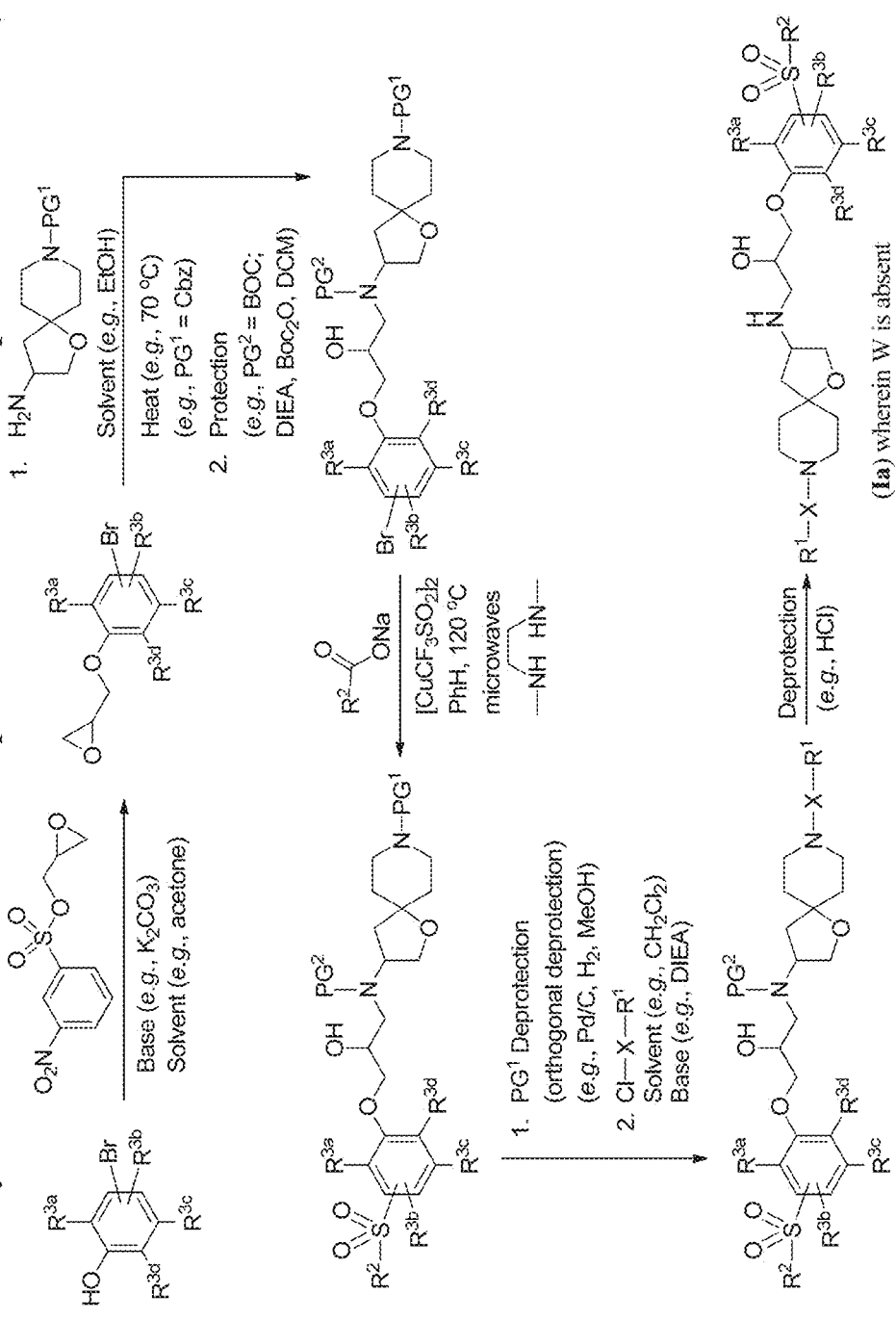
FIG. 24 shows a general synthetic scheme for introducing $R^2$ into Compounds of Formula (Ia) wherein W is a bond.

For clarity and consistency, the following definitions will be used throughout this patent document.

As used herein, "administering" refers to providing a compound of the invention or other therapy, remedy or treatment to the individual in need of treatment in a form that can be introduced into that individual's body in a therapeutically useful form and therapeutically useful amount, including, but not limited to: oral dosage forms, such as tablets, capsules, syrups, suspensions, and the like; injectable dosage forms, such as IV, IM, or IP, and the like; transdermal dosage forms, including creams, jellies, powders, or patches; buccal dosage forms; inhalation powders, sprays, suspensions, and the like; and rectal suppositories. A health care practitioner can directly provide a compound to an individual in the form of a sample, or can indirectly provide a compound to an individual by providing an oral or written prescription for the compound. Also, for example, an individual can obtain a compound by themselves without the involvement of a health care practitioner. When the compound is administered to the individual, the body is transformed by the compound in some way. When a compound of the invention is provided in combination with one or more other agents, "administration" is understood to include the compound and other agents are administered at the same time or at different times. When the agents of a combination are administered at the same time, they can be administered together in a single composition or they can be administered separately.

The term "antagonist" as used herein" refers to a moiety that can competitively bind to the $\beta_3$-adrenergic receptor as an agonist (for example, the endogenous ligand) but does not activate or substantially reduces the intracellular response compared to an agonist, and can thereby inhibit the intracellular responses by an agonist or partial agonist. An "antagonist" does not diminish the baseline intracellular response, or does so to a negligible extent, in the absence of an agonist or partial agonist.

The term "composition" refers to a compound or crystalline form thereof, including but not limited to, salts, solvates, and hydrates of a compound of the present invention, in combination with at least one additional component, such as, a composition obtained/prepared during synthesis, preformulation, in-process testing (i.e., TLC, HPLC, NMR samples), and the like.

The term "hydrate" as used herein means a compound of the invention or a salt thereof that further includes a stoichiometric or non-stoichiometric amount of water bound by non-covalent intermolecular forces.

The term "in need of treatment" and the term "in need thereof" when referring to treatment are used interchangeably to mean a judgment made by a caregiver (e.g. physician, nurse, nurse practitioner, etc. in the case of humans; veterinarian in the case of animals, including non-human mammals) that an individual or animal requires or will benefit from treatment. This judgment is made based on a variety of factors that are in the realm of a caregiver's expertise, but that includes the knowledge that the individual or animal is ill, or will become ill, as the result of a disease, condition or disorder that is treatable by the compounds of the invention. Accordingly, the compounds of the invention can be used in a protective or preventive manner; or compounds of the invention can be used to alleviate, inhibit, or ameliorate the disease, condition, or disorder.

The term "individual" refers to any animal, including mammals, such as, mice, rats, other rodents, rabbits, dogs, cats, swine, cattle, sheep, horses, primates, and humans. In some embodiment "individual" refers to humans.

The term "pharmaceutical composition" refers to a specific composition comprising at least one active ingredient; including but not limited to, salts, solvates, and hydrates of compounds of the present invention, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

The phrase "pharmaceutically acceptable salts, solvates, and hydrates" when referring to a compound/compounds as described herein embraces pharmaceutically acceptable solvates and/or hydrates of the compound/compounds, pharmaceutically acceptable salts of the compound/compounds, as well as pharmaceutically acceptable solvates and/or hydrates of pharmaceutically acceptable salts of the compound/compounds. It is also understood that when the phrase "pharmaceutically acceptable solvates and hydrates" or the phrase "pharmaceutically acceptable solvate or hydrate" is used when referring to a compound/compounds as described herein that are salts, it embraces pharmaceutically acceptable solvates and/or hydrates of such salts. It is also understood by a person of ordinary skill in the art that hydrates are a subgenus of solvates.

The term "prescribing" refers to order, authorize, or recommend the use of a drug or other therapy, remedy, or treatment. In some embodiments, a health care provider orally advises, recommends, or authorizes the use of a compound, dosage regimen, or other treatment to an individual.

The health care provider may or may not provide a written prescription for the compound, dosage regimen, or treatment. Further, the health care provider may or may not provide the compound or treatment to the individual. For example, the health care provider can advise the individual where to obtain the compound without providing the compound. In some embodiments, a health care provider can provide a written prescription for the compound, dosage regimen, or treatment to the individual. A prescription can be written on paper or recorded on electronic media. In addition, a prescription can be called in (oral) or faxed in (written) to a pharmacy or a dispensary. In some embodiments, a sample of the compound or treatment is given to the individual. As used herein, giving a sample of a compound constitutes an implicit prescription for the compound. Different health care systems around the world use different methods for prescribing and administering compounds or treatments, and these methods are encompassed by the disclosure herein.

A health care provider can include, for example, a physician, nurse, nurse practitioner, or other health care professional who can prescribe or administer compounds (drugs) for the disorders disclosed herein. In addition, a health care provider can include anyone who can recommend, prescribe, administer, or prevent an individual from receiving a compound or drug, including, for example, an insurance provider.

The terms "prevent," "preventing," and "prevention" refer to the elimination or reduction of the occurrence or onset of one or more symptoms associated with a particular disorder. For example, the terms "prevent," "preventing," and "prevention" can refer to the administration of therapy on a prophylactic or preventative basis to an individual who may ultimately manifest at least one symptom of a disorder but who has not yet done so. Such individuals can be identified on the basis of risk factors that are known to correlate with the subsequent occurrence of the disease, such as the presence of a biomarker. Alternatively, prevention therapy can be administered as a prophylactic measure without prior identification of a risk factor. Delaying the onset of the at least one episode and/or symptom of a disorder can also be considered prevention or prophylaxis.

The term "solvate" as used herein means a compound of the invention or a salt thereof that further includes a stoichiometric or non-stoichiometric amount of a solvent bound by non-covalent intermolecular forces. Preferred solvents are volatile, non-toxic, and/or acceptable for administration to humans in trace amounts.

The terms "treat," "treating," and "treatment" refer to the administration of therapy to an individual who already manifests, or who has previously manifested, at least one symptom of a disease, disorder, condition, dependence, or behavior. For example, "treating" can include any of the following with respect to a disease, disorder, condition, dependence, or behavior: alleviating, abating, ameliorating, improving, inhibiting (e.g., arresting the development), relieving, or causing regression. "Treating" can also include treating the symptoms, preventing additional symptoms, preventing the underlying physiological causes of the symptoms, or stopping the symptoms (either prophylactically and/or therapeutically) of a disease, disorder, condition, dependence, or behavior. For example, the term "treating" in reference to a disorder means a reduction in severity of one or more symptoms associated with a particular disorder. Therefore, treating a disorder does not necessarily mean a reduction in severity of all symptoms associated with a disorder and does not necessarily mean a complete reduction in the severity of one or more symptoms associated with a disorder.

The term "therapeutically effective amount" refers to the amount of active compound or pharmaceutical agent that elicits the biological or medicinal response in a tissue, system, animal, or human that is being sought by an individual, researcher, veterinarian, medical doctor, or other clinician or caregiver, which can include one or more of the following:

(1) preventing the disorder, for example, preventing a disease, condition, or disorder in an individual who may be predisposed to the disease, condition, or disorder but does not yet experience or display the relevant pathology or symptomatology;

(2) inhibiting the disorder, for example, inhibiting a disease, condition, or disorder in an individual who is experiencing or displaying the relevant pathology or symptomatology (i.e., arresting further development of the pathology and/or symptomatology); and (3) ameliorating the disorder, for example, ameliorating a disease, condition, or disorder in an individual who is experiencing or displaying the relevant pathology or symptomatology (i.e., reversing the pathology and/or symptomatology).

Chemical Group, Moiety or Radical

The term "$C_2$-$C_6$ alkenyl" denotes a radical containing 2 to 6 carbons wherein at least one carbon-carbon double bond is present. Some embodiments contain 2 to 5 carbons. Some embodiments contain 2 to 4 carbons. Some embodiments contain 2 to 3 carbons. Some embodiments contain 2 carbons (i.e., —CH=CH$_2$). Both E and Z isomers are embraced by the term "alkenyl." Furthermore, the term "alkenyl" includes di- and tri-alkenyls.

The terms "$C_1$-$C_6$ alkylene" and "$C_1$-$C_4$ alkylene" refers to a straight or branched, saturated aliphatic, divalent radical having the defined number of carbons, 1 to 6 carbon atoms or 1 to 4 carbon atoms respectively. Some embodiments contain 1 to 2 carbons. Some embodiments contain 1 to 5 carbons. Some embodiments contain 1 to 4 carbons. Some embodiments contain 1 to 3 carbons. Some embodiments contain 1 or 2 carbons. Some embodiments contain 1 carbon atom (i.e., —CH$_2$—). Examples include, but are not limited to, methylene, ethylene, n-propylene, isopropylene, n-butylene, s-butylene, isobutylene, t-butylene, pentylene, isopentylene, t-pentylene, neopentylene, 1-methylbutylene [i.e., —CH(CH$_3$)CH$_2$CH$_2$CH$_3$], 2-methylbutylene [i.e., —CH$_2$CH(CH$_3$)CH$_2$CH$_3$], n-hexylene, and the like.

The term "amino" refers to the group —NH$_2$.

The term "aryl" refers to a ring system containing 6 to 12 carbon atoms that may contain a single ring, two fused rings, or two rings bonded by a single bond (i.e., biphenyl) and wherein at least one ring is aromatic. Examples include phenyl, biphenyl, indanyl, tetrahydronaphthalenyl, naphthalenyl, and the like. Examples of biphenyl include: [1,1'-biphenyl]-2-yl (i.e., biphenyl-2-yl), [1,1'-biphenyl]-3-yl (i.e., biphenyl-3-yl), or [1,1'-biphenyl]-4-yl (i.e., biphenyl-4-yl) with the following structures respectively:

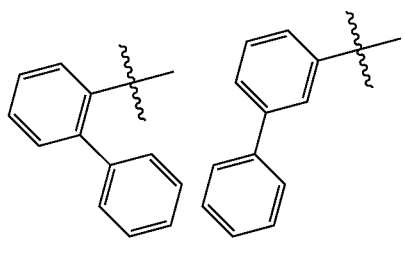

[1,1'-biphenyl]-2-yl    [1,1'-biphenyl]-3-yl

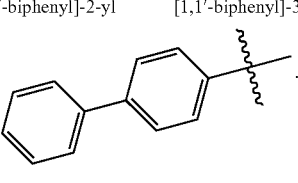

[1,1'-biphenyl]-4-yl

When a substituent is present on the aryl ring, the substituent can be bonded at any available ring carbon.

The term "$C_1$-$C_6$ alkoxy" refers to a radical comprising a $C_1$-$C_6$ alkyl group attached directly to an oxygen atom, wherein $C_1$-$C_6$ alkyl has the same definition as found herein. Some embodiments contain 1 to 5 carbons (i.e., $C_1$-$C_5$ alkoxy). Some embodiments contain 1 to 4 carbons (i.e., $C_1$-$C_4$ alkoxy). Some embodiments contain 1 to 3 carbons (i.e., $C_1$-$C_3$ alkoxy). Some embodiments contain 1 or 2 carbons. Examples include, but are not limited to methoxy, ethoxy, n-propoxy, isopropoxy, n-butoxy, t-butoxy, isobutoxy, s-butoxy, and the like.

The term "$C_1$-$C_6$ alkyl" refers to a straight or branched carbon radical containing 1 to 6 carbons. Some embodiments are 1 to 5 carbons (i.e., $C_1$-$C_5$ alkyl), some embodiments are 1 to 4 carbons (i.e., $C_1$-$C_4$ alkyl), some embodiments are 1 to 3 carbons (i.e., $C_1$-$C_3$ alkyl), and some embodiments are 1 or 2 carbons. Examples of an alkyl include, but are not limited to, methyl, ethyl, n-propyl, isopropyl, n-butyl, sec-butyl, isobutyl, tert-butyl, pentyl, isopentyl, tert-pentyl, neo-pentyl, 1-methylbutyl [i.e., —CH(CH$_3$)CH$_2$CH$_2$CH$_3$], 2-methylbutyl [i.e., —CH$_2$CH(CH$_3$)CH$_2$CH$_3$], n-hexyl and the like.

The term "$C_1$-$C_6$ alkylamino" refers to mean a radical comprising one $C_1$-$C_6$ alkyl group attached to an NH group, wherein $C_1$-$C_6$ alkyl has the same meaning as described herein. Some embodiments are "$C_1$-$C_2$ alkylamino." Some examples include methylamino, ethylamino, n-propylamino, isopropylamino, n-butylamino, s-butylamino, isobutylamino, t-butylamino, and the like.

The term "$C_1$-$C_6$ alkylcarboxamide" refers to mean a single $C_1$-$C_6$ alkyl group attached to either the carbon or the nitrogen of an amide group, wherein $C_1$-$C_6$ alkyl has the same definition as found herein. The $C_1$-$C_6$ alkylcarboxamido group may be represented by the following:

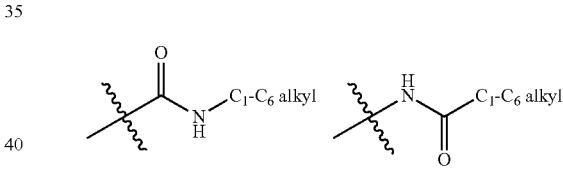

Examples include, N-methylcarboxamide, N-ethylcarboxamide, N-n-propylcarboxamide, N-isopropylcarboxamide, N-n-butylcarboxamide, N-s-butylcarboxamide, N-isobutylcarboxamide, N-t-butylcarboxamide, and the like.

The term "cyano" refers to the group —CN.

The term "$C_3$-$C_7$ cycloalkyl" refers to a saturated ring radical containing 3 to 7 carbons. Some embodiments contain 3 to 6 carbons. Some embodiments contain 3 to 5 carbons. Some embodiments contain 5 to 7 carbons. Some embodiments contain 3 to 4 carbons. Examples include cyclopropyl, cyclobutyl, cyclopentyl, cyclohexyl, cycloheptyl, and the like.

The term "$C_2$-$C_6$ dialkylamino" refers to a radical comprising an amino group substituted with two alkyl groups, the alkyl groups can be the same or different provided that two alkyl groups do not exceed a total of 6 carbon atoms between the two alkyl groups. Some embodiments are $C_2$-$C_4$ dialkylamino. Some examples include dimethylamino, methylethylamino, diethylamino, methylpropylamino, methylbutylamino, methylpentylamino, methylisopropylamino, ethylpropylamino, ethylisopropylamino, dipropylamino, propylisopropylamino, and the like.

The term "$C_1$-$C_6$ haloalkylamino" refers to a radical comprising one $C_1$-$C_6$ haloalkyl group attached to an NH group, wherein $C_1$-$C_6$ haloalkyl has the same meaning as described herein. Some embodiments are "$C_1$-$C_2$ haloalkylamino." Some examples include 2-fluoroethylamino, 2,2,2-trifluoroethylamino, (1,1,1-trifluoropropan-2-yl)amino, 3,3,3-trifluoropropylamino, 2,2,2-trifluoropropylamino, and the like.

The term "$C_1$-$C_6$ haloalkyl" refers to a radical comprising a $C_1$-$C_6$ alkyl group substituted with one or more halogens, wherein $C_1$-$C_6$ alkyl has the same definition as found herein. The $C_1$-$C_6$ haloalkyl may be fully substituted in which case it can be represented by the formula $C_nL_{2n+1}$, wherein L is a halogen and "n" is 1, 2, 3, 4, 5, or 6. When more than one halogen is present then they may be the same or different and selected from: fluorine, chlorine, bromine, and iodine. In some embodiments, haloalkyl contains 1 to 5 carbons (i.e., $C_1$-$C_5$ haloalkyl). In some embodiments, haloalkyl contains 1 to 4 carbons (i.e., $C_1$-$C_4$ haloalkyl). In some embodiments, haloalkyl contains 1 to 3 carbons (i.e., $C_1$-$C_3$ haloalkyl). In some embodiments, haloalkyl contains 1 or 2 carbons. Examples of haloalkyl groups include fluoromethyl, difluoromethyl, trifluoromethyl, chlorodifluoromethyl, 1-fluoroethyl, 2,2,2-trifluoroethyl, pentafluoroethyl, 4,4,4-trifluorobutyl, and the like.

The term "$C_3$-$C_7$ halocycloalkyl" refers to a radical comprising a $C_3$-$C_7$ cycloalkyl group substituted with one or more halogens, wherein $C_3$-$C_7$ cycloalkyl has the same definition as found herein. Examples of halocycloalkyl groups include 2,2-difluorocyclopropyl, 1-fluorocyclopropyl, 4,4-difluorocyclohexyl, and the like.

The term "halogen" refers to fluoro, chloro, bromo, or iodo group. In some embodiments, halogen is fluoro, chloro, or bromo. In some embodiments, halogen is fluoro or chloro. In some embodiments, halogen is fluoro.

The term "heteroaryl" refers to a ring system containing 5 to 14 ring atoms, that may contain a single ring, two fused rings, two rings bonded by a single bond, or three fused rings, and wherein at least one ring atom is a heteroatom, such as, O, S, and N, wherein N is optionally substituted with H, $C_1$-$C_4$ acyl, or $C_1$-$C_4$ alkyl and at least one ring is aromatic. When a heteroaryl group is substituted with an oxo group, the oxo group can be on any available ring atom, for example, a ring carbon to form a carbonyl group, a ring nitrogen to form an N-oxide, and a ring sulfur to form either a sulfoxide (i.e., —S(=O)—) or a sulfone (i.e., —S(=O)$_2$—). Some embodiments contain 5 to 6 ring atoms for example furanyl, thienyl, pyrrolyl, imidazolyl, oxazolyl, thiazolyl, isoxazolyl, pyrazolyl, isothiazolyl, oxadiazolyl, triazolyl, tetrazolyl, thiadiazolyl, pyridinyl, pyrazinyl, pyrimidinyl, pyridazinyl, triazinyl, and the like. Some embodiments contain 8 to 14 ring atoms for example quinolizinyl, quinolinyl, isoquinolinyl, cinnolinyl, phthalazinyl, quinazolinyl, quinoxalinyl, triazolyl, indolyl, isoindolyl, indazolyl, indolizinyl, purinyl, naphthyridinyl, pteridinyl, carbazolyl, acridinyl. phenazinyl, phenothiazinyl, phenoxazinyl, benzoxazolyl, benzothiazolyl, 1H-benzimidazolyl, imidazopyridinyl, benzothienyl, benzofuranyl, isobenzofuran, 2,3-dihydrobenzofuranyl, 4H-benzo[1,3]dioxinyl, 3,4-dihydro-1H-isoquinolinyl, 1,4,6,7-tetrahydro-imidazo[4,5-c]pyridinyl, 7,8-dihydro-5H-[1,6]naphthyridinyl, 5,6-dihydro-8H-[1,2,4]triazolo[4,3-a]pyrazinyl, benzo[1,3]dioxolyl, pyrazolo[1,5-a]pyrimidinyl, 1,2,3,4-tetrahydroquinolinyl, and the like. When the "heteroaryl" is a ring system containing two rings bonded by a single bond it is understood that the two rings can be bonded at any available ring carbon or available nitrogen atom. Some embodiments include 3-(1H-pyrazol-4-yl)phenyl, 3-(pyridin-4-yl)phenyl, 3-(pyridin-2-yl)phenyl, 5-phenylthiophen-2-yl, 3-(pyridin-3-yl)phenyl, 3-(pyrimidin-5-yl)phenyl, 5-(phenyl)pyridin-3-yl, 5-(1H-pyrazol-4-yl)pyridin-3-yl, 4-(pyridin-3-yl)phenyl, 4-(pyridin-4-yl)phenyl, 4-(pyridin-2-yl)phenyl, (corresponding to the following chemical structures) and the like.

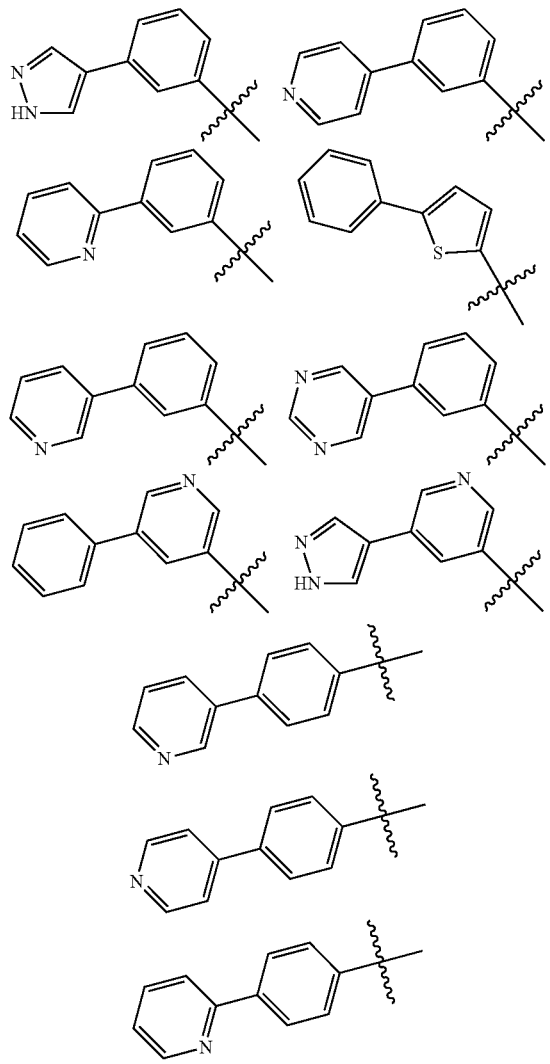

In some embodiments, "heteroaryl" is selected from the group: (1H-pyrazolyl)phenyl, (1H-pyrazolyl)pyridinyl, (pyridinyl)phenyl, (pyrimidinyl)phenyl, 1,2,3,4-tetrahydropyrido[3,2-b]pyrazinyl, 1,2-dihydroquinolinyl, 1,4-dihydroquinolinyl, 1H-benzo[d]imidazolyl, 1H-indazolyl, 1H-indolyl, 1H-pyrazolo[4,3-b]pyridinyl, 1H-pyrazolyl, 1H-pyrrolo[2,3-b]pyridinyl, 1H-pyrrolo[3,2-b]pyridinyl, 2,3-dihydro-[1,4]dioxino[2,3-b]pyridinyl, 2,3-dihydro-1H-imidazo[4,5-b]pyridinyl, 2,3-dihydro-1H-pyrido[2,3-b][1,4]oxazinyl, 2,3-dihydro-1H-pyrrolo[2,3-b]pyridinyl, 2,3-dihydrobenzofuranyl, 3,4-dihydro-2H-benzo[b][1,4]oxazinyl, 3,4-dihydro-2H-pyrano[2,3-b]pyridinyl, 3,4-dihydro-2H-pyrido[3,2-b][1,4]oxazinyl, 3H-imidazo[4,5-b]pyridinyl, (phenyl)pyridinyl, 5,6,7,8-tetrahydroquinolinyl, 6,7-dihydro-5H-pyrrolo[3,4-b]pyridin-3-yl, benzo[c][1,2,5]oxadiazolyl, benzofuranyl, chromanyl, isoquinolinyl, isoxazolyl, phenylthiophenyl, pyridinyl, pyrrolo[1,2-a]pyrimidinyl, quinolinyl, and thiazolyl. In some embodiments, "heteroaryl" is selected from the group: 1,2,3,4-tetrahydropyrido[3,2-b]pyrazin-7-yl, 1,2-dihydroquinolin-6-yl, 1,4-dihydroquinolin-3-yl, 1H-benzo[d]imidazol-5-yl, 1H-indazol-5-yl, 1H-indol-2-yl, 1H-indol-3-yl, 1H-indol-5-yl, 1H-indol-6-yl, 1H-pyrazol-4-yl, 1H-pyrazolo[4,3-b]pyridin-6-yl, 1H-pyrrolo[2,3-b]pyridin-3-yl, 1H-pyrrolo[3,2-b]pyridin-6-yl, 2,3-dihydro-[1,4]dioxino[2,3-b]pyridin-7-yl, 2,3-dihydro-1H-imidazo[4,5-b]pyridin-6-yl, 2,3-dihydro-1H-pyrido[2,3-b][1,4]oxazin-6-yl, 2,3-dihydro-1H-pyrido[2,3-b][1,4]oxazin-7-yl, 1,4-dihydroquinolin-3-yl, 2,3-dihydro-1H-pyrrolo[2,3-b]pyridin-5-yl, 2,3-dihydrobenzofuran-5-yl, 3-(1H-pyrazol-4-yl)phenyl, 3-(pyridin-2-yl)phenyl, 3-(pyridin-3-yl)phenyl, 3-(pyridin-4-yl)phenyl, 3-(pyrimidin-5-yl)phenyl, 3,4-dihydro-2H-benzo[b][1,4]oxazin-6-yl, 3,4-dihydro-2H-benzo[b][1,4]oxazin-7-yl, 3,4-dihydro-2H-pyrano[2,3-b]pyridin-6-yl, 3,4-dihydro-2H-pyrido[3,2-b][1,4]oxazin-7-yl, 3H-imidazo[4,5-b]pyridin-5-yl, 3H-imidazo[4,5-b]pyridin-6-yl, 4-(pyridin-2-yl)phenyl, 4-(pyridin-3-yl)phenyl, 4-(pyridin-4-yl)phenyl, 5-(1H-pyrazol-4-yl)pyridin-3-yl, 5-(phenyl)pyridin-3-yl, 5,6,7,8-tetrahydroquinolin-3-yl, 5-phenylthiophen-2-yl, 6,7-dihydro-5H-pyrrolo[3,4-b]pyridin-3-yl, benzo[c][1,2,5]oxadiazol-4-yl, benzofuran-2-yl, benzofuran-5-yl, chroman-6-yl, chroman-7-yl, isoquinolin-5-yl, isoxazol-4-yl, pyridin-2-yl, pyridin-3-yl, pyrrolo[1,2-a]pyrimidin-3-yl, quinolin-3-yl, quinolin-6-yl, quinolin-7-yl, and thiazol-4-yl. When referring to a heteroaryl group, it is understood that the terms thiophenyl, thiophen-2-yl, thiophen-3-yl, and the like, refer to the following heteroaryl groups respectively:

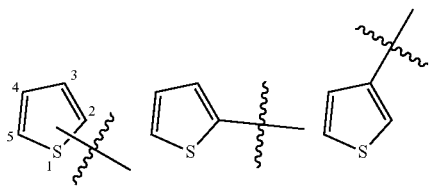

The term "heterocyclyl" refers to a non-aromatic ring radical containing 3 to 8 ring atoms, wherein one, two, or three of the ring atoms are heteroatoms selected from, for example: O, S, and N, wherein N is optionally substituted with H, $C_1$-$C_4$ acyl, or $C_1$-$C_4$ alkyl. In some embodiments, "heterocyclyl" refers to a non-aromatic ring radical containing 3 to 8 ring atoms, wherein one or two of the ring atoms are heteroatoms selected from, for example: O, S, and NH. Examples of a heterocyclyl group include aziridinyl, azetidinyl, piperidinyl, morpholinyl, oxetanyl, imidazolidinyl, piperazinyl, pyrrolidinyl, thiomorpholinyl, [1,4]oxazepanyl, azepanyl, tetrahydrofuranyl, tetrahydropyranyl, tetrahydrothiopyranyl, and the like.

The term "hydroxyl" refers to the group —OH.

The term "$C_1$-$C_6$ alkylenehydroxyl" refers to a radical consisting of a hydroxyl group bonded to a $C_1$-$C_6$ alkylene radical, wherein hydroxyl and $C_1$-$C_6$ alkylene have the same definitions as described herein. Examples include hydroxymethyl, 2-hydroxyethyl, 1-hydroxyethyl, and the like.

The term "oxo" refers to the diradical =O.

The term "sulfamoyl" refers to the group —S(=O)$_2$NH$_2$.

Compounds of the Invention

One aspect of the present invention encompasses, inter alia, certain 1-oxa-8-azaspiro[4.5]decan-3-yl-aminopropanyl-ether derivatives selected from compounds of Formula (Ia) and pharmaceutically acceptable salts, solvates, and hydrates thereof:

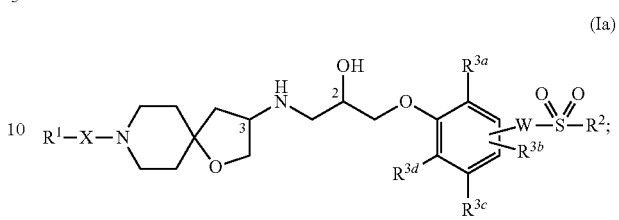

wherein: $R^1$ (as well as Y and Z that are both related to $R^1$), X, W, $R^2$, $R^{3a}$, $R^{3b}$, $R^{3c}$, and $R^{3d}$ all have the same definitions as described herein, supra and infra. It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination. All combinations of the embodiments pertaining to the chemical groups represented by the variables (e.g., $R^1$, X, W, $R^2$, $R^{3a}$, $R^{3b}$, $R^{3c}$, and $R^{3d}$; as well as $R^4$, $R^{5a}$, $R^{5b}$, $R^{5c}$, and $R^{5d}$) contained within the generic chemical formulae described herein, for example, Formulae (Ia), (Ia$^1$), (Ia$^2$), (Ia$^3$), (Ia$^4$), (Ib), (Ic), (Ie), (Ig), (Ii), and the formulae disclosed in the figures, are specifically embraced by the present invention just as if each and every combination was individually and explicitly recited, to the extent that such combinations embrace compounds that result in stable compounds (i.e., compounds that can be isolated, characterized, and tested for biological activity). In addition, all subcombinations of the chemical groups listed in the embodiments describing such variables, as well as all subcombinations of uses and medical indications described herein, are also specifically embraced by the present invention just as if each and every subcombination of chemical groups and subcombination of uses and medical indications was individually and explicitly recited herein.

As used herein, "substituted" indicates that at least one hydrogen atom of the chemical group is replaced by a non-hydrogen substituent or group, the non-hydrogen substituent or group can be monovalent or divalent. When the substituent or group is divalent, then it is understood that this group is further substituted with another substituent or group. When a chemical group herein is "substituted" it may have up to the full valance of substitution; for example, a methyl group can be substituted by 1, 2, or 3 substituents, a methylene group can be substituted by 1 or 2 substituents, a phenyl group can be substituted by 1, 2, 3, 4, or 5 substituents, a naphthyl group can be substituted by 1, 2, 3, 4, 5, 6, or 7 substituents, and the like. Likewise, "substituted with one or more substituents" refers to the substitution of a group substituted with one substituent up to the total number of substituents physically allowed by the group. Further, when a group is substituted with more than one group they can be identical or they can be different.

Compounds of the invention can also include tautomeric forms, such as keto-enol tautomers and the like. Tautomeric forms can be in equilibrium or sterically locked into one form by appropriate substitution. It is understood that the various tautomeric forms are within the scope of the compounds of the present invention. One example relates to compounds containing the group described herein as 4-oxo-1,4-dihydroquinolin-3-yl, such as Compound 326. Even thou one tautomer is shown for a compound, such as shown in Table A, it is understood that the compound embraces all such tautomers; below are two representative tautomers of 4-oxo-1,4-dihydroquinolin-3-yl:

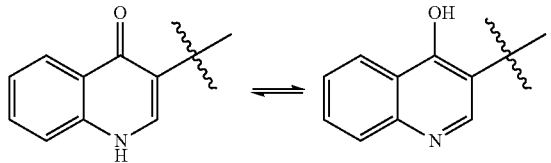 [SMILES: *c1c[nH]c2ccccc2c1=O ; *c1cnc2ccccc2c1O]

It is understood and appreciated that compounds of Formula (Ia) and formulae related thereto may have one or more chiral centers and therefore can exist as enantiomers and/or diastereoisomers. The invention is understood to extend to and embrace all such enantiomers, diastereoisomers, and mixtures thereof, including but not limited to racemates.

In some embodiments, compounds of the present can have the following defined stereochemistry as shown in Formula (Ia$^1$):

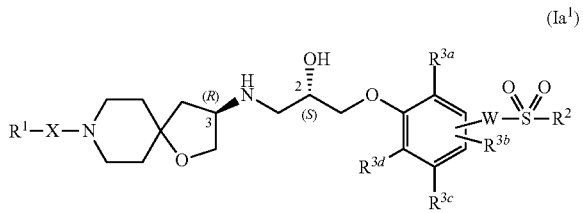

wherein: $R^1$, X, W, $R^2$, $R^{3a}$, $R^{3b}$, $R^{3c}$, and $R^{3d}$, have the same definitions as described herein, supra and infra, and wherein the carbon designated as C(3) of the oxa-azaspiro[4.5]decanyl group bonded to the nitrogen has the (R) stereochemistry and the carbon designated as C(2) of the propyl group bonded to the hydroxyl group has the (S) stereochemistry.

In some embodiments, compounds of the present can have the following defined stereochemistry as shown in Formula (Ia$^2$):

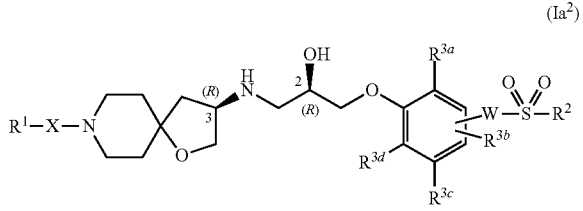

wherein: $R^1$, X, W, $R^2$, $R^{3a}$, $R^{3b}$, $R^{3c}$, and $R^{3d}$, have the same definitions as described herein, supra and infra, and wherein the carbon designated as C(3) of the oxa-azaspiro[4.5]decanyl group bonded to the nitrogen has the (R) stereochemistry and the carbon designated as C(2) of the propyl group bonded to the hydroxyl group has the (R) stereochemistry.

In some embodiments, compounds of the present can have the following defined stereochemistry as shown in Formula (Ia$^3$):

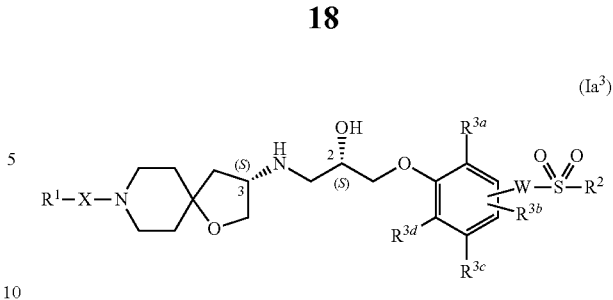

wherein: $R^1$, X, W, $R^2$, $R^{3a}$, $R^{3b}$, $R^{3c}$, and $R^{3d}$, have the same definitions as described herein, supra and infra, and wherein the carbon designated as C(3) of the oxa-azaspiro[4.5]decanyl group bonded to the nitrogen has the (S) stereochemistry and the carbon designated as C(2) of the propyl group bonded to the hydroxyl group has the (S) stereochemistry.

In some embodiments, compounds of the present can have the following defined stereochemistry as shown in Formula (Ia$^4$):

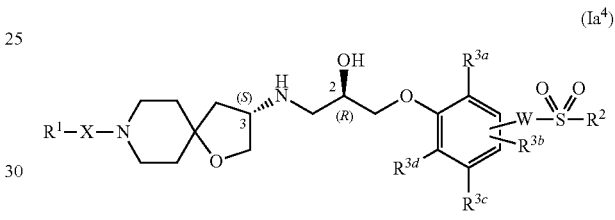

wherein: $R^1$, X, W, $R^2$, $R^{3a}$, $R^{3b}$, $R^{3c}$, and $R^{3d}$, have the same definitions as described herein, supra and infra, and wherein the carbon designated as C(3) of the oxa-azaspiro[4.5]decanyl group bonded to the nitrogen has the (S) stereochemistry and the carbon designated as C(2) of the propyl group bonded to the hydroxyl group has the (R) stereochemistry.

It is understood that any formulae described herein for which the stereochemistry is not specifically shown can be written to specifically show the stereochemistry as (R) and (S), (R) and (R), (S) and (S), or (S) and (R) for C(3) and C(2) respectively in a similar manner as Formulae (Ia$^1$), (Ia$^2$), (Ia$^3$), and (Ia$^4$) shows the respective stereochemistry for Formula (Ia), supra. Similarly, any formulae described herein for which the stereochemistry is not specifically shown can alternatively be defined using the language as described for Formulae (Ia$^1$), (Ia$^2$), (Ia$^3$), and (Ia$^4$), supra, to define the stereochemistry as (R) and (S), (R) and (R), (S) and (S), and (S) and (R) respectively.

Accordingly, in some embodiments, the stereochemistry for the C(3) carbon of the oxa-azaspiro[4.5]decanyl group bonded to the nitrogen is (R) and the stereochemistry for the C(2) carbon of the propyl group bonded to the hydroxyl group is (S). In some embodiments, the stereochemistry for the C(3) carbon of the oxa-azaspiro[4.5]decanyl group bonded to the nitrogen is (R) and the stereochemistry for the C(2) carbon of the propyl group bonded to the hydroxyl group is (R). In some embodiments, the stereochemistry for the C(3) carbon of the oxa-azaspiro[4.5]decanyl group bonded to the nitrogen is (S) and the stereochemistry for the C(2) carbon of the propyl group bonded to the hydroxyl group is (S). In some embodiments, the stereochemistry for the C(3) carbon of the oxa-azaspiro[4.5]decanyl group bonded to the nitrogen is (S) and the stereochemistry for the C(2) carbon of the propyl group bonded to the hydroxyl group is (R).

It is understood that compounds of Formula (Ia) and formulae used throughout this disclosure represent all individual enantiomers and mixtures thereof, unless specifically stated or shown otherwise.

The X Group

In some embodiments, X is —$SO_2$—, —C(=O)—, or —$CH_2$C(=O)—.

In some embodiments, X is —$SO_2$—.

In some embodiments, X is —C(=O)—.

In some embodiments, X is —$CH_2$C(=O)—.

Ring W

In some embodiments, W is absent or $C_1$-$C_3$ alkylene.

In some embodiments, W is absent.

In some embodiments, W is $C_1$-$C_3$ alkylene.

In some embodiments, W is —$CH_2$—.

The Y and Z Groups

The Y and Z groups are related to certain substituents on $R^1$ where the substituent is selected from $C_1$-$C_6$ alkyl and $C_3$-$C_7$ cycloalkyl group and each can be further optionally substituted with one or more substituents selected from a group consisting of the following that contain either the Y group or both the Y and Z groups: —Y—$C_3$-$C_7$-cycloalkyl and —Y—$C_1$-$C_6$-alkylene-Z.

In some embodiments, Y is independently selected from: —O—, —NH—, and —N—($C_1$-$C_4$ alkyl)-.

In some embodiments, Z is independently selected from: hydroxyl, $C_1$-$C_6$ alkoxy, amino, $C_1$-$C_6$ alkylamino, and $C_2$-$C_6$ dialkylamino.

It is understood that when more than one —Y—$C_3$-$C_7$-cycloalkyl and/or —Y—$C_1$-$C_6$-alkylene-Z group is present then Y and Z may be the same or different.

In some embodiments, Y is —O—.

In some embodiments, Y is —NH—.

In some embodiments, Y is —N—($C_1$-$C_4$ alkyl)-.

In some embodiments, Z is independently selected from: $C_1$-$C_6$ alkoxy, amino, and $C_1$-$C_6$ alkylamino.

In some embodiments, Z is hydroxyl.

In some embodiments, Z is $C_1$-$C_6$ alkoxy.

In some embodiments, Z is amino.

In some embodiments, Z is $C_1$-$C_6$ alkylamino.

In some embodiments, Z is $C_2$-$C_6$ dialkylamino.

The $R^1$ Group (Aryl and Heteroaryl)

In some embodiments, $R^1$ is aryl or heteroaryl, wherein each is optionally substituted with one or more substituents selected from: $C_1$-$C_6$ alkoxy, $C_1$-$C_6$ alkyl, amino, cyano, $C_3$-$C_7$ cycloalkyl, $C_1$-$C_6$ haloalkyl, halogen, hydroxyl, oxo, and sulfamoyl; and wherein said $C_1$-$C_6$ alkyl and $C_3$-$C_7$ cycloalkyl are each optionally substituted with one or more substituents selected from: amino, $C_1$-$C_6$ alkoxy, $C_1$-$C_6$ alkylcarboxamide, —Y—$C_3$-$C_7$-cycloalkyl, —Y—$C_1$-$C_6$-alkylene-Z, $C_1$-$C_6$ alkylamino, $C_1$-$C_6$ haloalkylamino, and heterocyclyl.

In some embodiments, $R^1$ is aryl or heteroaryl, wherein each is optionally substituted with one or more substituents selected from: $C_1$-$C_6$ alkoxy, $C_1$-$C_6$ alkyl, amino, cyano, $C_3$-$C_7$ cycloalkyl, $C_1$-$C_6$ haloalkyl, halogen, hydroxyl, oxo, and sulfamoyl; and wherein said $C_1$-$C_6$ alkyl and $C_3$-$C_7$ cycloalkyl are each optionally substituted with one or more substituents selected from: amino, $C_1$-$C_6$ alkoxy, $C_1$-$C_6$ alkylcarboxamide, —NH—$C_3$-$C_7$-cycloalkyl, —NH—$C_1$-$C_6$-alkylene-$NH_2$, —NH—$C_1$-$C_6$-alkylene-O—$C_1$-$C_6$-alkyl, —NH—$C_1$-$C_6$-alkylene-NH—$C_1$-$C_6$-alkyl, $C_1$-$C_6$ alkylamino, $C_1$-$C_6$ haloalkylamino, and heterocyclyl.

In some embodiments, $R^1$ is selected from: (1H-pyrazolyl)phenyl, (1H-pyrazolyl)pyridinyl, (pyridinyl)phenyl, (pyrimidinyl)phenyl, 1,2,3,4-tetrahydropyrido[3,2-b]pyrazinyl, 1,2-dihydroquinolinyl, 1,4-dihydroquinolinyl, 1H-benzo[d]imidazolyl, 1H-indazolyl, 1H-indolyl, 1H-pyrazolo[4,3-b]pyridinyl, 1H-pyrazolyl, 1H-pyrrolo[2,3-b]pyridinyl, 1H-pyrrolo[3,2-b]pyridinyl, 2,3-dihydro-[1,4]dioxino[2,3-b]pyridinyl, 2,3-dihydro-1H-imidazo[4,5-b]pyridinyl, 2,3-dihydro-1H-pyrido[2,3-b][1,4]oxazinyl, 2,3-dihydro-1H-pyrrolo[2,3-b]pyridinyl, 2,3-dihydrobenzofuranyl, 3,4-dihydro-2H-benzo[b][1,4]oxazinyl, 3,4-dihydro-2H-pyrano[2,3-b]pyridinyl, 3,4-dihydro-2H-pyrido[3,2-b][1,4]oxazinyl, 3H-imidazo[4,5-b]pyridinyl, (phenyl)pyridinyl, 5,6,7,8-tetrahydronaphthalenyl, 5,6,7,8-tetrahydroquinolinyl, 6,7-dihydro-5H-pyrrolo[3,4-b]pyridin-3-yl, benzo[c][1,2,5]oxadiazolyl, benzofuranyl, biphenyl, chromanyl, isoquinolinyl, isoxazolyl, naphthalenyl, phenyl, phenylthiophenyl, pyridinyl, pyrrolo[1,2-a]pyrimidinyl, quinolinyl, and thiazolyl; wherein each is optionally substituted with one or more substituents selected from: 2-methylpropan-2-yl, amino, bromo, chloro, cyclopropyl, ethoxy, ethyl, fluoro, hydroxy, isopropoxy, methoxy, methyl, oxo, propan-2-yl, propan-1-yl, sulfamoyl, and trifluoromethyl; and wherein said 2-methylpropan-2-yl, cyclopropyl, ethyl, methyl, and propan-2-yl are each optionally substituted with one or more substituents selected from: 2,2,2-trifluoroethylamino, 2-aminoethylamino, 2-methoxyethylamino, 3-aminopropylamino, acetamido, amino, azetidin-1-yl, butylamino, cyclobutylamino, ethylamino, isobutylamino, isopropylamino, methoxy, methylamino, morpholino, propylamino, tert-butylamino, and tert-pentylamino.

In some embodiments, $R^1$ is selected from: (1H-pyrazolyl)phenyl, (1H-pyrazolyl)pyridinyl, (pyridinyl)phenyl, (pyrimidinyl)phenyl, 1,2,3,4-tetrahydropyrido[3,2-b]pyrazinyl, 1,2-dihydroquinolinyl, 1,4-dihydroquinolinyl, 1H-benzo[d]imidazolyl, 1H-indazolyl, 1H-indolyl, 1H-pyrazolo[4,3-b]pyridinyl, 1H-pyrazolyl, 1H-pyrrolo[2,3-b]pyridinyl, 1H-pyrrolo[3,2-b]pyridinyl, 2,3-dihydro-[1,4]dioxino[2,3-b]pyridinyl, 2,3-dihydro-1H-imidazo[4,5-b]pyridinyl, 2,3-dihydro-1H-pyrido[2,3-b][1,4]oxazinyl, 2,3-dihydro-1H-pyrrolo[2,3-b]pyridinyl, 2,3-dihydrobenzofuranyl, 3,4-dihydro-2H-benzo[b][1,4]oxazinyl, 3,4-dihydro-2H-pyrano[2,3-b]pyridinyl, 3,4-dihydro-2H-pyrido[3,2-b][1,4]oxazinyl, 3H-imidazo[4,5-b]pyridinyl, (phenyl)pyridinyl, 5,6,7,8-tetrahydronaphthalenyl, 5,6,7,8-tetrahydroquinolinyl, 6,7-dihydro-5H-pyrrolo[3,4-b]pyridin-3-yl, benzo[c][1,2,5]oxadiazolyl, benzofuranyl, biphenyl, chromanyl, isoquinolinyl, isoxazolyl, naphthalenyl, phenyl, phenylthiophenyl, pyridinyl, pyrrolo[1,2-a]pyrimidinyl, quinolinyl, and thiazolyl; wherein each is optionally substituted with one or more substituents selected from: (2,2,2-trifluoroethylamino)methyl, (2-aminoethylamino)methyl, (2-methoxyethylamino)methyl, (3-aminopropylamino)methyl, (butylamino)methyl, (cyclobutylamino)methyl, (ethylamino)methyl, (isobutylamino)methyl, (isopropylamino)methyl, (methylamino)methyl, (propylamino)methyl, (tert-butylamino)methyl, (tert-pentylamino)methyl, 1-amino-2-methylpropan-2-yl, 1-aminocyclopropyl, 2-acetamidoethyl, 2-aminoethyl, 2-aminopropan-2-yl, 2-methoxyethyl, amino, aminomethyl, azetidin-1-ylmethyl, bromo, chloro, cyano, cyclopropyl, ethoxy, ethyl, fluoro, hydroxy, isopropoxy, methoxy, methyl, morpholinomethyl, oxo, propan-1-yl, sulfamoyl, and trifluoromethyl.

In some embodiments, $R^1$ is selected from: 1,2,3,4-tetrahydropyrido[3,2-b]pyrazin-7-yl, 1,2-dihydroquinolin-6-yl, 1,4-dihydroquinolin-3-yl, 1H-benzo[d]imidazol-5-yl, 1H-indazol-5-yl, 1H-indol-2-yl, 1H-indol-3-yl, 1H-indol-5-yl, 1H-indol-6-yl, 1H-pyrazol-4-yl, 1H-pyrazolo[4,3-b]pyridin-6-yl, 1H-pyrrolo[2,3-b]pyridin-3-yl, 1H-pyrrolo[3,2-b]pyridin-6-yl, 2,3-dihydro-[1,4]dioxino[2,3-b]pyridin-7-yl, 2,3-dihydro-1H-imidazo[4,5-b]pyridin-6-yl, 2,3-dihydro-1H-pyrido[2,3-b][1,4]oxazin-6-yl, 2,3-dihydro-1H-pyrido[2,3-b][1,4]oxazin-7-yl, 2,3-dihydro-1H-pyrrolo[2,3-b]pyridin-5-yl, 2,3-dihydrobenzofuran-5-yl, 3-(1H-pyrazol-4-yl)phenyl, 3-(pyridin-2-yl)phenyl, 3-(pyridin-3-yl)phenyl, 3-(pyridin-4-yl)phenyl, 3-(pyrimidin-5-yl)phenyl, 3,4-dihydro-2H-benzo[b][1,4]oxazin-6-yl, 3,4-dihydro-2H-benzo[b][1,4]oxazin-7-yl, 3,4-dihydro-2H-pyrano[2,3-b]pyridin-6-yl, 3,4-dihydro-2H-pyrido[3,2-b][1,4]oxazin-7-yl, 3H-imidazo[4,5-b]pyridin-5-yl, 3H-imidazo[4,5-b]pyridin-6-yl, 4-(pyridin-2-yl)phenyl, 4-(pyridin-3-yl)phenyl, 4-(pyridin-4-yl)phenyl, 5-(1H-pyrazol-4-yl)pyridin-3-yl, 5-(phenyl)pyridin-3-yl, 5,6,7,8-tetrahydronaphthalen-2-yl, 5,6,7,8-tetrahydroquinolin-3-yl, 5-phenylthiophen-2-yl, 6,7-dihydro-5H-pyrrolo[3,4-b]pyridin-3-yl, benzo[c][1,2,5]oxadiazol-4-yl, benzofuran-2-yl, benzofuran-5-yl, biphenyl-3-yl, biphenyl-4-yl, chroman-6-yl, chroman-7-yl, isoquinolin-5-yl, isoxazol-4-yl, naphthalen-2-yl, phenyl, pyridin-2-yl, pyridin-3-yl, pyrrolo[1,2-a]pyrimidin-3-yl, quinolin-3-yl, quinolin-6-yl, quinolin-7-yl, and thiazol-4-yl; wherein each is optionally substituted with one or more substituents selected from: (2,2,2-trifluoroethylamino)methyl, (2-aminoethylamino)methyl, (2-methoxyethylamino)methyl, (3-aminopropylamino)methyl, (butylamino)methyl, (cyclobutylamino)methyl, (ethylamino)methyl, (isobutylamino)methyl, (isopropylamino)methyl, (methylamino)methyl, (propylamino)methyl, (tert-butylamino)methyl, (tert-pentylamino)methyl, 1-amino-2-methylpropan-2-yl, 1-aminocyclopropyl, 2-acetamidoethyl, 2-aminoethyl, 2-aminopropan-2-yl, 2-methoxyethyl, amino, aminomethyl, azetidin-1-ylmethyl, bromo, chloro, cyano, cyclopropyl, ethoxy, ethyl, fluoro, hydroxy, isopropoxy, methoxy, methyl, morpholinomethyl, oxo, propan-1-yl, sulfamoyl, and trifluoromethyl.

In some embodiments, $R^1$ is selected from: (R)-1,3-dimethyl-2,3-dihydro-1H-pyrido[2,3-b][1,4]oxazin-7-yl, (S)-1,3-dimethyl-2,3-dihydro-1H-pyrido[2,3-b][1,4]oxazin-7-yl, 1-(2-methoxyethyl)-2,3-dihydro-1H-pyrido[2,3-b][1,4]oxazin-7-yl, 1,3,3-trimethyl-2,3-dihydro-1H-pyrido[2,3-b][1,4]oxazin-6-yl, 1,4-dimethyl-1,2,3,4-tetrahydropyrido[3,2-b]pyrazin-7-yl, 1,6-dimethyl-2,3-dihydro-1H-pyrido[2,3-b][1,4]oxazin-7-yl, 1,8-dimethyl-2,3-dihydro-1H-pyrido[2,3-b][1,4]oxazin-7-yl, 1-ethoxynaphthalen-2-yl, 1-ethyl-2,3-dihydro-1H-pyrido[2,3-b][1,4]oxazin-7-yl, 1-ethyl-4-oxo-1,4-dihydroquinolin-3-yl, 1-ethyl-5-methyl-1H-pyrazol-4-yl, 1-ethyl-6-fluoro-4-oxo-1,4-dihydroquinolin-3-yl, 1-ethyl-6-methyl-4-oxo-1,4-dihydroquinolin-3-yl, 1-ethyl-7-fluoro-4-oxo-1,4-dihydroquinolin-3-yl, 1-ethyl-7-methyl-4-oxo-1,4-dihydroquinolin-3-yl, 1-ethyl-8-fluoro-4-oxo-1,4-dihydroquinolin-3-yl, 1-ethyl-8-methyl-4-oxo-1,4-dihydroquinolin-3-yl, 1H-benzo[d]imidazol-5-yl, 1H-indazol-5-yl, 1H-indol-2-yl, 1H-indol-3-yl, 1H-indol-5-yl, 1H-indol-6-yl, 1H-pyrazolo[4,3-b]pyridin-6-yl, 1H-pyrrolo[2,3-b]pyridin-3-yl, 1H-pyrrolo[3,2-b]pyridin-6-yl, 1-methyl-2,3-dihydro-1H-pyrido[2,3-b][1,4]oxazin-7-yl, 1-methyl-4-oxo-1,4-dihydroquinolin-3-yl, 2,3-dihydro-[1,4]dioxino[2,3-b]pyridin-7-yl, 2,3-dihydro-1H-pyrido[2,3-b][1,4]oxazin-7-yl, 2,3-dihydrobenzofuran-5-yl, 2-aminothiazol-4-yl, 2-oxo-2,3-dihydro-1H-imidazo[4,5-b]pyridin-6-yl, 2-oxo-2,3-dihydro-1H-pyrrolo[2,3-b]pyridin-5-yl, 3-(1-cyclopropyl-1H-pyrazol-4-yl)phenyl, 3-(1-ethyl-1H-pyrazol-4-yl)phenyl, 3-(1H-pyrazol-4-yl)phenyl, 3-(1-methyl-1H-pyrazol-4-yl)phenyl, 3-(1-propyl-1H-pyrazol-4-yl)phenyl, 3-(2-methylpyridin-4-yl)phenyl, 3-(3-fluoropyridin-2-yl)phenyl, 3-(4-methylpyridin-2-yl)phenyl, 3-(5-methylpyridin-2-yl)phenyl, 3-(6-(trifluoromethyl)pyridin-2-yl)phenyl, 3-(6-aminopyridin-3-yl)phenyl, 3-(6-fluoropyridin-2-yl)phenyl, 3-(6-methylpyridin-2-yl)phenyl, 3-(pyridin-2-yl)phenyl, 3-(pyridin-3-yl)phenyl, 3-(pyridin-4-yl)phenyl, 3-(pyrimidin-5-yl)phenyl, 3-(trifluoromethyl)phenyl, 3,4-dihydro-2H-pyrano[2,3-b]pyridin-6-yl, 3,5-dimethylisoxazol-4-yl, 3-bromo-2-methylphenyl, 3-bromo-4-methoxyphenyl, 3-bromophenyl, 3-chlorophenyl, 3-cyanophenyl, 3-fluorophenyl, 3-methoxyphenyl, 3-methyl-3H-imidazo[4,5-b]pyridin-5-yl, 3-methyl-3H-imidazo[4,5-b]pyridin-6-yl, 3-oxo-3,4-dihydro-2H-benzo[b][1,4]oxazin-6-yl, 4'-(2,2,2-trifluoroethylamino)methyl)biphenyl-3-yl, 4'-((2-aminoethylamino)methyl)biphenyl-3-yl, 4'-((2-methoxyethylamino)methyl)biphenyl-3-yl, 4'-((3-aminopropylamino)methyl)biphenyl-3-yl, 4'-((butylamino)methyl)biphenyl-3-yl, 4'-((cyclobutylamino)methyl)biphenyl-3-yl, 4'-((ethylamino)methyl)biphenyl-3-yl, 4'-((isobutylamino)methyl)biphenyl-3-yl, 4'-((isopropylamino)methyl)biphenyl-3-yl, 4'-((methylamino)methyl)biphenyl-3-yl, 4'-((propylamino)methyl)biphenyl-3-yl, 4'-((tert-butylamino)methyl)biphenyl-3-yl, 4'-((tert-pentylamino)methyl)biphenyl-3-yl, 4'-(1-amino-2-methylpropan-2-yl)-4-ethoxybiphenyl-3-yl, 4'-(1-amino-2-methylpropan-2-yl)biphenyl-3-yl, 4'-(1-aminocyclopropyl)-2-methylbiphenyl-3-yl, 4'-(1-aminocyclopropyl)-4-ethoxybiphenyl-3-yl, 4'-(1-aminocyclopropyl)-6-fluorobiphenyl-3-yl, 4'-(1-aminocyclopropyl)-6-methoxybiphenyl-3-yl, 4'-(1-aminocyclopropyl)biphenyl-3-yl, 4'-(2-acetamidoethyl)-4-ethoxy-biphenyl-3-yl, 4'-(2-acetamidoethyl)-biphenyl-3-yl, 4'-(2-aminoethyl)-4-ethoxybiphenyl-3-yl, 4'-(2-aminoethyl)-6-methoxybiphenyl-3-yl, 4'-(2-aminoethyl)biphenyl-3-yl, 4'-(2-aminopropan-2-yl)-4-ethoxybiphenyl-3-yl, 4'-(aminomethyl)-2-methoxybiphenyl-3-yl, 4'-(aminomethyl)-2-methylbiphenyl-3-yl, 4'-(aminomethyl)-3'-fluorobiphenyl-3-yl, 4'-(aminomethyl)-4-ethoxy-3'-fluorobiphenyl-3-yl, 4'-(aminomethyl)-4-ethoxybiphenyl-3-yl, 4'-(aminomethyl)-4-fluorobiphenyl-3-yl, 4'-(aminomethyl)-4-isopropoxybiphenyl-3-yl, 4'-(aminomethyl)-5-methoxybiphenyl-3-yl, 4'-(aminomethyl)-6-ethoxybiphenyl-3-yl, 4'-(aminomethyl)-6-fluorobiphenyl-3-yl, 4'-(aminomethyl)-6-methoxybiphenyl-3-yl, 4'-(aminomethyl)biphenyl-3-yl, 4'-(aminomethyl)biphenyl-4-yl, 4'-(azetidin-1-ylmethyl)biphenyl-3-yl, 4'-(morpholinomethyl)biphenyl-3-yl, 4-(pyridin-2-yl)phenyl, 4-(pyridin-3-yl)phenyl, 4-(pyridin-4-yl)phenyl, 4'-(sulfamoyl)biphenyl-3-yl, 4-bromo-3-methylphenyl, 4-ethoxy-4'-((isopropylamino)methyl)biphenyl-3-yl, 4-hydroxy-6-methylquinolin-3-yl, 4-hydroxy-7-methylquinolin-3-yl, 4-hydroxy-8-methylquinolin-3-yl, 4-hydroxyquinolin-3-yl, 4-methoxyquinolin-3-yl, 4-methyl-2-oxo-1,2-dihydroquinolin-6-yl, 4-methyl-3,4-dihydro-2H-benzo[b][1,4]oxazin-6-yl, 4-methyl-3,4-dihydro-2H-benzo[b][1,4]oxazin-7-yl, 4-methyl-3,4-dihydro-2H-pyrido[3,2-b][1,4]oxazin-7-yl, 4'-methylbiphenyl-3-yl, 4-oxo-1,4-dihydroquinolin-3-yl, 5-(1-methyl-1H-pyrazol-4-yl)pyridin-3-yl, 5-(4-(aminomethyl)phenyl)pyridin-3-yl, 5,6,7,8-tetrahydronaphthalen-2-yl, 5,6,7,8-tetrahydroquinolin-3-yl, 5-bromo-6-chloropyridin-3-yl, 5-bromopyridin-3-yl, 5-chloronaphthalen-2-yl, 5-oxo-6,7-dihydro-5H-pyrrolo[3,4-b]pyridin-3-yl, 5-phenylthiophen-2-yl, 6-chloronaphthalen-2-yl, 6-fluoro-4-hydroxyquinolin-3-yl, 7-chlorobenzo[c][1,2,5]oxadiazol-4-yl, 7-fluoro-4-hydroxyquinolin-3-yl, 8-fluoro-4-hydroxyquinolin-3-yl, benzofuran-2-yl, benzofuran-5-yl, chroman-6-yl, chroman-7-yl, isoquinolin-5-yl, m-tolyl, naphthalen-2-yl, phenyl, pyridin-2-yl, pyridin-3-yl, pyrrolo[1,2-a]pyrimidin-3-yl, quinolin-3-yl, quinolin-6-yl, and quinolin-7-yl.

In some embodiments, $R^1$ is (R)-1,3-dimethyl-2,3-dihydro-1H-pyrido[2,3-b][1,4]oxazin-7-yl.

In some embodiments, $R^1$ is (S)-1,3-dimethyl-2,3-dihydro-1H-pyrido[2,3-b][1,4]oxazin-7-yl.

In some embodiments, $R^1$ is 1-(2-methoxyethyl)-2,3-dihydro-1H-pyrido[2,3-b][1,4]oxazin-7-yl.

In some embodiments, $R^1$ is 1,3,3-trimethyl-2,3-dihydro-1H-pyrido[2,3-b][1,4]oxazin-6-yl.

In some embodiments, $R^1$ is 1,4-dimethyl-1,2,3,4-tetrahydropyrido[3,2-b]pyrazin-7-yl.

In some embodiments, $R^1$ is 1,6-dimethyl-2,3-dihydro-1H-pyrido[2,3-b][1,4]oxazin-7-yl.

In some embodiments, $R^1$ is 1,8-dimethyl-2,3-dihydro-1H-pyrido[2,3-b][1,4]oxazin-7-yl.

In some embodiments, $R^1$ is 1-ethoxynaphthalen-2-yl.

In some embodiments, $R^1$ is 1-ethyl-2,3-dihydro-1H-pyrido[2,3-b][1,4]oxazin-7-yl.

In some embodiments, $R^1$ is 1-ethyl-4-oxo-1,4-dihydroquinolin-3-yl.

In some embodiments, $R^1$ is 1-ethyl-5-methyl-1H-pyrazol-4-yl.

In some embodiments, $R^1$ is 1-ethyl-6-fluoro-4-oxo-1,4-dihydroquinolin-3-yl.

In some embodiments, $R^1$ is 1-ethyl-6-methyl-4-oxo-1,4-dihydroquinolin-3-yl.

In some embodiments, $R^1$ is 1-ethyl-7-fluoro-4-oxo-1,4-dihydroquinolin-3-yl.

In some embodiments, $R^1$ is 1-ethyl-7-methyl-4-oxo-1,4-dihydroquinolin-3-yl.

In some embodiments, $R^1$ is 1-ethyl-8-fluoro-4-oxo-1,4-dihydroquinolin-3-yl.

In some embodiments, $R^1$ is 1-ethyl-8-methyl-4-oxo-1,4-dihydroquinolin-3-yl.

In some embodiments, $R^1$ is 1H-benzo[d]imidazol-5-yl.

In some embodiments, $R^1$ is 1H-indazol-5-yl.

In some embodiments, $R^1$ is 1H-indol-2-yl.

In some embodiments, $R^1$ is 1H-indol-3-yl.

In some embodiments, $R^1$ is 1H-indol-5-yl.

In some embodiments, $R^1$ is 1H-indol-6-yl.

In some embodiments, $R^1$ is 1H-pyrazolo[4,3-b]pyridin-6-yl.

In some embodiments, $R^1$ is 1H-pyrrolo[2,3-b]pyridin-3-yl.

In some embodiments, $R^1$ is 1H-pyrrolo[3,2-b]pyridin-6-yl.

In some embodiments, $R^1$ is 1-methyl-2,3-dihydro-1H-pyrido[2,3-b][1,4]oxazin-7-yl.

In some embodiments, $R^1$ is 1-methyl-4-oxo-1,4-dihydroquinolin-3-yl.

In some embodiments, $R^1$ is 2,3-dihydro-[1,4]dioxino[2,3-b]pyridin-7-yl.

In some embodiments, $R^1$ is 2,3-dihydro-1H-pyrido[2,3-b][1,4]oxazin-7-yl.

In some embodiments, $R^1$ is 2,3-dihydrobenzofuran-5-yl.

In some embodiments, $R^1$ is 2-aminothiazol-4-yl.

In some embodiments, $R^1$ is 2-oxo-2,3-dihydro-1H-imidazo[4,5-b]pyridin-6-yl.

In some embodiments, $R^1$ is 2-oxo-2,3-dihydro-1H-pyrrolo[2,3-b]pyridin-5-yl.

In some embodiments, $R^1$ is 3-(1-cyclopropyl-1H-pyrazol-4-yl)phenyl.

In some embodiments, $R^1$ is 3-(1-ethyl-1H-pyrazol-4-yl)phenyl.

In some embodiments, $R^1$ is 3-(1H-pyrazol-4-yl)phenyl.

In some embodiments, $R^1$ is 3-(1-methyl-1H-pyrazol-4-yl)phenyl.

In some embodiments, $R^1$ is 3-(1-propyl-1H-pyrazol-4-yl)phenyl.

In some embodiments, $R^1$ is 3-(2-methylpyridin-4-yl)phenyl.

In some embodiments, $R^1$ is 3-(3-fluoropyridin-2-yl)phenyl.

In some embodiments, $R^1$ is 3-(4-methylpyridin-2-yl)phenyl.

In some embodiments, $R^1$ is 3-(5-methylpyridin-2-yl)phenyl.

In some embodiments, $R^1$ is 3-(6-(trifluoromethyl)pyridin-2-yl)phenyl.

In some embodiments, $R^1$ is 3-(6-aminopyridin-3-yl)phenyl.

In some embodiments, $R^1$ is 3-(6-fluoropyridin-2-yl)phenyl.

In some embodiments, $R^1$ is 3-(6-methylpyridin-2-yl)phenyl.

In some embodiments, $R^1$ is 3-(pyridin-2-yl)phenyl.

In some embodiments, $R^1$ is 3-(pyridin-3-yl)phenyl.

In some embodiments, $R^1$ is 3-(pyridin-4-yl)phenyl.

In some embodiments, $R^1$ is 3-(pyrimidin-5-yl)phenyl.

In some embodiments, $R^1$ is 3-(trifluoromethyl)phenyl.

In some embodiments, $R^1$ is 3,4-dihydro-2H-pyrano[2,3-b]pyridin-6-yl.

In some embodiments, $R^1$ is 3,5-dimethylisoxazol-4-yl.

In some embodiments, $R^1$ is 3-bromo-2-methylphenyl.

In some embodiments, $R^1$ is 3-bromo-4-methoxyphenyl.

In some embodiments, $R^1$ is 3-bromophenyl.

In some embodiments, $R^1$ is 3-chlorophenyl.

In some embodiments, $R^1$ is 3-cyanophenyl.

In some embodiments, $R^1$ is 3-fluorophenyl.

In some embodiments, $R^1$ is 3-methoxyphenyl.

In some embodiments, $R^1$ is 3-methyl-3H-imidazo[4,5-b]pyridin-5-yl.

In some embodiments, $R^1$ is 3-methyl-3H-imidazo[4,5-b]pyridin-6-yl.

In some embodiments, $R^1$ is 3-oxo-3,4-dihydro-2H-benzo[b][1,4]oxazin-6-yl.

In some embodiments, $R^1$ is 4'-((2,2,2-trifluoroethylamino)methyl)biphenyl-3-yl.

In some embodiments, $R^1$ is 4'-((2-aminoethylamino)methyl)biphenyl-3-yl.

In some embodiments, $R^1$ is 4'-((2-methoxyethylamino)methyl)biphenyl-3-yl.

In some embodiments, $R^1$ is 4'-((3-aminopropylamino)methyl)biphenyl-3-yl.

In some embodiments, $R^1$ is 4'-((butylamino)methyl)biphenyl-3-yl.

In some embodiments, $R^1$ is 4'-((cyclobutylamino)methyl)biphenyl-3-yl.

In some embodiments, $R^1$ is 4'-((ethylamino)methyl)biphenyl-3-yl.

In some embodiments, $R^1$ is 4'-((isobutylamino)methyl)biphenyl-3-yl.

In some embodiments, $R^1$ is 4'-((isopropylamino)methyl)biphenyl-3-yl.

In some embodiments, $R^1$ is 4'-((methylamino)methyl)biphenyl-3-yl.

In some embodiments, $R^1$ is 4'-((propylamino)methyl)biphenyl-3-yl.

In some embodiments, $R^1$ is 4'-((tert-butylamino)methyl)biphenyl-3-yl.

In some embodiments, $R^1$ is 4'-((tert-pentylamino)methyl)biphenyl-3-yl.

In some embodiments, $R^1$ is 4'-(1-amino-2-methylpropan-2-yl)-4-ethoxybiphenyl-3-yl.

In some embodiments, $R^1$ is 4'-(1-amino-2-methylpropan-2-yl)biphenyl-3-yl.

In some embodiments, $R^1$ is 4'-(1-aminocyclopropyl)-2-methylbiphenyl-3-yl.

In some embodiments, $R^1$ is 4'-(1-aminocyclopropyl)-4-ethoxybiphenyl-3-yl.

In some embodiments, $R^1$ is 4'(1-aminocyclopropyl)-6-fluorobiphenyl-3-yl.

In some embodiments, $R^1$ is 4'-(1-aminocyclopropyl)-6-methoxybiphenyl-3-yl.

In some embodiments, $R^1$ is 4'-(1-aminocyclopropyl)biphenyl-3-yl.

In some embodiments, $R^1$ is 4'-(2-acetamidoethyl)-4-ethoxy-biphenyl-3-yl.

In some embodiments, $R^1$ is 4'-(2-acetamidoethyl)-biphenyl-3-yl.

In some embodiments, $R^1$ is 4'-(2-aminoethyl)-4-ethoxybiphenyl-3-yl.

In some embodiments, $R^1$ is 4'-(2-aminoethyl)-6-methoxybiphenyl-3-yl.

In some embodiments, $R^1$ is 4'-(2-aminoethyl)biphenyl-3-yl.

In some embodiments, $R^1$ is 4'-(2-aminopropan-2-yl)-4-ethoxybiphenyl-3-yl.

In some embodiments, $R^1$ is 4'-(aminomethyl)-2-methoxybiphenyl-3-yl.

In some embodiments, $R^1$ is 4'-(aminomethyl)-2-methylbiphenyl-3-yl.

In some embodiments, $R^1$ is 4'-(aminomethyl)-3'-fluorobiphenyl-3-yl.

In some embodiments, $R^1$ is 4'-(aminomethyl)-4-ethoxy-3'-fluorobiphenyl-3-yl.

In some embodiments, $R^1$ is 4'-(aminomethyl)-4-ethoxybiphenyl-3-yl.

In some embodiments, $R^1$ is 4'-(aminomethyl)-4-fluorobiphenyl-3-yl.

In some embodiments, $R^1$ is 4'-(aminomethyl)-4-isopropoxybiphenyl-3-yl.

In some embodiments, $R^1$ is 4'-(aminomethyl)-5-methoxybiphenyl-3-yl.

In some embodiments, $R^1$ is 4'-(aminomethyl)-6-ethoxybiphenyl-3-yl.

In some embodiments, $R^1$ is 4'-(aminomethyl)-6-fluorobiphenyl-3-yl.

In some embodiments, $R^1$ is 4'-(aminomethyl)-6-methoxybiphenyl-3-yl.

In some embodiments, $R^1$ is 4'-(aminomethyl)biphenyl-3-yl.

In some embodiments, $R^1$ is 4'-(aminomethyl)biphenyl-4-yl.

In some embodiments, $R^1$ is 4'-(azetidin-1-ylmethyl)biphenyl-3-yl.

In some embodiments, $R^1$ is 4'-(morpholinomethyl)biphenyl-3-yl.

In some embodiments, $R^1$ is 4-(pyridin-2-yl)phenyl.

In some embodiments, $R^1$ is 4-(pyridin-3-yl)phenyl.

In some embodiments, $R^1$ is 4-(pyridin-4-yl)phenyl.

In some embodiments, $R^1$ is 4'-(sulfamoyl)biphenyl-3-yl.

In some embodiments, $R^1$ is 4-bromo-3-methylphenyl.

In some embodiments, $R^1$ is 4-ethoxy-4'-((isopropylamino)methyl)biphenyl-3-yl.

In some embodiments, $R^1$ is 4-hydroxy-6-methylquinolin-3-yl.

In some embodiments, $R^1$ is 4-hydroxy-7-methylquinolin-3-yl.

In some embodiments, $R^1$ is 4-hydroxy-8-methylquinolin-3-yl.

In some embodiments, $R^1$ is 4-hydroxyquinolin-3-yl.

In some embodiments, $R^1$ is 4-methoxyquinolin-3-yl.

In some embodiments, $R^1$ is 4-methyl-2-oxo-1,2-dihydroquinolin-6-yl.

In some embodiments, $R^1$ is 4-methyl-3,4-dihydro-2H-benzo[b][1,4]oxazin-6-yl.

In some embodiments, $R^1$ is 4-methyl-3,4-dihydro-2H-benzo[b][1,4]oxazin-7-yl.

In some embodiments, $R^1$ is 4-methyl-3,4-dihydro-2H-pyrido[3,2-b][1,4]oxazin-7-yl.

In some embodiments, $R^1$ is 4'-methylbiphenyl-3-yl.

In some embodiments, $R^1$ is 4-oxo-1,4-dihydroquinolin-3-yl.

In some embodiments, $R^1$ is 5-(1-methyl-1H-pyrazol-4-yl)pyridin-3-yl.

In some embodiments, $R^1$ is 5-(4-(aminomethyl)phenyl)pyridin-3-yl.

In some embodiments, $R^1$ is 5,6,7,8-tetrahydronaphthalen-2-yl.

In some embodiments, $R^1$ is 5,6,7,8-tetrahydroquinolin-3-yl.

In some embodiments, $R^1$ is 5-bromo-6-chloropyridin-3-yl.

In some embodiments, $R^1$ is 5-bromopyridin-3-yl.

In some embodiments, $R^1$ is 5-chloronaphthalen-2-yl.

In some embodiments, $R^1$ is 5-oxo-6,7-dihydro-5H-pyrrolo[3,4-b]pyridin-3-yl.

In some embodiments, $R^1$ is 5-phenylthiophen-2-yl.

In some embodiments, $R^1$ is 6-chloronaphthalen-2-yl.

In some embodiments, $R^1$ is 6-fluoro-4-hydroxyquinolin-3-yl.

In some embodiments, $R^1$ is 7-chlorobenzo[c][1,2,5]oxadiazol-4-yl.

In some embodiments, $R^1$ is 7-fluoro-4-hydroxyquinolin-3-yl.

In some embodiments, $R^1$ is 8-fluoro-4-hydroxyquinolin-3-yl.

In some embodiments, $R^1$ is benzofuran-2-yl.

In some embodiments, $R^1$ is benzofuran-5-yl.

In some embodiments, $R^1$ is chroman-6-yl.

In some embodiments, $R^1$ is chroman-7-yl.

In some embodiments, $R^1$ is isoquinolin-5-yl.

In some embodiments, $R^1$ is m-tolyl.

In some embodiments, $R^1$ is naphthalen-2-yl.

In some embodiments, $R^1$ is phenyl.

In some embodiments, $R^1$ is pyridin-2-yl.

In some embodiments, $R^1$ is pyridin-3-yl.

In some embodiments, $R^1$ is pyrrolo[1,2-a]pyrimidin-3-yl.

In some embodiments, $R^1$ is quinolin-3-yl.

In some embodiments, $R^1$ is quinolin-6-yl.

In some embodiments, $R^1$ is and quinolin-7-yl.

The $R^1$ Group (Aryl)

In some embodiments, $R^1$ is aryl, wherein each is optionally substituted with one or more substituents selected from: $C_1$-$C_6$ alkoxy, $C_1$-$C_6$ alkyl, amino, cyano, $C_3$-$C_7$ cycloalkyl, $C_1$-$C_6$ haloalkyl, halogen, hydroxyl, oxo, and sulfamoyl; and wherein said $C_1$-$C_6$ alkyl and $C_3$-$C_7$ cycloalkyl are each optionally substituted with one or more substituents selected from: amino, $C_1$-$C_6$ alkoxy, $C_1$-$C_6$ alkylcarboxamide, —Y—$C_3$-$C_7$-cycloalkyl, —Y—$C_1$-$C_6$-alkylene-Z, $C_1$-$C_6$ alkylamino, $C_1$-$C_6$ haloalkylamino, and heterocyclyl.

In some embodiments, $R^1$ is aryl optionally substituted with one or more substituents selected from: $C_1$-$C_6$ alkoxy, $C_1$-$C_6$ alkyl, cyano, $C_3$-$C_7$ cycloalkyl, $C_1$-$C_6$ haloalkyl, halogen, and sulfamoyl; and wherein said $C_1$-$C_6$ alkyl and $C_3$-$C_7$ cycloalkyl are each optionally substituted with one or more substituents selected from: amino, $C_1$-$C_6$ alkylcarboxamide, —NH—$C_3$-$C_7$-cycloalkyl, —NH—$C_1$-$C_6$-alkylene-NH$_2$, —NH—$C_1$-$C_6$-alkylene-O—$C_1$-$C_6$-alkyl, $C_1$-$C_6$ alkylamino, $C_1$-$C_6$ haloalkylamino, and heterocyclyl.

In some embodiments, $R^1$ is selected from: 5,6,7,8-tetrahydronaphthalenyl, biphenyl, naphthalenyl, and phenyl; wherein each is optionally substituted with one or more substituents selected from: 2-methylpropan-2-yl, bromo, chloro, cyano, cyclopropyl, ethoxy, ethyl, fluoro, isopropoxy, methoxy, methyl, propan-2-yl, sulfamoyl, and trifluoromethyl; and wherein said 2-methylpropan-2-yl, cyclopropyl, ethyl, methyl, and propan-2-yl are each optionally substituted with one or more substituents selected from: 2,2,2-trifluoroethylamino, 2-aminoethylamino, 2-methoxyethylamino, 3-aminopropylamino, acetamido, amino, azetidin-1-yl, butylamino, cyclobutylamino, ethylamino, isobutylamino, isopropylamino, methylamino, morpholino, propylamino, tert-butylamino, and tert-pentylamino.

In some embodiments, $R^1$ is selected from: 5,6,7,8-tetrahydronaphthalenyl, biphenyl, naphthalenyl, and phenyl; wherein each is optionally substituted with one or more substituents selected from: (2,2,2-trifluoroethylamino) methyl, (2-aminoethylamino)methyl, (2-methoxyethylamino)methyl, (3-aminopropylamino)methyl, (butylamino) methyl, (cyclobutylamino)methyl, (ethylamino)methyl, (isobutylamino)methyl, (isopropylamino)methyl, (methylamino)methyl, (propylamino)methyl, (tert-butylamino) methyl, (tert-pentylamino)methyl, 1-amino-2-methylpropan-2-yl, 1-aminocyclopropyl, 2-acetamidoethyl, 2-aminoethyl, 2-aminopropan-2-yl, aminomethyl, azetidin-1-ylmethyl, bromo, chloro, cyano, ethoxy, fluoro, isopropoxy, methoxy, methyl, morpholinomethyl, sulfamoyl, and trifluoromethyl.

In some embodiments, $R^1$ is selected from: 5,6,7,8-tetrahydronaphthalen-2-yl, biphenyl-3-yl, biphenyl-4-yl, naphthalen-2-yl, and phenyl; wherein each is optionally substituted with one or more substituents selected from: (2,2,2-trifluoroethylamino)methyl, (2-aminoethylamino)methyl, (2-methoxyethylamino)methyl, (3-aminopropylamino) methyl, (butylamino)methyl, (cyclobutylamino)methyl, (ethylamino)methyl, (isobutylamino)methyl, (isopropylamino)methyl, (methylamino)methyl, (propylamino)methyl, (tert-butylamino)methyl, (tert-pentylamino)methyl, 1-amino-2-methylpropan-2-yl, 1-aminocyclopropyl, 2-acetamidoethyl, 2-aminoethyl, 2-aminopropan-2-yl, aminomethyl, azetidin-1-ylmethyl, bromo, chloro, cyano, ethoxy, fluoro, isopropoxy, methoxy, methyl, morpholinomethyl, sulfamoyl, and trifluoromethyl.

In some embodiments, $R^1$ is selected from: 1-ethoxynaphthalen-2-yl, 3-(trifluoromethyl)phenyl, 3-bromo-2-methylphenyl, 3-bromo-4-methoxyphenyl, 3-bromophenyl, 3-chlorophenyl, 3-cyanophenyl, 3-fluorophenyl, 3-methoxyphenyl, 4'-((2,2,2-trifluoroethylamino)methyl)biphenyl-3-yl, 4'-((2-aminoethylamino)methyl)biphenyl-3-yl, 4'-((2-methoxyethylamino)methyl)biphenyl-3-yl, 4'-((3-amino-propylamino)methyl)biphenyl-3-yl, 4'-((butylamino)methyl)biphenyl-3-yl, 4'-((cyclobutylamino)methyl)biphenyl-3-yl, 4'-((ethylamino)methyl)biphenyl-3-yl, 4'-((isobutylamino)methyl)biphenyl-3-yl, 4'-((isopropylamino)methyl) biphenyl-3-yl, 4'-((methylamino)methyl)biphenyl-3-yl, 4'-((propylamino)methyl)biphenyl-3-yl, 4'-((tert-butylamino) methyl)biphenyl-3-yl, 4'-((tert-pentylamino)methyl)biphenyl-3-yl, 4'-(1-amino-2-methylpropan-2-yl)-4-ethoxybiphenyl-3-yl, 4'-(1-amino-2-methylpropan-2-yl)biphenyl-3-yl, 4'-(1-aminocyclopropyl)-2-methylbiphenyl-3-yl, 4'-(1-aminocyclopropyl)-4-ethoxybiphenyl-3-yl, 4'-(1-aminocyclopropyl)-6-fluorobiphenyl-3-yl, 4'-(1-aminocyclopropyl)-6-methoxybiphenyl-3-yl, 4'-(1-aminocyclopropyl)biphenyl-3-yl, 4'-(2-acetamidoethyl)-4-ethoxy-biphenyl-3-yl, 4'-(2-acetamidoethyl)-biphenyl-3-yl, 4'-(2-aminoethyl)-4-ethoxybiphenyl-3-yl, 4'-(2-aminoethyl)-6-methoxybiphenyl-3-yl, 4'-(2-aminoethyl)biphenyl-3-yl, 4'-(2-aminopropan-2-yl)-4-ethoxybiphenyl-3-yl, 4'-(aminomethyl)-2-methoxybiphenyl-3-yl, 4'-(aminomethyl)-2-methylbiphenyl-3-yl, 4'-(aminomethyl)-3'-fluorobiphenyl-3-yl, 4'-(aminomethyl)-4-ethoxy-3'-fluorobiphenyl-3-yl, 4'-(aminomethyl)-4-ethoxybiphenyl-3-yl, 4'-(aminomethyl)-4-fluorobiphenyl-3-yl, 4'-(aminomethyl)-4-isopropoxybiphenyl-3-yl, 4'-(aminomethyl)-5-methoxybiphenyl-3-yl, 4'-(aminomethyl)-6-ethoxybiphenyl-3-yl, 4'-(aminomethyl)-6-fluorobiphenyl-3-yl, 4'-(aminomethyl)-6-methoxybiphenyl-3-yl, 4'-(aminomethyl)biphenyl-3-yl, 4'-(aminomethyl)biphenyl-4-yl, 4'-(azetidin-1-ylmethyl)biphenyl-3-yl, 4'-(morpholinomethyl) biphenyl-3-yl, 4'-(sulfamoyl)biphenyl-3-yl, 4-bromo-3-methylphenyl, 4-ethoxy-4'-((isopropylamino)methyl)biphenyl-3-yl, 4'-methylbiphenyl-3-yl, 5,6,7,8-tetrahydronaphthalen-2-yl, 5-chloronaphthalen-2-yl, 6-chloronaphthalen-2-yl, m-tolyl, naphthalen-2-yl, and phenyl.

The $R^1$ Group (Heteroaryl)

In some embodiments, $R^1$ is heteroaryl, wherein each is optionally substituted with one or more substituents selected from: $C_1$-$C_6$ alkoxy, $C_1$-$C_6$ alkyl, amino, cyano, $C_3$-$C_7$ cycloalkyl, $C_1$-$C_6$ haloalkyl, halogen, hydroxyl, oxo, and sulfamoyl; and wherein said $C_1$-$C_6$ alkyl and $C_3$-$C_7$ cycloalkyl are each optionally substituted with one or more substituents selected from: amino, $C_1$-$C_6$ alkoxy, $C_1$-$C_6$ alkylcarboxamide, —Y—$C_3$-$C_7$-cycloalkyl, —Y—$C_1$-$C_6$-alkylene-Z, $C_1$-$C_6$ alkylamino, $C_1$-$C_6$ haloalkylamino, and heterocyclyl.

In some embodiments, $R^1$ is heteroaryl optionally substituted with one or more substituents selected from: $C_1$-$C_6$ alkoxy, $C_1$-$C_6$ alkyl, amino, $C_3$-$C_7$ cycloalkyl, $C_1$-$C_6$ haloalkyl, halogen, hydroxyl, and oxo; and wherein said $C_1$-$C_6$ alkyl is optionally substituted with one or more substituents selected from: amino and $C_1$-$C_6$ alkoxy.

In some embodiments, $R^1$ is selected from: (1H-pyrazolyl)phenyl, (1H-pyrazolyl)pyridinyl, (pyridinyl)phenyl, (pyrimidinyl)phenyl, 1,2,3,4-tetrahydropyrido[3,2-b]pyrazinyl, 1,2-dihydroquinolinyl, 1,4-dihydroquinolinyl, 1H-benzo[d]imidazolyl, 1H-indazolyl, 1H-indolyl, 1H-pyrazolo[4,3-b]pyridinyl, 1H-pyrazolyl, 1H-pyrrolo[2,3-b]pyridinyl, 1H-pyrrolo[3,2-b]pyridinyl, 2,3-dihydro-[1,4]dioxino[2,3-b]pyridinyl, 2,3-dihydro-1H-imidazo[4,5-b] pyridinyl, 2,3-dihydro-1H-pyrido[2,3-b][1,4]oxazinyl, 2,3-dihydro-1H-pyrrolo[2,3-b]pyridinyl, 2,3-dihydrobenzofuranyl, 3,4-dihydro-2H-benzo[b][1,4]oxazinyl, 3,4-dihydro-2H-pyrano[2,3-b]pyridinyl, 3,4-dihydro-2H-pyrido[3,2-b][1,4]oxazinyl, 3H-imidazo[4,5-b]pyridinyl, (phenyl) pyridinyl, 5,6,7,8-tetrahydroquinolinyl, 6,7-dihydro-5H-pyrrolo[3,4-b]pyridin-3-yl, benzo[c][1,2,5]oxadiazolyl, benzofuranyl, chromanyl, isoquinolinyl, isoxazolyl, phenylthiophenyl, pyridinyl, pyrrolo[1,2-a]pyrimidinyl, quinolinyl, and thiazolyl; wherein each is optionally substituted with one or more substituents selected from: amino, bromo, chloro, cyclopropyl, ethyl, fluoro, hydroxy, methoxy, methyl, oxo, propan-1-yl, and trifluoromethyl; and wherein said ethyl and methyl are each optionally substituted with one or more substituents selected from: amino and methoxy.

In some embodiments, $R^1$ is selected from: (1H-pyrazolyl)phenyl, (1H-pyrazolyl)pyridinyl, (pyridinyl)phenyl, (pyrimidinyl)phenyl, 1,2,3,4-tetrahydropyrido[3,2-b]pyrazinyl, 1,2-dihydroquinolinyl, 1,4-dihydroquinolinyl, 1H-benzo[d]imidazolyl, 1H-indazolyl, 1H-indolyl, 1H-pyrazolo[4,3-b]pyridinyl, 1H-pyrazolyl, 1H-pyrrolo[2,3-b]pyridinyl, 1H-pyrrolo[3,2-b]pyridinyl, 2,3-dihydro-[1,4]dioxino[2,3-b]pyridinyl, 2,3-dihydro-1H-imidazo[4,5-b]pyridinyl, 2,3-dihydro-1H-pyrido[2,3-b][1,4]oxazinyl, 2,3-dihydro-1H-pyrrolo[2,3-b]pyridinyl, 2,3-dihydrobenzofuranyl, 3,4-dihydro-2H-benzo[b][1,4]oxazinyl, 3,4-dihydro-2H-pyrano[2,3-b]pyridinyl, 3,4-dihydro-2H-pyrido[3,2-b][1,4]oxazinyl, 3H-imidazo[4,5-b]pyridinyl, (phenyl)pyridinyl, 5,6,7,8-tetrahydroquinolinyl, 6,7-dihydro-5H-pyrrolo[3,4-b]pyridin-3-yl, benzo[c][1,2,5]oxadiazolyl, benzofuranyl, chromanyl, isoquinolinyl, isoxazolyl, phenylthiophenyl, pyridinyl, pyrrolo[1,2-a]pyrimidinyl, quinolinyl, and thiazolyl; wherein each is optionally substituted with one or more substituents selected from: 2-methoxyethyl, amino, aminomethyl, bromo, chloro, cyclopropyl, ethyl, fluoro, hydroxy, methoxy, methyl, oxo, propan-1-yl, and trifluoromethyl.

In some embodiments, $R^1$ is selected from: 1,2,3,4-tetrahydropyrido[3,2-b]pyrazin-7-yl, 1,2-dihydroquinolin-6-yl, 1,4-dihydroquinolin-3-yl, 1H-benzo[d]imidazol-5-yl, 1H-indazol-5-yl, 1H-indol-2-yl, 1H-indol-3-yl, 1H-indol-5-yl, 1H-indol-6-yl, 1H-pyrazol-4-yl, 1H-pyrazolo[4,3-b]pyridin-6-yl, 1H-pyrrolo[2,3-b]pyridin-3-yl, 1H-pyrrolo[3,2-b]pyridin-6-yl, 2,3-dihydro-[1,4]dioxino[2,3-b]pyridin-7-yl, 2,3-dihydro-1H-imidazo[4,5-b]pyridin-6-yl, 2,3-dihydro-1H-pyrido[2,3-b][1,4]oxazin-6-yl, 2,3-dihydro-1H-pyrido[2,3-b][1,4]oxazin-7-yl, 2,3-dihydro-1H-pyrrolo[2,3-b]pyridin-5-yl, 2,3-dihydrobenzofuran-5-yl, 3-(1H-pyrazol-4-yl)phenyl, 3-(pyridin-2-yl)phenyl, 3-(pyridin-3-yl)phenyl, 3-(pyridin-4-yl)phenyl, 3-(pyrimidin-5-yl)phenyl, 3,4-dihydro-2H-benzo[b][1,4]oxazin-6-yl, 3,4-dihydro-2H-benzo[b][1,4]oxazin-7-yl, 3,4-dihydro-2H-pyrano[2,3-b]pyridin-6-yl, 3,4-dihydro-2H-pyrido[3,2-b][1,4]oxazin-7-yl, 3H-imidazo[4,5-b]pyridin-5-yl, 3H-imidazo[4,5-b]pyridin-6-yl, 4-(pyridin-2-yl)phenyl, 4-(pyridin-3-yl)phenyl, 4-(pyridin-4-yl)phenyl, 5-(1H-pyrazol-4-yl)pyridin-3-yl, 5-(phenyl)pyridin-3-yl, 5,6,7,8-tetrahydroquinolin-3-yl, 5-phenylthiophen-2-yl, 6,7-dihydro-5H-pyrrolo[3,4-b]pyridin-3-yl, benzo[c][1,2,5]oxadiazol-4-yl, benzofuran-2-yl, benzofuran-5-yl, chroman-6-yl, chroman-7-yl, isoquinolin-5-yl, isoxazol-4-yl, pyridin-2-yl, pyridin-3-yl, pyrrolo[1,2-a]pyrimidin-3-yl, quinolin-3-yl, quinolin-6-yl, quinolin-7-yl, and thiazol-4-yl; wherein each is optionally substituted with one or more substituents selected from: 2-methoxyethyl, amino, aminomethyl, bromo, chloro, cyclopropyl, ethyl, fluoro, hydroxy, methoxy, methyl, oxo, propan-1-yl, and trifluoromethyl.

In some embodiments, $R^1$ is selected from: (R)-1,3-dimethyl-2,3-dihydro-1H-pyrido[2,3-b][1,4]oxazin-7-yl, (S)-1,3-dimethyl-2,3-dihydro-1H-pyrido[2,3-b][1,4]oxazin-7-yl, 1-(2-methoxyethyl)-2,3-dihydro-1H-pyrido[2,3-b][1,4]oxazin-7-yl, 1,3,3-trimethyl-2,3-dihydro-1H-pyrido[2,3-b][1,4]oxazin-6-yl, 1,4-dimethyl-1,2,3,4-tetrahydropyrido[3,2-b]pyrazin-7-yl, 1,6-dimethyl-2,3-dihydro-1H-pyrido[2,3-b][1,4]oxazin-7-yl, 1,8-dimethyl-2,3-dihydro-1H-pyrido[2,3-b][1,4]oxazin-7-yl, 1-ethyl-2,3-dihydro-1H-pyrido[2,3-b][1,4]oxazin-7-yl, 1-ethyl-4-oxo-1,4-dihydroquinolin-3-yl, 1-ethyl-5-methyl-1H-pyrazol-4-yl, 1-ethyl-6-fluoro-4-oxo-1,4-dihydroquinolin-3-yl, 1-ethyl-6-methyl-4-oxo-1,4-dihydroquinolin-3-yl, 1-ethyl-7-fluoro-4-oxo-1,4-dihydroquinolin-3-yl, 1-ethyl-7-methyl-4-oxo-1,4-dihydroquinolin-3-yl, 1-ethyl-8-fluoro-4-oxo-1,4-dihydroquinolin-3-yl, 1-ethyl-8-methyl-4-oxo-1,4-dihydroquinolin-3-yl, 1H-benzo[d]imidazol-5-yl, 1H-indazol-5-yl, 1H-indol-2-yl, 1H-indol-3-yl, 1H-indol-5-yl, 1H-indol-6-yl, 1H-pyrazolo[4,3-b]pyridin-6-yl, 1H-pyrrolo[2,3-b]pyridin-3-yl, 1H-pyrrolo[3,2-b]pyridin-6-yl, 1-methyl-2,3-dihydro-1H-pyrido[2,3-b][1,4]oxazin-7-yl, 1-methyl-4-oxo-1,4-dihydroquinolin-3-yl, 2,3-dihydro-[1,4]dioxino[2,3-b]pyridin-7-yl, 2,3-dihydro-1H-pyrido[2,3-b][1,4]oxazin-7-yl, 2,3-dihydrobenzofuran-5-yl, 2-aminothiazol-4-yl, 2-oxo-2,3-dihydro-1H-imidazo[4,5-b]pyridin-6-yl, 2-oxo-2,3-dihydro-1H-pyrrolo[2,3-b]pyridin-5-yl, 3-(1-cyclopropyl-1H-pyrazol-4-yl)phenyl, 3-(1-ethyl-1H-pyrazol-4-yl)phenyl, 3-(1H-pyrazol-4-yl)phenyl, 3-(1-methyl-1H-pyrazol-4-yl)phenyl, 3-(1-propyl-1H-pyrazol-4-yl)phenyl, 3-(2-methylpyridin-4-yl)phenyl, 3-(3-fluoropyridin-2-yl)phenyl, 3-(4-methylpyridin-2-yl)phenyl, 3-(5-methylpyridin-2-yl)phenyl, 3-(6-(trifluoromethyl)pyridin-2-yl)phenyl, 3-(6-aminopyridin-3-yl)phenyl, 3-(6-fluoropyridin-2-yl)phenyl, 3-(6-methylpyridin-2-yl)phenyl, 3-(pyridin-2-yl)phenyl, 3-(pyridin-3-yl)phenyl, 3-(pyridin-4-yl)phenyl, 3-(pyrimidin-5-yl)phenyl, 3,4-dihydro-2H-pyrano[2,3-b]pyridin-6-yl, 3,5-dimethylisoxazol-4-yl, 3-methyl-3H-imidazo[4,5-b]pyridin-5-yl, 3-methyl-3H-imidazo[4,5-b]pyridin-6-yl, 3-oxo-3,4-dihydro-2H-benzo[b][1,4]oxazin-6-yl, 4-(pyridin-2-yl)phenyl, 4-(pyridin-3-yl)phenyl, 4-(pyridin-4-yl)phenyl, 4-hydroxy-6-methylquinolin-3-yl, 4-hydroxy-7-methylquinolin-3-yl, 4-hydroxy-8-methylquinolin-3-yl, 4-hydroxyquinolin-3-yl, 4-methoxyquinolin-3-yl, 4-methyl-2-oxo-1,2-dihydroquinolin-6-yl, 4-methyl-3,4-dihydro-2H-benzo[b][1,4]oxazin-6-yl, 4-methyl-3,4-dihydro-2H-benzo[b][1,4]oxazin-7-yl, 4-methyl-3,4-dihydro-2H-pyrido[3,2-b][1,4]oxazin-7-yl, 4-oxo-1,4-dihydroquinolin-3-yl, 5-(1-methyl-1H-pyrazol-4-yl)pyridin-3-yl, 5-(4-(aminomethyl)phenyl)pyridin-3-yl, 5,6,7,8-tetrahydroquinolin-3-yl, 5-bromo-6-chloropyridin-3-yl, 5-bromopyridin-3-yl, 5-oxo-6,7-dihydro-5H-pyrrolo[3,4-b]pyridin-3-yl, 5-phenylthiophen-2-yl, 6-fluoro-4-hydroxyquinolin-3-yl, 7-chlorobenzo[c][1,2,5]oxadiazol-4-yl, 7-fluoro-4-hydroxyquinolin-3-yl, 8-fluoro-4-hydroxyquinolin-3-yl, benzofuran-2-yl, benzofuran-5-yl, chroman-6-yl, chroman-7-yl, isoquinolin-5-yl, pyridin-2-yl, pyridin-3-yl, pyrrolo[1,2-a]pyrimidin-3-yl, quinolin-3-yl, quinolin-6-yl, and quinolin-7-yl.

The $R^2$ Group

In some embodiments, $R^2$ is selected from: $C_2$-$C_6$ alkenyl, $C_1$-$C_6$ alkyl, $C_3$-$C_7$ cycloalkyl, heterocyclyl, and $C_1$-$C_6$ haloalkyl; each optionally substituted with one or more substituents selected from: $C_1$-$C_6$ alkoxy, $C_1$-$C_6$ alkylenehydroxyl, amino, aryl, $C_3$-$C_7$ cycloalkyl, cyano, $C_3$-$C_7$ halocycloalkyl, hydroxyl, and oxo.

In some embodiments, $R^2$ is selected from: 1,1-difluoroethyl, 1-fluoroethyl, 2-methylpropan-2-yl, 3,3,3-trifluoropropyl, 4,4,4-trifluorobutyl, azetidin-3-yl, cyclobutyl, cyclopentyl, cyclopropyl, ethyl, fluoromethyl, isobutyl, isopentyl, isopropyl, methyl, oxetan-3-yl, propan-1-yl, sec-butyl, and vinyl; each optionally substituted with one or more substituents selected from: 2,2-difluorocyclopropyl, amino, cyano, cyclobutyl, cyclohexyl, cyclopropyl, ethoxy, hydroxy, hydroxymethyl, methoxy, oxo, and phenyl.

In some embodiments, $R^2$ is selected from: (2,2-difluorocyclopropyl)methyl, 1-(hydroxymethyl)cyclobutyl, 1-(hydroxymethyl)cyclopropyl, 1,1-difluoro-2-hydroxyethyl, 1-amino-2-methyl-1-oxopropan-2-yl, 1-ethoxy-2-methyl-1-oxopropan-2-yl, 1-fluoroethyl, 1-hydroxy-2-methylpropan-2-yl, 2-amino-2-oxoethyl, 2-aminoethyl, 2-hydroxyethyl, 3,3,3-trifluoropropyl, 3-amino-3-oxopropyl, 3-hydroxycyclobutyl, 3-hydroxypropyl, 3-methoxypropyl, 4,4,4-trifluorobutyl, azetidin-3-yl, benzyl, carboxymethyl, cyanomethyl, cyclobutyl, cyclobutylmethyl, cyclohexylmethyl, cyclopentyl, cyclopropyl, cyclopropylmethyl, ethyl, fluoromethyl, isobutyl, isopentyl, isopropyl, methoxymethyl, methyl, oxetan-3-yl, propan-1-yl, sec-butyl, and vinyl.

In some embodiments, $R^2$ is selected from: 1-(hydroxymethyl)cyclobutyl, 1-(hydroxymethyl)cyclopropyl, 1,1-difluoro-2-hydroxyethyl, 1-fluoroethyl, 1-hydroxy-2-methylpropan-2-yl, 2-amino-2-oxoethyl, 2-hydroxyethyl, 3-amino-3-oxopropyl, 3-hydroxypropyl, 3-methoxypropyl, cyclobutyl, cyclopropyl, cyclopropylmethyl, ethyl, isobutyl, isopropyl, methoxymethyl, methyl, and propan-1-yl.

In some embodiments, $R^2$ is (2,2-difluorocyclopropyl)methyl.

In some embodiments, $R^2$ is 1-(hydroxymethyl)cyclobutyl.

In some embodiments, $R^2$ is 1-(hydroxymethyl)cyclopropyl.

In some embodiments, $R^2$ is 1,1-difluoro-2-hydroxyethyl.

In some embodiments, $R^2$ is 1-amino-2-methyl-1-oxopropan-2-yl.

In some embodiments, $R^2$ is 1-ethoxy-2-methyl-1-oxopropan-2-yl.

In some embodiments, $R^2$ is 1-fluoroethyl.

In some embodiments, $R^2$ is 1-hydroxy-2-methylpropan-2-yl.

In some embodiments, $R^2$ is 2-amino-2-oxoethyl.
In some embodiments, $R^2$ is 2-aminoethyl.
In some embodiments, $R^2$ is 2-hydroxyethyl.
In some embodiments, $R^2$ is 3,3,3-trifluoropropyl.
In some embodiments, $R^2$ is 3-amino-3-oxopropyl.
In some embodiments, $R^2$ is 3-hydroxycyclobutyl.
In some embodiments, $R^2$ is 3-hydroxypropyl.
In some embodiments, $R^2$ is 3-methoxypropyl.
In some embodiments, $R^2$ is 4,4,4-trifluorobutyl.
In some embodiments, $R^2$ is azetidin-3-yl.
In some embodiments, $R^2$ is benzyl.
In some embodiments, $R^2$ is carboxymethyl.
In some embodiments, $R^2$ is cyanomethyl.
In some embodiments, $R^2$ is s cyclobutyl.
In some embodiments, $R^2$ is cyclobutylmethyl.
In some embodiments, $R^2$ is cyclohexylmethyl.
In some embodiments, $R^2$ is cyclopentyl.
In some embodiments, $R^2$ is cyclopropyl.
In some embodiments, $R^2$ is cyclopropylmethyl.
In some embodiments, $R^2$ is ethyl.
In some embodiments, $R^2$ is fluoromethyl.
In some embodiments, $R^2$ is isobutyl.
In some embodiments, $R^2$ is isopentyl.
In some embodiments, $R^2$ is isopropyl.
In some embodiments, $R^2$ is methoxymethyl.
In some embodiments, $R^2$ is methyl.
In some embodiments, $R^2$ is oxetan-3-yl.
In some embodiments, $R^2$ is propan-1-yl.
In some embodiments, $R^2$ is sec-butyl.
In some embodiments, $R^2$ is vinyl.

The $R^{3a}$, $R^{3b}$, $R^{3c}$, and $R^{3d}$ Groups

In some embodiments, $R^{3a}$, $R^{3b}$, $R^{3c}$, and $R^{3d}$ are each independently H or halogen.

In some embodiments, $R^{3a}$ is H or halogen; $R^{3b}$ is H; $R^{3c}$ is H or halogen; and $R^{3d}$ is H.

In some embodiments, $R^{3a}$ is halogen; $R^{3b}$ is H; $R^{3c}$ is H or halogen; and $R^{3d}$ is H.

In some embodiments, $R^{3a}$ is H; $R^{3b}$ is H; $R^{3c}$ is halogen; and $R^{3d}$ is H.

In some embodiments, $R^{3a}$, $R^{3b}$, $R^{3c}$, and $R^{3d}$ are each independently H or F.

In some embodiments, $R^{3a}$ is H or F; $R^{3b}$ is H; $R^{3c}$ is H or F; and $R^{3d}$ is H.

In some embodiments, $R^{3a}$ is F; $R^{3b}$ is H; $R^{3c}$ is H; and $R^{3d}$ is H.

In some embodiments, $R^{3a}$ is H; $R^{3b}$ is H; $R^{3c}$ is F; and $R^{3d}$ is H.

In some embodiments, $R^{3a}$, $R^{3b}$, $R^{3c}$, and $R^{3d}$ are each H.
In some embodiments, $R^{3a}$ is halogen.
In some embodiments, $R^{3b}$ is halogen.
In some embodiments, $R^{3c}$ is halogen.
In some embodiments, $R^{3d}$ is halogen.
In some embodiments, $R^{3a}$ is F.
In some embodiments, $R^{3b}$ is F.
In some embodiments, $R^{3c}$ is F.
In some embodiments, $R^{3d}$ is F.
In some embodiments, $R^{3a}$ is H.
In some embodiments, $R^{3b}$ is H.
In some embodiments, $R^{3c}$ is H.
In some embodiments, $R^{3d}$ is H.

Certain Combinations

One aspect of the present invention pertains to compounds of Formula (Ib) and pharmaceutically acceptable salts, solvates, and hydrates thereof:

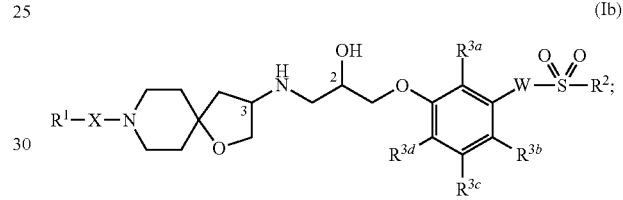

(Ib)

wherein: $R^1$ (as well as Y and Z that are both related to $R^1$), X, W, $R^2$, $R^{3a}$, $R^{3b}$, $R^{3c}$, and $R^{3d}$ all have the same definitions as described herein, supra and infra.

One aspect of the present invention pertains to compounds of Formula (Ic) and pharmaceutically acceptable salts, solvates, and hydrates thereof:

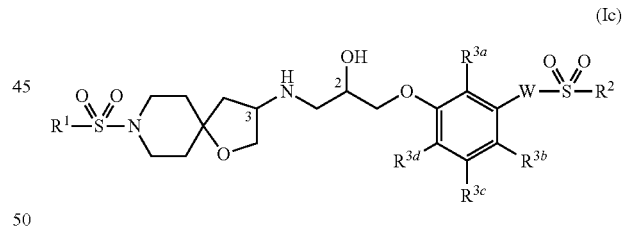

(Ic)

wherein:

W is absent or —$CH_2$—;

$R^1$ is aryl or heteroaryl, wherein each is optionally substituted with one or more substituents selected from: $C_1$-$C_6$ alkoxy, $C_1$-$C_6$ alkyl, amino, cyano, $C_3$-$C_7$ cycloalkyl, $C_1$-$C_6$ haloalkyl, halogen, hydroxyl, oxo, and sulfamoyl; and wherein said $C_1$-$C_6$ alkyl and $C_3$-$C_7$ cycloalkyl are each optionally substituted with one or more substituents selected from: amino, $C_1$-$C_6$ alkoxy, $C_1$-$C_6$ alkylcarboxamide, —NH—$C_3$-$C_7$-cycloalkyl, —NH—$C_1$-$C_6$-alkylene-$NH_2$, —NH—$C_1$-$C_6$-alkylene-O—$C_1$-$C_6$-alkyl, —NH—$C_1$-$C_6$-alkylene-NH—$C_1$-$C_6$-alkyl, $C_1$-$C_6$ alkylamino, $C_1$-$C_6$ haloalkylamino, and heterocyclyl;

$R^2$ is selected from: $C_2$-$C_6$ alkenyl, $C_1$-$C_6$ alkyl, $C_3$-$C_7$ cycloalkyl, heterocyclyl, and $C_1$-$C_6$ haloalkyl; each optionally substituted with one or more substituents selected from:

$C_1$-$C_6$ alkoxy, $C_1$-$C_6$ alkylenehydroxyl, amino, aryl, $C_3$-$C_7$ cycloalkyl, cyano, $C_3$-$C_7$ halocycloalkyl, hydroxyl, and oxo; and $R^{3a}$, $R^{3b}$, $R^{3c}$, and $R^{3d}$ are each independently H or halogen.

One aspect of the present invention pertains to compounds of Formula (Ic) and pharmaceutically acceptable salts, solvates, and hydrates thereof:

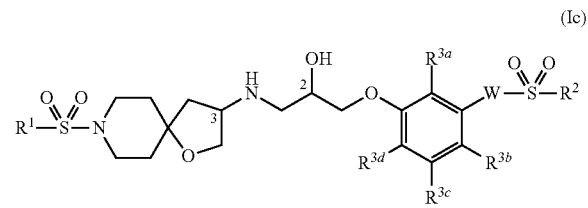

(Ic)

wherein:

W is absent or —$CH_2$—;

$R^1$ is selected from: (1H-pyrazolyl)phenyl, (1H-pyrazolyl)pyridinyl, (pyridinyl)phenyl, (pyrimidinyl)phenyl, 1,2,3,4-tetrahydropyrido[3,2-b]pyrazinyl, 1,2-dihydroquinolinyl, 1,4-dihydroquinolinyl, 1H-benzo[d]imidazolyl, 1H-indazolyl, 1H-indolyl, 1H-pyrazolo[4,3-b]pyridinyl, 1H-pyrazolyl, 1H-pyrrolo[2,3-b]pyridinyl, 1H-pyrrolo[3,2-b]pyridinyl, 2,3-dihydro-[1,4]dioxino[2,3-b]pyridinyl, 2,3-dihydro-1H-imidazo[4,5-b]pyridinyl, 2,3-dihydro-1H-pyrido[2,3-b][1,4]oxazinyl, 2,3-dihydro-1H-pyrrolo[2,3-b]pyridinyl, 2,3-dihydrobenzofuranyl, 3,4-dihydro-2H-benzo[b][1,4]oxazinyl, 3,4-dihydro-2H-pyrano[2,3-b]pyridinyl, 3,4-dihydro-2H-pyrido[3,2-b][1,4]oxazinyl, 3H-imidazo[4,5-b]pyridinyl, (phenyl)pyridinyl, 5,6,7,8-tetrahydronaphthalenyl, 5,6,7,8-tetrahydroquinolinyl, 6,7-dihydro-5H-pyrrolo[3,4-b]pyridin-3-yl, benzo[c][1,2,5]oxadiazolyl, benzofuranyl, biphenyl, chromanyl, isoquinolinyl, isoxazolyl, naphthalenyl, phenyl, phenylthiophenyl, pyridinyl, pyrrolo[1,2-a]pyrimidinyl, quinolinyl, and thiazolyl; wherein each is optionally substituted with one or more substituents selected from: 2-methylpropan-2-yl, amino, bromo, chloro, cyclopropyl, ethoxy, ethyl, fluoro, hydroxy, isopropoxy, methoxy, methyl, oxo, propan-2-yl, propan-1-yl, sulfamoyl, and trifluoromethyl; and wherein said 2-methylpropan-2-yl, cyclopropyl, ethyl, methyl, and propan-2-yl are each optionally substituted with one or more substituents selected from: 2,2,2-trifluoroethylamino, 2-aminoethylamino, 2-methoxyethylamino, 3-aminopropylamino, acetamido, amino, azetidin-1-yl, butylamino, cyclobutylamino, ethylamino, isobutylamino, isopropylamino, methoxy, methylamino, morpholino, propylamino, tert-butylamino, and tert-pentylamino;

$R^2$ is selected from: 1,1-difluoroethyl, 1-fluoroethyl, 2-methylpropan-2-yl, 3,3,3-trifluoropropyl, 4,4,4-trifluorobutyl, azetidin-3-yl, cyclobutyl, cyclopentyl, cyclopropyl, ethyl, fluoromethyl, isobutyl, isopentyl, isopropyl, methyl, oxetan-3-yl, propan-1-yl, sec-butyl, and vinyl; each optionally substituted with one or more substituents selected from: 2,2-difluorocyclopropyl, amino, cyano, cyclobutyl, cyclohexyl, cyclopropyl, ethoxy, hydroxy, hydroxymethyl, methoxy, oxo, and phenyl; and $R^{3a}$, $R^{3b}$, $R^{3c}$, and $R^{3d}$ are each independently H or F.

One aspect of the present invention pertains to compounds of Formula (Ic) and pharmaceutically acceptable salts, solvates, and hydrates thereof:

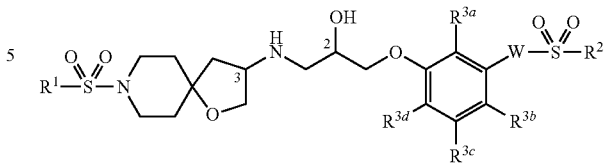

(Ic)

wherein:

W is absent or —$CH_2$—;

$R^1$ is selected from: (R)-1,3-dimethyl-2,3-dihydro-1H-pyrido[2,3-b][1,4]oxazin-7-yl, (S)-1,3-dimethyl-2,3-dihydro-1H-pyrido[2,3-b][1,4]oxazin-7-yl, 1-(2-methoxyethyl)-2,3-dihydro-1H-pyrido[2,3-b][1,4]oxazin-7-yl, 1,3,3-trimethyl-2,3-dihydro-1H-pyrido[2,3-b][1,4]oxazin-6-yl, 1,4-dimethyl-1,2,3,4-tetrahydropyrido[3,2-b]pyrazin-7-yl, 1,6-dimethyl-2,3-dihydro-1H-pyrido[2,3-b][1,4]oxazin-7-yl, 1,8-dimethyl-2,3-dihydro-1H-pyrido[2,3-b][1,4]oxazin-7-yl, 1-ethyl-2,3-dihydro-1H-pyrido[2,3-b][1,4]oxazin-7-yl, 1-ethyl-4-oxo-1,4-dihydroquinolin-3-yl, 1-ethyl-5-methyl-1H-pyrazol-4-yl, 1-ethyl-6-fluoro-4-oxo-1,4-dihydroquinolin-3-yl, 1-ethyl-6-methyl-4-oxo-1,4-dihydroquinolin-3-yl, 1-ethyl-7-fluoro-4-oxo-1,4-dihydroquinolin-3-yl, 1-ethyl-7-methyl-4-oxo-1,4-dihydroquinolin-3-yl, 1-ethyl-8-fluoro-4-oxo-1,4-dihydroquinolin-3-yl, 1-ethyl-8-methyl-4-oxo-1,4-dihydroquinolin-3-yl, 1H-benzo[d]imidazol-5-yl, 1H-indazol-5-yl, 1H-indol-2-yl, 1H-indol-3-yl, 1H-indol-5-yl, 1H-indol-6-yl, 1H-pyrazolo[4,3-b]pyridin-6-yl, 1H-pyrrolo[2,3-b]pyridin-3-yl, 1H-pyrrolo[3,2-b]pyridin-6-yl, 1-methyl-2,3-dihydro-1H-pyrido[2,3-b][1,4]oxazin-7-yl, 1-methyl-4-oxo-1,4-dihydroquinolin-3-yl, 2,3-dihydro-[1,4]dioxino[2,3-b]pyridin-7-yl, 2,3-dihydro-1H-pyrido[2,3-b][1,4]oxazin-7-yl, 2,3-dihydrobenzofuran-5-yl, 2-aminothiazol-4-yl, 2-oxo-2,3-dihydro-1H-imidazo[4,5-b]pyridin-6-yl, 2-oxo-2,3-dihydro-1H-pyrrolo[2,3-b]pyridin-5-yl, 3-(1-cyclopropyl-1H-pyrazol-4-yl)phenyl, 3-(1-ethyl-1H-pyrazol-4-yl)phenyl, 3-(1H-pyrazol-4-yl)phenyl, 3-(1-methyl-1H-pyrazol-4-yl)phenyl, 3-(1-propyl-1H-pyrazol-4-yl)phenyl, 3-(2-methylpyridin-4-yl)phenyl, 3-(3-fluoropyridin-2-yl)phenyl, 3-(4-methylpyridin-2-yl)phenyl, 3-(5-methylpyridin-2-yl)phenyl, 3-(6-(trifluoromethyl)pyridin-2-yl)phenyl, 3-(6-aminopyridin-3-yl)phenyl, 3-(6-fluoropyridin-2-yl)phenyl, 3-(6-methylpyridin-2-yl)phenyl, 3-(pyridin-2-yl)phenyl, 3-(pyridin-3-yl)phenyl, 3-(pyridin-4-yl)phenyl, 3-(pyrimidin-5-yl)phenyl, 3,4-dihydro-2H-pyrano[2,3-b]pyridin-6-yl, 3,5-dimethylisoxazol-4-yl, 3-methyl-3H-imidazo[4,5-b]pyridin-5-yl, 3-methyl-3H-imidazo[4,5-b]pyridin-6-yl, 3-oxo-3,4-dihydro-2H-benzo[b][1,4]oxazin-6-yl, 4-(pyridin-2-yl)phenyl, 4-(pyridin-3-yl)phenyl, 4-(pyridin-4-yl)phenyl, 4-hydroxy-6-methylquinolin-3-yl, 4-hydroxy-7-methylquinolin-3-yl, 4-hydroxy-8-methylquinolin-3-yl, 4-hydroxyquinolin-3-yl, 4-methoxyquinolin-3-yl, 4-methyl-2-oxo-1,2-dihydroquinolin-6-yl, 4-methyl-3,4-dihydro-2H-benzo[b][1,4]oxazin-6-yl, 4-methyl-3,4-dihydro-2H-benzo[b][1,4]oxazin-7-yl, 4-methyl-3,4-dihydro-2H-pyrido[3,2-b][1,4]oxazin-7-yl, 4-oxo-1,4-dihydroquinolin-3-yl, 5-(1-methyl-1H-pyrazol-4-yl)pyridin-3-yl, 5-(4-(aminomethyl)phenyl)pyridin-3-yl, 5,6,7,8-tetrahydroquinolin-3-yl, 5-bromo-6-chloropyridin-3-yl, 5-bromopyridin-3-yl, 5-oxo-6,7-dihydro-5H-pyrrolo[3,4-b]pyridin-3-yl, 5-phenylthiophen-2-yl, 6-fluoro-4-hydroxyquinolin-3-yl, 7-chlorobenzo[c][1,2,5]oxadiazol-4-yl, 7-fluoro-4-hydroxyquinolin-3-yl, 8-fluoro-4-hydroxyquinolin-3-yl, benzofuran-2-yl, benzofuran-5-yl, chroman-6-yl, chroman-7-yl, isoquinolin-5-yl, pyridin-2-yl, pyridin-3-yl, pyrrolo[1,2-a]pyrimidin-3-yl, quinolin-3-yl, quinolin-6-yl, and quinolin-7-yl;

$R^2$ is selected from: (2,2-difluorocyclopropyl)methyl, 1-(hydroxymethyl)cyclobutyl, 1-(hydroxymethyl)cyclopropyl, 1,1-difluoro-2-hydroxyethyl, 1-amino-2-methyl-1-oxopropan-2-yl, 1-ethoxy-2-methyl-1-oxopropan-2-yl, 1-fluoroethyl, 1-hydroxy-2-methylpropan-2-yl, 2-amino-2-oxoethyl, 2-aminoethyl, 2-hydroxyethyl, 3,3,3-trifluoropropyl, 3-amino-3-oxopropyl, 3-hydroxycyclobutyl, 3-hydroxypropyl, 3-methoxypropyl, 4,4,4-trifluorobutyl, azetidin-3-yl, benzyl, carboxymethyl, cyanomethyl, cyclobutyl, cyclobutylmethyl, cyclohexylmethyl, cyclopentyl, cyclopropyl, cyclopropylmethyl, ethyl, fluoromethyl, isobutyl, isopentyl, isopropyl, methoxymethyl, methyl, oxetan-3-yl, propan-1-yl, sec-butyl, and vinyl; and $R^{3a}$, $R^{3b}$, $R^{3c}$, and $R^{3d}$ are each independently H or F.

One aspect of the present invention pertains to compounds of Formula (Ie) and pharmaceutically acceptable salts, solvates, and hydrates thereof:

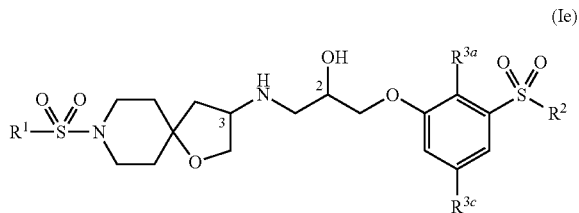

(Ie)

wherein:

$R^1$ is aryl or heteroaryl, wherein each is optionally substituted with one or more substituents selected from: $C_1$-$C_6$ alkoxy, $C_1$-$C_6$ alkyl, amino, cyano, $C_3$-$C_7$ cycloalkyl, $C_1$-$C_6$ haloalkyl, halogen, hydroxyl, oxo, and sulfamoyl; and wherein said $C_1$-$C_6$ alkyl and $C_3$-$C_7$ cycloalkyl are each optionally substituted with one or more substituents selected from: amino, $C_1$-$C_6$ alkoxy, $C_1$-$C_6$ alkylcarboxamide, —NH—$C_3$-$C_7$-cycloalkyl, —NH—$C_1$-$C_6$-alkylene-NH$_2$, —NH—$C_1$-$C_6$-alkylene-O—$C_1$-$C_6$-alkyl, —NH—$C_1$-$C_6$-alkylene-NH—$C_1$-$C_6$-alkyl, $C_1$-$C_6$ alkylamino, $C_1$-$C_6$ haloalkylamino, and heterocyclyl;

$R^2$ is selected from: $C_2$-$C_6$ alkenyl, $C_1$-$C_6$ alkyl, $C_3$-$C_7$ cycloalkyl, heterocyclyl, and $C_1$-$C_6$ haloalkyl; each optionally substituted with one or more substituents selected from: $C_1$-$C_6$ alkoxy, $C_1$-$C_6$ alkylenehydroxyl, amino, aryl, $C_3$-$C_7$ cycloalkyl, cyano, $C_3$-$C_7$ halocycloalkyl, hydroxyl, and oxo; and $R^{3a}$ and $R^{3c}$ are each independently H or halogen.

One aspect of the present invention pertains to compounds of Formula (Ie) and pharmaceutically acceptable salts, solvates, and hydrates thereof:

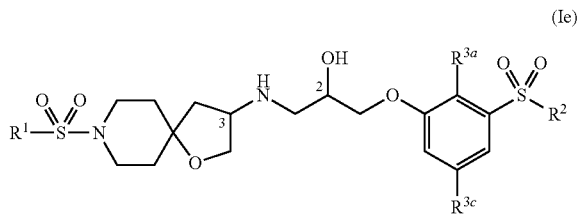

(Ie)

wherein:

$R^1$ is selected from: (1H-pyrazolyl)phenyl, (1H-pyrazolyl)pyridinyl, (pyridinyl)phenyl, (pyrimidinyl)phenyl, 1,2,3,4-tetrahydropyrido[3,2-b]pyrazinyl, 1,2-dihydroquinolinyl, 1,4-dihydroquinolinyl, 1H-benzo[d]imidazolyl, 1H-indazolyl, 1H-indolyl, 1H-pyrazolo[4,3-b]pyridinyl, 1H-pyrazolyl, 1H-pyrrolo[2,3-b]pyridinyl, 1H-pyrrolo[3,2-b]pyridinyl, 2,3-dihydro-[1,4]dioxino[2,3-b]pyridinyl, 2,3-dihydro-1H-imidazo[4,5-b]pyridinyl, 2,3-dihydro-1H-pyrido[2,3-b][1,4]oxazinyl, 2,3-dihydro-1H-pyrrolo[2,3-b]pyridinyl, 2,3-dihydrobenzofuranyl, 3,4-dihydro-2H-benzo[b][1,4]oxazinyl, 3,4-dihydro-2H-pyrano[2,3-b]pyridinyl, 3,4-dihydro-2H-pyrido[3,2-b][1,4]oxazinyl, 3H-imidazo[4,5-b]pyridinyl, (phenyl)pyridinyl, 5,6,7,8-tetrahydronaphthalenyl, 5,6,7,8-tetrahydroquinolinyl, 6,7-dihydro-5H-pyrrolo[3,4-b]pyridin-3-yl, benzo[c][1,2,5]oxadiazolyl, benzofuranyl, biphenyl, chromanyl, isoquinolinyl, isoxazolyl, naphthalenyl, phenyl, phenylthiophenyl, pyridinyl, pyrrolo[1,2-a]pyrimidinyl, quinolinyl, and thiazolyl; wherein each is optionally substituted with one or more substituents selected from: 2-methylpropan-2-yl, amino, bromo, chloro, cyclopropyl, ethoxy, ethyl, fluoro, hydroxy, isopropoxy, methoxy, methyl, oxo, propan-2-yl, propan-1-yl, sulfamoyl, and trifluoromethyl; and wherein said 2-methylpropan-2-yl, cyclopropyl, ethyl, methyl, and propan-2-yl are each optionally substituted with one or more substituents selected from: 2,2,2-trifluoroethylamino, 2-aminoethylamino, 2-methoxyethylamino, 3-aminopropylamino, acetamido, amino, azetidin-1-yl, butylamino, cyclobutylamino, ethylamino, isobutylamino, isopropylamino, methoxy, methylamino, morpholino, propylamino, tert-butylamino, and tert-pentylamino;

$R^2$ is selected from: 1,1-difluoroethyl, 1-fluoroethyl, 2-methylpropan-2-yl, 3,3,3-trifluoropropyl, 4,4,4-trifluorobutyl, azetidin-3-yl, cyclobutyl, cyclopentyl, cyclopropyl, ethyl, fluoromethyl, isobutyl, isopentyl, isopropyl, methyl, oxetan-3-yl, propan-1-yl, sec-butyl, and vinyl; each optionally substituted with one or more substituents selected from: 2,2-difluorocyclopropyl, amino, cyano, cyclobutyl, cyclohexyl, cyclopropyl, ethoxy, hydroxy, hydroxymethyl, methoxy, oxo, and phenyl; and $R^{3a}$ and $R^{3c}$ are each independently H or F.

One aspect of the present invention pertains to compounds of Formula (Ie) and pharmaceutically acceptable salts, solvates, and hydrates thereof:

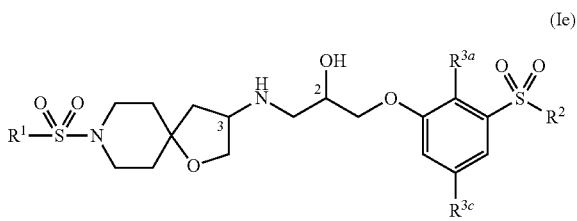

(Ie)

wherein:

$R^1$ is selected from: (R)-1,3-dimethyl-2,3-dihydro-1H-pyrido[2,3-b][1,4]oxazin-7-yl, (S)-1,3-dimethyl-2,3-dihydro-1H-pyrido[2,3-b][1,4]oxazin-7-yl, 1-(2-methoxyethyl)-2,3-dihydro-1H-pyrido[2,3-b][1,4]oxazin-7-yl, 1,3,3-trimethyl-2,3-dihydro-1H-pyrido[2,3-b][1,4]oxazin-6-yl, 1,4-dimethyl-1,2,3,4-tetrahydropyrido[3,2-b]pyrazin-7-yl, 1,6-dimethyl-2,3-dihydro-1H-pyrido[2,3-b][1,4]oxazin-7-yl, 1,8-dimethyl-2,3-dihydro-1H-pyrido[2,3-b][1,4]oxazin-7-yl, 1-ethyl-2,3-dihydro-1H-pyrido[2,3-b][1,4]oxazin-7-yl, 1-ethyl-4-oxo-1,4-dihydroquinolin-3-yl, 1-ethyl-5-methyl- 1H-pyrazol-4-yl, 1-ethyl-6-fluoro-4-oxo-1,4-dihydroquinolin-3-yl, 1-ethyl-6-methyl-4-oxo-1,4-dihydroquinolin-3-yl, 1-ethyl-7-fluoro-4-oxo-1,4-dihydroquinolin-3-yl, 1-ethyl-7-methyl-4-oxo-1,4-dihydroquinolin-3-yl, 1-ethyl-8-fluoro-4-oxo-1,4-dihydroquinolin-3-yl, 1-ethyl-8-methyl-4-oxo-1,4-dihydroquinolin-3-yl, 1H-benzo[d]imidazol-5-yl, 1H-indazol-5-yl, 1H-indol-2-yl, 1H-indol-3-yl, 1H-indol-5-yl, 1H-indol-6-yl, 1H-pyrazolo[4,3-b]pyridin-6-yl, 1H-pyrrolo[2,3-b]pyridin-3-yl, 1H-pyrrolo[3,2-b]pyridin-6-yl, 1-methyl-2,3-dihydro-1H-pyrido[2,3-b][1,4]oxazin-7-yl, 1-methyl-4-oxo-1,4-dihydroquinolin-3-yl, 2,3-dihydro-[1,4]dioxino[2,3-b]pyridin-7-yl, 2,3-dihydro-1H-pyrido[2,3-b][1,4]oxazin-7-yl, 2,3-dihydrobenzofuran-5-yl, 2-aminothiazol-4-yl, 2-oxo-2,3-dihydro-1H-imidazo[4,5-b]pyridin-6-yl, 2-oxo-2,3-dihydro-1H-pyrrolo[2,3-b]pyridin-5-yl, 3-(1-cyclopropyl-1H-pyrazol-4-yl)phenyl, 3-(1-ethyl-1H-pyrazol-4-yl)phenyl, 3-(1H-pyrazol-4-yl)phenyl, 3-(1-methyl-1H-pyrazol-4-yl)phenyl, 3-(1-propyl-1H-pyrazol-4-yl)phenyl, 3-(2-methylpyridin-4-yl)phenyl, 3-(3-fluoropyridin-2-yl)phenyl, 3-(4-methylpyridin-2-yl)phenyl, 3-(5-methylpyridin-2-yl)phenyl, 3-(6-(trifluoromethyl)pyridin-2-yl)phenyl, 3-(6-aminopyridin-3-yl)phenyl, 3-(6-fluoropyridin-2-yl)phenyl, 3-(6-methylpyridin-2-yl)phenyl, 3-(pyridin-2-yl)phenyl, 3-(pyridin-3-yl)phenyl, 3-(pyridin-4-yl)phenyl, 3-(pyrimidin-5-yl)phenyl, 3,4-dihydro-2H-pyrano[2,3-b]pyridin-6-yl, 3,5-dimethylisoxazol-4-yl, 3-methyl-3H-imidazo[4,5-b]pyridin-5-yl, 3-methyl-3H-imidazo[4,5-b]pyridin-6-yl, 3-oxo-3,4-dihydro-2H-benzo[b][1,4]oxazin-6-yl, 4-(pyridin-2-yl)phenyl, 4-(pyridin-3-yl)phenyl, 4-(pyridin-4-yl)phenyl, 4-hydroxy-6-methylquinolin-3-yl, 4-hydroxy-7-methylquinolin-3-yl, 4-hydroxy-8-methylquinolin-3-yl, 4-hydroxyquinolin-3-yl, 4-methoxyquinolin-3-yl, 4-methyl-2-oxo-1,2-dihydroquinolin-6-yl, 4-methyl-3,4-dihydro-2H-benzo[b][1,4]oxazin-6-yl, 4-methyl-3,4-dihydro-2H-benzo[b][1,4]oxazin-7-yl, 4-methyl-3,4-dihydro-2H-pyrido[3,2-b][1,4]oxazin-7-yl, 4-oxo-1,4-dihydroquinolin-3-yl, 5-(1-methyl-1H-pyrazol-4-yl)pyridin-3-yl, 5-(4-(aminomethyl)phenyl)pyridin-3-yl, 5,6,7,8-tetrahydroquinolin-3-yl, 5-bromo-6-chloropyridin-3-yl, 5-bromopyridin-3-yl, 5-oxo-6,7-dihydro-5H-pyrrolo[3,4-b]pyridin-3-yl, 5-phenylthiophen-2-yl, 6-fluoro-4-hydroxyquinolin-3-yl, 7-chlorobenzo[c][1,2,5]oxadiazol-4-yl, 7-fluoro-4-hydroxyquinolin-3-yl, 8-fluoro-4-hydroxyquinolin-3-yl, benzofuran-2-yl, benzofuran-5-yl, chroman-6-yl, chroman-7-yl, isoquinolin-5-yl, pyridin-2-yl, pyridin-3-yl, pyrrolo[1,2-a]pyrimidin-3-yl, quinolin-3-yl, quinolin-6-yl, and quinolin-7-yl;

$R^2$ is selected from: (2,2-difluorocyclopropyl)methyl, 1-(hydroxymethyl)cyclobutyl, 1-(hydroxymethyl)cyclopropyl, 1,1-difluoro-2-hydroxyethyl, 1-amino-2-methyl-1-oxopropan-2-yl, 1-ethoxy-2-methyl-1-oxopropan-2-yl, 1-fluoroethyl, 1-hydroxy-2-methylpropan-2-yl, 2-amino-2-oxoethyl, 2-aminoethyl, 2-hydroxyethyl, 3,3,3-trifluoropropyl, 3-amino-3-oxopropyl, 3-hydroxycyclobutyl, 3-hydroxypropyl, 3-methoxypropyl, 4,4,4-trifluorobutyl, azetidin-3-yl, benzyl, carboxymethyl, cyanomethyl, cyclobutyl, cyclobutylmethyl, cyclohexylmethyl, cyclopentyl, cyclopropyl, cyclopropylmethyl, ethyl, fluoromethyl, isobutyl, isopentyl, isopropyl, methoxymethyl, methyl, oxetan-3-yl, propan-1-yl, sec-butyl, and vinyl; and $R^{3a}$ and $R^{3c}$ are each independently H or F.

One aspect of the present invention pertains to compounds of Formula (Ig) and pharmaceutically acceptable salts, solvates, and hydrates thereof:

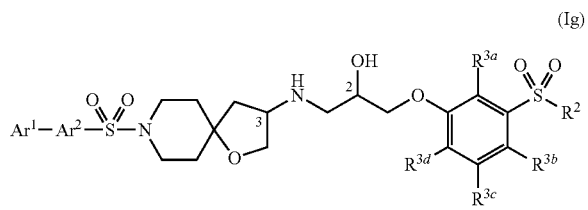

(Ig)

wherein:

$Ar^1$ and $Ar^2$ are independently 1H-pyrazolyl, phenyl, pyridinyl, pyrimidinyl, and thiophenyl, wherein each is optionally substituted with one or more substituents selected from: $C_1$-$C_6$ alkoxy, $C_1$-$C_6$ alkyl, amino, $C_3$-$C_7$ cycloalkyl, $C_1$-$C_6$ haloalkyl, halogen, and sulfamoyl; and wherein said $C_1$-$C_6$ alkyl and $C_3$-$C_7$ cycloalkyl are each optionally substituted with one or more substituents selected from: amino, $C_1$-$C_6$ alkylcarboxamide, —NH—$C_3$-$C_7$-cycloalkyl, —NH—$C_1$-$C_6$-alkylene-NH$_2$, —NH—$C_1$-$C_6$-alkylene-O—$C_1$-$C_6$-alkyl, $C_1$-$C_6$ alkylamino, $C_1$-$C_6$ haloalkylamino, and heterocyclyl;

$R^2$ is selected from: $C_1$-$C_6$ alkyl, $C_3$-$C_7$ cycloalkyl, and $C_1$-$C_6$ haloalkyl; each optionally substituted with one or more substituents selected from: $C_1$-$C_6$ alkoxy, $C_1$-$C_6$ alkylenehydroxyl, amino, hydroxyl, and oxo; and $R^{3a}$, $R^{3b}$, $R^{3c}$, and $R^{3d}$ are each independently H or halogen.

One aspect of the present invention pertains to compounds of Formula (Ig) and pharmaceutically acceptable salts, solvates, and hydrates thereof:

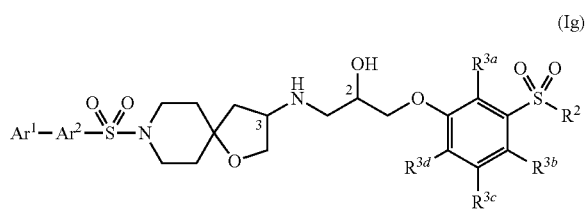

(Ig)

wherein:

$Ar^1$ and $Ar^2$ together form a group selected from: (1H-pyrazolyl)phenyl, (1H-pyrazolyl)pyridinyl, (phenyl)pyridinyl, (pyridinyl)phenyl, (pyrimidinyl)phenyl, biphenyl, and phenylthiophenyl, wherein each is optionally substituted with one or more substituents selected from: 2-methylpropan-2-yl, amino, cyclopropyl, ethoxy, ethyl, fluoro, isopropoxy, methoxy, methyl, n-propyl, propan-2-yl, sulfamoyl, and trifluoromethyl; and wherein said 2-methylpropan-2-yl, cyclopropyl, ethyl, methyl, and propan-2-yl are each optionally substituted with 2,2,2-trifluoroethylamino, 2-aminoethylamino, 2-methoxyethylamino, 3-aminopropylamino, acetamido, amino, azetidin-1-yl, butylamino, cyclobutylamino, ethylamino, isobutylamino, isopropylamino, isopropylamino, methylamino, morpholino, propylamino, tert-butylamino, and tert-pentylamino;

$R^2$ is selected from: 1,1-difluoroethyl, 2-methylpropan-2-yl, cyclopropyl, ethyl, isopropyl, and methyl; each optionally substituted with one or more substituents selected from: amino, hydroxy, hydroxymethyl, methoxy, and oxo; and $R^{3a}$, $R^{3b}$, $R^{3c}$, and $R^{3d}$ are each H.

One aspect of the present invention pertains to compounds of Formula (Ig) and pharmaceutically acceptable salts, solvates, and hydrates thereof:

(Ig)

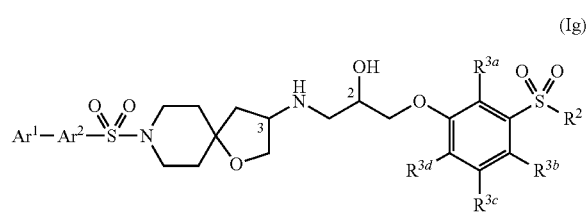

wherein:

Ar¹ and Ar² together form a group selected from: 3-(1H-pyrazol-4-yl)phenyl, 3-(pyridin-2-yl)phenyl, 3-(pyridin-3-yl)phenyl, 3-(pyridin-4-yl)phenyl, 3-(pyrimidin-5-yl)phenyl, 4-(pyridin-2-yl)phenyl, 4-(pyridin-3-yl)phenyl, 4-(pyridin-4-yl)phenyl, 5-(1H-pyrazol-4-yl)pyridin-3-yl, 5-(phenyl)pyridin-3-yl, 5-phenylthiophen-2-yl, biphenyl-3-yl, and biphenyl-4-yl, wherein each is optionally substituted with one or more substituents selected from: (2,2,2-trifluoroethylamino)methyl, (2-aminoethylamino)methyl, (2-methoxyethylamino)methyl, (3-aminopropylamino)methyl, (butylamino)methyl, (cyclobutylamino)methyl, (ethylamino)methyl, (isobutylamino)methyl, (isopropylamino)methyl, (methylamino)methyl, (propylamino)methyl, (tert-butylamino)methyl, (tert-pentylamino)methyl, 1-amino-2-methylpropan-2-yl, 1-aminocyclopropyl, 2-acetamidoethyl, 2-aminoethyl, 2-aminopropan-2-yl, amino, aminomethyl, azetidin-1-ylmethyl, cyclopropyl, ethoxy, ethyl, fluoro, isopropoxy, methoxy, methyl, morpholinomethyl, propyl, sulfamoyl, and trifluoromethyl;

R² is selected from: 1-(hydroxymethyl)cyclopropyl, 1,1-difluoro-2-hydroxyethyl, 1-hydroxy-2-methylpropan-2-yl, 2-amino-2-oxoethyl, 2-hydroxyethyl, cyclopropyl, ethyl, isopropyl, methoxymethyl, and methyl; and R³ᵃ, R³ᵇ, R³ᶜ, and R³ᵈ are each H.

One aspect of the present invention pertains to compounds of Formula (Ig) and pharmaceutically acceptable salts, solvates, and hydrates thereof:

(Ig)

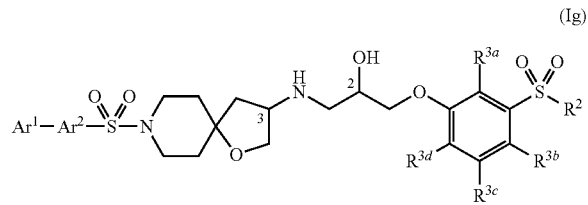

wherein:

Ar¹ and Ar² together form a group selected from: 3-(1-cyclopropyl-1H-pyrazol-4-yl)phenyl, 3-(1-ethyl-1H-pyrazol-4-yl)phenyl, 3-(1H-pyrazol-4-yl)phenyl, 3-(1-methyl-1H-pyrazol-4-yl)phenyl, 3-(1-propyl-1H-pyrazol-4-yl)phenyl, 3-(2-methylpyridin-4-yl)phenyl, 3-(3-fluoropyridin-2-yl)phenyl, 3-(4-methylpyridin-2-yl)phenyl, 3-(5-methylpyridin-2-yl)phenyl, 3-(6-(trifluoromethyl)pyridin-2-yl)phenyl, 3-(6-aminopyridin-3-yl)phenyl, 3-(6-fluoropyridin-2-yl)phenyl, 3-(6-methylpyridin-2-yl)phenyl, 3-(pyridin-2-yl)phenyl, 3-(pyridin-3-yl)phenyl, 3-(pyridin-4-yl)phenyl, 3-(pyrimidin-5-yl)phenyl, 4'-((2,2,2-trifluoroethylamino)methyl)biphenyl-3-yl, 4'-((2-aminoethylamino)methyl)biphenyl-3-yl, 4'-((2-methoxyethylamino)methyl)biphenyl-3-yl, 4'-((3-aminopropylamino)methyl)biphenyl-3-yl, 4'-((butylamino)methyl)biphenyl-3-yl, 4'-((cyclobutylamino)methyl)biphenyl-3-yl, 4'-((ethylamino)methyl)biphenyl-3-yl, 4'-((isobutylamino)methyl)biphenyl-3-yl, 4'-((isopropylamino)methyl)biphenyl-3-yl, 4'-((methylamino)methyl)biphenyl-3-yl, 4'-((propylamino)methyl)biphenyl-3-yl, 4'-((tert-butylamino)methyl)biphenyl-3-yl, 4'-((tert-pentylamino)methyl)biphenyl-3-yl, 4'-(1-amino-2-methylpropan-2-yl)-4-ethoxybiphenyl-3-yl, 4'-(1-amino-2-methylpropan-2-yl)biphenyl-3-yl, 4'-(1-aminocyclopropyl)-2-methylbiphenyl-3-yl, 4'-(1-aminocyclopropyl)-4-ethoxybiphenyl-3-yl, 4'-(1-aminocyclopropyl)-6-fluorobiphenyl-3-yl, 4'-(1-aminocyclopropyl)-6-methoxybiphenyl-3-yl, 4'-(1-aminocyclopropyl)biphenyl-3-yl, 4'-(2-acetamidoethyl)-4-ethoxy-biphenyl-3-yl, 4'-(2-acetamidoethyl)-biphenyl-3-yl, 4'-(2-aminoethyl)-4-ethoxybiphenyl-3-yl, 4'-(2-aminoethyl)-6-methoxybiphenyl-3-yl, 4'-(2-aminoethyl)biphenyl-3-yl, 4'-(2-aminopropan-2-yl)-4-ethoxybiphenyl-3-yl, 4'-(aminomethyl)-2-methoxybiphenyl-3-yl, 4'-(aminomethyl)-2-methylbiphenyl-3-yl, 4'-(aminomethyl)-3'-fluorobiphenyl-3-yl, 4'-(aminomethyl)-4-ethoxy-3'-fluorobiphenyl-3-yl, 4'-(aminomethyl)-4-ethoxybiphenyl-3-yl, 4'-(aminomethyl)-4-fluorobiphenyl-3-yl, 4'-(aminomethyl)-4-isopropoxybiphenyl-3-yl, 4'-(aminomethyl)-5-methoxybiphenyl-3-yl, 4'-(aminomethyl)-6-ethoxybiphenyl-3-yl, 4'-(aminomethyl)-6-fluorobiphenyl-3-yl, 4'-(aminomethyl)-6-methoxybiphenyl-3-yl, 4'-(aminomethyl)biphenyl-3-yl, 4'-(aminomethyl)biphenyl-4-yl, 4'-(azetidin-1-ylmethyl)biphenyl-3-yl, 4'-(morpholinomethyl)biphenyl-3-yl, 4-(pyridin-2-yl)phenyl, 4-(pyridin-3-yl)phenyl, 4-(pyridin-4-yl)phenyl, 4'-(sulfamoyl)biphenyl-3-yl, 4-ethoxy-4'-((isopropylamino)methyl)biphenyl-3-yl, 4'-methylbiphenyl-3-yl, 5-(1-methyl-1H-pyrazol-4-yl)pyridin-3-yl, 5-(4-(aminomethyl)phenyl)pyridin-3-yl, and 5-phenylthiophen-2-yl;

R² is selected from: 1-(hydroxymethyl)cyclopropyl, 1,1-difluoro-2-hydroxyethyl, 1-hydroxy-2-methylpropan-2-yl, 2-amino-2-oxoethyl, 2-hydroxyethyl, cyclopropyl, ethyl, isopropyl, methoxymethyl, and methyl; and R³ᵃ, R³ᵇ, R³ᶜ, and R³ᵈ are each H.

One aspect of the present invention pertains to compounds of Formula (Ii) and pharmaceutically acceptable salts, solvates, and hydrates thereof:

(Ii)

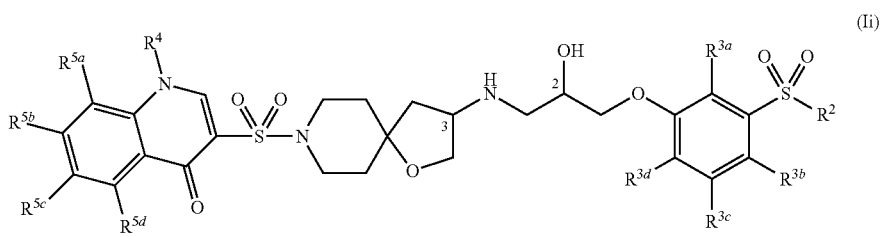

wherein:

$R^2$ is selected from: $C_1$-$C_6$ alkyl, $C_3$-$C_7$ cycloalkyl, and $C_1$-$C_6$ haloalkyl; each optionally substituted with one or more substituents selected from: $C_1$-$C_6$ alkoxy, $C_1$-$C_6$ alkylenehydroxyl, and hydroxyl;

$R^{3a}$, $R^{3b}$, $R^{3c}$, and $R^{3d}$ are each independently H or halogen;

$R^4$ is H or $C_1$-$C_6$ alkyl; and $R^{5a}$, $R^{5b}$, $R^{5c}$, and $R^{5d}$ are independently H, $C_1$-$C_6$ alkyl, and halogen.

One aspect of the present invention pertains to compounds of Formula (Ii) and pharmaceutically acceptable salts, solvates, and hydrates thereof:

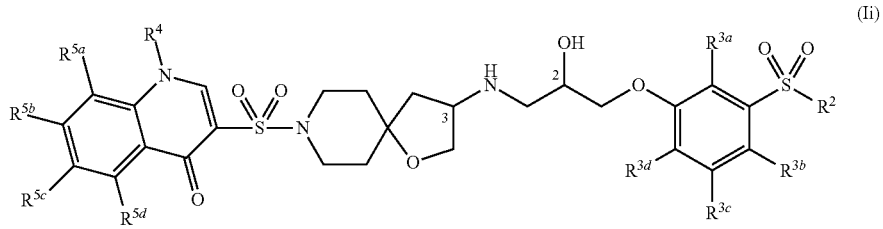

(Ii)

wherein:

$R^2$ is selected from: 1,1-difluoroethyl, 2-methylpropan-2-yl, cyclopropyl, ethyl, 1-fluoroethyl, isopropyl, and methyl; each optionally substituted with one or more substituents selected from: hydroxy, hydroxymethyl, and methoxy;

$R^{3a}$, $R^{3b}$, $R^{3c}$, and $R^{3d}$ are each H;

$R^4$ is selected from: H, methyl, and ethyl; and $R^{5a}$, $R^{5b}$, $R^{5c}$, and $R^{5d}$ are independently H, methyl, and fluoro.

One aspect of the present invention pertains to compounds of Formula (Ii) and pharmaceutically acceptable salts, solvates, and hydrates thereof:

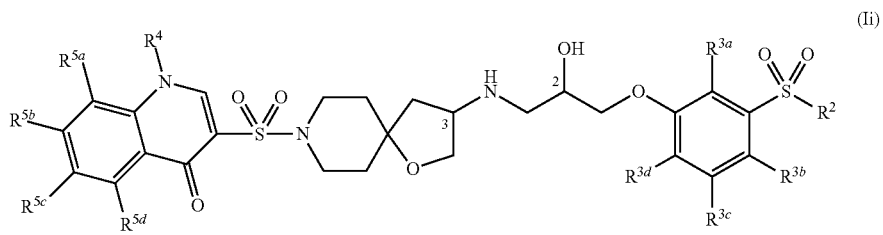

(Ii)

wherein:

$R^2$ is selected from: 1-(hydroxymethyl)cyclopropyl, 1,1-difluoro-2-hydroxyethyl, 1-fluoroethyl, 1-hydroxy-2-methylpropan-2-yl, cyclopropyl, isopropyl, methoxymethyl, and methyl;

$R^{3a}$, $R^{3b}$, $R^{3c}$, and $R^{3d}$ are each H;

$R^4$ is selected from: H, methyl, and ethyl;

$R^{5a}$, $R^{5b}$, and $R^{5c}$ are independently H, methyl, and fluoro; and $R^{5d}$ is H.

Some embodiments of the present invention include every combination of one or more compounds and pharmaceutically acceptable salts, solvates, and hydrates thereof selected from the following group shown in Table A.

TABLE A

| Cmpd No. | Chemical Structure | Chemical Name |
|---|---|---|
| 5 | 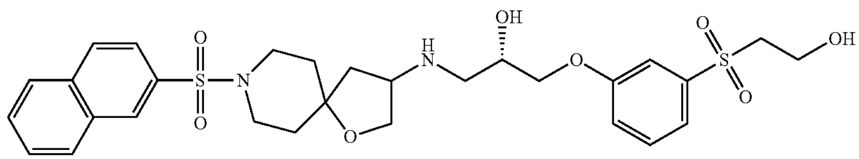 [SMILES: O=S(=O)(CCO)c1cccc(OC[C@@H](O)CNC2COC3(CCN(S(=O)(=O)c4ccc5ccccc5c4)CC3)C2)c1] | 2(S)-1-(3-(2-hydroxyethylsulfonyl)phenoxy)-3-(8-(naphthalen-2-ylsulfonyl)-1-oxa-8-azaspiro[4.5]decan-3-ylamino)propan-2-ol |
| 88 | 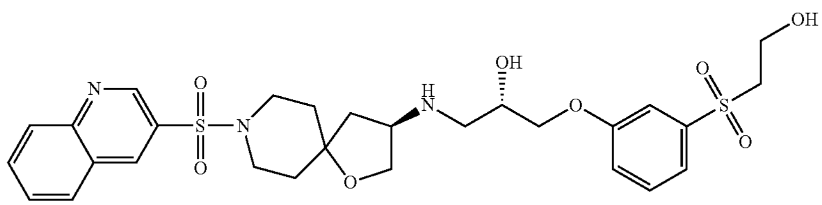 [SMILES: O=S(=O)(CCO)c1cccc(OC[C@@H](O)CN[C@H]2COC3(CCN(S(=O)(=O)c4cnc5ccccc5c4)CC3)C2)c1] | (S)-1-(3-(2-hydroxyethylsulfonyl)phenoxy)-3-((R)-8-(quinolin-3-ylsulfonyl)-1-oxa-8-azaspiro[4.5]decan-3-ylamino)propan-2-ol |
| 123 | 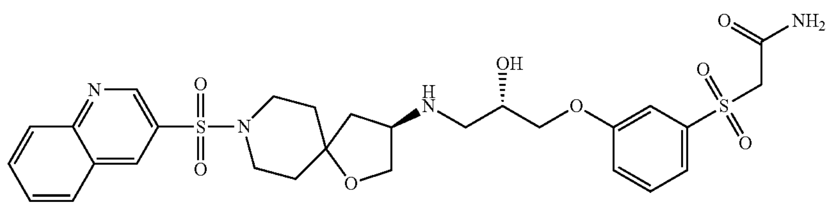 [SMILES: NC(=O)CS(=O)(=O)c1cccc(OC[C@@H](O)CN[C@H]2COC3(CCN(S(=O)(=O)c4cnc5ccccc5c4)CC3)C2)c1] | 2-(3-((S)-2-hydroxy-3-((R)-8-(quinolin-3-ylsulfonyl)-1-oxa-8-aaspiro[4.5]decan-3-ylamino)propoxy)phenylsulfonyl)acetamide |
| 136 | 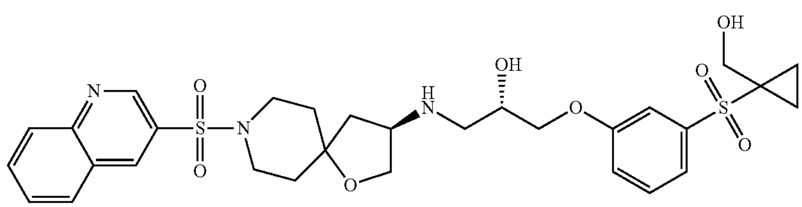 [SMILES: O=S(=O)(c1cnc2ccccc2c1)N1CCC2(CC1)C[C@@H](NC[C@H](O)COc1cccc(S(=O)(=O)C3(CO)CC3)c1)CO2] | (S)-1-(3-(1-(hydroxymethyl)cyclopropylsulfonyl)phenoxy)-3-((R)-8-(quinolin-3-ylsulfonyl)-1-oxa-8-azaspiro[4.5]decan-3-ylamino)propan-2-ol |
| 154 | 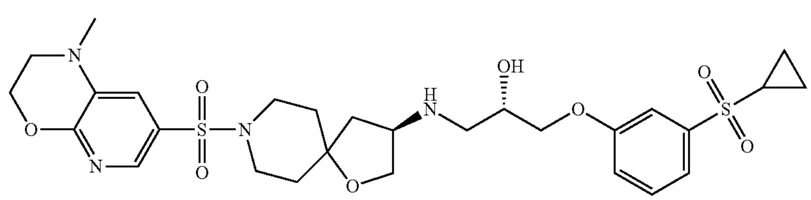 [SMILES: CN1CCOc2ncc(S(=O)(=O)N3CCC4(CC3)C[C@@H](NC[C@H](O)COc3cccc(S(=O)(=O)C5CC5)c3)CO4)cc21] | (S)-1-(3-(cyclopropylsulfonyl)phenoxy)-3-((R)-8-(1-methyl-2,3-dihydro-1H-pyrido[2,3-b][1,4]oxazin-7-ylsulfonyl)-1-oxa-8-azaspiro[4.5]decan-3-ylamino)propan-2-ol |
| 161 | 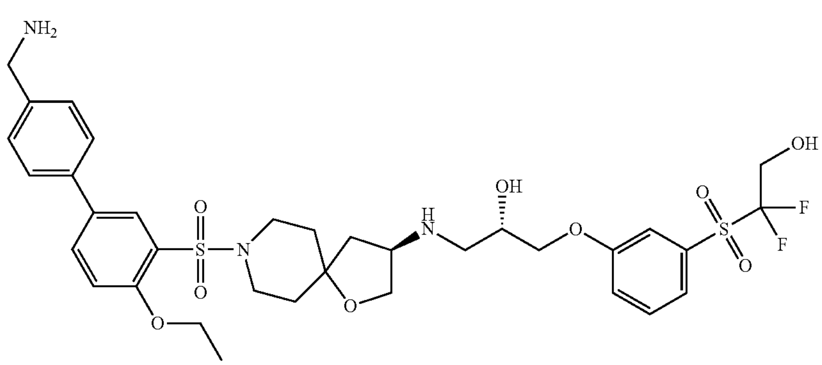 [SMILES: CCOc1ccc(-c2ccc(CN)cc2)cc1S(=O)(=O)N1CCC2(CC1)C[C@@H](NC[C@H](O)COc1cccc(S(=O)(=O)C(F)(F)CO)c1)CO2] | (S)-1-((R)-8-(4'-(aminomethyl)-4-ethoxybiphenyl-3-ylsulfonyl)-1-oxa-8-azaspiro[4.5]decan-3-ylamino)-3-(3-(1,1-difluoro-2-hydroxyethylsulfonyl)phenoxy)propan-2-ol |

TABLE A-continued

| Cmpd No. | Chemical Structure | Chemical Name |
|---|---|---|
| 163 | 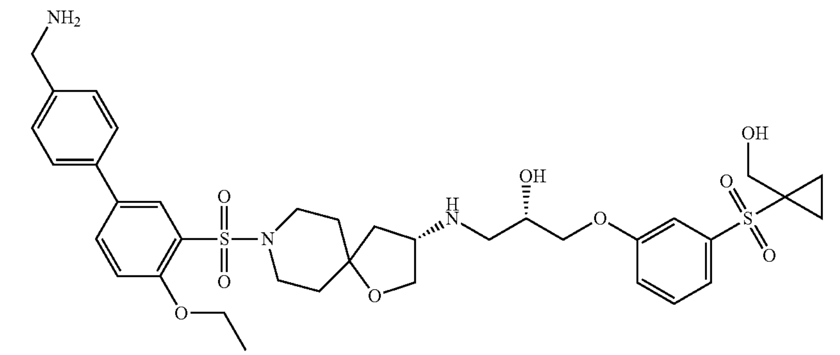 [SMILES: CCOc1ccc(-c2ccc(CN)cc2)cc1S(=O)(=O)N1CCC2(CC1)C[C@H](NC[C@H](O)COc1cccc(S(=O)(=O)C3(CO)CC3)c1)CO2] | (S)-1-((S)-8-(4'-(aminomethyl)-4-ethoxybiphenyl-3-ylsulfonyl)-1-oxa-8-azaspiro[4.5]decan-3-ylamino)-3-(3-(1-(hydroxymethyl)cyclopropylsulfonyl)phenoxy)propan-2-ol |
| 169 | 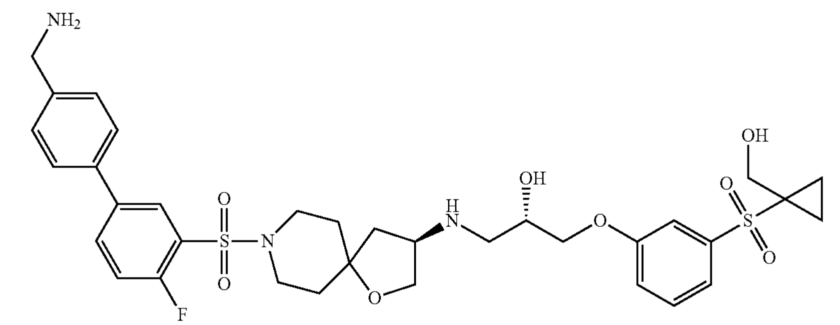 [SMILES: NCc1ccc(-c2ccc(F)c(S(=O)(=O)N3CCC4(CC3)C[C@@H](NC[C@H](O)COc3cccc(S(=O)(=O)C5(CO)CC5)c3)CO4)c2)cc1] | (S)-1-((R)-8-(4'-(aminomethyl)-4-fluorobiphenyl-3-ylsulfonyl)-1-oxa-8-azaspiro[4.5]decan-3-ylamino)-3-(3-(1-(hydroxymethyl)cyclopropylsulfonyl)phenoxy)propan-2-ol |
| 199 | 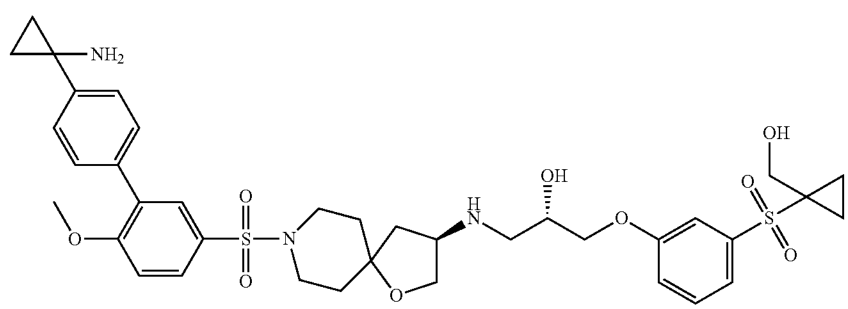 [SMILES: COc1ccc(S(=O)(=O)N2CCC3(CC2)C[C@@H](NC[C@H](O)COc2cccc(S(=O)(=O)C4(CO)CC4)c2)CO3)cc1-c1ccc(C2(N)CC2)cc1] | (S)-1-((R)-8-(4'-(1-aminocyclopropyl)-6-methoxybiphenyl-3-ylsulfonyl)-1-oxa-8-azaspiro[4.5]decan-3-ylamino)-3-(3-(1-(hydroxymethyl)cyclopropylsulfonyl)phenoxy)propan-2-ol |
| 210 | 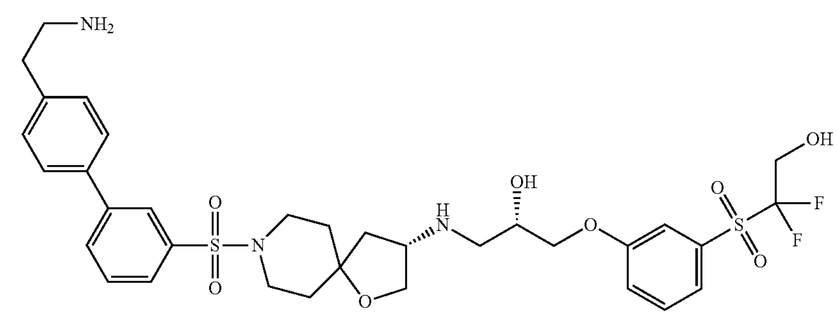 [SMILES: NCCc1ccc(-c2cccc(S(=O)(=O)N3CCC4(CC3)C[C@H](NC[C@H](O)COc3cccc(S(=O)(=O)C(F)(F)CO)c3)CO4)c2)cc1] | (S)-1-((S)-8-(4'-(2-aminoethyl)biphenyl-3-ylsulfonyl)-1-oxa-8-azaspiro[4.5]decan-3-ylamino)-3-(3-((1,1-difluoro-2-hydroxyethylsulfonyl)phenoxy)propan-2-ol |

TABLE A-continued

| Cmpd No. | Chemical Structure | Chemical Name |
|---|---|---|
| 211 | 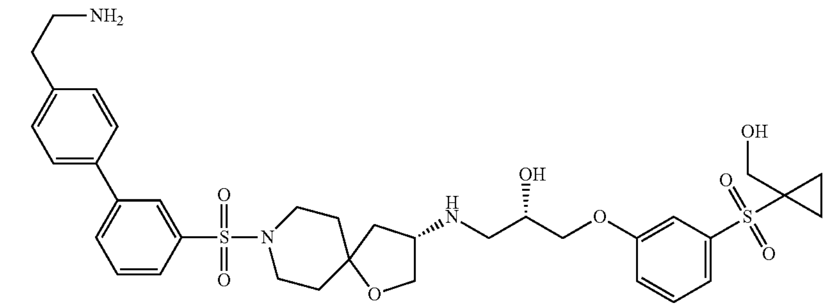 [SMILES: NCCc1ccc(-c2cccc(S(=O)(=O)N3CCC4(CC3)C[C@H](NC[C@H](O)COc3cccc(S(=O)(=O)C5(CO)CC5)c3)CO4)c2)cc1] | (S)-1-((S)-8-(4'-(2-aminoethyl)biphenyl-3-ylsulfonyl)-1-oxa-8-azaspiro[4.5]decan-3-ylamino)-3-(3-(1-(hydroxymethyl)cyclopropylsulfonyl)phenoxy)propan-2-ol |
| 217 | 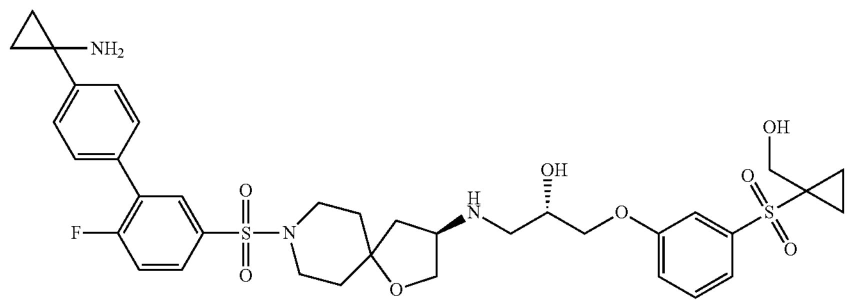 [SMILES: NC1(c2ccc(-c3cc(S(=O)(=O)N4CCC5(CC4)C[C@@H](NC[C@H](O)COc4cccc(S(=O)(=O)C6(CO)CC6)c4)CO5)ccc3F)cc2)CC1] | (S)-1-((R)-8-(4'-(1-aminocyclopropyl)-6-fluorobiphenyl-3-ylsulfonyl)-1-oxa-8-azaspiro[4.5]decan-3-ylamino)-3-(3-(1-(hydroxymethyl)cyclopropylsulfonyl)phenoxy)propan-2-ol |
| 220 | 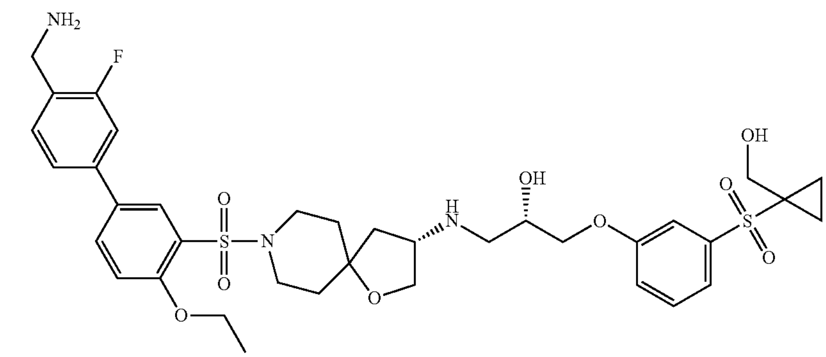 [SMILES: CCOc1ccc(-c2ccc(CN)c(F)c2)cc1S(=O)(=O)N1CCC2(CC1)C[C@H](NC[C@H](O)COc1cccc(S(=O)(=O)C3(CO)CC3)c1)CO2] | (S)-1-((S)-8-(4'-(aminomethyl)-4-ethoxy-3'-fluorobiphenyl-3-ylsulfonyl)-1-oxa-8-azaspiro[4.5]decan-3-ylamino)-3-(3-(1-(hydroxymethyl)cyclopropylsulfonyl)phenoxy)propan-2-ol |
| 225 | 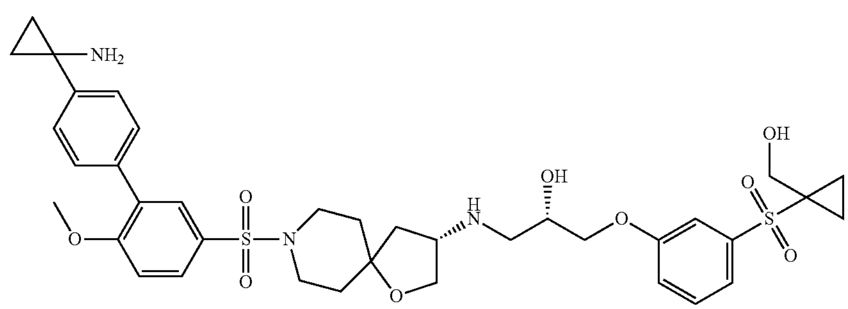 [SMILES: COc1ccc(S(=O)(=O)N2CCC3(CC2)C[C@H](NC[C@H](O)COc2cccc(S(=O)(=O)C4(CO)CC4)c2)CO3)cc1-c1ccc(C2(N)CC2)cc1] | (S)-1-((S)-8-(4'-(1-aminocyclopropyl)-6-methoxybiphenyl-3-ylsulfonyl)-1-oxa-8-azaspiro[4.5]decan-3-ylamino)-3-(3-(1-(hydroxymethyl)cyclopropylsulfonyl)phenoxy)propan-2-ol |
| 227 | 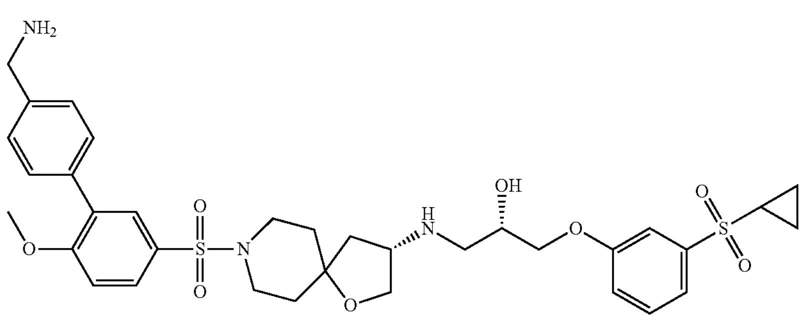 [SMILES: COc1ccc(S(=O)(=O)N2CCC3(CC2)C[C@H](NC[C@H](O)COc2cccc(S(=O)(=O)C4CC4)c2)CO3)cc1-c1ccc(CN)cc1] | (S)-1-((S)-8-(4'-(aminomethyl)-6-methoxybiphenyl-3-ylsulfonyl)-1-oxa-8-azaspiro[4.5]decan-3-ylamino)-3-(3-(cyclopropylsulfonyl)phenoxy)propan-2-ol |

TABLE A-continued

| Cmpd No. | Chemical Structure | Chemical Name |
|---|---|---|
| 229 | 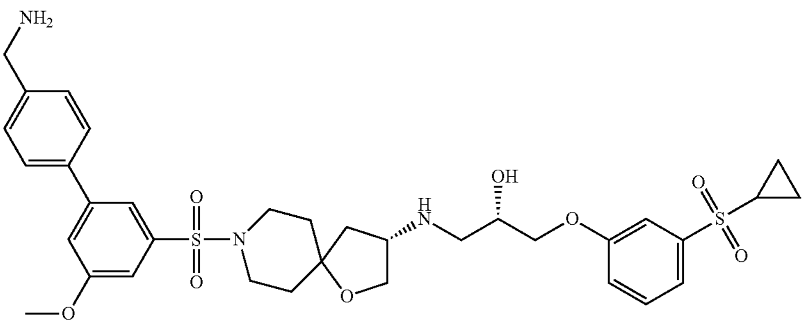 [SMILES: COc1cc(-c2ccc(CN)cc2)cc(S(=O)(=O)N2CCC3(CC2)C[C@H](NC[C@H](O)COc2cccc(S(=O)(=O)C4CC4)c2)CO3)c1] | (S)-1-((S)-8-(4'-(aminomethyl)-5-methoxybiphenyl-3-ylsulfonyl)-1-oxa-8-azaspiro[4.5]decan-3-ylamino)-3-(3-(cyclopropylsulfonyl)phenoxy)propan-2-ol |
| 230 | 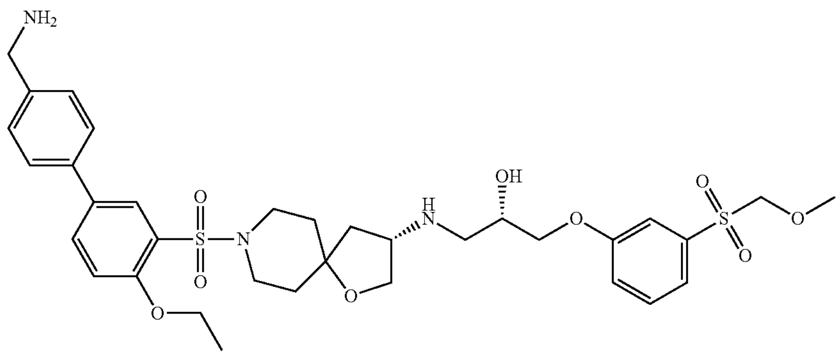 [SMILES: CCOc1ccc(-c2ccc(CN)cc2)cc1S(=O)(=O)N1CCC2(CC1)C[C@H](NC[C@H](O)COc1cccc(S(=O)(=O)COC)c1)CO2] | (S)-1-((S)-8-(4'-(aminomethyl)-4-ethoxybiphenyl-3-ylsulfonyl)-1-oxa-8-azaspiro[4.5]decan-3-ylamino)-3-(3-(methoxymethylsulfonyl)phenoxy)propan-2-ol |
| 232 | 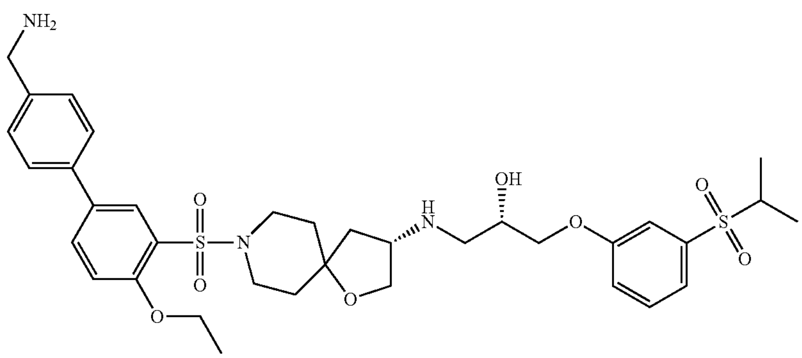 [SMILES: CCOc1ccc(-c2ccc(CN)cc2)cc1S(=O)(=O)N1CCC2(CC1)C[C@H](NC[C@H](O)COc1cccc(S(=O)(=O)C(C)C)c1)CO2] | (S)-1-((S)-8-(4'-(aminomethyl)-4-ethoxybiphenyl-3-ylsulfonyl)-1-oxa-8-azaspiro[4.5]decan-3-ylamino)-3-(3-(isopropylsulfonyl)phenoxy)propan-2-ol |
| 234 | 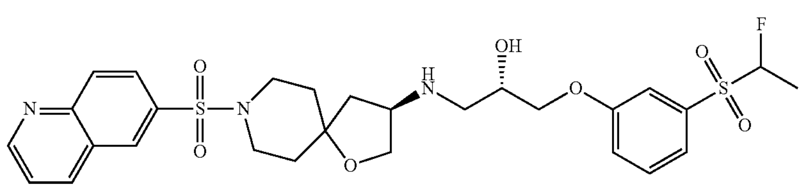 [SMILES: CC(F)S(=O)(=O)c1cccc(OC[C@@H](O)CN[C@H]2COC3(CCN(S(=O)(=O)c4ccc5ncccc5c4)CC3)C2)c1] | (2S)-1-(3-(1-fluoroethylsulfonyl)phenoxy)-3-((R)-8-(quinolin-6-ylsulfonyl)-1-oxa-8-azaspiro[4.5]decan-3-ylamino)propan-2-ol |
| 240 | 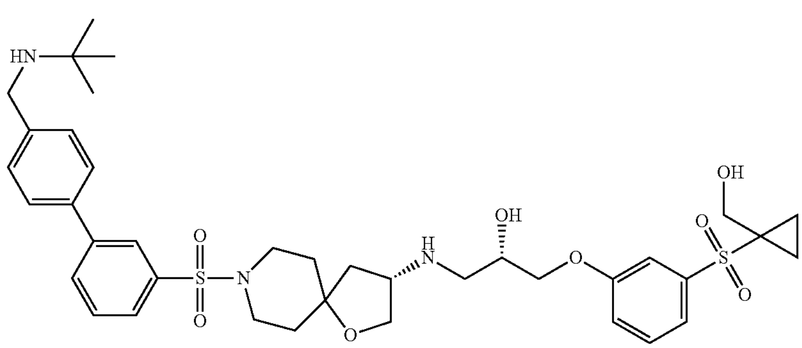 [SMILES: CC(C)(C)NCc1ccc(-c2cccc(S(=O)(=O)N3CCC4(CC3)C[C@H](NC[C@H](O)COc3cccc(S(=O)(=O)C5(CO)CC5)c3)CO4)c2)cc1] | (S)-1-((S)-8-(4'-((tert-butylamino)methyl)biphenyl-3-ylsulfonyl)-1-oxa-8-azaspiro[4.5]decan-3-ylamino)-3-(3-(1-(hydroxymethyl)cyclopropylsulfonyl)phenoxy)propan-2-ol |

TABLE A-continued

| Cmpd No. | Chemical Structure | Chemical Name |
|---|---|---|
| 241 | 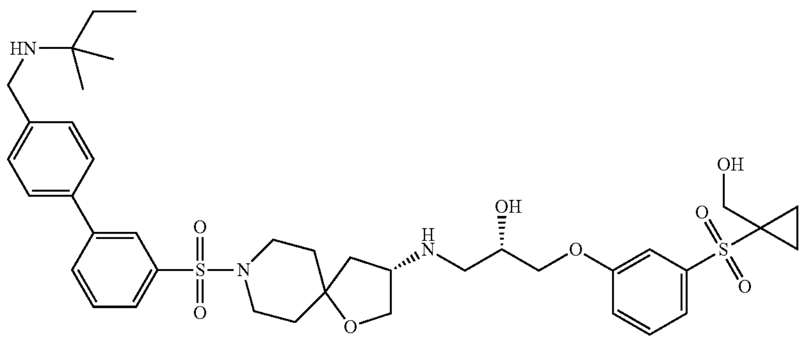 [SMILES: CCC(C)(C)NCc1ccc(-c2cccc(S(=O)(=O)N3CCC4(CC3)C[C@H](NC[C@H](O)COc3cccc(S(=O)(=O)C5(CO)CC5)c3)CO4)c2)cc1] | (S)-1-(3-(1-(hydroxymethyl)cyclopropylsulfonyl)phenoxy)-3-((S)-8-(4'-((tert-pentylamino)methyl)biphenyl-3-ylsulfonyl)-1-oxa-8-azaspiro[4.5]decan-3-ylamino)propan-2-ol |
| 243 | 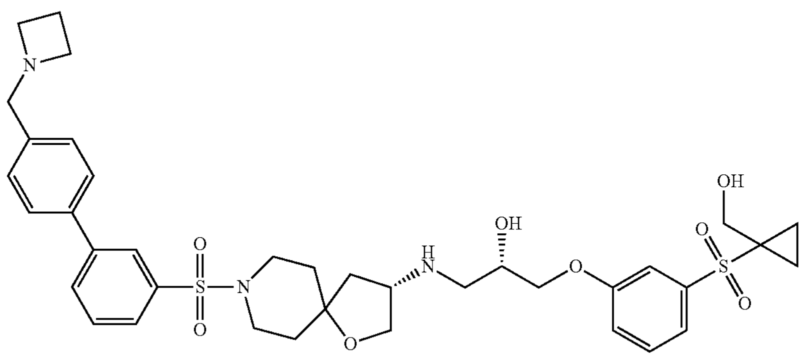 [SMILES: O=S(=O)(c1cccc(-c2ccc(CN3CCC3)cc2)c1)N1CCC2(CC1)C[C@H](NC[C@H](O)COc1cccc(S(=O)(=O)C3(CO)CC3)c1)CO2] | (S)-1-((S)-8-(4'-(azetidin-1-ylmethyl)biphenyl-3-ylsulfonyl)-1-oxa-8-azaspiro[4.5]decan-3-ylamino)-3-(3-(1-(hydroxymethyl)cyclopropylsulfonyl)phenoxy)propan-2-ol |
| 244 | 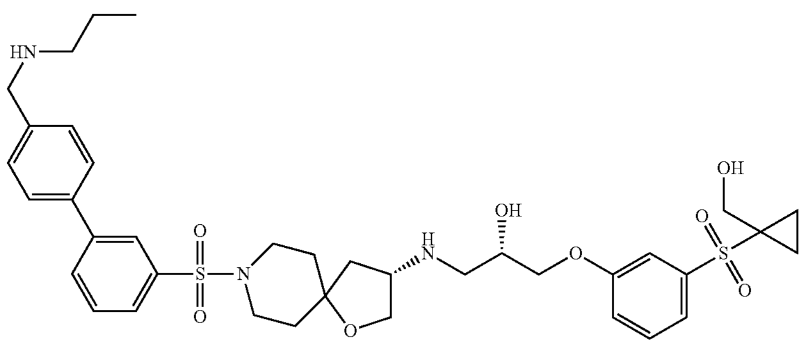 [SMILES: CCCNCc1ccc(-c2cccc(S(=O)(=O)N3CCC4(CC3)C[C@H](NC[C@H](O)COc3cccc(S(=O)(=O)C5(CO)CC5)c3)CO4)c2)cc1] | (S)-1-(3-(1-(hydroxymethyl)cyclopropylsulfonyl)phenoxy)-3-((S)-8-(4'-((propylamino)methyl)biphenyl-3-ylsulfonyl)-1-oxa-8-azaspiro[4.5]decan-3-ylamino)propan-2-ol |
| 245 | 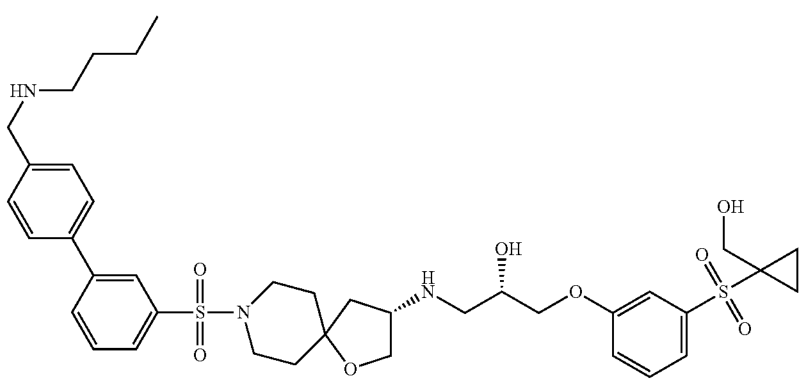 [SMILES: CCCCNCc1ccc(-c2cccc(S(=O)(=O)N3CCC4(CC3)C[C@H](NC[C@H](O)COc3cccc(S(=O)(=O)C5(CO)CC5)c3)CO4)c2)cc1] | (S)-1-((S)-8-(4'-((butylamino)methyl)biphenyl-3-ylsulfonyl)-1-oxa-8-azaspiro[4.5]decan-3-ylamino)-3-(3-(1-(hydroxymethyl)cyclopropylsulfonyl)phenoxy)propan-2-ol |

TABLE A-continued

| Cmpd No. | Chemical Structure | Chemical Name |
|---|---|---|
| 247 | 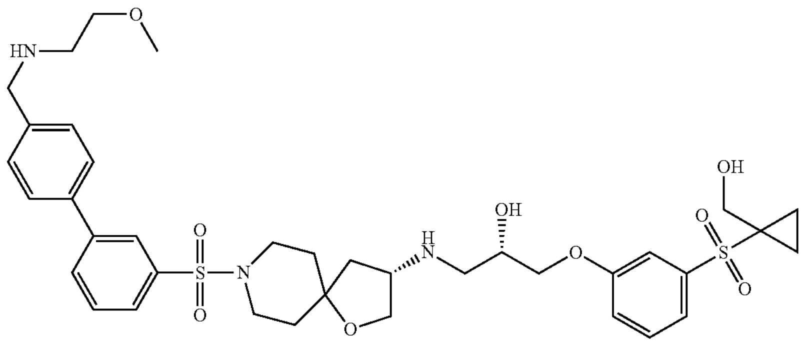 [SMILES: COCCNCc1ccc(-c2cccc(S(=O)(=O)N3CCC4(CC3)C[C@H](NC[C@H](O)COc3cccc(S(=O)(=O)C5(CO)CC5)c3)CO4)c2)cc1] | (S)-1-(3-(1-(hydroxymethyl)cyclopropylsulfonyl)phenoxy)-3-((S)-8-(4'-((2-methoxyethylamino)methyl)biphenyl-3-ylsulfonyl)-1-oxa-8-azaspiro[4.5]decan-3-ylamino)propan-2-ol |
| 296 | 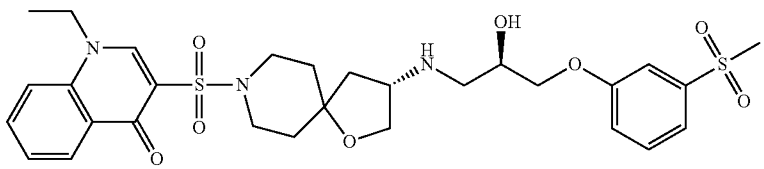 [SMILES: CCn1cc(S(=O)(=O)N2CCC3(CC2)C[C@H](NC[C@@H](O)COc2cccc(S(C)(=O)=O)c2)CO3)c(=O)c2ccccc21] | 1-ethyl-3-((S)-3-((R)-2-hydroxy-3-(3-(methylsulfonyl)phenoxy)propylamino)-1-oxa-8-azaspiro[4.5]decan-8-ylsulfonyl)quinolin-4(1H)-one |
| 297 | 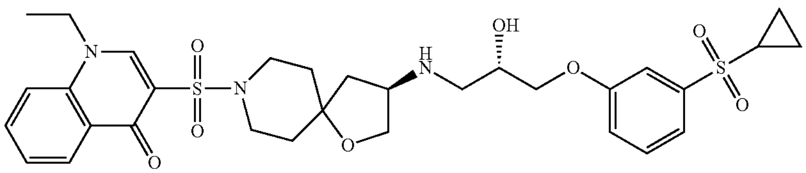 [SMILES: CCn1cc(S(=O)(=O)N2CCC3(CC2)C[C@@H](NC[C@H](O)COc2cccc(S(=O)(=O)C4CC4)c2)CO3)c(=O)c2ccccc21] | 3-((R)-3-((S)-3-(3-(cyclopropylsulfonyl)phenoxy)-2-hydroxypropylamino)-1-oxa-8-azaspiro[4.5]decan-8-ylsulfonyl)-1-ethylquinolin-4(1H)-one |
| 300 | 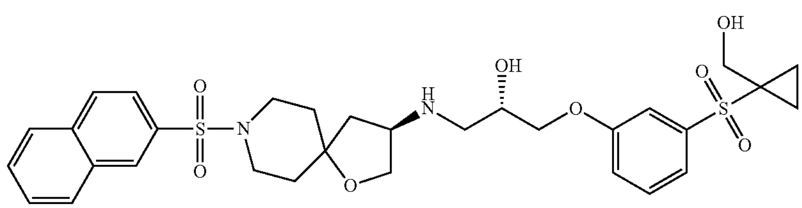 [SMILES: O=S(=O)(c1ccc2ccccc2c1)N1CCC2(CC1)C[C@@H](NC[C@H](O)COc1cccc(S(=O)(=O)C3(CO)CC3)c1)CO2] | (S)-1-(3-(1-(hydroxymethyl)cyclopropylsulfonyl)phenoxy)-3-((R)-8-(naphthalen-2-ylsulfonyl)-1-oxa-8-azaspiro[4.5]decan-3-ylamino)propan-2-ol |
| 309 | 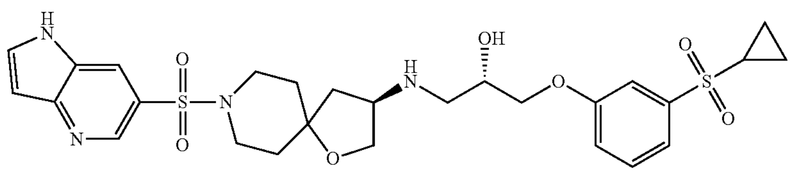 [SMILES: O=S(=O)(c1cccc(OC[C@@H](O)CN[C@H]2COC3(CCN(S(=O)(=O)c4cnc5cc[nH]c5c4)CC3)C2)c1)C1CC1] | (S)-1-((R)-8-(1H-pyrrolo[3,2-b]pyridin-6-ylsulfonyl)-1-oxa-8-azaspiro[4.5]decan-3-ylamino)-3-(3-(cyclopropylsulfonyl)phenoxy)propan-2-ol |
| 310 | 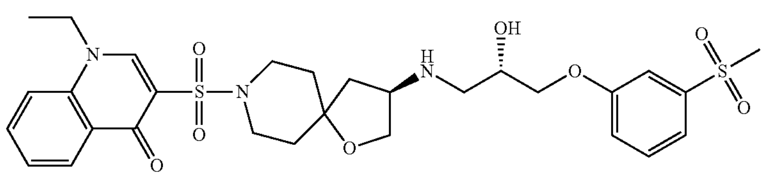 [SMILES: CCn1cc(S(=O)(=O)N2CCC3(CC2)C[C@@H](NC[C@H](O)COc2cccc(S(C)(=O)=O)c2)CO3)c(=O)c2ccccc21] | 1-ethyl-3-((R)-3-((S)-2-hydroxy-3-(3-(methylsulfonyl)phenoxy)propylamino)-1-oxa-8-azaspiro[4.5]decan-8-ylsulfonyl)quinolin-4(1H)-one |
| 320 | 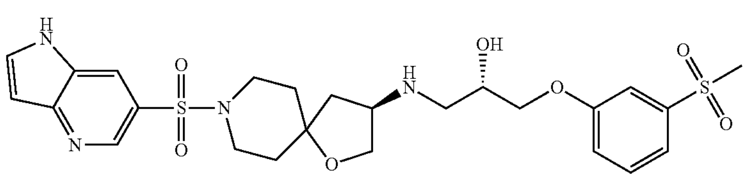 [SMILES: CS(=O)(=O)c1cccc(OC[C@@H](O)CN[C@H]2COC3(CCN(S(=O)(=O)c4cnc5cc[nH]c5c4)CC3)C2)c1] | (S)-1-((R)-8-(1H-pyrrolo[3,2-b]pyridin-6-ylsulfonyl)-1-oxa-8-aaspiro[4.5]decan-3-ylamino)-3-(3-(methylsulfonyl)phenoxy)propan-2-ol |

TABLE A-continued

| Cmpd No. | Chemical Structure | Chemical Name |
|---|---|---|
| 321 | 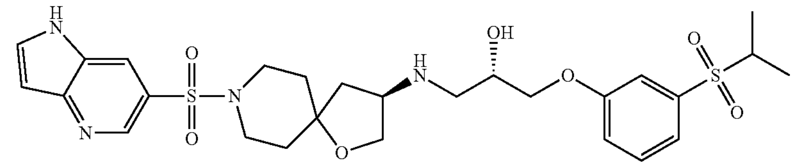 [SMILES: CC(C)S(=O)(=O)c1cccc(OC[C@@H](O)CN[C@H]2COC3(CCN(S(=O)(=O)c4cnc5cc[nH]c5c4)CC3)C2)c1] | (S)-1-((R)-8-(1H-pyrrolo[3,2-b]pyridin-6-ylsulfonyl)-1-oxa-8-azaspiro[4.5]decan-3-ylamino)-3-(3-(isopropylsulfonyl)phenoxy)propan-2-ol |
| 322 | 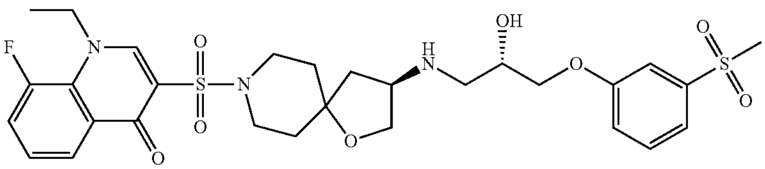 [SMILES: CCn1cc(S(=O)(=O)N2CCC3(CC2)C[C@@H](NC[C@H](O)COc2cccc(S(C)(=O)=O)c2)CO3)c(=O)c2cccc(F)c21] | 1-ethyl-8-fluoro-3-((R)-3-((S)-2-hydroxy-3-(3-(methylsulfonyl)phenoxy)propylamino)-1-oxa-8-azaspiro[4.5]decan-8-ylsulfonyl)quinolin-4(1H)-one |
| 326 | 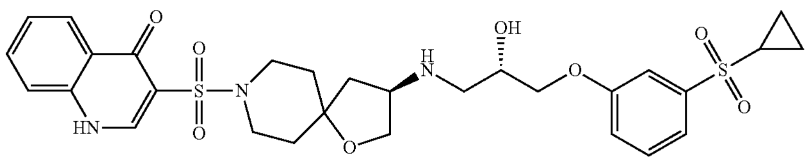 [SMILES: O=c1c(S(=O)(=O)N2CCC3(CC2)C[C@@H](NC[C@H](O)COc2cccc(S(=O)(=O)C4CC4)c2)CO3)c[nH]c2ccccc12] | 3-((R)-3-((S)-3-(3-(cyclopropylsulfonyl)pheonxy)-2-hydroxypropylamino)-1-oxa-8-azaspiro[4.5]decan-8-ylsulfonyl)quinolin-4(1H)-one |
| 327 | 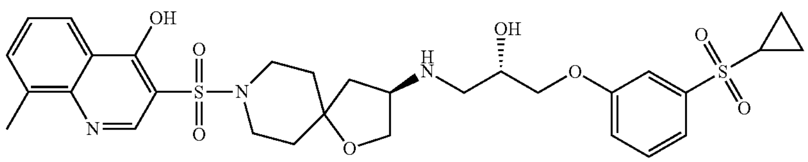 [SMILES: Cc1cccc2c(O)c(S(=O)(=O)N3CCC4(CC3)C[C@@H](NC[C@H](O)COc3cccc(S(=O)(=O)C5CC5)c3)CO4)cnc12] | 3-((R)-3-((S)-3-(3-(cyclopropylsulfonyl)pheonxy)-2-hydroxypropylamino)-1-oxa-8-aaspiro[4.5]decan-8-ylsulfonyl)-8-methylquinolin-4-ol |
| 329 | 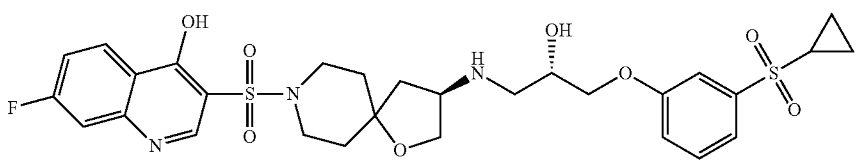 [SMILES: O=S(=O)(c1cccc(OC[C@@H](O)CN[C@H]2COC3(CCN(S(=O)(=O)c4cnc5cc(F)ccc5c4O)CC3)C2)c1)C1CC1] | 3-((R)-3-((S)-3-(3-(cyclopropylsulfonyl)phenoxy)-2-hydorxypropylamino)-1-oxa-8-azaspiro[4.5]decan-8-ylsulfonyl)-7-fluoroquinolin-4-ol |
| 331 | 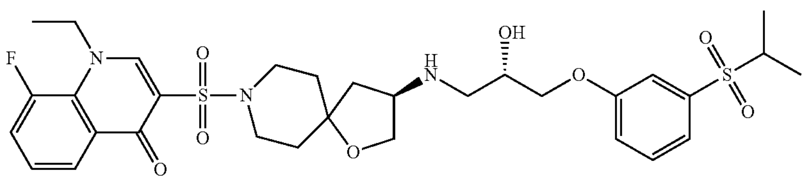 [SMILES: CCn1cc(S(=O)(=O)N2CCC3(CC2)C[C@@H](NC[C@H](O)COc2cccc(S(=O)(=O)C(C)C)c2)CO3)c(=O)c2cccc(F)c21] | 1-ethyl-8-fluoro-3-((R)-3-((S)-2-hydroxy-3-(3-(isopropylsulfonyl)phenoxy)propylamino)-1-oxa-8-azaspiro[4.5]decan-8-ylsulfonyl)quinolin-4(1H)-one |

Some embodiments of the present invention include every combination of one or more compounds and pharmaceutically acceptable salts, solvates, and hydrates thereof selected from the following group, wherein the Compound Number in bold directly preceding the chemical name is used elsewhere in this disclosure:

Compound 5: (2S)-1-(3-(2-hydroxyethylsulfonyl)phenoxy)-3-(8-(naphthalen-2-ylsulfonyl)-1-oxa-8-azaspiro[4.5]decan-3-ylamino)propan-2-ol; Compound 88: (S)-1-(3-(2-hydroxyethylsulfonyl)phenoxy)-3-((R)-8-(quinolin-3-ylsulfonyl)-1-oxa-8-azaspiro[4.5]decan-3-ylamino)propan-2-ol; Compound 123: 2-(3-((S)-2-hydroxy-3-((R)-8-(quinolin-3-ylsulfonyl)-1-oxa-8-azaspiro[4.5]decan-3-ylamino)propoxy)phenylsulfonyl)acetamide; Compound 136: (S)-1-(3-(1-(hydroxymethyl)cyclopropylsulfonyl)phenoxy)-3-((R)-8-(quinolin-3-ylsulfonyl)-1-oxa-8-azaspiro[4.5]decan-3-ylamino)propan-2-ol; Compound 154: (S)-1-(3-(cyclopropylsulfonyl)phenoxy)-3-((R)-8-(1-methyl-2,3-dihydro-1H-pyrido[2,3-b][1,4]oxazin-7-ylsulfonyl)-1-oxa-8-azaspiro[4.5]decan-3-ylamino)propan-2-ol; Compound 161: (S)-1-((R)-8-(4'-(aminomethyl)-4-ethoxybiphenyl-3-ylsulfonyl)-1-oxa-8-azaspiro[4.5]decan-3-ylamino)-3-(3-(1,1-difluoro-2-hydroxyethylsulfonyl)phenoxy)propan-2-ol; Compound 163: (S)-1-((S)-8-(4'-(aminomethyl)-4-ethoxybiphenyl-3-ylsulfonyl)-1-oxa-8-azaspiro[4.5]decan-3-ylamino)-3-(3-(1-(hydroxymethyl)cyclopropylsulfonyl)phenoxy)propan-2-ol; Compound 169: (S)-1-((R)-8-(4'-(aminomethyl)-4-fluorobiphenyl-3-ylsulfonyl)-1-oxa-8-azaspiro[4.5]decan-3-ylamino)-3-(3-(1-(hydroxymethyl)cyclopropylsulfonyl)phenoxy)propan-2-ol; Compound 199: (S)-1-((R)-8-(4'-(1-aminocyclopropyl)-6-methoxybiphenyl-3-ylsulfonyl)-1-oxa-8-azaspiro[4.5]decan-3-ylamino)-3-(3-(1-(hydroxymethyl)cyclopropylsulfonyl)phenoxy)propan-2-ol; Compound 210: (S)-1-((S)-8-(4'-(2-aminoethyl)biphenyl-3-ylsulfonyl)-1-oxa-8-azaspiro[4.5]decan-3-ylamino)-3-(3-(1,1-difluoro-2-hydroxyethylsulfonyl)

phenoxy)propan-2-ol; Compound 211: (S)-1-((S)-8-(4'-(2-aminoethyl)biphenyl-3-ylsulfonyl)-1-oxa-8-azaspiro[4.5]decan-3-ylamino)-3-(3-(1-(hydroxymethyl)cyclopropylsulfonyl)phenoxy)propan-2-ol; Compound 217: (S)-1-((R)-8-(4'-(1-aminocyclopropyl)-6-fluorobiphenyl-3-ylsulfonyl)-1-oxa-8-azaspiro[4.5]decan-3-ylamino)-3-(3-(1-(hydroxymethyl)cyclopropylsulfonyl)phenoxy)propan-2-ol; Compound 220: (S)-1-((S)-8-(4'-(aminomethyl)-4-ethoxy-3'-fluorobiphenyl-3-ylsulfonyl)-1-oxa-8-azaspiro[4.5]decan-3-ylamino)-3-(3-(1-(hydroxymethyl)cyclopropylsulfonyl)phenoxy)propan-2-ol; Compound 225: (S)-1-((S)-8-(4'-(1-aminocyclopropyl)-6-methoxybiphenyl-3-ylsulfonyl)-1-oxa-8-azaspiro[4.5]decan-3-ylamino)-3-(3-(1-(hydroxymethyl)cyclopropylsulfonyl)phenoxy)propan-2-ol; Compound 227: (S)-1-((S)-8-(4'-(aminomethyl)-6-methoxybiphenyl-3-ylsulfonyl)-1-oxa-8-azaspiro[4.5]decan-3-ylamino)-3-(3-(cyclopropylsulfonyl)phenoxy)propan-2-ol; Compound 229: (S)-1-((S)-8-(4'-(aminomethyl)-5-methoxybiphenyl-3-ylsulfonyl)-1-oxa-8-azaspiro[4.5]decan-3-ylamino)-3-(3-(cyclopropylsulfonyl)phenoxy)propan-2-ol; Compound 230: (S)-1-((S)-8-(4'-(aminomethyl)-4-ethoxybiphenyl-3-ylsulfonyl)-1-oxa-8-azaspiro[4.5]decan-3-ylamino)-3-(3-(methoxymethylsulfonyl)phenoxy)propan-2-ol; Compound 232: (S)-1-((S)-8-(4'-(aminomethyl)-4-ethoxybiphenyl-3-ylsulfonyl)-1-oxa-8-azaspiro[4.5]decan-3-ylamino)-3-(3-(isopropylsulfonyl)phenoxy)propan-2-ol; Compound 234: (2S)-1-(3-(1-fluoroethylsulfonyl)phenoxy)-3-((R)-8-(quinolin-6-ylsulfonyl)-1-oxa-8-azaspiro[4.5]decan-3-ylamino)propan-2-ol; Compound 240: (S)-1-((S)-8-(4'-((tert-butylamino)methyl)biphenyl-3-ylsulfonyl)-1-oxa-8-azaspiro[4.5]decan-3-ylamino)-3-(3-(1-(hydroxymethyl)cyclopropylsulfonyl)phenoxy)propan-2-ol; Compound 241: (S)-1-(3-(1-(hydroxymethyl)cyclopropylsulfonyl)phenoxy)-3-((S)-8-(4'-((tert-pentylamino)methyl)biphenyl-3-ylsulfonyl)-1-oxa-8-azaspiro[4.5]decan-3-ylamino)propan-2-ol; Compound 243: (S)-1-((S)-8-(4'-(azetidin-1-ylmethyl)biphenyl-3-ylsulfonyl)-1-oxa-8-azaspiro[4.5]decan-3-ylamino)-3-(3-(1-(hydroxymethyl)cyclopropylsulfonyl)phenoxy)propan-2-ol; Compound 244: (S)-1-(3-(1-(hydroxymethyl)cyclopropylsulfonyl)phenoxy)-3-((S)-8-(4'-((propylamino)methyl)biphenyl-3-ylsulfonyl)-1-oxa-8-azaspiro[4.5]decan-3-ylamino)propan-2-ol; Compound 245: (S)-1-((S)-8-(4'-((butylamino)methyl)biphenyl-3-ylsulfonyl)-1-oxa-8-azaspiro[4.5]decan-3-ylamino)-3-(3-(1-(hydroxymethyl)cyclopropylsulfonyl)phenoxy)propan-2-ol; Compound 247: (S)-1-(3-(1-(hydroxymethyl)cyclopropylsulfonyl)phenoxy)-3-((S)-8-(4'-((2-methoxyethylamino)methyl)biphenyl-3-ylsulfonyl)-1-oxa-8-azaspiro[4.5]decan-3-ylamino)propan-2-ol; Compound 296: 1-ethyl-3-((S)-3-((R)-2-hydroxy-3-(3-(methylsulfonyl)phenoxy)propylamino)-1-oxa-8-azaspiro[4.5]decan-8-ylsulfonyl)quinolin-4(1H)-one; Compound 297: 3-((R)-3-((S)-3-(3-(cyclopropylsulfonyl)phenoxy)-2-hydroxypropylamino)-1-oxa-8-azaspiro[4.5]decan-8-ylsulfonyl)-1-ethylquinolin-4(1H)-one; Compound 300: (S)-1-(3-(1-(hydroxymethyl)cyclopropylsulfonyl)phenoxy)-3-((R)-8-(naphthalen-2-ylsulfonyl)-1-oxa-8-azaspiro[4.5]decan-3-ylamino)propan-2-ol; Compound 309: (S)-1-((R)-8-(1H-pyrrolo[3,2-b]pyridin-6-ylsulfonyl)-1-oxa-8-azaspiro[4.5]decan-3-ylamino)-3-(3-(cyclopropylsulfonyl)phenoxy)propan-2-ol; Compound 310: 1-ethyl-3-((R)-3-((S)-2-hydroxy-3-(3-(methylsulfonyl)phenoxy)propylamino)-1-oxa-8-azaspiro[4.5]decan-8-ylsulfonyl)quinolin-4(1H)-one; Compound 320: (S)-1-((R)-8-(1H-pyrrolo[3,2-b]pyridin-6-ylsulfonyl)-1-oxa-8-azaspiro[4.5]decan-3-ylamino)-3-(3-(methylsulfonyl)phenoxy)propan-2-ol; Compound 321: (S)-1-((R)-8-(1H-pyrrolo[3,2-b]pyridin-6-ylsulfonyl)-1-oxa-8-azaspiro[4.5]decan-3-ylamino)-3-(3-(isopropylsulfonyl)phenoxy)propan-2-ol; Compound 322: 1-ethyl-8-fluoro-3-((R)-3-((S)-2-hydroxy-3-(3-(methylsulfonyl)phenoxy)propylamino)-1-oxa-8-azaspiro[4.5]decan-8-ylsulfonyl)quinolin-4(1H)-one; Compound 326: 3-((R)-3-((S)-3-(3-(cyclopropylsulfonyl)phenoxy)-2-hydroxypropylamino)-1-oxa-8-azaspiro[4.5]decan-8-ylsulfonyl)quinolin-4(1H)-one; Compound 327: 3-((R)-3-((S)-3-(3-(cyclopropylsulfonyl)phenoxy)-2-hydroxypropylamino)-1-oxa-8-azaspiro[4.5]decan-8-ylsulfonyl)-8-methylquinolin-4-ol; Compound 329: 3-((R)-3-((S)-3-(3-(cyclopropylsulfonyl)phenoxy)-2-hydroxypropylamino)-1-oxa-8-azaspiro[4.5]decan-8-ylsulfonyl)-7-fluoroquinolin-4-ol; and Compound 331: 1-ethyl-8-fluoro-3-((R)-3-((S)-2-hydroxy-3-(3-(isopropylsulfonyl)phenoxy)propylamino)-1-oxa-8-azaspiro[4.5]decan-8-ylsulfonyl)quinolin-4(1H)-one.

Some embodiments of the present invention include every combination of one or more compounds and pharmaceutically acceptable salts, solvates, and hydrates thereof selected from the following group, wherein the Compound Number in bold directly preceding the chemical name is used elsewhere in this disclosure:

Compound 1: (2S)-1-(3-(methylsulfonyl)phenoxy)-3-(8-(naphthalen-2-ylsulfonyl)-1-oxa-8-azaspiro[4.5]decan-3-ylamino)propan-2-ol; Compound 2: (2R)-1-(3-(methylsulfonyl)phenoxy)-3-(8-(naphthalen-2-ylsulfonyl)-1-oxa-8-azaspiro[4.5]decan-3-ylamino)propan-2-ol; Compound 3: (S)-1-(3-(methylsulfonyl)phenoxy)-3-((R)-8-(naphthalen-2-ylsulfonyl)-1-oxa-8-azaspiro[4.5]decan-3-ylamino)propan-2-ol; Compound 4: (S)-1-(3-(methylsulfonyl)phenoxy)-3-((S)-8-(naphthalen-2-ylsulfonyl)-1-oxa-8-azaspiro[4.5]decan-3-ylamino)propan-2-ol; Compound 6: (2S)-1-(8-(naphthalen-2-ylsulfonyl)-1-oxa-8-azaspiro[4.5]decan-3-ylamino)-3-(3-(propylsulfonyl)phenoxy)propan-2-ol; Compound 7: (2S)-1-(3-(cyclopropylmethylsulfonyl)phenoxy)-3-(8-(naphthalen-2-ylsulfonyl)-1-oxa-8-azaspiro[4.5]decan-3-ylamino)propan-2-ol; Compound 8: (2S)-1-(3-(isopropylsulfonyl)phenoxy)-3-(8-(naphthalen-2-ylsulfonyl)-1-oxa-8-azaspiro[4.5]decan-3-ylamino)propan-2-ol; Compound 9: (2S)-1-(8-(naphthalen-2-ylsulfonyl)-1-oxa-8-azaspiro[4.5]decan-3-ylamino)-3-(3-(3,3,3-trifluoropropylsulfonyl)phenoxy)propan-2-ol; Compound 10: (2S)-1-(3-(isobutylsulfonyl)phenoxy)-3-(8-(naphthalen-2-ylsulfonyl)-1-oxa-8-azaspiro[4.5]decan-3-ylamino)propan-2-ol; Compound 11: (2S)-1-(3-(isopentylsulfonyl)phenoxy)-3-(8-(naphthalen-2-ylsulfonyl)-1-oxa-8-azaspiro[4.5]decan-3-ylamino)propan-2-ol; Compound 12: 2-(34(2S)-2-hydroxy-3-(8-(naphthalen-2-ylsulfonyl)-1-oxa-8-azaspiro[4.5]decan-3-ylamino)propoxy)phenylsulfonyl)acetonitrile; Compound 13: (2S)-1-(3-(cyclobutylmethylsulfonyl)phenoxy)-3-(8-(naphthalen-2-ylsulfonyl)-1-oxa-8-azaspiro[4.5]decan-3-ylamino)propan-2-ol; Compound 14: (2S)-1-(8-(naphthalen-2-ylsulfonyl)-1-oxa-8-azaspiro[4.5]decan-3-ylamino)-3-(3-(4,4,4-trifluorobutylsulfonyl)phenoxy)propan-2-ol; Compound 15: (2S)-1-(3-(ethylsulfonyl)phenoxy)-3-(8-(naphthalen-2-ylsulfonyl)-1-oxa-8-azaspiro[4.5]decan-3-ylamino)propan-2-ol; Compound 16: (2S)-1-(3-(cyclohexylmethylsulfonyl)phenoxy)-3-(8-(naphthalen-2-ylsulfonyl)-1-oxa-8-azaspiro[4.5]decan-3-ylamino)propan-2-ol; Compound 17: (2S)-1-(3-((2,2-difluorocyclopropyl)methylsulfonyl)phenoxy)-3-(8-(naphthalen-2-ylsulfonyl)-1-oxa-8-azaspiro[4.5]decan-3-ylamino)propan-2-ol; Compound 18: (2S)-1-(3-(cyclobutylsulfonyl)phenoxy)-3-(8-(naphthalen-2-ylsulfonyl)-1-oxa-8-azaspiro[4.5]decan-3-ylamino)propan-2-ol; Compound 19: (2S)-1-(3-(cyclopentylsulfonyl)phenoxy)-3-(8-(naphthalen-2-ylsulfonyl)-1-oxa-8-azaspiro

[4.5]decan-3-ylamino)propan-2-ol; Compound 20: (2S)-1-(3-(benzylsulfonyl)phenoxy)-3-(8-(naphthalen-2-ylsulfonyl)-1-oxa-8-azaspiro[4.5]decan-3-ylamino)propan-2-ol; Compound 21: (2S)-1-(3-(azetidin-3-ylsulfonyl)phenoxy)-3-(8-(naphthalen-2-ylsulfonyl)-1-oxa-8-azaspiro[4.5]decan-3-ylamino)propan-2-ol; Compound 22: (2S)-1-(3-(2-aminoethylsulfonyl)phenoxy)-3-(8-(naphthalen-2-ylsulfonyl)-1-oxa-8-azaspiro[4.5]decan-3-ylamino)propan-2-ol; Compound 23: (R)-1-(3-(methylsulfonyl)phenoxy)-3-((R)-8-(naphthalen-2-ylsulfonyl)-1-oxa-8-azaspiro[4.5]decan-3-ylamino)propan-2-ol; Compound 24: (2S)-1-(8-(naphthalen-2-ylsulfonyl)-1-oxa-8-azaspiro[4.5]decan-3-ylamino)-3-(3-(oxetan-3-ylsulfonyl)phenoxy)propan-2-ol; Compound 25: (2S)-1-(3-(sec-butylsulfonyl)phenoxy)-3-(8-(naphthalen-2-ylsulfonyl)-1-oxa-8-azaspiro[4.5]decan-3-ylamino)propan-2-ol; Compound 26: (S)-1-(3-(ethylsulfonyl)phenoxy)-3-((R)-8-(naphthalen-2-ylsulfonyl)-1-oxa-8-azaspiro[4.5]decan-3-ylamino)propan-2-ol; Compound 27: (S)-1-(3-(ethylsulfonyl)phenoxy)-3-((S)-8-(naphthalen-2-ylsulfonyl)-1-oxa-8-azaspiro[4.5]decan-3-ylamino)propan-2-ol; Compound 28: (2S)-1-(8-(chroman-6-ylsulfonyl)-1-oxa-8-azaspiro[4.5]decan-3-ylamino)-3-(3-(methylsulfonyl)phenoxy)propan-2-ol; Compound 29: (2S)-1-(3-(methylsulfonyl)phenoxy)-3-(8-(5,6,7,8-tetrahydronaphthalen-2-ylsulfonyl)-1-oxa-8-azaspiro[4.5]decan-3-ylamino)propan-2-ol; Compound 30: (2S)-1-(8-(7-chlorobenzo[c][1,2,5]oxadiazol-4-ylsulfonyl)-1-oxa-8-azaspiro[4.5]decan-3-ylamino)-3-(3-(methylsulfonyl)phenoxy)propan-2-ol; Compound 31: (2S)-1-(8-(3-chlorophenylsulfonyl)-1-oxa-8-azaspiro[4.5]decan-3-ylamino)-3-(3-(methylsulfonyl)phenoxy)propan-2-ol; Compound 32: (2S)-1-(8-(4-methyl-3,4-dihydro-2H-benzo[b][1,4]oxazin-6-ylsulfonyl)-1-oxa-8-azaspiro[4.5]decan-3-ylamino)-3-(3-(methylsulfonyl)phenoxy)propan-2-ol; Compound 33: (R)-1-(3-(methylsulfonyl)phenoxy)-3-((S)-8-(naphthalen-2-ylsulfonyl)-1-oxa-8-azaspiro[4.5]decan-3-ylamino)propan-2-ol; Compound 34: (S)-1-(3-(2-hydroxyethylsulfonyl)phenoxy)-3-((S)-8-(naphthalen-2-ylsulfonyl)-1-oxa-8-azaspiro[4.5]decan-3-ylamino)propan-2-ol; Compound 35: (S)-1-(3-(2-hydroxyethylsulfonyl)phenoxy)-3-((R)-8-(naphthalen-2-ylsulfonyl)-1-oxa-8-azaspiro[4.5]decan-3-ylamino)propan-2-ol; Compound 36: (2S)-1-(8-(3-(1-ethyl-1H-pyrazol-4-yl)phenylsulfonyl)-1-oxa-8-azaspiro[4.5]decan-3-ylamino)-3-(3-(methylsulfonyl)phenoxy)propan-2-ol; Compound 37: (2S)-1-(8-(3-(1H-pyrazol-4-yl)phenylsulfonyl)-1-oxa-8-azaspiro[4.5]decan-3-ylamino)-3-(3-(methylsulfonyl)phenoxy)propan-2-ol; Compound 38: (2S)-1-(3-(methylsulfonyl)phenoxy)-3-(8-(3-(1-propyl-1H-pyrazol-4-yl)phenylsulfonyl)-1-oxa-8-azaspiro[4.5]decan-3-ylamino)propan-2-ol; Compound 39: (2S)-1-(8-(3-(1-cyclopropyl-1H-pyrazol-4-yl)phenylsulfonyl)-1-oxa-8-azaspiro[4.5]decan-3-ylamino)-3-(3-(methylsulfonyl)phenoxy)propan-2-ol; Compound 40: (2S)-1-(8-(3-(1-methyl-1H-pyrazol-4-yl)phenylsulfonyl)-1-oxa-8-azaspiro[4.5]decan-3-ylamino)-3-(3-(methylsulfonyl)phenoxy)propan-2-ol; Compound 41: (2S)-1-(8-(4'-(aminomethyl)biphenyl-3-ylsulfonyl)-1-oxa-8-azaspiro[4.5]decan-3-ylamino)-3-(3-(methylsulfonyl)phenoxy)propan-2-ol; Compound 42: 3'-(3-((S)-2-hydroxy-3-(3-(methylsulfonyl)phenoxy)propylamino)-1-oxa-8-azaspiro[4.5]decan-8-ylsulfonyl)biphenyl-4-sulfonamide; Compound 43: (2S)-1-(3-(methylsulfonyl)phenoxy)-3-(8-(3-(pyridin-4-yl)phenylsulfonyl)-1-oxa-8-azaspiro[4.5]decan-3-ylamino)propan-2-ol; Compound 44: (2S)-1-(8-(3-(2-methylpyridin-4-yl)phenylsulfonyl)-1-oxa-8-azaspiro[4.5]decan-3-ylamino)-3-(3-(methylsulfonyl)phenoxy)propan-2-ol; Compound 45: (2S)-1-(3-(methylsulfonyl)phenoxy)-3-(8-(3-(pyridin-2-yl)phenylsulfonyl)-1-oxa-8-azaspiro[4.5]decan-3-ylamino)propan-2-ol; Compound 46: (2S)-1-(3-(methylsulfonyl)phenoxy)-3-(8-(pyridin-3-ylsulfonyl)-1-oxa-8-azaspiro[4.5]decan-3-ylamino)propan-2-ol; Compound 47: (2S)-1-(3-(methylsulfonyl)phenoxy)-3-(8-(phenylsulfonyl)-1-oxa-8-azaspiro[4.5]decan-3-ylamino)propan-2-ol; Compound 48: (2S)-1-(3-(methylsulfonyl)phenoxy)-3-(8-(m-tolylsulfonyl)-1-oxa-8-azaspiro[4.5]decan-3-ylamino)propan-2-ol; Compound 49: (2S)-1-(8-(3-methoxyphenylsulfonyl)-1-oxa-8-azaspiro[4.5]decan-3-ylamino)-3-(3-(methylsulfonyl)phenoxy)propan-2-ol; Compound 50: (2S)-1-(3-(methylsulfonyl)phenoxy)-3-(8-(3-(trifluoromethyl)phenylsulfonyl)-1-oxa-8-azaspiro[4.5]decan-3-ylamino)propan-2-ol; Compound 51: (2S)-1-(3-(methylsulfonyl)phenoxy)-3-(8-(5-phenylthiophen-2-ylsulfonyl)-1-oxa-8-azaspiro[4.5]decan-3-ylamino)propan-2-ol; Compound 52: (2S)-1-(8-(3,5-dimethylisoxazol-4-ylsulfonyl)-1-oxa-8-azaspiro[4.5]decan-3-ylamino)-3-(3-(methylsulfonyl)phenoxy)propan-2-ol; Compound 53: 6-(3-((S)-2-hydroxy-3-(3-(methylsulfonyl)phenoxy)propylamino)-1-oxa-8-azaspiro[4.5]decan-8-ylsulfonyl)-2H-benzo[b][1,4]oxazin-3(4H)-one; Compound 54: (2S)-1-(8-(3-fluorophenylsulfonyl)-1-oxa-8-azaspiro[4.5]decan-3-ylamino)-3-(3-(methylsulfonyl)phenoxy)propan-2-ol; Compound 55: 3-(3-((S)-2-hydroxy-3-(3-(methylsulfonyl)phenoxy)propylamino)-1-oxa-8-azaspiro[4.5]decan-8-ylsulfonyl)benzonitrile; Compound 56: 2-(2-aminothiazol-4-yl)-1-(3-((S)-2-hydroxy-3-(3-(methylsulfonyl)phenoxy)propylamino)-1-oxa-8-azaspiro[4.5]decan-8-yl)ethanone; Compound 57: (3-((S)-2-hydroxy-3-(3-(methylsulfonyl)phenoxy)propylamino)-1-oxa-8-azaspiro[4.5]decan-8-yl)(naphthalen-2-yl)methanone; Compound 58: (2S)-1-(8-(1-ethyl-5-methyl-1H-pyrazol-4-ylsulfonyl)-1-oxa-8-azaspiro[4.5]decan-3-ylamino)-3-(3-(methylsulfonyl)phenoxy)propan-2-ol; Compound 59: (2S)-1-(8-(5-chloronaphthalen-2-ylsulfonyl)-1-oxa-8-azaspiro[4.5]decan-3-ylamino)-3-(3-(methylsulfonyl)phenoxy)propan-2-ol; Compound 60: (2S)-1-(8-(benzofuran-2-ylsulfonyl)-1-oxa-8-azaspiro[4.5]decan-3-ylamino)-3-(3-(methylsulfonyl)phenoxy)propan-2-ol; Compound 61: (2S)-1-(8-(benzofuran-5-ylsulfonyl)-1-oxa-8-azaspiro[4.5]decan-3-ylamino)-3-(3-(methylsulfonyl)phenoxy)propan-2-ol; Compound 62: (2S)-1-(8-(1H-indol-5-ylsulfonyl)-1-oxa-8-azaspiro[4.5]decan-3-ylamino)-3-(3-(methylsulfonyl)phenoxy)propan-2-ol; Compound 63: (2S)-1-(3-(methylsulfonyl)phenoxy)-3-(8-(3-(pyridin-3-yl)phenylsulfonyl)-1-oxa-8-azaspiro[4.5]decan-3-ylamino)propan-2-ol; Compound 64: (3-((S)-2-hydroxy-3-(3-(methylsulfonyl)phenoxy)propylamino)-1-oxa-8-azaspiro[4.5]decan-8-yl)(4-methyl-3,4-dihydro-2H-benzo[b][1,4]oxazin-7-yl)methanone; Compound 65: (3-((S)-2-hydroxy-3-(3-(methylsulfonyl)phenoxy)propylamino)-1-oxa-8-azaspiro[4.5]decan-8-yl)(1H-indol-2-yl)methanone; Compound 66: (3-((S)-2-hydroxy-3-(3-(methylsulfonyl)phenoxy)propylamino)-1-oxa-8-azaspiro[4.5]decan-8-yl)(1H-indol-3-yl)methanone; Compound 67: (3-((S)-2-hydroxy-3-(3-(methylsulfonyl)phenoxy)propylamino)-1-oxa-8-azaspiro[4.5]decan-8-yl)(1H-indol-5-yl)methanone; Compound 68: (3-((S)-2-hydroxy-3-(3-(methylsulfonyl)phenoxy)propylamino)-1-oxa-8-azaspiro[4.5]decan-8-yl)(1H-indol-6-yl)methanone; Compound 69: (2S)-1-(8-(3-bromophenylsulfonyl)-1-oxa-8-azaspiro[4.5]decan-3-ylamino)-3-(3-(methylsulfonyl)phenoxy)propan-2-ol; Compound 70: (2S)-1-(8-(3-(6-aminopyridin-3-yl)phenylsulfonyl)-1-oxa-8-azaspiro[4.5]decan-3-ylamino)-3-(3-(methylsulfonyl)phenoxy)propan-2-ol; Compound 71: (2S)-1-(3-(methylsulfonyl)phenoxy)-3-(8-(3-(pyrimidin-5-yl)phenylsulfonyl)-1-oxa-8-azaspiro[4.5]decan-3-ylamino)

propan-2-ol; Compound 72: (2S)-1-(3-(methylsulfonyl)phenoxy)-3-(8-(pyridin-2-ylsulfonyl)-1-oxa-8-azaspiro[4.5]decan-3-ylamino)propan-2-ol; Compound 73: (2S)-1-(8-(6-chloronaphthalen-2-ylsulfonyl)-1-oxa-8-azaspiro[4.5]decan-3-ylamino)-3-(3-(methylsulfonyl)phenoxy)propan-2-ol; Compound 74: (2S)-1-(8-(2,3-dihydrobenzofuran-5-ylsulfonyl)-1-oxa-8-azaspiro[4.5]decan-3-ylamino)-3-(3-(methylsulfonyl)phenoxy)propan-2-ol; Compound 75: (2S)-1-(3-(methylsulfonyl)phenoxy)-3-(8-(quinolin-6-ylsulfonyl)-1-oxa-8-azaspiro[4.5]decan-3-ylamino)propan-2-ol; Compound 76: (2S)-1-(8-(1H-benzo[d]imidazol-5-ylsulfonyl)-1-oxa-8-azaspiro[4.5]decan-3-ylamino)-3-(3-(methylsulfonyl)phenoxy)propan-2-ol; Compound 77: (2S)-1-(8-(1H-indazol-5-ylsulfonyl)-1-oxa-8-azaspiro[4.5]decan-3-ylamino)-3-(3-(methylsulfonyl)phenoxy)propan-2-ol; Compound 78: (2S)-1-(8-(4'-((methylamino)methyl)biphenyl-3-ylsulfonyl)-1-oxa-8-azaspiro[4.5]decan-3-ylamino)-3-(3-(methylsulfonyl)phenoxy)propan-2-ol; Compound 79: (2S)-1-(8-(4'-((ethylamino)methyl)biphenyl-3-ylsulfonyl)-1-oxa-8-azaspiro[4.5]decan-3-ylamino)-3-(3-(methylsulfonyl)phenoxy)propan-2-ol; Compound 80: (2S)-1-(8-(4'-((isopropylamino)methyl)biphenyl-3-ylsulfonyl)-1-oxa-8-azaspiro[4.5]decan-3-ylamino)-3-(3-(methylsulfonyl)phenoxy)propan-2-ol; Compound 81: (2S)-1-(8-(4'-((isobutylamino)methyl)biphenyl-3-ylsulfonyl)-1-oxa-8-azaspiro[4.5]decan-3-ylamino)-3-(3-(methylsulfonyl)phenoxy)propan-2-ol; Compound 82: (2S)-1-(3-(methylsulfonyl)phenoxy)-3-(8-(4'-((2,2,2-trifluoroethylamino)methyl)biphenyl-3-ylsulfonyl)-1-oxa-8-azaspiro[4.5]decan-3-ylamino)propan-2-ol; Compound 83: (S)-1-((R)-8-(chroman-6-ylsulfonyl)-1-oxa-8-azaspiro[4.5]decan-3-ylamino)-3-(3-(2-hydroxyethylsulfonyl)phenoxy)propan-2-ol; Compound 84: (5)-1-(3-(2-hydroxyethylsulfonyl)phenoxy)-3-((R)-8-(4-methyl-3,4-dihydro-2H-benzo[b][1,4]oxazin-6-ylsulfonyl)-1-oxa-8-azaspiro[4.5]decan-3-ylamino)propan-2-ol; Compound 85: (S)-1-(3-(methylsulfonyl)phenoxy)-3-((S)-8-(quinolin-3-ylsulfonyl)-1-oxa-8-azaspiro[4.5]decan-3-ylamino)propan-2-ol; Compound 86: (2S)-1-(3-(fluoromethylsulfonyl)phenoxy)-3-(8-(naphthalen-2-ylsulfonyl)-1-oxa-8-azaspiro[4.5]decan-3-ylamino)propan-2-ol; Compound 87: (S)-1-((R)-8-(chroman-7-ylsulfonyl)-1-oxa-8-azaspiro[4.5]decan-3-ylamino)-3-(3-(2-hydroxyethylsulfonyl)phenoxy)propan-2-ol; Compound 88: (S)-1-(3-(2-hydroxyethylsulfonyl)phenoxy)-3-((R)-8-(quinolin-3-ylsulfonyl)-1-oxa-8-azaspiro[4.5]decan-3-ylamino)propan-2-ol; Compound 89: (S)-1-((R)-8-(5-(4-(aminomethyl)phenyl)pyridin-3-ylsulfonyl)-1-oxa-8-azaspiro[4.5]decan-3-ylamino)-3-(3-(2-hydroxyethylsulfonyl)phenoxy)propan-2-ol; Compound 90: (S)-1-(3-(2-hydroxyethylsulfonyl)phenoxy)-3-((R)-8-(5-(1-methyl-1H-pyrazol-4-yl)pyridin-3-ylsulfonyl)-1-oxa-8-azaspiro[4.5]decan-3-ylamino)propan-2-ol; Compound 91: (S)-1-((R)-8-(4'-(aminomethyl)biphenyl-3-ylsulfonyl)-1-oxa-8-azaspiro[4.5]decan-3-ylamino)-3-(3-(2-hydroxyethylsulfonyl)phenoxy)propan-2-ol; Compound 92: (S)-1-((R)-8-(quinolin-3-ylsulfonyl)-1-oxa-8-azaspiro[4.5]decan-3-ylamino)-3-(vinylsulfonyl)phenoxy)propan-2-ol; Compound 93: (S)-1-(3-(2-hydroxyethylsulfonyl)phenoxy)-3-((R)-8-(quinolin-6-ylsulfonyl)-1-oxa-8-azaspiro[4.5]decan-3-ylamino)propan-2-ol; Compound 94: (2R)-1-(3-(methylsulfonylmethyl)phenoxy)-3-(8-(naphthalen-2-ylsulfonyl)-1-oxa-8-azaspiro[4.5]decan-3-ylamino)propan-2-ol; Compound 95: (S)-1-(3-(methylsulfonylmethyl)phenoxy)-3-((R)-8-(quinolin-3-ylsulfonyl)-1-oxa-8-azaspiro[4.5]decan-3-ylamino)propan-2-ol; Compound 96: (S)-1-(3-(2-hydroxyethylsulfonyl)phenoxy)-3-((R)-8-(3-(pyridin-4-yl)phenylsulfonyl)-1-oxa-8-azaspiro[4.5]decan-3-ylamino)propan-2-ol; Compound 97: (S)-1-(3-(2-hydroxyethylsulfonyl)phenoxy)-3-((R)-8-(3-(pyridin-3-yl)phenylsulfonyl)-1-oxa-8-azaspiro[4.5]decan-3-ylamino)propan-2-ol; Compound 98: (S)-1-(3-(2-hydroxyethylsulfonyl)phenoxy)-3-((R)-8-(quinolin-7-ylsulfonyl)-1-oxa-8-azaspiro[4.5]decan-3-ylamino)propan-2-ol; Compound 99: (S)-1-(3-(2-hydroxyethylsulfonyl)phenoxy)-3-((R)-8-(4-(pyridin-3-yl)phenylsulfonyl)-1-oxa-8-azaspiro[4.5]decan-3-ylamino)propan-2-ol; Compound 100: (S)-1-(3-(2-hydroxyethylsulfonyl)phenoxy)-3-((R)-8-(3-(pyridin-2-yl)phenylsulfonyl)-1-oxa-8-azaspiro[4.5]decan-3-ylamino)propan-2-ol; Compound 101: (S)-1-(3-(2-hydroxyethylsulfonyl)phenoxy)-3-((R)-8-(4-(pyridin-4-yl)phenylsulfonyl)-1-oxa-8-azaspiro[4.5]decan-3-ylamino)propan-2-ol; Compound 102: (S)-1-(3-(2-hydroxyethylsulfonyl)phenoxy)-3-((R)-8-(4-(pyridin-2-yl)phenylsulfonyl)-1-oxa-8-azaspiro[4.5]decan-3-ylamino)propan-2-ol; Compound 103: (S)-1-((R)-8-(4'-(aminomethyl)biphenyl-4-ylsulfonyl)-1-oxa-8-azaspiro[4.5]decan-3-ylamino)-3-(3-(2-hydroxyethylsulfonyl)phenoxy)propan-2-ol; Compound 104: (S)-1-((R)-8-(1-methyl-2,3-dihydro-1H-pyrido[2,3-b][1,4]oxazin-7-ylsulfonyl)-1-oxa-8-azaspiro[4.5]decan-3-ylamino)-3-(3-(methylsulfonylmethyl)phenoxy)propan-2-ol; Compound 105: (S)-1-(3-(2-hydroxyethylsulfonyl)phenoxy)-3-((R)-8-(isoquinolin-5-ylsulfonyl)-1-oxa-8-azaspiro[4.5]decan-3-ylamino)propan-2-ol; Compound 106: 2-(3-((S)-2-hydroxy-3-((R)-8-(quinolin-3-ylsulfonyl)-1-oxa-8-azaspiro[4.5]decan-3-ylamino)propoxy)phenylsulfonyl)-2-methylpropan-1-ol; Compound 107: (S)-1-(3-(1-(hydroxymethyl)cyclobutylsulfonyl)phenoxy)-3-((R)-8-(quinolin-3-ylsulfonyl)-1-oxa-8-azaspiro[4.5]decan-3-ylamino)propan-2-ol; Compound 108: 2-(3-((S)-2-hydroxy-3-((R)-8-(quinolin-3-ylsulfonyl)-1-oxa-8-azaspiro[4.5]decan-3-ylamino)propoxy)phenylsulfonyl)-2-methylpropanamide; Compound 109: 2-(3-((S)-2-hydroxy-3-((R)-8-(quinolin-6-ylsulfonyl)-1-oxa-8-azaspiro[4.5]decan-3-ylamino)propoxy)phenylsulfonyl)-2-methylpropan-1-ol; Compound 110: (S)-1-(3-(1-(hydroxymethyl)cyclobutylsulfonyl)phenoxy)-3-((R)-8-(quinolin-6-ylsulfonyl)-1-oxa-8-azaspiro[4.5]decan-3-ylamino)propan-2-ol; Compound 111: (S)-1-(3-(methylsulfonyl)phenoxy)-3-((R)-8-(quinolin-6-ylsulfonyl)-1-oxa-8-azaspiro[4.5]decan-3-ylamino)propan-2-ol; Compound 112: (S)-1-(3-(ethylsulfonyl)phenoxy)-3-((R)-8-(quinolin-6-ylsulfonyl)-1-oxa-8-azaspiro[4.5]decan-3-ylamino)propan-2-ol; Compound 113: (S)-1-(3-(isopropylsulfonyl)phenoxy)-3-((R)-8-(quinolin-6-ylsulfonyl)-1-oxa-8-azaspiro[4.5]decan-3-ylamino)propan-2-ol; Compound 114: (S)-1-(3-(cyclobutylsulfonyl)phenoxy)-3-((R)-8-(quinolin-6-ylsulfonyl)-1-oxa-8-azaspiro[4.5]decan-3-ylamino)propan-2-ol; Compound 115: (S)-1-(3-(propylsulfonyl)phenoxy)-3-((R)-8-(quinolin-6-ylsulfonyl)-1-oxa-8-azaspiro[4.5]decan-3-ylamino)propan-2-ol; Compound 116: (S)-1-(3-(isobutylsulfonyl)phenoxy)-3-((R)-8-(quinolin-6-ylsulfonyl)-1-oxa-8-azaspiro[4.5]decan-3-ylamino)propan-2-ol; Compound 117: (S)-1-(3-(cyclopropylmethylsulfonyl)phenoxy)-3-((R)-8-(quinolin-6-ylsulfonyl)-1-oxa-8-azaspiro[4.5]decan-3-ylamino)propan-2-ol; Compound 118: (S)-1-(3-(methylsulfonyl)phenoxy)-3-((R)-8-(quinolin-3-ylsulfonyl)-1-oxa-8-azaspiro[4.5]decan-3-ylamino)propan-2-ol; Compound 119: (S)-1-(3-(isopropylsulfonyl)phenoxy)-3-((R)-8-(quinolin-3-ylsulfonyl)-1-oxa-8-azaspiro[4.5]decan-3-ylamino)propan-2-ol; Compound 120: (5)-1-(3-(2-hydroxyethylsulfonyl)phenoxy)-3-((S)-8-(3-(6-methylpyridin-2-yl)phenylsulfonyl)-1-oxa-8-azaspiro[4.5]decan-3-ylamino propan-2-ol; Compound 121: 3-(3-((S)-2-hydroxy-3-((R)-8-(quinolin-6-ylsulfonyl)-1-oxa-8-azaspiro[4.5]decan-3-ylamino)propoxy)phenylsulfonyl)propan-1-ol; Compound 122: (S)-1-(3-(ethylsulfonyl)phenoxy)-3-((R)-8-(quinolin-3-ylsulfonyl)-1-oxa-8-azaspiro[4.5]decan-3-ylamino)propan-2-ol; Compound 123: 2-(3-((S)-2-hydroxy-3-((R)-8-(quinolin-3-ylsulfonyl)-1-oxa-8-azaspiro[4.5]decan-3-ylamino)propoxy)phenylsulfonyl)acetamide; Compound 124: (S)-1-(3-(isobutylsulfonyl)phenoxy)-3-((R)-8-(quinolin-3-ylsulfonyl)-1-oxa-8-azaspiro[4.5]decan-3-ylamino)propan-2-ol; Compound 125: (S)-1-(3-(2-hydroxyethylsulfonyl)phenoxy)-3-((R)-8-(3-(6-(trifluoromethyl)pyridin-2-yl)phenylsulfonyl)-1-oxa-8-azaspiro[4.5]decan-3-ylamino)propan-2-ol; Compound 126: (S)-1-((R)-8-(3-(3-fluoropyridin-2-yl)phenylsulfonyl)-1-oxa-8-azaspiro[4.5]decan-3-ylamino)-3-(3-(2-hydroxyethylsulfonyl)phenoxy)propan-2-ol; Compound 127: (S)-1-(3-(2-hydroxyethylsulfonyl)phenoxy)-3-((R)-8-(3-(5-methylpyridin-2-yl)phenylsulfonyl)-1-oxa-8-azaspiro[4.5]decan-3-ylamino)propan-2-ol; Compound 128: (S)-1-(3-(2-hydroxyethylsulfonyl)phenoxy)-3-((R)-8-(3-(6-methylpyridin-2-yl)phenylsulfonyl)-1-oxa-8-azaspiro[4.5]decan-3-ylamino)propan-2-ol; Compound 129: (S)-1-(3-(2-hydroxyethylsulfonyl)phenoxy)-3-((R)-8-(3-(4-methylpyridin-2-yl)phenylsulfonyl)-1-oxa-8-azaspiro[4.5]decan-3-ylamino)propan-2-ol; Compound 130: (S)-1-(3-(1,1-difluoro-2-hydroxyethylsulfonyl)phenoxy)-3-((R)-8-(quinolin-3-ylsulfonyl)-1-oxa-8-azaspiro[4.5]decan-3-ylamino)propan-2-ol; Compound 131: (S)-1-(3-(methoxymethylsulfonyl)phenoxy)-3-((R)-8-(quinolin-6-ylsulfonyl)-1-oxa-8-azaspiro[4.5]decan-3-ylamino)propan-2-ol; Compound 132: (S)-1-(3-(3-methoxypropylsulfonyl)phenoxy)-3-((R)-8-(quinolin-6-ylsulfonyl)-1-oxa-8-azaspiro[4.5]decan-3-ylamino)propan-2-ol; Compound 133: 3-(3-((S)-2-hydroxy-3-((R)-8-(quinolin-6-ylsulfonyl)-1-oxa-8-azaspiro[4.5]decan-3-ylamino)propoxy)phenylsulfonyl)propanamide; Compound 134: (S)-1-((R)-8-(3-(6-fluoropyridin-2-yl)phenylsulfonyl)-1-oxa-8-azaspiro[4.5]decan-3-ylamino)-3-(3-(2-hydroxyethylsulfonyl)phenoxy)propan-2-ol; Compound 135: 3-(3-((S)-2-hydroxy-3-((R)-8-(quinolin-3-ylsulfonyl)-1-oxa-8-azaspiro[4.5]decan-3-ylamino)propoxy)phenylsulfonyl)propan-1-ol; Compound 136: (S)-1-(3-(1-(hydroxymethyl)cyclopropylsulfonyl)phenoxy)-3-((R)-8-(quinolin-3-ylsulfonyl)-1-oxa-8-azaspiro[4.5]decan-3-ylamino)propan-2-ol; Compound 137: 2-(3-((S)-2-hydroxy-3-((R)-8-(quinolin-6-ylsulfonyl)-1-oxa-8-azaspiro[4.5]decan-3-ylamino)propoxy)phenylsulfonyl)acetamide; Compound 138: (S)-1-(3-(cyclobutylsulfonyl)phenoxy)-3-((R)-8-(quinolin-3-ylsulfonyl)-1-oxa-8-azaspiro[4.5]decan-3-ylamino)propan-2-ol; Compound 139: (S)-1-(3-(propylsulfonyl)phenoxy)-3-((R)-8-(quinolin-3-ylsulfonyl)-1-oxa-8-azaspiro[4.5]decan-3-ylamino)propan-2-ol; Compound 140: (S)-1-(3-(cyclopropylmethylsulfonyl)phenoxy)-3-((R)-8-(quinolin-3-ylsulfonyl)-1-oxa-8-azaspiro[4.5]decan-3-ylamino)propan-2-ol; Compound 141: (S)-1-(3-(methoxymethylsulfonyl)phenoxy)-3-((R)-8-(quinolin-3-ylsulfonyl)-1-oxa-8-azaspiro[4.5]decan-3-ylamino)propan-2-ol; Compound 142: 3-(3-((S)-2-hydroxy-3-((R)-8-(quinolin-3-ylsulfonyl)-1-oxa-8-azaspiro[4.5]decan-3-ylamino)propoxy)phenylsulfonyl)propanamide; Compound 143: (S)-1-(3-(cyclopropylsulfonyl)phenoxy)-3-((R)-8-(quinolin-6-ylsulfonyl)-1-oxa-8-azaspiro[4.5]decan-3-ylamino)propan-2-ol; Compound 144: (S)-1-(3-(cyclopropylsulfonyl)phenoxy)-3-((R)-8-(quinolin-3-ylsulfonyl)-1-oxa-8-azaspiro[4.5]decan-3-ylamino)propan-2-ol; Compound 145: ethyl 2-(3-((S)-2-hydroxy-3-((R)-8-(quinolin-3-ylsulfonyl)-1-oxa-8-azaspiro[4.5]decan-3-ylamino)propoxy)phenylsulfonyl)-2-methylpropanoate; Compound 146: 3-(3-((S)-2-hydroxy-3-((R)-8-(quinolin-3-ylsulfonyl)-1-oxa-8-azaspiro[4.5]decan-3-ylamino)propoxy)phenylsulfonyl)cyclobutanol; Compound 147: (S)-1-(3-(1-(hydroxymethyl)cyclopropylsulfonyl)phenoxy)-3-((R)-8-(quinolin-6-ylsulfonyl)-1-oxa-8-azaspiro[4.5]decan-3-ylamino)propan-2-ol; Compound 148: (S)-1-(3-(1,1-difluoro-2-hydroxyethylsulfonyl)phenoxy)-3-((R)-8-(quinolin-6-ylsulfonyl)-1-oxa-8-azaspiro[4.5]decan-3-ylamino)propan-2-ol; Compound 149: (S)-1-(3-(3-methoxypropylsulfonyl)phenoxy)-3-((R)-8-(quinolin-3-ylsulfonyl)-1-oxa-8-azaspiro[4.5]decan-3-ylamino)propan-2-ol; Compound 150: 3-(3-((S)-2-hydroxy-3-((R)-8-(1-methyl-2,3-dihydro-1H-pyrido[2,3-b][1,4]oxazin-7-ylsulfonyl)-1-oxa-8-azaspiro[4.5]decan-3-ylamino)propoxy)phenylsulfonyl)propan-1-ol; Compound 151: (S)-1-(3-(2-hydroxyethylsulfonyl)phenoxy)-3-((R)-8-(1-methyl-2,3-dihydro-1H-pyrido[2,3-b][1,4]oxazin-7-ylsulfonyl)-1-oxa-8-azaspiro[4.5]decan-3-ylamino)propan-2-ol; Compound 152: (S)-1-((R)-8-(1-methyl-2,3-dihydro-1H-pyrido[2,3-b][1,4]oxazin-7-ylsulfonyl)-1-oxa-8-azaspiro[4.5]decan-3-ylamino)-3-(3-(methylsulfonyl)phenoxy)propan-2-ol; Compound 153: (S)-1-(3-(isopropylsulfonyl)phenoxy)-3-((R)-8-(1-methyl-2,3-dihydro-1H-pyrido[2,3-b][1,4]oxazin-7-ylsulfonyl)-1-oxa-8-azaspiro[4.5]decan-3-ylamino)propan-2-ol; Compound 154: (S)-1-(3-(cyclopropylsulfonyl)phenoxy)-3-((R)-8-(1-methyl-2,3-dihydro-1H-pyrido[2,3-b][1,4]oxazin-7-ylsulfonyl)-1-oxa-8-azaspiro[4.5]decan-3-ylamino)propan-2-ol; Compound 155: (S)-1-(3-(1-(hydroxymethyl)cyclopropylsulfonyl)phenoxy)-3-((R)-8-(1-methyl-2,3-dihydro-1H-pyrido[2,3-b][1,4]oxazin-7-ylsulfonyl)-1-oxa-8-azaspiro[4.5]decan-3-ylamino)propan-2-ol; Compound 156: (S)-1-(3-(1,1-difluoro-2-hydroxyethylsulfonyl)phenoxy)-3-((R)-8-(1-methyl-2,3-dihydro-1H-pyrido[2,3-b][1,4]oxazin-7-ylsulfonyl)-1-oxa-8-azaspiro[4.5]decan-3-ylamino)propan-2-ol; Compound 157: (S)-1-((R)-8-(4'-(aminomethyl)biphenyl-3-ylsulfonyl)-1-oxa-8-azaspiro[4.5]decan-3-ylamino)-3-(3-(1-(hydroxymethyl)cyclopropylsulfonyl)phenoxy)propan-2-ol; Compound 158: (S)-1-((R)-8-(4'-(aminomethyl)-4-ethoxybiphenyl-3-ylsulfonyl)-1-oxa-8-azaspiro[4.5]decan-3-ylamino)-3-(3-(1-(hydroxymethyl)cyclopropylsulfonyl)phenoxy)propan-2-ol; Compound 159: 2-(3-((S)-2-hydroxy-3-((R)-8-(1-methyl-2,3-dihydro-1H-pyrido[2,3-b][1,4]oxazin-7-ylsulfonyl)-1-oxa-8-azaspiro[4.5]decan-3-ylamino)propoxy)phenylsulfonyl)acetamide; Compound 160: (S)-1-((S)-8-(4'-(aminomethyl)-4-ethoxybiphenyl-3-ylsulfonyl)-1-oxa-8-azaspiro[4.5]decan-3-ylamino)-3-(3-(cyclopropylsulfonyl)phenoxy)propan-2-ol; Compound 161: (S)-1-((R)-8-(4'-(aminomethyl)-4-ethoxybiphenyl-3-ylsulfonyl)-1-oxa-8-azaspiro[4.5]decan-3-ylamino)-3-(3-(1,1-difluoro-2-hydroxyethylsulfonyl)phenoxy)propan-2-ol; Compound 162: (S)-1-((S)-8-(4'-(aminomethyl)-4-fluorobiphenyl-3-ylsulfonyl)-1-oxa-8-azaspiro[4.5]decan-3-ylamino)-3-(3-(1-(hydroxymethyl)cyclopropylsulfonyl)phenoxy)propan-2-ol; Compound 163: (S)-1-((S)-8-(4'-(aminomethyl)-4-ethoxybiphenyl-3-ylsulfonyl)-1-oxa-8-azaspiro[4.5]decan-3-ylamino)-3-(3-(1-(hydroxymethyl)cyclopropylsulfonyl)phenoxy)propan-2-ol; Compound 164: (S)-1-((S)-8-(4'-(aminomethyl)biphenyl-3-ylsulfonyl)-1-oxa-8-azaspiro[4.5]decan-3-ylamino)-3-(3-(1-(hydroxymethyl)cyclopropylsulfonyl)phenoxy)propan-2-ol; Compound 165: (S)-1-((R)-8-(4-ethoxy-4'-((isopropylamino)methyl)biphenyl-3-ylsulfonyl)-1-oxa-8-azaspiro[4.5]decan-3-ylamino)-3-(3-(1-(hydroxymethyl)cyclopropylsulfonyl)phenoxy)propan-2-ol; Compound 166: (S)-1-((S)-8-(4'-(aminomethyl)-4-isopropoxybiphenyl-3-ylsulfonyl)-1-oxa-8-azaspiro[4.5]decan-3-ylamino)-3-(3-(cyclopropylsulfonyl)phenoxy)propan-2-ol; Compound 167: (S)-1-((R)-8-(4'-(aminomethyl)-4-ethoxybiphenyl-3-ylsulfonyl)-1-oxa-8-azaspiro[4.5]decan-3-ylamino)-3-(3-(cyclopropylsulfonyl)phenoxy)propan-2-ol; Compound 168: (S)-1-((S)-8-(4'-(aminomethyl)-4-ethoxybiphenyl-3-ylsulfonyl)-1-oxa-8-azaspiro[4.5]decan-3-ylamino)-3-(3-(1,1-difluoro-2-hydroxyethylsulfonyl)phenoxy)propan-2-ol; Compound 169: (S)-1-((R)-8-(4'-(aminomethyl)-4-fluorobiphenyl-3-ylsulfonyl)-1-oxa-8-azaspiro[4.5]decan-3-ylamino)-3-(3-(1-(hydroxymethyl)cyclopropylsulfonyl)phenoxy)propan-2-ol; Compound 170: (S)-1-(3-(1-(hydroxymethyl)cyclopropylsulfonyl)phenoxy)-3-((R)-8-(4'-methylbiphenyl-3-ylsulfonyl)-1-oxa-8-azaspiro[4.5]decan-3-ylamino)propan-2-ol; Compound 171: (S)-1-((R)-8-(4'-(aminomethyl)-4-isopropoxybiphenyl-3-ylsulfonyl)-1-oxa-8-azaspiro[4.5]decan-3-ylamino)-3-(3-(cyclopropylsulfonyl)phenoxy)propan-2-ol; Compound 172: (S)-1-((R)-8-(4'-(1-aminocyclopropyl)-4-ethoxybiphenyl-3-ylsulfonyl)-1-oxa-8-azaspiro[4.5]decan-3-ylamino)-3-(3-(1-(hydroxymethyl)cyclopropylsulfonyl)phenoxy)propan-2-ol; Compound 173: (S)-1-((R)-8-(4'-(1-aminocyclopropyl)biphenyl-3-ylsulfonyl)-1-oxa-8-azaspiro[4.5]decan-3-ylamino)-3-(3-(1-(hydroxymethyl)cyclopropylsulfonyl)phenoxy)propan-2-ol; Compound 174: (S)-1-((R)-8-(4'-(1-amino-2-methylpropan-2-yl)-4-ethoxybiphenyl-3-ylsulfonyl)-1-oxa-8-azaspiro[4.5]decan-3-ylamino)-3-(3-(1-(hydroxymethyl)cyclopropylsulfonyl)phenoxy)propan-2-ol; Compound 175: N-(2-(4'-ethoxy-3'-((R)-3-((S)-2-hydroxy-3-(3-(1-(hydroxymethyl)cyclopropylsulfonyl)phenoxy)propylamino)-1-oxa-8-azaspiro[4.5]decan-8-ylsulfonyl)biphenyl-4-yl)ethyl)acetamide; Compound 176: (S)-1-((S)-8-(4'-(1-amino-2-methylpropan-2-yl)-4-ethoxybiphenyl-3-ylsulfonyl)-1-oxa-8-azaspiro[4.5]decan-3-ylamino)-3-(3-(1-(hydroxymethyl)cyclopropylsulfonyl)phenoxy)propan-2-ol; Compound 177: N-(2-(4'-ethoxy-3'-((S)-3-((S)-2-hydroxy-3-(3-(1-(hydroxymethyl)cyclopropylsulfonyl)phenoxy)propylamino)-1-oxa-8-azaspiro[4.5]decan-8-ylsulfonyl)biphenyl-4-yl)ethyl)acetamide; Compound 178: 2-(3-((S)-3-((R)-8-(4'-(aminomethyl)biphenyl-3-ylsulfonyl)-1-oxa-8-azaspiro[4.5]decan-3-ylamino)-2-hydroxypropoxy)phenylsulfonyl)acetamide; Compound 179: 2-(3-((S)-3-((R)-8-(4'-(aminomethyl)-4-ethoxybiphenyl-3-ylsulfonyl)-1-oxa-8-azaspiro[4.5]decan-3-ylamino)-2-hydroxypropoxy)phenylsulfonyl)acetamide; Compound 180: (S)-1-((S)-8-(4'-(1-amino-2-methylpropan-2-yl)biphenyl-3-ylsulfonyl)-1-oxa-8-azaspiro[4.5]decan-3-ylamino)-3-(3-(1-(hydroxymethyl)cyclopropylsulfonyl)phenoxy)propan-2-ol; Compound 181: (S)-1-((R)-8-(4'-(1-amino-2-methylpropan-2-yl)biphenyl-3-ylsulfonyl)-1-oxa-8-azaspiro[4.5]decan-3-ylamino)-3-(3-(1-(hydroxymethyl)cyclopropylsulfonyl)phenoxy)propan-2-ol; Compound 182: (S)-1-((S)-8-(4'-(aminomethyl)-3'-fluorobiphenyl-3-ylsulfonyl)-1-oxa-8-azaspiro[4.5]decan-3-ylamino)-3-(3-(1-(hydroxymethyl)cyclopropylsulfonyl)phenoxy)propan-2-ol; Compound 183: 2-(3-((S)-2-hydroxy-3-((R)-8-(quinolin-3-ylsulfonyl)-1-oxa-8-azaspiro[4.5]decan-3-ylamino)propoxy)phenylsulfonyl)acetic acid; Compound 184: (S)-1-((S)-8-(4'-(1-aminocyclopropyl)biphenyl-3-ylsulfonyl)-1-oxa-8-azaspiro[4.5]decan-3-ylamino)-3-(3-(1-(hydroxymethyl)cyclopropylsulfonyl)phenoxy)propan-2-ol; Compound 185: (S)-1-((R)-8-(5-bromopyridin-3-ylsulfonyl)-1-oxa-8-azaspiro[4.5]decan-3-ylamino)-3-(3-(1-(hydroxymethyl)cyclopropylsulfonyl)phenoxy)propan-2-ol; Compound 186: (S)-1-((S)-8-(5-bromopyridin-3-ylsulfonyl)-1-oxa-8-azaspiro[4.5]decan-3-ylamino)-3-(3-(1-(hydroxymethyl)cyclopropylsulfonyl)phenoxy)propan-2-ol; Compound 187: 2-(3-((S)-3-((S)-8-(4'-(aminomethyl)-4-ethoxybiphenyl-3-ylsulfonyl)-1-oxa-8-azaspiro[4.5]decan-3-ylamino)-2-hydroxypropoxy)phenylsulfonyl)-2-methylpropan-1-ol; Compound 188: (S)-1-((S)-8-(4'-(1-aminocyclopropyl)-4-ethoxybiphenyl-3-ylsulfonyl)-1-oxa-8-azaspiro[4.5]decan-3-ylamino)-3-(3-(1-(hydroxymethyl)cyclopropylsulfonyl)phenoxy)propan-2-ol; Compound 189: (S)-1-((R)-8-(4'-(aminomethyl)biphenyl-3-ylsulfonyl)-1-oxa-8-azaspiro[4.5]decan-3-ylamino)-3-(3-(cyclopropylsulfonyl)phenoxy)propan-2-ol; Compound 190: N-(2-(3'-((S)-3-((S)-2-hydroxy-3-(3-(1-(hydroxymethyl)cyclopropylsulfonyl)phenoxy)propylamino)-1-oxa-8-azaspiro[4.5]decan-8-ylsulfonyl)biphenyl-4-yl)ethyl)acetamide; Compound 191: N-(2-(3'-((R)-3-((S)-2-hydroxy-3-(3-(1-(hydroxymethyl)cyclopropylsulfonyl)phenoxy)propylamino)-1-oxa-8-azaspiro[4.5]decan-8-ylsulfonyl)biphenyl-4-yl)ethyl)acetamide; Compound 192: (S)-1-((R)-8-(3-bromo-2-methylphenylsulfonyl)-1-oxa-8-azaspiro[4.5]decan-3-ylamino)-3-(3-(1-(hydroxymethyl)cyclopropylsulfonyl)phenoxy)propan-2-ol; Compound 193: (S)-1-((R)-8-(3-bromo-4-methoxyphenylsulfonyl)-1-oxa-8-azaspiro[4.5]decan-3-ylamino)-3-(3-(1-(hydroxymethyl)cyclopropylsulfonyl)phenoxy)propan-2-ol; Compound 194: (S)-1-((R)-8-(4-bromo-3-methylphenylsulfonyl)-1-oxa-8-azaspiro[4.5]decan-3-ylamino)-3-(3-(1-(hydroxymethyl)cyclopropylsulfonyl)phenoxy)propan-2-ol; Compound 195: (S)-1-(3-(1-(hydroxymethyl)cyclopropylsulfonyl)phenoxy)-3-((R)-8-(pyridin-3-ylsulfonyl)-1-oxa-8-azaspiro[4.5]decan-3-ylamino)propan-2-ol; Compound 196: (S)-1-((S)-8-(4-bromo-3-methylphenylsulfonyl)-1-oxa-8-azaspiro[4.5]decan-3-ylamino)-3-(3-(1-(hydroxymethyl)cyclopropylsulfonyl)phenoxy)propan-2-ol; Compound 197: (S)-1-((S)-8-(4'-(aminomethyl)-2-methylbiphenyl-3-ylsulfonyl)-1-oxa-8-azaspiro[4.5]decan-3-ylamino)-3-(3-(1-(hydroxymethyl)cyclopropylsulfonyl)phenoxy)propan-2-ol; Compound 198: (S)-1-((S)-8-(4'-(1-aminocyclopropyl)-2-methylbiphenyl-3-ylsulfonyl)-1-oxa-8-azaspiro[4.5]decan-3-ylamino)-3-(3-(1-(hydroxymethyl)cyclopropylsulfonyl)phenoxy)propan-2-ol; Compound 199: (S)-1-((R)-8-(4'-(1-aminocyclopropyl)-6-methoxybiphenyl-3-ylsulfonyl)-1-oxa-8-azaspiro[4.5]decan-3-ylamino)-3-(3-(1-(hydroxymethyl)cyclopropylsulfonyl)phenoxy)propan-2-ol; Compound 200: (S)-1-((S)-8-(3-bromo-2-methylphenylsulfonyl)-1-oxa-8-azaspiro[4.5]decan-3-ylamino)-3-(3-(1-(hydroxymethyl)cyclopropylsulfonyl)phenoxy)propan-2-ol; Compound 201: (S)-1-((S)-8-(3-bromo-4-methoxyphenylsulfonyl)-1-oxa-8-azaspiro[4.5]decan-3-ylamino)-3-(3-(1-(hydroxymethyl)cyclopropylsulfonyl)phenoxy)propan-2-ol; Compound 202: (S)-1-(3-(1-(hydroxymethyl)cyclopropylsulfonyl)phenoxy)-3-((S)-8-(pyridin-3-ylsulfonyl)-1-oxa-8-azaspiro[4.5]decan-3-ylamino)propan-2-ol; Compound 203: (S)-1-((R)-8-(4'-(aminomethyl)-2-methylbiphenyl-3-ylsulfonyl)-1-oxa-8-azaspiro[4.5]decan-3-ylamino)-3-(3-(1-(hydroxymethyl)cyclopropylsulfonyl)phenoxy)propan-2-ol; Compound 204: (S)-1-((R)-8-(4'-(1-aminocyclopropyl)-2-methylbiphenyl-3-ylsulfonyl)-1-oxa-8-azaspiro[4.5]decan-3-ylamino)-3-(3-(1-(hydroxymethyl)cyclopropylsulfonyl)phenoxy)propan-2-ol; Compound 205: 2-(3-((S)-3-((S)-8-(4'-(aminomethyl)-4-ethoxybiphenyl-3-ylsulfonyl)-1-oxa-8-azaspiro[4.5]decan-3-ylamino)-2-hydroxypropoxy)phenylsulfonyl)acetamide; Compound 206: 2-(3-((S)-3-((S)-8-(4'-(aminomethyl)-2-methoxybiphenyl-3-ylsulfonyl)-1-oxa-8-azaspiro[4.5]decan-3-ylamino)-2-hydroxypropoxy)phenylsulfonyl)acetamide; Compound 207: (S)-1-((S)-8-(4'-(aminomethyl)-6-methoxybiphenyl-3-ylsulfonyl)-1-oxa-8-azaspiro[4.5]decan-3-ylamino)-3-(3-(1-(hydroxymethyl)cyclopropylsulfonyl)phenoxy)propan-2-ol; Compound 208: (S)-1-((R)-8-(4'-(aminomethyl)-6- methoxybiphenyl-3-ylsulfonyl)-1-oxa-8-azaspiro[4.5]decan-3-ylamino)-3-(3-(1-(hydroxymethyl)cyclopropylsulfonyl)phenoxy)propan-2-ol; Compound 209: (S)-1-((S)-8-(4'-(aminomethyl)-4-ethoxybiphenyl-3-ylsulfonyl)-1-oxa-8-azaspiro[4.5]decan-3-ylamino)-3-(2-fluoro-3-(methylsulfonyl)phenoxy)propan-2-ol; Compound 210: (S)-1-((S)-8-(4'-(2-aminoethyl)biphenyl-3-ylsulfonyl)-1-oxa-8-azaspiro[4.5]decan-3-ylamino)-3-(3-(1,1-difluoro-2-hydroxyethylsulfonyl)phenoxy)propan-2-ol; Compound 211: (S)-1-((S)-8-(4'-(2-aminoethyl)biphenyl-3-ylsulfonyl)-1-oxa-8-azaspiro[4.5]decan-3-ylamino)-3-(3-(1-(hydroxymethyl)cyclopropylsulfonyl)phenoxy)propan-2-ol; Compound 212: (S)-1-((R)-8-(4'-(2-aminoethyl)biphenyl-3-ylsulfonyl)-1-oxa-8-azaspiro[4.5]decan-3-ylamino)-3-(3-(1-(hydroxymethyl)cyclopropylsulfonyl)phenoxy)propan-2-ol; Compound 213: (S)-1-((R)-8-(4'-(2-aminoethyl)biphenyl-3-ylsulfonyl)-1-oxa-8-azaspiro[4.5]decan-3-ylamino)-3-(3-(1,1-difluoro-2-hydroxyethylsulfonyl)phenoxy)propan-2-ol; Compound 214: (S)-1-((S)-8-(4'-(2-aminoethyl)-4-ethoxybiphenyl-3-ylsulfonyl)-1-oxa-8-azaspiro[4.5]decan-3-ylamino)-3-(3-(1-(hydroxymethyl)cyclopropylsulfonyl)phenoxy)propan-2-ol; Compound 215: (S)-1-((S)-8-(4'-(2-aminoethyl)-6-methoxybiphenyl-3-ylsulfonyl)-1-oxa-8-azaspiro[4.5]decan-3-ylamino)-3-(3-(1-(hydroxymethyl)cyclopropylsulfonyl)phenoxy)propan-2-ol; Compound 216: (S)-1-((R)-8-(4'-(aminomethyl)-6-fluorobiphenyl-3-ylsulfonyl)-1-oxa-8-azaspiro[4.5]decan-3-ylamino)-3-(3-(1-(hydroxymethyl)cyclopropylsulfonyl)phenoxy)propan-2-ol; Compound 217: (S)-1-((R)-8-(4'-(1-aminocyclopropyl)-6-fluorobiphenyl-3-ylsulfonyl)-1-oxa-8-azaspiro[4.5]decan-3-ylamino)-3-(3-(1-(hydroxymethyl)cyclopropylsulfonyl)phenoxy)propan-2-ol; Compound 218: (S)-1-((S)-8-(4'-(aminomethyl)-6-fluorobiphenyl-3-ylsulfonyl)-1-oxa-8-azaspiro[4.5]decan-3-ylamino)-3-(3-(1-(hydroxymethyl)cyclopropylsulfonyl)phenoxy)propan-2-ol; Compound 219: (S)-1-((S)-8-(4'-(1-aminocyclopropyl)-6-fluorobiphenyl-3-ylsulfonyl)-1-oxa-8-azaspiro[4.5]decan-3-ylamino)-3-(3-(1-(hydroxymethyl)cyclopropylsulfonyl)phenoxy)propan-2-ol; Compound 220: (S)-1-((S)-8-(4'-(aminomethyl)-4-ethoxy-3'-fluorobiphenyl-3-ylsulfonyl)-1-oxa-8-azaspiro[4.5]decan-3-ylamino)-3-(3-(1-(hydroxymethyl)cyclopropylsulfonyl)phenoxy)propan-2-ol; Compound 221: (S)-1-((R)-8-(5-bromo-6-chloropyridin-3-ylsulfonyl)-1-oxa-8-azaspiro[4.5]decan-3-ylamino)-3-(3-(1-(hydroxymethyl)cyclopropylsulfonyl)phenoxy)propan-2-ol; Compound 222: (S)-1-((R)-8-(1,4-dimethyl-1,2,3,4-tetrahydropyrido[3,2-b]pyrazin-7-ylsulfonyl)-1-oxa-8-azaspiro[4.5]decan-3-ylamino)-3-(3-(1-(hydroxymethyl)cyclopropylsulfonyl)phenoxy)propan-2-ol; Compound 223: 2-(3-((S)-3-((S)-8-(4'-(aminomethyl)-6-methoxybiphenyl-3-ylsulfonyl)-1-oxa-8-azaspiro[4.5]decan-3-ylamino)-2-hydroxypropoxy)phenylsulfonyl)-2-methylpropan-1-ol; Compound 224: 2-(3-((S)-3-((S)-8-(4'-(1-aminocyclopropyl)-6-methoxybiphenyl-3-ylsulfonyl)-1-oxa-8-azaspiro[4.5]decan-3-ylamino)-2-hydroxypropoxy)phenylsulfonyl)-2-methylpropan-1-ol; Compound 225: (S)-1-((S)-8-(4'-(1-aminocyclopropyl)-6-methoxybiphenyl-3-ylsulfonyl)-1-oxa-8-azaspiro[4.5]decan-3-ylamino)-3-(3-(1-(hydroxymethyl)cyclopropylsulfonyl)phenoxy)propan-2-ol; Compound 226: (S)-1-((S)-8-(4'-(aminomethyl)-4-ethoxybiphenyl-3-ylsulfonyl)-1-oxa-8-azaspiro[4.5]decan-3-ylamino)-3-(3-(ethylsulfonyl)phenoxy)propan-2-ol; Compound 227: (S)-1-((S)-8-(4'-(aminomethyl)-6-methoxybiphenyl-3-ylsulfonyl)-1-oxa-8-azaspiro[4.5]decan-3-ylamino)-3-(3-(cyclopropylsulfonyl)phenoxy)propan-2-ol; Compound 228: (S)-1-((S)-8-(4'-(aminomethyl)-2-methoxybiphenyl-3-ylsulfonyl)-1-oxa-8-azaspiro[4.5]decan-3-ylamino)-3-(3-(cyclopropylsulfonyl)phenoxy)propan-2-ol; Compound 229: (S)-1-((S)-8-(4'-(aminomethyl)-5-methoxybiphenyl-3-ylsulfonyl)-1-oxa-8-azaspiro[4.5]decan-3-ylamino)-3-(3-(cyclopropylsulfonyl)phenoxy)propan-2-ol; Compound 230: (S)-1-((S)-8-(4'-(aminomethyl)-4-ethoxybiphenyl-3-ylsulfonyl)-1-oxa-8-azaspiro[4.5]decan-3-ylamino)-3-(3-(methoxymethylsulfonyl)phenoxy)propan-2-ol; Compound 231: (S)-1-((S)-8-(4'-(aminomethyl)-4-ethoxybiphenyl-3-ylsulfonyl)-1-oxa-8-azaspiro[4.5]decan-3-ylamino)-3-(3-(methylsulfonyl)phenoxy)propan-2-ol; Compound 232: (S)-1-((S)-8-(4'-(aminomethyl)-4-ethoxybiphenyl-3-ylsulfonyl)-1-oxa-8-azaspiro[4.5]decan-3-ylamino)-3-(3-(isopropylsulfonyl)phenoxy)propan-2-ol; Compound 233: (2S)-1-(3-(1-fluoroethylsulfonyl)phenoxy)-3-((R)-8-(quinolin-3-ylsulfonyl)-1-oxa-8-azaspiro[4.5]decan-3-ylamino)propan-2-ol; Compound 234: (2S)-1-(3-(1-fluoroethylsulfonyl)phenoxy)-3-((R)-8-(quinolin-6-ylsulfonyl)-1-oxa-8-azaspiro[4.5]decan-3-ylamino)propan-2-ol; Compound 235: (2S)-1-(3-(1-fluoroethylsulfonyl)phenoxy)-3-((R)-8-(1-methyl-2,3-dihydro-1H-pyrido[2,3-b][1,4]oxazin-7-ylsulfonyl)-1-oxa-8-azaspiro[4.5]decan-3-ylamino)propan-2-ol; Compound 236: 6-((R)-3-((S)-2-hydroxy-3-(3-(1-(hydroxymethyl)cyclopropylsulfonyl)phenoxy)propylamino)-1-oxa-8-azaspiro[4.5]decan-8-ylsulfonyl)-4-methylquinolin-2(1H)-one; Compound 237: (S)-1-((S)-8-(4'-(aminomethyl)-6-ethoxybiphenyl-3-ylsulfonyl)-1-oxa-8-azaspiro[4.5]decan-3-ylamino)-3-(3-(1-(hydroxymethyl)cyclopropylsulfonyl)phenoxy)propan-2-ol; Compound 238: (S)-1-((S)-8-(4'-(aminomethyl)-6-methoxybiphenyl-3-ylsulfonyl)-1-oxa-8-azaspiro[4.5]decan-3-ylamino)-3-(3-(1,1-difluoro-2-hydroxyethylsulfonyl)phenoxy)propan-2-ol; Compound 239: (S)-1-((S)-8-(4'-(1-aminocyclopropyl)-6-methoxybiphenyl-3-ylsulfonyl)-1-oxa-8-azaspiro[4.5]decan-3-ylamino)-3-(3-(1,1-difluoro-2-hydroxyethylsulfonyl)phenoxy)propan-2-ol; Compound 240: (S)-1-((S)-8-(4'-((tert-butylamino)methyl)biphenyl-3-ylsulfonyl)-1-oxa-8-azaspiro[4.5]decan-3-ylamino)-3-(3-(1-(hydroxymethyl)cyclopropylsulfonyl)phenoxy)propan-2-ol; Compound 241: (S)-1-(3-(1-(hydroxymethyl)cyclopropylsulfonyl)phenoxy)-3-((S)-8-(4'-((tert-pentylamino)methyl)biphenyl-3-ylsulfonyl)-1-oxa-8-azaspiro[4.5]decan-3-ylamino)propan-2-ol; Compound 242: (S)-1-(3-(1-(hydroxymethyl)cyclopropylsulfonyl)phenoxy)-3-((S)-8-(4'-((2,2,2-trifluoroethylamino)methyl)biphenyl-3-ylsulfonyl)-1-oxa-8-azaspiro[4.5]decan-3-ylamino)propan-2-ol; Compound 243: (S)-1-((S)-8-(4'-(azetidin-1-ylmethyl)biphenyl-3-ylsulfonyl)-1-oxa-8-azaspiro[4.5]decan-3-ylamino)-3-(3-(1-(hydroxymethyl)cyclopropylsulfonyl)phenoxy)propan-2-ol; Compound 244: (S)-1-(3-(1-(hydroxymethyl)cyclopropylsulfonyl)phenoxy)-3-((S)-8-(4'-((propylamino)methyl)biphenyl-3-ylsulfonyl)-1-oxa-8-azaspiro[4.5]decan-3-ylamino)propan-2-ol; Compound 245: (S)-1-((S)-8-(4'-((butylamino)methyl)biphenyl-3-ylsulfonyl)-1-oxa-8-azaspiro[4.5]decan-3-ylamino)-3-(3-(1-(hydroxymethyl)cyclopropylsulfonyl)phenoxy)propan-2-ol; Compound 246: (S)-1-(3-(1-(hydroxymethyl)cyclopropylsulfonyl)phenoxy)-3-((S)-8-(4'-(morpholinomethyl)biphenyl-3-ylsulfonyl)-1-oxa-8-azaspiro[4.5]decan-3-ylamino)propan-2-ol; Compound 247: (S)-1-(3-(1-(hydroxymethyl)cyclopropylsulfonyl)phenoxy)-3-((S)-8-(4'-((2-methoxyethylamino)methyl)biphenyl-3-ylsulfonyl)-1-oxa-8-azaspiro[4.5]decan-3-ylamino)propan-2-ol; Compound 248: (S)-1-(3-fluoro-5-(2-hydroxyethylsulfonyl)phenoxy)-3-((R)-8-(quinolin-3-ylsulfonyl)-1-oxa-8-azaspiro[4.5]decan-3-ylamino)propan-2-ol; Compound 249: (S)-1-(3-fluoro-5-(2-hydroxyethylsulfonyl)phenoxy)-3-((R)-8-

(quinolin-6-ylsulfonyl)-1-oxa-8-azaspiro[4.5]decan-3-ylamino)propan-2-ol; Compound 250: (S)-1-((S)-8-(1,8-dimethyl-2,3-dihydro-1H-pyrido[2,3-b][1,4]oxazin-7-ylsulfonyl)-1-oxa-8-azaspiro[4.5]decan-3-ylamino)-3-(3-(1-(hydroxymethyl)cyclopropylsulfonyl)phenoxy)propan-2-ol; Compound 251: (S)-1-((S)-8-(4'-(2-aminopropan-2-yl)-4-ethoxybiphenyl-3-ylsulfonyl)-1-oxa-8-azaspiro[4.5]decan-3-ylamino)-3-(3-(1-(hydroxymethyl)cyclopropylsulfonyl)phenoxy)propan-2-ol; Compound 252: (S)-1-((S)-8-(4'-(1-aminocyclopropyl)-4-ethoxybiphenyl-3-ylsulfonyl)-1-oxa-8-azaspiro[4.5]decan-3-ylamino)-3-(3-(cyclopropylsulfonyl)phenoxy)propan-2-ol; Compound 253: (S)-1-((S)-8-(4'-(1-aminocyclopropyl)-6-methoxybiphenyl-3-ylsulfonyl)-1-oxa-8-azaspiro[4.5]decan-3-ylamino)-3-(3-(cyclopropylsulfonyl)phenoxy)propan-2-ol; Compound 254: (S)-1-((R)-8-(4'-(1-aminocyclopropyl)-4-ethoxybiphenyl-3-ylsulfonyl)-1-oxa-8-azaspiro[4.5]decan-3-ylamino)-3-(3-(cyclopropylsulfonyl)phenoxy)propan-2-ol; Compound 255: (S)-1-((R)-8-(4'-(1-aminocyclopropyl)-6-methoxybiphenyl-3-ylsulfonyl)-1-oxa-8-azaspiro[4.5]decan-3-ylamino)-3-(3-(cyclopropylsulfonyl)phenoxy)propan-2-ol; Compound 256: (S)-1-((S)-8-(4'-(1-aminocyclopropyl)-4-ethoxybiphenyl-3-ylsulfonyl)-1-oxa-8-azaspiro[4.5]decan-3-ylamino)-3-(3-(ethylsulfonyl)phenoxy)propan-2-ol; Compound 257: (S)-1-((R)-8-(4'-(1-aminocyclopropyl)-4-ethoxybiphenyl-3-ylsulfonyl)-1-oxa-8-azaspiro[4.5]decan-3-ylamino)-3-(3-(ethylsulfonyl)phenoxy)propan-2-ol; Compound 258: (S)-1-((R)-8-(4'-(1-aminocyclopropyl)-6-methoxybiphenyl-3-ylsulfonyl)-1-oxa-8-azaspiro[4.5]decan-3-ylamino)-3-(3-(ethylsulfonyl)phenoxy)propan-2-ol; Compound 259: (S)-1-(3-(cyclopropylsulfonyl)phenoxy)-3-((R)-8-(1,6-dimethyl-2,3-dihydro-1H-pyrido[2,3-b][1,4]oxazin-7-ylsulfonyl)-1-oxa-8-azaspiro[4.5]decan-3-ylamino)propan-2-ol; Compound 260: (S)-1-((R)-8-(1,8-dimethyl-2,3-dihydro-1H-pyrido[2,3-b][1,4]oxazin-7-ylsulfonyl)-1-oxa-8-azaspiro[4.5]decan-3-ylamino)-3-(3-(1-(hydroxymethyl)cyclopropylsulfonyl)phenoxy)propan-2-ol; Compound 261: (S)-1-((S)-8-(4'-(1-aminocyclopropyl)-6-methoxybiphenyl-3-ylsulfonyl)-1-oxa-8-azaspiro[4.5]decan-3-ylamino)-3-(3-(ethylsulfonyl)phenoxy)propan-2-ol; Compound 262: (S)-1-((R)-8-(4'-((tert-butylamino)methyl)biphenyl-3-ylsulfonyl)-1-oxa-8-azaspiro[4.5]decan-3-ylamino)-3-(3-(1-(hydroxymethyl)cyclopropylsulfonyl)phenoxy)propan-2-ol; Compound 263: (S)-1-(3-(1-(hydroxymethyl)cyclopropylsulfonyl)phenoxy)-3-((R)-8-(4'-((tert-pentylamino)methyl)biphenyl-3-ylsulfonyl)-1-oxa-8-azaspiro[4.5]decan-3-ylamino)propan-2-ol; Compound 264: (S)-1-(3-(1-(hydroxymethyl)cyclopropylsulfonyl)phenoxy)-3-((R)-8-(4'-((2,2,2-trifluoroethylamino)methyl)biphenyl-3-ylsulfonyl)-1-oxa-8-azaspiro[4.5]decan-3-ylamino)propan-2-ol; Compound 265: (S)-1-((R)-8-(4'-(azetidin-1-ylmethyl)biphenyl-3-ylsulfonyl)-1-oxa-8-azaspiro[4.5]decan-3-ylamino)-3-(3-(1-(hydroxymethyl)cyclopropylsulfonyl)phenoxy)propan-2-ol; Compound 266: (S)-1-(3-(1-(hydroxymethyl)cyclopropylsulfonyl)phenoxy)-3-((R)-8-(4'-(morpholinomethyl)biphenyl-3-ylsulfonyl)-1-oxa-8-azaspiro[4.5]decan-3-ylamino)propan-2-ol; Compound 267: (S)-1-(3-(1-(hydroxymethyl)cyclopropylsulfonyl)phenoxy)-3-((R)-8-(4'-((2-methoxyethylamino)methyl)biphenyl-3-ylsulfonyl)-1-oxa-8-azaspiro[4.5]decan-3-ylamino)propan-2-ol; Compound 268: (S)-1-((R)-8-(4'-((ethylamino)methyl)biphenyl-3-ylsulfonyl)-1-oxa-8-azaspiro[4.5]decan-3-ylamino)-3-(3-(1-(hydroxymethyl)cyclopropylsulfonyl)phenoxy)propan-2-ol; Compound 269: (S)-1-((R)-8-(4'-((cyclobutylamino)methyl)biphenyl-3-ylsulfonyl)-1-oxa-8-azaspiro[4.5]decan-3-ylamino)-3-(3-(1-(hydroxymethyl)cyclopropylsulfonyl)phenoxy)propan-2-ol; Compound 270: (S)-1-((R)-8-(4'-((2-aminoethylamino)methyl)biphenyl-3-ylsulfonyl)-1-oxa-8-azaspiro[4.5]decan-3-ylamino)-3-(3-(1-(hydroxymethyl)cyclopropylsulfonyl)phenoxy)propan-2-ol; Compound 271: (S)-1-((R)-8-(4'-((3-aminopropylamino)methyl)biphenyl-3-ylsulfonyl)-1-oxa-8-azaspiro[4.5]decan-3-ylamino)-3-(3-(1-(hydroxymethyl)cyclopropylsulfonyl)phenoxy)propan-2-ol; Compound 272: (S)-1-(3-(1-(hydroxymethyl)cyclopropylsulfonyl)phenoxy)-3-((R)-8-(4'-((isobutylamino)methyl)biphenyl-3-ylsulfonyl)-1-oxa-8-azaspiro[4.5]decan-3-ylamino)propan-2-ol; Compound 273: (S)-1-(3-(cyclopropylsulfonyl)phenoxy)-3-((R)-8-(1-ethyl-2,3-dihydro-1H-pyrido[2,3-b][1,4]oxazin-7-ylsulfonyl)-1-oxa-8-azaspiro[4.5]decan-3-ylamino)propan-2-ol; Compound 274: (S)-1-(3-(cyclopropylsulfonyl)phenoxy)-3-((R)-8-((S)-1,3-dimethyl-2,3-dihydro-1H-pyrido[2,3-b][1,4]oxazin-7-ylsulfonyl)-1-oxa-8-azaspiro[4.5]decan-3-ylamino)propan-2-ol; Compound 275: (S)-1-(3-(cyclopropylsulfonyl)phenoxy)-3-((R)-8-(1,8-dimethyl-2,3-dihydro-1H-pyrido[2,3-b][1,4]oxazin-7-ylsulfonyl)-1-oxa-8-azaspiro[4.5]decan-3-ylamino)propan-2-ol; Compound 276: 2-(3-((S)-3-((R)-8-(1,8-dimethyl-2,3-dihydro-1H-pyrido[2,3-b][1,4]oxazin-7-ylsulfonyl)-1-oxa-8-azaspiro[4.5]decan-3-ylamino)-2-hydroxypropoxy)phenylsulfonyl)acetamide; Compound 277: (S)-1-(3-(cyclopropylsulfonyl)phenoxy)-3-((S)-8-((S)-1,3-dimethyl-2,3-dihydro-1H-pyrido[2,3-b][1,4]oxazin-7-ylsulfonyl)-1-oxa-8-azaspiro[4.5]decan-3-ylamino)propan-2-ol; Compound 278: 2-(3-((S)-3-((R)-8-((S)-1,3-dimethyl-2,3-dihydro-1H-pyrido[2,3-b][1,4]oxazin-7-ylsulfonyl)-1-oxa-8-azaspiro[4.5]decan-3-ylamino)-2-hydroxypropoxy)phenylsulfonyl)acetamide; Compound 279: (S)-1-(3-(cyclopropylsulfonyl)phenoxy)-3-((R)-8-(3-methyl-3H-imidazo[4,5-b]pyridin-6-ylsulfonyl)-1-oxa-8-azaspiro[4.5]decan-3-ylamino)propan-2-ol; Compound 280: 3-((R)-3-((S)-3-(3-(cyclopropylsulfonyl)phenoxy)-2-hydroxypropylamino)-1-oxa-8-azaspiro[4.5]decan-8-ylsulfonyl)-6,7-dihydro-5H-pyrrolo[3,4-b]pyridin-5-one; Compound 281: 6-((R)-3-((S)-3-(3-(cyclopropylsulfonyl)phenoxy)-2-hydroxypropylamino)-1-oxa-8-azaspiro[4.5]decan-8-ylsulfonyl)-1H-imidazo[4,5-b]pyridin-2(3H)-one; Compound 282: (S)-1-(3-(cyclopropylsulfonyl)phenoxy)-3-((R)-8-(5,6,7,8-tetrahydroquinolin-3-ylsulfonyl)-1-oxa-8-azaspiro[4.5]decan-3-ylamino)propan-2-ol; Compound 283: (S)-1-((R)-8-((R)-1,3-dimethyl-2,3-dihydro-1H-pyrido[2,3-b][1,4]oxazin-7-ylsulfonyl)-1-oxa-8-azaspiro[4.5]decan-3-ylamino)-3-(3-(1-(hydroxymethyl)cyclopropylsulfonyl)phenoxy)propan-2-ol; Compound 284: (S)-1-((R)-8-(3,4-dihydro-2H-pyrano[2,3-b]pyridin-6-ylsulfonyl)-1-oxa-8-azaspiro[4.5]decan-3-ylamino)-3-(3-(1-(hydroxymethyl)cyclopropylsulfonyl)phenoxy)propan-2-ol; Compound 285: (S)-1-((R)-8-(2,3-dihydro-[1,4]dioxino[2,3-b]pyridin-7-ylsulfonyl)-1-oxa-8-azaspiro[4.5]decan-3-ylamino)-3-(3-(1-(hydroxymethyl)cyclopropylsulfonyl)phenoxy)propan-2-ol; Compound 286: (S)-1-(3-(1-(hydroxymethyl)cyclopropylsulfonyl)phenoxy)-3-((R)-8-(4-methyl-3,4-dihydro-2H-pyrido[3,2-b][1,4]oxazin-7-ylsulfonyl)-1-oxa-8-azaspiro[4.5]decan-3-ylamino)propan-2-ol; Compound 287: (S)-1-(3-(1-(hydroxymethyl)cyclopropylsulfonyl)phenoxy)-3-((R)-8-(3-methyl-3H-imidazo[4,5-b]pyridin-5-ylsulfonyl)-1-oxa-8-azaspiro[4.5]decan-3-ylamino)propan-2-ol; Compound 288: (S)-1-(3-(1-(hydroxymethyl)cyclopropylsulfonyl)phenoxy)-3-((R)-8-(1,3,3-trimethyl-2,3-dihydro-1H-pyrido[2,3-b][1,4]oxazin-6-ylsulfonyl)-1-oxa-8-azaspiro[4.5]decan-3-ylamino)propan-2-ol; Compound 289: (S)-1-(3-(cyclopropylsulfonyl)phenoxy)-3-((R)-8-(2,3-dihydro-[1,4]dioxino[2,3-b]pyridin-7-ylsulfonyl)-1-oxa-8-azaspiro[4.5]decan-3-ylamino)propan-2-ol; Compound 290:

(S)-1-(3-(cyclopropylsulfonyl)phenoxy)-3-((R)-8-(4-methyl-3,4-dihydro-2H-pyrido[3,2-b][1,4]oxazin-7-ylsulfonyl)-1-oxa-8-azaspiro[4.5]decan-3-ylamino)propan-2-ol; Compound 291: (5)-1-(3-(cyclopropylsulfonyl)phenoxy)-3-((R)-8-(3,4-dihydro-2H-pyrano[2,3-b]pyridin-6-ylsulfonyl)-1-oxa-8-azaspiro[4.5]decan-3-ylamino)propan-2-ol; Compound 292: 1-ethyl-3-((R)-3-((S)-2-hydroxy-3-(3-(1-(hydroxymethyl)cyclopropylsulfonyl)phenoxy)propylamino)-1-oxa-8-azaspiro[4.5]decan-8-ylsulfonyl)quinolin-4(1H)-one; Compound 293: 1-ethyl-3-((S)-3-((S)-2-hydroxy-3-(3-(1-(hydroxymethyl)cyclopropylsulfonyl)phenoxy)propylamino)-1-oxa-8-azaspiro[4.5]decan-8-ylsulfonyl)quinolin-4(1H)-one; Compound 294: 1-ethyl-3-((R)-3-((S)-2-hydroxy-3-(3-(1-hydroxy-2-methylpropan-2-ylsulfonyl)phenoxy)propylamino)-1-oxa-8-azaspiro[4.5]decan-8-ylsulfonyl)quinolin-4(1H)-one; Compound 295: 3-((R)-3-((S)-2-hydroxy-3-(3-(1-(hydroxymethyl)cyclopropylsulfonyl)phenoxy)propylamino)-1-oxa-8-azaspiro[4.5]decan-8-ylsulfonyl)-1-methylquinolin-4(1H)-one; Compound 297: 3-((R)-3-((S)-3-(3-(cyclopropylsulfonyl)phenoxy)-2-hydroxypropylamino)-1-oxa-8-azaspiro[4.5]decan-8-ylsulfonyl)-1-ethylquinolin-4(1H)-one; Compound 298: 3-((R)-3-((S)-3-(3-(1,1-difluoro-2-hydroxyethylsulfonyl)phenoxy)-2-hydroxypropylamino)-1-oxa-8-azaspiro[4.5]decan-8-ylsulfonyl)-1-ethylquinolin-4(1H)-one; Compound 299: 1-ethyl-3-((3R)-3-((2S)-3-(3-(1-fluoroethylsulfonyl)phenoxy)-2-hydroxypropylamino)-1-oxa-8-azaspiro[4.5]decan-8-ylsulfonyl)quinolin-4(1H)-one; Compound 300: (S)-1-(3-(1-(hydroxymethyl)cyclopropylsulfonyl)phenoxy)-3-((R)-8-(naphthalen-2-ylsulfonyl)-1-oxa-8-azaspiro[4.5]decan-3-ylamino)propan-2-ol; Compound 301: (S)-1-((R)-8-(1-ethoxynaphthalen-2-ylsulfonyl)-1-oxa-8-azaspiro[4.5]decan-3-ylamino)-3-(3-(1-(hydroxymethyl)cyclopropylsulfonyl)phenoxy)propan-2-ol; Compound 302: (S)-1-(3-(1-(hydroxymethyl)cyclopropylsulfonyl)phenoxy)-3-((R)-8-(pyrrolo[1,2-a]pyrimidin-3-ylsulfonyl)-1-oxa-8-azaspiro[4.5]decan-3-ylamino)propan-2-ol; Compound 303: (S)-1-(3-(cyclopropylsulfonyl)phenoxy)-3-((R)-8-(2,3-dihydro-1H-pyrido[2,3-b][1,4]oxazin-7-ylsulfonyl)-1-oxa-8-azaspiro[4.5]decan-3-ylamino)propan-2-ol; Compound 304: (S)-1-(3-(cyclopropylsulfonyl)phenoxy)-3-((R)-8-(1-(2-methoxyethyl)-2,3-dihydro-1H-pyrido[2,3-b][1,4]oxazin-7-ylsulfonyl)-1-oxa-8-azaspiro[4.5]decan-3-ylamino)propan-2-ol; Compound 305: (S)-1-(3-(cyclopropylsulfonyl)phenoxy)-3-((R)-8-((R)-1,3-dimethyl-2,3-dihydro-1H-pyrido[2,3-b][1,4]oxazin-7-ylsulfonyl)-1-oxa-8-azaspiro[4.5]decan-3-ylamino)propan-2-ol; Compound 306: 1-ethyl-3-((R)-3-((S)-2-hydroxy-3-(3-(methoxymethylsulfonyl)phenoxy)propylamino)-1-oxa-8-azaspiro[4.5]decan-8-ylsulfonyl)quinolin-4(1H)-one; Compound 307: (S)-1-((R)-8-(1H-pyrrolo[2,3-b]pyridin-3-ylsulfonyl)-1-oxa-8-azaspiro[4.5]decan-3-ylamino)-3-(3-(cyclopropylsulfonyl)phenoxy)propan-2-ol; Compound 308: (S)-1-((R)-8-(1H-indol-3-ylsulfonyl)-1-oxa-8-azaspiro[4.5]decan-3-ylamino)-3-(3-(cyclopropylsulfonyl)phenoxy)propan-2-ol; Compound 309: (S)-1-((R)-8-(1H-pyrrolo[3,2-b]pyridin-6-ylsulfonyl)-1-oxa-8-azaspiro[4.5]decan-3-ylamino)-3-(3-(cyclopropylsulfonyl)phenoxy)propan-2-ol; Compound 310: 1-ethyl-3-((R)-3-((S)-2-hydroxy-3-(3-(methylsulfonyl)phenoxy)propylamino)-1-oxa-8-azaspiro[4.5]decan-8-ylsulfonyl)quinolin-4(1H)-one; Compound 311: (S)-1-((R)-8-(1H-indol-3-ylsulfonyl)-1-oxa-8-azaspiro[4.5]decan-3-ylamino)-3-(3-(methylsulfonyl)phenoxy)propan-2-ol; Compound 312: (S)-1-((R)-8-(1H-indol-3-ylsulfonyl)-1-oxa-8-azaspiro[4.5]decan-3-ylamino)-3-(3-(methoxymethylsulfonyl)phenoxy)propan-2-ol; Compound 313: 5-((R)-3-((S)-3-(3-(cyclopropylsulfonyl)phenoxy)-2-hydroxypropylamino)-1-oxa-8-azaspiro[4.5]decan-8-ylsulfonyl)-1H-pyrrolo[2,3-b]pyridin-2(3H)-one; Compound 314: 3-((R)-3-((S)-3-(3-(cyclopropylsulfonyl)phenoxy)-2-hydroxypropylamino)-1-oxa-8-azaspiro[4.5]decan-8-ylsulfonyl)-1-ethyl-6-fluoroquinolin-4(1H)-one; Compound 315: 3-((R)-3-((S)-3-(3-(cyclopropylsulfonyl)phenoxy)-2-hydroxypropylamino)-1-oxa-8-azaspiro[4.5]decan-8-ylsulfonyl)-1-ethyl-8-methylquinolin-4(1H)-one; Compound 316: 3-((R)-3-((S)-3-(3-(cyclopropylsulfonyl)phenoxy)-2-hydroxypropylamino)-1-oxa-8-azaspiro[4.5]decan-8-ylsulfonyl)-1-ethyl-7-fluoroquinolin-4(1H)-one; Compound 317: 3-((R)-3-((S)-3-(3-(cyclopropylsulfonyl)phenoxy)-2-hydroxypropylamino)-1-oxa-8-azaspiro[4.5]decan-8-ylsulfonyl)-1-ethyl-6-methylquinolin-4(1H)-one; Compound 318: 3-((R)-3-((S)-3-(3-(cyclopropylsulfonyl)phenoxy)-2-hydroxypropylamino)-1-oxa-8-azaspiro[4.5]decan-8-ylsulfonyl)-1-ethyl-7-methylquinolin-4(1H)-one; Compound 319: (S)-1-((R)-8-(1H-pyrazolo[4,3-b]pyridin-6-ylsulfonyl)-1-oxa-8-azaspiro[4.5]decan-3-ylamino)-3-(3-(cyclopropylsulfonyl)phenoxy)propan-2-ol; Compound 320: (S)-1-((R)-8-(1H-pyrrolo[3,2-b]pyridin-6-ylsulfonyl)-1-oxa-8-azaspiro[4.5]decan-3-ylamino)-3-(3-(methylsulfonyl)phenoxy)propan-2-ol; Compound 321: (S)-1-((R)-8-(1H-pyrrolo[3,2-b]pyridin-6-ylsulfonyl)-1-oxa-8-azaspiro[4.5]decan-3-ylamino)-3-(3-(isopropylsulfonyl)phenoxy)propan-2-ol; Compound 322: 1-ethyl-8-fluoro-3-((R)-3-((S)-2-hydroxy-3-(3-(methylsulfonyl)phenoxy)propylamino)-1-oxa-8-azaspiro[4.5]decan-8-ylsulfonyl)quinolin-4(1H)-one; Compound 323: 8-fluoro-3-((R)-3-((S)-2-hydroxy-3-(3-(isopropylsulfonyl)phenoxy)propylamino)-1-oxa-8-azaspiro[4.5]decan-8-ylsulfonyl)quinolin-4-ol; Compound 324: 3-((R)-3-((S)-3-(3-(cyclopropylsulfonyl)phenoxy)-2-hydroxypropylamino)-1-oxa-8-azaspiro[4.5]decan-8-ylsulfonyl)-6-methylquinolin-4-ol; Compound 325: 3-((R)-3-((S)-3-(3-(cyclopropylsulfonyl)phenoxy)-2-hydroxypropylamino)-1-oxa-8-azaspiro[4.5]decan-8-ylsulfonyl)-6-fluoroquinolin-4-ol; Compound 326: 3-((R)-3-((S)-3-(3-(cyclopropylsulfonyl)phenoxy)-2-hydroxypropylamino)-1-oxa-8-azaspiro[4.5]decan-8-ylsulfonyl)quinolin-4(1H)-one; Compound 327: 3-((R)-3-((S)-3-(3-(cyclopropylsulfonyl)phenoxy)-2-hydroxypropylamino)-1-oxa-8-azaspiro[4.5]decan-8-ylsulfonyl)-8-methylquinolin-4-ol; Compound 328: 3-((R)-3-((S)-3-(3-(cyclopropylsulfonyl)phenoxy)-2-hydroxypropylamino)-1-oxa-8-azaspiro[4.5]decan-8-ylsulfonyl)-8-fluoroquinolin-4-ol; Compound 329: 3-((R)-3-((S)-3-(3-(cyclopropylsulfonyl)phenoxy)-2-hydroxypropylamino)-1-oxa-8-azaspiro[4.5]decan-8-ylsulfonyl)-7-fluoroquinolin-4-ol; Compound 330: 3-((R)-3-((S)-3-(3-(cyclopropylsulfonyl)phenoxy)-2-hydroxypropylamino)-1-oxa-8-azaspiro[4.5]decan-8-ylsulfonyl)-7-methylquinolin-4-ol; Compound 331: 1-ethyl-8-fluoro-3-((R)-3-((S)-2-hydroxy-3-(3-(isopropylsulfonyl)phenoxy)propylamino)-1-oxa-8-azaspiro[4.5]decan-8-ylsulfonyl)quinolin-4(1H)-one; Compound 332: 1-ethyl-3-((R)-3-((S)-2-hydroxy-3-(3-(isopropylsulfonyl)phenoxy)propylamino)-1-oxa-8-azaspiro[4.5]decan-8-ylsulfonyl)quinolin-4(1H)-one; Compound 333: 3-((R)-3-((S)-3-(3-(cyclopropylsulfonyl)phenoxy)-2-hydroxypropylamino)-1-oxa-8-azaspiro[4.5]decan-8-ylsulfonyl)-1-ethyl-8-fluoroquinolin-4(1H)-one; Compound 334: (2S)-1-(4-(methylsulfonyl)phenoxy)-3-(8-(naphthalen-2-ylsulfonyl)-1-oxa-8-azaspiro[4.5]decan-3-ylamino)propan-2-ol; Compound 335: (2S)-1-(3-(methylsulfonylmethyl)phenoxy)-3-(8-(naphthalen-2-ylsulfonyl)-1-oxa-8-azaspiro[4.5]decan-3-ylamino)propan-2-ol; Compound 336: (S)-1-(3-

(methylsulfonylmethyl)phenoxy)-3-((R)-8-(quinolin-6-ylsulfonyl)-1-oxa-8-azaspiro[4.5]decan-3-ylamino)propan-2-ol; Compound 337: 1-ethyl-3-((R)-3-((R)-2-hydroxy-3-(3-(methylsulfonyl)propylamino)-1-oxa-8-azaspiro[4.5]decan-8-ylsulfonyl)quinolin-4(1H)-one; and Compound 338: 1-ethyl-3-((S)-3-((S)-2-hydroxy-3-(3-(methylsulfonyl)phenoxy)propylamino)-1-oxa-8-azaspiro[4.5]decan-8-ylsulfonyl)quinolin-4(1H)-one.

Additionally, chemical genera of the present invention and individual compounds, for example those compounds found in the above list and Table A, including diastereoisomers and enantiomers thereof, encompass all pharmaceutically acceptable salts, solvates, hydrates, and N-oxides thereof.

The compounds of Formula (Ia) of the present invention may be prepared according to relevant published literature procedures that are used by one skilled in the art. Exemplary reagents and procedures for these reactions appear hereinafter in the working Examples. Protection and deprotection may be carried out by procedures generally known in the art (see, for example, Greene, T. W. and Wuts, P. G. M., *Protecting Groups in Organic Synthesis*, 3$^{rd}$ Edition, 1999 [Wiley]).

It is understood that the present invention embraces each isomer, each diastereoisomer, each enantiomer and mixtures thereof of each compound and generic formulae disclosed herein just as if they were each individually disclosed with the specific stereochemical designation for each chiral carbon. Individual isomers and enantiomers can be prepared by selective synthesis, such as, by enantiomeric selective syntheses; or they can be obtained using separation techniques which are well known to practitioners in the art, such as, by HPLC (including, normal phase, reverse phase, and chiral), recrystallization (i.e., diastereoisomeric mixtures) and the like techniques.

Disorders and Methods of Treatment

The compounds disclosed herein are useful in the treatment or prevention of several diseases, disorders, conditions, and/or indications (which are cumulatively referred to herein as "disorders"). One of skill in the art will recognize that when a disorder, or a method of treatment or prevention, is disclosed herein, such disclosure encompasses second medical uses (e.g., a compound for use in the treatment of the disorder, use of a compound for the treatment of the disorder, and use of a compound in the manufacture of a medicament for the treatment of the disorder).

In some embodiments, the compounds disclosed herein are useful for the treatment or prevention of a disorder. In some embodiments, the compounds disclosed herein are useful for the treatment or prevention of a subtype of a disorder. In some embodiments, the compounds disclosed herein are useful for the treatment or prevention of a symptom of a disorder.

Provided herein are methods for treating or preventing a beta-3 adrenergic receptor-mediated disorder. In some embodiments, the compounds disclosed herein are useful for the prevention of a beta-3 adrenergic receptor-mediated disorder. In some embodiments, the compounds disclosed herein are useful for the treatment or prevention of a beta-3 adrenergic receptor-mediated disorder.

One aspect of the present invention relates to methods for treating or preventing a beta-3 adrenergic receptor-mediated disorder in an individual, comprising administering to the individual in need thereof, a therapeutically effective amount of a compound of the present invention; a pharmaceutical product of the present invention; or a pharmaceutical composition of the present invention.

One aspect of the present invention relates to methods for treating or preventing heart failure in an individual, comprising administering to the individual in need thereof, a therapeutically effective amount of a compound of the present invention; a pharmaceutical product of the present invention; or a pharmaceutical composition of the present invention.

One aspect of the present invention relates to methods for treating a hypotensive patient or a borderline hypotensive patient, comprising administering to the patient in need thereof, a therapeutically effective amount of a compound of the present invention; a pharmaceutical product of the present invention; or a pharmaceutical composition of the present invention. One aspect of the present invention relates to uses of a compound of the present invention in the manufacture of a medicament for treating or preventing a beta-3 adrenergic receptor-mediated disorder in an individual.

One aspect of the present invention relates to uses of a compound of the present invention in the manufacture of a medicament for treating or preventing heart failure in an individual.

One aspect of the present invention relates to uses of a compound of the present invention in the manufacture of a medicament for treating a hypotensive patient or a borderline hypotensive patient.

One aspect of the present invention relates to uses of a compound of the present invention in the manufacture of a medicament for treating a normotensive patient.

One aspect of the present invention relates to uses of a compound of the present invention in the manufacture of a medicament for treating a hypertensive patient.

One aspect of the present invention relates to uses of a compound of the present invention in the manufacture of a medicament for treating a patient following myocardial infarction.

One aspect of the present invention relates to compounds of the present invention; a pharmaceutical product of the present invention; or a pharmaceutical composition of the present invention; for use in a method of treatment of the human or animal body by therapy.

One aspect of the present invention relates to compounds of the present invention; pharmaceutical products of the present invention; or pharmaceutical compositions of the present invention; for use in a method for treating or preventing a beta-3 adrenergic receptor-mediated disorder in an individual.

In some embodiments, the beta-3 adrenergic receptor-mediated disorder is selected from the list consisting of: heart failure; reduced cardiac performance in heart failure; mortality, reinfarction, and/or hospitalization in connection with heart failure; acute heart failure; acute decompensated heart failure; congestive heart failure; severe congestive heart failure; organ damage associated with heart failure (e.g., kidney damage or failure, heart valve problems, heart rhythm problems, and/or liver damage); heart failure due to left ventricular dysfunction; heart failure with normal ejection fraction; cardiovascular mortality following myocardial infarction; cardiovascular mortality in patients with left ventricular failure or left ventricular dysfunction; a condition following myocardial infarction; left ventricular failure; left ventricular dysfunction; class II heart failure using the New York Heart Association (NYHA) classification system; class III heart failure using the New York Heart Association (NYHA) classification system; class IV heart failure using the New York Heart Association (NYHA) classification system; LVEF<40% by radionuclide ventriculography; and LVEF≤35% by echocardiography or ventricular contrast angiography.

In some embodiments, the beta-3 adrenergic receptor-mediated disorder is heart failure.

In some embodiments, the beta-3 adrenergic receptor-mediated disorder is reduced cardiac performance in heart failure.

In some embodiments, the beta-3 adrenergic receptor-mediated disorder is mortality, reinfarction, and/or hospitalization in connection with heart failure.

In some embodiments, the beta-3 adrenergic receptor-mediated disorder is acute heart failure.

In some embodiments, the beta-3 adrenergic receptor-mediated disorder is acute decompensated heart failure.

In some embodiments, the beta-3 adrenergic receptor-mediated disorder is congestive heart failure.

In some embodiments, the beta-3 adrenergic receptor-mediated disorder is severe congestive heart failure.

In some embodiments, the beta-3 adrenergic receptor-mediated disorder is organ damage associated with heart failure (e.g., kidney damage or failure, heart valve problems, heart rhythm problems, and/or liver damage).

In some embodiments, the beta-3 adrenergic receptor-mediated disorder is heart failure due to left ventricular dysfunction.

In some embodiments, the beta-3 adrenergic receptor-mediated disorder is heart failure with normal ejection fraction.

In some embodiments, the beta-3 adrenergic receptor-mediated disorder is cardiovascular mortality following myocardial infarction.

In some embodiments, the beta-3 adrenergic receptor-mediated disorder is cardiovascular mortality in patients with left ventricular failure or left ventricular dysfunction.

In some embodiments, the beta-3 adrenergic receptor-mediated disorder is following myocardial infarction.

In some embodiments, the beta-3 adrenergic receptor-mediated disorder is left ventricular failure.

In some embodiments, the beta-3 adrenergic receptor-mediated disorder is left ventricular dysfunction.

Doctors can classify the patient's heart failure according to the severity of their symptoms. The table below describes the most commonly used classification system, the New York Heart Association (NYHA) Functional Classification. It places patients in one of four categories based on how much they are limited during physical activity.

| Class | Patient Symptoms |
|---|---|
| I | No limitation of physical activity. Ordinary physical activity does not cause undue fatigue, palpitation, dyspnea (shortness of breath). |
| II | Slight limitation of physical activity. Comfortable at rest. Ordinary physical activity results in fatigue, palpitation, dyspnea (shortness of breath). |
| III | Marked limitation of physical activity. Comfortable at rest. Less than ordinary activity causes fatigue, palpitation, or dyspnea. |
| IV | Unable to carry on any physical activity without discomfort. Symptoms of heart failure at rest. If any physical activity is undertaken, discomfort increases. |

Accordingly, in some embodiments, the beta-3 adrenergic receptor-mediated disorder is class II heart failure using the New York Heart Association (NYHA) classification system.

In some embodiments, the beta-3 adrenergic receptor-mediated disorder is class III heart failure using the New York Heart Association (NYHA) classification system.

In some embodiments, the beta-3 adrenergic receptor-mediated disorder is class IV heart failure using the New York Heart Association (NYHA) classification system.

In some embodiments, the beta-3 adrenergic receptor-mediated disorder is LVEF<40% by radionuclide ventriculography.

In some embodiments, the beta-3 adrenergic receptor-mediated disorder is LVEF≤35% by echocardiography or ventricular contrast angiography.

Polymorphs and Pseudopolymorphs

Polymorphism is the ability of a substance to exist as two or more crystalline phases that have different arrangements and/or conformations of the molecules in the crystal lattice. Polymorphs show the same properties in the liquid or gaseous state but they behave differently in the solid state.

Besides single-component polymorphs, drugs can also exist as salts and other multicomponent crystalline phases. For example, solvates and hydrates may contain an API host and either solvent or water molecules, respectively, as guests. Analogously, when the guest compound is a solid at room temperature, the resulting form is often called a cocrystal. Salts, solvates, hydrates, and cocrystals may show polymorphism as well. Crystalline phases that share the same API host, but differ with respect to their guests, may be referred to as pseudopolymorphs of one another.

Solvates contain molecules of the solvent of crystallization in a definite crystal lattice. Solvates, in which the solvent of crystallization is water, are termed hydrates. Because water is a constituent of the atmosphere, hydrates of drugs may be formed rather easily.

By way of example, Stably published a polymorph screen of 245 compounds consisting of a "wide variety of structural types" that revealed about 90% of them exhibited multiple solid forms. Overall, approximately half of the compounds were polymorphic, often having one to three forms. About one-third of the compounds formed hydrates, and about one-third formed solvates. Data from cocrystal screens of 64 compounds showed that 60% formed cocrystals other than hydrates or solvates. (G. P. Stahly, *Crystal Growth & Design* (2007), 7(6), 1007-1026).

Isotopes

The present disclosure includes all isotopes of atoms occurring in the compounds provided herein. Isotopes include those atoms having the same atomic number but different mass numbers. It is appreciated that certain features of the invention(s) include every combination of one or more atoms in the compounds provided herein that is replaced with an atom having the same atomic number but a different mass number. One such example is the replacement of an atom that is the most naturally abundant isotope, such as $^1H$ or $^{12}C$, found in one of the compounds provided herein with a different atom that is not the most naturally abundant isotope, such as $^2H$ or $^3H$ (replacing $^1H$), or $^{11}C$, $^{13}C$, or $^{14}C$ (replacing $^{12}C$). A compound wherein such a replacement has taken place is commonly referred to as being isotopically-labeled. Isotopic-labeling of the present compounds can be accomplished using any one of a variety of different synthetic methods know to those of ordinary skill in the art and they are readily credited with understanding the synthetic methods and available reagents needed to conduct such isotopic-labeling. By way of general example, and without limitation, isotopes of hydrogen include $^2H$ (deuterium) and $^3H$ (tritium). Isotopes of carbon include $^{11}C$, $^{13}C$, and $^{14}C$. Isotopes of nitrogen include $^{13}N$ and $^{15}N$.

Isotopes of oxygen include $^{15}O$, $^{17}O$, and $^{18}O$. An isotope of fluorine includes $^{18}F$. An isotope of sulfur includes $^{35}S$. An isotope of chlorine includes $^{36}Cl$. Isotopes of bromine include $^{75}Br$, $^{76}Br$, $^{77}Br$, and $^{82}Br$. Isotopes of iodine include $^{123}I$, $^{124}I$, $^{125}I$, and $^{131}I$. Also provided are compositions, such as, those prepared during synthesis, preformulation, and the like, and pharmaceutical compositions, such as, those prepared with the intent of using in a mammal for the treatment of one or more of the disorders described herein, comprising one or more of the present compounds, wherein the naturally occurring distribution of the isotopes in the composition is perturbed. Also provided herein are compositions and pharmaceutical compositions comprising compounds of the invention as described herein, wherein the salt is enriched at one or more positions with an isotope other than the most naturally abundant isotope. Methods are readily available to measure such isotope perturbations or enrichments, such as, mass spectrometry, and for isotopes that are radio-isotopes additional methods are available, such as, radio-detectors used in connection with HPLC or GC.

One challenge in drug development is improving absorption, distribution, metabolism, excretion, and toxicity (ADMET) properties while maintaining a desired pharmacological profile. Structural changes to improve ADMET properties often alter the pharmacology of a lead compound. While the effects of deuterium substitution on ADMET properties are unpredictable, in select cases deuterium can improve a compound's ADMET properties with minimal perturbation of its pharmacology. Two examples where deuterium has enabled improvements in therapeutic entities are: CTP-347 and CTP-354. CTP-347 is a deuterated version of paroxetine with a reduced liability for mechanism-based inactivation of CYP2D6 that is observed clinically with paroxetine. CTP-354 is a deuterated version of a promising preclinical gamma-aminobutyric acid A receptor (GABAA) modulator (L-838417) that was not developed due to poor pharmacokinetic (PK) properties. In both cases, deuterium substitution resulted in improved ADMET profiles that provide the potential for improved safety, efficacy, and/or tolerability without significantly altering the biochemical potency and selectivity versus the all-hydrogen compounds. Provided are deuterium substituted compounds of the present invention with improved ADMET profiles and substantially similar biochemical potency and selectivity versus the corresponding all-hydrogen compounds.

OTHER UTILITIES

Another object of the present invention relates to radio-labeled compounds of the present invention that would be useful not only in radio-imaging but also in assays, both in vitro and in vivo, for localizing and quantitating beta-3 adrenergic receptors in tissue samples, including human and for identifying beta-3 adrenergic receptor ligands by inhibition binding of a radio-labeled compound. It is a further object of this invention to develop novel beta-3 adrenergic receptor assays of which comprise such radio-labeled compounds.

The present disclosure includes all isotopes of atoms occurring in the present compounds, intermediates, salts and crystalline forms thereof. Isotopes include those atoms having the same atomic number but different mass numbers. One aspect of the present invention includes every combination of one or more atoms in the present compounds, intermediates, salts, and crystalline forms thereof that is replaced with an atom having the same atomic number but a different mass number. One such example is the replacement of an atom that is the most naturally abundant isotope, such as $^1H$ or $^{12}C$, found in one the present compounds, intermediates, salts, and crystalline forms thereof, with a different atom that is not the most naturally abundant isotope, such as $^2H$ or $^3H$ (replacing $^1H$), or $^{11}C$, $^{13}C$, or $^{14}C$ (replacing $^{12}C$). A compound wherein such a replacement has taken place is commonly referred to as being an isotopically-labeled compound. Isotopic-labeling of the present compounds, intermediates, salts, and crystalline forms thereof can be accomplished using any one of a variety of different synthetic methods know to those of ordinary skill in the art and they are readily credited with understanding the synthetic methods and available reagents needed to conduct such isotopic-labeling. By way of general example, and without limitation, isotopes of hydrogen include $^2H$ (deuterium) and $^3H$ (tritium). Isotopes of carbon include 11C, $^{13}C$, and $^{14}C$. Isotopes of nitrogen include $^{13}N$ and $^{15}N$. Isotopes of oxygen include $^{15}O$, $^{17}O$, and $^{18}O$. An isotope of fluorine includes $^{18}F$. An isotope of sulfur includes $^{35}S$. An isotope of chlorine includes $^{36}Cl$. Isotopes of bromine include $^{75}Br$, $^{76}Br$, $^{77}Br$, and $^{82}Br$. Isotopes of iodine include $^{123}I$, $^{124}I$, $^{125}I$, and $^{131}I$. Another aspect of the present invention includes compositions, such as, those prepared during synthesis, preformulation, and the like, and pharmaceutical compositions, such as, those prepared with the intent of using in a mammal for the treatment of one or more of the disorders described herein, comprising one or more of the present compounds, intermediates, salts, and crystalline forms thereof, wherein the naturally occurring distribution of the isotopes in the composition is perturbed. Another aspect of the present invention includes compositions and pharmaceutical compositions comprising compounds as described herein wherein the compound is enriched at one or more positions with an isotope other than the most naturally abundant isotope. Methods are readily available to measure such isotope perturbations or enrichments, such as, mass spectrometry, and for isotopes that are radio-isotopes additional methods are available, such as, radio-detectors used in connection with HPLC or GC.

Certain isotopically-labeled compounds of the present invention are useful in compound and/or substrate tissue distribution assays. In some embodiments the radionuclide $^3H$ and/or $^{14}C$ isotopes are useful in these studies. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labeled compounds of the present invention can generally be prepared by following procedures analogous to those disclosed in the Drawings and Examples infra, by substituting an isotopically labeled reagent for a non-isotopically labeled reagent. Other synthetic methods that are useful are discussed infra. Moreover, it should be understood that all of the atoms represented in the compounds of the invention can be either the most commonly occurring isotope of such atoms or the scarcer radio-isotope or nonradioactive isotope.

Synthetic methods for incorporating radio-isotopes into organic compounds are applicable to compounds of the invention and are well known in the art. Representative synthetic methods for incorporating activity levels of tritium into target molecules include, for example:

A. Catalytic Reduction with Tritium Gas: This procedure normally yields high specific activity products and requires halogenated or unsaturated precursors.

B. Reduction with Sodium Borohydride [$^3$H]: This procedure is rather inexpensive and requires precursors containing reducible functional groups such as aldehydes, ketones, lactones, esters and the like.

C. Reduction with Lithium Aluminum Hydride [$^3$H]: This procedure offers products at almost theoretical specific activities. It also requires precursors containing reducible functional groups such as aldehydes, ketones, lactones, esters and the like.

D. Tritium Gas Exposure Labeling: This procedure involves exposing precursors containing exchangeable protons to tritium gas in the presence of a suitable catalyst.

E. N-Methylation using Methyl Iodide [$^3$H]: This procedure is usually employed to prepare O-methyl or N-methyl ($^3$H) products by treating appropriate precursors with high specific activity methyl iodide ($^3$H). This method in general allows for higher specific activity, such as for example, about 70-90 Ci/mmol.

Synthetic methods for incorporating activity levels of $^{125}$I into target molecules include:

A. Sandmeyer and like reactions: This procedure transforms an aryl amine or a heteroaryl amine into a diazonium salt, such as a diazonium tetrafluoroborate salt and subsequently to $^{125}$I labeled compound using Na$^{125}$I. A representative procedure was reported by Zhu, G-D. and co-workers in *J. Org. Chem.*, 2002, 67, 943-948.

B. Ortho $^{125}$Iodination of phenols: This procedure allows for the incorporation of $^{125}$I at the ortho position of a phenol as reported by Collier, T. L. and co-workers in *J. Labelled Compd. Radiopharm.*, 1999, 42, S264-S266.

C. Aryl and heteroaryl bromide exchange with $^{125}$I: This method is generally a two step process. The first step is the conversion of the aryl or heteroaryl bromide to the corresponding tri-alkyltin intermediate using for example, a Pd catalyzed reaction [i.e. Pd(Ph$_3$P)$_4$] or through an aryl or heteroaryl lithium, in the presence of a tri-alkyltinhalide or hexaalkylditin [e.g., (CH$_3$)$_3$SnSn(CH$_3$)$_3$]. A representative procedure was reported by Le Bas, M.-D. and co-workers in *J. Labelled Compd. Radiopharm.* 2001, 44, S280-S282.

A radiolabeled beta-3 adrenergic receptor compound of Formula (Ia) can be used in a screening assay to identify/evaluate compounds. In general terms, a newly synthesized or identified compound (i.e., test compound) can be evaluated for its ability to reduce binding of the "radiolabeled compound of Formula (Ia)" to a beta-3 adrenergic receptor. Accordingly, the ability of a test compound to compete with the "radiolabeled compound of Formula (Ia)" for the binding to a beta-3 adrenergic receptor directly correlates to its binding affinity.

Certain labeled compounds of the present invention bind to certain beta-3 adrenergic receptors. In one embodiment the labeled compound has an IC$_{50}$ less than about 500 µM, in another embodiment the labeled compound has an IC$_{50}$ less than about 100 µM, in yet another embodiment the labeled compound has an IC$_{50}$ less than about 10 µM, in yet another embodiment the labeled compound has an IC$_{50}$ less than about 1 µM and in still yet another embodiment the labeled compound has an IC$_{50}$ less than about 0.1 µM.

Compositions and Formulations

Formulations may be prepared by any suitable method, typically by uniformly mixing the active compound(s) with liquids or finely divided solid carriers, or both, in the required proportions and then, if necessary, forming the resulting mixture into a desired shape.

Conventional excipients, such as binding agents, fillers, acceptable wetting agents, tabletting lubricants and disintegrants may be used in tablets and capsules for oral administration. Liquid preparations for oral administration may be in the form of solutions, emulsions, aqueous or oily suspensions and syrups. Alternatively, the oral preparations may be in the form of dry powder that can be reconstituted with water or another suitable liquid vehicle before use. Additional additives such as suspending or emulsifying agents, non-aqueous vehicles (including edible oils), preservatives and flavorings and colorants may be added to the liquid preparations. Parenteral dosage forms may be prepared by dissolving the compound provided herein in a suitable liquid vehicle and filter sterilizing the solution before filling and sealing an appropriate vial or ampule. These are just a few examples of the many appropriate methods well known in the art for preparing dosage forms.

A compound of the present invention can be formulated into pharmaceutical compositions using techniques well known to those in the art. Suitable pharmaceutically-acceptable carriers, outside those mentioned herein, are known in the art; for example, see Remington, The Science and Practice of Pharmacy, 20th Edition, 2000, Lippincott Williams & Wilkins, (Editors: Gennaro et. al.).

While it is possible that, for use in the prophylaxis or treatment, a compound provided herein may, in an alternative use, be administered as a raw or pure chemical, it is preferable however to present the compound or active ingredient as a pharmaceutical formulation or composition further comprising a pharmaceutically acceptable carrier.

Pharmaceutical formulations include those suitable for oral, rectal, nasal, topical (including buccal and sub-lingual), vaginal or parenteral (including intramuscular, sub-cutaneous and intravenous) administration or in a form suitable for administration by inhalation, insufflation or by a transdermal patch. Transdermal patches dispense a drug at a controlled rate by presenting the drug for absorption in an efficient manner with minimal degradation of the drug. Typically, transdermal patches comprise an impermeable backing layer, a single pressure sensitive adhesive and a removable protective layer with a release liner. One of ordinary skill in the art will understand and appreciate the techniques appropriate for manufacturing a desired efficacious transdermal patch based upon the needs of the artisan.

The compounds provided herein, together with a conventional adjuvant, carrier, or diluent, may thus be placed into the form of pharmaceutical formulations and unit dosages thereof and in such form may be employed as solids, such as tablets or filled capsules, or liquids such as solutions, suspensions, emulsions, elixirs, gels or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles and such unit dosage forms may contain any suitable effective amount of the active ingredient commensurate with the intended daily dosage range to be employed.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are capsules, tablets, powders, granules or a suspension, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethyl-cellulose; and with lubricants such as talc or magnesium stearate. The active ingredient may also be administered by injection as a composition wherein, for example, saline, dextrose or water may be used as a suitable pharmaceutically acceptable carrier.

Compounds provided herein or a salt, solvate, or hydrate thereof can be used as active ingredients in pharmaceutical compositions, specifically as beta-3 adrenergic receptor modulators. The term "active ingredient", defined in the context of a "pharmaceutical composition", refers to a component of a pharmaceutical composition that provides the primary pharmacological effect, as opposed to an "inactive ingredient" which would generally be recognized as providing no pharmaceutical benefit.

The dose when using the compounds provided herein can vary within wide limits and as is customary and is known to the physician or other clinician, it is to be tailored to the individual conditions in each individual case. It depends, for example, on the nature and severity of the illness to be treated, on the condition of the patient, on the compound employed or on whether an acute or chronic disease state is treated, or prophylaxis conducted, or on whether further active compounds are administered in addition to the compounds provided herein. Representative doses include, but are not limited to, about 0.001 mg to about 5000 mg, about 0.001 mg to about 2500 mg, about 0.001 mg to about 1000 mg, about 0.001 mg to about 500 mg, about 0.001 mg to about 250 mg, about 0.001 mg to 100 mg, about 0.001 mg to about 50 mg and about 0.001 mg to about 25 mg. Multiple doses may be administered during the day, especially when relatively large amounts are deemed to be needed, for example 2, 3, or 4 doses. Depending on the individual and as deemed appropriate from the healthcare provider it may be necessary to deviate upward or downward from the doses described herein.

The amount of active ingredient, or an active salt or derivative thereof, required for use in treatment will vary not only with the particular salt selected but also with the route of administration, the nature of the condition being treated and the age and condition of the patient and will ultimately be at the discretion of the attendant physician or clinician. In general, one skilled in the art understands how to extrapolate in vivo data obtained in a model system, typically an animal model, to another, such as a human. In some circumstances, these extrapolations may merely be based on the weight of the animal model in comparison to another, such as a mammal, preferably a human, however, more often, these extrapolations are not simply based on weights, but rather incorporate a variety of factors. Representative factors include the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized, on whether an acute or chronic disease state is being treated, or prophylaxis conducted, or on whether further active compounds are administered in addition to the compounds provided herein and as part of a drug combination. The dosage regimen for treating a disease condition with the compounds and/or compositions provided herein is selected in accordance with a variety factors as cited above. Thus, the actual dosage regimen employed may vary widely and therefore may deviate from a preferred dosage regimen and one skilled in the art will recognize that dosage and dosage regimen outside these typical ranges can be tested and, where appropriate, may be used in the methods provided herein.

The desired dose may conveniently be presented in a single dose or as divided doses administered at appropriate intervals, for example, as two, three, four, or more sub-doses per day. The sub-dose itself may be further divided, e.g., into a number of discrete loosely spaced administrations.

The daily dose can be divided, especially when relatively large amounts are administered as deemed appropriate, into several, for example two, three, or four-part administrations. If appropriate, depending on individual behavior, it may be necessary to deviate upward or downward from the daily dose indicated.

The compounds provided herein can be administered in a wide variety of oral and parenteral dosage forms. It will be obvious to those skilled in the art that the dosage forms may comprise, as the active component, either a compound provided herein or a pharmaceutically acceptable salt, hydrate, or solvate of a compound provided herein.

For preparing pharmaceutical compositions from the compounds provided herein, the selection of a suitable pharmaceutically acceptable carrier can be either solid, liquid or a mixture of both. Solid form preparations include powders, tablets, pills, capsules, cachets, suppositories and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is admixed with the carrier having the necessary binding capacity in suitable proportions and compacted to the desire shape and size.

The powders and tablets may contain varying percentage amounts of the active compound. A representative amount in a powder or tablet may contain from 0.5 to about 90 percent of the active compound; however, an artisan would know when amounts outside of this range are necessary. Suitable carriers for powders and tablets are magnesium carbonate, magnesium stearate, talc, sugar, lactose, pectin, dextrin, starch, gelatin, tragacanth, methylcellulose, sodium carboxymethyl cellulose, a low melting wax, cocoa butter and the like. The term "preparation" refers to the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as an admixture of fatty acid glycerides or cocoa butter, is first melted and the active component is dispersed homogeneously therein, as by stirring. The molten homogenous mixture is then poured into convenient sized molds, allowed to cool and thereby to solidify.

Formulations suitable for vaginal administration may be presented as pessaries, tampons, creams, gels, pastes, foams, or sprays containing in addition to the active ingredient such carriers as are known in the art to be appropriate.

Liquid form preparations include solutions, suspensions, and emulsions, for example, water or water-propylene glycol solutions. For example, parenteral injection liquid preparations can be formulated as solutions in aqueous polyethylene glycol solution. Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds provided herein may thus be formulated for parenteral administration (e.g. by injection, for example bolus injection or continuous infusion) and may be presented in unit dose form in ampoules, pre-filled syringes, small volume infusion or in multi-dose containers with an added preservative. The pharmaceutical compositions may take such forms as suspensions, solutions, or emulsions in oily or aqueous vehicles and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous formulations suitable for oral use can be prepared by dissolving or suspending the active component in water and adding suitable colorants, flavors, stabilizing and thickening agents, as desired.

Aqueous suspensions suitable for oral use can be made by dispersing the finely divided active component in water with viscous material, such as natural or synthetic gums, resins, methylcellulose, sodium carboxymethyl cellulose, or other well-known suspending agents.

Also included are solid form preparations which are intended to be converted, shortly before use, to liquid form preparations for oral administration. Such liquid forms include solutions, suspensions and emulsions. These preparations may contain, in addition to the active component, colorants, flavors, stabilizers, buffers, artificial and natural sweeteners, dispersants, thickeners, solubilizing agents and the like.

For topical administration to the epidermis the compounds provided herein may be formulated as ointments, creams or lotions, or as a transdermal patch.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents.

Formulations suitable for topical administration in the mouth include lozenges comprising active agent in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multi-dose form. In the latter case of a dropper or pipette, this may be achieved by the patient administering an appropriate, predetermined volume of the solution or suspension. In the case of a spray, this may be achieved for example by means of a metering atomizing spray pump.

Administration to the respiratory tract may also be achieved by means of an aerosol formulation in which the active ingredient is provided in a pressurized pack with a suitable propellant. If the compounds provided herein or pharmaceutical compositions comprising them are administered as aerosols, for example as nasal aerosols or by inhalation, this can be carried out, for example, using a spray, a nebulizer, a pump nebulizer, an inhalation apparatus, a metered inhaler or a dry powder inhaler. Pharmaceutical forms for administration of the compounds provided herein as an aerosol can be prepared by processes well known to the person skilled in the art. For their preparation, for example, solutions or dispersions of the compounds provided herein in water, water/alcohol mixtures or suitable saline solutions can be employed using customary additives, for example benzyl alcohol or other suitable preservatives, absorption enhancers for increasing the bioavailability, solubilizers, dispersants and others and, if appropriate, customary propellants, for example include carbon dioxide, CFCs, such as, dichlorodifluoromethane, trichlorofluoromethane, or dichlorotetrafluoroethane; and the like. The aerosol may conveniently also contain a surfactant such as lecithin. The dose of drug may be controlled by provision of a metered valve.

In formulations intended for administration to the respiratory tract, including intranasal formulations, the compound will generally have a small particle size for example of the order of 10 microns or less. Such a particle size may be obtained by means known in the art, for example by micronization. When desired, formulations adapted to give sustained release of the active ingredient may be employed.

Alternatively the active ingredients may be provided in the form of a dry powder, for example, a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration are preferred compositions.

The compounds provided herein may optionally exist as pharmaceutically acceptable salts including pharmaceutically acceptable acid addition salts prepared from pharmaceutically acceptable non-toxic acids including inorganic and organic acids. Representative acids include, but are not limited to, acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfiric, tartaric, oxalic, p-toluenesulfonic and the like. Certain compounds provided herein which contain a carboxylic acid functional group may optionally exist as pharmaceutically acceptable salts containing non-toxic, pharmaceutically acceptable metal cations and cations derived from organic bases. Representative metals include, but are not limited to, aluminium, calcium, lithium, magnesium, potassium, sodium, zinc and the like. In some embodiments the pharmaceutically acceptable metal is sodium. Representative organic bases include, but are not limited to, benzathine ($N^1,N^2$-dibenzylethane-1,2-diamine), chloroprocaine (2-(diethylamino)ethyl 4-(chloroamino)benzoate), choline, diethanolamine, ethylenediamine, meglumine ((2R,3R,4R,5S)-6-(methylamino)hexane-1,2,3,4,5-pentaol), procaine (2-(diethylamino)ethyl 4-aminobenzoate), and the like. Certain pharmaceutically acceptable salts are listed in Berge, et. al., Journal of Pharmaceutical Sciences, 66:1-19 (1977).

The acid addition salts may be obtained as the direct products of compound synthesis. In the alternative, the free base may be dissolved in a suitable solvent containing the appropriate acid and the salt isolated by evaporating the solvent or otherwise separating the salt and solvent. The compounds provided herein may form solvates with standard low molecular weight solvents using methods known to the skilled artisan.

Compounds provided herein can be converted to "pro-drugs." The term "pro-drugs" refers to compounds that have been modified with specific chemical groups known in the art and when administered into an individual these groups undergo biotransformation to give the parent compound. Pro-drugs can thus be viewed as compounds provided herein containing one or more specialized non-toxic protective groups used in a transient manner to alter or to eliminate a property of the compound. In one general aspect, the "pro-drug" approach is utilized to facilitate oral absorption. A thorough discussion is provided in T. Higuchi and V. Stella, Pro-drugs as Novel Delivery Systems Vol. 14 of the A.C.S. Symposium Series; and in Bioreversible Carriers in Drug Design, ed. Edward B. Roche, American Pharmaceutical Association and Pergamon Press, 1987.

Some embodiments include a method of producing a pharmaceutical composition for "combination-therapy" comprising admixing at least one compound according to any of the compound embodiments disclosed herein, together with at least one known pharmaceutical agent and a pharmaceutically acceptable carrier.

It is noted that when the beta-3 adrenergic receptor modulators are utilized as active ingredients in pharmaceutical compositions, these are not intended for use in humans only, but in non-human mammals as well. Recent advances in the area of animal health-care mandate that consideration be given for the use of active agents, such as beta-3 adrenergic receptor modulators, for the treatment of a beta-3 adrenergic receptor-associated disease or disorder in companionship animals (e.g., cats, dogs, etc.) and in livestock animals (e.g., horses, cows, etc.) Those of ordinary skill in the art are readily credited with understanding the utility of such compounds in such settings.

Other uses of the disclosed receptors and methods will become apparent to those skilled in the art based upon, inter alia, a review of this disclosure.

As will be recognized, the steps of the methods of the present invention need not be performed any particular number of times or in any particular sequence. Additional objects, advantages and novel features of this invention will become apparent to those skilled in the art upon examination of the following examples thereof, which are intended to be illustrative and not intended to be limiting.

EXAMPLES

Example 1: Syntheses of Compounds of the Present Invention

The compounds disclosed herein and their syntheses are further illustrated by the following examples. Additional illustrated syntheses for compounds of the present invention are shown in FIGS. 1 to 24 where the symbols have the same definitions as used throughout this disclosure. The following examples are provided to further define the invention without, however, limiting the invention to the particulars of these examples. The compounds described herein, supra and infra, are named according to the AutoNom version 2.2, CS ChemDraw Ultra Version 9.0.7, or ChemBioDraw Ultra 12.0.2.1076. In certain instances common names are used and it is understood that these common names would be recognized by those skilled in the art.

Chemistry: Proton nuclear magnetic resonance ($^1H$ NMR) spectra were recorded on a Bruker Avance 111-400 equipped with a 5 mm BBFO probe. Chemical shifts are given in parts per million (ppm) with the residual solvent signal used as reference. NMR abbreviations are used as follows: s=singlet, d=doublet, dd=doublet of doublets, ddd=doublet of doublet of doublets, dddd=doublet of doublet of doublet of doublets, dt=doublet of triplets, t=triplet, q=quartet, m=multiplet, bs=broad singlet, sxt=sextet. Microwave irradiations were carried out using an Initiator$^{+TM}$ (Biotage®). Thin-layer chromatography (TLC) was performed on silica gel 60 $F_{254}$ (Merck), preparatory thin-layer chromatography (prep TLC) was performed on PK6F silica gel 60 Å 1 mm plates (Whatman) and column chromatography was carried out on a silica gel column using Kieselgel 60, 0.063-0.200 mm (Merck). Evaporation was done under reduced pressure on a Blichi rotary evaporator. Celite® 545 was used for filtration of palladium.

LCMS spec: HPLC-Agilent 1200; pumps: G1312A; DAD:G1315B; Autosampler: G1367B; Mass spectrometer-Agilent G1956A; ionization source: ESI; Drying Gas Flow: 10 L/min; Nebulizer Pressure: 40 psig; Drying Gas Temperature: 350° C.; Capillary Voltage: 2500 V) Software: Agilent Chemstation Rev.B.04.03.

Example 1.1: Preparation of Benzyl 3-((tert-Butoxycarbonyl)amino)-1-oxa-8-azaspiro[4.5]decane-8-carboxylate Step A: Preparation of Benzyl 4-Allyl-4-hydroxypiperidine-1-carboxylate To a mixture of benzyl 4-oxopiperidine-1-carboxylate (51 g, 218.6 mmol) in THF (36.44 mL) were added 3-bromoprop-1-ene (54.72 mL, 655.92 mmol) and saturated $NH_4Cl$ (114 mL, 218.6 mmol) aqueous solution. Then Zinc dust (31.59 g, 483.1 mmol) was added portion wise while the internal reaction temperature was kept below 40° C. The reaction was stirred at room temperature overnight. After the reaction was completed, it was quenched with $H_2SO_4$ (10%, 225 mL). The reaction mixture was filtered through a pad of Celite® and washed with MTBE (1 L). The aqueous layer was extracted with MTBE (2×) and EtOAc (1×). The combined organic layers were washed with water and brine, and then dried over $MgSO_4$, filtered and concentrated to give the title compound (62.39 g, 104% yield). This material was used in the next step without further purification. LCMS m/z=276.2 [M+H]$^+$; $^1H$ NMR (400 MHz, $CDCl_3$) δ ppm 1.55-1.63 (m, 5H), 2.24 (d, J=7.33 Hz, 2H), 3.25 (bs, 2H), 3.93 (bs, 2H), 5.14 (s, 2H), 5.21 (td, J=9.54, 1.89 Hz, 1H), 5.79-5.93 (m, 1H), 7.33 (dd, J=5.18, 3.41 Hz, 1H), 7.35-7.40 (m, 4H).

Step B: Preparation of Benzyl 4-(2,3-Dihydroxypropyl)-4-hydroxypiperidine-1-carboxylate A mixture of $K_3Fe(CN)_6$ (62.64 g, 190.3 mmol), $K_2CO_3$ (26.29 g, 190.3 mmol), quinuclidine (0.25 g, 2.25 mmol), K₂OsO₂(OH)₄ (0.20 g, 0.53 mmol) was dissolved in H₂O (354.0 mL) and then stirred at room temperature for 20 min. (Note: Not all of the salts dissolved in water). A solution of benzyl 4-allyl-4-hydroxypiperidine-1-carboxylate (14.72 g, 53.44 mmol) in t-BuOH (354 mL) was prepared then added into the aqueous salt solution via addition funnel portion wise at room temperature. (Note: All of the salts went into the solution as benzyl 4-allyl-4-hydroxypiperidine-1-carboxylate solution was added.) Then methanesulfonamide (5.08 g, 53.44 mmol) was added. The reaction mixture changed color from reddish to green, and was stirred at room temperature for 5 h. The reaction was quenched with Na₂SO₃ (51.5 g). The organic layer was separated and concentrated. The residue was dissolved in EtOAc and extracted with water and brine, then dried over MgSO₄, and filtered. The filtrate was concentrated to give the title compound (19 g, 115% yield) as an oil which was used in the next step without further purification. LCMS m/z=310.4 [M+H]⁺; ¹H NMR (400 MHz, CDCl₃) δ ppm 1.47 (dd, J=14.65, 2.27 Hz, 1H), 1.57 (s, 2H), 1.72 (dd, J=14.65, 11.12 Hz, 1H), 1.81 (d, J=12.63 Hz, 1H), 1.88 (t, J=5.43 Hz, 1H), 3.12 (s, 2H), 3.16-3.23 (m, 1H), 3.25-3.37 (m, 1H), 3.48 (ddd, J=10.86, 6.95, 5.68 Hz, 1H), 3.65 (ddd, J=10.80, 4.61, 3.54 Hz, 1H), 3.92 (bs, 2H), 4.14 (bs, 1H), 4.68 (bs, 1H), 5.14 (s, 2H), 7.29-7.40 (m, 5H).

Step C: Preparation of Benzyl 3-Hydroxy-1-oxa-8-azaspiro[4.5]decane-8-carboxylate To a solution of benzyl 4-(2,3-dihydroxypropyl)-4-hydroxypiperidine-1-carboxylate (17.80 g, 57.55 mmol) in CH₂Cl₂ (16 mL) and pyridine (8.90 mL) under nitrogen were added N,N-dimethylpyridin-4-amine (1.41 g, 11.51 mmol) and 4-methylbenzene-1-sulfonyl chloride (12.07 g, 63.30 mmol) at 0° C. The reaction was stirred at room temperature overnight. After the reaction was completed, it was quenched with water and extracted with DCM (5×). The combined organic layers were washed with 1M HCl aqueous solution, water and brine, then dried over MgSO₄ and concentrated. The residue was purified by silica gel column chromatography to give the title compound (12.5 g, 75% yield) as a yellow oil. LCMS m/z=292.2 [M+H]⁺; ¹H NMR (400 MHz, CD₃OD) δ ppm 1.53-1.60 (m, 2H), 1.63-1.72 (m, 1H), 1.79 (ddd, J=13.52, 1.26, 1.14 Hz, 1H), 1.82-1.89 (m, 1H), 1.98 (dd, J=13.52, 6.44 Hz, 1H), 3.41 (bs, 2H), 3.67 (dd, J=12.51, 6.44 Hz, 2H), 3.74 (ddd, J=9.60, 2.53, 1.01 Hz, 1H), 3.90 (dd, J=9.60, 4.55 Hz, 1H), 4.39-4.48 (m, 1H), 5.11 (s, 2H), 7.26-7.39 (m, 5H).

Step D: Preparation of Benzyl 3-Azido-1-oxa-8-azaspiro[4.5]decane-8-carboxylate

Benzyl 3-hydroxy-1-oxa-8-azaspiro[4.5]decane-8-carboxylate (10 g, 34.31 mmol) was dissolved in pyridine (22 mL) under nitrogen then cooled down to 0° C. Methanesulfonyl chloride (8.76 mL, 113.2 mmol) was added. The reaction mixture was stirred at room temperature overnight. (Note: Precipitation was formed.). After the reaction was completed, it was diluted with EtOAc then washed with H₂O (40 mL), HCl (1N, 30 mL), and brine (30 mL). The aqueous layers were back extracted with EtOAc (2×). The combined organic layers were dried over MgSO₄, filtered and concentrated to give benzyl 3-((methylsulfonyl)oxy)-1-oxa-8-azaspiro[4.5]decane-8-carboxylate as a brown oil which was used in the next step without further purification. LCMS m/z=370.0 [M+H]⁺.

Benzyl 3-((methylsulfonyl)oxy)-1-oxa-8-azaspiro[4.5]decane-8-carboxylate from the previous step was dissolved in DMF (30 mL) under nitrogen. Sodium azide (5.13 g, 78.91 mmol) was added. The reaction was heated at 50° C. overnight. After the reaction was cooled down to room temperature, it was diluted with EtOAc and washed with water and brine. The aqueous layer was back extracted with EtOAc (2×). The combined organic layers were dried over MgSO₄, filtered and concentrated. The residue was purified by silica gel column chromatography to give the title compound (10.02 g, 92% yield). LCMS m/z=317.2 [M+H]⁺; ¹H NMR (400 MHz, CDCl₃) δ ppm 1.56-1.70 (m, 3H), 1.78-1.85 (m, 1H), 1.85-1.91 (m, 1H), 2.03 (dd, J=13.64, 7.07 Hz, 1H), 3.29-3.41 (m, 2H), 3.72-3.83 (m, 2H), 3.85 (ddd, J=9.98, 3.16, 1.01 Hz, 1H), 3.94-4.00 (m, 1H), 4.15-4.21 (m, 1H), 5.14 (s, 2H), 7.29-7.40 (m, 5H).

Step E: Preparation of Benzyl 3-((tert-Butoxycarbonyl)amino)-1-oxa-8-azaspiro[4.5]decane-8-carboxylate To a solution of benzyl 3-azido-1-oxa-8-azaspiro[4.5]decane-8-carboxylate (13.11 g, 41.43 mmol) in THF (220 mL) were added acetic acid (16.59 mL, 290.0 mmol) and zinc dust (10.84 g, 165.7 mmol). The reaction was heated at 70° C. for 1 h. After the reaction was cooled down to room temperature, it was neutralized with NaHCO₃ to pH 7. The mixture was passed through a pad of Celite®, and washed with EtOAc and IPA/DCM (30%). The aqueous layer was back extracted with EtOAc (3×). (Note: The product was still remained in the aqueous layer which was then back extracted with IPA/DCM (30%). The combined extracts were dried over MgSO₄ and concentrated to give benzyl 3-amino-1-oxa-8-azaspiro[4.5]decane-8-carboxylate, as a white gummy solid which was used in the next step without further purification. LCMS m/z=291.2 [M+H]⁺.

The benzyl 3-amino-1-oxa-8-azaspiro[4.5]decane-8-carboxylate from the previous step was dissolved in CH₂Cl₂ (220 mL) followed by addition of DIEA (14.43 mL, 82.86 mmol) and (BOC)₂O (13.56 g, 62.15 mmol). The reaction was stirred at room temperature overnight. After the reaction was completed, the solvent was removed then purified by flash column chromatography to give the title compound (11.55 g, 71% yield) as a white solid. LCMS m/z=391.4 [M+H]⁺; ¹H NMR (400 MHz, CD₃OD) δ ppm 1.44 (s, 9H), 1.50-1.54 (m, 1H), 1.58-1.74 (m, 4H), 2.12 (dd, J=13.14, 8.08 Hz, 1H), 3.32-3.43 (m, 2H), 3.63 (dd, J=9.09, 5.56 Hz, 1H), 3.67-3.79 (m, 2H), 3.99 (dd, J=8.97, 6.19 Hz, 1H), 4.21-4.43 (m, 1H), 4.67-4.70 (m, 1H), 5.11 (s, 2H), 7.28-7.39 (m, 5H).

Step F: Chiral HPLC Resolution of Enantiomers of Benzyl 3-((tert-Butoxycarbonyl)amino)-1-oxa-8-azaspiro[4.5]decane-8-carboxylate The racemic benzyl 3-((tert-butoxycarbonyl)amino)-1-oxa-8-azaspiro[4.5]decane-8-carboxylate (11.55 g, 29.58 mmol) was resolved to give two enantiomers by normal phase preparative chiral HPLC under the following conditions:

Column: Chiralcel OD, 5 cm×50 cm ID, 20 μm particle size
Eluent: EtOH/Hex (10%) with TEA (0.1%)
Injection: 800 mg/6 mL per injection
Gradient: isocratic
Flow rate: 60 mL/min
Detector: 250 nm Retention time: 1st enantiomer 28.98 min, 2nd enantiomer 39.38 min The 1st enantiomer (28.98 min on Chiralcel OD column) and 2nd enantiomer (39.38 min on Chiralcel OD column) was checked by analytical normal phase preparative chiral HPLC under the following conditions:

Column: ChiralPak IC, 250×20 mm ID, 5 µm particle size
Eluent: EtOH/Hex (10%) with TEA (0.1%)
Injection: 2 mg/mL per injection
Gradient: isocratic
Flow rate: 1 mL/min
Detector: 250 nm
Retention time of 1st enantiomer (28.97 min on Chiralcel OD) & % ee: 31.13 min; 100% ee.
Retention time of 2nd enantiomer (39.382 min on Chiralcel OD) & % ee: 28.14 min; 100% ee.

(S)-benzyl 3-((tert-butoxycarbonyl) amino)-1-oxa-8-azaspiro[4.5]decane-8-carboxylate (1st enantiomer, 5.14 g, 45% yield, 100% ee). $^1$H NMR (400 MHz, CD$_3$OD) δ ppm 1.43 (s, 9H), 1.49-1.59 (m, 1H), 1.59-1.75 (m, 4H), 2.10 (dd, J=13.14, 8.08 Hz, 1H), 3.33-3.46 (m, 2H), 3.58 (dd, J=9.09, 5.56 Hz, 1H), 3.63-3.72 (m, 2H), 3.99 (dd, J=9.09, 6.32 Hz, 1H), 4.11-4.20 (m, 1H), 5.11 (s, 2H), 6.86 (br.s., 1H), 7.26-7.39 (m, 5H).

(R)-benzyl 3-((tert-butoxycarbonyl)amino)-1-oxa-8-azaspiro[4.5]decane-8-carboxylate (2nd enantiomer, 4.86 g, 42% yield, 100% ee): NMR (400 MHz, CD$_3$OD) δ ppm 1.43 (s, 9H), 1.50-1.58 (m, 1H), 1.60-1.75 (m, 4H), 2.10 (dd, J=13.14, 8.08 Hz, 1H), 3.33-3.46 (m, 2H), 3.58 (dd, J=9.09, 5.56 Hz, 1H), 3.63-3.72 (m, 2H), 3.99 (dd, J=9.09, 6.32 Hz, 1H), 4.10-4.20 (m, 1H), 5.11 (s, 2H), 6.86 (br.s., 1H), 7.24-7.40 (m, 5H).

The stereochemistry was elucidated using Mosher amide as show in Example 1.2 and Example 1.3, respectively.

Example 1.2: Preparation of (S)-3,3,3-Trifluoro-2-methoxy-N—((S)-8-(naphthalen-2-ylsulfonyl)-1-oxa-8-azaspiro[4.5]decan-3-yl)-2-phenylpropanamide and (R)-3,3,3-Trifluoro-2-methoxy-N—((S)-8-(naphthalen-2-ylsulfonyl)-1-oxa-8-azaspiro[4.5]decan-3-yl)-2-phenylpropanamide Step A: Preparation of one Enantiomer of tert-Butyl (8-(Naphthalen-2-ylsulfonyl)-1-oxa-8-azaspiro[4.5]decan-3-yl)carbamate (from Pt enantiomer)

The 1st enantiomer of benzyl 3-((tert-butoxycarbonyl) amino)-1-oxa-8-azaspiro[4.5]decane-8-carboxylate (1.13 g, 2.89 mmol) from chiral HPLC in Example 1.1 was dissolved in MeOH (10 mL). Palladium/C (30.72 mg, 0.289 mmol) and a H$_2$ balloon were applied. The reaction was stirred at room temperature overnight at room temperature. The next day, the H$_2$ balloon was removed. The reaction mixture was filtered through a pad of Celite®, washed with EtOAc and MeOH, and concentrated to give an enantiomer of tert-butyl 1-oxa-8-azaspiro[4.5]decan-3-ylcarbamate (0.64 g, 86% yield) as a colorless gum which was used in the next step without further purification. LCMS m/z=257.4 [M+H]$^+$; $^1$H NMR (400 MHz, DMSO-d$_6$) δ ppm 1.37 (s, 9H), 1.39-1.42 (m, 2H), 1.46-1.59 (m, 4H), 1.95 (dd, J=12.63, 8.34 Hz, 1H), 2.70-2.82 (m, 2H), 3.17 (d, J=2.78 Hz, 1H), 3.40 (dd, J=8.59, 6.57 Hz, 1H), 3.84 (t, J=8.00 Hz, 1H), 3.93-4.10 (m, 1H), 6.99 (d, J=5.56 Hz, 1H).

The above obtained enantiomer of tert-butyl 1-oxa-8-azaspiro[4.5]decan-3-ylcarbamate (0.64 g, 2.49 mmol) was dissolved in CH$_2$Cl$_2$ (12 mL). DIEA (1.00 mL, 5.77 mmol) was added then the resulting mixture was cooled on an ice bath. To the cooled solution was added naphthalene-2-sulfonyl chloride (0.92 g, 4.04 mmol). The reaction was warmed up to room temperature and stirred overnight. The reaction mixture was concentrated and purified by silica gel column chromatography to give the title compound (1.12 g, 87% yield) as a white solid. LCMS m/z=447.4 [M+H]$^+$; $^1$HNMR (400 MHz, DMSO-d$_6$) δ ppm 1.34 (s, 9H), 1.52 (dd, J=13.01, 6.44 Hz, 1H), 1.57-1.63 (m, 2H), 1.65-1.73 (m, 2H), 1.89 (dd, J=12.88, 8.34 Hz, 1H), 2.62-2.70 (m, 2H), 3.27-3.35 (m, 3H), 3.70 (dd, J=8.97, 6.44 Hz, 1H), 3.87-3.99 (m, 1H), 6.93-7.01 (m, 1H), 7.66-7.78 (m, 3H), 8.08 (d, J=8.08 Hz, 1H), 8.17 (d, J=8.84 Hz, 1H), 8.21 (d, J=7.83 Hz, 1H), 8.42 (d, J=1.52 Hz, 1H).

Step B: Preparation of one Enantiomer of 8-(Naphthalen-2-ylsulfonyl)-1-oxa-8-azaspiro[4.5]decan-3-amine To a solution of tert-butyl (8-(naphthalen-2-ylsulfonyl)-1-oxa-8-azaspiro[4.5]decan-3-yl)carbamate (1.12 g, 2.50 mmol) obtained in Step A above in CH$_2$Cl$_2$ (20 mL) at room temperature was added 4N HCl (in dioxane, 6.25 mL, 25.01 mmol). The reaction mixture was stirred at room temperature for 16 h. After the reaction was completed, it was concentrated to give the title compound (1.19 g, 125% yield) as a white solid which was used in the next step without further purification. LCMS m/z=347.0 [M+H]$^+$; $^1$H NMR (400 MHz, DMSO-d$_6$) δ ppm 1.52-1.72 (m, 3H), 1.73-1.90 (m, 2H), 2.06 (dd, J=13.64, 8.08 Hz, 1H), 2.53-2.70 (m, 2H), 3.33-3.44 (m, 2H), 3.58 (dd, J=9.60, 4.29 Hz, 1H), 3.69-3.82 (m, 2H), 7.64-7.83 (m, 3H), 8.09 (d, J=8.08 Hz, 1H), 8.13-8.27 (m, 2H), 8.44 (d, J=1.52 Hz, 1H).

Step C: Preparation of (S)-3,3,3-Trifluoro-2-methoxy-N—((S)-8-(naphthalen-2-ylsulfonyl)-1-oxa-8-azaspiro[4.5]decan-3-yl)-2-phenylpropanamide To a solution of the above obtained 8-(naphthalen-2-ylsulfonyl)-1-oxa-8-azaspiro[4.5]decan-3-amine (10 mg, 26.12 µmol) and DIEA (7.54 µL, 43.30 µmol) in THF (1 mL) was added (R)-3,3,3-trifluoro-2-methoxy-2-phenylpropanoyl chloride (7.92 mg, 31.34 µmol) then stirred for 1.5 h. The reaction was quenched with water then extracted with DCM. The aqueous layer was back extracted with DCM (3×). The combined organics were dried over MgSO$_4$, filtered and concentrated. The residue was purified by flash column chromatography to give the title compound (12 mg, 82% yield) as a white solid. The stereochemistry of the title compound was elucidated by NMR. LCMS m/z=563.4 [M+H]$^+$; $^1$H NMR (400 MHz, CDCl$_3$) δ ppm 1.53-1.64 (m, 3H), 1.67-1.76 (m, 2H), 2.07 (dd, J=13.52, 7.45 Hz, 1H), 2.79 (qd, J=5.68, 3.41 Hz, 2H), 3.39 (t, J=1.52 Hz, 3H), 3.49 (td, J=11.62, 8.59 Hz, 2H), 3.59 (dd, J=9.73, 3.41 Hz, 1H), 3.89 (dd, J=9.73, 5.43 Hz, 1H), 4.42-4.51 (m, 1H), 6.81 (d, J=7.33 Hz, 1H), 7.36-7.43 (m, 3H), 7.46 (d, J=2.27 Hz, 2H), 7.64 (qd, J=7.71, 7.45 Hz, 2H), 7.75 (dd, J=8.59, 1.77 Hz, 1H), 7.93 (d, J=7.83 Hz, 1H), 7.98 (d, J=8.34 Hz, 2H), 8.33 (d, J=1.26 Hz, 1H).

Step D: Preparation of (R)-3,3,3-Trifluoro-2-methoxy-N—((S)-8-(naphthalen-2-ylsulfonyl)-1-oxa-8-azaspiro[4.5]decan-3-yl)-2-phenylpropanamide To a solution of the above obtained 8-(naphthalen-2-ylsulfonyl)-1-oxa-8-azaspiro[4.5]decan-3-amine (10 mg, 26.12 µmol) and DIEA (6.82 µL, 39.17 µmol) in THF (1 mL) was added (S)-3,3,3-trifluoro-2-methoxy-2-phenylpropanoyl chloride (7.92 mg, 31.34 µmol). The reaction was stirred at room temperature for 1.5 h. It was quenched with water then extracted with DCM. The aqueous layer was back extracted with DCM (3×). The combined organic layers were dried over MgSO$_4$, filtered and concentrated. The residue was purified by flash column chromatography to give the title compound (12 mg, 82% yield) as a white solid. The stereochemistry of the title compound was elucidated by NMR. LCMS m/z=563.4 [M+H]$^+$; $^1$H NMR (400 MHz, CDCl$_3$) δ ppm 1.64-1.80 (m, 4H), 1.82-1.92 (m, 1H), 2.13 (dd, J=13.52, 7.45 Hz, 1H), 2.78-2.90 (m, 2H), 3.33 (d, J=1.26 Hz, 3H), 3.47-3.60 (m, 3H), 3.88 (dd, J=9.85, 5.56 Hz, 1H), 4.48 (dq, J=5.24, 3.81 Hz, 1H), 6.98 (d, J=7.33 Hz, 1H), 7.39 (d, J=2.78 Hz, 3H), 7.42-7.48 (m, 2H), 7.64 (qd, J=7.71, 7.45 Hz, 2H), 7.76 (dd, J=8.59, 1.77 Hz, 1H), 7.93 (d, J=8.08 Hz, 1H), 7.98 (d, J=8.34 Hz, 2H), 8.34 (d, J=1.26 Hz, 1H).

Example 1.3: Preparation of (S)-3,3,3-Trifluoro-2-methoxy-N—((R)-8-(naphthalen-2-ylsulfonyl)-1-oxa-8-azaspiro[4.5]decan-3-yl)-2-phenylpropanamide and (R)-3,3,3-Trifluoro-2-methoxy-N—((R)-8-(naphthalen-2-ylsulfonyl)-1-oxa-8-azaspiro[4.5]decan-3-yl)-2-phenylpropanamide Step A: Preparation of one Enantiomer of tert-Butyl (8-(naphthalen-2-ylsulfonyl)-1-oxa-8-azaspiro[4.5]decan-3-yl)carbamate (from 2$^{nd}$ enantiomer)

The 2$^{nd}$ enantiomer of benzyl 3-((tert-butoxycarbonyl)amino)-1-oxa-8-azaspiro[4.5]decane-8-carboxylate (1.14 g, 2.92 mmol) from chiral HPLC in Example 1.1 was dissolved in MeOH (10 mL). To the resulting solution Palladium/C (31.07 mg, 0.29 mmol) and balloon H$_2$ were applied. The reaction was stirred at room temperature for 16 h. The next day, H$_2$ balloon was removed. The reaction mixture was filtered through a pad of Celite®, washed with EtOAc and MeOH, and concentrated to give an enantiomer of tert-butyl 1-oxa-8-azaspiro[4.5]decan-3-ylcarbamate (Peak 2, 735 mg, 98% yield) as a colorless gum which was used in the next step without further purification. LCMS m/z=257.4 [M+H]$^+$; $^1$H NMR (400 MHz, DMSO-d$_6$) δ ppm 1.34-1.45 (m, 11H), 1.52 (dd, J=6.69, 3.41 Hz, 4H), 1.96 (dd, J=12.63, 8.34 Hz, 1H), 2.51-2.59 (m, 2H), 2.71-2.84 (m, 2H), 3.41 (dd, J=8.59, 6.57 Hz, 1H), 3.83 (dd, J=8.59, 6.82 Hz, 1H), 3.91-4.07 (m, 1H), 6.99 (bs, 1H).

The above obtained enantiomer of tert-butyl 1-oxa-8-azaspiro[4.5]decan-3-ylcarbamate was re-dissolved in CH$_2$Cl$_2$ (12 mL) following by addition of DIEA (1.02 mL, 5.84 mmol). The reaction was cooled in an ice bath then naphthalene-2-sulfonyl chloride (0.93 g, 4.09 mmol) was added. The resulting mixture was stirred at room temperature overnight then concentrated. The residue was purified by silica gel column chromatography to yield the title compound (1.07 g, 82% yield) as a white solid. LCMS m/z=447.4 [M+H]$^+$; $^1$H NMR (400 MHz, DMSO-d$_6$) δ ppm 1.34 (s, 9H), 1.52 (dd, J=12.88, 6.32 Hz, 1H), 1.56-1.62 (m, 2H), 1.65-1.72 (m, 2H), 1.89 (dd, J=12.88, 8.34 Hz, 1H), 2.60-2.71 (m, 2H), 3.27-3.35 (m, 3H), 3.70 (dd, J=8.72, 6.44 Hz, 1H), 3.88-3.99 (m, 1H), 6.93-7.02 (m, 1H), 7.67-7.78 (m, 3H), 8.08 (d, J=8.34 Hz, 1H), 8.17 (d, J=8.84 Hz, 1H), 8.21 (d, J=8.08 Hz, 1H), 8.42 (d, J=1.26 Hz, 1H).

Step B: Preparation of one Enantiomer of 8-(Naphthalen-2-ylsulfonyl)-1-oxa-8-azaspiro[4.5]decan-3-amine To a solution of tert-butyl (8-(naphthalen-2-ylsulfonyl)-1-oxa-8-azaspiro[4.5]decan-3-yl)carbamate (1.07 g, 2.39 mmol) obtained in Step A above in DCM at room temperature was added HCl (4 N in dioxane, 5.97 mL, 23.89 mmol). The reaction was stirred at room temperature for 16 h. After the reaction was completed, it was concentrated to give the title compound (934 mg, 102% yield) as a white solid which was used in the next step without further purification. LCMS m/z=347.2 [M+H]$^+$; $^1$H NMR (400 MHz, DMSO-d$_6$) δ ppm 1.53-1.72 (m, 3H), 1.80 (d, J=3.79 Hz, 2H), 2.01-2.12 (m, 1H), 2.54-2.73 (m, 6H), 3.39 (d, J=15.41 Hz, 3H), 3.57 (d, J=5.05 Hz, 1H), 3.76 (d, J=8.84 Hz, 2H), 7.66-7.80 (m, 3H), 8.09 (d, J=8.08 Hz, 1H), 8.17 (d, J=8.84 Hz, 1H), 8.21 (d, J=8.08 Hz, 1H), 8.44 (s, 1H).

Step C: Preparation of (S)-3,3,3-Trifluoro-2-methoxy-N—((R)-8-(naphthalen-2-ylsulfonyl)-1-oxa-8-azaspiro[4.5]decan-3-yl)-2-phenylpropanamide To a solution of the above obtained 8-(naphthalen-2-ylsulfonyl)-1-oxa-8-azaspiro[4.5]decan-3-amine (10 mg, 26.12 µmol) and DIEA (7.54 µL, 43.30 µmol) in THF (1 mL) was added (R)-3,3,3-trifluoro-2-methoxy-2-phenylpropanoyl chloride (7.92 mg, 31.34 µmol). The reaction was stirred for 1.5 h at room temperature. Then the reaction was quenched with water and extracted with DCM. The aqueous layer was back extracted with DCM (3×). The combined organics were dried over MgSO$_4$, filtered and concentrated. The residue was purified by flash column chromatography to yield the title compound (11 mg, 75% yield) as a white solid. The stereochemistry of the title compound was elucidated by NMR. LCMS m/z=563.2 [M+H]$^+$; $^1$H NMR (400 MHz, CDCl$_3$) δ ppm 1.65-1.80 (m, 4H), 1.82-1.92 (m, 1H), 2.13 (dd, J=13.64, 7.58 Hz, 1H), 2.79-2.89 (m, 2H), 3.33 (d, J=1.52 Hz, 3H), 3.48-3.60 (m, 3H), 3.88 (dd, J=9.73, 5.43 Hz, 1H), 4.43-4.53 (m, 1H), 6.98 (d, J=7.33 Hz, 1H), 7.37-7.41 (m, 3H), 7.43-7.47 (m, 2H), 7.60-7.69 (m, 2H), 7.76 (dd, J=8.72, 1.89 Hz, 1H), 7.93 (d, J=7.83 Hz, 1H), 7.98 (d, J=8.34 Hz, 2H), 8.34 (d, J=1.26 Hz, 1H).

Step D: Preparation of (R)-3,3,3-Trifluoro-2-methoxy-N—((R)-8-(naphthalen-2-ylsulfonyl)-1-oxa-8-azaspiro[4.5]decan-3-yl)-2-phenylpropanamide To a solution of the above obtained 8-(naphthalen-2-ylsulfonyl)-1-oxa-8-azaspiro[4.5]decan-3-amine (10 mg, 26.12 µmol) and DIEA (7.54 µL, 43.30 µmol) in THF (1 mL) was added (S)-3,3,3-trifluoro-2-methoxy-2-phenylpropanoyl chloride (7.92 mg, 31.34 µmol). The reaction was stirred at room temperature for 1.5 h. Then it was quenched with water and extracted with DCM. The aqueous was back extracted with DCM (3×). The combined organic layers were dried over MgSO$_4$, filtered and concentrated. The residue was purified by flash column chromatography to give the title compound (12 mg, 82% yield) as a white solid. The stereochemistry of the title compound was elucidated by NMR. LCMS m/z=563.2 [M+H]$^+$; $^1$H NMR (400 MHz, CDCl$_3$) δ ppm 1.54-1.66 (m, 3H), 1.67-1.79 (m, 3H), 2.06 (dd, J=13.52, 7.45 Hz, 1H), 2.73-2.85 (m, 2H), 3.39 (d, J=1.52 Hz, 3H), 3.44-3.55 (m, 2H), 3.59 (dd, J=9.60, 3.54 Hz, 1H), 3.89 (dd, J=9.73, 5.43 Hz, 1H), 4.41-4.52 (m, 1H), 6.81 (d, J=7.33 Hz, 1H), 7.37-7.44 (m, 3H), 7.45-7.53 (m, 2H), 7.60-7.71 (m, 2H), 7.75 (dd, J=8.59, 1.77 Hz, 1H), 7.93 (d, J=7.83 Hz, 1H), 7.97 (d, J=8.34 Hz, 2H), 8.33 (s, 1H).

Example 1.4: Preparation of (R)-Benzyl 3-((tert-Butoxycarbonyl)amino)-1-oxa-8-azaspiro[4.5]decane-8-carboxylate Step A: Preparation of Benzyl 4-Allyl-4-hydroxypiperidine-1-carboxylate To an ice-cooled mixture of benzyl 4-oxopiperidine-1-carboxylate (900.00 g, 3.86 mol), 3-bromoprop-1-ene (1.17 kg, 9.65 mol) and $NH_4Cl$ (3.30 L) in THF (750.00 mL) was added Zn (630.74 g, 9.65 mol) portion wise at 5-10° C. After the addition, the mixture was kept at 30° C. for 3 h. After benzyl 4-oxopiperidine-1-carboxylate was consumed, the mixture was filtered. The filtrate was extracted with ethyl acetate (2 L×3). The combined organic layer was washed with brine (1 L×2), dried over anhydrous $Na_2SO_4$, and concentrated to give the title compound (1.02 kg, crude) as a yellow oil which was used in the next step without further purification. $^1$H NMR (400 MHz, $CDCl_3$) δ ppm 1.45-1.75 (m, 4H), 2.22 (d, J=4.0 Hz, 2H), 3.23 (bs, 1H), 3.92 (bs, 2H), 5.05-5.25 (m, 4H), 5.75-5.95 (m, 1H), 7.25-7.45 (m, 5H).

Step B: Preparation of Benzyl 4-(2,3-Dihydroxypropyl)-4-hydroxypiperidine-1-carboxylate To a solution of benzyl 4-allyl-4-hydroxypiperidine-1-carboxylate (1.16 kg, 4.21 mol) in THF (2.20 L), acetone (2.20 L) and $H_2O$ (2.20 L) were added $K_2OsO_4.2H_2O$ (7.76 g, 21.05 mmol) and NMO (1.04 kg, 8.84 mol, 933.08 mL). Then the reaction was stirred at 30° C. for 12 h. The mixture was diluted with saturated $Na_2SO_3$ aqueous solution (5 L) and extracted with ethyl acetate (2 L×2). The combined organics were washed with brine (2 L), dried over $Na_2SO_4$, filtered and concentrated to give the title compound as an off-white solid without further purification (1.10 kg, 83.14% yield). $^1$H NMR (400 MHz, DMSO-$d_6$) δ ppm 1.40-1.60 (m, 6H), 3.00-3.30 (m, 4H), 3.65-3.86 (m, 3H), 4.52-4.62 (m, 2H), 4.67-4.74 (m, 1H), 5.06 (s, 2H), 7.28-7.42 (m, 5H).

Step C: Preparation of Benzyl 3-((Methylsulfonyl)oxy)-1-oxa-8-azaspiro[4.5]decane-8-carboxylate To a solution of benzyl 4-(2,3-dihydroxypropyl)-4-hydroxypiperidine-1-carboxylate (1.34 kg, 4.33 mol), DMAP (158.75 g, 1.30 mol) and pyridine (1.03 kg, 12.99 mol, 1.05 L) in DCM (5.36 L) was added MsCl (1.13 kg, 9.86 mol, 763.51 mL) at 0° C. The reaction was stirred at 25° C. for 3 hrs. Then the reaction mixture was heated and stirred at 40° C. for 12 h. Then the mixture was added additional MsCl (319.00 g, 2.78 mol, 215.54 mL) at 25° C. and the resulting mixture was stirred at 40° C. for 24 h. The mixture was diluted with DCM (5 L), washed with 1 N HCl (4 L) and brine (4 L) in sequence. The organic phase was dried over $Na_2SO_4$ and filtered. The filtrate was concentrated to give the title compound (1.55 kg) as brown oil, which was used directly for the next step without further purification. $^1$H NMR (400 MHz, DMSO-$d_6$) δ ppm 1.38-1.75 (m, 6H), 1.96-2.20 (m, 2H), 3.12-3.41 (m, 5H), 3.50-3.67 (m, 2H), 3.94-3.95 (m, 2H), 5.06 (s, 2H), 5.29 (s, 1H), 7.25-7.44 (m, 5H).

Step D: Preparation of Benzyl 3-Amino-1-oxa-8-azaspiro[4.5]decane-8-carboxylate

To a solution of benzyl 3-((methylsulfonyl)oxy)-1-oxa-8-azaspiro[4.5]decane-8-carboxylate (300.00 g, 812.06 mmol) in DMF (1.50 L) was added $NaN_3$ (61.00 g, 938.32 mmol, 32.97 mL) in $H_2O$ (150.00 mL) and the resultant mixture was stirred at 70° C. for 16 h. $PPh_3$ (425.99 g, 1.62 mol, 2.00 eq) was added portion wise at 70° C. (Caution: gas generated). The mixture was stirred at 70° C. for another 2 h. After cooled to 15° C., water (6 L) was added and the mixture was basified to pH=10 with $Na_2CO_3$. The mixture was extracted with ethyl acetate (3 L×3) and the combined organics layers were washed with 1 N HCl (3 L×3). The combined aqueous phase was basified to pH=10 with NaOH, extracted with ethyl acetate (3 L×3). The combined organics were washed with brine (3 L), dried over $Na_2SO_4$, filtered and concentrated to give the title compound (153.00 g, 58.4% yield). $^1$H NMR (400 MHz, $CDCl_3$) δ ppm 1.37 (s, 1H), 1.42-1.85 (m, 5H), 2.05 (dd, J=12.8 Hz, 5.4 Hz, 1H), 3.25-3.45 (m, 2H), 3.45-3.56 (m, 1H), 3.57-3.80 (m, 3H), 3.93 (dd, J=6.4 Hz, 5.7 Hz, 1H), 5.11 (s, 2H), 7.24-7.42 (m, 5H).

Step E: Preparation of (R)-Benzyl 3-Amino-1-oxa-8-azaspiro[4.5]decane-8-carboxylate To a solution of benzyl 3-amino-1-oxa-8-azaspiro[4.5]decane-8-carboxylate (126 g, 434 mmol, 1.0 eq) in MeOH (2.5 L) was added di-p-toluoyl-D-tartaric acid (37 g, 95.5 mmol, 0.44 eq) and the mixture was heated to 78° C. After stirred at this temperature for 5 h, the mixture was cooled to 25° C. slowly and stirred at this temperature for 1 h. The white solid was collected by filtration and the solid was washed with MeOH (500 mL). The filter cake was added to $NaHCO_3$ aqueous solution (500 mL) and extracted with DCM (1 L×2). The combined organics were washed with brine, dried over $Na_2SO_4$, filtered and concentrated to give the title compound (54 g) which was analyzed by supercritical fluid chromatography (SFC) (AD-3S_4_25_3 ML; Column: Chiralpak AD-3 100×4.6 mm I.D., 3 μm; Mobile phase: 25% isopropanol (0.05% DEA) in $CO_2$; Flow rate: 3 mL/min; Wavelength: 220 nm) to have ee value of 93%. The above material (42 g, 145 mmol, 1.0 eq) was dissolved with MeOH (800 mL), followed by the addition of di-p-toluoyl-D-tartaric acid (27 g, 69 mmol, 0.96 eq). The mixture was heated to 78° C. After stirred at this temperature for 5 h, the mixture was cooled to 25° C. slowly and stirred at this temperature for 1 h. The white solid was collected by filtration, washed with EtOH (500 mL). The cake was added to $NaHCO_3$ aqueous (500 mL) and extracted with DCM (1 L×2). The combined organics were washed with brine, dried over $Na_2SO_4$, filtered and concentrated to give the title compound (36 g, 97.5% ee) as colorless oil.

Step F: Preparation of (R)-Benzyl 3-((tert-Butoxycarbonyl)amino)-1-oxa-8-azaspiro[4.5]decane-8-carboxylate To a solution of (R)-benzyl 3-amino-1-oxa-8-azaspiro[4.5]decane-8-carboxylate (36 g, 124 mmol, 1.0 eq) in DCM (600 mL) were added TEA (25 g, 248 mmol, 2.0 eq) and $Boc_2O$ (30 g, 136 mmol, 1.1 eq). The reaction was stirred at 20° C. for 6 h. The mixture was washed with cold HCl aqueous solution (1N, 200 mL) and brine, dried over $Na_2SO_4$, filtered and concentrated. The residue was triturated with petroleum ether to give the title compound (44 g, 91% yield) as a white solid. LCMS m/z=335.1 (M-tBu+H); $^1$H NMR (400 MHz, DMSO-$d_6$) δ 1.38 (s, 9H), 1.44-1.64 (m, 5H), 1.95-2.05 (m, 1H), 3.39-3.36 (m, 2H), 3.53-3.55 (m, 3H), 3.89 (t, J=6.4 Hz, 1H), 4.01-4.10 (m, 1H), 5.06 (s, 2H), 7.10 (d, J=6.0 Hz, 1H), 7.38-7.32 (m, 5H).

SFC analysis: (AD-3S_5_40_3 ML; Column: Chiralpak AD-3 100×4.6 mm I.D., 3 μm; Mobile phase: 40% ethanol (0.05% DEA) in $CO_2$; Flow rate: 3 mL/min; Wave length: 220 nm) 100% ee.

Example 1.5: Preparation of (S)-Benzyl 3-((tert-Butoxycarbonyl)amino)-1-oxa-8-azaspiro[4.5]decane-8-carboxylate

Step A: Preparation of (S)-benzyl 3-amino-1-oxa-8-azaspiro[4.5]decane-8-carboxylate To a solution of benzyl 3-amino-1-oxa-8-azaspiro[4.5]decane-8-carboxylate (97 g, 0.334 mol, 1.0 eq) in MeOH (2.5 L) was added di-p-toluoyl-L-tartaric acid (40 g, 104 mmol, 0.62 eq) and the mixture was heated to 78° C. After stirred at this temperature for 5 h, the mixture was cooled to 25° C. slowly and stirred at this temperature for 1 h. The white solid was collected by filtration and the solid was washed with MeOH (250 mL). The filter cake was added to $NaHCO_3$ aqueous solution (300 mL) and extracted with DCM (500 mL×2). The combined organics were washed with brine, dried over $Na_2SO_4$, filtered and concentrated to give the residue (45 g) which was analyzed by SFC (AD-3S_4_25_3 ML; Column: Chiralpak AD-3 100×4.6 mm I.D., 3 μm; Mobile phase: 25% isopropanol (0.05% DEA) in $CO_2$; Flow rate: 3 mL/min, wavelength: 220 nm) to have ee value of 95%. The above material (45 g, 150 mmol, 1.0 eq) was dissolved with MeOH (1.2 L), followed by the addition of di-p-toluoyl-L-tartaric acid (28 g, 72 mmol, 0.96 eq.) and the mixture was heated to 78° C. After stirred at this temperature for 5 h, the mixture was cooled to 25° C. slowly and stirred at this temperature for 1 h. The white solid was collected by filtration, washed with EtOH (500 mL). The cake was added to $NaHCO_3$ aqueous solution (300 mL) and extracted with DCM (500 mL×2). The combined organics were washed with brine, dried over $Na_2SO_4$, filtered and concentrated to give the title compound (40 g, 97.5% ee) as a colorless oil.

Step B: Preparation of (S)-Benzyl 3-((tert-Butoxycarbonyl)amino)-1-oxa-8-azaspiro[4.5]decane-8-carboxylate To a solution of (S)-benzyl 3-amino-1-oxa-8-azaspiro[4.5]decane-8-carboxylate (40 g, 138 mmol, 1.0 eq) in DCM (600 mL) were added TEA (28 g, 276 mmol, 2.0 eq) and $Boc_2O$ (33 g, 152 mmol, 1.1 eq). The reaction was stirred at 20° C. for 6 h. The mixture was washed with cold HCl aq. (1 N, 200 mL) and brine, dried over $Na_2SO_4$, filtered and concentrated. The residue was triturated with petroleum ether to give the title compound (51 g, 131 mmol, 95% yield) as a white solid. LCMS m/z=335.1 (M-tBu+H); $^1H$ NMR (400 MHz DMSO-$d_6$) δ 1.38 (s, 9H), 1.48-1.62 (m, 5H), 1.96-2.07 (m, 1H), 3.19-3.36 (m, 2H), 3.53-3.43 (m, 3H), 3.89 (t, J=6.4 Hz, 1H), 4.04-4.11 (m, 1H), 5.06 (s, 2H), 7.10-7.09 (d, J=6.0 Hz, 1H), 7.38-7.32 (m, 5H).

SFC analysis: (AD-3S_5_40_3 ML; Column: Chiralpak AD-3 100×4.6 mm I.D., 3 μm; Mobile phase: 40% ethanol (0.05% DEA) in $CO_2$; Flow rate: 3 mL/min; Wave length: 220 nm) 100% ee.

Example 1.6: Preparation of (S)-2-((3-((Cyclopropylmethyl)sulfonyl)phenoxy)methyl)oxirane (Method BB1)

Step A: Preparation of Sodium 3-Methoxybenzenesulfinate (Method BB1A)

To a solution of sodium sulfite (3.56 g, 28.26 mmol) and sodium carbonate (3 g, 28.26 mmol) in $H_2O$ (18.84 mL) was added 3-methoxybenzene-1-sulfonyl chloride (2 mL, 14.13 mmol) and EtOH (9.42 mL). The reaction was heated at 60° C. for 3 h. The mixture was concentrated and azeotroped with toluene (2×) to give the title compound as a light yellow solid which was used in the next step without further purification. LCMS m/z=170.8 [M–H]+; $^1H$ NMR (400 MHz, DMSO-$d_6$) δ ppm 3.75 (s, 3H), 6.77 (d, J=1.01 Hz, 1H), 6.99-7.06 (m, 2H), 7.20 (t, J=7.71 Hz, 1H).

Step B: Preparation of 1-((Cyclopropylmethyl)sulfonyl)-3-methoxybenzene (Method BB1B)

To a solution of sodium 3-methoxybenzenesulfinate (300 mg, 1.55 mmol) in DMF (6.0 mL) was added (bromomethyl)cyclopropane (0.63 g, 1.55 mmol). The reaction was heated under microwave irradiation for 1.5 h at 120° C. Then it was filtered through a pad of Celite®, washed with EtOAc and concentrated. The residue was purified by silica gel column chromatography to give the title compound (289 mg, 83% yield). LCMS m/z=227.0 [M+H]$^+$; $^1H$ NMR (400 MHz, $CDCl_3$) δ ppm 0.17 (q, J=5.31 Hz, 2H), 0.59 (td, J=7.20, 5.05 Hz, 2H), 1.02 (tt, J=8.08, 4.80 Hz, 1H), 3.03 (d, J=7.07 Hz, 2H), 3.88 (s, 3H), 7.18 (ddd, J=8.15, 2.59, 1.14 Hz, 1H), 7.44-7.50 (m, 2H), 7.53 (dt, J=8.00, 1.39 Hz, 1H).

Step C: Preparation of 3-((Cyclopropylmethyl)sulfonyl)phenol (Method BB1C)

To a solution of 1-((cyclopropylmethyl)sulfonyl)-3-methoxybenzene (290 mg, 1.28 mmol) in DCM (6.4 mL) at −20° C. under nitrogen, boron tribromide (176 μl, 2.56 mmol) in DCM (2.6 mL) was added drop wise. The reaction mixture was stirred at room temperature overnight. After the reaction was completed, it was cooled down to −20° C. then quenched with MeOH and neutralized with 7N $NH_3$ in MeOH. The resulting mixture was filtered through a pad of Celite® to remove $NH_4Br$ salt; the organic layer was washed with water and brine, then dried over $Na_2SO_4$, filtered and concentrated. The residue was purified by silica gel column chromatography to give the title compound (229 mg, 72% yield). LCMS m/z=212.8 [M]$^+$; NMR (400 MHz, $CDCl_3$) δ ppm 0.12-0.24 (m, 2H), 0.52-0.65 (m, 2H), 0.95-1.07 (m, 1H), 3.05 (d, J=7.33 Hz, 2H), 6.12 (s, 1H), 7.15 (ddd, J=7.83, 2.40, 1.39 Hz, 1H), 7.44 (t, J=8.08 Hz, 1H), 7.47-7.52 (m, 2H).

Step D: Preparation of (S)-2-((3-((Cyclopropylmethyl)sulfonyl)phenoxy)methyl)oxirane. (Method BB1D)

In a 5 mL microwave vial were added 3-((cyclopropylmethyl)sulfonyl)phenol (100 mg, 0.47 mmol), potassium carbonate (195 mg, 1.41 mmol) and acetone (2 mL). The reaction was stirred at room temperature for 10 min then (S)-oxiran-2-ylmethyl 3-nitrobenzenesulfonate (122 mg, 0.47 mmol) was added. The reaction was heated at 70° C. overnight. After cooling down to room temperature, the mixture was filtered through a pad of Celite®, washed with EtOAc and concentrated. The residue was purified by silica gel column chromatography to give the title compound (121 mg, 87% yield) as a colorless oil. LCMS m/z=269.0 [M+H]$^+$.

Example 1.7: Preparation of (S)-2-((3-(Oxiran-2-ylmethoxy)phenyl)sulfonyl)ethanol. (Method BB2)

Step A: Preparation of 3-((2-Hydroxyethyl)thio)phenol

To a solution of 3-mercaptophenol (14.6 g, 115.7 mmol) in DCM (400 mL) containing DIEA (40.31 mL, 231.4 mmol) at 0° C. under nitrogen was added a solution of 2-bromoethanol (17.35 g, 138.9 mmol) in DCM (75 mL) via additional funnel. The reaction was stirred at room temperature overnight. After the reaction was completed, it was neutralized with HCl (0.5N) aqueous solution to pH 6 then the organic layer was separated. The aqueous layer was back extracted with DCM. The combined organic layers were washed with brine, then dried over $Na_2SO_4$, filtered and concentrated. The residue was purified by silica gel column chromatography to give the title compound (21.65 g, 62% yield). LCMS m/z=171.2 [M+H]$^+$; $^1$H NMR (400 MHz, DMSO-d$_6$) δ ppm 2.97 (t, J=6.95 Hz, 2H), 3.51-3.58 (m, 2H), 4.91 (t, J=5.56 Hz, 1H), 6.57 (ddd, J=8.72, 1.39, 1.26 Hz, 1H), 6.70-6.75 (m, 2H), 7.09 (t, J=8.08 Hz, 1H), 9.49 (s, 1H).

Step B: Preparation of 3-((2-Hydroxyethyl)sulfonyl)phenol

To a solution of 3-((2-hydroxyethyl)thio)phenol (21.65 g, 78.9 mmol) in MeOH (217.5 mL) and $H_2O$ (54.38 mL) at 0° C. was added potassium peroxymonosulfate, Oxone® (72.95 g, 157.7 mmol) portion wise. The reaction mixture was stirred at room temperature overnight. It was filtered through a pad of Celite®, washed with MeOH, and concentrated. The residue was diluted in water then adjust pH to pH 8-9 using $NaHCO_3$. The aqueous solution was extracted with DCM. The combined organic layers were washed with water (1×) and brine (1×), then dried over $Na_2SO_4$, filtered and concentrated. The residue was purified by silica gel column chromatography to give the title compound (14.02 g, 88% yield) as a yellow solid. LCMS m/z=203.2 [M+H]$^+$; $^1$H NMR (400 MHz, DMSO-d$_6$) δ ppm 3.39 (t, J=6.44 Hz, 2H), 3.61-3.70 (m, 2H), 4.87 (t, J=5.43 Hz, 1H), 7.09 (ddd, J=8.15, 2.46, 1.01 Hz, 1H), 7.23 (d, J=2.27 Hz, 1H), 7.30 (dd, J=8.97, 1.39 Hz, 1H), 7.44 (t, J=7.96 Hz, 1H), 10.19 (s, 1H).

Step C: Preparation of (S)-2-((3-(Oxiran-2-ylmethoxy)phenyl)sulfonyl)ethanol

To a mixture of 3-((2-hydroxyethyl)sulfonyl)phenol (14.02 g, 45.76 mmol) and potassium carbonate (18.97 g, 137.3 mmol) in acetone (91.51 mL) under nitrogen was added (S)-oxiran-2-ylmethyl 3-nitrobenzenesulfonate (11.86 g, 45.76 mmol) at room temperature. The reaction was heated at 80° C. overnight. After the reaction was cooled down to room temperature, the mixture was filtered through a pad of Celite®, washed with acetone then concentrated. The residue was re-dissolved in EtOAc and washed with aqueous NaOH (1N) solution, water and brine. The aqueous layer was back extracted with EtOAc (2×). The combined organic layers were washed with water and brine, then dried over $Na_2SO_4$, filtered and concentrated. The residue was purified by silica gel column chromatography to give the title compound (15.23 g, 85% yield). LCMS m/z=259.2 [M+H]$^+$; $^1$H NMR (400 MHz, DMSO-d$_6$) δ ppm 2.74 (dd, J=5.05, 2.53 Hz, 1H), 2.86 (t, J=4.29 Hz, 1H), 3.33-3.38 (m, 1H), 3.46 (t, J=6.44 Hz, 2H), 3.63-3.70 (m, 2H), 3.94 (dd, J=11.37, 6.57 Hz, 1H), 4.46 (dd, J=11.37, 2.53 Hz, 1H), 4.87 (t, J=5.56 Hz, 1H), 7.32 (dt, J=8.27, 1.29 Hz, 1H), 7.42 (d, J=2.27 Hz, 1H), 7.46-7.49 (m, 1H), 7.56 (t, J=7.96 Hz, 1H).

Example 1.8: Preparation of (S)-2-((3-(Methylsulfonyl)phenoxy)methyl)oxirane (Method BB3)

Step A: Preparation of 3-(Methylsulfonyl)phenol (Method BB3A)

To a solution of 1-methoxy-3-(methylsulfonyl)benzene (2.58 g, 13.86 mmol) in $CH_2Cl_2$ (12 mL) at below −20° C. was added slowly a solution of boron tribromide (2.63 mL, 27.72 mmol) under nitrogen. The reaction changed color from pale yellow to red color. The reaction was slowly warmed up to room temperature overnight. After the reaction was completed, the mixture was cooled down to −20° C., then quenched with MeOH, and then diluted with $CH_2Cl_2$. The reaction mixture was neutralized with $NaHCO_3$ by slowly adding into the saturated $NaHCO_3$ aqueous solution followed by addition of $NaHCO_3$ solid. The organic layer was separated and the aqueous layer was back extracted with $CH_2Cl_2$. The combined organic layers were dried over $Na_2SO_4$, filtered and concentrated. The residue was purified by silica gel column chromatography to give the title compound (2.46 g, 103% yield) as a white solid. LCMS m/z=173.2 [M+H]$^+$; $^1$H NMR (400 MHz, CDCl$_3$) δ ppm 3.09 (s, 3H), 7.15 (ddd, J=7.83, 2.53, 1.52 Hz, 1H), 7.41-7.53 (m, 3H).

Step B: Preparation of (S)-2-((3-(Methylsulfonyl)phenoxy)methyl)oxirane

To a solution of 3-(methylsulfonyl)phenol (2.46 g, 14.29 mmol) in acetone (70 mL) was added potassium carbonate (3.95 g, 28.57 mmol). The reaction was stirred at room temperature for 10 min. Then (S)-oxiran-2-ylmethyl 3-nitrobenzenesulfonate (3.70 g, 14.29 mmol) was added. The reaction was heated at 70° C. overnight under nitrogen. After cooling down to room temperature, the mixture was filtered through a pad of Celite®, washed with acetone, and concentrated. The residue was purified by silica gel column chromatography to give the title compound (3.03 g, 93% yield) as a colorless oil. LCMS m/z=229.4 [M+H]$^+$; $^1$H NMR (400 MHz, CDCl$_3$) δ ppm 2.79 (dd, J=4.80, 2.78 Hz, 1H), 2.94 (t, J=4 Hz, 1H), 3.06 (s, 3H), 3.33-3.42 (m, 1H), 3.99 (dd, J=11.12, 6.06 Hz, 1H), 4.37 (dd, J=11.12, 2.78 Hz, 1H), 7.22 (ddd, J=8.21, 2.65, 1.01 Hz, 1H), 7.46-7.52 (m, 2H), 7.54-7.58 (m, 1H).

Example 1.9: Preparation of (S)-2-((3-(Cyclopropylsulfonyl)phenoxy)methyl)oxirane (Method BB4)

Step A: Preparation of 3-(Cyclopropylthio)phenol

To a stirred suspension of potassium tert-butoxide (8.00 g, 71.33 mmol) in DMSO (70 mL) under nitrogen was added 3-mercaptophenol (5 g, 39.63 mmol) at 0° C.; the reaction was stirred at room temperature for 30 min. Then bromocyclopropane (5.72 mL, 71.33 mmol) was added into the reaction mixture. The reaction was heated at 90° C. overnight. After the reaction was completed, it was diluted with EtOAc. The organic layer was washed with water, saturated $NH_4Cl$ aqueous solution (2×), and brine. The aqueous layer was back extracted with EtOAc (1×). The combined organic layers were dried over $Na_2SO_4$, filtered and concentrated. The residue was purified by silica gel column chromatography to give the title compound (6.19 g, 85% yield). LCMS m/z=167.2 [M+H]⁺; ¹H NMR (400 MHz, CDCl₃) δ ppm 0.68-0.74 (m, 2H), 1.05-1.12 (m, 2H), 2.13-2.22 (m, 1H), 4.75 (s, 1H), 6.60 (dt, J=8.08, 1.26 Hz, 1H), 6.89 (t, J=2.27 Hz, 1H), 6.93 (ddd, J=7.83, 1.64, 0.88 Hz, 1H), 7.15 (t, J=7.96 Hz, 1H).

Step B: Preparation of (S)-2-((3-(Cyclopropylsulfonyl)phenoxy)methyl)oxirane To a round bottom flask containing Al₂O₃ (56 g) was added water (71 mL). To this mixture a solution of 3-(cyclopropylthio)phenol (6.19 g, 33.60 mmol) in CCl₄ (170 mL) was added followed by addition of potassium peroxymonosulfate (Oxone®) (31.09 g, 67.21 mmol). The reaction was heated at 40° C. for 8 h; then the reaction was stirred at room temperature overnight. After the reaction was completed, the mixture was filtered through a pad of Celite® and washed with CH₂Cl₂. The organic layer was washed with water and brine, then dried over Na₂SO₄, filtered and concentrated to give 3-(cyclopropylsulfonyl)phenol (7.07 g, 106% yield) as a solid. This material was used in the next step without further purification. LCMS m/z=199.2 [M+H]⁺; ¹H NMR (400 MHz, CDCl₃) δ ppm 1.02-1.10 (m, 2H), 1.33-1.39 (m, 2H), 2.49 (tt, J=8.05, 4.83 Hz, 1H), 6.18 (bs, 1H), 7.13 (dt, J=6.51, 2.56 Hz, 1H), 7.40-7.48 (m, 3H).

To a solution of 3-(cyclopropylsulfonyl)phenol in acetone (170.0 mL) was added potassium carbonate (9.29 g, 67.21 mmol) and (S)-oxiran-2-ylmethyl 3-nitrobenzenesulfonate (8.71 g, 33.60 mmol). The reaction was heated at 70° C. overnight under nitrogen. After the reaction was completed, the mixture was filtered through a pad of Celite®, washed with acetone and concentrated. The residue was purified by silica gel column chromatography to give the title compound (7.63 g, 89% yield) as a light yellow oil. LCMS m/z=255.2 [M+H]⁺; ¹H NMR (400 MHz, CDCl₃) δ ppm 1.01-1.08 (m, 2H), 1.33-1.39 (m, 2H), 2.47 (tt, J=7.99, 4.89 Hz, 1H), 2.79 (dd, J=4.80, 2.53 Hz, 1H), 2.93 (t, J=4.29 Hz, 1H), 3.35-3.41 (m, 1H), 3.99 (dd, J=11.12, 5.81 Hz, 1H), 4.36 (dd, J=11.12, 2.78 Hz, 1H), 7.20 (ddd, J=8.02, 2.59, 1.26 Hz, 1H), 7.44 (t, J=2.27 Hz, 1H), 7.47 (t, J=7.71 Hz, 1H), 7.50-7.54 (m, 1H).

Example 1.10: Preparation of (S)-2-((3-(Oxiran-2-ylmethoxy)phenyl)sulfonyl)acetamide (Method BB5)

Step A: Preparation of 2-((3-Hydroxyphenyl)thio)acetamide (Method BB5A)

To a solution of sodium hydroxide (4.82 g, 123.6 mmol) in MeOH (120 mL) at 0° C. was added a solution of 3-mercaptophenol (10.51 mL, 103.0 mmol) in MeOH (20 mL). The reaction was warmed up to room temperature then stirred for 30 min. A solution of 2-bromoacetamide (31.28 g, 226.6 mmol) in MeOH (100 mL) was added into the reaction mixture. The reaction was stirred at room temperature overnight. After the reaction was completed, the mixture was filtered through a pad of Celite® then washed with MeOH. The filtrate was concentrated then the residue was re-dissolved in water and extracted with IPA/DCM (10%, 2×). The combined organic layers were washed with water and brine, then dried over Na₂SO₄, filtered and concentrated. The residue was triturated with DCM/Hex (2:1 ratio) to give the title compound (17.19 g, 96% yield) as a light brown solid. LCMS m/z=184.2 [M+H]⁺; ¹H NMR (400 MHz, CD₃OD) δ ppm 3.59 (s, 2H), 6.64 (ddd, J=8.15, 2.34, 0.88 Hz, 1H), 6.80-6.86 (m, 2H), 7.11 (t, J=7.83 Hz, 1H).

Step B: Preparation of 2-((3-Hydroxyphenyl)sulfonyl)acetamide (Method BB5B)

To a solution of 2-((3-hydroxyphenyl)thio)acetamide (18.04 g, 98.46 mmol) in MeOH (272 mL) and H₂O (68 mL) at 0° C. was added a solution of potassium peroxymonosulfate (Oxone®) (91.09 g, 196.9 mmol) portion wise. The reaction was stirred at room temperature overnight. The reaction mixture was filtered through a pad of Celite®, washed with MeOH and then concentrated. The residue was dissolved in water and neutralized with saturated NaHCO₃ aqueous to pH 8. (Note: The aqueous layer changed color to light pink.) The aqueous layer was extracted with IPA/DCM (10%). The organic layer was washed with water and brine, dried over Na₂SO₄, filtered and concentrate to give the title compound (15.11 g, 71% yield) as a white solid. LCMS m/z=216.0 [M+H]⁺; ¹H NMR (400 MHz, CD₃OD) δ ppm 4.10 (s, 2H), 7.11 (ddd, J=7.83, 2.53, 1.26 Hz, 1H), 7.33 (t, J=2.02 Hz, 1H), 7.39 (t, J=1.52 Hz, 1H), 7.42 (t, J=7.58 Hz, 1H).

Step C: Preparation of (S)-2-((3-(Oxiran-2-ylmethoxy)phenyl)sulfonyl)acetamide To a solution of 2-((3-hydroxyphenyl)sulfonyl)acetamide (24.35 g, 70.2 mmol) in acetone (351 mL) was added potassium carbonate (19.39 g, 140.3 mmol) and (S)-oxiran-2-ylmethyl 3-nitrobenzenesulfonate (28.5 g, 104.4 mmol). The reaction was heated at 80° C. for 23 h. After cooling down to room temperature, the reaction mixture was filtered through a pad of Celite®, washed with Acetone, and then concentrated. The residue was purified by silica gel column chromatography to give the title compound (13.9 g, 73% yield) as a light yellow solid. LCMS m/z=272.0 [M+H]⁺; ¹H NMR (400 MHz, CDCl₃) δ ppm 2.78 (dd, J=4.80, 2.78 Hz, 1H), 2.94 (t, J=4.04 Hz, 1H), 3.38 (dddd, J=6.13, 3.85, 2.91, 2.78 Hz, 1H), 3.96-4.04 (m, 3H), 4.36 (dd, J=11.12, 2.78 Hz, 1H), 5.61 (bs, 1H), 6.72 (bs, 1H), 7.24-7.29 (m, 1H), 7.47 (t, J=1.77 Hz, 1H), 7.52 (t, J=7.83 Hz, 1H), 7.54 (dt, J=7.83, 1.52 Hz, 1H).

Example 1.11: Preparation of (S)-(1-((3-(Oxiran-2-ylmethoxy)phenyl)sulfonyl)cyclopropyl)methanol (Method BB6)

Step A: Preparation of 3-((3-Chloropropyl)thio)phenol

To a solution of 3-mercaptophenol (4.5 g, 35.66 mmol) in CH₂Cl₂ (60 mL, 0.6M) was added triethylamine (9.94 mL, 71.33 mmol) at 0° C. with vigorous stirring. The resulting suspension was added 1-bromo-3-chloropropane (6.74 g, 42.80 mmol) drop wise at 0° C. The reaction was stirred at room temperature for 1 h. The mixture was added DCM (100 mL) and water (60 mL). The organic layer was separated, and the aqueous layer was extracted with DCM (2×). The organic extracts were combined and washed with water (2×), brine, dried over Na₂SO₄, and filtered. The filtrate was concentrated to give the title compound as a thick yellowish liquid without further purification.

Step B: Preparation of 3-((3-Chloropropyl)sulfonyl)phenol

The crude 3-((3-chloropropyl)thio)phenol from Step A above was dissolved in dioxane and water (4:1, 100 mL). To this solution was added Oxone® (65.78 g, 107.0 mmol) portion wise. The white suspension was stirred at room temperature for 1 h. The white solid was filtered and washed with EtOAc (50 mL). The filtrate was concentrated under reduced pressure to remove the organic solvents. The resulting aqueous solution was extracted with EtOAc (3×75 mL). The combined organic extracts were washed with saturated aqueous NaHCO$_3$ solution, brine, dried over Na$_2$SO$_4$ and filtered. The filtrate was concentrated. The residue was purified by silica gel column chromatography to give the title compound (7.77 g, 89.7% yield). LCMS m/z=235.2 [M+H]$^+$; $^1$H NMR (400 M Hz, CDCl$_3$) δ ppm 2.18-2.25 (m, 2H), 3.27-3.31 (m, 2H), 3.61 (t, J=6.20 Hz, 2H), 7.14-7.19 (m, 1H), 7.43-7.47 (m, 3H).

Step C: Preparation of 3-(Cyclopropylsulfonyl)phenol

To a solution of 3-((3-chloropropyl)sulfonyl)phenol (5.0 g, 21.30 mmol) in THF (150 mL) was added drop wise potassium bis(trimethylsilyl)amide (1.0 M in MTBE, 46.87 mL, 46.87 mmol) at −78° C., which resulted formation of a thick suspension. The reaction was vigorously stirred for 30 min, then warmed up to room temperature overnight. The mixture was quenched with 2N HCl (50 mL) and the aqueous layer was extracted with 5% of MeOH/EtOAc (3×). The combined organic extract was washed with brine, dried over Na$_2$SO$_4$, and filtered. The filtrate was concentrated. The residue was purified by silica gel column chromatography to give the title compound (3.6 g, 85.2% yield) as a light yellow solid. LCMS m/z=199.4 [M+H]$^+$; $^1$H NMR (400 M Hz, CDCl$_3$) δ ppm 1.03-1.09 (m, 2H), 1.33-1.38 (m, 2H), 2.45-2.52 (m, 1H), 6.44 (s, 1H), 7.10-7.15 (m, 1H), 7.40-7.46 (m, 3H).

Step D: Preparation of ethyl 1-((3-((Ethoxycarbonyl)oxy)phenyl)sulfonyl)cyclopropane carboxylate To a solution of 3-(cyclopropylsulfonyl)phenol (3.6 g, 18.16 mmol) in THF (100 mL) was added n-butyllithium (18.75 mL, 46.87 mmol) drop wise at −78° C. The reaction was stirred for 30 min at the same temperature. Ethyl chloroformate (5.27 mL, 55.39 mmol) was then added drop wise to the reaction mixture at −78° C. The reaction mixture was allowed to warm up to room temperature and stirring was continued at room temperature for 2 h. After the reaction was completed, the mixture was quenched with saturated aqueous NH$_4$Cl solution. The aqueous layer was extracted with EtOAc (3×). The organic extracts were combined and washed with brine, dried over Na$_2$SO$_4$, and filtered. The filtrate was concentrated to give the title compound (6.4 g, 87.7% yield) without further purification. LCMS m/z=343.2 [M+H]$^+$.

Step E: Preparation of 3-((1-(Hydroxymethyl)cyclopropyl)sulfonyl)phenol (Method BB6E)

To a solution of ethyl 14(3-((ethoxycarbonyl)oxy)phenyl)sulfonyl)cyclopropanecarboxylate (6.4 g, 18.69 mmol) in THF (20 mL) was added 2.0 M solution of lithium aluminum hydride (23.43 mL, 46.87 mmol) at 0° C. After stirring at 0° C. for 10 min, the reaction mixture was warmed up to room temperature then stirred for another 3 h. The reaction mixture was carefully quenched with 1N NaOH at 0° C. to result in a thick suspension. To the suspension was added EtOAc (150 mL) and the reaction was stirred for 1 h at room temperature. The EtOAc layer was decanted from the suspension. 6N HCl (100 mL) was added and the mixture was stirred for 1 h to give a clear layer. The layers were separated and the aqueous layer was extracted with EtOAc (3×). The combined organic extracts were washed with water and brine, dried over Na$_2$SO$_4$, and concentrated. The residue was purified by silica gel column chromatography to give the title compound (3.74 g, 76.9% yield) as a light yellow solid. LCMS m/z=229.4 [M+H]$^+$; $^1$H NMR (400 M Hz, CDCl$_3$) δ ppm 1.04-1.07 (m, 2H), 1.58-1.61 (m, 2H), 3.67 (s, 2H), 7.12-7.15 (m, 1H), 7.34 (dt, J=1.41, 7.70 Hz, 1H), 7.37 (d, J=7.76 Hz, 1H), 7.38-7.40 (m, 1H), 9.18 (s, 1H).

Step F: Preparation of (S)-(1-((3-(Oxiran-2-ylmethoxy)phenyl)sulfonyl)cyclopropyl)methanol To a mixture of 3-((1-(hydroxymethyl)cyclopropyl)sulfonyl)phenol (2.0 g, 8.76 mmol) and potassium carbonate (3.63 g, 26.29 mmol) in acetone (30 mL) was added (S)-oxiran-2-ylmethyl 3-nitrobenzenesulfonate (2.50 g, 9.638 mmol). The reaction was heated at 75° C. overnight. The reaction mixture was cooled down to room temperature. The solid was separated by filtration and washed with acetone (2×10 mL). The filtrate was concentrated. The residue was purified by silica gel column chromatography to give the title compound (2.55 g, 90.5% yield) as a yellowish liquid. LCMS m/z=285.0 [M+H]$^+$; $^1$H NMR (400 M Hz, CDCl$_3$) δ ppm 1.05-1.08 (m, 2H), 1.62-1.66 (m, 2H), 2.64-2.74 (m, 1H), 2.78 (dd, J=2.69, 4.94 Hz, 1H), 2.94 (dd, J=4.19, 4.79 Hz, 1H), 3.35-3.39 (m, 1H), 3.66 (bs, 2H), 3.98 (dd, J=6.08, 11.60 Hz, 1H), 4.37 (dd, J=2.76, 11.05 Hz, 1H), 7.21-7.25 (m, 1H), 7.44-7.45 (m, 1H), 7.48-7.51 (m, 2H).

Example 1.12: Preparation of (S)-2,2-Difluoro-2-((3-(oxiran-2-ylmethoxy)phenyl)sulfonyl)ethanol (Method BB7)

Step A: Preparation of Ethyl 2,2-Difluoro-2-((3-methoxyphenyl)thio)acetate

To a suspension of sodium hydride (0.28 g, 6.99 mmol,) in THF at 0° C. was added 3-methoxybenzenethiol (0.7 g, 4.99 mmol) in THF (2 mL) drop wise and stirred at room temperature for 30 min. The reaction was cooled back to 0° C. and added a solution of ethyl 2-bromo-2,2-difluoroacetate (0.70 mL, 5.49 mmol) in THF (0.5 mL) drop wise. The reaction was stirred at 0° C. for 2 h and quenched with ice. The aqueous layer was separated and extracted with EtOAc (3×). The combined organic extracts were washed with brine, dried over Na$_2$SO$_4$, and concentrated. The residue was purified by silica gel column chromatography to give the title compound (1.26 g, 82% yield). LCMS m/z=263.2 [M+H]$^+$; $^1$H NMR (400 M Hz, CDCl$_3$) δ ppm 1.27 (t, J=7.15 Hz, 3H), 3.81 (s, 3H), 4.26 (q, J=7.15 Hz, 2H), 6.98-7.01 (m, 1H), 7.14-7.15 (m, 1H), 7.18-7.20 (m, 1H), 7.29 (q, J=7.86 Hz, 1H).

Step B: Preparation of Ethyl 2,2-Difluoro-2-((3-methoxyphenyl)sulfonyl)acetate To a solution of ethyl 2,2-difluoro-2-((3-methoxyphenyl) thio)acetate (1.26 g, 4.09 mmol) in DCM (75 mL) at 0° C. was added 3-chlorobenzoperoxoic acid (3.36 g, 14.98 mmol) portion wise. The reaction was stirred at room temperature overnight. The mixture was filtered through a pad of Celite® then washed with DCM. The filtrate was added NaHCO$_3$ then stirred for 30 min. The mixture was filtered through a pad of Celite®. The filtrate was washed once with saturated NaHCO$_3$ aqueous solution, brine, dried over Na$_2$SO$_4$, and concentrated. The residue was purified by silica gel column chromatography to give the title compound (1.01 g, 69% yield). LCMS m/z=295.2 [M+H]$^+$.

Step C: Preparation of 2,2-Difluoro-2-((3-methoxyphenyl)sulfonyl)ethanol

To a solution of ethyl 2,2-difluoro-2-((3-methoxyphenyl)sulfonyl)acetate (261 mg, 0.887 mmol) at 0° C. was added of lithium aluminum hydride (2.0M, 0.375 mL, 0.750 mmol,). After stirring at 0° C. for 10 min and at room temperature for 3 h, the reaction mixture was quenched with 1N NaOH at 0° C. The suspension was added 10% of MeOH in DCM and stirred for 30 minutes at room temperature. The mixture was filtered and washed with 10% of MeOH in DCM (3×). Aqueous layer was extracted with 10% of MeOH in DCM (3×). The combined organic extracts were washed with brine, dried over Na$_2$SO$_4$, filtered and concentrated. The residue was purified by silica gel silica gel column chromatography to give the title compound (0.201 g, 89% yield). LCMS m/z=253.0 [M+H]$^+$; $^1$H NMR (400 M Hz, CDCl$_3$) δ ppm 3.89 (s, 3H), 4.29 (t, J=12.70 Hz, 2H), 7.29-7.32 (m, 1H), 7.46-7.47 (m, 1H), 7.54 (t, J=7.88 Hz, 1H), 7.59 (m, 1H).

Step D: Preparation of 3-((1,1-Difluoro-2-hydroxyethyl)sulfonyl)phenol

To a solution of 2,2-difluoro-2-((3-methoxyphenyl)sulfonyl)ethanol (0.201 g, 0.668 mmol) in DCM (2 mL) at −78° C. under N$_2$ was added a solution of boron tribromide (0.142 mL, 1.501 mmol) slowly. The reaction was stirred at −78° C. for 1 h then warmed up to room temperature and stirred for 1 h. After the reaction was completed, the mixture was cooled down to −20° C. then quenched with $^i$PrOH. The mixture was neutralized with NaHCO$_3$ aqueous solution to pH 7 then extracted with 20% of $^i$PrOH in DCM. The combined organic extracts were washed once with brine, separated, dried over Na$_2$SO$_4$, and filtered. The filtrate was concentrated to give the title compound without further purification. LCMS m/z=239.2 [M+H]$^+$; $^1$H NMR (400 M Hz, CDCl$_3$) δ ppm 4.29 (t, J=12.72 Hz, 2H), 7.24-7.27 (m, 1H), 7.45-7.46 (m, 1H), 7.49 (t, J=7.84 Hz, 1H), 7.53-7.56 (m, 1H).

Step E: Preparation of (S)-2,2-Difluoro-2-((3-(oxiran-2-ylmethoxy)phenyl)sulfonyl)ethanol To a mixture of 3-((1,1-difluoro-2-hydroxyethyl)sulfonyl)phenol (0.132 g, 0.555 mmol) and potassium carbonate (0.207 g, 1.501 mmol) in acetone (15 mL) was added (S)-oxiran-2-ylmethyl 3-nitrobenzenesulfonate (0.214 g, 0.826 mmol). The reaction was heated at 75° C. overnight. The mixture was cooled down to room temperature, filtered, and washed with acetone (2×5 mL). The filtrate was concentrated and the residue was purified by silica gel column chromatography to give the title compound (0.205 g, 69% yield). LCMS m/z=295.4 [M+H]$^+$; $^1$H NMR (400 M Hz, CDCl$_3$) δ ppm 2.47 (t, J=7.33 Hz, 1H), 2.79 (dd, J=2.18, 4.79 Hz, 1H), 2.95 (t, J=4.04 Hz, 1H), 3.36-3.40 (m, 1H), 4.00 (dd, J=11.24, 5.94 Hz, 1H), 4.22-4.33 (m, 2H), 4.38 (dd, J=11.12, 2.78 Hz, 1H), 7.31-7.39 (m, 1H), 7.47-7.52 (m, 1H), 7.55 (t, J=7.96 Hz, 1H), 7.58-7.64 (m, 1H).

Example 1.13: Preparation of Quinoline-6-sulfonyl chloride

Step A: Preparation of Methyl 3-(Quinolin-6-ylsulfonyl)propanoate

To a 5 mL microwave vial were added 6-bromoquinoline (200 mg, 0.96 mmol), sodium 3-methoxy-3-oxopropane-1-sulfinate (0.84 g, 4.81 mmol), and copper (I) iodide (0.92 g, 4.81 mmol) followed by DMSO (2 mL). The reaction was degassed (2×) with nitrogen then heated at 110° C. overnight. After the reaction was cooled down room temperature, it was diluted with EtOAc. The resulting mixture was filtered through a pad of silica gel, washed with EtOAc, and then concentrated. The residue was purified by silica gel column chromatography to give the title compound (95 mg, 33% yield) as a yellow oil. LCMS m/z=280.2 [M+H]$^+$; $^1$H NMR (400 MHz, CD$_3$OD) δ ppm 2.77 (t, J=7.20 Hz, 2H), 3.55 (s, 3H), 3.65 (t, J=7.20 Hz, 2H), 7.72 (dd, J=8.46, 4.42 Hz, 1H), 8.17-8.22 (m, 1H), 8.24-8.29 (m, 1H), 8.61 (dd, J=8.46, 1.14 Hz, 1H), 8.64 (d, J=2.02 Hz, 1H), 9.07 (dd, J=4.29, 1.77 Hz, 1H).

Step B: Preparation of Quinoline-6-sulfonyl Chloride

To a solution of methyl 3-(quinolin-6-ylsulfonyl)propanoate (425 mg, 1.52 mmol) in THF (15 mL) at room temperature was added sodium methoxide (0.35 µL 1.52 mmol). The reaction mixture was stirred for 30 min then concentrated to give methyl quinoline-6-sulfonate as a yellow solid. LCMS m/z=266.0 [M+H]$^+$.

Methyl quinoline-6-sulfonate obtained above was dissolved in CH$_2$Cl$_2$ (15.00 mL) at 0° C. Then NCS (0.20 g, 1.52 mmol) was added. The reaction was stirred for 2 h. The reaction was quenched with brine then allowed to warm up to room temperature. The organic layer was separated and aqueous layer was washed with DCM. The combined organic layers were washed with water and brine, dried over Na$_2$SO$_4$, filtered and concentrated. The residue was purified by silica gel column chromatography to give the title compound (199 mg, 57% yield) as a beige solid. LCMS m/z=228.2 [M+H]$^+$; $^1$H NMR (400 MHz, CD$_3$OD) δ ppm 7.78 (dd, J=8.59, 4.29 Hz, 1H), 8.35 (d, J=1.52 Hz, 2H), 8.69 (dd, J=8.59, 1.52 Hz, 1H), 8.86 (s, 1H), 9.14 (dd, J=4.29, 1.77 Hz, 1H).

Example 1.14: Preparation of tert-Butyl 6-(Chlorosulfonyl)-1H-pyrrolo[3,2-b]pyridine-1-carboxylate Step A: Preparation of 6-(Benzylthio)-1H-pyrrolo[3,2-b]pyridine A mixture of 6-bromo-1H-pyrrolo[3,2-b]pyridine (1.970 g, 10 mmol), phenylmethanethiol (1.291 mL, 11.00 mmol), DIEA (3.484 mL, 20.00 mmol), and Pd$_2$(dba)$_3$ (0.458 g, 0.500 mmol) in dioxane (10 mL) was added (9,9-dimethyl-9H-xanthene-4,5-diyl)bis(diphenylphosphine) (0.579 g, 1.000 mmol). The reaction was heated to 150° C. for 2 h under microwave irradiation. After the reaction was cooled to room temperature, it was taken up in EtOAc. The mixture was washed with NaHCO$_3$(3×) and brine, dried over MgSO$_4$ and concentrated. The residue was purified by silica gel column chromatography to give the title compound (2.31 g, 96.1% yield) as an orange solid. LCMS m/z=241.2 [M+H]$^+$; $^1$H NMR (400 M Hz, CD$_3$OD) δ 4.05 (s, 2H), 6.55 (d, J=4.04 Hz, 1H), 7.10-7.16 (m, 2H), 7.16-7.25 (m, 3H), 7.56 (d, J=3.28 Hz, 1H), 7.73 (d, J=1.01 Hz, 1H), 8.17 (d, J=1.77 Hz, 1H).

Step B: Preparation of tert-Butyl 6-(Benzylthio)-1H-pyrrolo[3,2-b]pyridine-1-carboxylate To a solution of 6-(benzylthio)-1H-pyrrolo[3,2-b]pyridine (2.304 g, 9.587 mmol) and pyridine (1.551 mL, 19.17 mmol) in THF (20 mL) was added (BOC)$_2$O (2.511 g, 11.50 mmol). The reaction was stirred at room temperature for 18 h. The mixture was diluted with EtOAc, washed with water (3×) and brine, dried over MgSO$_4$ and concentrated. The residue was purified by silica gel column chromatography to give the title compound (2.59 g, 79.4% yield) as a yellow solid. LCMS m/z=341.4 [M+H]$^+$; $^1$H NMR (400 M Hz, CDCl$_3$) δ ppm 1.65 (s, 9H), 4.10 (s, 2H), 6.73 (d, J=3.28 Hz, 1H), 7.14-7.33 (m, 5H), 7.79 (d, J=3.79 Hz, 1H), 8.34 (bs, 1H), 8.45 (d, J=2.02 Hz, 1H).

Step C: Preparation of tert-Butyl 6-(Chlorosulfonyl)-1H-pyrrolo[3,2-b]pyridine-1-carboxylate (Method BB8C)

To a solution of tert-butyl 6-(benzylthio)-1H-pyrrolo[3,2-b]pyridine-1-carboxylate (2.583 g, 7.587 mmol) in AcOH (10 mL)/H$_2$O (3.333 mL) was added NCS (3.039 g, 22.76 mmol). The reaction was stirred for 5 hours. The mixture was concentrated. The residue was dissolved in DCM and washed with aqueous NaHCO$_3$. The aqueous layer was extracted with DCM (2×). The combined organics were dried over MgSO$_4$, filtered and concentrated. The residue was purified by silica gel column chromatography to give the title compound (0.54 0 g, 22.5% yield) as a yellow solid. LCMS m/z=317.2 [M+H]$^+$; $^1$H NMR (400 M Hz, CDCl$_3$) δ ppm 1.72 (s, 9H), 6.94 (d, J=3.03 Hz, 1H), 8.16 (d, J=3.54 Hz, 1H), 9.02 (bs, 1H), 9.16 (d, J=2.27 Hz, 1H).

Example 1.15: Preparation of 1-Methyl-2,3-dihydro-1H-pyrido[2,3-b][1,4]oxazine-7-sulfonyl Chloride (Method BB9)

Step A: Preparation of 7-(Benzylthio)-1-methyl-2,3-dihydro-1H-pyrido[2,3-b][1,4]oxazine From 7-bromo-1-methyl-2,3-dihydro-1H-pyrido[2,3-b][1,4]oxazine, the title compound was prepared using a similar method to the one described in Example 1.14, Step A. LCMS m/z=272.8 [M+H]$^+$.

Step B: Preparation of 1-Methyl-2,3-dihydro-1H-pyrido[2,3-b][1,4]oxazine-7-sulfonyl chloride From 7-(benzylthio)-1-methyl-2,3-dihydro-1H-pyrido[2,3-b][1,4]oxazine, the title compound was prepared using a similar method to the one described in Example 1.14, Step C. LCMS m/z=249.2 [M+H]$^+$; $^1$H NMR (400 M Hz, CDCl$_3$) δ ppm 3.00 (s, 3H), 3.39-3.42 (m, 2H), 4.54-4.57 (m, 2H), 7.24 (d, J=2.27 Hz, 1H), 8.22 (d, J=2.02 Hz, 1H).

Example 1.16: Preparation of 3-Methyl-3H-imidazo[4,5-b]pyridine-6-sulfonyl chloride (Method BB10)

Step A: Preparation of 5-(Benzylthio)-N$^2$-methyl-pyridine-2,3-diamine

From 5-bromo-N$^2$-methylpyridine-2,3-diamine, the title compound was prepared using a similar method to the one described in Example 1.14, Step A. LCMS m/z=246.2 [M+H]$^+$; $^1$H NMR (400 MHz, DMSO-d$_6$) δ ppm 2.80 (d, J=4.55 Hz, 3H), 3.91 (s, 2H), 4.72 (s, 2H), 5.79 (q, J=4.55 Hz, 1H), 6.72 (d, J=2.27 Hz, 1H), 7.17-7.22 (m, 3H), 7.24-7.29 (m, 2H), 7.31 (d, J=2.27 Hz, 1H)

Step B: Preparation of 6-(Benzylthio)-3-methyl-3H-imidazo[4,5-b]pyridine

To a solution of 5-(benzylthio)-N$^2$-methylpyridine-2,3-diamine (0.195 g, 0.795 mmol) in THF (5 mL) was added trimethoxymethane (4 mL, 36.56 mol) followed by addition of a few drops of TFA. The reaction was stirred overnight. The mixture was diluted with EtOAc, washed with water (3×) and brine, dried over MgSO$_4$ and concentrated. The residue was purified by silica gel column chromatography (1:1 EtOAc/hexane) to give the title compound (1.74 g, 87.5% yield) as a tan solid. LCMS m/z=256.4 [M+H]$^+$; $^1$H NMR (400 M Hz, CDCl$_3$) δ ppm 3.91 (s, 3H), 4.06 (s, 2H), 7.14-7.26 (m, 5H), 8.03 (d, J=2.02 Hz, 1H), 8.08 (s, 1H), 8.35 (d, 1H).

Step C: Preparation of 3-Methyl-3H-imidazo[4,5-b]pyridine-6-sulfonyl chloride From 6-(benzylthio)-3-methyl-3H-imidazo[4,5-b]pyridine, the title compound was prepared using a similar method to the one described in Example 1.14, Step C. LCMS m/z=232.2 [M+H]$^+$; $^1$H NMR (400 MHz, CDCl$_3$) δ ppm 4.02 (s, 3H), 8.29 (s, 1H), 8.71 (d, J=2.02 Hz, 1H), 9.10 (d, J=2.02 Hz, 1H).

Example 1.17: Preparation of 1-(2-Methoxyethyl)-2,3-dihydro-1H-pyrido[2,3-b][1,4]oxazine-7-sulfonyl chloride (Method BB11)

Step A: Preparation of 7-Bromo-1-(2-methoxyethyl)-2,3-dihydro-1H-pyrido[2,3-b][1,4]oxazine To a solution of 7-bromo-2,3-dihydro-1H-pyrido[2,3-b][1,4]oxazine (0.430 g, 2 mmol) in DMF was added sodium hydride (0.120 g, 3.000 mmol). The reaction was stirred for 20 minutes. 1-Bromo-2-methoxyethane (0.207 mL, 2.200 mmol) was added. The reaction was heated to 60° C. for 2 hours. The mixture was concentrated. The residue was taken up in EtOAc, washed with water (3×) and brine, dried over MgSO$_4$ and concentrated. The residue was purified by silica gel column chromatography to give the title compound (0.451 g, 82.6% yield) as a white solid. LCMS m/z=273.0 [M+H]$^+$; $^1$H NMR (400 M Hz, CDCl$_3$) δ ppm 3.36 (s, 3H), 3.39-3.47 (m, 4H), 3.58 (t, J=5.43 Hz, 2H), 4.35 (t, J=4.80 Hz, 2H), 6.97 (d, J=2.02 Hz, 1H), 7.55 (d, J=2.27 Hz, 1H).

Step B: Preparation of 7-(Benzylthio)-1-(2-methoxyethyl)-2,3-dihydro-1H-pyrido[2,3-b][1,4]oxazine From 7-bromo-1-(2-methoxyethyl)-2,3-dihydro-1H-pyrido[2,3-b][1,4]oxazine, the title compound was prepared using a similar method to the one described in Example 1.14, Step A. LCMS m/z=317.0 [M+H]$^+$; $^1$H NMR (400 M Hz, CDCl$_3$) δ ppm 3.29 (t, J=5.31 Hz, 2H), 3.32 (s, 3H), 3.37-3.45 (m, 4H), 3.96 (s, 2H), 4.35 (t, J=4.55 Hz, 2H), 6.70 (d, J=2.02 Hz, 1H), 7.15-7.32 (m, 5H), 7.53 (d, J=2.02 Hz, 1H).

Step C: Preparation of 1-(2-Methoxyethyl)-2,3-dihydro-1H-pyrido[2,3-b][1,4]oxazine-7-sulfonyl Chloride From 7-(benzylthio)-1-(2-methoxyethyl)-2,3-dihydro-1H-pyrido[2,3-b][1,4]oxazine, the title compound was prepared using a similar method to the one described in Example 1.14, Step C. LCMS m/z=292.8 [M+H]$^+$; $^1$H NMR (400 M Hz, CDCl$_3$) δ ppm 3.36 (s, 3H), 3.52-3.56 (m, 4H), 3.63 (t, J=5.05 Hz, 2H), 4.46-4.50 (m, 2H), 7.34 (d, J=2.27 Hz, 1H), 8.17 (d, J=2.02 Hz, 1H).

Example 1.18: Preparation of 7-Fluoro-4-hydroxyquinoline-3-sulfonyl Chloride (Method BB12)

To sulfurochloridic acid (10.71 g, 91.9 mmol, 30 eq) at 0° C. was added 7-fluoroquinolin-4-ol (500 mg, 3.06 mmol, 1.0 eq) under N$_2$ atmosphere. The resulting solution was stirred at 90° C. for 16 h. After cooling to room temperature, the reaction mixture was added onto ice drop wise. The resulting precipitate was filtered and the filter cake was washed with CH$_3$CN/H$_2$O (2:1), the filtrate was lyophilized to give the title compound (550 mg, 65% yield) as a white solid. LCMS m/z=261.9 [M+H]$^+$; $^1$H NMR (400 MHz, DMSO-d$_6$): δ ppm 6.90 (br.s, 1H), 7.59 (td, J=8.9, 2.4 Hz, 1H), 7.78 (dd, J=9.8, 2.5 Hz, 1H), 8.41 (dd, J=9.3, 6.0 Hz, 1H), 8.99 (s, 1H).

Example 1.19: Preparation of 4-Hydroxy-7-methylquinoline-3-sulfonyl Chloride (Method BB13)

To sulfurochloridic acid (10.98 g, 94.2 mmol) at 0° C. was added 7-methylquinolin-4-ol (500 mg, 3.14 mmol) under N$_2$ atmosphere. The resulting solution was stirred at 80° C. for 16 h. After cooling to room temperature, the reaction mixture was added onto ice drop wise. The resulting precipitate was filtered and the filter cake was washed with CH$_3$CN/H$_2$O (3:1), the filtrate was lyophilized to give the title compound (250 mg, 17% yield) as a yellow solid, further purification could not improve the purity. LCMS m/z=258.0 [M+H]$^+$; $^1$H NMR (400 MHz, DMSO-d$_6$): δ ppm 2.57 (s, 3H), 7.64 (d, J=8.3 Hz, 1H), 7.82 (br.s., 1H), 8.26 (d, J=8.4 Hz, 1H), 9.07-9.15 (m, 1H).

Example 1.20: Preparation of 1H-Indole-3-sulfonyl Chloride (Method BB14)

Step A: Preparation of 1H-Indole-sulfonic Acid

A solution of 1H-indole (2.0 g, 17.07 mmol) and sulfur trioxide pyridine complex (2.72 g, 17.07 mmol) in pyridine (10 mL) was refluxed under stirring for 2 h and then was cooled to room temperature. The reaction mixture was diluted with water (20 mL) and washed with diethyl ether (2×20 mL). The aqueous phase was concentrated to give the title compound which was used in the next step without further purification.

Step B: Preparation of 1H-Indole-3-sulfonyl Chloride

The 1H-indole-sulfonic acid pyridinium salt from the previous step was dissolved in 40 mL of a 1:1 sulfolane (20 mL)-MeCN (20 mL) mixture. The solution was cooled to 0° C., and phosphoryl trichloride (6 mL, 64.57 mmol) was added drop wise with stirring. The reaction mixture was heated to 70° C. for 2 h, and then cooled to 0° C. Cold water (10 mL) was added drop wise to the reaction mixture. The precipitate was filtered, washed with water and dried under reduced pressure to afford the title compound (1.7 g, 40% yield) as a brown color solid. LCMS m/z=216.0 [M+H]$^+$; NMR (400 MHz, Acetone-d$_6$) δ ppm 7.38-7.46 (m, 2H), 7.69 (dd, J=6.57, 2.78 Hz, 1H), 7.95 (dd, J=6.57, 2.78 Hz, 1H), 8.38 (s, 1H), 11.77 (bs, 1H).

Example 1.21: Preparation of 3-((3-Methoxyphenyl)sulfonyl)cyclobutanol

To a solution of 1-methoxy-3-(methylsulfonyl)benzene (200 mg, 1.074 mmol) in THF (10 mL) at 0° C. was added dropwise n-butyllithium (2.5 M in hexane, 0.86 mL, 2.15 mmol), which resulted in formation of yellowish suspension and stirring was continued for 1 h at 0° C. Then 2-(chloromethyl)oxirane (99.37 mg, 1.07 mmol) was added drop wise at 0° C. The reaction was stirred at room temperature overnight and quenched with saturated aqueous NH$_4$Cl solution. The aqueous layer was extracted with EtOAc (3×). The combined organic phase was washed with brine, dried over Na$_2$SO$_4$, and concentrated. The residue was purified by silica gel column chromatography to give the title compound (0.248 g, 86% yield) as a thick liquid. LCMS m/z=243.0 [M+H]$^+$; $^1$H NMR (400 MHz, CDCl$_3$) δ ppm 2.40-2.52 (m, 2H), 2.56-2.67 (m, 2H), 3.36 (quin, J=8.21 Hz, 1H), 3.87 (s, 3H), 4.20 (quin, J=7.70 Hz, 1H), 7.17 (dt, J=7.14, 2.37 Hz, 1H), 7.34-7.40 (m, 1H), 7.40-7.51 (m, 2H).

Example 1.22: Preparation of 2-((3-Fluoro-5-methoxyphenyl)thio)ethanol

A mixture of 1-bromo-3-fluoro-5-methoxybenzene (0.5 g, 2.44 mmol), 2-mercaptoethanol (0.210 g, 2.683 mmol), DIEA (0.94 mL, 5.37 mmol), Pd2(dba)3 (0.22 g, 0.24 mmol), and (9,9-dimethyl-9H-xanthene-4,5-diyl)bis(diphenylphosphine) (0.14 g, 0.24 mmol) in DMF (2 mL) was heated to 110° C. overnight. After cooling down to room temperature, the mixture was diluted with EtOAc and water. The mixture was filtered through a pad of celite. The aqueous layer was extracted with EtOAc (3×). The combined organic layer was washed with brine, dried over Na$_2$SO$_4$, and filtered. The filtrate was concentrated to give the title compound without further purification.

Example 1.23: Preparation of 7-(Benzylthio)-1,8-dimethyl-2,3-dihydro-1H-pyrido[2,3-b][1,4]oxazine

Step A: Preparation of Ethyl 2-((5-Bromo-4-methyl-3-nitropyridin-2-yl)oxy)acetate To a solution of 5-bromo-2-chloro-4-methyl-3-nitro-pyridine (5.00 g, 19.9 mmol) in ethyl 2-hydroxyacetate (12.42 g, 119 mmol) at room temperature was added DBU (9.08 g, 59.7 mmol) dropwise. The color of the reaction mixture changed from yellow to puce. The mixture was stirred at 100° C. for 8 hours and then cooled to room temperature. The reaction was then quenched with 30 mL of water and extracted with ethyl acetate (2×20 mL). The combined organic phase was washed with brine (30 mL), dried over anhydrous Na$_2$SO$_4$, filtered and concentrated in vacuo. The residue was purified by silica gel column chromatography to give the title compound (2.0 g, 29% yield, 91% purity) as a yellow solid.

Step B: Preparation of 7-Bromo-8-methyl-1H-pyrido[2,3-b][1,4]oxazin-2(3H)-one To a solution of ethyl 2-((5-bromo-4-methyl-3-nitropyridin-2-yl)oxy)acetate (2.00 g, 5.70 mmol, 91% purity 1.0 eq) in EtOH (4 mL) and AcOH (10 mL) at room temperature was added zinc powder (2.05 g, 31.4 mmol). The reaction was stirred at 100° C. for 1 hour. After cooling to room temperature, the solution was concentrated in vacuo. To the residue was added MeOH (20 mL) and pH was adjusted to 9 by ammonia. The mixture was filtered and the filtrate was concentrated in vacuo to give the title compound (1.40 g, crude) as a brown solid, which was used in the next step without further purification.

Step C: Preparation of 7-Bromo-8-methyl-2,3-dihydro-1H-pyrido[2,3-b][1,4]oxazine To the solution of 7-bromo-8-methyl-1H-pyrido[2,3-b][1,4]oxazin-2(3H)-one (1.40 g crude, 5.76 mmol, 1.0 eq) in THF (5 mL) was added $BH_3$·THF (23 mL, 1 M solution in THF, 23 mmol, 4.0 eq) at 0° C. under $N_2$ atmosphere. The mixture was then heated to 80° C. for 6 hours. After cooling to room temperature, the reaction was quenched by adding 3 mL of $H_2O$ and 3 mL of MeOH. The mixture was concentrated in vacuo and purified by silica gel column chromatography to give the title compound (800 mg, 54% yield, 89% purity) as a white solid.

Step D: Preparation of 7-Bromo-1,8-dimethyl-2,3-dihydro-1H-pyrido[2,3-b][1,4]oxazine To a solution of 7-bromo-8-methyl-2,3-dihydro-1H-pyrido[2,3-b][1,4]oxazine (800 mg, 3.11 mmol, 89% purity) in DMF (6 mL) under $N_2$ atmosphere was added NaH (167.60 mg, 60% purity, 4.19 mmol) and then stirred at 0° C. for 1 hour. To the above solution was added iodomethane (13.00 g, 91.4 mmol) at 0° C. and then stirred at 20° C. for additional 1 h. The reaction mixture was quenched by addition of saturated aqueous solution of $NH_4Cl$ (4 mL), diluted with $H_2O$ (4 mL) and extracted with ethyl acetate (3×8 mL). The combined organic layer was washed with brine (10 mL), dried over anhydrous $Na_2SO_4$, filtered and concentrated in vacuo. The residue was purified by silica gel column chromatography to give the title compound (690 mg, 65% yield, 80% purity) as a white oil.

Step E: Preparation of 7-(Benzylthio)-1,8-dimethyl-2,3-dihydro-1H-pyrido[2,3-b][1,4]oxazine To a microwave tube were added phenylmethanethiol (1.46 g, 11.7 mmol, 3.0 eq), 7-bromo-1,8-dimethyl-2,3-dihydro-1H-pyrido[2,3-b][1,4]oxazine (950 mg, 3.91 mmol), dioxane (6.00 mL), Pd(dppf)$Cl_2$·$CH_2Cl_2$ (1.43 g, 1.96 mmol, 0.50 eq), tri-tert-butylphosphine (791 mg, 3.91 mmol, 1.0 eq) and DIEA (2.02 g, 15.6 mmol, 4.0 eq) under $N_2$ atmosphere. The sealed tube was heated at 150° C. for 6 hours under microwave irradiation. After cooling, the mixture was diluted with $H_2O$ (20 mL) and extracted with ethyl acetate (3×20 mL). The combined organic phase was washed with brine (30 mL), dried over anhydrous $Na_2SO_4$, filtered and concentrated in vacuo. The residue was purified by prep-HPLC (basic condition) to give the title compound (500 mg, 44% yield) as a brown oil. LCMS m/z 287.4 [M+H]$^+$; $^1$H NMR (CDCl$_3$, 400 MHz): δ ppm 2.17 (s, 3H), 2.62 (s, 3H), 3.03-3.11 (m, 2H), 3.89 (s, 2H), 4.31-4.38 (m, 2H), 7.06-7.15 (m, 2H), 7.18-7.26 (m, 3H), 7.94 (s, 1H).

Example 1.24: Preparation of (R)-7-(Benzylthio)-1,3-dimethyl-2,3-dihydro-1H-pyrido[2,3-b][1,4]oxazine

Step A: Preparation of (R)-Methyl 2-((5-bromo-3-nitropyridin-2-yl)oxy)propanoate To a solution of 5-bromo-2-chloro-3-nitropyridine (8.00 g, 33.7 mmol, 1.0 eq), methyl (2R)-2-hydroxypropanoate (10.52 g, 101 mmol, 3.0 eq) in MeCN (250 mL) was added $K_2CO_3$ (18.63 g, 135 mmol, 4.0 eq). The reaction was stirred at 75° C. for 15 h. After cooling, the mixture was filtered and the filtrate was concentrated in vacuo. The residue was purified by silica gel chromatography to give the title compound (4.84 g, 47% yield) as yellow oil.

Step B: Preparation of (R)-7-Bromo-3-methyl-1H-pyrido[2,3-b][1,4]oxazin-2(3H)-one To a solution of (R)-methyl 2-((5-bromo-3-nitropyridin-2-yl)oxy)propanoate (4.80 g, 15.7 mmol) in AcOH (250 mL) was added Fe powder (4.39 g, 78.7 mmol), and then the mixture was heated to 80° C. for 1 h. After cooling to room temperature, the mixture was filtered and the filtrate was concentrated in vacuo to give the title compound (10 g) without further purification.

Step C: Preparation of (R)-7-Bromo-1,3-dimethyl-1H-pyrido[2,3-b][1,4]oxazin-2(3H)-one To a solution of (R)-7-bromo-3-methyl-1H-pyrido[2,3-b][1,4]oxazin-2(3H)-one (4.81 g crude, 19.8 mmol) in acetone (80 mL) was added MeI (3.98 g, 28.0 mmol) and $K_2CO_3$ (2.74 g, 19.8 mmol). The mixture was stirred at 50-70° C. for 15 h. After cooling, the reaction mixture was filtered, and the filtrate was concentrated in vacuo. The residue was purified by silica gel chromatography to give the title compound (1.24 g, 24% yield, 88% purity) as a white solid. LCMS m/z=256.9 [M+H]$^+$.

Step D: Preparation of (R)-7-Bromo-1,3-dimethyl-2,3-dihydro-1H-pyrido[2,3-b][1,4]oxazine To a solution of (R)-7-bromo-1,3-dimethyl-1H-pyrido[2,3-b][1,4]oxazin-2(3H)-one (400 mg, 1.37 mmol, 88% purity) in THF (40 mL) was added $BH_3$·THF (15.6 mL, 1 M solution in THF, 15.6 mmol) dropwise at 0° C. under $N_2$ atmosphere. The mixture was then stirred at 25° C. for 15 h. The reaction mixture was quenched by adding MeOH (4 mL) at 0° C., and then 1 M HCl was added to adjust pH<7. The mixture was then heated to reflux for 1 hour. After cooling, 1 M NaOH aqueous solution was added to adjust pH>7. The reaction mixture was diluted with $H_2O$ (20 mL) and extracted with ethyl acetate (3×20 mL). The combined organic phase was washed with brine (30 mL), dried over anhydrous $Na_2SO_4$, filtered and concentrated in vacuo. The residue was purified by silica gel chromatography to give the title compound (269 mg, 71% yield) as a yellow solid. LCMS (ESI): m/z=242.9 [M+H]$^+$.

Step E: Preparation of (R)-7-(Benzylthio)-1,3-dimethyl-2,3-dihydro-1H-pyrido[2,3-b][1,4]oxazine From (R)-7-bromo-1,3-dimethyl-2,3-dihydro-1H-pyrido[2,3-b][1,4]oxazine, the title compound was prepared using a similar method to the one described in Example 1.23, Step E. LCMS m/z=287.1 [M+H]⁺; ¹H NMR (CDCl₃, 400 MHz): δ ppm 1.42 (d, J=6.4 Hz, 3H), 2.73 (s, 3H), 2.98 (dd, J=11.5, 8.4 Hz, 1H), 3.16 (dd, J=11.6, 2.6 Hz, 1H), 3.97 (s, 2H), 4.48 (dqd, J=8.5, 6.3, 2.6 Hz, 1H), 6.66 (d, J=2.0 Hz, 1H), 7.18-7.32 (m, 5H), 7.57 (d, J=2.0 Hz, 1H).

Example 1.25: Preparation of (3S)-7-Benzylsulfanyl-1,3-dimethyl-2,3-dihydropyrido[2,3-b][1,4]oxazine Step A: Preparation of Methyl (2S)-2-[(5-Bromo-3-nitro-2-pyridyl)oxy]propanoate To a solution of 5-bromo-2-chloro-3-nitro-pyridine (8.00 g, 33.7 mmol), methyl (2S)-2-hydroxypropanoate (10.52 g, 101 mmol) in MeCN (100 mL) was added K₂CO₃ (18.63 g, 135 mmol). The mixture was stirred at 75° C. for 15 hours. After cooling, the reaction mixture was filtered and concentrated in vacuo. The residue was purified by silica gel chromatography to give the title compound (6.10 g, 59% yield) as a yellow oil.

Step B: Preparation of (3S)-7-Bromo-3-methyl-1H-pyrido[2,3-b][1,4]oxazin-2-one

To a solution of (S)-methyl 2-((5-bromo-3-nitropyridin-2-yl)oxy)propanoate (5.00 g, 16.4 mmol) in AcOH (50 mL) was added Fe powder (4.58 g, 82.0 mmol), and then the mixture was heated to 80° C. for 1 h. The reaction mixture was filtered and concentrated in vacuo. The residue was purified by basic resin to give the title compound (3.58 g, 90% yield) without further purification.

Step C: Preparation of (3S)-7-Bromo-3-methyl-2,3-dihydro-1H-pyrido[2,3-b][1,4]oxazine To a solution of (3S)-7-bromo-3-methyl-1H-pyrido[2,3-b][1,4]oxazin-2-one (2.20 g, 9.05 mmol) in THF (100 mL) was added BH₃.THF (90.5 mL, 1 M solution in THF, 90.5 mmol) at 0° C. The reaction was then stirred at 25° C. for 15 h. The reaction mixture was quenched by adding MeOH (4.0 mL) at 0° C., and then HCl (1 M, 2.0 mL) was added to adjust pH<7. The mixture was refluxed for 1 h and then cooled to room temperature. NaOH (1 M aqueous solution, 4.0 mL) was added to make pH>7. The aqueous phase was extracted with DCM (3×100 mL). The combined organic phase was washed with brine (2×30 mL), dried over anhydrous Na₂SO₄, filtered and concentrated in vacuo. The residue was purified by silica gel chromatography to give the title compound (679 mg, 33% yield) as a white solid.

Step D: Preparation of (3S)-7-Bromo-1,3-dimethyl-2,3-dihydropyrido[2,3-b][1,4]oxazine To a solution of (3S)-7-bromo-3-methyl-1H-pyrido[2,3-b][1,4]oxazin-2-one (100 mg, 411 μmol) in DMF (20 mL) was added NaH (104 mg, 2.59 mmol, 60% purity) at 0° C. under N₂ atmosphere. The mixture was stirred at 25° C. for 15 h before quenching with ice water. The mixture was then extracted with ethyl acetate (3×20 mL). The combined organic phase was washed with brine (20 mL), dried over anhydrous Na₂SO₄, filtered and concentrated in vacuo. The residue was purified by silica gel chromatography to give the title compound (80 mg, 80% yield) as a white solid.

Step E: Preparation of (3S)-7-Benzylsulfanyl-1,3-dimethyl-2,3-dihydropyrido[2,3-b][1,4]oxazine From (3S)-7-bromo-1,3-dimethyl-2,3-dihydropyrido[2,3-b][1,4]oxazine, the title compound was prepared using a similar method to the one described in Example 1.23, Step E. LCMS m/z=287.1 [M+H]⁺; ¹H NMR (CDCl₃, 400 MHz): δ ppm 1.41 (d, J=6.4 Hz, 3H), 2.72 (s, 3H), 2.97 (dd, J=11.5, 8.4 Hz, 1H), 3.15 (dd, J=11.5, 2.5 Hz, 1H), 3.96 (s, 2H), 4.43-4.53 (m, 1H), 6.64 (d, J=1.9 Hz, 1H), 7.16-7.30 (m, 5H), 7.55 (d, J=2.0 Hz, 1H).

Example 1.26: Preparation of 7-Benzylsulfanyl-1,3,3-trimethyl-2H-pyrido[2,3-b][1,4]oxazine Step A: Preparation of 2-Bromo-N-(5-bromo-2-hydroxypyridin-3-yl)-2-methylpropanamide To a solution of 3-amino-5-bromopyridin-2-ol (4.00 g, 21.2 mmol, 1.0 eq) in THF (40 mL) was added TEA (6.42 g, 63.5 mmol) and 2-bromo-2-methyl-propanoyl bromide (5.35 g, 23.3 mmol) at 0° C. The reaction was stirred at 17° C. for 2 h. The mixture was diluted with H₂O (60 mL) and extracted with ethyl acetate (2×30 mL). The combined organic phase was washed with brine (30 mL), dried over anhydrous Na₂SO₄, filtered and concentrated in vacuo to give the title compound (6.30 g, crude) as a white solid without further purification. LCMS: m/z=336.9. [M+H]⁺.

Step B: Preparation of 7-Bromo-3,3-dimethyl-1H-pyrido[2,3-b][1,4]oxazin-2(3H)-one To a solution of 2-bromo-N-(5-bromo-2-hydroxypyridin-3-yl)-2-methylpropanamide (5.30 g, 15.7 mmol) in DMF (130 mL) was added K₂CO₃ (6.50 g, 47.0 mmol). The mixture was stirred at 70° C. for 8 h under N₂ atmosphere. After cooling, the reaction mixture was concentrated in vacuo. The residue was purified by silica gel column chromatography to give the title compound (2.70 g, 67% yield) as a yellow solid.

Step C: Preparation of 7-Bromo-3,3-dimethyl-1,2-dihydropyrido[2,3-b][1,4]oxazine To a solution of 7-bromo-3,3-dimethyl-1H-pyrido[2,3-b][1,4]oxazin-2(3H)-one (2.70 g, 10.5 mmol) in THF (20 mL) was added BH₃.THF (31.5 mL, 1 M solution in THF, 31.5 mmol) at 0° C. under N₂ atmosphere. The reaction was stirred at 80° C. for 4 h. After cooling, the reaction mixture was quenched by addition of H₂O (3 mL) and MeOH (3 mL). The mixture was concentrated in vacuo to give the title compound (2.80 g, crude) as a yellow solid. LCMS m/z=243.0 [M+H]⁺.

Step D: Preparation of 7-Bromo-1,3,3-trimethyl-2H-pyrido[2,3-b][1,4]oxazine

To a solution of 7-bromo-3,3-dimethyl-1,2-dihydropyrido[2,3-b][1,4]oxazine (2.80 g, 11.5 mmol) in DMF (30 mL) was added NaH (691 mg, 17.3 mmol, 60% purity) at 0° C. for 30 minutes under N₂ atmosphere. Then iodomethane (2.45 g, 17.3 mmol) was added at 0° C. The reaction was stirred at 15° C. for 1 h. The mixture was quenched by addition of saturated aqueous solution of NH₄Cl (20 mL), and then extracted with ethyl acetate (2×20 mL). The combined organic phase was washed with brine (20 mL), dried over anhydrous Na₂SO₄, filtered and concentrated in vacuo. The residue was purified by silica gel column chromatography to give the title compound (150 mg) as a white solid.

Step E: Preparation of 7-Benzylsulfanyl-1,3,3-trimethyl-2H-pyrido[2,3-b][1,4]oxazine From 7-bromo-1,3,3-trimethyl-2H-pyrido[2,3-b][1,4]oxazine, the title compound was prepared using a similar method to the one described in Example 1.23, Step E. LCMS m/z=301.1 [M+H]$^+$; $^1$H NMR (CDCl$_3$, 400 MHz): δ ppm 1.38 (s, 6H), 2.75 (s, 3H), 2.91-2.98 (m, 2H), 3.96 (s, 2H), 6.65 (d, J=2.0 Hz, 1H), 7.16-7.32 (m, 5H), 7.59 (d, J=2.0 Hz, 1H).

Example 1.27: Preparation of 7-Benzylsulfanyl-1-methyl-spiro[2H-pyrido[2,3-b][1,4]oxazine-3,1'-cyclopropane]

Step A: Preparation of Methyl 1-[(5-Bromo-3-nitro-2-pyridyl)oxy]cyclopropanecarboxylate To a mixture of methyl 1-hydroxycyclopropanecarboxylate (3.00 g, 25.82 mmol) in THF (100 mL) was added NaH (1.55 g, 38.7 mmol, 60% purity) in portions at 0° C. under N$_2$ atmosphere. The mixture was stirred at 0° C. for 30 minutes, then 5-bromo-2-chloro-3-nitro-pyridine (6.13 g, 25.8 mmol) in THF (20 mL) was added dropwise. The mixture was stirred at 0° C. for 1.5 h. The solution was quenched with water (50 mL) and then extracted with ethyl acetate (3×100 mL). The combined organic layers was washed with brine (2×200 mL), dried over Na$_2$SO$_4$, filtered, and then concentrated in vacuo. The residue was purified by chromatography to give the title compound (5.35 g, 65% yield) as a red solid. LCMS m/z=316.9 [M+H]$^+$.

Step B: Preparation of 7-Bromospiro[1H-pyrido[2,3-b][1,4]oxazine-3,1'-cyclopropane]-2-one To a mixture of methyl 1-[(5-bromo-3-nitro-2-pyridyl) oxy]cyclopropanecarboxylate (2.00 g, 6.31 mmol) in AcOH (8 mL) and EtOH (3 mL) was added zinc powder (2.10 g, 32.1 mmol). The reaction was then stirred at 100° C. for 1 h. After cooling, the mixture was filtered, and the filtrate was concentrated in vacuo to give the title compound (2.20 g) as a yellow solid without further purification. LCMS m/z=255.0 [M+H]$^+$.

Step C: Preparation of 7-Bromospiro[1,2-dihydropyrido[2,3-b][1,4]oxazine-3,1'-cyclopropane]

To a solution of 7-bromospiro[1H-pyrido[2,3-b][1,4]oxazine-3,1'-cyclopropane]-2-one (3.00 g, 10.2 mmol) in THF (20 mL) was added borane; tetrahydrofuran (40.9 mL, 1 M solution in THF, 40.9 mmol) at 0° C. under N$_2$ atmosphere. The reaction was then stirred at 80° C. for 3 h. After cooling to 20° C., methanol (10 mL) was added, and the resulting solution was concentrated in vacuo. The residue was diluted in ethyl acetate (15 mL) and washed with saturated aqueous NaHCO$_3$ (2×20 mL), water (2×20 mL), brine (2×20 mL). The organic layer was then concentrated in vacuo to give the title compound (1.50 g, 28% yield) as a yellow oil. LCMS m/z=240.9 [M+H]$^+$.

Step D: Preparation of 7-Bromo-1-methyl-spiro[2H-pyrido[2,3-b][1,4]oxazine-3,1'-cyclopropane]

To a solution of 7-bromospiro[1,2-dihydropyrido[2,3-b] [1,4]oxazine-3,1'-cyclopropane] (1.00 g, 1.91 mmol, 46% purity, 1.0 eq) in DMF (25 mL) was added NaH (60 mg, 2.48 mmol, 60% purity, 0.78 eq) at 0° C., after stirring for 5 minutes, iodomethane (542 mg, 3.82 mmol, 2.0 eq) was added. The reaction was stirred at 0° C. for 1.5 hours and then quenched with water (30 mL) and brine (30 mL). The reaction solution was extracted with ethyl acetate (2×50 mL). The combined organic layers was washed with water (2×50 mL) and brine (2×50 mL), and then concentrated in vacuo. The residue was purified by chromatography to give the title compound (400 mg, 66% yield) as a yellow oil. LCMS m/z=255.0 [M+H]$^+$; $^1$H NMR (300 MHz, CDCl$_3$): δ ppm 0.71-0.79 (m, 2H), 1.13-1.22 (m, 2H), 2.91 (s, 3H), 3.22 (s, 2H), 6.97 (d, J=2.1 Hz, 1H), 7.56 (d, J=2.1 Hz, 1H).

Step E: Preparation of 7-Benzylsulfanyl-1-methyl-spiro[2H-pyrido[2,3-b][1,4]oxazine-3,1'-cyclopropane]

From 7-bromo-1-methyl-spiro[2H-pyrido[2,3-b][1,4]oxazine-3,1'-cyclopropane], the title compound was prepared using a similar method to the one described in Example 1.23, Step E (except acidic HPLC condition). LCMS m/z=299.1 [M+H]$^+$; $^1$H NMR (400 MHz, DMSO-d$_6$): δ ppm 0.72-0.82 (m, 2H), 0.91-1.00 (m, 2H), 2.79 (s, 3H), 3.20 (s, 2H), 4.13 (s, 2H), 6.93 (d, J=1.8 Hz, 1H), 7.19-7.30 (m, 5H), 7.31 (d, J=2.0 Hz, 1H).

Example 1.28: Preparation of (S)-(1-((3-(Oxiran-2-ylmethoxy)phenyl)sulfonyl)cyclobutyl)methanol

Step A: Preparation of Ethyl 1-((3-Methoxyphenyl)thio)cyclobutanecarboxylate To a solution of 3-methoxybenzenethiol (0.88 mL, 7.13 mmol) in EtOH (20 mL) was added powdered potassium hydroxide (0.44 g, 7.85 mmol), followed by ethyl 1-bromo-cyclobutanecarboxylate (1.63 g, 7.85 mmol). The reaction was heated to reflux for 3 h and then cooled to room temperature. The solid was separated by filtration and rinsed with EtOH (20 mL). The filtrate was concentrated under reduced pressure. The residue was dissolved in DCM (50 mL) and washed with saturated NaHCO$_3$ aqueous solution (50 mL). The aqueous layer was back extracted with DCM (50 mL). The combined organic extracts were washed with brine, dried over Na$_2$SO$_4$, and filtered. The filtrate was concentrated to give the title compound (1.7 g, 90% yield) without further purification. LCMS m/z=267.4 [M+H]$^+$; $^1$H NMR (400 MHz, CDCl$_3$) δ ppm 1.21 (t, J=7.07 Hz, 3H), 1.86-1.97 (m, 1H), 2.14-2.32 (m, 3H), 2.66-2.75 (m, 2H), 3.79 (s, 3H), 4.16 (q, J=7.07 Hz, 2H), 6.82 (dd, J=8.34, 2.53 Hz, 1H), 6.91-6.98 (m, 2H), 7.20 (t, J=8.08 Hz, 1H).

Step B: Preparation of Ethyl 1-((3-Methoxyphenyl) sulfonyl)cyclobutanecarboxylate To a solution of ethyl 1-((3-methoxyphenyl)thio)cyclobutanecarboxylate (0.60 g, 2.25 mmol) in dioxane/H$_2$O (20 mL/5 mL, 4:1) was added in several portions of Oxone® (4.15 g, 6.76 mmol). The white suspension was stirred at room temperature for 3 h. The white solid was separated by filtration and washed with dioxane (20 mL). The filtrate was concentrated and the resulting aqueous solution was extracted with DCM (3×40 mL). The combined organic extracts were washed with saturated NaHCO$_3$ aqueous solution, brine and dried over Na$_2$SO$_4$ then filtered. The filtrate was concentrated to give the title compound (0.6 g, 88% yield) as a solid without further purification. LCMS m/z=299.4 [M+H]⁺; ¹H NMR (400 MHz, CDCl₃) δ ppm 1.17 (t, J=7.07 Hz, 3H), 1.88-2.05 (m, 1H), 2.05-2.19 (m, 1H), 2.55-2.66 (m, 2H), 2.98 (ddd, J=13.89, 9.98, 7.71 Hz, 2H), 3.86 (s, 3H), 4.12 (q, J=7.07 Hz, 2H), 7.18 (ddd, J=6.95, 2.53, 2.40 Hz, 1H), 7.33 (t, J=1.01 Hz, 1H), 7.39-7.47 (m, 2H).

Step C: Preparation of (1-((3-Methoxyphenyl)sulfonyl)cyclobutyl)methanol

To a solution of ethyl 1-((3-methoxyphenyl)sulfonyl)cyclobutanecarboxylate (0.6 g, 1.99 mmol) in THF at 0° C. was added lithium aluminum hydride (2.0 M, 1.13 mL, 2.25 mmol). After stirring at 0° C. for 10 min and at room temperature for 2 h, the reaction was quenched with 1N NaOH at 0° C. To the suspension was added MeOH/DCM (10%) and stirred for 30 min at room temperature. The suspension was filtered and washed with MeOH/DCM (10%, 3×). The aqueous layer was extracted with MeOH/DCM (3×). The combined organic extracts were washed with brine, dried over Na₂SO₄, and filtered. The filtrate was concentrated to give the title compound (0.55 g, 92% yield) without further purification. LCMS m/z=257.2 [M+H]⁺; ¹H NMR (400 MHz, CDCl₃) δ ppm 1.94-2.10 (m, 4H), 2.65-2.80 (m, 2H), 3.49 (s, 1H), 3.83 (s, 2H), 3.88 (s, 3H), 7.21 (dt, J=7.52, 1.17 Hz, 1H), 7.38 (t, J=2.27 Hz, 1H), 7.42-7.55 (m, 2H).

Step D: Preparation of 3-((1-(hydroxymethyl)cyclobutyl)sulfonyl)phenol

To a solution of (1-((3-methoxyphenyl)sulfonyl)cyclobutyl)methanol (0.55 g, 2.08 mmol) in CH₂Cl₂ (2 mL) at −78° C. was added a solution of boron tribromide (0.43 mL, 4.51 mmol) slowly under N₂. The reaction mixture was stirred at −78° C. for 5 h then stirred at room temperature for 2 h. The reaction was cooled down to −20° C. and quenched with ⁱPrOH. The mixture was neutralized with aqueous NaHCO₃ solution to pH 7. The resulting mixture was extracted with ⁱPrOH/DCM (20%). The combined organic extracts were washed with brine, dried over Na₂SO₄, and filtered then concentrated to give the title compound (0.49 g, 84% yield) without further purification. LCMS m/z=243.0 [M+H]⁺.

Step E: Preparation of (S)-(1-((3-(Oxiran-2-ylmethoxy)phenyl)sulfonyl)cyclobutyl)methanol To a mixture of 3-((1-(hydroxymethyl)cyclobutyl)sulfonyl)phenol (280 mg, 1.16 mmol) and potassium carbonate (0.48 g, 3.47 mmol) in acetone (10 mL) was added (S)-oxiran-2-ylmethyl 3-nitrobenzenesulfonate (0.30 g, 1.16 mmol). The reaction mixture was heated at 70° C. overnight. After cooling down to room temperature, the solid material was filtered through a pad of Celite® and washed with acetone (2×5 mL). The filtrate was concentrated. The residue was purified by silica gel column chromatography to give the title compound (0.30 g, 84% yield). LCMS m/z=299.4 [M+H]⁺; ¹H NMR (400 MHz, CDCl₃) δ ppm 1.91-2.09 (m, 4H), 2.67-2.76 (m, 2H), 2.78 (dd, J=4.80, 2.53 Hz, 1H), 2.87 (t, J=6.32 Hz, 1H), 2.93 (d, J=4.04 Hz, 1H), 3.30-3.40 (m, 1H), 3.83 (d, J=6.32 Hz, 2H), 3.98 (dd, J=11.12, 6.06 Hz, 1H), 4.37 (dd, J=11.24, 2.65 Hz, 1H), 7.22-7.26 (m, 1H), 7.41 (t, J=1.26 Hz, 1H), 7.45-7.53 (m, 2H).

Example 1.29: Preparation of (S)-2-Methyl-2-((3-(oxiran-2-ylmethoxy)phenyl)sulfonyl)propan-1-ol Step A: Preparation of Ethyl 2-((3-Hydroxyphenyl)thio)-2-methylpropanoate A solution of 3-mercaptophenol (1.0 g, 7.93 mmol) in MeOH (20 mL) was added aqueous 1.0 N sodium hydroxide (8.72 mL, 8.72 mmol) dropwise over a period of 30 min at −5° C. The reaction was stirred at −5° C. for 1 h. A solution of ethyl 2-bromo-2-methylpropanoate (1.70 g, 8.72 mmol) in MeOH (5 mL) was added at −5° C. over a period of 15 min. The reaction was stirred at room temperature for 24 h. The mixture was concentrated. The residue was treated with 25 mL of water and 100 mL of TBME. After extraction and phase separation, the organic phase was washed with 50 mL of saturated NaHCO₃ and 50 mL of brine. The combined organic phase was dried over Na₂SO₄ and filtered. The filtrate was concentrated. The residue was purified by silica gel column chromatography to give the title compound (1.47 g, 77% yield). LCMS m/z=241.2 [M+H]⁺; ¹H NMR (400 MHz, CDCl₃) δ ppm 1.23 (t, J=7.07 Hz, 3H), 1.51 (s, 6H), 4.13 (q, J=7.24 Hz, 2H), 6.85 (ddd, J=8.08, 2.53, 1.01 Hz, 1H), 6.98 (t, J=2.53 Hz, 1H), 7.03 (dt, J=7.64, 1.36 Hz, 1H), 7.18 (t, J=7.83 Hz, 1H).

Step B: Preparation of Ethyl 2-((3-Hydroxyphenyl)sulfonyl)-2-methylpropanoate

To a solution of ethyl 2-((3-hydroxyphenyl)thio)-2-methylpropanoate (500 mg, 2.08 mmol) in dioxane/water (4:1, 30 mL) were added in several portions of Oxone® (3.84 g, 6.24 mmol). The white suspension was stirred at room temperature for 3-4 h. The white solid was filtered and washed with dioxane (20 mL) and the filtrate was concentrated. The resulting aqueous solution was extracted with DCM (3×40 mL). The combined organic extracts were washed with saturated NaHCO₃ aqueous solution, brine, dried over Na₂SO₄ and filtered. The filtrate was concentrated. The residue was purified by silica gel column chromatography to give the title compound (0.54 g, 91% yield). LCMS m/z=273.4 [M+H]⁺; ¹H NMR (400 MHz, CDCl₃) δ ppm 1.17 (t, J=7.07 Hz, 3H), 1.64 (s, 6H), 4.13 (q, J=7.16 Hz, 2H), 6.77 (s, 1H), 7.16-7.20 (m, 1H), 7.36-7.47 (m, 3H).

Step C: Preparation of 3-((1-Hydroxy-2-methylpropan-2-yl)sulfonyl)phenol

To a solution of ethyl 2-((3-hydroxyphenyl)sulfonyl)-2-methylpropanoate (500 mg, 1.84 mmol) in THF (30 mL) at 0° C. was added lithium aluminum hydride (2.0 M in THF, 1.10 mL, 2.20 mmol). After stirring at 0° C. for 10 min and at room temperature for 3 h, the reaction was quenched with water and aqueous HCl (6.0 M) at 0° C. then warmed up to room temperature. To the resulting mixture was added ⁱPrOH/DCM (20%) then it was stirred for 30 min at room temperature. The aqueous layer was extracted with ⁱPrOH/DCM (20%, 3×). The combined organic layer was washed with brine, dried over Na₂SO₄, and filtered. The filtrate was concentrated to give the title compound (411 mg, 97% yield) without further purification. LCMS m/z=231.0 [M+H]⁺; ¹H NMR (400 MHz, CD₃OD) δ ppm 1.29 (s, 6H), 3.65 (s, 2H), 7.12 (ddd, J=8.15, 2.46, 1.01 Hz, 1H), 7.26 (t, J=2.27 Hz, 1H), 7.29-7.34 (m, 1H), 7.43 (t, J=7.96 Hz, 1H).

Step D: Preparation of (S)-2-Methyl-2-((3-(oxiran-2-ylmethoxy)phenyl)sulfonyl)propan-1-ol To a mixture of 34(1-hydroxy-2-methylpropan-2-yl)sulfonyl)phenol (411 mg, 1.79 mmol) and potassium carbonate (0.76 g, 5.51 mmol) in acetone (30 mL) was added (S)-oxiran-2-ylmethyl 3-nitrobenzenesulfonate (0.52 g, 2.02 mmol). The reaction mixture was heated at 70° C. overnight. The reaction mixture was cooled down to room temperature. The solid was filtered and washed with acetone (2×10 mL).

The filtrate was concentrated. The residue was purified by silica gel column chromatography to give the title compound (0.50 g, 95% yield) as a thick liquid. LCMS m/z=287.0 [M+H]+; 1H NMR (400 MHz, CDCl3) δ ppm 1.31 (s, 6H), 2.78 (dd, J=4.80, 2.78 Hz, 1H), 2.87-2.97 (m, 2H), 3.34-3.40 (m, 1H), 3.74 (d, J=4.29 Hz, 2H), 3.98 (dd, J=11.24, 5.94 Hz, 1H), 4.36 (dd, J=11.12, 2.78 Hz, 1H), 7.22-7.26 (m, 1H), 7.41 (t, J=1.01 Hz, 1H), 7.45-7.51 (m, 2H).

Example 1.30: Preparation of (R)-8-((1-Methyl-2,3-dihydro-1H-pyrido[2,3-b][1,4]oxazin-7-yl)sulfonyl)-1-oxa-8-azaspiro[4.5]decan-3-amine Step A: Preparation of (R)-tert-Butyl 1-Oxa-8-azaspiro[4.5]decan-3-ylcarbamate The title compound was prepared using a similar method to the one described in Method B, Step A.

Step B: Preparation of (R)-tert-Butyl (8-((1-Methyl-2,3-dihydro-1H-pyrido[2,3-b][1,4]oxazin-7-yl)sulfonyl)-1-oxa-8-azaspiro[4.5]decan-3-yl)carbamate From 1-methyl-2,3-dihydro-1H-pyrido[2,3-b][1,4]oxazine-7-sulfonyl chloride and (R)-tert-butyl 1-oxa-8-azaspiro[4.5]decan-3-ylcarbamate, the title compound was prepared using a similar method to the one described in Method B, Step B. LCMS m/z=469.4 [M+H]+; 1H NMR (400 MHz, CD3OD) δ ppm 1.42 (s, 9H), 1.59-1.83 (m, 5H), 2.05 (dd, J=13.14, 8.08 Hz, 1H), 2.73-2.84 (m, 2H), 2.98 (s, 3H), 3.33-3.42 (m, 5H), 3.51 (dd, J=9.09, 5.56 Hz, 1H), 3.85-3.93 (m, 1H), 4.05-4.15 (m, 1H), 4.51 (t, J=4.55 Hz, 1H), 7.13 (d, J=2.02 Hz, 1H), 7.75 (d, J=2.02 Hz, 1H).

Step C: Preparation of (R)-8-((1-Methyl-2,3-dihydro-1H-pyrido[2,3-b][1,4]oxazin-7-yl)sulfonyl)-1-oxa-8-azaspiro[4.5]decan-3-amine To a solution of (R)-tert-butyl (8-((1-methyl-2,3-dihydro-1H-pyrido[2,3-b][1,4]oxazin-7-yl)sulfonyl)-1-oxa-8-azaspiro[4.5]decan-3-yl)carbamate (189.0 mg, 0.40 mmol) in CH2Cl2 (10 mL) was added HCl (1.01 mL, 4.03 mmol) in dioxane. The reaction mixture was stirred at room temperature overnight. Next day, a white precipitation was observed. The reaction was quenched with water then neutralized with saturated NaHCO3 aqueous solution. The resulting solution was extracted with iPrOH/DCM (20%, 2×). The combined organic layers were dried over Na2SO4, filtered and concentrated to give the title compound (149 mg, 92% yield) as a pale solid. LCMS m/z=369.4 [M+H]+; 1H NMR (400 MHz, CD3OD) δ ppm 1.50 (dd, J=13.01, 6.19 Hz, 1H), 1.60-1.78 (m, 2H), 1.78-1.86 (m, 2H), 2.07 (dd, J=12.88, 7.58 Hz, 1H), 2.74-2.87 (m, 2H), 2.97 (s, 3H), 3.33-3.46 (m, 6H), 3.50-3.57 (m, 1H), 3.86 (dd, J=8.84, 5.81 Hz, 1H), 4.51 (t, J=4.55 Hz, 2H), 7.13 (d, J=2.02 Hz, 1H), 7.75 (d, J=2.27 Hz, 1H).

Example 1.31: Preparation of (R)-8-(Quinolin-6-ylsulfonyl)-1-oxa-8-azaspiro[4.5]decan-3-amine Step A: Preparation of (R)-tert-Butyl 1-oxa-8-azaspiro[4.5]decan-3-ylcarbamate The title compound was prepared using a similar method to the one described in Method B, Step A.

Step B: Preparation of (R)-tert-Butyl (8-(quinolin-6-ylsulfonyl)-1-oxa-8-azaspiro[4.5]decan-3-yl)carbamate From quinoline-6-sulfonyl chloride and (R)-tert-butyl 1-oxa-8-azaspiro[4.5]decan-3-ylcarbamate, the title compound was prepared using a similar method to the one described in Method B, Step B. LCMS m/z=448.4 [M+H]+; 1H NMR (400 MHz, CD3OD) δ ppm 1.40 (s, 9H), 1.59 (dd, J=13.14, 6.06 Hz, 1H), 1.66-1.74 (m, 2H), 1.75-1.83 (m, 2H), 1.97-2.05 (m, 1H), 2.77-2.89 (m, 2H), 3.41-3.51 (m, 3H), 3.84 (dd, J=9.22, 6.19 Hz, 1H), 4.01-4.12 (m, 1H), 7.69 (dd, J=8.34, 4.29 Hz, 1H), 8.07 (dd, J=8.84, 2.02 Hz, 1H), 8.23 (d, J=8.84 Hz, 1H), 8.48 (d, J=2.02 Hz, 1H), 8.58 (d, J=7.58 Hz, 1H), 9.03 (dd, J=4.29, 1.77 Hz, 1H).

Step C: Preparation of (R)-8-(Quinolin-6-ylsulfonyl)-1-oxa-8-azaspiro[4.5]decan-3-amine To a solution of (R)-tert-butyl (8-(quinolin-6-ylsulfonyl)-1-oxa-8-azaspiro[4.5]decan-3-yl)carbamate (398 mg, 0.89 mmol) in DCM (12 mL) at room temperature was added TFA (0.68 mL, 8.89 mmol). The reaction mixture was stirred at room temperature overnight. The reaction was quenched with water then netraulized with saturated NaHCO3 aqueous to pH 7. The resulting solution was extracted with iPrOH/DCM. The organic layer was washed with brine, dried over Na2SO4, and filtered then concentrate to give the title compound which was used in the next step without purification (350 mg, 106% yield). LCMS m/z=348.2 [M+H]+; 1H NMR (400 MHz, CD3OD) δ ppm 1.58 (dd, J=13.64, 5.31 Hz, 1H), 1.61-1.70 (m, 1H), 1.76 (dt, J=17.43, 14.15 Hz, 1H), 1.85 (dd, J=7.45, 4.42 Hz, 2H), 2.13 (dd, J=13.52, 7.96 Hz, 1H), 2.76-2.90 (m, 2H), 3.45-3.56 (m, 3H), 3.63-3.71 (m, 1H), 3.85 (dd, J=9.73, 5.68 Hz, 1H), 7.70 (dd, J=8.34, 4.29 Hz, 1H), 8.07 (dd, J=8.97, 2.15 Hz, 1H), 8.23 (d, J=8.84 Hz, 1H), 8.48 (d, J=2.02 Hz, 1H), 8.58 (d, J=8.59 Hz, 1H), 9.04 (dd, J=4.29, 1.77 Hz, 1H).

Example 1.32: Preparation of Other Intermediates of the Present Invention

The following chemicals were prepared using similar methods to the ones described in the above examples from proper intermediate(s) obtained through commercial sources or synthesized according to literature preparation. The specific method(s) applicable were listed in the following table:

| Building Block No. | Chemical Structure | Chemical Name | Method of Preparation | LCMS Data [M + 1] |
|---|---|---|---|---|
| C1 | 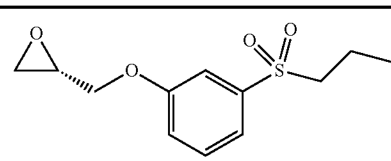 | (S)-2-((3-(propylsulfonyl)phenoxy)methyl)oxirane | BB1 | 257.4 |

-continued

| Building Block No. | Chemical Structure | Chemical Name | Method of Preparation | LCMS Data [M + 1] |
|---|---|---|---|---|
| C2 | 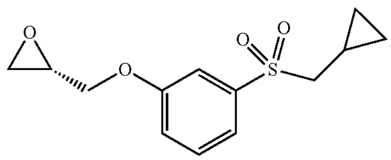 [SMILES: O=S(=O)(CC1CC1)c1cccc(OC[C@@H]2CO2)c1] | (S)-2-((3-((cyclopropylmethyl)sulfonyl)phenoxy)methyl)oxirane | BB1 | 269.0 |
| C3 | 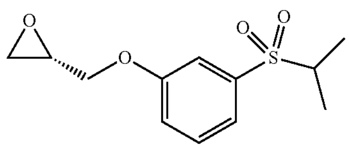 [SMILES: CC(C)S(=O)(=O)c1cccc(OC[C@@H]2CO2)c1] | (S)-2-((3-(isopropylsulfonyl)phenoxy)methyl)oxirane | BB1 | 257.6 |
| C4 | 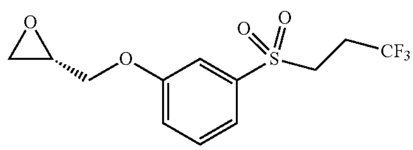 [SMILES: O=S(=O)(CCC(F)(F)F)c1cccc(OC[C@@H]2CO2)c1] | (S)-2-((3-((3,3,3-trifluoropropyl)sulfonyl)phenoxy)methyl)oxirane | BB1 | 311.4 |
| C5 | 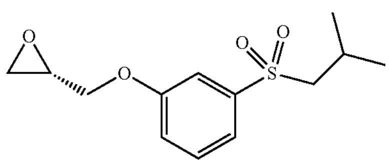 [SMILES: CC(C)CS(=O)(=O)c1cccc(OC[C@@H]2CO2)c1] | (S)-2-((3-(isobutylsulfonyl)phenoxy)methyl)oxirane | BB1 | 271.2 |
| C6 | 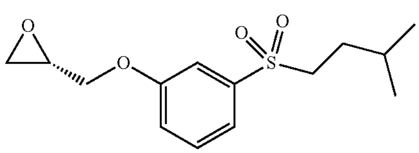 [SMILES: CC(C)CCS(=O)(=O)c1cccc(OC[C@@H]2CO2)c1] | (S)-2-((3-(isopentylsulfonyl)phenoxy)methyl)oxirane | BB1 | 285.2 |
| C7 | 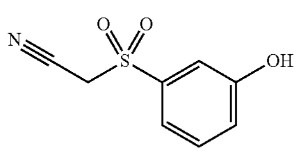 [SMILES: N#CCS(=O)(=O)c1cccc(O)c1] | 2-((3-hydroxyphenyl)sulfonyl)acetonitrile | BB1A BB1B BB1C | 198.0 |
| C8 | 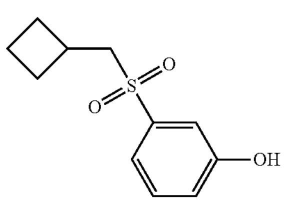 [SMILES: O=S(=O)(CC1CCC1)c1cccc(O)c1] | 3-((cyclobutylmethyl)sulfonyl)phenol | BB1A BB1B BB1C | 227.2 |
| C9 | 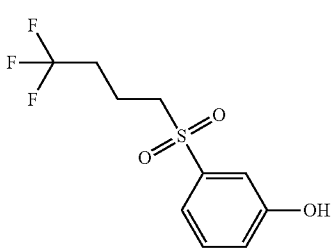 [SMILES: O=S(=O)(CCCC(F)(F)F)c1cccc(O)c1] | 3-((4,4,4-trifluorobutyl)sulfonyl)phenol | BB1A BB1B BB1C | 269.0 |

-continued

| Building Block No. | Chemical Structure | Chemical Name | Method of Preparation | LCMS Data [M + 1] |
|---|---|---|---|---|
| C10 | 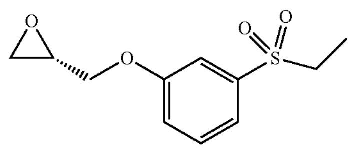 [SMILES: CCS(=O)(=O)c1cccc(OC[C@@H]2CO2)c1] | (S)-2-((3-(ethylsulfonyl)phenoxy)methyl)oxirane | BB1 | 243.2 |
| C11 | 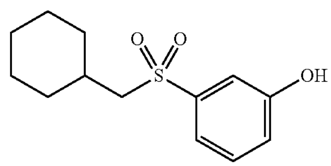 [SMILES: O=S(=O)(CC1CCCCC1)c1cccc(O)c1] | 3-((cyclohexylmethyl)sulfonyl)phenol | BB1A BB1B BB1C | 255.4 |
| C12 | 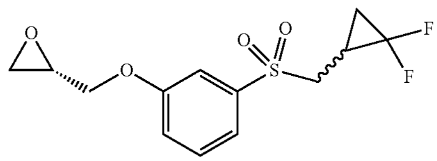 [SMILES: O=S(=O)(CC1CC1(F)F)c1cccc(OC[C@@H]2CO2)c1] | (2S)-2-((3-(((2,2-difluorocyclopropyl)methyl)sulfonyl)phenoxy)methyl)oxirane | BB1 | 305.2 |
| C13 | 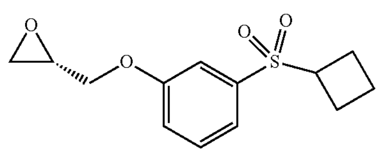 [SMILES: O=S(=O)(c1cccc(OC[C@@H]2CO2)c1)C1CCC1] | (S)-2-((3-(cyclobutylsulfonyl)phenoxy)methyl)oxirane | BB1 | 269.2 |
| C14 | 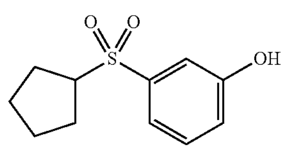 [SMILES: O=S(=O)(c1cccc(O)c1)C1CCCC1] | 3-(cyclopentylsulfonyl)phenol | BB1A BB1B BB1C | 227.2 |
| C15 | 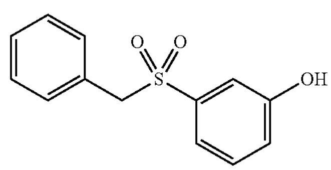 [SMILES: O=S(=O)(Cc1ccccc1)c1cccc(O)c1] | 3-(benzylsulfonyl)phenol | BB1A BB1B BB1C | 249.0 |
| C16 | 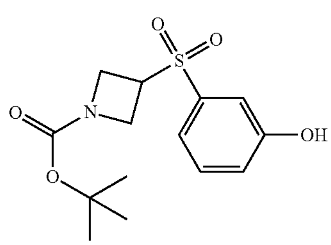 | tert-butyl 3-((3-hydroxyphenyl)sulfonyl)azetidine-1-carboxylate | BB1A BB1B BB1C | 332.6 [M + 18]+ |
| C17 | 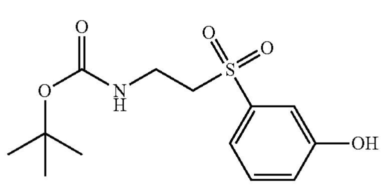 [SMILES: CC(C)(C)OC(=O)NCCS(=O)(=O)c1cccc(O)c1] | tert-butyl (2-((3-hydroxyphenyl)sulfonyl)ethyl)carbamate | BB1A BB1B BB1C | 302.4 |
| C18 | 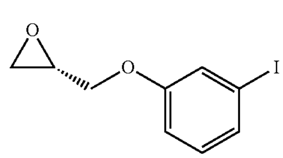 [SMILES: Ic1cccc(OC[C@@H]2CO2)c1] | (S)-2-((3-iodophenoxy)methyl)oxirane | BB1D | 277.0 |

-continued

| Building Block No. | Chemical Structure | Chemical Name | Method of Preparation | LCMS Data [M + 1] |
|---|---|---|---|---|
| C19 | 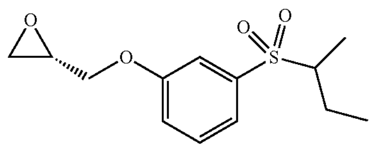 [SMILES: CCC(C)S(=O)(=O)c1cccc(OC[C@@H]2CO2)c1] | (2S)-2-((3-(sec-butylsulfonyl)phenoxy)methyl)oxirane | BB1 | 271.2 |
| C20 | 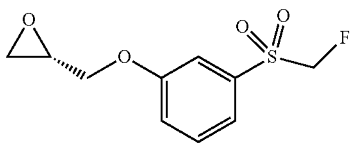 | (S)-2-((3-((fluoromethyl)sulfonyl)phenoxy)methyl)oxirane | BB3 | NA See NMR Below |
| C21 | 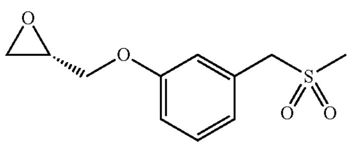 [SMILES: CS(=O)(=O)Cc1cccc(OC[C@@H]2CO2)c1] | (S)-2-((3-((methylsulfonyl)methyl)phenoxy)methyl)oxirane | BB1 | NA See NMR Below |
| C22 | 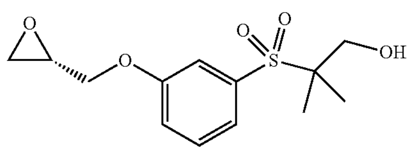 [SMILES: CC(C)(CO)S(=O)(=O)c1cccc(OC[C@@H]2CO2)c1] | (S)-2-methyl-2-((3-(oxiran-2-ylmethoxy)phenyl)sulfonyl)propan-1-ol | Described in Example 1.29 | 287.0 |
| C23 | 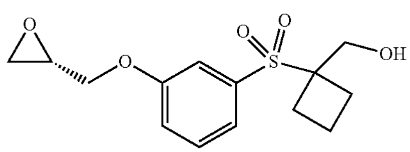 [SMILES: O=S(=O)(c1cccc(OC[C@@H]2CO2)c1)C1(CO)CCC1] | (S)-(1-((3-(oxiran-2-ylmethoxy)phenyl)sulfonyl)cyclobutyl)methanol | Described in Example 1.28 | 299.4 |
| C24 | 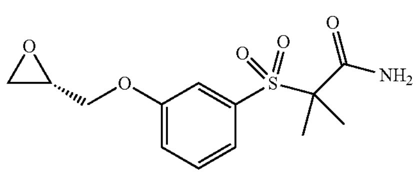 [SMILES: CC(C)(C(N)=O)S(=O)(=O)c1cccc(OC[C@@H]2CO2)c1] | (S)-2-methyl-2-((3-(oxiran-2-ylmethoxy)phenyl)sulfonyl)propanamide | BB5A BB5B BB1D | 300.2 |
| C25 | 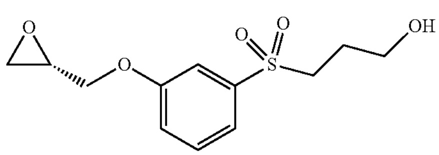 [SMILES: O=S(=O)(CCCO)c1cccc(OC[C@@H]2CO2)c1] | (S)-3-((3-(oxiran-2-ylmethoxy)phenyl)sulfonyl)propan-1-ol | BB1 | 273.2 |
| C26 | 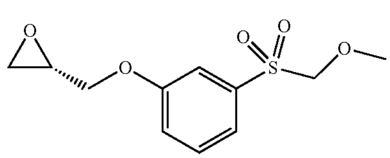 | (S)-2-((3-((methoxymethyl)sulfonyl)phenoxy)methyl)oxirane | BB5 | 276.0 [M + 18] |
| C27 | 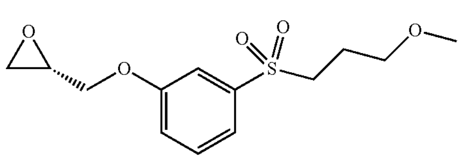 [SMILES: COCCCS(=O)(=O)c1cccc(OC[C@@H]2CO2)c1] | (S)-2-((3-((3-methoxypropyl)sulfonyl)phenoxy)methyl)oxirane | BB5 | 287.0 |

-continued

| Building Block No. | Chemical Structure | Chemical Name | Method of Preparation | LCMS Data [M + 1] |
|---|---|---|---|---|
| C28 | 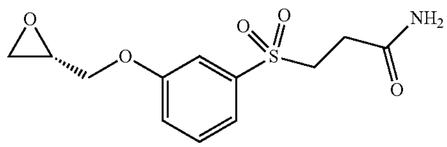 [SMILES: NC(=O)CCS(=O)(=O)c1cccc(OC[C@@H]2CO2)c1] | (S)-3-((3-(oxiran-2-ylmethoxy)phenyl)sulfonyl)propanamide | BB1 | 286.2 |
| C29 | 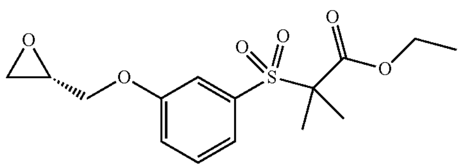 [SMILES: CCOC(=O)C(C)(C)S(=O)(=O)c1cccc(OC[C@@H]2CO2)c1] | (S)-ethyl 2-methyl-2-((3-(oxiran-2-ylmethoxy)phenyl)sulfonyl)propanoate | BB5A BB5B BB1D | 329.4 |
| C30 | 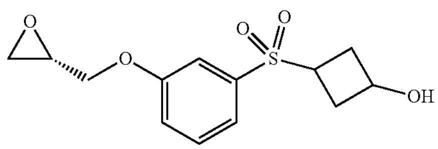 [SMILES: O=S(=O)(c1cccc(OC[C@@H]2CO2)c1)C1CC(O)C1] | (S)-3-((3-(oxiran-2-ylmethoxy)phenyl)sulfonyl)cyclobutanol | BB3A BB1D | 285.2 |
| C31 | 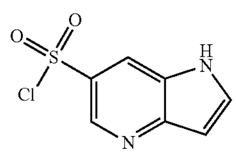 [SMILES: O=S(=O)(Cl)c1cnc2cc[nH]c2c1] | 1H-pyrrolo[3,2-b]pyridine-6-sulfonyl chloride | BB9 | 217.2 |
| C32 | 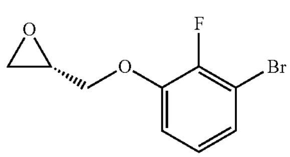 [SMILES: Fc1c(Br)cccc1OC[C@@H]1CO1] | (S)-2-((3-bromo-2-fluorophenoxy)methyl)oxirane | BB1D | 245.2 |
| C33 | 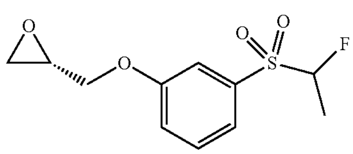 [SMILES: CC(F)S(=O)(=O)c1cccc(OC[C@@H]2CO2)c1] | (2S)-2-((3-((1-fluoroethyl)sulfonyl)phenoxy)methyl)oxirane | BB6A BB6B BB6E BB1D | 260.8 |
| C34 | 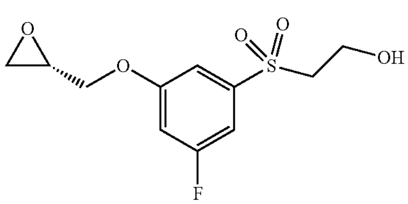 [SMILES: O=S(=O)(CCO)c1cc(F)cc(OC[C@@H]2CO2)c1] | (S)-2-((3-fluoro-5-(oxiran-2-ylmethoxy)phenyl)sulfonyl)ethanol | BB5B BB3A BB1D | 277.2 |
| C35 | 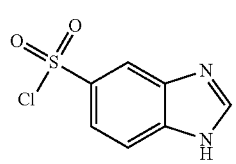 [SMILES: O=S(=O)(Cl)c1ccc2[nH]cnc2c1] | 1H-benzo[d]imidazole-5-sulfonyl chloride | BB9 | 217.0 |
| C36 | 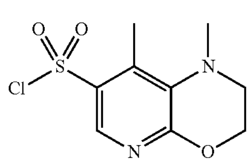 [SMILES: Cc1c(S(=O)(=O)Cl)cnc2c1N(C)CCO2] | 1,8-dimethyl-2,3-dihydro-1H-pyrido[2,3-b][1,4]oxazine-7-sulfonyl chloride | BB8C | 263.2 |

-continued

| Building Block No. | Chemical Structure | Chemical Name | Method of Preparation | LCMS Data [M + 1] |
|---|---|---|---|---|
| C37 | 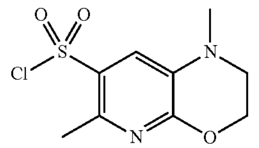 [SMILES: Cc1nc2c(cc1S(=O)(=O)Cl)N(C)CCO2] | 1,6-dimethyl-2,3-dihydro-1H-pyrido[2,3-b][1,4]oxazine-7-sulfonyl chloride | BB9 | 263.0 |
| C38 | 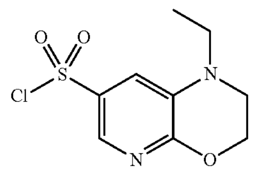 [SMILES: CCN1CCOc2ncc(S(=O)(=O)Cl)cc21] | 1-ethyl-2,3-dihydro-1H-pyrido[2,3-b][1,4]oxazine-7-sulfonyl chloride | BB9 | 263.2 |
| C39 | 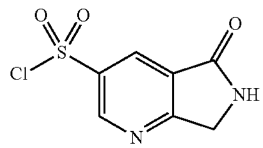 [SMILES: O=C1NCc2ncc(S(=O)(=O)Cl)cc21] | 5-oxo-6,7-dihydro-5H-pyrrolo[3,4-b]pyridine-3-sulfonyl chloride | BB9 | 233.2 |
| C40 | 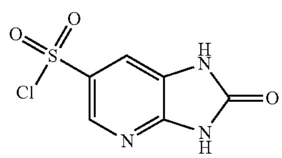 [SMILES: O=c1[nH]c2cc(S(=O)(=O)Cl)cnc2[nH]1] | 2-oxo-2,3-dihydro-1H-imidazo[4,5-b]pyridine-6-sulfonyl chloride | BB9 | 234.0 |
| C41 | 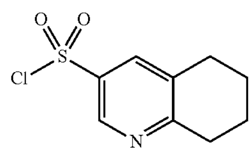 [SMILES: O=S(=O)(Cl)c1cnc2c(c1)CCCC2] | 5,6,7,8-tetrahydroquinoline-3-sulfonyl chloride | BB9 | 232.2 |
| C42 | 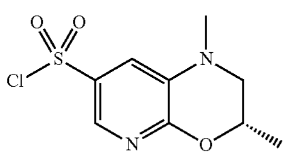 [SMILES: C[C@H]1CN(C)c2cc(S(=O)(=O)Cl)cnc2O1] | (S)-1,3-dimethyl-2,3-dihydro-1H-pyrido[2,3-b][1,4]oxazine-7-sulfonyl chloride | BB8C | 263.0 |
| C43 | 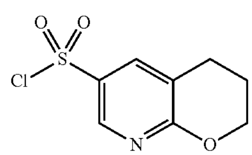 [SMILES: O=S(=O)(Cl)c1cnc2c(c1)CCCO2] | 3,4-dihydro-2H-pyrano[2,3-b]pyridine-6-sulfonyl chloride | BB9 | 234.0 |
| C44 | 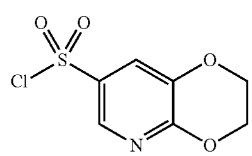 [SMILES: O=S(=O)(Cl)c1cnc2c(c1)OCCO2] | 2,3-dihydro-[1,4]dioxino[2,3-b]pyridine-7-sulfonyl chloride | BB9 | 236.0 |
| C45 | 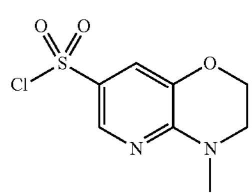 | 4-methyl-3,4-dihydro-2H-pyrido[3,2-b][1,4]oxazine-7-sulfonyl chloride | BB9 | 249.2 |

-continued

| Building Block No. | Chemical Structure | Chemical Name | Method of Preparation | LCMS Data [M + 1] |
|---|---|---|---|---|
| C46 | 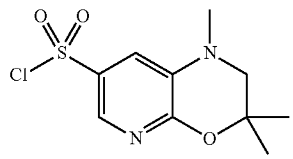 [SMILES: CN1CC(C)(C)Oc2ncc(S(=O)(=O)Cl)cc21] | 1,3,3-trimethyl-2,3-dihydro-1H-pyrido[2,3-b][1,4]oxazine-7-sulfonyl chloride | BB8C | 277.2 |
| C47 | 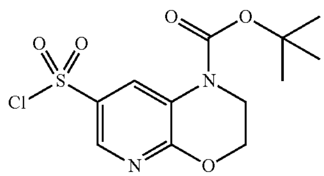 [SMILES: CC(C)(C)OC(=O)N1CCOc2ncc(S(=O)(=O)Cl)cc21] | tert-butyl 7-(chlorosulfonyl)-2,3-dihydro-1H-pyrido[2,3-b][1,4]oxazine-1-carboxylate | BB9 | 335.4 |
| C48 | 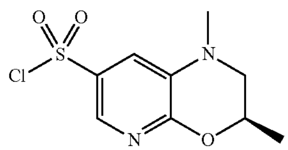 [SMILES: C[C@@H]1CN(C)c2cc(S(=O)(=O)Cl)cnc2O1] | (R)-1,3-dimthyl-2,3-dihydro-1H-pyrido[2,3-b][1,4]oxazine-7-sulfonyl chloride | BB8C | 263.2 |
| C49 | 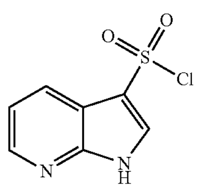 [SMILES: O=S(=O)(Cl)c1c[nH]c2ncccc12] | 1H-pyrrolo[2,3-b]pyridine-3-sulfonyl chloride | BB9 | 217.2 |
| C50 | 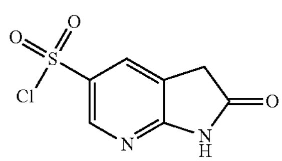 [SMILES: O=C1Cc2cc(S(=O)(=O)Cl)cnc2N1] | 2-oxo-2,3-dihydro-1H-pyrrolo[2,3-b]pyridine-5-sulfonyl chloride | BB9 | 233.2 |
| C51 | 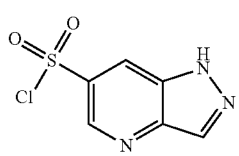 [SMILES: O=S(=O)(Cl)c1cnc2cn[nH]c2c1] | 1H-pyraolo[4,3-b]pyridine-6-sulfonyl chloride | BB9 | 218.0 |
| C52 | 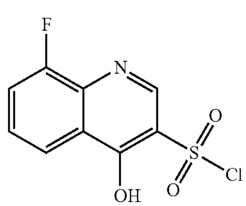 [SMILES: O=S(=O)(Cl)c1cnc2c(F)cccc2c1O] | 8-fluoro-4-hydroxyquinoline-3-sulfonyl chloride | BB12 | 261.9 |
| C53 | 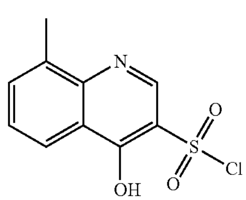 [SMILES: Cc1cccc2c(O)c(S(=O)(=O)Cl)cnc12] | 4-hydroxy-8-methylquinoline-3-sulfonyl chloride | BB13 | 258.0 |

-continued

| Building Block No. | Chemical Structure | Chemical Name | Method of Preparation | LCMS Data [M + 1] |
|---|---|---|---|---|
| C54 | 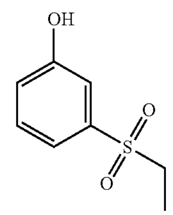 | 3-(ethylsulfonyl) phenol | BB1A BB1B BB1C | 187.0 |
| C55 | 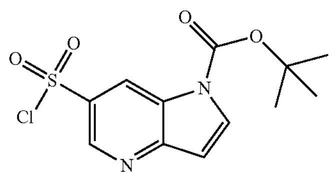 [SMILES: CC(C)(C)OC(=O)n1ccc2ncc(S(=O)(=O)Cl)cc21] | tert-butyl 6-(chlorosulfonyl)-1H-pyrrolo[3,2-b]pyridine-1-carboxylate | BB8C | 317.0 |
| C56 | 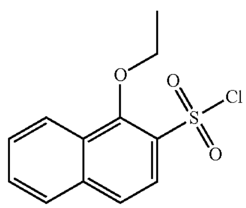 [SMILES: CCOc1c(S(=O)(=O)Cl)ccc2ccccc12] | 1-ethoxynaphthalene-2-sulfonyl chloride | BB9 | 270.8 |
| C57 | 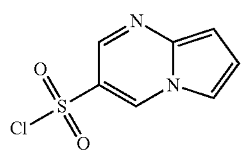 [SMILES: O=S(=O)(Cl)c1cnc2cccn2c1] | pyrrolo[1,2-a]pyrimidine-3-sulfonyl chloride | BB9 | 216.8 |
| C58 | 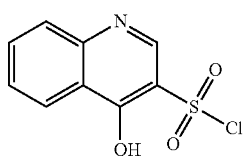 [SMILES: O=S(=O)(Cl)c1cnc2ccccc2c1O] | 4-hydroxyquinoline-3-sulfonyl chloride | A: STEP E | 244.2 |
| C59 | 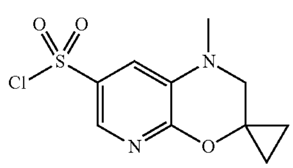 [SMILES: CN1CC2(CC2)Oc2ncc(S(=O)(=O)Cl)cc21] | 1'-methyl-1',2'-dihydrospiro[cyclopropane-1,3'-pyrido[2,3-b][1,4]oxazine]-7'-sulfonyl chloride | BB8C | 275.2 |
| C60 | 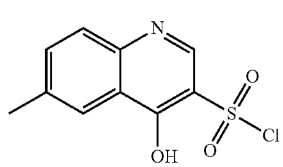 [SMILES: Cc1ccc2ncc(S(=O)(=O)Cl)c(O)c2c1] | 4-hydroxy-6-methylquinoline-3-sulfonyl chloride | BB13 | 258.1 |
| C61 | 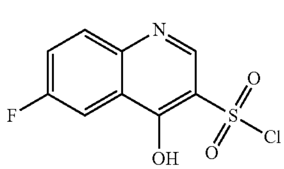 [SMILES: O=S(=O)(Cl)c1cnc2ccc(F)cc2c1O] | 6-fluoro-4-hydroxyquinoline-3-sulfonyl chloride | BB12 | 262.0 |

| Building Block No. | Chemical Structure | Chemical Name | Method of Preparation | LCMS Data [M + 1] |
|---|---|---|---|---|
| C62 | 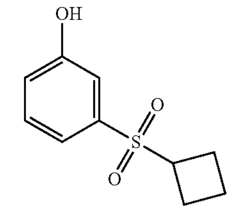 [SMILES: O=S(=O)(c1cccc(O)c1)C1CCC1] | 3-(cyclobutylsulfonyl) phenol | BB1A BB1B BB1C | 213.0 |
| C63 | 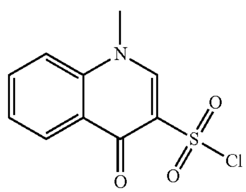 [SMILES: Cn1cc(S(=O)(=O)Cl)c(=O)c2ccccc21] | 1-methyl-4-oxo-1,4-dihydroquinoline-3-sulfonyl chloride | A: STEP D, E | 258.2 |

(S)-2-((3-((fluoromethyl)sulfonyl)phenoxy)methyl)oxirane (Building Block No. C20): $^1$H NMR (400 MHz, CDCl$_3$) δ ppm 2.74 (dd, J=5.05, 2.78 Hz, 1H), 2.86 (dd, J=5.05, 4.29 Hz, 1H), 3.36 (dddd, J=6.66, 4.39, 2.53, 2.34 Hz, 1H), 3.96 (dd, J=11.37, 6.57 Hz, 1H), 4.48 (dd, J=11.37, 2.53 Hz, 1H), 5.75 (d, J=45.73 Hz, 2H), 7.41-7.46 (m, 2H), 7.53 (ddd, J=7.71, 1.26, 1.14 Hz, 1H), 7.64 (t, J=7.58 Hz, 1H).

(S)-2-((3-((methylsulfonyl)methyl)phenoxy)methyl)oxirane (Building Block No. C21): $^1$H NMR (400 MHz, CDCl$_3$) δ ppm 2.75-2.79 (m, 4H), 2.92 (dd, J=4.8, 4.28 Hz, 1H), 3.36 (dddd, J=5.78, 4.20, 2.91, 2.78 Hz, 1H), 3.96 (dd, J=11.12, 5.81 Hz, 1H), 4.22 (s, 2H), 4.29 (dd, J=11.12, 2.78 Hz, 1H), 6.95-6.99 (m, 1H), 6.99-7.03 (m, 2H), 7.33 (t, J=8.08 Hz, 1H).

Example 1.33: Preparation of 1-Ethyl-3-((R)-3-((S)-2-hydroxy-3-(3-(methylsulfonyl)phenoxy) propylamino)-1-oxa-8-azaspiro[4.5]decan-8-ylsulfonyl) quinolin-4(1H)-one (Compound 310) as the Mesylic Acid Salt. (Method A)

Step A: Preparation of (R)-Benzyl 3-(((S)-2-Hydroxy-3-(3-(methylsulfonyl)phenoxy)propyl)amino)-1-oxa-8-azaspiro[4.5]decane-8-carboxylate Into a solution of (S)-2-((3-(methylsulfonyl)phenoxy)methyl)oxirane (11.26 g, 49.32 mmol) and (R)-benzyl 3-amino-1-oxa-8-azaspiro[4.5]decane-8-carboxylate (28.64 g, 98.63 mmol) in EtOH (978 mL) was bubbled with nitrogen for 1 h. The reaction was heated at 70° C. for 2 days. After cooling down to room temperature, solvent was removed under vacuum. The residue was dissolved in EtOAc (500 mL) and extracted with saturated NaHCO$_3$ aqueous solution. The EtOAc layer was separated. The aqueous layer was washed with EtOAc (1×). The combined organic layer was washed with water and brine, dried over Na$_2$SO$_4$, filtered and concentrated. The residue was purified by silica gel column chromatography to give the title compound (22.17 g, 87% yield). LCMS m/z=519.4 [M+H]$^+$; NMR (400 MHz, CD$_3$OD) δ ppm 1.48-1.58 (m, 1H), 1.58-1.77 (m, 4H), 2.12 (dd, J=12.88, 7.58 Hz, 1H), 2.71-2.82 (m, 2H), 3.11 (s, 3H), 3.34-3.44 (m, 2H), 3.45-3.52 (m, 1H), 3.61-3.70 (m, 3H), 3.96-4.14 (m, 4H), 5.11 (s, 2H), 7.26-7.33 (m, 2H), 7.34-7.37 (m, 4H), 7.48-7.51 (m, 1H), 7.51-7.57 (m, 2H).

Step B: Preparation of (R)-Benzyl 3-((tert-Butoxycarbonyl)((S)-2-hydroxy-3-(3-(methylsulfonyl)phenoxy)propyl)amino)-1-oxa-8-azaspiro[4.5]decane-8-carboxylate To a solution of (R)-benzyl 3-(((S)-2-hydroxy-3-(3-(methylsulfonyl)phenoxy)propyl)amino)-1-oxa-8-azaspiro[4.5]decane-8-carboxylate (23.20 g, 44.73 mmol) in CH$_2$Cl$_2$ (300 mL) was added DIEA (23.37 mL, 134.2 mmol) and (BOC)$_2$O (29.29 g, 134.2 mmol). The reaction was stirred under nitrogen at room temperature overnight. After the reaction was completed, the mixture was washed with saturated NH$_4$Cl aqueous solution, water, and then brine. The organic layer was dried over Na$_2$SO$_4$, filtered, and concentrated. The residue was purified by silica gel column chromatography to give the title compound (25.21 g, 91% yield). LCMS m/z=619.6 [M+H]$^+$; NMR (400 MHz, CD$_3$OD) δ ppm 1.46 (s, 9H), 1.48-1.57 (m, 1H), 1.60-1.74 (m, 3H), 1.89 (dd, J=12.76, 8.21 Hz, 1H), 2.11 (dd, J=12.76, 8.46 Hz, 1H), 3.11 (s, 3H), 3.22-3.29 (m, 1H), 3.34-3.46 (m, 2H), 3.56 (dd, J=14.53, 4.42 Hz, 1H), 3.60-3.71 (m, 2H), 3.89-3.97 (m, 1H), 3.99-4.11 (m, 3H), 4.13-4.23 (m, 1H), 4.48-4.61 (m, 1H), 5.11 (s, 2H), 7.25-7.38 (m, 6H), 7.50 (t, J=1.26 Hz, 1H), 7.51-7.59 (m, 2H).

Step C: Preparation of tert-Butyl ((S)-2-Hydroxy-3-(3-(methylsulfonyl)phenoxy)propyl)((R)-1-oxa-8-azaspiro[4.5]decan-3-yl)carbamate To a solution of (R)-benzyl 3-((tert-butoxycarbonyl)((S)-2-hydroxy-3-(3-(methylsulfonyl)phenoxy)propyl)amino)-1-oxa-8-azaspiro[4.5]decane-8-carboxylate (20.8 g, 33.62 mmol) in MeOH (336.2 mL) under H$_2$ balloon was added Palladium/C (3.59 g, 3.36 mmol). The reaction was stirred at room temperature. After the reaction was completed, the mixture was filtered through a pad of Celite® then washed with MeOH. The filtrate was concentrated to give the title compound (15.43 g, 88% yield) as a white foam. LCMS m/z=485.4 [M+H]$^+$; $^1$H NMR (400 MHz, DMSO-d$_6$) δ ppm 1.38 (s, 9H), 1.41 (d, J=6.82 Hz, 2H), 1.49-1.58 (m, 2H), 1.66 (dd, J=12.38, 8.59 Hz, 1H), 2.01 (dd, J=12.38, 8.34 Hz, 1H), 2.52-2.58 (m, 1H), 2.71-2.84 (m, 2H), 3.01-3.13 (m, 1H), 3.21 (s, 3H), 3.42 (dd, J=14.27, 4.17 Hz, 1H), 3.75-3.89 (m, 2H), 3.92-4.11 (m, 3H), 4.44 (bs, 1H), 5.25 (d, J=3.79 Hz, 1H), 7.27 (dd, J=8.21, 1.64 Hz, 1H), 7.41 (t, J=2.02 Hz, 1H), 7.49 (d, J=7.83 Hz, 1H), 7.57 (t, J=7.96 Hz, 1H).

Step D: Preparation of 1-Ethylquinolin-4(1H)-one

To a solution of quinolin-4-ol (25 g, 172.2 mmol) in DMF (100 mL) was added potassium carbonate (47.61 g, 344.5 mmol). The reaction was stirred at room temperature for 30 min. Bromoethane (17.87 mL, 241.1 mmol) was added. The reaction mixture was heated to 80° C. overnight. After the reaction was completed and cooled down to room temperature, the mixture was filtered through a pad of celite and washed with DCM. The filtrate was concentrated. The residue was purified by silica gel column chromatography to give the title compound (13.65 g, 46% yield) as a yellow solid. LCMS m/z=174.2 [M+H]$^+$; $^1$H NMR (400 MHz, DMSO-$d_6$) δ ppm 1.34 (t, J=7.07 Hz, 3H), 4.28 (q, J=7.16 Hz, 2H), 6.05 (d, J=7.58 Hz, 1H), 7.37 (ddd, J=7.96, 4.93, 3.03 Hz, 1H), 7.69-7.76 (m, 2H), 7.99 (d, J=7.58 Hz, 1H), 8.19 (d, J=7.83 Hz, 1H).

Step E: Preparation of 1-Ethyl-4-oxo-1,4-dihydroquinoline-3-sulfonyl Chloride

Freshly distilled sulfurochloridic acid (9.21 mL, 138.6 mmol) was added drop wise under $N_2$ into a 3 necks round bottom flask containing 1-ethylquinolin-4(1H)-one (4 g, 23.09 mmol) until the bubbles slowed down. (Note: A lot of smoke formed and gas evolved.) The resulting clear brown solution was stirred at room temperature for 30 min and then heated at 100° C. under $N_2$ overnight. The reaction was cooled down to room temperature. The mixture was slowly poured into crushed ice in a 500 mL beaker with vigorously stirring. The precipitate was filtered and washed with cold water to give the title compound (3.86 g, 54% yield) as a beige solid. LCMS m/z=271.8 [M]$^+$; $^1$H NMR (400 MHz, DMSO-$d_6$) δ ppm 1.46 (t, J=7.07 Hz, 3H), 4.76 (q, J=7.07 Hz, 2H), 7.79 (t, J=7.58 Hz, 1H), 8.08 (dd, J=15.66, 1.52 Hz, 1H), 8.22 (d, J=8.84 Hz, 1H), 8.43 (dd, J=8.34, 1.52 Hz, 1H), 9.26 (s, 1H).

Step F: Preparation of tert-Butyl ((R)-8-((1-Ethyl-4-oxo-1,4-dihydroquinolin-3-yl)sulfonyl)-1-oxa-8-azaspiro[4.5]decan-3-yl)((S)-2-hydroxy-3-(3-(methylsulfonyl)phenoxy)propyl)carbamate To a solution of tert-butyl ((S)-2-hydroxy-3-(3-(methylsulfonyl)phenoxy)propyl)((R)-1-oxa-8-azaspiro[4.5]decan-3-yl)carbamate (15.51 g, 32.01 mmol) in $CH_2Cl_2$ (160 mL) were added DIEA (12.94 mL, 74.18 mmol) and 1-ethyl-4-oxo-1,4-dihydroquinoline-3-sulfonyl chloride (85.4% pure, 12.07 g, 37.94 mmol). The reaction was stirred at room temperature for 4 h, then quenched with water, and washed with 10% of IPA/DCM. The aqueous layer was back extracted with IPA/DCM (10%). The combined organic layer was dried over $Na_2SO_4$, filtered and concentrated. The residue was purified by silica gel column chromatography to give the title compound (21.2 g, 82% yield) as a white foam. LCMS m/z=720.6 [M+H]$^+$; $^1$H NMR (400 MHz, DMSO-$d_6$) δ ppm 1.36 (s, 9H), 1.37-1.42 (m, 3H), 1.47-1.57 (m, 1H), 1.58-1.76 (m, 4H), 2.98-3.17 (m, 3H), 3.19 (s, 3H), 3.35 (d, J=4.04 Hz, 1H), 3.41 (dd, J=14.27, 3.92 Hz, 1H), 3.77 (t, J=8.21 Hz, 1H), 3.84 (d, J=7.07 Hz, 1H), 3.89-4.06 (m, 4H), 4.45 (q, J=7.07 Hz, 3H), 5.22 (d, J=5.05 Hz, 1H), 7.25 (ddd, J=6.82, 1.52, 1.26 Hz, 1H), 7.39 (d, J=2.53 Hz, 1H), 7.44-7.49 (m, 1H), 7.50-7.58 (m, 2H), 7.86 (d, J=1.26 Hz, 2H), 8.26 (d, J=7.58 Hz, 1H), 8.61 (s, 1H).

Step G: Preparation of 1-Ethyl-3-((R)-3-((S)-2-hydroxy-3-(3-(methylsulfonyl)phenoxy)propylamino)-1-oxa-8-azaspiro[4.5]decan-8-ylsulfonyl)quinolin-4(1H)-one (Compound 310) as the Mesylic Acid Salt A solution of tert-butyl ((R)-8-((1-ethyl-4-oxo-1,4-dihydroquinolin-3-yl)sulfonyl)-1-oxa-8-azaspiro[4.5]decan-3-yl)((S)-2-hydroxy-3-(3-(methylsulfonyl)phenoxy)propyl) carbamate (17.42 g, 24.19 mmol) in acetone (78.81 mL) was prepared in a 500 mL round bottom flask assembled with a condenser and a needle outlet septum to give a clear light yellow solution. The resulting solution was heated to 60° C. Methanesulfonic acid (2.02 mL, 31.45 mmol) was added drop wise into the reaction solution stirred vigorously. After 1 h of stirring, white precipitation formed; a seed crystal of mesylate salt of the title compound (15 mg) was added into the reaction mixture. After adding the seed crystal, there was more precipitation formed within 20 minutes. The stir bar stopped moving. The precipitated cake was broken by a spatula and more acetone (84 mL) was added. Heating was continued overnight with stirring. Heating was turned off next day. The reaction mixture was stirred at room temperature overnight. Next day, the reaction was reheated up to 60° C. with stirring for 1 h then precipitation was collected via vacuum filtration while still hot. The cake was washed with acetone (3×100 mL) at room temperature and dried under heated vacuum oven at 50° C. to give the tile compound (15.24 g, 88% yield) as a white solid. LCMS m/z=620.4 [M+H]$^+$; $^1$H NMR (400 MHz, DMSO-$d_6$) δ ppm 1.38 (t, J=7.07 Hz, 3H), 1.51-1.61 (m, 1H), 1.62-1.71 (m, 1H), 1.71-1.82 (m, 3H), 2.20 (dd, J=13.26, 8.21 Hz, 1H), 2.30 (s, 3H), 2.94-3.05 (m, 1H), 3.06-3.20 (m, 3H), 3.21 (s, 3H), 3.30-3.43 (m, 1H), 3.76-3.85 (m, 1H), 3.90-3.99 (m, 2H), 4.07 (d, J=5.05 Hz, 2H), 4.10-4.19 (m, 1H), 4.46 (q, J=7.07 Hz, 2H), 5.91 (bs, 1H), 7.30 (ddd, J=8.15, 2.46, 0.76 Hz, 1H), 7.44 (t, J=2.27 Hz, 1H), 7.50-7.56 (m, 2H), 7.59 (t, J=7.96 Hz, 1H), 7.82-7.91 (m, 2H), 8.25 (dd, J=7.83, 1.26 Hz, 1H), 8.63 (s, 1H), 8.76 (bs, 2H). $^{13}$C NMR (400 MHz, DMSO-$d_6$) δ ppm 14.30, 35.68, 36.35, 42.54, 43.10, 43.21, 43.35, 48.09, 50.44, 58.11, 67.65, 70.45, 71.00, 78.90, 112.31, 117.02, 117.43, 118.81, 120.05, 125.12, 126.17, 127.71, 130.58, 133.31, 138.91, 142.03, 147.53, 158.91, 171.53.

Example 1.34: Preparation of (S)-1-(3-(2-Hydroxyethylsulfonyl)phenoxy)-3-((R)-8-(quinolin-3-ylsulfonyl)-1-oxa-8-azaspiro[4.5]decan-3-ylamino)propan-2-ol (Compound 88). (Method B)

Step A: Preparation of (R)-tert-Butyl 1-Oxa-8-azaspiro[4.5]decan-3-ylcarbamate

To a solution of (R)-benzyl 3-((tert-butoxycarbonyl)amino)-1-oxa-8-azaspiro[4.5]decane-8-carboxylate (39.8 g, 101.9 mmol) in MeOH (254.8 mL) under $H_2$ balloon was added Palladium/C (10.85 g, 10.19 mmol) at room temperature. The reaction was stirred at room temperature overnight. After the reaction was completed, the mixture was filtered through a pad of Celite®, washed with MeOH, and concentrated. The residue was triturated with EtOAc/Hex (10%) to give the title compound (21.02 g, 80% yield) as a yellow gum. LCMS m/z=257.4 [M+H]+; 1H NMR (400 MHz, DMSO-d6) δ ppm 1.37 (s, 9H), 1.41 (t, J=5.68 Hz, 2H), 1.52 (dd, J=6.69, 3.41 Hz, 3H), 1.96 (dd, J=12.63, 8.34 Hz, 1H), 2.52-2.58 (m, 2H), 2.72-2.84 (m, 2H), 3.41 (dd, J=8.59, 6.57 Hz, 1H), 3.83 (dd, J=8.59, 6.82 Hz, 1H), 3.92-4.08 (m, 1H), 6.99 (bs, 1H).

Step B: Preparation of (R)-tert-Butyl (8-(Quinolin-3-ylsulfonyl)-1-oxa-8-azaspiro[4.5]decan-3-yl)carbamate To a solution of (R)-tert-butyl 1-oxa-8-azaspiro[4.5]decan-3-ylcarbamate (21.02 g, 82.00 mmol) in CH2Cl2 (370 mL) under nitrogen was added DIEA (14.28 mL, 82.00 mmol) at 0° C. followed by addition of a quinoline-3-sulfonyl chloride (20.54 g, 90.20 mmol) solution in CH2Cl2 via addition funnel. The reaction mixture was slowly warmed up to room temperature overnight. After the reaction was completed, the mixture was washed with water and then brine. The organic layer was dried over Na2SO4, filtered, and concentrated. The residue was triturated with hexane to give the title compound (42.31 g, 112% yield) as a light yellow solid. LCMS m/z=448.4 [M+H]+; 1H NMR (400 MHz, DMSO-d6) δ ppm 1.34 (s, 9H), 1.53 (dd, J=13.01, 6.44 Hz, 1H), 1.62 (t, J=4.29 Hz, 2H), 1.71 (t, J=4.55 Hz, 2H), 1.91 (dd, J=12.88, 8.34 Hz, 1H), 2.65-2.83 (m, 2H), 3.31-3.39 (m, 2H), 3.72 (dd, J=8.84, 6.57 Hz, 1H), 3.87-4.01 (m, 1H), 6.99 (d, J=5.81 Hz, 1H), 7.81 (ddd, J=8.15, 7.01, 1.01 Hz, 1H), 8.00 (ddd, J=8.46, 6.95, 1.52 Hz, 1H), 8.17 (d, J=8.34 Hz, 1H), 8.29 (d, J=7.58 Hz, 1H), 8.92 (d, J=1.77 Hz, 1H), 9.13 (d, J=2.27 Hz, 1H).

Step C: Preparation of (R)-8-(Quinolin-3-ylsulfonyl)-1-oxa-8-azaspiro[4.5]decan-3-amine To a solution of (R)-tert-butyl (8-(quinolin-3-ylsulfonyl)-1-oxa-8-azaspiro[4.5]decan-3-yl)carbamate (42.52 g, 95.01 mmol) in CH2Cl2 (237.5 mL) was slowly added TFA (79 mL, 1.032 mol) at 0° C. The reaction was stirred at room temperature for 2.5 h. After the reaction was completed, the mixture was concentrated. The reddish brown oil residue was triturated with MTBE to give the title compound (30.34 g, 92% yield) as a light brown solid. LCMS m/z=348.2 [M+H]+; 1H NMR (400 MHz, DMSO-d6) δ ppm 1.45 (dd, J=13.01, 5.68 Hz, 1H), 1.53-1.67 (m, 2H), 1.70-1.84 (m, 2H), 1.94 (dd, J=13.01, 7.71 Hz, 1H), 2.65-2.80 (m, 2H), 3.16-3.45 (m, 3H), 3.53 (dq, J=7.71, 5.68 Hz, 1H), 3.69 (dd, J=9.09, 6.06 Hz, 1H), 7.81 (td, J=7.58, 1.01 Hz, 1H), 8.00 (td, J=8.46, 6.95, 1.52 Hz, 1H), 8.18 (d, J=8.59 Hz, 1H), 8.28 (d, J=1.01 Hz, 1H), 8.93 (d, J=2.02 Hz, 1H), 9.13 (d, J=2.27 Hz, 1H).

Step D: Preparation of (S)-1-(3-(2-Hydroxyethylsulfonyl)phenoxy)-3-((R)-8-(quinolin-3-ylsulfonyl)-1-oxa-8-azaspiro[4.5]decan-3-ylamino)propan-2-ol (Compound 88). (Method BD)

A solution of (S)-2-((3-(oxiran-2-ylmethoxy)phenyl)sulfonyl)ethanol (15.23 g, 38.91 mmol) and (R)-8-(quinolin-3-ylsulfonyl)-1-oxa-8-azaspiro[4.5]decan-3-amine (27.04 g, 77.82 mmol) in EtOH (160 mL) was heated at 70° C. for 24 h. After the reaction was completed, the mixture was concentrated. The residue was purified by prep-HPLC. The fractions were combined and neutralized with saturated NaHCO3 aqueous solution. The volatile was evaporated, and then the aqueous layer was extracted with IPA/CH2Cl2 (10%). The organic layer was dried over Na2SO4, filtered, and concentrated to give the title compound (9.70 g, 41% yield) as a white solid. LCMS m/z=606.4 [M+H]+; 1H NMR (400 MHz, DMSO-d6) δ ppm 1.46 (dd, J=12.63 5.31 Hz, 1H), 1.60 (t, J=5.68 Hz, 2H), 1.65-1.81 (m, 2H), 1.88 (dd, J=12.25, 7.20 Hz, 1H), 2.53-2.61 (m, 2H), 2.68-2.79 (m, 2H), 3.32-3.40 (m, 3H), 3.44 (t, J=6.44 Hz, 2H), 3.62-3.73 (m, 3H), 3.78-3.86 (m, 1H), 3.89-3.95 (m, 1H), 3.98-4.04 (m, 1H), 4.86 (t, J=5.56 Hz, 1H), 5.02 (bs, 1H), 7.25 (dd, J=8.21, 2.53, 0.88 Hz, 1H), 7.36 (t, J=2.53 Hz, 1H), 7.43 (dd, J=8.34, 1.77 Hz, 1H), 7.52 (t, J=7.96 Hz, 1H), 7.81 (ddd, J=8.15, 7.01, 1.01 Hz, 1H), 8.00 (ddd, J=8.46, 6.95, 1.52 Hz, 1H), 8.18 (d, J=8.34 Hz, 1H), 8.29 (dd, J=8.46, 0.88 Hz, 1H), 8.92 (d, J=1.77 Hz, 1H), 9.13 (d, J=2.27 Hz, 1H).

Example 1.35: Preparation of (2S)-1-(4-(Methylsulfonyl)phenoxy)-3-(8-(naphthalen-2-ylsulfonyl)-1-oxa-8-azaspiro[4.5]decan-3-ylamino)propan-2-ol (Compound 334). (Method C)

Step A: Preparation of tert-Butyl (8-(Naphthalen-2-ylsulfonyl)-1-oxa-8-azaspiro[4.5]decan-3-yl)carbamate Benzyl 3-((tert-butoxycarbonyl)amino)-1-oxa-8-azaspiro[4.5]decane-8-carboxylate (4.1 g, 10.50 mmol) was dissolved in MeOH (15 mL). Palladium/C (0.11 g, 1.05 mmol) and a double balloon of hydrogen (gas) were applied. The reaction was vigorously stirred at room temperature for 2 h. After this time, the reaction was complete. The reaction was filtered through a plug of celite. The solvent was completely removed. The resulting viscous oil was re-dissolved in CH2Cl2 (30 mL). DIEA (2.74 mL, 15.75 mmol) was added, followed by naphthalene-2-sulfonyl chloride (2.62 g, 11.55 mmol) (a slightly exothermic reaction, and bubbling, took place). The reaction was stirred at room temperature for a half hour. After this time, the reaction was complete. The solvent was removed, and the residue was purified by silica gel column chromatography to give the title compound (4.5 g, 95.0% yield) as a white solid. LCMS m/z=447.6 [M+H]+. 1H NMR (400 MHz, DMSO-d6) δ ppm 1.34 (s, 9H), 1.48-1.56 (m, 1H), 1.56-1.63 (m, 2H), 1.64-1.74 (m, 2H), 1.85-1.94 (m, 1H), 2.59-2.72 (m, 2H), 3.25-3.33 (m, 3H), 3.67-3.75 (m, 1H), 3.88-3.99 (m, 1H), 6.97 (d, J=8.7 Hz, 1H), 7.67-7.79 (m, 3H), 8.08 (d, J=8.0 Hz, 1H), 8.17 (d, J=8.7 Hz, 1H), 8.21 (d, J=8.0 Hz, 1H), 8.42 (d, J=1.4 Hz, 1H).

Step B: Preparation of tert-Butyl (8-(Naphthalen-2-ylsulfonyl)-1-oxa-8-azaspiro[4.5]decan-3-yl)((S)-oxiran-2-ylmethyl)carbamate tert-Butyl (8-(naphthalen-2-ylsulfonyl)-1-oxa-8-azaspiro[4.5]decan-3-yl)carbamate (2.0 g, 4.48 mmol) was dissolved in DMF (6 mL; the solution remained slightly cloudy). Sodium Hydride (0.32 g, 13.44 mmol) was added at room temperature (bubbling was observed). The reaction was stirred at room temperature for a half hour. Then, (S)-2-(chloromethyl)oxirane (2.07 g, 22.39 mmol) was added to the stirring solution. The reaction was stirred at room temperature for an hour. After this time, the reaction was around 50% complete by TLC analysis. The reaction was warmed in an oil bath to 40° C., and stirred at this temperature for 2 h. After this time, the starting material was consumed. The reaction was cooled and diluted with EtOAc (20 mL). The reaction was poured into a separatory funnel with H2O (30 mL), and extracted with EtOAc. The combined organic layer was dried, concentrated, and the residue was purified by silica gel column chromatography to give the title compound (1.47 g, 2.63 mmol, 58.8% yield) as a white foamy solid. LCMS m/z=503.6 [M+H]$^+$; $^1$H NMR (400 MHz, DMSO-d$_6$) δ ppm 1.37 (s, 9H), 1.50-1.81 (m, 5H), 1.88-1.99 (m, 1H), 2.41-2.48 (m, 1H), 2.57-2.75 (m, 3H), 2.92-3.00 (m, 1H), 3.23-3.43 (m, 3H), 3.43-3.50 (m, 1H), 3.52-3.59 (m, 1H), 3.63-3.73 (m, 1H), 4.35-4.51 (m, 1H), 7.66-7.79 (m, 3H), 8.09 (d, J=7.9 Hz, 1H), 8.17 (d, J=8.8 Hz, 1H), 8.21 (d, J=8.0 Hz, 1H), 8.43 (s, 1H).

Step C: Preparation of (2S)-1-(4-(Methylsulfonyl)phenoxy)-3-(8-(naphthalen-2-ylsulfonyl)-1-oxa-8-azaspiro[4.5]decan-3-ylamino)propan-2-ol (Compound 334)

tert-Butyl (8-(naphthalen-2-ylsulfonyl)-1-oxa-8-azaspiro[4.5]decan-3-yl)((S)-oxiran-2-ylmethyl)carbamate (10 mg, 19.90 µmol), 4-(methylsulfonyl)phenol (4.11 mg, 23.87 µmol), and potassium carbonate (8.25 mg, 59.69 µmol) were dissolved/suspended in DMF (0.2 mL). The reaction was heated to 100° C. overnight. The mixture was filtered through a plug of Celite®. The filtrate was concentrated and purified by Prep LC/MS to give tert-butyl ((S)-2-hydroxy-3-(4-(methylsulfonyl)phenoxy)propyl)(8-(naphthalen-2-ylsulfonyl)-1-oxa-8-azaspiro[4.5]decan-3-yl)carbamate. After lyophilizing, the material was dissolved in ACN (1.5 mL). 4N HCl in dioxane (100 µl, 0.400 mmol) was added, and the reaction was allowed to stand until the Boc-group was completely cleaved. The solvents were removed completely, and the resulting material was dissolved in ACN (0.2 mL) and H$_2$O (0.5 mL), frozen, and lyophilized again to give the HCl salt of the title compound. Due to the presence of an impurity observed in the LC/MS after the lyophilized step, the material was again purified by Prep LC/MS to give the title compound (3.3 mg, 23.8% yield) as a white solid (TFA salt). LCMS m/z=575.4 [M+H]$^+$.

Example 1.36: Preparation of (2S)-1-(3-(Ethylsulfonyl)phenoxy)-3-(8-(naphthalen-2-ylsulfonyl)-1-oxa-8-azaspiro[4.5]decan-3-ylamino)propan-2-ol (Compound 15)

Step A: Preparation of tert-Butyl (8-(Naphthalen-2-ylsulfonyl)-1-oxa-8-azaspiro[4.5]decan-3-yl)((S)-oxiran-2-ylmethyl)carbamate tert-Butyl (8-(naphthalen-2-ylsulfonyl)-1-oxa-8-azaspiro[4.5]decan-3-yl)carbamate (1.5 g, 3.36 mmol)) was dissolved anhydrous DMF (12 mL) under N$_2$ to give a clear colorless solution. Sodium hydride (0.61 g, 15.12 mmol) was added. The grayish suspension was stirred at room temperature for 30 min followed by addition of (S)-2-(chloromethyl)oxirane (1.32 mL, 16.80 mmol). The reaction was stirred at room temperature under N$_2$ for 2 h. The reaction was quenched with water, then poured into a saturated NaHCO$_3$ aqueous solution (25 mL). The resulting mixture was extracted with EtOAc (3×). The combined organic layer was washed with water and brine, dried over MgSO$_4$, filtered and concentrated. The residue was purified by silica gel column chromatography to the title compound (323 mg, 22% yield). LCMS m/z=503.4 [M+H]$^+$; $^1$H NMR (400 MHz, CD$_3$OD) δ ppm 1.44 (s, 9H), 1.56-1.69 (m, 1H), 1.69-1.88 (m, 4H), 1.97-2.05 (m, 1H), 2.50 (dt, J=4.80, 2.40 Hz, 1H), 2.72-2.77 (m, 1H), 2.77-2.88 (m, 2H), 2.98-3.07 (m, 1H), 3.32-3.38 (m, 2H), 3.38-3.50 (m, 2H), 3.56 (dd, J=14.78, 1.89 Hz, 1H), 3.70-3.81 (m, 1H), 4.49 (bs, 1H), 7.63-7.73 (m, 2H), 7.77 (dd, J=8.59, 1.77 Hz, 1H), 8.01 (d, J=7.83 Hz, 1H), 8.08 (d, J=8.34 Hz, 2H), 8.37 (d, J=1.26 Hz, 1H).

Step B: Preparation of (2S)-1-(3-(Ethylsulfonyl)phenoxy)-3-(8-(naphthalen-2-ylsulfonyl)-1-oxa-8-azaspiro[4.5]decan-3-ylamino)propan-2-ol (Compound 15)

A solution of tert-butyl (8-(naphthalen-2-ylsulfonyl)-1-oxa-8-azaspiro[4.5]decan-3-yl)((S)-oxiran-2-ylmethyl)carbamate (15 mg, 29.84 µmol) in DMF (0.2 mL) was added into a 5 mL scintillation vial containing 3-(ethylsulfonyl)phenol (10.28 mg, 59.69 µmol) and K$_2$CO$_3$ (12.37 mg, 89.53 µmol). The reaction was heated at 70° C. overnight. After the reaction was completed, the mixture was filtered through a pad of Celite® then concentrated. The residue was purified by mass directed prep-HPLC to give tert-butyl ((S)-2-hydroxy-3-(3-(ethylsulfonyl)phenoxy)propyl)(8-(naphthalen-2-ylsulfonyl)-1-oxa-8-azaspiro[4.5]decan-3-yl)carbamate. LCMS m/z=689.4 [M+H]$^+$.

To a solution of tert-butyl ((S)-2-hydroxy-3-(3-(ethylsulfonyl)phenoxy)propyl)(8-(naphthalen-2-ylsulfonyl)-1-oxa-8-azaspiro[4.5]decan-3-yl)carbamate in ACN (2 mL) was added 4N HCl (in Dioxane, 75 µL, 0.30 mmol). The reaction was gently shaken for 2 h at room temperature and concentrated. The residue was purified by mass directed prep-HPLC to give the title compound (8.1 mg, 39% yield) as an off white solid. LCMS m/z=589.4 [M+H]$^+$; $^1$H NMR (400 MHz, CD$_3$OD) δ ppm 1.20 (t, J=8.00 Hz, 3H), 1.67 (dd, J=10.86, 4.29 Hz, 1H), 1.75-1.96 (m, 4H), 2.28 (ddd, J=13.58, 8.02, 2.40 Hz, 1H), 2.73-2.90 (m, 2H), 3.06-3.29 (m, 4H), 3.49 (t, J=12.63 Hz, 2H), 3.79-3.88 (m, 1H), 3.92-4.03 (m, 2H), 4.04-4.13 (m, 2H), 4.18-4.27 (m, 1H), 7.29 (ddd, J=8.08, 2.53, 1.26 Hz, 1H), 7.44 (t, J=4.00 Hz, 1H), 7.48-7.52 (m, 1H), 7.55 (t, J=8.00 Hz, 1H), 7.68 (qd, J=8.25, 8.08 Hz, 2H), 7.77 (dd, J=8.72, 1.89 Hz, 1H), 8.01 (d, J=7.83 Hz, 1H), 8.08 (d, J=8.84 Hz, 2H), 8.38 (d, J=1.52 Hz, 1H).

Example 1.37: Preparation of (2S)-1-(3-(Methylsulfonyl)phenoxy)-3-(8-(naphthalen-2-ylsulfonyl)-1-oxa-8-azaspiro[4.5]decan-3-ylamino)propan-2-ol (Compound 1). (Method D)

(S)-2-((3-(Methylsulfonyl)phenoxy)methyl)oxirane (20 mg, 87.62 µmol) and 8-(naphthalen-2-ylsulfonyl)-1-oxa-8-azaspiro[4.5]decan-3-amine (33.39 mg, 96.38 nmol, prepared from benzyl 3-((tert-butoxycarbonyl)amino)-1-oxa-8-azaspiro[4.5]decane-8-carboxylate using a similar method to the one described in Example 1.2, Step A and B) were dissolved in EtOH (2.5 mL). The reaction was heated at 60° C. overnight. After the reaction was completed and cooled down to room temperature, it was concentrated and purified by mass direct prep-HPLC to give the title compound (7 mg, 12% yield). LCMS m/z=575.4 [M+H]$^+$; $^1$H NMR (400 MHz, CD$_3$OD) δ ppm 1.31-1.38 (m, 1H), 1.61-1.72 (m, 1H), 1.77-1.96 (m, 4H), 2.29 (dd, J=13.77, 8.21 Hz, 1H), 2.74-2.91 (m, 2H), 3.10 (s, 3H), 3.44-3.55 (m, 4H), 3.79-3.87 (m, 1H), 3.93-4.03 (m, 2H), 4.09 (d, J=4.80 Hz, 2H), 4.20-4.29 (m, 1H), 7.26-7.33 (m, 1H), 7.49 (s, 1H), 7.55 (d, J=5.05 Hz, 2H), 7.62-7.74 (m, 2H), 7.77 (d, J=8.59 Hz, 1H), 8.01 (d, J=8.08 Hz, 1H), 8.09 (d, J=8.59 Hz, 2H), 8.38 (s, 1H).

Example 1.38: Preparation of (S)-1-(3-(Cyclopropylsulfonyl)phenoxy)-3-((R)-8-(1-methyl-2,3-dihydro-1H-pyrido[2,3-b][1,4]oxazin-7-ylsulfonyl)-1-oxa-8-azaspiro[4.5]decan-3-ylamino)propan-2-ol (Compound 154). (Method E)

Step A: Preparation of (R)-Benzyl 3-((tert-butoxycarbonyl)((S)-3-(3-(cyclopropylsulfonyl)phenoxy)-2-hydroxypropyl)amino)-1-oxa-8-azaspiro[4.5]decane-8-carboxylate A solution of (S)-2-((3-(cyclopropylsulfonyl)phenoxy)methyl)oxirane (7.63 g, 30.00 mmol) and (R)-benzyl 3-amino-1-oxa-8-azaspiro[4.5]decane-8-carboxylate (17.42 g, 60.01 mmol) in EtOH (150 mL) was heated at 70° C. overnight. After the reaction was completed, the mixture was concentrated. The residue was purified by silica gel column chromatography to give (R)-benzyl 3-(((S)-3-(3-(cyclopropylsulfonyl)phenoxy)-2-hydroxypropyl)amino)-1-oxa-8-azaspiro[4.5]decane-8-carboxylate (6.34 g, 61% yield). LCMS m/z=545.6 [M+H]$^+$; $^1$H NMR (400 MHz, CDCl$_3$) δ ppm 1.00-1.09 (m, 2H), 1.32-1.39 (m, 2H), 1.46-1.58 (m, 1H), 1.60-1.74 (m, 2H), 1.79 (dd, J=13.14, 5.81 Hz, 2H), 2.10-2.17 (m, 1H), 2.48 (tt, J=7.96, 4.93 Hz, 1H), 2.92-3.09 (m, 2H), 3.35 (q, J=10.78 Hz, 2H), 3.61-3.70 (m, 1H), 3.70-3.81 (m, 2H), 3.84-3.92 (m, 1H), 4.01-4.14 (m, 3H), 4.21-4.31 (m, 1H), 5.13 (s, 2H), 7.17 (ddd, J=7.89, 2.46, 1.26 Hz, 1H), 7.28-7.39 (m, 5H), 7.40-7.55 (m, 3H).

To a solution of (R)-benzyl 3-(((S)-3-(3-(cyclopropylsulfonyl)phenoxy)-2-hydroxypropyl)amino)-1-oxa-8-azaspiro[4.5]decane-8-carboxylate (6.34 g, 11.63 mmol) in CH$_2$Cl$_2$ (150.0 mL) was added DIEA (3.7 mL, 21.2 mmol) and (BOC)$_2$O (4.4 g, 20.2 mmol). The reaction was stirred at room temperature overnight. After the reaction was completed, the mixture was concentrated. The residue was purified by silica gel column chromatography to give the title compound (5.81 g). LCMS m/z=645.4 [M+H]$^+$; $^1$H NMR (400 MHz, CDCl$_3$) δ ppm 1.00-1.08 (m, 2H), 1.31-1.39 (m, 2H), 1.50 (s, 10H), 1.63-1.76 (m, 3H), 1.82 (dd, J=13.01, 8.21 Hz, 1H), 2.09 (dd, J=12.88, 8.59 Hz, 1H), 2.41-2.52 (m, 1H), 3.27-3.54 (m, 4H), 3.66-3.79 (m, 2H), 3.80-3.90 (m, 1H), 3.92-4.07 (m, 3H), 4.11-4.20 (m, 1H), 4.57-4.69 (m, 1H), 5.14 (s, 2H), 7.16 (ddd, J=8.02, 2.59, 1.26 Hz, 1H), 7.29-7.40 (m, 5H), 7.42 (t, J=2.27 Hz, 1H), 7.45-7.54 (m, 2H).

Step B: Preparation of tert-Butyl ((S)-3-(3-(Cyclopropylsulfonyl)phenoxy)-2-hydroxypropyl)((R)-1-oxa-8-azaspiro[4.5]decan-3-yl)carbamate To a solution of (R)-benzyl 3-((tert-butoxycarbonyl)((S)-3-(3-(cyclopropylsulfonyl)phenoxy)-2-hydroxypropyl)amino)-1-oxa-8-azaspiro[4.5]decane-8-carboxylate (5.80 g, 9.00 mmol) in MeOH (45 mL) under nitrogen was added palladium/C (0.96 g, 0.90 mmol). The reaction was stirred at room temperature overnight under H$_2$ balloons. After the reaction was completed, the mixture was filtered through a pad of Celite® and washed with MeOH. The filtrate was concentrated to give the title compound (4.6 g, 100% yield) as a white foam LCMS m/z=511.6 [M+H]$^+$; $^1$H NMR (400 MHz, CDCl$_3$) δ ppm 1.00-1.09 (m, 2H), 1.32-1.38 (m, 2H), 1.50 (s, 9H), 1.56-1.80 (m, 6H), 2.13 (dd, J=12.88, 8.84 Hz, 1H), 2.46 (tt, J=7.96, 4.80 Hz, 1H), 2.71-2.81 (m, 2H), 2.93-3.07 (m, 2H), 3.38-3.56 (m, 2H), 3.76-3.87 (m, 1H), 3.93-4.07 (m, 3H), 4.12-4.20 (m, 1H), 4.59-4.71 (m, 1H), 7.16 (ddd, J=7.83, 2.53, 1.52 Hz, 1H), 7.42 (t, J=1.52 Hz, 1H), 7.45-7.55 (m, 2H).

Step C: Preparation of tert-Butyl ((S)-3-(3-(Cyclopropylsulfonyl)phenoxy)-2-hydroxypropyl)((R)-8-((1-methyl-2,3-dihydro-1H-pyrido[2,3-b][1,4]oxazin-7-yl)sulfonyl)-1-oxa-8-azaspiro[4.5]decan-3-yl)carbamate To a solution of tert-butyl ((S)-3-(3-(cyclopropylsulfonyl)phenoxy)-2-hydroxypropyl)((R)-1-oxa-8-azaspiro[4.5]decan-3-yl)carbamate (1.96 g, 3.84 mmol) in CH$_2$Cl$_2$ (19.18 mL) was added DIEA (0.80 mL, 4.60 mmol) and 1-methyl-2,3-dihydro-1H-pyrido[2,3-b][1,4]oxazine-7-sulfonyl chloride (1.10 g, 4.41 mmol). The reaction was stirred at room temperature overnight. After the reaction was completed, the mixture was concentrated. The residue was then purified by silica gel column chromatography to give the title compound (2.5 g, 90% yield). LCMS m/z=723.6 [M+H]$^+$.

Step D: Preparation of (S)-1-(3-(Cyclopropylsulfonyl)phenoxy)-3-((R)-8-(1-methyl-2,3-dihydro-1H-pyrido[2,3-b][1,4]oxazin-7-ylsulfonyl)-1-oxa-8-azaspiro[4.5]decan-3-ylamino)propan-2-ol (Compound 154)

To a solution of tert-Butyl ((S)-3-(3-(cyclopropylsulfonyl)phenoxy)-2-hydroxypropyl)((R)-8-((1-methyl-2,3-dihydro-1H-pyrido[2,3-b][1,4]oxazin-7-yl)sulfonyl)-1-oxa-8-azaspiro[4.5]decan-3-yl)carbamate (2.5 g, 3.46 mmol) in DCM (19 mL) was added TFA (7 mL, 91.41 mmol). The reaction was stirred at room temperature for 1 h. The mixture was concentrated. The residue was diluted with water. The mixture was neutralized with saturated NaHCO$_3$ aqueous solution then extracted with IPA/DCM (10%). The organic layer was washed with water and brine, then dried over Na$_2$SO$_4$, and filtered. The filtrate was concentrated to give the title compound (2.1 g, 88% yield) as a foam. LCMS m/z=623.4 [M+H]$^+$; $^1$H NMR (400 MHz, DMSO-d$_6$) δ ppm 1.00-1.07 (m, 2H), 1.09-1.13 (m, 2H), 1.47 (dd, J=12.76, 5.43 Hz, 1H), 1.56-1.61 (m, 2H), 1.67 (dd, J=10.61, 4.29 Hz, 1H), 1.72-1.80 (m, 1H), 1.89 (dd, J=12.76, 7.45 Hz, 1H), 2.53-2.68 (m, 4H), 2.87 (dd, J=12.63, 3.03 Hz, 1H), 2.91 (s, 3H), 3.23 (dd, J=10.74, 5.94 Hz, 2H), 3.33-3.43 (m, 4H), 3.75 (dd, J=8.59, 5.81 Hz, 1H), 3.80-3.88 (m, 1H), 3.91-3.98 (m, 1H), 4.02-4.07 (m, 1H), 4.45 (t, J=4.8 Hz, 2H), 4.96-5.06 (m, 1H), 7.02 (d, J=2.27 Hz, 1H), 7.28 (dd, J=7.83, 2.02 Hz, 1H), 7.35 (t, J=1.77 Hz, 1H), 7.43 (d, J=8.34 Hz, 1H), 7.55 (t, J=7.96 Hz, 1H), 7.71 (d, J=2.02 Hz, 1H). $^{13}$C NMR (400 MHz, CD$_3$OD) δ ppm 6.51, 25.39, 33.55, 35.28, 36.97, 38.42, 41.06, 44.42, 44.81, 48.12, 50.51, 59.71, 66.69, 67.80, 68.45, 71.71, 80.99, 114.62, 117.44, 121.12, 121.26, 129.23, 131.54, 132.03, 135.13, 143.44, 154.96, 160.46.

Example 1.39: Preparation of 3-((R)-3-((S)-3-(3-(Cyclopropylsulfonyl)phenoxy)-2-hydroxypropylamino)-1-oxa-8-azaspiro[4.5]decan-8-ylsulfonyl)-1-ethylquinolin-4(1H)-one (Compound 297)

Step A: Preparation of tert-Butyl ((S)-3-(3-(Cyclopropylsulfonyl)phenoxy)-2-hydroxypropyl)((R)-8-((1-ethyl-4-oxo-1,4-dihydroquinolin-3-yl)sulfonyl)-1-oxa-8-azaspiro[4.5]decan-3-yl)carbamate To a solution of tert-butyl ((S)-3-(3-(cyclopropylsulfonyl)phenoxy)-2-hydroxypropyl)((R)-1-oxa-8-azaspiro[4.5]decan-3-yl)carbamate (294 mg, 0.58 mmol) in CH$_2$Cl$_2$ (5 mL) was added DIEA (0.22 mL, 1.26 mmol) followed by 1-ethyl-4-oxo-1,4-dihydroquinoline-3-sulfonyl chloride (0.27 g, 0.98 mmol). The reaction was stirred at room temperature overnight. The mixture was concentrated. The residue was purified by silica gel column chromatography to give the title compound. LCMS m/z=746.4 [M+H]$^+$.

Step B: Preparation of 3-((R)-3-((S)-3-(3-(Cyclopropylsulfonyl)phenoxy)-2-hydroxypropylamino)-1-oxa-8-azaspiro[4.5]decan-8-ylsulfonyl)-1-ethylquinolin-4(1H)-one (Compound 297)

tert-Butyl ((S)-3-(3-(cyclopropylsulfonyl)phenoxy)-2-hydroxypropyl)((R)-8-((1-ethyl-4-oxo-1,4-dihydroquinolin-3-yl)sulfonyl)-1-oxa-8-azaspiro[4.5]decan-3-yl)carbamate (from the previous Step) was stirred in TFA/DCM (14%, 5 mL) at room temperature overnight. The mixture was concentrated and the residue was purified by prep-HPLC. The combined fractions were neutralized with aqueous NaHCO$_3$ then MeCN was removed under pressure. The aqueous layer was extracted with IPA/DCM (10%, 2×150 mL). The combined organic layer was washed with brine, then dried over Na$_2$SO$_4$, filtered and concentrated. The residue was dissolved in ACN (14 mL) then HCl (4N in dioxane, 2.3 equiv.) was added. The solution was stirred at room temperature for 1 h followed by addition of water (21 mL). The mixture was then lyophilized to give the title compound (356 mg, 86% yield). LCMS m/z=646.4 [M+H]$^+$; $^1$H NMR (400 MHz, DMSO-d$_6$) δ ppm 1.00-1.08 (m, 2H), 1.08-1.15 (m, 2H), 1.38 (t, J=7.07 Hz, 3H), 1.51-1.60 (m, 1H), 1.62-1.70 (m, 1H), 1.72-1.84 (m, 3H), 2.20 (dd, J=13.39, 8.08 Hz, 1H), 2.87 (tt, J=7.80, 4.83 Hz, 1H), 2.93-3.04 (m, 1H), 3.05-3.22 (m, 3H), 3.29-3.42 (m, 2H), 3.78-3.87 (m, 1H), 3.87-3.99 (m, 2H), 4.07 (d, J=5.05 Hz, 2H), 4.14-4.23 (m, 1H), 4.46 (q, J=7.07 Hz, 2H), 7.31 (dd, J=8.08, 1.77 Hz, 1H), 7.38 (t, J=1.77 Hz, 1H), 7.48 (d, J=7.83 Hz, 1H), 7.53 (ddd, J=7.96, 6.32, 1.64 Hz, 1H), 7.58 (t, J=7.96 Hz, 1H), 7.82-7.92 (m, 2H), 8.24 (d, J=1.26 Hz, 1H), 8.63 (s, 1H), 8.96 (bs, 1H), 9.09 (bs, 1H).

Example 1.40: Preparation of 2-(3-((S)-2-Hydroxy-3-((R)-8-(quinolin-3-ylsulfonyl)-1-oxa-8-azaspiro[4.5]decan-3-ylamino)propoxy)phenylsulfonyl)acetamide (Compound 123). (Method E2)

Step A: Preparation of (R)-Benzyl 3-(((S)-3-(3-((2-amino-2-oxoethyl)sulfonyl)phenoxy)-2-hydroxypropyl)amino)-1-oxa-8-azaspiro[4.5]decane-8-carboxylate A solution of (S)-2-((3-(oxiran-2-ylmethoxy)phenyl)sulfonyl)acetamide (14.75 g, 54.38 mmol) and (R)-benzyl 3-amino-1-oxa-8-azaspiro[4.5]decane-8-carboxylate (62.5 g, 98.8 mmol) in EtOH (550 mL) was heated at 70° C. for 40 h. After the reaction was completed and cooled down to room temperature, the mixture was concentrated. The residue was used in the next step without purification. LCMS m/z=562.4 [M+H]$^+$.

Step B: Preparation of (R)-Benzyl 3-(((S)-3-(3-((2-amino-2-oxoethyl)sulfonyl)phenoxy)-2-hydroxypropyl)(tert-butoxycarbonyl)amino)-1-oxa-8-azaspiro[4.5]decane-8-carboxylate (R)-benzyl 3-(((S)-3-(3-((2-amino-2-oxoethyl)sulfonyl)phenoxy)-2-hydroxypropyl)amino)-1-oxa-8-azaspiro[4.5]decane-8-carboxylate from the previous step was dissolved in CH$_2$Cl$_2$ (550 mL) then cooled down to 0° C. DIEA (37.89 mL, 217.5 mmol) and (BOC)$_2$O (71.21 g, 326.3 mmol) were added. The reaction was stirred at room temperature. The mixture was concentrated. The residue was purified by silica gel column chromatography to give the title compound (22.1 g, 61% yield) as a yellow foam. LCMS m/z=662.6 [M+H]$^+$; $^1$H NMR (400 MHz, CDCl$_3$) δ ppm 1.50 (s, 10H), 1.64-1.85 (m, 4H), 2.09 (dd, J=13.14, 8.84 Hz, 1H), 3.29-3.55 (m, 4H), 3.68-3.87 (m, 3H), 3.92-4.01 (m, 4H), 4.02-4.08 (m, 1H), 4.11-4.19 (m, 1H), 4.61-4.71 (m, 1H), 5.13 (s, 2H), 5.58-5.93 (m, 1H), 6.62-6.73 (m, 1H), 7.21 (ddd, J=7.83, 2.53, 1.52 Hz, 1H), 7.30-7.39 (m, 5H), 7.43 (t, J=1.77 Hz, 1H), 7.48-7.58 (m, 2H).

Step C: Preparation of tert-Butyl ((S)-3-(3-((2-Amino-2-oxoethyl)sulfonyl)phenoxy)-2-hydroxypropyl)((R)-1-oxa-8-azaspiro[4.5]decan-3-yl)carbamate To a solution of (R)-benzyl 3-(((S)-3-(3-((2-amino-2-oxoethyl)sulfonyl)phenoxy)-2-hydroxypropyl)(tert-butoxycarbonyl)amino)-1-oxa-8-azaspiro[4.5]decane-8-carboxylate (22.1 g, 32.40 mmol) in MeOH (324 mL) under N$_2$ was added Palladium/C (3.45 g, 3.24 mmol). The reaction was stirred overnight under H$_2$ balloons. The mixture was passed through a pad of Celite® and washed with MeOH. The filtrate was concentrated to give the title compound (17.6 g, 103% yield) as a white foam which was used in the next step without purification. LCMS m/z=528.6 [M+H]$^+$; $^1$H NMR (400 MHz, CDCl$_3$) δ ppm 1.50 (s, 9H), 1.54-1.69 (m, 2H), 1.71-1.83 (m, 3H), 2.10 (dd, J=13.01, 8.97 Hz, 1H), 2.72-2.88 (m, 2H), 3.00 (dddd, J=17.27, 8.56, 8.40, 4.17 Hz, 2H), 3.38-3.56 (m, 2H), 3.66-3.85 (m, 1H), 3.92-4.09 (m, 5H), 4.10-4.18 (m, 1H), 4.58-4.73 (m, 1H), 6.19-6.51 (m, 1H), 6.75 (bs, 1H), 7.22 (dd, J=7.58, 2.53 Hz, 1H), 7.44 (t, J=1.77 Hz, 1H), 7.48-7.58 (m, 2H).

Step D: Preparation of tert-Butyl ((S)-3-(3-((2-Amino-2-oxoethyl)sulfonyl)phenoxy)-2-hydroxypropyl)((R)-8-(quinolin-3-ylsulfonyl)-1-oxa-8-azaspiro[4.5]decan-3-yl)carbamate To a solution of tert-butyl ((S)-3-(3-((2-amino-2-oxoethyl)sulfonyl)phenoxy)-2-hydroxypropyl)((R)-1-oxa-8-azaspiro[4.5]decan-3-yl)carbamate (15.93 g, 30.20 mmol) in CH$_2$Cl$_2$ (151 mL) under nitrogen were added DIEA (7.89 mL, 45.29 mmol) and quinoline-3-sulfonyl chloride (8.25 g, 36.23 mmol) portion wise at room temperature. The reaction was stirred for 1 h. The mixture was concentrated. The residue was purified by silica gel column chromatography to give the title compound (18.89 g, 87% yield) as a light yellow foam. LCMS m/z=719.4 [M+H]$^+$; $^1$H NMR (400 MHz, CDCl$_3$) δ ppm 1.47 (s, 9H), 1.56-1.73 (m, 1H), 1.75-1.84 (m, 2H), 1.85-1.94 (m, 2H), 2.05 (dd, J=13.14, 8.84 Hz, 1H), 2.75-2.90 (m, 2H), 3.30-3.42 (m, 1H), 3.42-3.49 (m, 1H), 3.56-3.76 (m, 3H), 3.77-3.84 (m, 1H), 3.88-3.96 (m, 1H), 3.97-4.04 (m, 3H), 4.07-4.15 (m, 1H), 4.58 (quin, J=7.52 Hz, 1H), 5.81 (bs, 1H), 6.75 (bs, 1H), 7.18 (ddd, J=7.83, 2.65, 1.39 Hz, 1H), 7.39 (t, J=2.27 Hz, 1H), 7.47-7.57 (m, 2H), 7.71 (ddd, J=8.15, 7.01, 1.26 Hz, 1H), 7.91 (ddd, J=8.53, 7.01, 1.39 Hz, 1H), 7.99 (d, J=8.34 Hz, 1H), 8.22 (d, J=8.34 Hz, 1H), 8.65 (d, J=1.77 Hz, 1H), 9.20 (d, J=2.27 Hz, 1H).

Step E: Preparation of 2-(3-((S)-2-Hydroxy-3-((R)-8-(quinolin-3-ylsulfonyl)-1-oxa-8-azaspiro[4.5]decan-3-ylamino)propoxy)phenylsulfonyl)acetamide (Compound 123)

tert-Butyl ((S)-3-(3-((2-amino-2-oxoethyl)sulfonyl)phenoxy)-2-hydroxypropyl)((R)-8-(quinolin-3-ylsulfonyl)-1- oxa-8-azaspiro[4.5]decan-3-yl)carbamate from the previous step (18.89 g, 26.28 mmol) was dissolved in dioxane (100 mL) to give a clear yellow solution at 0° C. 4N HCl (in dioxane, 35 mL, 140 mmol) was added slowly with vigorous stirring. A yellow lump was formed; the reaction flask was removed from the ice bath; then it was sonicated to break the lump then continued stirring at room temperature. A white solid was formed and collected to give the title compound (16.18 g, 87% yield). LCMS m/z=619.4 [M+H]$^+$; $^1$H NMR (400 MHz, DMSO-d$_6$) δ ppm 1.57-1.74 (m, 2H), 1.74-1.86 (m, 3H), 2.16 (dd, J=13.39, 8.08 Hz, 1H), 2.68-2.82 (m, 2H), 2.90-3.01 (m, 1H), 3.04-3.15 (m, 1H), 3.3-3.45 (m, 2H), 3.72-3.80 (m, 1H), 3.82-3.93 (m, 2H), 4.04 (d, J=4.80 Hz, 2H), 4.14-4.22 (m, 1H), 4.25 (s, 2H), 4.71 (bs, 2H), 7.26-7.33 (m, 2H), 7.39 (t, J=1.77 Hz, 1H), 7.46 (d, J=8.08 Hz, 1H), 7.55 (t, J=7.96 Hz, 1H), 7.60 (bs, 1H), 7.81 (td, J=7.58, 1.01 Hz, 1H), 8.01 (ddd, J=8.46, 6.95, 1.52 Hz, 1H), 8.18 (d, J=8.59 Hz, 1H), 8.29 (d, J=7.58 Hz, 1H), 8.94 (d, J=1.77 Hz, 1H), 9.00 (bs, 1H), 9.11-9.21 (m, 2H). $^{13}$C NMR (400 MHz, CD$_3$OD) δ ppm 35.09, 37.00, 41.12, 44.33, 44.76, 50.34, 59.77, 62.50, 66.61, 68.35, 71.57, 80.99, 115.36, 122.02, 122.29, 128.33, 129.58, 130.06, 130.84, 131.61, 131.82, 134.46, 139.42, 141.86, 148.02, 149.86, 160.26, 166.00.

Example 1.41: Preparation of (S)-1-((S)-8-(4'-(Aminomethyl)-4-ethoxybiphenyl-3-ylsulfonyl)-1-oxa-8-azaspiro[4.5]decan-3-ylamino)-3-(3-(1-(hydroxymethyl)cyclopropylsulfonyl)phenoxy) propan-2-ol (Compound 163). (Method F)

Step A: Preparation of (S)-Benzyl 3-(((S)-2-Hydroxy-3-(3-((1-(hydroxymethyl)cyclopropyl)sulfonyl)phenoxy)propyl)amino)-1-oxa-8-azaspiro[4.5]decane-8-carboxylate (S)-(1-((3-(oxiran-2-ylmethoxy)phenyl)sulfonyl)cyclopropyl)methanol (380 mg, 1.34 mmol) and (S)-benzyl 3-amino-1-oxa-8-azaspiro[4.5]decane-8-carboxylate (0.70 g, 2.41 mmol) were dissolved in EtOH (10 mL). The reaction was heated at 80° C. overnight. After cooling down to room temperature, the mixture was concentrated to give the title compound which was used directly in the next step without further purification. LCMS m/z=575.6 [M+H]$^+$.

Step B: Preparation of (S)-Benzyl 3-((tert-Butoxycarbonyl)((S)-2-hydroxy-3-(3-((1-(hydroxymethyl) cyclopropyl)sulfonyl)phenoxy)propyl)amino)-1-oxa-8-azaspiro[4.5]decane-8-carboxylate To a solution of (S)-benzyl 3-(((S)-2-hydroxy-3-(3-((1-(hydroxymethyl)cyclopropyl)sulfonyl)phenoxy)propyl) amino)-1-oxa-8-azaspiro[4.5]decane-8-carboxylate in CH$_2$Cl$_2$ (20 mL) were added DIEA (1.397 mL, 8.019 mmol) and (BOC)$_2$O (1.167 g, 5.346 mmol) at room temperature. Upon completion of the reaction monitored by TLC, the reaction was quenched with water. The water layer was extracted with CH$_2$Cl$_2$ (3×). The organic layers were combined and washed with brine, dried over Na$_2$SO$_4$, filtered, and concentrated. The residue was purified by silica gel column chromatography to give the title compound (720 mg, 72.1% yield). LCMS m/z=675.2 [M+H]$^+$; $^1$H NMR (400 M Hz, CDCl$_3$) δ ppm 1.04-1.08 (m, 2H), 1.44-1.47 (m, 1H), 1.49 (s, 9H), 1.61-1.64 (m, 2H), 1.65-1.73 (m, 4H), 1.77-1.84 (m, 1H), 2.08 (dd, J=8.85, 12.87 Hz, 1H), 3.30-3.40 (m, 2H), 3.44-3.51 (t, J=4.20 Hz, 1H), 3.66 (s, 2H), 3.68-3.75 (m, 2H), 3.81 (dd, J=5.63, 9.65 Hz, 1H), 3.91-4.06 (m, 3H), 4.09-4.15 (m, 1H), 4.62 (t, J=6.98 Hz, 1H), 5.12 (s, 2H), 7.18-7.21 (m, 1H), 7.28-7.36 (m, 5H), 7.41-7.42 (m, 1H), 7.46-7.52 (m, 2H).

Step C: Preparation of tert-Butyl ((S)-2-Hydroxy-3-(3-((1-(hydroxymethyl)cyclopropyl)sulfonyl)phenoxy)propyl)((S)-1-oxa-8-azaspiro[4.5]decan-3-yl) carbamate Palladium/C (0.142 g, 1.336 mmol) was taken in to 50 mL round bottom flask with a septa and the vessel was evacuated and backfilled with argon. To that was added MeOH (20 mL) followed by (S)-benzyl 3-((tert-butoxycarbonyl)((S)-2-hydroxy-3-(34(1-(hydroxymethyl)cyclopropyl)sulfonyl)phenoxy) propyl)amino)-1-oxa-8-azaspiro[4.5]decane-8-carboxylate (720 mg, 0.963 mmol) in MeOH (5 mL). The reaction was stirred at room temperature for 2 min, flushed with hydrogen and stirred at room temperature under hydrogen balloon for 5 h. The mixture was filtered through a pad of celite and washed with MeOH. The filtrate was concentrated to give the title compound (620 mg, 85.1% yield) as a white solid and used in the next step without further purification. LCMS m/z=541.4 [M+H]$^+$; $^1$H NMR (400 M Hz, CD$_3$OD) δ ppm 1.07-1.11 (m, 2H), 1.47 (s, 9H), 1.47-1.52 (m, 2H), 1.53-1.64 (m, 1H), 1.65-1.75 (m, 1H), 1.75-1.85 (m, 2H), 2.06-2.15 (m, 2H), 2.80-2.91 (m, 2H), 2.95-3.08 (m, 2H), 3.25-3.36 (m, 1H), 3.57 (dd, J=5.22, 15.09 Hz, 1H), 3.73 (s, 2H), 3.83 (dd, J=7.55, 9.29 Hz, 1H), 3.94-4.05 (m, 2H), 4.05-4.11 (m, 1H), 4.14-4.20 (m, 1H), 4.52 (quin, J=7.58 Hz, 1H), 7.29 (ddd, J=7.89, 2.59, 1.39 Hz, 1H), 7.45-7.56 (m, 3H).

Step D: Preparation of tert-Butyl ((S)-8-((5-Bromo-2-ethoxyphenyl)sulfonyl)-1-oxa-8-azaspiro[4.5]decan-3-yl)((S)-2-hydroxy-3-(3-((1-(hydroxymethyl) cyclopropyl)sulfonyl)phenoxy)propyl)carbamate To a solution of tert-butyl ((S)-2-hydroxy-3-(3-((1-(hydroxymethyl)cyclopropyl)sulfonyl) phenoxy)propyl)((S)-1-oxa-8-azaspiro[4.5]decan-3-yl)carbamate (380 mg, 0.703 mmol) in CH$_2$Cl$_2$ (3.0 mL) was added DIEA (0.122 mL, 0.703 mmol) followed by addition of 5-bromo-2-ethoxybenzene-1-sulfonyl chloride (0.211 g, 0.703 mmol) at 0° C. The reaction was stirred at room temperature overnight. The mixture was concentrated and the residue was purified by silica gel column chromatography to give the title compound (0.521 g, 86% yield) as a white solid. LCMS m/z=803.4 [M+H]$^+$; $^1$H NMR (400 M Hz, CDCl$_3$) δ ppm 1.05-1.08 (m, 2H), 1.45 (t, J=7.00 Hz, 3H), 1.49 (s, 9H), 1.58-1.65 (m, 3H), 1.71-1.86 (m, 5H), 2.07 (dd, J=8.62, 12.93 Hz, 1H), 3.04-3.14 (m, 2H), 3.46 (d, J=3.72 Hz, 2H), 3.53-3.58 (m, 2H), 3.66 (s, 2H), 3.77 (dd, J=6.03, 9.48 Hz, 1H), 3.91 (dd, J=6.90, 9.48 Hz, 1H), 3.96-4.04 (m, 2H), 4.09-4.15 (m, 3H), 4.55-4.62 (m, 1H), 6.86 (d, J=8.84 Hz, 1H), 7.18 (dt, J=2.31, 7.17 Hz, 1H), 7.40-7.41 (m, 1H), 7.46-7.52 (m, 2H), 7.56 (dd, J=2.54, 8.80 Hz, 1H), 8.00 (d, J=2.52 Hz, 1H).

Step E: Preparation of tert-Butyl ((S)-8-((4'-(((tert-Butoxycarbonyl)amino)methyl)-4-ethoxy-[1,1'-biphenyl]-3-yl)sulfonyl)-1-oxa-8-azaspiro[4.5]decan-3-yl)((S)-2-hydroxy-3-(3-((1-(hydroxymethyl) cyclopropyl)sulfonyl)phenoxy)propyl)carbamate To a solution of tert-butyl ((S)-8-((5-bromo-2-ethoxyphenyl)sulfonyl)-1-oxa-8-azaspiro[4.5]decan-3-yl)((S)-2-hydroxy-3-(3-((1-(hydroxymethyl)cyclopropyl)sulfonyl)phenoxy) propyl)carbamate (0.521 g, 0.604 mmol) in EtOH/

H₂O (4.5 mL, 2:1 ratio) were added potassium carbonate (97.14 mg, 0.703 mmol), Pd(dppf)₂ complex with DCM (0.578 g, 0.703 mmol) and (4-(((tert-butoxycarbonyl)amino)methyl)phenyl)boronic acid (0.176 g, 0.703 mmol). The reaction was heated to 80° C. for 1 h. After cooling down to room temperature, the reaction was diluted with EtOAc and washed with water (3×) and brine then dried over Na₂SO₄, filtered and concentrated. The residue was purified by silica gel column chromatography to give the title compound (440 mg, 61.5% yield) as a white solid. LCMS m/z=930.6 [M+H]⁺.

Step F: Preparation of (S)-1-((S)-8-(4'-(Aminomethyl)-4-ethoxybiphenyl-3-ylsulfonyl)-1-oxa-8-azaspiro[4.5]decan-3-ylamino)-3-(3-(1-(hydroxymethyl)cyclopropylsulfonyl)phenoxy)propan-2-ol (Compound 163)

tert-Butyl ((S)-8-((4'-(((tert-butoxycarbonyl)amino)methyl)-4-ethoxy-[1,1'-biphenyl]-3-yl)sulfonyl)-1-oxa-8-azaspiro[4.5]decan-3-yl)((S)-2-hydroxy-3-(3-((1-(hydroxymethyl)cyclopropyl) sulfonyl)phenoxy)propyl)carbamate (380 mg, 0.409 mmol) was dissolved in MeOH (1.0 mL) followed by addition of HCl (4N in dioxane, 1.5 mL, 6.128 mmol) at room temperature. The reaction was stirred at room temperature until the Boc-groups were cleaved (~30 min). The mixture was concentrated and the residue was purified by prep-HPLC. Combined fractions were concentrated and the residue was dissolved in water and neutralized with saturated aqueous NaHCO₃ (pH~8). The aqueous layer was extracted with 5% of MeOH/CH₂Cl₂ (3×). The organic layer was washed with brine, dried over Na₂SO₄, filtered and concentrated. The residue was dissolved in MeOH (1.0 mL) and added HCl (4N in dioxane, 1.532 mL, 6.128 mmol). The solution was stood for 1 hour, concentrated then lyophilized to give the title compound (263 mg, 80.2% yield) as a white solid. LCMS m/z=730.6 [M+H]⁺; ¹H NMR (400 M Hz, CD₃OD) δ ppm 1.07-1.10 (m, 2H), 1.48 (t, J=7.00 Hz, 3H), 1.49-1.51 (m, 2H), 1.61-1.68 (m, 1H), 1.79-1.92 (m, 4H), 2.36 (dd, J=8.09, 13.75 Hz, 1H), 3.08-3.21 (m, 3H), 3.32-3.36 (m, 1H), 3.53-3.61 (m, 2H), 3.72 (s, 2H), 3.94 (dd, J=4.05, 9.71 Hz, 1H), 4.01-4.08 (m, 1H), 4.08-4.14 (m, 3H), 4.16 (s, 2H), 4.26 (q, J=7.00 Hz, 2H), 4.24-4.31 (m, 1H), 7.30 (d, J=8.72 Hz, 1H), 7.28-7.32 (m, 1H), 7.47-7.52 (m, 3H), 7.55 (d, J=7.20 Hz, 2H), 7.69 (d, J=8.24 Hz, 2H), 7.87 (dd, J=2.32, 8.71 Hz, 1H), 8.08 (d, J=2.36 Hz, 1H).

Example 1.42: Preparation of 3-((R)-3-((S)-3-(3-(Cyclopropylsulfonyl)phenoxy)-2-hydroxy propylamino)-1-oxa-8-azaspiro[4.5]decan-8-ylsulfonyl)-1-ethyl-8-fluoroquinolin-4(1H)-one (Compound 333). (Method G)

Step A: Preparation of tert-Butyl ((S)-3-(3-(Cyclopropylsulfonyl)phenoxy)-2-hydroxypropyl)((R)-8-((8-fluoro-4-hydroxyquinolin-3-yl)sulfonyl)-1-oxa-8-azaspiro[4.5]decan-3-yl)carbamate To a solution of tert-butyl ((S)-3-(3-(cyclopropylsulfonyl)phenoxy)-2-hydroxypropyl) ((R)-1-oxa-8-azaspiro[4.5]decan-3-yl)carbamate (50 mg, 97.92 μmol) in CH₂Cl₂ (3.26 mL) under nitrogen were added DIEA (34.11 μL 0.20 mmol) and 8-fluoro-4-hydroxyquinoline-3-sulfonyl chloride (28.18 mg, 0.11 mmol). The reaction was stirred at room temperature until completion. It was then concentrated and purified by silica gel column chromatography to give the title compound (76 mg, 95% yield) as a white solid. LCMS m/z=736.4 [M+H]⁺; ¹H NMR (400 MHz, CD₃OD) δ ppm 1.01-1.09 (m, 2H), 1.18-1.23 (m, 2H), 1.32-1.36 (m, 1H), 1.45 (s, 9H), 1.57-1.65 (m, 1H), 1.69-1.76 (m, 1H), 1.79 (t, J=5.94 Hz, 2H), 1.86 (dd, J=12.63, 8.08 Hz, 1H), 2.07 (dd, J=12.63, 8.59 Hz, 1H), 2.66 (tt, J=7.83, 4.80 Hz, 1H), 3.21-3.28 (m, 3H), 3.42-3.56 (m, 3H), 3.85-3.92 (m, 1H), 3.94-4.08 (m, 3H), 4.11-4.19 (m, 1H), 4.52 (dd, J=13.89, 7.07 Hz, 1H), 7.27 (ddd, J=8.15, 2.59, 1.14 Hz, 1H), 7.42 (t, J=2.27 Hz, 1H), 7.43-7.53 (m, 3H), 7.60 (ddd, J=10.80, 7.89, 1.26 Hz, 1H), 8.08 (d, J=8.34 Hz, 1H), 8.47 (s, 1H).

Step B: Preparation of tert-Butyl ((S)-3-(3-(Cyclopropylsulfonyl)phenoxy)-2-hydroxypropyl)((R)-8-((1-ethyl-8-fluoro-4-oxo-1,4-dihydroquinolin-3-yl)sulfonyl)-1-oxa-8-azaspiro[4.5]decan-3-yl)carbamate To a solution of tert-butyl ((S)-3-(3-(cyclopropylsulfonyl)phenoxy)-2-hydroxypropyl)((R)-8-((8-fluoro-4-hydroxyquinolin-3-yl)sulfonyl)-1-oxa-8-azaspiro[4.5]decan-3-yl)carbamate (76 mg, 0.10 mmol) in DMF (1.5 mL) under nitrogen was added DIEA (44.98 μL, 0.258 mmol). The reaction was stirred at room temperature for 30 min. Then bromoethane (43.3 μL, 0.77 mmol) was added. The reaction was heated under microwave irradiation at 110° C. for 4 h. The mixture was purified by semi-prep HPLC to give the title compound (44 mg, 56% yield) as a white solid. LCMS m/z=764.4[M+H]⁺; ¹H NMR (400 MHz, CD₃OD) δ ppm 1.01-1.08 (m, 2H), 1.17-1.23 (m, 2H), 1.45 (s, 9H), 1.52 (t, J=6.57 Hz, 3H), 1.61 (ddd, J=13.39, 9.73, 3.92 Hz, 1H), 1.73 (ddd, J=13.52, 4.04, 3.92 Hz, 1H), 1.79 (t, J=5.81 Hz, 2H), 1.86 (dd, J=12.76, 8.21 Hz, 1H), 2.07 (dd, J=12.63, 8.59 Hz, 1H), 2.66 (tt, J=7.86, 4.77 Hz, 1H), 3.20-3.30 (m, 3H), 3.41-3.57 (m, 3H), 3.83-3.91 (m, 1H), 3.94-4.08 (m, 3H), 4.11-4.21 (m, 1H), 4.45-4.61 (m, 3H), 7.27 (ddd, J=8.08, 2.53, 1.01 Hz, 1H), 7.42 (t, J=2.53 Hz, 1H), 7.43-7.47 (m, 1H), 7.49-7.55 (m, 2H), 7.65 (ddd, J=14.91, 8.08, 1.52 Hz, 1H), 8.22 (dd, J=8.08, 1.01 Hz, 1H), 8.56 (s, 1H).

Step C: Preparation of 3-((R)-3-((S)-3-(3-(Cyclopropylsulfonyl)phenoxy)-2-hydroxy propylamino)-1-oxa-8-azaspiro[4.5]decan-8-ylsulfonyl)-1-ethyl-8-fluoroquinolin-4(1H)-one (Compound 333)

To a solution of tert-butyl ((S)-3-(3-(cyclopropylsulfonyl)phenoxy)-2-hydroxypropyl)((R)-8-((1-ethyl-8-fluoro-4-oxo-1,4-dihydroquinolin-3-yl)sulfonyl)-1-oxa-8-azaspiro[4.5]decan-3-yl)carbamate (33 mg, 44.85 μmol) in THF (2 mL) was added HCl (2N in dioxane, 1 mL, 2.0 mmol). The reaction was stirred at room temperature overnight. DCM (2 mL) was added to improve solubility and more of 2N HCl (in dioxane, 0.5 mL) was added. After the reaction was completed, the mixture was concentrated and the residue was purified by prep-HPLC to give the title compound (26.3 mg, 87% yield) which was then converted to its HCl salt. LCMS m/z=664.6 [M+H]⁺; ¹H NMR (400 MHz, CD₃OD) δ ppm 1.02-1.10 (m, 2H), 1.19-1.25 (m, 2H), 1.52 (t, J=6.57 Hz, 3H), 1.59-1.70 (m, 1H), 1.77-1.91 (m, 4H), 2.35 (dd, J=13.64, 8.08 Hz, 1H), 2.67 (tt, J=7.96, 4.80 Hz, 1H), 3.17-3.30 (m, 4H), 3.52-3.65 (m, 2H), 3.90-3.97 (m, 1H), 3.98-4.06 (m, 1H), 4.06-4.15 (m, 3H), 4.21-4.30 (m, 1H), 4.55 (qd, J=7.07, 3.03 Hz, 2H), 7.30 (ddd, J=7.89, 2.59, 1.39 Hz, 1H), 7.45 (t, J=2.27 Hz, 1H), 7.49-7.59 (m, 3H), 7.67 (ddd, J=14.91, 8.08, 1.52 Hz, 1H), 8.22 (dd, J=8.46, 1.14 Hz, 1H), 8.58 (s, 1H). ¹³C NMR (400 MHz, CD₃OD) δ ppm 6.42, 33.52, 35.72, 37.66, 41.14, 44.25, 44.68, 50.39, 59.86, 66.71, 68.37, 71.62, 81.65, 114.53, 119.17, 119.33, 120.17, 121.10, 121.38, 122.44, 122.48, 126.61, 126.68, 130.19, 130.57, 130.71, 132.02, 143.59, 145.09, 152.63, 155.12, 160.48, 174.52, 174.55.

Example 1.43: Preparation of (S)-1-(3-(1,1-Difluoro-2-hydroxyethylsulfonyl)phenoxy)-3-((R)-8-(quinolin-3-ylsulfonyl)-1-oxa-8-azaspiro[4.5]decan-3-ylamino)propan-2-ol (Compound 130)

Step A: Preparation of tert-Butyl ((S)-3-(3-((1,1-Difluoro-2-hydroxyethyl)sulfonyl)phenoxy)-2-hydroxypropyl)((R)-8-(quinolin-3-ylsulfonyl)-1-oxa-8-azaspiro[4.5]decan-3-yl)carbamate (S)-2,2-difluoro-2-((3-(oxiran-2-ylmethoxy)phenyl)sulfonyl)ethanol (20 mg, 67.96 μmol) and (R)-8-(quinolin-3-ylsulfonyl)-1-oxa-8-azaspiro[4.5]decan-3-amine (37.78 mg, 0.109 mmol) were dissolved in EtOH (0.5 mL). The reaction was heated at 75° C. overnight. The mixture was concentrated and the residue was purified by flash chromatography to give the title compound as a white solid.

Step B: Preparation of (S)-1-(3-(1,1-Difluoro-2-hydroxyethylsulfonyl)phenoxy)-3-((R)-8-(quinolin-3-ylsulfonyl)-1-oxa-8-azaspiro[4.5]decan-3-ylamino)propan-2-ol (Compound 130)

tert-Butyl ((S)-3-(3-((1,1-difluoro-2-hydroxyethyl)sulfonyl)phenoxy)-2-hydroxypropyl)((R)-8-(quinolin-3-ylsulfonyl)-1-oxa-8-azaspiro[4.5]decan-3-yl)carbamate was dissolved in HCl (4N in Dioxane, 0.34 mL, 1.36 mmol) and stood for 2 h. The mixture was concentrated to give the title compound (25.5 mg, 50.5% yield) as a white solid. LCMS m/z=642.4 [M+H]$^+$; $^1$H NMR (400 M Hz, CD$_3$OD) δ ppm 1.68-1.75 (m, 1H), 1.83-1.99 (m, 4H), 2.34 (dd, J=7.24, 13.45 Hz, 1H), 2.89-3.00 (m, 2H), 3.13-3.18 (m, 1H), 3.25-3.33 (m, 1H), 3.57-3.60 (m, 2H), 3.61-3.68 (m, 5H), 3.72-3.75 (m, 2H), 3.86-3.91 (m, 1H), 3.99-4.05 (m, 2H), 4.09-4.12 (m, 1H), 4.14 (t, J=13.97 Hz, 2H), 4.24-4.29 (m, 1H), 7.42-7.45 (m, 1H), 7.51 (bs, 1H), 7.59 (d, J=7.76 Hz, 1H), 7.63 (t, J=7.76 Hz, 1H), 7.94 (t, J=7.50 Hz, 1H), 8.16 (t, J=7.54 Hz, 1H), 8.27 (d, J=8.52 Hz, 1H), 8.35 (d, J=8.20 Hz, 1H), 9.21 (bs, 1H), 9.36 (bs, 1H).

Example 1.44: Preparation of (S)-1-(3-(Methylsulfonyl)phenoxy)-3-((R)-8-(naphthalen-2-ylsulfonyl)-1-oxa-8-azaspiro[4.5]decan-3-ylamino)propan-2-ol (Compound 3)

(S)-2-((3-(methylsulfonyl)phenoxy)methyl)oxirane (8 mg, 35.05 μmol) and (R)-8-(naphthalen-2-ylsulfonyl)-1-oxa-8-azaspiro[4.5]decan-3-amine (24.28 mg, 70.09 μmol) were dissolved in EtOH (1.5 mL). The reaction was heated at 60° C. overnight. After the reaction was completed and cooled down to room temperature, it was concentrated and purified by mass direct prep-HPLC to give the title compound (15.1 mg, 62% yield). LCMS m/z=575.4 [M+H]$^+$; $^1$H NMR (400 MHz, CD$_3$OD) δ ppm 1.60-1.71 (m, 1H), 1.76-1.95 (m, 4H), 2.29 (dd, J=13.77, 8.21 Hz, 1H), 2.73-2.91 (m, 2H), 3.10 (s, 3H), 3.11-3.16 (m, 1H), 3.25 (dd, J=12.88, 3.03 Hz, 1H), 3.43-3.55 (m, 2H), 3.80-3.88 (m, 1H), 3.92-4.02 (m, 2H), 4.04-4.13 (m, 2H), 4.17-4.27 (m, 1H), 7.25-7.33 (m, 1H), 7.49 (d, J=1.52 Hz, 1H), 7.55 (d, J=5.56 Hz, 2H), 7.68 (qd, J=8.25, 8.08 Hz, 2H), 7.77 (dd, J=8.72, 1.89 Hz, 1H), 8.01 (d, J=8.08 Hz, 1H), 8.06-8.12 (m, 2H), 8.38 (d, J=1.26 Hz, 1H).

Example 1.45: Preparation of (S)-1-(3-(Methylsulfonyl)phenoxy)-3-((S)-8-(naphthalen-2-ylsulfonyl)-1-oxa-8-azaspiro[4.5]decan-3-ylamino)propan-2-ol (Compound 4)

(S)-2-((3-(methylsulfonyl)phenoxy)methyl)oxirane (50 mg, 0.22 mmol) and (S)-8-(naphthalen-2-ylsulfonyl)-1-oxa-8-azaspiro[4.5]decan-3-amine hydrochloride (0.17 g, 0.44 mmol) were dissolved in EtOH (3 mL) followed by addition of DIEA (83.94 μL, 0.482 mmol). The reaction was heated at 60° C. overnight. After the reaction was completed, it was cooled down to room temperature, concentrated, and then purified by mass direct prep-HPLC. The TFA salt obtained was lyophilized and re-dissolved in MeOH. The solution was passed through a SCX cartridge and washed with 2N NH$_3$ in MeOH. The filtrate was added HCl (4N in dioxane, 400 μL) and concentrated to give the title compound (27 mg, 20% yield) as a white solid. LCMS m/z=575.4 [M+H]$^+$; $^1$H NMR (400 MHz, CD$_3$OD) δ ppm 1.61-1.71 (m, 1H), 1.76-1.96 (m, 4H), 2.29 (dd, J=13.64, 8.34 Hz, 1H), 2.73-2.89 (m, 2H), 3.05-3.15 (m, 4H), 3.27 (dd, J=12.88, 3.03 Hz, 1H), 3.44-3.56 (m, 2H), 3.78-3.86 (m, 1H), 3.92-4.02 (m, 2H), 4.04-4.13 (m, 2H), 4.18-4.26 (m, 1H), 7.25-7.32 (m, 1H), 7.49 (d, J=1.52 Hz, 1H), 7.54-7.58 (m, 2H), 7.63-7.74 (m, 2H), 7.77 (dd, J=8.72, 1.89 Hz, 1H), 8.01 (d, J=8.08 Hz, 1H), 8.05-8.12 (m, 2H), 8.38 (d, J=1.52 Hz, 1H).

Example 1.46: Preparation of (2S)-1-(8-(4'-((Methylamino)methyl)biphenyl-3-ylsulfonyl)-1-oxa-8-azaspiro[4.5]decan-3-ylamino)-3-(3-(methylsulfonyl)phenoxy)propan-2-ol (Compound 78). (Method H)

Step A: Preparation of tert-Butyl ((S)-2-Hydroxy-3-(3-(methylsulfonyl)phenoxy)propyl)(1-oxa-8-azaspiro[4.5]decan-3-yl)carbamate From (S)-2-((3-(methylsulfonyl)phenoxy)methyl)oxirane and benzyl 3-amino-1-oxa-8-azaspiro[4.5]decane-8-carboxylate, the title compound was prepared using a similar method to the one described in Method A, Step A, B, and C.

Step B: Preparation of tert-Butyl (8-((3-Bromophenyl)sulfonyl)-1-oxa-8-azaspiro[4.5]decan-3-yl)((S)-2-hydroxy-3-(3-(methylsulfonyl)phenoxy)propyl)carbamate To a solution of tert-butyl ((S)-2-hydroxy-3-(3-(methylsulfonyl)phenoxy)propyl)(1-oxa-8-azaspiro[4.5]decan-3-yl)carbamate (243 mg, 0.50 mmol) in THF (7 mL) under nitrogen was added DIEA (0.18 mL, 1.00 mmol) and 3-bromobenzene-1-sulfonyl chloride (0.17 g, 0.65 mmol). The reaction was stirred at room temperature overnight. After the reaction was completed, the mixture was concentrated. The residue was purified by silica gel column chromatography to give the title compound (313 mg, 89% yield) as a white foam. LCMS m/z=705.3 [M+H]$^+$; $^1$H NMR (400 MHz, CD$_3$OD) δ ppm 1.44 (s, 9H), 1.57-1.67 (m, 1H), 1.71-1.79 (m, 1H), 1.79-1.87 (m, 2H), 1.98-2.05 (m, 1H), 2.77 (ddd, J=15.03, 11.87, 11.75 Hz, 2H), 3.11 (s, 3H), 3.21-3.27 (m, 1H), 3.34-3.41 (m, 3H), 3.53 (dd, J=14.65, 4.55 Hz, 1H), 3.80-3.90 (m, 1H), 3.93-4.10 (m, 3H), 4.11-4.18 (m, 1H), 4.43-4.51 (m, 1H), 7.28 (dt, J=5.87, 3.00 Hz, 1H), 7.48 (d, J=1.52 Hz, 1H), 7.51-7.58 (m, 3H), 7.75 (d, J=7.83 Hz, 1H), 7.84 (d, J=8.08 Hz, 1H), 7.90 (t, J=1.77 Hz, 1H).

Step C: Preparation of tert-Butyl ((S)-2-Hydroxy-3-(3-(methylsulfonyl)phenoxy)propyl)(8-((4'-(hydroxymethyl)-[1,1'-biphenyl]-3-yl)sulfonyl)-1-oxa-8-azaspiro[4.5]decan-3-yl)carbamate To a 20 mL microwave vial containing a magnetic stir bar were added Pd(dppf)$_2$, DCM (0.54 g, 0.65 mmol) and (4-(hydroxymethyl)phenyl)boronic acid (59.34 mg, 0.39 mmol). A solution of tert-butyl (84(3-bromophenyl)sulfonyl)-1-oxa-8-azaspiro[4.5]decan-3-yl)((S)-2-hydroxy-3-(3-(methylsulfonyl)phenoxy)propyl)carbamate (229 mg, 0.33 mmol) and a solution of sodium carbonate (0.358 mL, 0.716 mmol) were then added to the reaction vial. The resulting mixture was heated at 90° C. overnight. After the reaction was completed, it was diluted in EtOAc then washed with water and brine. The organic layer was dried over Mg$_2$SO$_4$, filtered and concentrated. The residue was purified by silica gel column chromatography to give the title compound (209 mg, 87% yield). LCMS m/z=731.5 [M+H]$^+$; $^1$H NMR (400 MHz, CD$_3$OD) δ ppm 1.43 (s, 9H), 1.56-1.69 (m, 1H), 1.70-1.79 (m, 1H), 1.79-1.89 (m, 2H), 1.95-2.10 (m, 2H), 2.74-2.85 (m, 2H), 3.09 (s, 3H), 3.16-3.27 (m, 1H), 3.35-3.44 (m, 2H), 3.46-3.55 (m, 1H), 3.70-4.07 (m, 4H), 4.09-4.18 (m, 1H), 4.42-4.51 (m, 1H), 4.67 (s, 2H), 7.21-7.31 (m, 1H), 7.45-7.54 (m, 5H), 7.63-7.72 (m, 3H), 7.72-7.77 (m, 1H), 7.92-8.00 (m, 3H).

Step D: Preparation of tert-Butyl ((S)-2-Hydroxy-3-(3-(methylsulfonyl)phenoxy)propyl)(8-((4'-((methylamino)methyl)-[1,1'-biphenyl]-3-yl)sulfonyl)-1-oxa-8-azaspiro[4.5]decan-3-yl)carbamate To a solution of tert-butyl ((S)-2-hydroxy-3-(3-(methylsulfonyl)phenoxy)propyl)(8-((4'-(hydroxymethyl)-[1,1'-biphenyl]-3-yl)sulfonyl)-1-oxa-8-azaspiro[4.5]decan-3-yl)carbamate (10 mg, 13.68 µmol) in dioxane (1 mL) was added methanesulfonyl chloride (9.53 µL, 123.15 µmol). The reaction was stirred at room temperature overnight. Next day, methanamine (637.4 µg, 20.52 µmol) was added and the reaction was stirred overnight. After the reaction was completed, it was quenched with water and purified via mass directed prep-HPLC. The appropriated fractions were lyophilized to give the title compound as a white solid. LCMS m/z=744.4 [M+H]$^+$.

Step E: Preparation of (2S)-1-(8-(4'-((Methylamino)methyl)biphenyl-3-ylsulfonyl)-1-oxa-8-azaspiro[4.5]decan-3-ylamino)-3-(3-(methylsulfonyl)phenoxy)propan-2-ol (Compound 78)

The TFA salt of tert-butyl ((S)-2-hydroxy-3-(3-(methylsulfonyl)phenoxy)propyl)(8-((4'-((methylamino)methyl)-[1,1'-biphenyl]-3-yl)sulfonyl)-1-oxa-8-azaspiro[4.5]decan-3-yl)carbamate was dissolved in ACN (2 mL) and added HCl (4N in dioxane, 51.31 µL, 0.21 mmol). The reaction was stirred at room temperature for 3 h. The mixture was then concentrated and purified by prep-HPLC to give the title compound (4.8 mg, 46% yield). LCMS m/z=644.4 [M+H]$^+$; $^1$H NMR (400 MHz, CD$_3$OD) δ ppm 1.68 (m, 1H), 1.79-1.97 (m, 4H), 2.31 (ddd, J=13.77, 8.21, 2.02 Hz, 1H), 2.69-2.85 (m, 5H), 3.11 (s, 3H), 3.12-3.19 (m, 1H), 3.25-3.29 (m, 1H), 3.42-3.55 (m, 2H), 3.83-3.93 (m, 1H), 3.95-4.07 (m, 2H), 4.07-4.15 (m, 2H), 4.21-4.30 (m, 3H,) 7.26-7.33 (m, 1H), 7.49 (t, J=1.25 Hz, 1H), 7.56 (d, J=5.05 Hz, 2H), 7.62 (d, J=8.34 Hz, 2H), 7.74 (t, J=8.34 Hz, 1H), 7.76-7.83 (m, 3H), 7.94-8.01 (m, 2H).

Example 1.47: Preparation of (S)-1-((R)-8-(1H-Pyrrolo[3,2-b]pyridin-6-ylsulfonyl)-1-oxa-8-azaspiro[4.5]decan-3-ylamino)-3-(3-(methylsulfonyl)phenoxy)propan-2-ol (Compound 320)

Step A: Preparation of tert-Butyl ((R)-8-((1H-Pyrrolo[3,2-b]pyridin-6-yl)sulfonyl)-1-oxa-8-azaspiro[4.5]decan-3-yl)((S)-2-hydroxy-3-(3-(methylsulfonyl)phenoxy)propyl)carbamate To a solution of tert-butyl ((S)-2-hydroxy-3-(3-(methylsulfonyl)phenoxy)propyl)((R)-1-oxa-8-azaspiro[4.5]decan-3-yl)carbamate (30 mg, 61.91 µmol) in CH$_2$Cl$_2$ (5 mL) was added DIEA (12.94 µL, 74.29 µmol) and 1H-pyrrolo[3,2-b]pyridine-6-sulfonyl chloride (16.09 mg, 74.29 µmol). The reaction was stirred at room temperature under nitrogen. After the reaction was completed, the mixture was concentrated. The residue was purified by silica gel column chromatography to give the title compound (14 mg, 34% yield). LCMS m/z=665.4 [M+H]$^+$.

Step B: Preparation of (S)-1-((R)-8-(1H-Pyrrolo[3,2-b]pyridin-6-ylsulfonyl)-1-oxa-8-azaspiro[4.5]decan-3-ylamino)-3-(3-(methylsulfonyl)phenoxy)propan-2-ol (Compound 320)

tert-Butyl ((R)-8-((1H-pyrrolo[3,2-b]pyridin-6-yl)sulfonyl)-1-oxa-8-azaspiro[4.5]decan-3-yl)((S)-2-hydroxy-3-(3-(methylsulfonyl)phenoxy)propyl)carbamate (14 mg, 21.1 µmol) was dissolved in DCM (3 mL) following by addition of HCl (4N in dioxane, 0.2 mL). The reaction was stirred at room temperature until completion. The mixture was concentrated to give a white solid which was then triturated with MeCN to give the title compound (11.2 mg, 28% yield) as a solid. LCMS m/z=565.4 [M+H]$^+$; $^1$H NMR (400 MHz, DMSO-d$_6$) δ ppm 1.56-1.87 (m, 5H), 2.15 (dd, J=13.64, 8.08 Hz, 1H), 2.57-2.73 (m, 2H), 2.89-3.01 (m, 1H), 3.07-3.15 (m, 1H), 3.21 (s, 3H), 3.25-3.37 (m, 2H), 3.64-3.98 (m, 4H), 4.06 (d, J=5.05 Hz, 2H), 4.13-4.20 (m, 1H), 6.78 (bs, 1H), 7.29 (ddd, J=8.08, 2.53, 1.01 Hz, 1H), 7.43 (d, J=1.77 Hz, 1H), 7.48-7.54 (m, 1H), 7.58 (t, J=7.96 Hz, 1H), 8.06 (d, J=2.27 Hz, 1H), 8.20 (bs, 1H), 8.68 (s, 1H), 8.95 (bs, 1H), 9.08 (bs, 1H), 12.05 (bs, 1H).

Example 1.48: Preparation of (S)-1-((R)-8-(1H-Pyrrolo[3,2-b]pyridin-6-ylsulfonyl)-1-oxa-8-azaspiro[4.5]decan-3-ylamino)-3-(3-(isopropylsulfonyl)phenoxy)propan-2-ol (Compound 321). (Method E3)

Step A: Preparation of tert-butyl ((R)-8-((1H-Pyrrolo[3,2-b]pyridin-6-yl)sulfonyl)-1-oxa-8-azaspiro[4.5]decan-3-yl)((S)-2-hydroxy-3-(3-(isopropylsulfonyl)phenoxy)propyl)carbamate From (S)-2-((3-(isopropylsulfonyl)phenoxy)methyl)oxirane, (R)-benzyl 3-amino-1-oxa-8-azaspiro[4.5]decane-8-carboxylate and tert-butyl 6-(chlorosulfonyl)-1H-pyrrolo[3,2-b]pyridine-1-carboxylate, the title compound was prepared using a similar method to the one described in Method E, Step A, B and C. LCMS m/z=793.6 [M+H]+.

Step B: Preparation of (S)-1-((R)-8-(1H-Pyrrolo[3,2-b]pyridin-6-ylsulfonyl)-1-oxa-8-azaspiro[4.5]decan-3-ylamino)-3-(3-(isopropylsulfonyl)phenoxy)propan-2-ol (Compound 321)

From tert-butyl ((R)-8-((1H-pyrrolo[3,2-b]pyridin-6-yl)sulfonyl)-1-oxa-8-azaspiro[4.5]decan-3-yl)((S)-2-hydroxy-3-(isopropylsulfonyl)phenoxy)propyl)carbamate, the title compound was prepared using a similar method to the one described in Method G, Step C. LCMS m/z=593.4 [M+H]+; $^1$H NMR (400 MHz, CD$_3$OD) δ ppm 1.24 (d, J=6.82 Hz, 6H), 1.65-1.78 (m, 1H), 1.83-1.99 (m, 4H), 2.36 (dd, J=13.64, 7.83 Hz, 1H), 2.83-2.99 (m, 2H), 3.16 (dd, J=12.63, 9.85 Hz, 1H), 3.27 (d, J=3.03 Hz, 1H), 3.32-3.37 (m, 1H), 3.55-3.64 (m, 2H), 3.64-3.76 (m, 1H), 3.86-3.95 (m, 1H), 3.99-4.07 (m, 2H), 4.07-4.15 (m, 2H), 4.23-4.32 (m, 1H), 7.04 (d, J=3.23 Hz, 1H), 7.33 (dd, J=8.34, 1.77 Hz, 1H), 7.42 (t, J=1.52 Hz, 1H), 7.48 (d, J=7.83 Hz, 1H), 7.57 (t, J=7.96 Hz, 1H), 8.42 (d, J=3.28 Hz, 1H), 8.86 (s, 1H), 9.05 (d, J=1.26 Hz, 1H).

Example 1.49: Preparation of 1-Ethyl-8-fluoro-3-((R)-3-((S)-2-hydroxy-3-(3-(methylsulfonyl)phenoxy)propylamino)-1-oxa-8-azaspiro[4.5]decan-8-ylsulfonyl)quinolin-4(1H)-one (Compound 322)

Step A: Preparation of tert-Butyl ((R)-8-((8-Fluoro-4-hydroxyquinolin-3-yl)sulfonyl)-1-oxa-8-azaspiro[4.5]decan-3-yl)((S)-2-hydroxy-3-(3-(methylsulfonyl)phenoxy)propyl)carbamate From tert-butyl ((S)-2-hydroxy-3-(3-(methylsulfonyl)phenoxy)propyl)((R)-1-oxa-8-azaspiro[4.5]decan-3-yl)carbamate (40.0 mg, 82.54 μmol) and 8-fluoro-4-hydroxyquinoline-3-sulfonyl chloride, the title compound was prepared using a similar method to the one described in Method G, Step A. LCMS m/z=710.6 [M+H]+; $^1$H NMR (400 MHz, CD$_3$OD) δ ppm 1.45 (s, 9H), 1.61 (ddd, J=13.39, 5.18, 4.93 Hz, 1H), 1.69-1.77 (m, 1H), 1.80 (t, J=8 Hz, 2H), 1.86 (dd, J=12.63, 8.08 Hz, 1H), 2.08 (dd, J=12.76, 8.46 Hz, 1H), 3.09 (s, 3H), 3.22-3.29 (m, 3H), 3.42-3.56 (m, 4H), 3.85-3.92 (m, 1H), 3.96-4.08 (m, 3H), 4.12-4.19 (m, 1H), 4.47-4.57 (m, 1H), 7.28 (dt, J=7.39, 2.24 Hz, 1H), 7.43-7.55 (m, 4H), 7.61 (ddd, J=10.80, 8.02, 1.14 Hz, 1H), 8.08 (d, J=8.34 Hz, 1H), 8.47 (s, 1H).

Step B: Preparation of 1-Ethyl-8-fluoro-3-((R)-3-((S)-2-hydroxy-3-(3-(methylsulfonyl)phenoxy)propylamino)-1-oxa-8-azaspiro[4.5]decan-8-ylsulfonyl)quinolin-4(1H)-one (Compound 322)

To a solution of tert-butyl ((R)-8-((8-fluoro-4-hydroxyquinolin-3-yl)sulfonyl)-1-oxa-8-azaspiro[4.5]decan-3-yl)((S)-2-hydroxy-3-(3-(methylsulfonyl)phenoxy)propyl)carbamate (48 mg, 67.62 μmol) in DMF (2 mL) was added iodoethane (81.13 μL, 1.01 mmol) and DIEA (0.18 mL, 1.01 mmol). The reaction was heated at 120° C. for 2.5 h. After the reaction was completed, it was diluted in EtOAc then washed with water (2×) and brine. The organic layer was dried over Na$_2$SO$_4$, filtered and concentrated. The residue was purified by silica gel column chromatography to give tert-butyl ((R)-8-((1-ethyl-8-fluoro-4-oxo-1,4-dihydroquinolin-3-yl)sulfonyl)-1-oxa-8-azaspiro[4.5]decan-3-yl)((S)-2-hydroxy-3-(3-(methylsulfonyl)phenoxy)propyl)carbamate. LCMS m/z=738.6 [M+H]+.

tert-Butyl ((R)-8-((1-ethyl-8-fluoro-4-oxo-1,4-dihydroquinolin-3-yl)sulfonyl)-1-oxa-8-azaspiro[4.5]decan-3-yl)((S)-2-hydroxy-3-(3-(methylsulfonyl)phenoxy)propyl)carbamate from the previous step was dissolved in EtOAc (2 mL) followed by addition of HCl (4N in dioxane, 0.4 mL). The reaction was stirred at room temperature until completion. The mixture was concentrated and the residue was purified by HPLC to give the FTA salt of the title compound. The TFA salt was lyophilized then neutralized. The obtained material was dissolved in EtOAc (2 mL) and treated with HCl (4N in dioxane, 0.1 mL). The mixture was concentrated to give HCl salt of the title compound (36.2 mg, 75% yield) as a white solid. LCMS m/z=638.6 [M+H]+; $^1$H NMR (400 MHz, DMSO-d$_6$) δ ppm 1.40 (t, J=6.69 Hz, 3H), 1.52-1.61 (m, 1H), 1.62-1.71 (m, 1H), 1.72-1.83 (m, 3H), 2.20 (dd, J=13.26, 7.96 Hz, 1H), 2.94-3.05 (m, 1H), 3.06-3.20 (m, 3H), 3.22 (s, 3H), 3.33-3.43 (m, 2H), 3.77-3.86 (m, 1H), 3.87-3.99 (m, 2H), 4.07 (d, J=5.05 Hz, 2H), 4.13-4.22 (m, 1H), 4.44-4.54 (m, 1H), 5.91 (d, J=4.80 Hz, 1H), 7.30 (dd, J=8.08, 1.77 Hz, 1H), 7.44 (t, J=2.02 Hz, 1H), 7.49-7.56 (m, 2H), 7.59 (t, J=7.96 Hz, 1H), 7.76 (ddd, J=15.03, 7.96, 1.52 Hz, 1H), 8.11 (d, J=7.83 Hz, 1H), 8.56 (s, 1H), 8.91 (bs, 1H), 8.98 (bs, 1H).

Example 1.50: Preparation of 3-((R)-3-((S)-3-(3-(cyclopropylsulfonyl)phenoxy)-2-hydroxypropylamino)-1-oxa-8-azaspiro[4.5]decan-8-ylsulfonyl)quinolin-4(1H)-one (Compound 326) as the HCl Salt Step A: Preparation of tert-Butyl ((S)-3-(3-(Cyclopropylsulfonyl)phenoxy)-2-hydroxypropyl)((R)-8-((4-hydroxyquinolin-3-yl)sulfonyl)-1-oxa-8-azaspiro[4.5]decan-3-yl)carbamate From tert-butyl ((S)-3-(3-(cyclopropylsulfonyl)phenoxy)-2-hydroxypropyl)((R)-1-oxa-8-azaspiro[4.5]decan-3-yl)carbamate and 4-hydroxyquinoline-3-sulfonyl chloride, the title compound was prepared using a similar method to the one described in Method G, Step A. LCMS m/z=718.6 [M+H]+; $^1$H NMR (400 MHz, CD$_3$OD) δ ppm 1.00-1.09 (m, 2H), 1.18-1.23 (m, 2H), 1.45 (s, 9H), 1.56-1.66 (m, 1H), 1.68-1.76 (m, 1H), 1.80 (t, J=6.82 Hz, 2H), 1.86 (dd, J=12.88, 8.34 Hz, 1H), 2.07 (dd, J=12.76, 8.46 Hz, 1H), 2.62-2.71 (m, 1H), 3.20-3.28 (m, 3H), 3.38-3.57 (m, 4H), 3.84-3.92 (m, 1H), 3.95-4.06 (m, 3H), 4.11-4.19 (m, 1H), 4.44-4.56 (m, 1H), 7.26 (dt, J=8.08, 1.26 Hz, 1H), 7.39-7.46 (m, 2H), 7.47-7.54 (m, 2H), 7.62 (d, J=7.83 Hz, 1H), 7.76-7.82 (m, 1H), 8.29 (dd, J=8.08, 1.01 Hz, 1H), 8.51 (s, 1H).

Step B: Preparation of 3-((R)-3-((S)-3-(3-(cyclopropylsulfonyl)phenoxy)-2-hydroxypropylamino)-1-oxa-8-azaspiro[4.5]decan-8-ylsulfonyl)quinolin-4(1H)-one (Compound 326) as the HCl Salt To a solution of tert-butyl ((S)-3-(3-(cyclopropylsulfonyl)phenoxy)-2-hydroxypropyl)((R)-8-((4-hydroxyquinolin-3-yl)sulfonyl)-1-oxa-8-azaspiro[4.5]decan-3-yl)carbamate (17 mg, 23.68 μmol) in THF/DCM (1:1 ratio, 4 mL) was added HCl (4N in dioxane, 1 mL, 1.0 mmol). The reaction was stirred at room temperature until completion. The mixture was concentrated and the residue was purified by prep-HPLC to give the TFA salt of the title compound. The TFA salt was lyophilized and converted to the HCl salt of the title compound (12.1 mg, 78.1% yield). LCMS m/z=618.4 [M+H]+; 1H NMR (400 MHz, CD3OD) δ ppm 1.02-1.10 (m, 2H), 1.19-1.25 (m, 2H), 1.31-1.34 (m, 1H), 1.56-1.72 (m, 1H), 1.77-1.91 (m, 4H), 2.33-2.39 (m, 1H), 2.62-2.71 (m, 1H), 3.14-3.29 (m, 3H), 3.50-3.63 (m, 2H), 3.90-3.97 (m, 1H), 3.98-4.06 (m, 1H), 4.07-4.15 (m, 3H), 4.22-4.29 (m, 1H), 7.30 (ddd, J=7.89, 2.59, 1.39 Hz, 1H), 7.45 (t, J=2.27 Hz, 1H), 7.49-7.59 (m, 3H), 7.63 (d, J=8.08 Hz, 1H), 7.80 (ddd, J=8.40, 7.01, 1.52 Hz, 1H), 8.29 (dd, J=8.08, 1.01 Hz, 1H), 8.53 (s, 1H).

Example 1.51: Preparation of 3-((R)-3-((S)-3-(3-(Cyclopropylsulfonyl)phenoxy)-2-hydroxypropylamino)-1-oxa-8-azaspiro[4.5]decan-8-ylsulfonyl)-8-methylquinolin-4-ol. (Compound 327)

Step A: Preparation of tert-Butyl ((S)-3-(3-(Cyclopropylsulfonyl)phenoxy)-2-hydroxypropyl)((R)-8-((4-hydroxy-8-methylquinolin-3-yl)sulfonyl)-1-oxa-8-azaspiro[4.5]decan-3-yl)carbamate From tert-butyl ((S)-3-(3-(cyclopropylsulfonyl)phenoxy)-2-hydroxypropyl)((R)-1-oxa-8-azaspiro[4.5]decan-3-yl)carbamate and 4-hydroxy-8-methylquinoline-3-sulfonyl chloride, the title compound was prepared using a similar method to the one described in Method G, Step A. LCMS m/z=732.6 [M+H]+; 1H NMR (400 MHz, CDCl3) δ ppm 1.01-1.10 (m, 2H), 1.30-1.37 (m, 2H), 1.47 (s, 9H), 1.66 (dd, J=11.24, 4.17 Hz, 1H), 1.75-1.92 (m, 5H), 2.04 (dd, J=13.01, 8.72 Hz, 1H), 2.47 (tt, J=7.93, 4.71 Hz, 1H), 2.63 (s, 3H), 2.65-2.78 (m, 2H), 3.36 (bs, 1H), 3.43-3.55 (m, 3H), 3.73-3.86 (m, 2H), 3.92-4.03 (m, 2H), 4.09-4.18 (m, 1H), 4.51-4.64 (m, 1H), 6.48 (d, J=7.33 Hz, 1H), 7.14 (dt, J=6.88, 2.49 Hz, 1H), 7.38 (d, J=1.52 Hz, 1H), 7.46-7.51 (m, 2H), 7.82 (d, J=1.26 Hz, 1H), 7.86 (d, J=7.58 Hz, 1H), 8.63 (d, J=1.77 Hz, 1H), 9.63 (bs, 1H).

Step B: Preparation of 3-((R)-3-((S)-3-(3-(Cyclopropylsulfonyl)phenoxy)-2-hydroxypropylamino)-1-oxa-8-azaspiro[4.5]decan-8-ylsulfonyl)-8-methylquinolin-4-ol. (Compound 327)

From tert-butyl ((S)-3-(3-(cyclopropylsulfonyl)phenoxy)-2-hydroxypropyl)((R)-8-((4-hydroxy-8-methylquinolin-3-yl)sulfonyl)-1-oxa-8-azaspiro[4.5]decan-3-yl)carbamate, the title compound was prepared using a similar method to the one described in Method G, Step C. LCMS m/z=632.6 [M+H]+; 1H NMR (400 MHz, CD3OD) δ ppm 1.02-1.10 (m, 2H), 1.18-1.25 (m, 2H), 1.64-1.75 (m, 1H), 1.80-1.98 (m, 4H), 2.33 (dd, J=13.77, 7.96 Hz, 1H), 2.67 (tt, J=7.96, 4.80 Hz, 1H), 2.71-2.87 (m, 5H), 3.15 (dd, J=12.76, 9.73 Hz, 1H), 3.24-3.30 (m, 1H), 3.49-3.61 (m, 2H), 3.82-3.91 (m, 1H), 3.96-4.04 (m, 2H), 4.06-4.14 (m, 2H), 4.21-4.29 (m, 1H), 6.99 (d, J=7.07 Hz, 1H), 7.29 (ddd, J=8.02, 2.46, 1.39 Hz, 1H), 7.44 (d, J=2.27 Hz, 1H), 7.48-7.59 (m, 2H), 8.09 (d, J=1.01 Hz, 1H), 8.55 (d, J=6.82 Hz, 1H), 8.61 (d, J=1.52 Hz, 1H).

Example 1.52: Preparation of 3-((R)-3-((S)-3-(3-(Cyclopropylsulfonyl)phenoxy)-2-hydroxypropylamino)-1-oxa-8-azaspiro[4.5]decan-8-ylsulfonyl)-7-fluoroquinolin-4-ol (Compound 329)

Step A: Preparation of tert-Butyl ((S)-3-(3-(Cyclopropylsulfonyl)phenoxy)-2-hydroxypropyl)((R)-8-((7-fluoro-4-hydroxyquinolin-3-yl)sulfonyl)-1-oxa-8-azaspiro[4.5]decan-3-yl)carbamate From tert-butyl ((S)-3-(3-(cyclopropylsulfonyl)phenoxy)-2-hydroxypropyl)((R)-1-oxa-8-azaspiro[4.5]decan-3-yl)carbamate and 7-fluoro-4-hydroxyquinoline-3-sulfonyl chloride, the title compound was prepared using a similar method to the one described in Method G, Step A. LCMS m/z=736.4 [M+H]+; 1H NMR (400 MHz, CD3OD) δ ppm 1.00-1.09 (m, 2H), 1.17-1.24 (m, 2H), 1.45 (s, 9H), 1.56-1.66 (m, 1H), 1.69-1.81 (m, 3H), 1.86 (dd, J=12.76, 8.21 Hz, 1H), 2.07 (dd, J=12.88, 8.59 Hz, 1H), 2.67 (tt, J=7.96, 4.80 Hz, 1H), 3.21-3.29 (m, 3H), 3.39-3.50 (m, 2H), 3.53 (dd, J=14.53, 4.67 Hz, 1H), 3.85-3.91 (m, 1H), 3.95-4.08 (m, 3H), 4.11-4.20 (m, 1H), 4.45-4.58 (m, 1H), 7.24-7.35 (m, 3H), 7.40-7.47 (m, 2H), 7.51 (t, J=7.96 Hz, 1H), 8.33 (dd, J=9.09, 6.06 Hz, 1H), 8.51 (s, 1H).

Step B: Preparation of 3-((R)-3-((S)-3-(3-(Cyclopropylsulfonyl)phenoxy)-2-hydroxypropylamino)-1-oxa-8-azaspiro[4.5]decan-8-ylsulfonyl)-7-fluoroquinolin-4-ol (Compound 329)

From tert-butyl ((S)-3-(3-(cyclopropylsulfonyl)phenoxy)-2-hydroxypropyl)((R)-8-((7-fluoro-4-hydroxyquinolin-3-yl)sulfonyl)-1-oxa-8-azaspiro[4.5]decan-3-yl)carbamate, the title compound was prepared using a similar method to the one described in Method E, Step D. LCMS m/z=636.6 [M+H]+; 1H NMR (400 MHz, CD3OD) δ ppm 1.03-1.11 (m, 2H), 1.18-1.26 (m, 2H), 1.59-1.71 (m, 1H), 1.76-1.90 (m, 4H), 2.35 (dd, J=13.89, 8.34 Hz, 1H), 2.67 (tt, J=7.96, 4.80 Hz, 1H), 3.16-3.30 (m, 3H), 3.51-3.62 (m, 2H), 3.64-3.70 (m, 1H), 3.72-3.76 (m, 1H), 3.91-3.97 (m, 1H), 3.98-4.06 (m, 1H), 4.06-4.15 (m, 3H), 4.26 (td, J=4.80, 3.03 Hz, 1H), 7.25-7.36 (m, 3H), 7.46 (t, J=2.27 Hz, 1H), 7.50-7.59 (m, 2H), 8.33 (dd, J=9.09, 5.81 Hz, 1H), 8.53 (s, 1H).

Example 1.53: Preparation of 1-Ethyl-8-fluoro-3-((R)-3-((S)-2-hydroxy-3-(3-(isopropylsulfonyl) phenoxy)propylamino)-1-oxa-8-azaspiro[4.5]decan-8-ylsulfonyl)quinolin-4(1H)-one (Compound 331)

Step A: Preparation of tert-Butyl ((R)-8-((8-Fluoro-4-hydroxyquinolin-3-yl)sulfonyl)-1-oxa-8-azaspiro[4.5]decan-3-yl)((S)-2-hydroxy-3-(3-(isopropylsulfonyl)phenoxy)propyl)carbamate From (S)-2-((3-(isopropylsulfonyl)phenoxy)methyl)oxirane, (R)-benzyl 3-amino-1-oxa-8-azaspiro[4.5]decane-8-carboxylate and 8-fluoro-4-hydroxyquinoline-3-sulfonyl chloride, the title compound was prepared using a similar method to the one described in Method E, Step A, B, and C. LCMS m/z=738.6 [M+H]+; 1H NMR (400 MHz, CD3OD) δ ppm 1.23 (d, J=6.82 Hz, 6H), 1.45 (s, 9H), 1.61 (ddd, J=13.64, 9.85, 4.04 Hz, 1H), 1.73 (ddd, J=13.52, 4.04, 3.92 Hz, 1H), 1.79 (t, J=5.81 Hz, 2H), 1.86 (dd, J=12.76, 8.21 Hz, 1H), 2.07 (dd, J=12.76, 8.46 Hz, 1H), 3.20-3.29 (m, 4H), 3.42-3.57 (m, 3H), 3.85-3.91 (m, 1H), 3.95-4.02 (m, 2H), 4.02-4.07 (m, 1H), 4.11-4.19 (m, 1H), 4.52 (dd, J=15.66, 8.34 Hz, 1H), 7.29 (ddd, J=8.34, 2.53, 1.01 Hz, 1H), 7.39 (t, J=2.53 Hz, 1H), 7.40-7.44 (m, 1H), 7.44-7.49 (m, 1H), 7.53 (t, J=7.96 Hz, 1H), 7.60 (ddd, J=10.86, 8.08, 1.26 Hz, 1H), 8.08 (d, J=8.08 Hz, 1H), 8.48 (s, 1H).

Step B: Preparation of tert-Butyl ((R)-8-((1-Ethyl-8-fluoro-4-oxo-1,4-dihydroquinolin-3-yl)sulfonyl)-1-oxa-8-azaspiro[4.5]decan-3-yl)((S)-2-hydroxy-3-(3-(isopropylsulfonyl)phenoxy)propyl)carbamate From tert-butyl ((R)-8-((8-fluoro-4-hydroxyquinolin-3-yl)sulfonyl)-1-oxa-8-azaspiro[4.5]decan-3-yl)((S)-2-hydroxy-3-(3-(isopropylsulfonyl)phenoxy)propyl)carbamate and ethyl iodide, the title compound was prepared using a similar method to the one described in Method G, Step B. LCMS m/z=766.6 [M+H]⁺.

Step C: Preparation of 1-Ethyl-8-fluoro-3-((R)-3-((S)-2-hydroxy-3-(3-(isopropylsulfonyl)phenoxy)propylamino)-1-oxa-8-azaspiro[4.5]decan-8-ylsulfonyl)quinolin-4(1H)-one (Compound 331)

From of tert-butyl ((R)-8-((1-ethyl-8-fluoro-4-oxo-1,4-dihydroquinolin-3-yl)sulfonyl)-1-oxa-8-azaspiro[4.5]decan-3-yl)((S)-2-hydroxy-3-(3-(isopropylsulfonyl)phenoxy)propyl)carbamate, the title compound was prepared using a similar method to the one described in Method E, Step D. LCMS m/z=666.6 [M+H]⁺; ¹H NMR (400 MHz, CD₃OD) δ ppm 1.25 (d, J=7.07 Hz, 6H), 1.52 (t, J=6.57 Hz, 3H), 1.60-1.69 (m, 1H), 1.77-1.90 (m, 4H), 2.35 (dd, J=13.77, 8.21 Hz, 1H), 3.16-3.29 (m, 4H), 3.53-3.69 (m, 3H), 3.91-3.97 (m, 1H), 3.99-4.15 (m, 4H), 4.26 (dddd, J=9.60, 4.99, 4.86, 3.28 Hz, 1H), 4.55 (qd, J=7.12, 2.91 Hz, 2H), 7.33 (ddd, J=8.15, 2.59, 0.88 Hz, 1H), 7.43 (t, J=2.53 Hz, 1H), 7.47-7.51 (m, 1H), 7.53 (dt, J=8.02, 3.95 Hz, 1H), 7.58 (t, J=7.96 Hz, 1H), 7.67 (ddd, J=14.91, 7.83, 1.52 Hz, 1H), 8.22 (d, J=8.08 Hz, 1H), 8.58 (s, 1H).

Example 1.54: Preparation of 1-Ethyl-3-((R)-3-((S)-2-hydroxy-3-(3-(isopropylsulfonyl)phenoxy)propylamino)-1-oxa-8-azaspiro[4.5]decan-8-ylsulfonyl)quinolin-4(1H)-one (Compound 332)

Step A: Preparation of tert-Butyl ((S)-2-Hydroxy-3-(3-(isopropylsulfonyl)phenoxy)propyl)((R)-1-oxa-8-azaspiro[4.5]decan-3-yl)carbamate From (S)-2-((3-(isopropylsulfonyl)phenoxy)methyl)oxirane and (R)-benzyl 3-amino-1-oxa-8-azaspiro[4.5]decane-8-carboxylate, the title compound was prepared using a similar method to the one described in Method A, Step A, B and C.

Step B: Preparation of 1-Ethyl-3-((R)-3-((S)-2-hydroxy-3-(3-(isopropylsulfonyl)phenoxy)propylamino)-1-oxa-8-azaspiro[4.5]decan-8-ylsulfonyl)quinolin-4(1H)-one (Compound 332)

From tert-butyl ((S)-2-hydroxy-3-(3-(isopropylsulfonyl)phenoxy)propyl)((R)-1-oxa-8-azaspiro[4.5]decan-3-yl)carbamate and 1-ethyl-4-oxo-1,4-dihydroquinoline-3-sulfonyl chloride, tert-butyl ((R)-8-((1-ethyl-4-oxo-1,4-dihydroquinolin-3-yl)sulfonyl)-1-oxa-8-azaspiro[4.5]decan-3-yl)((S)-2-hydroxy-3-(3-(isopropylsulfonyl)phenoxy)propyl)carbamate was prepared using a similar method to the one described in Method A, Step F.

From tert-butyl ((R)-8-((1-ethyl-4-oxo-1,4-dihydroquinolin-3-yl)sulfonyl)-1-oxa-8-azaspiro[4.5]decan-3-yl)((S)-2-hydroxy-3-(3-(isopropylsulfonyl)phenoxy)propyl)carbamate, the title compound was prepared in a similar method described in Method G, Step C. LCMS m/z=648.6 [M+H]⁺; ¹H NMR (400 MHz, CD₃OD) δ ppm 1.25 (d, J=6.82 Hz, 6H), 1.52 (t, J=7.20 Hz, 3H), 1.60-1.70 (m, 1H), 1.77-1.90 (m, 4H), 2.35 (dd, J=13.77, 8.21 Hz, 1H), 3.14-3.30 (m, 4H), 3.52-3.64 (m, 2H), 3.90-3.96 (m, 1H), 3.97-4.05 (m, 1H), 4.05-4.14 (m, 3H), 4.19-4.30 (m, 1H), 4.48 (q, J=7.07 Hz, 2H), 7.33 (ddd, J=8.27, 2.59, 1.01 Hz, 1H), 7.43 (t, J=2.27 Hz, 1H), 7.49 (dt, J=8.00, 1.26 Hz, 1H), 7.54-7.61 (m, 2H), 7.85-7.92 (m, 2H), 8.38 (d, J=7.83 Hz, 1H), 8.68 (s, 1H).

Example 1.55: Preparation of (S)-1-((R)-8-(4-(Aminomethyl)biphenyl-3-ylsulfonyl)-1-oxa-8-azaspiro[4.5]decan-3-ylamino)-3-(3-(cyclopropylsulfonyl)phenoxy)propan-2-ol (Compound 189)

Step A: Preparation of tert-Butyl ((R)-8-((3-Bromophenyl)sulfonyl)-1-oxa-8-azaspiro[4.5]decan-3-yl)((S)-3-(3-(cyclopropylsulfonyl)phenoxy)-2-hydroxypropyl)carbamate To a solution of tert-butyl ((S)-3-(3-(cyclopropylsulfonyl)phenoxy)-2-hydroxypropyl)((R)-1-oxa-8-azaspiro[4.5]decan-3-yl)carbamate (81 mg, 0.16 mmol) in CH₂Cl₂ (5 mL) was added DIEA (69.07 µL, 0.40 mmol) and 3-bromobenzene-1-sulfonyl chloride (48.64 mg, 0.19 mmol) under nitrogen. The reaction mixture was stirred at room temperature overnight. After the reaction was completed, the mixture was concentrated. The residue was purified by silica gel column chromatography to give the title compound (88 mg, 76% yield) as colorless oil. LCMS m/z=729.6 [M]+; ¹H NMR (400 MHz, CD₃OD) δ ppm 1.03-1.09 (m, 2H), 1.19-1.26 (m, 2H), 1.44 (s, 9H), 1.57-1.68 (m, 1H), 1.71-1.89 (m, 4H), 2.00-2.07 (m, 1H), 2.61-2.85 (m, 3H), 3.18-3.28 (m, 1H), 3.33-3.40 (m, 2H), 3.53 (dd, J=14.65, 4.55 Hz, 1H), 3.79-3.88 (m, 1H), 3.91-4.19 (m, 5H), 4.44-4.53 (m, 1H), 7.27 (ddd, J=7.89, 2.59, 1.14 Hz, 1H), 7.43 (t, J=2.27 Hz, 1H), 7.47-7.57 (m, 3H), 7.75 (ddd, J=7.83, 1.77, 1.01 Hz, 1H), 7.84 (ddd, J=7.89, 1.96, 1.01 Hz, 1H), 7.90 (t, J=1.77 Hz, 1H).

Step B: Preparation of (S)-1-((R)-8-(4'-(Aminomethyl)biphenyl-3-ylsulfonyl)-1-oxa-8-azaspiro[4.5]decan-3-ylamino)-3-(3-(cyclopropylsulfonyl)phenoxy)propan-2-ol (Compound 189)

A solution of tert-butyl ((R)-8-((3-bromophenyl)sulfonyl)-1-oxa-8-azaspiro[4.5]decan-3-yl)((S)-3-(3-(cyclopropylsulfonyl)phenoxy)-2-hydroxypropyl)carbamate (32 mg, 43.85 µmol), Pd(dppf)₂.DCM (5.41 mg, 6.6 µmol), sodium carbonate (48.24 µL, 96.48 µmol) and (4-(((tert-butoxycarbonyl)amino)methyl)phenyl)boronic acid (13.21 mg, 52.62 µmol) in dioxane (4 mL) was degassed with N₂ for 10 min then heated at 100° C. overnight. After the reaction was completed and cooled down to room temperature, solid Na₂SO₄ was added. The mixture was stirred for 2 h and filtered through a pad of Celite® and Na₂SO₄. The filtrate was washed with DCM/MeOH (5%) and concentrated. The residue was purified by silica gel column chromatography to give tert-butyl ((R)-8-((4'-(((tert-butoxycarbonyl)amino)methyl)-[1,1'-biphenyl]-3-yl)sulfonyl)-1-oxa-8-azaspiro[4.5]decan-3-yl)((S)-3-(3-(cyclopropylsulfonyl)phenoxy)-2-hydroxypropyl)carbamate. LCMS m/z=857.8 [M+H]⁺.

To a solution of tert-butyl ((R)-8-((4'-(((tert-butoxycarbonyl)amino)methyl)-[1,1'-biphenyl]-3-yl)sulfonyl)-1-oxa-8-azaspiro[4.5]decan-3-yl)((S)-3-(3-(cyclopropylsulfonyl)phenoxy)-2-hydroxypropyl)carbamate from the previous step in MeCN (4.0 mL) was added HCl (4N in dioxane, 0.3 mL). The reaction was stirred at room temperature until completion. The mixture was concentrated. The residue was purified by prep-HPLC. The collected fractions was added HCl (4N in dioxane, 200 µL) and lyophilized to give the title compound (24 mg, 74% yield) as a solid. LCMS m/z=656.6 [M+H]⁺; ¹H NMR (400 MHz, CD₃OD) δ ppm 1.03-1.10 (m, 2H), 1.19-1.25 (m, 2H), 1.61-1.74 (m, 1H), 1.79-1.94 (m, 4H), 2.33 (dd, J=13.77, 8.21 Hz, 1H), 2.63-2.71 (m, 1H), 2.71-2.84 (m, 2H), 3.16 (dd, J=12.38, 9.35 Hz, 1H), 3.45-3.56 (m, 2H), 3.56-3.77 (m, 2H), 3.86-3.92 (m, 1H), 3.96-

4.04 (m, 2H), 4.10 (dd, J=5.18, 2.91 Hz, 2H), 4.20 (s, 2H), 4.22-4.29 (m, 1H), 7.29 (ddd, J=7.89, 2.59, 1.39 Hz, 1H), 7.45 (t, J=2.27 Hz, 1H), 7.50-7.63 (m, 4H), 7.70-7.83 (m, 4H), 7.95-8.00 (m, 2H).

Example 1.56: Preparation of (S)-1-((S)-8-(4'-(Aminomethyl)-4-ethoxybiphenyl-3-ylsulfonyl)-1-oxa-8-azaspiro[4.5]decan-3-ylamino)-3-(2-fluoro-3-(methylsulfonyl)phenoxy)propan-2-ol (Compound 209). (Method I)

Step A: Preparation of (S)-Benzyl 3-(((S)-3-(3-Bromo-2-fluorophenoxy)-2-hydroxypropyl)(tert-butoxycarbonyl)amino)-1-oxa-8-azaspiro[4.5]decane-8-carboxylate A solution of (S)-benzyl 3-amino-1-oxa-8-azaspiro[4.5]decane-8-carboxylate (0.65 g, 2.23 mmol) and (S)-2-((3-bromo-2-fluorophenoxy)methyl)oxirane (0.28 g, 1.12 mmol) in EtOH (15 mL) was heated at 70° C. overnight under nitrogen. After the reaction was completed, the mixture was concentrated to give (S)-benzyl 3-(((S)-3-(3-bromo-2-fluorophenoxy)-2-hydroxypropyl)amino)-1-oxa-8-azaspiro[4.5]decane-8-carboxylate (0.55 g, 92% yield) as a yellow oil without further purification. LCMS m/z=537.2 [M]$^+$.

A solution of (S)-benzyl 3-(((S)-3-(3-bromo-2-fluorophenoxy)-2-hydroxypropyl)amino)-1-oxa-8-azaspiro[4.5]decane-8-carboxylate from the previous step (0.55 g, 1.02 mmol) in CH$_2$Cl$_2$ (15 mL) were added (BOC)$_2$O (0.49 g, 2.23 mmol) and DIEA (0.20 mL, 1.12 mmol). The reaction was stirred at room temperature overnight under nitrogen. After the reaction was completed, the mixture was concentrated. The residue was purified by silica gel column chromatography to give the title compound (565 mg, 79% yield) as a clear gum. LCMS m/z=637.4 [M]$^+$; $^1$H NMR (400 MHz, CD$_3$OD) δ ppm 1.42-1.54 (m, 11H), 1.59-1.68 (m, 1H), 1.69-1.77 (m, 2H), 2.02-2.14 (m, 2H), 3.40 (bs, 2H), 3.56 (dd, J=14.53, 4.67 Hz, 1H), 3.59-3.70 (m, 2H), 3.83 (dd, J=8.84, 7.33 Hz, 1H), 3.93-4.11 (m, 3H), 4.12-4.21 (m, 1H), 4.46-4.58 (m, 1H), 5.11 (s, 2H), 7.03 (td, J=8.21, 1.64 Hz, 1H), 7.09 (td, J=7.45, 1.64 Hz, 1H), 7.16 (ddd, J=7.89, 6.00, 1.52 Hz, 1H), 7.26-7.40 (m, 5H).

Step B: Preparation of (S)-Benzyl 3-((tert-Butoxycarbonyl)((S)-3-(2-fluoro-3-(methylsulfonyl)phenoxy)-2-hydroxypropyl)amino)-1-oxa-8-azaspiro[4.5]decane-8-carboxylate To a 5 mL microwave vial were added (S)-benzyl 3-(((S)-3-(3-bromo-2-fluorophenoxy)-2-hydroxypropyl)(tert-butoxycarbonyl)amino)-1-oxa-8-azaspiro[4.5]decane-8-carboxylate (150 mg, 0.24 mmol), Sodium methansulfinate (108.06 mg, 0.71 mmol), Copper(I) trifluoromethanesulfonate-benzene complex (26.06 mg, 70.56 μmol), and N$_1$,N$_2$-dimethylethane-1,2-diamine (12.45 mg, 141.22 μmol) under N$_2$ followed by DMSO (4 mL). The reaction was heated at 110° C. for 4 h under microwave irradiation. The mixture was diluted in EtOAc and washed with water and brine. The organic layer was dried over Na$_2$SO$_4$, filtered and concentrated. The residue was purified by silica gel column chromatography to give the title compound (96 mg, 64% yield) as a colorless oil. LCMS m/z=637.8 [M+H]$^+$; $^1$H NMR (400 MHz, CD$_3$OD) δ ppm 1.46 (s, 9H), 1.47-1.55 (m, 1H), 1.61-1.70 (m, 1H), 1.70-1.78 (m, 2H), 2.04-2.15 (m, 2H), 3.23 (s, 3H), 3.34-3.46 (m, 2H), 3.58 (dd, J=14.65, 4.55 Hz, 1H), 3.61-3.71 (m, 2H), 3.84 (dd, J=8.84, 7.33 Hz, 1H), 3.97 (dd, J=8.97, 7.71 Hz, 1H), 4.06-4.16 (m, 2H), 4.16-4.23 (m, 1H), 4.51-4.58 (m, 1H), 5.11 (s, 2H), 7.27-7.38 (m, 6H), 7.43-7.53 (m, 2H).

Step C: Preparation of tert-Butyl ((S)-3-(2-Fluoro-3-(methylsulfonyl)phenoxy)-2-hydroxypropyl)((S)-1-oxa-8-azaspiro[4.5]decan-3-yl)carbamate To a solution of (S)-benzyl 3-((tert-butoxycarbonyl)((S)-3-(2-fluoro-3-(methylsulfonyl)phenoxy)-2-hydroxypropyl)amino)-1-oxa-8-azaspiro[4.5]decane-8-carboxylate (96 mg, 0.15 mmol) in MeOH (10 mL) under N$_2$ was added Palladium/C (16.05 mg, 15.08 μmol) followed by addition of H$_2$ balloon. The reaction was stirred at room temperature overnight. After the reaction was completed, it was filtered through a pad of Celite®, washed with MeOH and concentrated to give the title compound (76 mg, 100% yield) as a white foam which was used in the next step without further purification. LCMS m/z=503.4 [M+H]$^+$.

Step D: Preparation of tert-Butyl ((S)-8-((5-Bromo-2-ethoxyphenyl)sulfonyl)-1-oxa-8-azaspiro[4.5]decan-3-yl)((S)-3-(2-fluoro-3-(methylsulfonyl)phenoxy)-2-hydroxypropyl)carbamate To a solution of tert-butyl ((S)-3-(2-fluoro-3-(methylsulfonyl)phenoxy)-2-hydroxypropyl)((S)-1-oxa-8-azaspiro[4.5]decan-3-yl)carbamate and DIEA (65.85 μL, 0.38 mmol) in CH$_2$Cl$_2$ (10 mL) was added 5-bromo-2-ethoxybenzene-1-sulfonyl chloride (70.78 mg, 0.23 mmol) under nitrogen. The reaction was stirred at room temperature for 6 h. The mixture was concentrated. The residue was purified by silica gel column chromatography to give the title compound (55 mg, 48% yield) as a white foam. LCMS m/z=767.4 [M+2H]$^+$; $^1$H NMR (400 MHz, CDCl$_3$) δ ppm 1.42-1.52 (m, 12H), 1.60-1.89 (m, 6H), 2.04-2.12 (m, 1H), 3.03-3.16 (m, 2H), 3.21 (s, 3H), 3.44-3.52 (m, 2H), 3.59 (dd, J=13.01, 4.42 Hz, 2H), 3.78 (dd, J=9.60, 6.57 Hz, 1H), 3.92 (dd, J=9.47, 7.45 Hz, 1H), 3.98-4.05 (m, 1H), 4.05-4.19 (m, 4H), 4.48-4.67 (m, 1H), 6.87 (d, J=8.59 Hz, 1H), 7.21-7.32 (m, 2H), 7.56 (dd, J=11.87, 9.35 Hz, 2H), 8.01 (d, J=2.53 Hz, 1H).

Step E: Preparation of (S)-1-((S)-8-(4'-(Aminomethyl)-4-ethoxybiphenyl-3-ylsulfonyl)-1-oxa-8-azaspiro[4.5]decan-3-ylamino)-3-(2-fluoro-3-(methylsulfonyl)phenoxy)propan-2-ol (Compound 209) as the di-HCl Salt A mixture of tert-butyl ((S)-8-((5-bromo-2-ethoxyphenyl)sulfonyl)-1-oxa-8-azaspiro[4.5]decan-3-yl)((S)-3-(2-fluoro-3-(methylsulfonyl)phenoxy)-2-hydroxypropyl)carbamate (55 mg, 71.83 μmol), (4-(((tert-butoxycarbonyl)amino)methyl)phenyl)boronic acid (27.05 mg, 108 μmol), Sodium carbonate, Pd(dppf)$_2$, DCM (11.82 mg, 14.34 μmol) in dioxane (5 mL) was degassed with N$_2$ for 5 min. The reaction was heated at 100° C. overnight. After cooling down to room temperature, solid Na$_2$SO$_4$ was added. The mixture was stirred at room temperature for 2 h. The mixture was filtered through a pad of Celite® and Na$_2$SO$_4$, washed with DCM, and then concentrated. The residue was purified by silica gel column chromatography to give tert-butyl ((S)-8-((4'-(((tert-butoxycarbonyl)amino)methyl)-4-ethoxy-[1,1'-biphenyl]-3-yl)sulfonyl)-1-oxa-8-azaspiro[4.5]decan-3-yl)((S)-3-(2-fluoro-3-(methylsulfonyl)phenoxy)-2-hydroxypropyl)carbamate. LCMS m/z=892.6 [M+H]$^+$.

tert-Butyl ((S)-8-((4'-(((tert-butoxycarbonyl)amino)methyl)-4-ethoxy-[1,1'-biphenyl]-3-yl)sulfonyl)-1-oxa-8- azaspiro[4.5]decan-3-yl)((S)-3-(2-fluoro-3-(methylsulfonyl)phenoxy)-2-hydroxypropyl)carbamate from the previous step was dissolved in DCM (5 mL). Then HCl (4N in dioxane, 180 µL) was added. The reaction was stirred at room temperature until completion. The mixture was concentration. The residue was purified by prep-HPLC. The combined fractions were added HCl (4N in dioxane, 200 µL) and lyophilized to give the title compound (27.5 mg, 50% yield) as a white foam. LCMS m/z=692.4 [M+H]$^+$; $^1$H NMR (400 MHz, CD$_3$OD) δ ppm 1.49 (t, J=7.07 Hz, 3H), 1.60-1.70 (m, 1H), 1.78-1.93 (m, 4H), 2.37 (dd, J=13.64, 8.34 Hz, 1H), 3.07-3.22 (m, 4H), 3.24 (s, 3H), 3.51-3.63 (m, 2H), 3.94 (dd, J=10.11, 4.04 Hz, 1H), 4.01-4.09 (m, 1H), 4.09-4.33 (m, 8H), 7.30 (d, J=8.59 Hz, 1H), 7.35 (td, J=8.08, 1.52 Hz, 1H), 7.47-7.58 (m, 4H), 7.70 (d, J=8.34 Hz, 2H), 7.88 (dd, J=8.59, 2.53 Hz, 1H), 8.08 (d, J=2.53 Hz, 1H).

Example 1.57: Preparation of (2S)-1-(8-(Chroman-6-ylsulfonyl)-1-oxa-8-azaspiro[4.5]decan-3-ylamino)-3-(3-(methylsulfonyl)phenoxy)propan-2-ol (Compound 28). (Method J)

Step A: Preparation of (2S)-1-(1-Oxa-8-azaspiro[4.5]decan-3-ylamino)-3-(3-(methylsulfonyl)phenoxy)propan-2-ol From (S)-2-((3-(methylsulfonyl)phenoxy)methyl)oxirane and benzyl 3-amino-1-oxa-8-azaspiro[4.5]decane-8-carboxylate, the title compound was prepared using a method similar to the ones described in Method A, Step A and C. LCMS m/z=385.2 [M+H]$^+$.

Step B: Preparation of (2S)-1-(8-(Chroman-6-ylsulfonyl)-1-oxa-8-azaspiro[4.5]decan-3-ylamino)-3-(3-(methylsulfonyl)phenoxy)propan-2-ol (Compound 28)

To a solution of (2S)-1-(1-oxa-8-azaspiro[4.5]decan-3-ylamino)-3-(3-(methylsulfonyl)phenoxy)propan-2-ol (10 mg, 26.01 µmol) and DIEA (9.060 µl, 52.02 µmol) in dioxane (0.4 mL) was added chroman-6-sulfonyl chloride (7.26 mg, 31.21 µmol). The reaction mixture was stirred overnight at room temperature for 16 h. The reaction was quenched with water then purified via mass directed prep-HPLC. Collected fractions were lyophilized to give the title compound (9.1 mg, 50% yield). LCMS m/z=581.2 [M+H]$^+$; $^1$H NMR (400 MHz, CD$_3$OD) δ ppm 1.66 (td, J=10.99, 4.17 Hz, 1H), 1.76-1.90 (m, 4H), 1.99-2.06 (m, 2H), 2.31 (ddd, J=13.83, 8.27, 2.40 Hz, 1H), 2.63-2.78 (m, 2H), 2.85 (t, J=6.44 Hz, 2H), 3.11 (s, 3H), 3.13-3.20 (m, 1H), 3.25-3.42 (m, 3H), 3.89 (td, J=8.59, 5.81 Hz, 1H), 3.96-4.08 (m, 2H), 4.11 (dd, J=4.93, 1.64 Hz, 2H), 4.21-4.30 (m, 3H), 6.90 (d, J=8.34 Hz, 1H), 7.26-7.34 (m, 1H), 7.43-7.48 (m, 2H), 7.50 (t, J=1.26 Hz, 1H), 7.56 (d, J=5.05 Hz, 2H).

Example 1.58: Preparation of (3-((S)-2-Hydroxy-3-(3-(methylsulfonyl)phenoxy)propylamino)-1-oxa-8-azaspiro[4.5]decan-8-yl)(4-methyl-3,4-dihydro-2H-benzo[b][1,4]oxazin-7-yl)methanone (Compound 64). (Method K)

Step A: Preparation of tert-Butyl ((S)-2-Hydroxy-3-(3-(methylsulfonyl)phenoxy)propyl)(8-(4-methyl-3,4-dihydro-2H-benzo[b][1,4]oxazine-7-carbonyl)-1-oxa-8-azaspiro[4.5]decan-3-yl)carbamate tert-Butyl ((S)-2-hydroxy-3-(3-(methylsulfonyl)phenoxy)propyl)(1-oxa-8-azaspiro[4.5]decan-3-yl)carbamate (15 mg, 30.95 µmol), 4-methyl-3,4-dihydro-2H-benzo[b][1,4]oxazine-7-carboxylic acid (7.18 mg, 37.14 µmol), HATU (14.12 mg, 37.14 µmol) and triethylamine in DMF (1M, 61.91 µL, 61.91 µmol) solution were added in 5 mL scintillation vial following by addition of DMF (1 mL). The reaction mixture was heated at 70° C. for 16 h. The reaction mixture was filtered and purified by mass direct pre-HPLC. The collected fractions were lyophilized to give the title compound. LCMS m/z=660.6 [M+H]$^+$.

Step B: Preparation of (3-((S)-2-Hydroxy-3-(3-(methylsulfonyl)phenoxy)propylamino)-1-oxa-8-azaspiro[4.5]decan-8-yl)(4-methyl-3,4-dihydro-2H-benzo[b][1,4]oxazin-7-yl)methanone (Compound 64) as the HCl Salt To a solution of tert-butyl ((S)-2-hydroxy-3-(3-(methylsulfonyl)phenoxy)propyl)(8-(4-methyl-3,4-dihydro-2H-benzo[b][1,4]oxazine-7-carbonyl)-1-oxa-8-azaspiro[4.5]decan-3-yl)carbamate in ACN (3 mL) was added HCl (4N in dioxane, 100 µL). The reaction was stirred for 4 h. The mixture was concentrated. The residue was triturated with hexane to give the title compound (11 mg, 60% yield). LCMS m/z=560.4 [M+H]$^+$; $^1$H NMR (400 MHz, CD$_3$OD) δ ppm 1.61 (t, J=10.36 Hz, 1H), 1.69-1.86 (m, 3H), 1.91 (dt, J=13.58, 5.72 Hz, 1H), 2.40 (ddd, J=13.64, 8.21, 2.15 Hz, 1H), 2.92 (s, 3H), 3.12 (s, 3H), 3.19 (dt, J=12.82, 9.25 Hz, 1H), 3.32-3.38 (m, 2H), 3.40-3.53 (m, 2H), 3.95-4.20 (m, 6H), 4.22-4.33 (m, 3H), 6.70 (d, J=8.34 Hz, 1H), 6.78 (d, J=2.02 Hz, 1H), 6.91 (dd, J=8.34, 2.02 Hz, 1H), 7.32 (td, J=3.73, 1.89 Hz, 1H), 7.52 (t, J=1.26 Hz, 1H), 7.57 (d, J=5.31 Hz, 2H).

Example 1.59: Preparation of (2S)-1-(3-(Fluoromethylsulfonyl)phenoxy)-3-(8-(naphthalen-2-ylsulfonyl)-1-oxa-8-azaspiro[4.5]decan-3-ylamino)propan-2-ol (Compound 86)

To a solution of 8-(naphthalen-2-ylsulfonyl)-1-oxa-8-azaspiro[4.5]decan-3-amine (14.07 mg, 40.61 µmol) was dissolved in EtOH (0.6 mL) was added (S)-2-((3-((fluoromethyl)sulfonyl)phenoxy) methyl)oxirane (5 mg, 20.30 µmol), pre-dissolved in EtOH (0.3 mL). The reaction was stirred at 90° C. overnight. The next day, the solvent was removed, and the residue was purified by PrepLC/MS to give the title compound (6.2 mg, 8.7 µmol, 42.8% yield) as a solid. LCMS m/z=593.4 [M+H]$^+$; $^1$H NMR (400 MHz, DMSO-d$_6$) δ ppm 1.55-1.65 (m, 1H), 1.66-1.85 (m, 4H), 2.07-2.19 (m, 1H), 2.58-2.75 (m, 2H), 2.86-3.02 (m, 1H), 3.03-3.16 (m, 1H), 3.27-3.43 (m, 3H), 3.65-3.74 (m, 1H), 3.80-3.94 (m, 2H), 4.01-4.07 (m, 2H), 4.07-4.16 (m, 1H), 5.66 (s, 1H), 5.78 (s, 1H), 7.35-7.44 (m, 2H), 7.54 (d, J=7.96 Hz, 1H), 7.64 (t, J=7.98 Hz, 1H), 7.67-7.80 (m, 3H), 8.09 (d, J=8.04 Hz, 1H), 8.18 (d, J=8.72 Hz, 1H), 8.21 (d, J=7.92 Hz, 1H), 8.44 (s, 1H), 8.73 (bs, 2H).

Example 1.60: Preparation of (S)-1-((R)-8-(4'-(1-Aminocyclopropyl)-6-methoxybiphenyl-3-ylsulfonyl)-1-oxa-8-azaspiro[4.5]decan-3-ylamino)-3-(3-(1-(hydroxymethyl)cyclopropylsulfonyl)phenoxy)propan-2-ol (Compound 199)

Step A: Preparation of tert-Butyl ((R)-8-((3-Bromo-4-methoxyphenyl)sulfonyl)-1-oxa-8-azaspiro[4.5]decan-3-yl)((S)-2-hydroxy-3-(3-((1-(hydroxymethyl)cyclopropyl)sulfonyl)phenoxy)propyl)carbamate From tert-butyl ((S)-2-hydroxy-3-(3-((1-(hydroxymethyl)cyclopropyl)sulfonyl)phenoxy)propyl)((S)-1-oxa-8- azaspiro[4.5]decan-3-yl)carbamate and 3-bromo-4-methoxybenzene-1-sulfonyl chloride, the title compound was prepared in a similar method described in Method F, Step D. LCMS m/z=789.4/791.4 [M+H]⁺.

Step B: Preparation of tert-Butyl ((R)-8-((4'-(1-((tert-Butoxycarbonyl)amino)cyclopropyl)-6-methoxy-[1,1'-biphenyl]-3-yl)sulfonyl)-1-oxa-8-azaspiro[4.5]decan-3-yl)((S)-2-hydroxy-3-(3-((1-(hydroxymethyl)cyclopropyl)sulfonyl)phenoxy)propyl)carbamate From tert-butyl ((R)-8-((3-bromo-4-methoxyphenyl)sulfonyl)-1-oxa-8-azaspiro[4.5]decan-3-yl)((S)-2-hydroxy-3-(3-((1-(hydroxymethyl)cyclopropyl)sulfonyl)phenoxy)propyl)carbamate and (4-(1-((tert-butoxycarbonyl)amino)cyclopropyl)phenyl)boronic acid, the title compound was prepared in a similar method described in Method F, Step E. LCMS m/z=942.6 [M+H]⁺.

Step C: Preparation of (S)-1-((R)-8-(4'-(1-Aminocyclopropyl)-6-methoxybiphenyl-3-ylsulfonyl)-1-oxa-8-azaspiro[4.5]decan-3-ylamino)-3-(3-(1-(hydroxymethyl)cyclopropylsulfonyl)phenoxy)propan-2-ol (Compound 199)

From tert-butyl ((R)-8-((4'-(1-((tert-butoxycarbonyl)amino)cyclopropyl)-6-methoxy-[1,1'-biphenyl]-3-yl)sulfonyl)-1-oxa-8-azaspiro[4.5]decan-3-yl)((S)-2-hydroxy-3-(3-((1-(hydroxymethyl)cyclopropyl)sulfonyl)phenoxy)propyl)carbamate, the title compound was prepared in a similar method described in Method F, Step F. LCMS m/z=742.8 [M+H]⁺; ¹H NMR (400 M Hz, CD₃OD) δ ppm 1.07-1.10 (m, 2H), 1.33-1.37 (m, 2H), 1.40-1.44 (m, 2H), 1.48-1.51 (q, J=3.77 Hz, 2H), 1.63-1.70 (m, 1H), 1.81-1.91 (m, 4H), 2.33 (dd, J=8.13, 13.55 Hz, 1H), 2.69-2.80 (m, 2H), 3.16 (dd, J=9.75, 13.00 Hz, 1H), 3.28 (d, J=2.96 Hz, 1H), 3.39-3.46 (m, 2H), 3.72 (s, 2H), 3.90 (s, 3H), 3.93 (d, J=3.52 Hz, 1H), 3.99-4.07 (m, 2H), 4.09-4.14 (m, 2H), 4.25-4.30 (m, 1H), 7.30 (m, 1H), 7.31 (d, J=8.64 Hz, 1H), 7.47-7.60 (m, 7H), 7.63 (d, J=2.32 Hz, 1H), 7.78 (dd, J=2.52, 9.00 Hz, 1H).

Example 1.61: Preparation of (S)-1-((R)-8-(4-Ethoxy-4'-((isopropylamino)methyl)biphenyl-3-ylsulfonyl)-1-oxa-8-azaspiro[4.5]decan-3-ylamino)-3-(3-(1-(hydroxymethyl)cyclopropylsulfonyl)phenoxy)propan-2-ol (Compound 165). (Method L)

Step A: Preparation of tert-Butyl ((R)-8-((5-Bromo-2-ethoxyphenyl)sulfonyl)-1-oxa-8-azaspiro[4.5]decan-3-yl)((S)-2-hydroxy-3-(3-((1-(hydroxymethyl)cyclopropyl)sulfonyl)phenoxy)propyl)carbamate From (S)-(1-((3-(oxiran-2-ylmethoxy)phenyl)sulfonyl)cyclopropyl)methanol, (R)-benzyl 3-amino-1-oxa-8-azaspiro[4.5]decane-8-carboxylate, and 5-bromo-2-ethoxybenzene-1-sulfonyl chloride, the title compound was prepared using a similar method to the one described in Method F, Step A, B, C, and D.

Step B: Preparation of tert-Butyl ((R)-8-((4-Ethoxy-4'-formyl-[1,1'-biphenyl]-3-yl)sulfonyl)-1-oxa-8-azaspiro[4.5]decan-3-yl)((S)-2-hydroxy-3-(3-((1-(hydroxymethyl)cyclopropyl)sulfonyl)phenoxy)propyl)carbamate To a solution of tert-butyl ((R)-8-((5-bromo-2-ethoxyphenyl)sulfonyl)-1-oxa-8-azaspiro[4.5]decan-3-yl)((S)-2-hydroxy-3-(3-((1-(hydroxymethyl)cyclopropyl)sulfonyl)phenoxy)propyl)carbamate (25 mg, 31.10 μmol) in EtOH (0.6 mL)/H₂O (0.300 mL) were added potassium carbonate (9.457 mg, 68.43 μmol), Pd(dppf)2, DCM (255.9 μg, 0.311 μmol) and (4-formylphenyl)boronic acid (6.529 mg, 43.54 μmol). The reaction was degassed for 5 min before heated to 80° C. for 1 h. The mixture was diluted with EtOAc, washed with water (3×) and brine, dried over Na₂SO₄ and concentrated. The residue was purified by silica gel column chromatography to give the title compound (21 mg, 78.2% yield) as a white solid. LCMS m/z=829.6 [M+H]⁺; ¹H NMR (400 M Hz, CDCl₃) δ ppm 1.03-1.09 (m, 2H), 1.48 (s, 9H), 1.52 (spt, 3H), 1.59-1.63 (m, 2H), 1.63-1.69 (m, 2H), 1.71-1.79 (m, 2H), 1.81-1.91 (m, 2H), 2.08 (dd, J=13.01, 8.72 Hz, 1H), 3.05-3.18 (m, 2H), 3.35-3.45 (m, 1H), 3.45-3.51 (m, 1H), 3.57-3.65 (m, 2H), 3.66 (s, 2H), 3.77-3.85 (m, 1H), 3.88-3.94 (m, 1H), 3.99 (t, J=5.18 Hz, 2H), 4.09-4.17 (m, 1H), 4.22 (q, J=6.99 Hz, 2H), 4.56-4.65 (m, 1H), 7.08 (d, J=8.84 Hz, 1H), 7.15-7.19 (m, 1H), 7.39-7.42 (m, 1H), 7.45-7.52 (m, 2H), 7.73 (d, J=8.34 Hz, 2H), 7.76 (dd, J=8.59, 2.53 Hz, 1H), 7.95 (d, J=8.34 Hz, 2H), 8.20 (d, J=2.53 Hz, 1H), 10.05 (s, 1H)

Step C: Preparation of tert-Butyl ((R)-8-((4-Ethoxy-4'-((isopropylamino)methyl)-[1,1'-biphenyl]-3-yl)sulfonyl)-1-oxa-8-azaspiro[4.5]decan-3-yl)((S)-2-hydroxy-3-(3-((1-(hydroxymethyl)cyclopropyl)sulfonyl)phenoxy)propyl)carbamate To a solution of tert-butyl ((R)-8-((4-ethoxy-4'-formyl-[1,1'-biphenyl]-3-yl)sulfonyl)-1-oxa-8-azaspiro[4.5]decan-3-yl)((S)-2-hydroxy-3-(3-((1-(hydroxymethyl)cyclopropyl)sulfonyl)phenoxy)propyl)carbamate (21 mg, 24.32 μmol, 78.2%) in dichloroethane (1 mL) were added acetic acid (8.894 μL 0.156 mmol), isopropylamine (12.73 μL 0.156 mmol) and stirred for 30 min. Sodium triacetoxyborohydride (13.18 mg, 62.21 μmol) was added in one portion and stirred for 2 h at room temperature and at 60° C. overnight. The reaction was quenched with water and extracted with DCM(×3). The combined organic layer was washed with brine, filtered, dried over Na₂SO₄ and concentrated. The residue was purified by silica gel column chromatography using EtOAc to give the title compound (18.28 mg, 67% yield) as a white solid. LCMS m/z=872.8 [M+H]⁺; ¹H NMR (400 M Hz, CDCl₃) δ ppm 1.03-1.08 (m, 2H), 1.14 (d, J=6.32 Hz, 6H), 1.20-1.36 (m, 2H) 1.47 (s, 9H), 1.49 (t, J=6.82 Hz, 3H), 1.57-1.62 (m, 2H), 1.62-1.67 (m, 1H), 1.71-1.77 (m, 1H), 1.78-1.89 (m, 2H), 2.07 (dd, J=12.88, 8.84 Hz, 1H), 2.86-2.94 (m, 1H), 3.04-3.16 (m, 2H), 3.35-3.44 (m, 1H), 3.45-3.51 (m, 1H), 3.54-3.65 (m, 2H), 3.66 (s, 2H), 3.83 (s, 2H), 3.87-3.92 (m, 1H), 3.95-4.04 (m, 2H), 4.09-4.23 (m, 1H), 4.16-4.22 (m, 2H), 4.54-4.65 (m, 1H), 7.03 (d, J=8.59 Hz, 1H), 7.16 (dt, J=7.01, 2.43 Hz, 1H), 7.38-7.42 (m, 3H), 7.44-7.54 (m, 4H), 7.68 (dd, J=8.59, 2.53 Hz, 1H), 8.11 (d, J=2.27 Hz, 1H).

Step D: Preparation of (S)-1-((R)-8-(4-Ethoxy-4'-((isopropylamino)methyl)biphenyl-3-ylsulfonyl)-1-oxa-8-azaspiro[4.5]decan-3-ylamino)-3-(3-(1-(hydroxymethyl)cyclopropylsulfonyl)phenoxy)propan-2-ol (Compound 165)

To a solution of tert-butyl ((R)-8-((4-ethoxy-4'-((isopropylamino)methyl)-[1,1'-biphenyl]-3-yl)sulfonyl)-1-oxa-8-azaspiro[4.5]decan-3-yl)((S)-2-hydroxy-3-(3-((1-(hydroxymethyl)cyclopropyl)sulfonyl)phenoxy)propyl)carbamate (18.28 mg, 20.84 μmol) in MeOH (1 mL) was added HCl in dioxane (0.156 mL, 0.622 mmol) at room temperature. The reaction was allowed to stand at room temperature until the Boc-group was cleaved. Then the solvent was removed and the residue was lyophilized to give the title compound (12 mg, 67% yield) as a white solid. LCMS m/z=772.6 [M+H]$^+$; $^1$H NMR (400 M Hz, CD$_3$OD) δ ppm 1.06-1.11 (m, 2H), 1.41 (d, J=6.57 Hz, 6H), 1.49 (t, J=6.95 Hz, 3H), 1.49-1.52 (m, 2H), 1.60-1.70 (m, 1H), 1.76-1.93 (m, 3H), 2.37 (dd, J=13.77, 8.21 Hz, 1H), 3.06-3.23 (m, 3H), 3.24-3.27 (m, 1H), 3.43-3.50 (m, 1H), 3.52-3.56 (m, 1H), 3.56-3.63 (m, 2H), 3.64-3.69 (m, 1H), 3.72 (s, 2H), 3.73-3.75 (m, 1H), 3.94-3.98 (m, 1H), 4.01-4.07 (m, 1H), 4.08-4.15 (m, 2H), 4.23-4.31 (m, 3H), 4.25 (s, 2H), 7.26-7.32 (m, 2H), 7.46-7.51 (m, 1H), 7.51-7.57 (m, 2H), 7.59 (d, J=8.34 Hz, 2H), 7.72 (d, J=8.34 Hz, 2H), 7.88 (dd, J=8.72, 2.40 Hz, 1H), 8.09 (d, J=2.53 Hz, 1H).

Example 1.62: Preparation of (S)-1-((R)-8-(1,4-Dimethyl-1,2,3,4-tetrahydropyrido[3,2-b]pyrazin-7-ylsulfonyl)-1-oxa-8-azaspiro[4.5]decan-3-ylamino)-3-(3-(1-(hydroxymethyl)cyclopropyl sulfonyl) phenoxy)propan-2-ol (Compound 222)

Step A: Preparation of tert-Butyl ((S)-2-Hydroxy-3-(3-((1-(hydroxymethyl)cyclopropyl)sulfonyl)phenoxy)propyl)((R)-1-oxa-8-azaspiro[4.5]decan-3-yl) carbamate From (S)-(1-((3-(oxiran-2-ylmethoxy)phenyl)sulfonyl)cyclopropyl)methanol and (R)-benzyl 3-amino-1-oxa-8-azaspiro[4.5]decane-8-carboxylate, the title compound was prepared using a similar method to the one described in Method F, Step A, B, C.

Step B: Preparation of tert-Butyl ((R)-8-((5-Bromo-6-chloropyridin-3-yl)sulfonyl)-1-oxa-8-azaspiro[4.5]decan-3-yl)((S)-2-hydroxy-3-(3-((1-(hydroxymethyl)cyclopropyl)sulfonyl)phenoxy)propyl)carbamate To a solution of tert-butyl ((S)-2-hydroxy-3-(3-((1-(hydroxymethyl)cyclopropyl)sulfonyl)phenoxy)propyl)((R)-1-oxa-8-azaspiro[4.5]decan-3-yl)carbamate (200 mg, 0.370 mmol) in CH$_2$Cl$_2$ (3.0 mL) was added DIEA (0.155 mL, 0.888 mmol) followed by addition of 5-bromo-6-chloropyridine-3-sulfonyl chloride (0.129 g, 0.444 mmol) at 0° C. The reaction was stirred at room temperature overnight. The mixture was concentrated. The residue was purified by silica gel column chromatography to give the title compound (230 mg, 73.7% yield) as a white solid. LCMS m/z=796.4 [M+H]$^+$.

Step C: Preparation of tert-Butyl ((R)-8-((1,4-Dimethyl-1,2,3,4-tetrahydropyrido[2,3-b]pyrazin-7-yl)sulfonyl)-1-oxa-8-azaspiro[4.5]decan-3-yl)((S)-2-hydroxy-3-(3-((1-(hydroxymethyl)cyclopropyl)sulfonyl)phenoxy)propyl)carbamate To a mixture of tert-Butyl ((R)-8-((5-bromo-6-chloropyridin-3-yl)sulfonyl)-1-oxa-8-azaspiro[4.5]decan-3-yl)((S)-2-hydroxy-3-(3-((1-(hydroxymethyl)cyclopropyl)sulfonyl)phenoxy)propyl)carbamate (25 mg, 31.44 μmol), potassium carbonate (13.04 mg, 94.32 μmol) in DMF (0.8 mL) was added N$^1$,N$^2$-dimethylethane-1,2-diamine (3.326 mg, 37.73 μmol) in a microwave vial. The reaction was heated at 160° C. for 15 min under microwave irradiation. The mixture was filtered and washed with MeOH. The filtrate was concentrated and purified by silica gel column chromatography to give the title compound (21 mg, 83.0% yield) as white solid. LCMS m/z=766.6 [M+H]$^+$.

Step D: Preparation of (S)-1-((R)-8-(1,4-Dimethyl-1,2,3,4-tetrahydropyrido[3,2-b]pyrazin-7-ylsulfonyl)-1-oxa-8-azaspiro[4.5]decan-3-ylamino)-3-(3-(1-(hydroxymethyl)cyclopropylsulfonyl)phenoxy) propan-2-ol (Compound 222)

To a solution of tert-butyl ((R)-8-((1,4-dimethyl-1,2,3,4-tetrahydropyrido[2,3-b]pyrazin-7-yl)sulfonyl)-1-oxa-8-azaspiro[4.5]decan-3-yl)((S)-2-hydroxy-3-(3-((1-(hydroxymethyl)cyclopropyl)sulfonyl)phenoxy)propyl)carbamate (21 mg, 26.10 μmol, 83.0%) was dissolved in MeOH (0.2 mL) was added HCl in dioxane (0.118 mL, 0.472 mmol) at room temperature. The reaction was allowed to stand at room temperature until the Boc-group was cleaved (~30 min). The mixture was concentrated and the residue was lyophilized to give the title compound (19 mg, 25.49 μmol, 81.1% yield) as a white solid. LCMS m/z=666.4 [M+H]$^+$; $^1$H NMR (400 MHz, CD$_3$OD) δ ppm 1.09-1.13 (m, 2H), 1.50-1.54 (m, 2H), 1.66-1.75 (m, 1H), 1.84-1.99 (m, 4H), 2.39 (dd, J=13.64, 8.34 Hz, 1H), 2.84-2.92 (m, 1H), 2.91-2.98 (m, 1H), 3.04 (s, 3H), 3.20 (dd, J=12.76, 9.47 Hz, 1H), 3.34-3.37 (m, 1H), 3.36 (s, 3H), 3.45-3.49 (m, 2H), 3.49-3.57 (m, 2H), 3.74 (s, 2H), 3.85 (t, J=5.18 Hz, 2H), 3.92-3.99 (m, 1H), 4.02-4.12 (m, 2H), 4.11-4.19 (m, 2H), 4.26-4.34 (m, 1H), 6.82 (d, J=1.52 Hz, 1H), 7.32 (ddd, J=7.83, 2.53, 1.52 Hz, 1H), 7.48-7.51 (m, 1H), 7.51-7.54 (m, 1H), 7.56 (d, J=7.83 Hz, 1H), 7.60 (d, J=1.77 Hz, 1H).

Example 1.63: Preparation of (S)-1-((S)-8-(4'-(Aminomethyl)-4-ethoxybiphenyl-3-ylsulfonyl)-1-oxa-8-azaspiro[4.5]decan-3-ylamino)-3-(3-(cyclopropylsulfonyl)phenoxy)propan-2-ol (Compound 160). (Method M)

Step A: Preparation of tert-Butyl ((S)-3-(3-(Cyclopropylsulfonyl)phenoxy)-2-hydroxypropyl)((S)-1-oxa-8-azaspiro[4.5]decan-3-yl)carbamate From (S)-2-((3-(cyclopropylsulfonyl)phenoxy)methyl) oxirane and (S)-benzyl 3-amino-1-oxa-8-azaspiro[4.5]decane-8-carboxylate, the title compound was prepared using a similar method to the one described in Method A, Step A, B, and C.

Step B: Preparation of tert-Butyl ((S)-8-((5-Bromo-2-ethoxyphenyl)sulfonyl)-1-oxa-8-azaspiro[4.5]decan-3-yl)((S)-3-(3-(cyclopropylsulfonyl)phenoxy)-2-hydroxypropyl)carbamate To a solution of tert-butyl ((S)-3-(3-(cyclopropylsulfonyl)phenoxy)-2-hydroxypropyl)((S)-1-oxa-8-azaspiro[4.5]decan-3-yl)carbamate (177 mg, 0.35 mmol) in DCM (15 mL) was added DIEA (0.17 mL, 0.98 mmol) and 5-bromo-2-ethoxybenzene-1-sulfonyl chloride (0.14 g, 0.45 mmol). The reaction was stirred at room temperature overnight. After the reaction was completed, the mixture was concentrated. The residue was purified by silica gel column chromatography to give the title compound (233 mg, 87% yield) as a colorless glass. LCMS m/z=773.6 [M]$^+$; $^1$H NMR (400 MHz, CD$_3$OD) δ ppm 1.03-1.10 (m, 2H), 1.19-1.25 (m, 2H), 1.43-1.47 (m, 12H), 1.50-1.63 (m, 1H), 1.71 (ddd, J=13.39, 3.92, 3.66 Hz, 1H), 1.81 (t, J=4.55 Hz, 2H), 1.99-2.13 (m, 2H), 2.62-2.71 (m, 1H), 3.06-3.22 (m, 2H), 3.24-3.29 (m, 1H), 3.36-3.50 (m, 2H), 3.55 (dd, J=14.65, 4.80 Hz, 1H), 3.80 (dd, J=8.84, 7.33 Hz, 1H), 3.92 (t, J=8.21 Hz, 1H), 3.98-4.03 (m, 1H), 4.04-4.10 (m, 1H), 4.11-4.22 (m, 3H), 4.49 (t, J=7.71 Hz, 1H), 7.12 (d, J=9.09 Hz, 1H), 7.28 (ddd, J=8.02, 2.59, 1.26 Hz, 1H), 7.44 (d, J=2.27 Hz, 1H), 7.47 (dt, J=8.0, 1.39 Hz, 1H), 7.52 (t, J=8.08 Hz, 1H), 7.69 (dd, J=8.84, 2.53 Hz, 1H), 7.90 (d, J=2.53 Hz, 1H).

Step C: Preparation of tert-Butyl ((S)-8-((4'-(((tert-Butoxycarbonyl)amino)methyl)-4-ethoxy-[1,1'-biphenyl]-3-yl)sulfonyl)-1-oxa-8-azaspiro[4.5]decan-3-yl)((S)-3-(3-(cyclopropylsulfonyl)phenoxy)-2-hydroxypropyl)carbamate A solution of tert-butyl ((S)-8-((5-bromo-2-ethoxyphenyl)sulfonyl)-1-oxa-8-azaspiro[4.5]decan-3-yl) ((S)-3-(3-(cyclopropylsulfonyl)phenoxy)-2-hydroxypropyl)carbamate (233 mg, 0.30 mmol), Pd(dppf)$_2$, DCM (24.77 mg, 30.11 µmol), sodium carbonate (0.33 mL, 0.66 mmol) and (4-(((tert-butoxycarbonyl)amino)methyl)phenyl)boronic acid (90.73 mg, 0.36 mmol) in dioxane (12 mL) was degassed with N$_2$ for 10 min. The reaction was heated at 100° C. for 18 h. After cooling down to room temperature, it was diluted with IPA/DCM (20%) and washed water. The aqueous layer was back extracted with IPA/DCM (20%, 2×). The combined organic layer was dried over Na$_2$SO$_4$, filtered and concentrated. The residue was purified by silica gel column chromatography to give the title compound (126 mg, 47% yield). LCMS m/z=900.8 [M+H]$^+$.

Step D: Preparation of (S)-1-((S)-8-(4'-(Aminomethyl)-4-ethoxybiphenyl-3-ylsulfonyl)-1-oxa-8-azaspiro[4.5]decan-3-ylamino)-3-(3-(cyclopropylsulfonyl)phenoxy)propan-2-ol (Compound 160)

To a solution of tert-butyl ((S)-8-((4'-(((tert-butoxycarbonyl)amino)methyl)-4-ethoxy-[1,1'-biphenyl]-3-yl)sulfonyl)-1-oxa-8-azaspiro[4.5]decan-3-yl)((S)-3-(3-(cyclopropylsulfonyl)phenoxy)-2-hydroxypropyl)carbamate (126 mg, 0.16 mmol) in ACN (4 mL) was added HCl (4N in dioxane, 0.3 mL, 1.2 mmol). The reaction was stirred at room temperature for 3 h. After the reaction was completed, the mixture was concentrated. The residue was purified by prep-HPLC to give TFA salt of the title compound. The TFA salt was converted to the HCl salt of the title compound (68.7 mg, 30% yield). LCMS m/z=700.4 [M+H]$^+$; $^1$H NMR (400 MHz, CD$_3$OD) δ ppm 1.03-1.10 (m, 2H), 1.19-1.25 (m, 2H), 1.49 (t, J=6.95 Hz, 3H), 1.60-1.70 (m, 1H), 1.77-1.85 (m, 1H), 1.85-1.94 (m, 3H), 2.37 (dd, J=13.64, 8.34 Hz, 1H), 2.68 (tt, J=7.96, 4.80 Hz, 1H), 3.06-3.23 (m, 3H), 3.32-3.37 (m, 1H), 3.51-3.64 (m, 2H), 3.91-3.97 (m, 1H), 4.00-4.08 (m, 1H), 4.09-4.15 (m, 3H), 4.17 (s, 2H), 4.22-4.33 (m, 3H), 7.27-7.33 (m, 2H), 7.46 (t, J=2.27 Hz, 1H), 7.50-7.59 (m, 4H), 7.66-7.73 (m, 2H), 7.88 (dd, J=8.72, 2.40 Hz, 1H), 8.08 (d, J=2.53 Hz, 1H).

Example 1.64: Preparation of (S)-1-(3-(Cyclopropylsulfonyl)phenoxy)-3-((R)-8-(3-methyl-3H-imidazo[4,5-b]pyridin-6-ylsulfonyl)-1-oxa-8-azaspiro[4.5]decan-3-ylamino)propan-2-ol (Compound 279). (Method N)

Step A: Preparation of tert-Butyl ((S)-3-(3-(Cyclopropylsulfonyl)phenoxy)-2-hydroxypropyl)((R)-8-((3-methyl-3H-imidazo[4,5-b]pyridin-6-yl)sulfonyl)-1-oxa-8-azaspiro[4.5]decan-3-yl)carbamate To a solution of tert-butyl ((S)-3-(3-(cyclopropylsulfonyl)phenoxy)-2-hydroxypropyl)((R)-1-oxa-8-azaspiro[4.5]decan-3-yl)carbamate (20 mg, 39.17 µmol) in THF (4 mL) was added DIEA (13.64 µL, 78.33 µmol), followed by addition of 3-methyl-3H-imidazo[4,5-b]pyridine-6-sulfonyl chloride (10.89 mg, 47.00 µmol). The reaction was stirred for 2 h. The mixture was diluted with EtOAc, washed with water (3×) and brine, and concentrated. The residue was purified by silica gel column chromatography to give a white solid. LCMS m/z=706.4 [M+H]$^+$; $^1$H NMR (400 M Hz, CD$_3$OD) δ ppm 1.02-1.08 (m, 2H), 1.18-1.24 (m, 2H), 1.43 (s, 9H), 1.60-1.68 (m, 1H), 1.73-1.88 (m, 4H), 1.99-2.04 (m, 1H), 2.71-2.82 (m, 2H), 3.20 (m, 1H), 3.38-3.44 (m, 2H), 3.48-3.52 (m, 2H), 3.76-3.80 (m, 1H), 3.89-3.92 (m, 1H), 3.95-3.97 (m, 1H), 3.99 (s, 3H), 4.01-4.04 (m, 1H), 4.09-4.14 (m, 1H), 4.42-4.50 (m, 1H), 7.23-7.26 (m, 1H), 7.40-7.41 (m, 1H), 7.47 (dt, J=7.96, 1.49 Hz, 1H), 7.52 (t, J=7.88 Hz, 1H), 8.40 (d, J=1.96 Hz, 1H), 8.55 (s, 1H), 8.80 (d, J=1.96 Hz, 1H).

Step B: Preparation of (S)-1-(3-(Cyclopropylsulfonyl)phenoxy)-3-((R)-8-(3-methyl-3H-imidazo[4,5-b]pyridin-6-ylsulfonyl)-1-oxa-8-azaspiro[4.5]decan-3-ylamino)propan-2-ol (Compound 279) as the di-HCl Salt To a solution of tert-butyl ((S)-3-(3-(cyclopropylsulfonyl)phenoxy)-2-hydroxypropyl)((R)-8-((3-methyl-3H-imidazo[4,5-b]pyridin-6-yl)sulfonyl)-1-oxa-8-azaspiro[4.5]decan-3-yl)carbamate (13 mg, 18.42 µmol) in EtOAc (10 mL) was added HCl (671.5 µg, 18.42 µmol). The reaction was stirred for 3 h. The mixture was concentrated to give the title compound as a white solid. LCMS m/z=606.6 [M+H]$^+$; $^1$H NMR (400 M Hz, CD$_3$OD) δ ppm 1.03-1.09 (m, 2H), 1.19-1.24 (m, 2H), 1.65-1.73 (m, 1H), 1.79-1.86 (m, 1H), 1.88-1.98 (m, 1H), 2.32 (dd, J=7.39, 12.94 Hz, 1H), 2.63-2.69 (m, 1H), 2.70-2.82 (m, 2H), 3.16 (d, J=8.53 Hz, 1H), 3.25-3.29 (m, 1H), 3.32-3.37 (m, 1H), 3.50-3.59 (m, 3H), 3.64-3.69 (m, 1H), 3.83-3.90 (m, 1H), 4.00 (d, J=6.64 Hz, 2H), 4.04 (s, 3H), 4.09 (dd, J=3.42, 4.95 Hz, 2H), 4.20-4.26 (m, 1H), 7.27-7.30 (m, 1H), 7.44 (dd, J=1.67, 2.39 Hz, 1H), 7.51 (dt, J=1.56, 7.81 Hz, 1H), 7.55 (t, J=7.82 Hz, 1H), 8.48 (d, J=1.88 Hz, 1H), 8.85 (s, 1H), 8.88 (d, J=1.92 Hz, 1H).

Example 1.65: Preparation of 1-Ethyl-3-((S)-3-((S)-2-hydroxy-3-(3-(methylsulfonyl)phenoxy)propylamino)-1-oxa-8-azaspiro[4.5]decan-8-ylsulfonyl)quinolin-4(1H)-one (Compound 338)

Step A: Preparation of (S)-Benzyl 3-(((S)-2-Hydroxy-3-(3-(methylsulfonyl)phenoxy)propyl)amino)-1-oxa-8-azaspiro[4.5]decane-8-carboxylate A solution of (S)-2-((3-(methylsulfonyl)phenoxy)methyl)oxirane (0.10 g, 0.44 mmol) and (S)-benzyl 3-amino-1-oxa-8-azaspiro[4.5]decane-8-carboxylate (0.25 g, 0.88 mmol) in EtOH (8.76 mL) was heated at 70° C. for 1 day. After cooling down to room temperature, the mixture was concentrated to give the title compound which was used in the next step without further purification. LCMS m/z=519.4 [M+H]$^+$.

Step B: Preparation of (S)-Benzyl 3-((tert-Butoxycarbonyl)((S)-2-hydroxy-3-(3-(methylsulfonyl)phenoxy)propyl)amino)-1-oxa-8-azaspiro[4.5]decane-8-carboxylate To a solution of (S)-benzyl 3-(((S)-2-hydroxy-3-(3-(methylsulfonyl)phenoxy)propyl)amino)-1-oxa-8-azaspiro[4.5]

decane-8-carboxylate (from the previous step) in DCM (8 mL) was added DIEA (0.23 mL, 1.31 mmol) and (Boc)$_2$O (0.29 g, 1.31 mmol). The reaction was stirred room temperature for 16 h. The mixture was extracted with water and brine. The organic layer was dried over Na$_2$SO$_4$, filtered and concentrated. The residue was purified by column chromatography to give the title compound (174.0 mg, 64.2%). LCMS m/z=619.4 [M+H]$^+$; $^1$H NMR (400 MHz, CD$_3$OD) δ ppm 1.47 (s, 9H), 1.48-1.54 (m, 1H), 1.59-1.68 (m, 1H), 1.69-1.77 (m, 2H), 2.04-2.15 (m, 2H), 3.11 (s, 3H), 3.40 (bs, 2H), 3.57 (dd, J=14.65, 4.80 Hz, 1H), 3.65 (t, J=13.01 Hz, 2H), 3.84 (dd, J=8.97, 7.20 Hz, 1H), 3.93-4.12 (m, 4H), 4.16 (ddd, J=7.26, 4.80, 4.61 Hz, 1H), 4.47-4.59 (m, 1H), 5.11 (s, 2H), 7.27-7.34 (m, 2H), 7.34-7.37 (m, 4H), 7.48-7.58 (m, 3H).

Step C: Preparation of tert-Butyl ((S)-2-Hydroxy-3-(3-(methylsulfonyl)phenoxy)propyl)((S)-1-oxa-8-azaspiro[4.5]decan-3-yl)carbamate (S)-Benzyl 3-((tert-butoxycarbonyl)((S)-2-hydroxy-3-(3-(methylsulfonyl)phenoxy)propyl)amino)-1-oxa-8-azaspiro[4.5]decane-8-carboxylate (162 mg, 0.26 mmol) was dissolved in MeOH (8 mL) under N$_2$ followed by addition of Pd/C (30 mg, 28.12 umol). The reaction was placed under H$_2$ balloon and stirred at room temperature overnight. The mixture was filtered through a pad of Celite® and washed with MeOH then concentrate to give the title compound (120 mg, 88.1%) as yellow solid. This material was used in the next step without further purification. LCMS m/z=485.4 [M+H]$^+$; $^1$H NMR (400 MHz, CDCl$_3$) δ ppm 1.50 (s, 9H), 1.53-1.68 (m, 1H), 1.69-1.77 (m, 3H), 1.80 (t, J=5.31 Hz, 1H), 2.04-2.19 (m, 1H), 2.31 (s, 1H), 2.38-2.56 (m, 3H), 2.79 (dd, J=11.12, 5.81 Hz, 1H), 2.95-3.04 (m, 1H), 3.06 (s, 3H), 3.49 (d, J=2.53 Hz, 2H), 3.80 (ddd, J=9.54, 6.25, 3.16 Hz, 1H), 3.89-4.02 (m, 2H), 4.02-4.08 (m, 1H), 4.12 (t, J=3.54 Hz, 1H), 4.56-4.69 (m, 1H), 7.20 (ddd, J=8.08, 2.53, 1.01 Hz, 1H), 7.43-7.52 (m, 2H), 7.53-7.58 (m, 1H).

Step D: Preparation of tert-Butyl ((S)-8-((1-Ethyl-4-oxo-1,4-dihydroquinolin-3-yl)sulfonyl)-1-oxa-8-azaspiro[4.5]decan-3-yl)((S)-2-hydroxy-3-(3-(methylsulfonyl)phenoxy)propyl)carbamate To a solution of tert-butyl ((S)-2-hydroxy-3-(3-(methylsulfonyl)phenoxy)propyl)((S)-1-oxa-8-azaspiro[4.5]decan-3-yl)carbamate (120 mg, 0.25 mmol) in CH$_2$Cl$_2$ (2 mL) at room temperature was added DIEA (86.26 μl, 0.50 mmol) then 1-ethyl-4-oxo-1,4-dihydroquinoline-3-sulfonyl chloride (0.10 g, 0.37 mmol). The reaction was stirred at room temperature overnight. The mixture was diluted with DCM then washed with water and brine. The organic layer was dried over Na$_2$SO$_4$, filtered and concentrated. The residue was purified by column chromatography to give the title compound (92 mg, 51.6%) as a yellow gum. LCMS m/z=720.6 [M+H]$^+$; $^1$H NMR (400 MHz, CD$_3$OD) δ ppm 1.45 (s, 9H), 1.52 (t, J=7.20 Hz, 3H), 1.56-1.63 (m, 1H), 1.72 (dt, J=13.58, 4.33 Hz, 1H), 1.83 (t, J=5.81 Hz, 2H), 1.98-2.10 (m, 2H), 3.08 (s, 3H), 3.20-3.29 (m, 3H), 3.39-3.57 (m, 3H), 3.78 (dd, J=8.84, 7.07 Hz, 1H), 3.91 (t, J=8.21 Hz, 1H), 3.97-4.09 (m, 2H), 4.10-4.18 (m, 1H), 4.48 (q, J=7.16 Hz, 3H), 7.27 (dt, J=7.39, 2.24 Hz, 1H), 7.45-7.52 (m, 3H), 7.56 (ddd, J=8.15, 4.99, 3.03 Hz, 1H), 7.85-7.89 (m, 2H), 8.39 (d, J=7.83 Hz, 1H), 8.66 (s, 1H).

Step E: Preparation of 1-Ethyl-3-((S)-3-((S)-2-hydroxy-3-(3-(methylsulfonyl)phenoxy)propylamino)-1-oxa-8-azaspiro[4.5]decan-8-ylsulfonyl)quinolin-4(1H)-one (Compound 338)

tert-Butyl ((S)-8-((1-ethyl-4-oxo-1,4-dihydroquinolin-3-yl)sulfonyl)-1-oxa-8-azaspiro[4.5]decan-3-yl)((S)-2-hydroxy-3-(3-(methylsulfonyl)phenoxy)propyl)carbamate (92 mg, 0.13 mmol) was stirred in TFA/DCM (1:3, 2 mL) at room temperature. After the reaction completed, solvent was removed. The residue was purified by prep-HPLC. The obtained material was dissolved in water and neutralized with saturated NaHCO$_3$ then extracted with IPA/DCM (10%, 2×100 mL). The organic layer was washed with brined, dried over Na$_2$SO$_4$, filtered and concentrated. The free base was dissolved in acetone and added HCl (4N, 0.2 mL). The resulting solution was stirred for 2 h then concentrated to give the title compound (63.5 mg, 75.1%). LCMS m/z=620.4 [M+H]$^+$; $^1$H NMR (400 MHz, DMSO-d$_6$) δ ppm 1.38 (t, J=7.07 Hz, 3H), 1.51-1.62 (m, 1H), 1.62-1.71 (m, 1H), 1.72-1.86 (m, 3H), 2.18 (dd, J=13.01, 8.46 Hz, 1H), 2.90-3.01 (m, 1H), 3.05-3.20 (m, 3H), 3.21 (s, 3H), 3.35-3.42 (m, 2H), 3.77-3.83 (m, 1H), 3.87-4.00 (m, 2H), 4.07 (d, J=5.05 Hz, 2H), 4.12-4.22 (m, 1H), 4.46 (q, J=6.82 Hz, 2H), 5.91 (bs, 1H), 7.30 (dd, J=7.71, 2.15 Hz, 1H), 7.44 (t, J=1.77 Hz, 1H), 7.49-7.56 (m, 2H), 7.57 (t, J=7.83 Hz, 1H), 7.82-7.90 (m, 2H), 8.24 (d, J=1.26 Hz, 1H), 8.63 (s, 1H), 8.85 (bs, 1H), 9.02 (bs, 1H).

Example 1.66: Preparation of 1-Ethyl-3-((S)-3-((R)-2-hydroxy-3-(3-(methylsulfonyl)phenoxy)propylamino)-1-oxa-8-azaspiro[4.5]decan-8-ylsulfonyl) quinolin-4(1H)-one (Compound 296)

Step A: Preparation of (R)-2-((3-(Methylsulfonyl) phenoxy)methyl)oxirane

To a solution of 3-(methylsulfonyl)phenol (1.34 g, 6.98 mmol) in acetone (34.87 mL) was added potassium carbonate (1.93 g, 13.95 mmol). The reaction mixture was stirred at room temperature for 10 min followed by addition of (R)-oxiran-2-ylmethyl 3-nitrobenzenesulfonate (1.90 g, 6.98 mmol). The reaction mixture was heated at 70° C. overnight. After cooling down to room temperature, the reaction mixture was filtered through a pad of Celite® and washed with acetone then concentrated. The residue was purified by silica gel column chromatography to give the title compound (1.43 g, 88.0% yield) as colorless oil then solidified after standing at room temperature. $^1$H NMR (400 MHz, CDCl$_3$) δ ppm 2.79 (dd, J=4.93, 2.65 Hz, 1H), 2.94 (t, J=4.04 Hz, 1H), 3.06 (s, 3H), 3.35-3.41 (m, 1H), 4.00 (dd, J=10.99, 5.94 Hz, 1H), 4.37 (dd, J=11.12, 2.78 Hz, 1H), 7.22 (ddd, J=8.08, 2.53, 1.01 Hz, 1H), 7.48 (t, J=2.27 Hz, 1H), 7.50 (d, J=8.08 Hz, 1H), 7.54-7.58 (m, 1H).

Step B: Preparation of (S)-Benzyl 3-(((R)-2-Hydroxy-3-(3-(methylsulfonyl)phenoxy)propyl)amino)-1-oxa-8-azaspiro[4.5]decane-8-carboxylate A solution of (R)-2-((3-(methylsulfonyl)phenoxy)methyl) oxirane (100 mg, 0.44 mmol) and (S)-benzyl 3-amino-1-oxa-8-azaspiro[4.5]decane-8-carboxylate (0.25 g, 0.88 mmol) in EtOH (8.8 mL) was heated at 70° C. overnight. After cooling down to room temperature, the mixture was concentrated. The residue was re-dissolved in DCM and washed with water and brine. The organic layer was dried over Na$_2$SO$_4$, filtered and concentrated to give the title compound which was used directly in the next step. LCMS m/z=519.6 [M+H]$^+$.

Step C: Preparation of (S)-Benzyl 3-((tert-Butoxycarbonyl)((R)-2-hydroxy-3-(3-(methylsulfonyl)phenoxy)propyl)amino)-1-oxa-8-azaspiro[4.5]decane-8-carboxylate To a solution of (S)-benzyl 3-(((R)-2-hydroxy-3-(3-(methylsulfonyl)phenoxy)propyl)amino)-1-oxa-8-azaspiro

[4.5]decane-8-carboxylate (326 mg, 0.63 mmol) in DCM (8.8 mL) at room temperature was added DIEA (0.15 mL, 0.88 mmol) and (Boc)$_2$O (0.19 g, 0.88 mmol). The reaction was stirred at room temperature until completion. The mixture was diluted with DCM and washed with water and brine. The organic layer was dried over Na$_2$SO$_4$, filtered and concentrated. The residue was purified by column chromatography to give the title compound (176 mg, 64.9%) as a white foam. LCMS m/z=619.6 [M+H]$^+$; $^1$H NMR (400 MHz, MeOD) δ ppm 1.40-1.52 (m, 11H), 1.59-1.74 (m, 3H), 1.80 (dd, J=12.88, 8.08 Hz, 1H), 2.06 (dd, J=12.76, 8.46 Hz, 1H), 3.03 (s, 3H), 3.17-3.29 (m, 1H), 3.33-3.42 (m, 2H), 3.50 (dd, J=14.65, 3.79 Hz, 1H), 3.59-3.69 (m, 2H), 3.89-4.00 (m, 4H), 4.49-4.60 (m, 1H), 5.07 (s, 2H), 7.18 (ddd, J=6.69, 2.65, 2.53 Hz, 1H), 7.25-7.35 (m, 5H), 7.42 (t, J=1.77 Hz, 1H), 7.46-7.51 (m, 2H).

Step D: Preparation of tert-Butyl ((R)-2-Hydroxy-3-(3-(methylsulfonyl)phenoxy)propyl)((S)-1-oxa-8-azaspiro[4.5]decan-3-yl)carbamate To a solution of (S)-benzyl 3-((tert-butoxycarbonyl)((R)-2-hydroxy-3-(3-(methylsulfonyl)phenoxy)propyl)amino)-1-oxa-8-azaspiro[4.5]decane-8-carboxylate (176 mg, 0.28 mmol) in MeOH (10 mL) was added Palladium/C (30.27 mg, 28.44 nmol). The reaction was placed under H$_2$ balloon and stirred at room temperature overnight. The mixture was filtered through a pad of Celite® and washed with MeOH. The filtrate was concentrated to give the title compound (137 mg, 68.9%) as a yellow foam. This material will be used in the next step without further purification. LCMS m/z=485.4 [M+H]$^+$; $^1$H NMR (400 MHz, CD$_3$OD) δ ppm 1.47 (s, 9H), 1.52-1.81 (m, 4H), 1.86 (dd, J=12.63, 8.34 Hz, 1H), 2.06-2.16 (m, 1H), 2.26 (s, 1H), 2.38-2.56 (m, 1H), 2.73-2.81 (m, 1H), 2.91-3.03 (m, 1H), 3.12 (s, 3H), 3.23-3.29 (m, 1H), 3.56 (ddd, J=14.53, 4.55, 1.89 Hz, 1H), 3.89-3.97 (m, 1H), 3.98-4.11 (m, 3H), 4.15-4.22 (m, 1H), 4.55 (dq, J=7.71, 7.54 Hz, 1H), 7.27-7.33 (m, 1H), 7.49-7.52 (m, 1H), 7.52-7.59 (m, 2H).

Step E: Preparation of tert-Butyl ((S)-8-((1-Ethyl-4-oxo-1,4-dihydroquinolin-3-yl)sulfonyl)-1-oxa-8-azaspiro[4.5]decan-3-yl)((R)-2-hydroxy-3-(3-(methylsulfonyl)phenoxy)propyl)carbamate To a solution of tert-butyl ((R)-2-hydroxy-3-(3-(methylsulfonyl)phenoxy)propyl)((S)-1-oxa-8-azaspiro[4.5]decan-3-yl)carbamate (73 mg, 0.15 mmol) in CH$_2$Cl$_2$ (2 mL) was added DIEA (89.21 µL, 0.51 mmol) and 1-ethyl-4-oxo-1,4-dihydroquinoline-3-sulfonyl chloride (82.27 mg, 0.18 mmol). The reaction was stirred at room temperature overnight. Next day, additional tert-butyl ((R)-2-hydroxy-3-(3-(methylsulfonyl)phenoxy)propyl)((S)-1-oxa-8-azaspiro[4.5]decan-3-yl)carbamate (23 mg, 0.05 mmol) and DIEA (30 uL, 0.17 mmol) were added. The reaction was stirred for another 5 h then concentrated. The residue was purified by silica gel column chromatography to give the title compound (67 mg, 61.8%) as a clear glass. LCMS m/z=720.6 [M+H]$^+$; $^1$H NMR (400 MHz, CD$_3$OD) δ ppm 1.45 (s, 9H), 1.52 (t, J=7.20 Hz, 3H), 1.57-1.66 (m, 1H), 1.69-1.77 (m, 1H), 1.77-1.82 (m, 2H), 1.85 (dd, J=12.76, 8.21 Hz, 1H), 2.07 (dd, J=12.88, 8.59 Hz, 1H), 3.08 (s, 3H), 3.20-3.30 (m, 3H), 3.41-3.49 (m, 2H), 3.50-3.56 (m, 1H), 3.88 (dd, J=7.58, 1.77 Hz, 1H), 3.95-4.02 (m, 2H), 4.03-4.08 (m, 1H), 4.12-4.19 (m, 1H), 4.44-4.56 (m, 3H), 7.27 (ddd, J=7.64, 2.08, 1.89 Hz, 1H), 7.45-7.52 (m, 3H), 7.53-7.58 (m, 1H), 7.85-7.91 (m, 2H), 8.39 (dt, J=7.89, 0.85 Hz, 1H), 8.65 (s, 1H).

Step F: Preparation of 1-Ethyl-3-((S)-3-((R)-2-hydroxy-3-(3-(methylsulfonyl)phenoxy)propylamino)-1-oxa-8-azaspiro[4.5]decan-8-ylsulfonyl)quinolin-4(1H)-one (Compound 296)

To a solution of tert-butyl ((S)-8-((1-ethyl-4-oxo-1,4-dihydroquinolin-3-yl)sulfonyl)-1-oxa-8-azaspiro[4.5]decan-3-yl)((R)-2-hydroxy-3-(3-(methylsulfonyl)phenoxy)propyl)carbamate (67 mg, 93.07 µmol) in CH$_2$Cl$_2$ (1.50 mL) was added TFA (0.5 mL). The resulting solution was stirred at ambient temperature for 2 h then concentrated. The residue was purified by prep-HPLC to give the title compound as TFA salt which was then converted to the HCl salt (53.5 mg, 87.6%) as a solid. LCMS m/z=620.4 [M+H]$^+$; $^1$H NMR (400 MHz, DMSO-d$_6$) δ ppm 1.38 (t, J=7.07 Hz, 3H), 1.52-1.61 (m, 1H) 1.62-1.70 (m, 1H), 1.71-1.82 (m, 3H), 2.20 (dd, J=12.88, 7.83 Hz, 1H), 2.94-3.05 (m, 1H), 3.05-3.20 (m, 4H), 3.21 (s, 3H), 3.26-3.42 (m, 1H), 3.78-3.86 (m, 1H), 3.88-3.99 (m, 2H), 4.07 (d, J=5.05 Hz, 2H), 4.12-4.21 (m, 1H), 4.46 (q, J=7.24 Hz, 2H), 5.90 (d, J=4.80 Hz, 1H), 7.30 (dd, J=8.08, 1.77 Hz, 1H), 7.44 (t, J=1.52 Hz, 1H), 7.49-7.56 (m, 2H), 7.59 (t, J=7.83 Hz, 1H), 7.82-7.91 (m, 2H), 8.24 (dd, J=7.33, 1.26 Hz, 1H), 8.63 (s, 1H), 8.88 (bs, 2H).

Example 1.67: Preparation of 1-Ethyl-3-((R)-3-((R)-2-hydroxy-3-(3-(methylsulfonyl)phenoxy)propylamino)-1-oxa-8-azaspiro[4.5]decan-8-ylsulfonyl)quinolin-4(1H)-one (Compound 337)

Step A: Preparation of (R)-Benzyl 3-(((R)-2-Hydroxy-3-(3-(methylsulfonyl)phenoxy)propyl)amino)-1-oxa-8-azaspiro[4.5]decane-8-carboxylate A solution of (R)-2-((3-(methylsulfonyl)phenoxy)methyl)oxirane (100 mg, 0.44 mmol) and (R)-benzyl 3-amino-1-oxa-8-azaspiro[4.5]decane-8-carboxylate (0.25 g, 0.88 mmol) in EtOH (8.8 mL) was heated at 70° C. overnight. After cooling down to room temperature, the mixture was concentrated. The residue was added ethyl acetate then washed with water and brine. The organic layer was dried over Na$_2$SO$_4$, filtered and concentrated to give the title compound which was used in the next step without purification. LCMS m/z=519.6 [M+H]$^+$.

Step B: Preparation of (R)-Benzyl 3-((tert-Butoxycarbonyl)((R)-2-hydroxy-3-(3-(methylsulfonyl)phenoxy)propyl)amino)-1-oxa-8-azaspiro[4.5]decane-8-carboxylate To a solution of (R)-benzyl 3-(((S)-2-hydroxy-3-(3-(methylsulfonyl)phenoxy)propyl)amino)-1-oxa-8-azaspiro[4.5]decane-8-carboxylate (176 mg, 0.34 mmol) in DCM (8.8 mL) at room temperature were added DIEA (0.15 mL, 0.88 mmol) and (Boc)$_2$O (0.19 g, 0.88 mmol). The reaction mixture was stirred at room temperature overnight. The mixture was diluted with DCM then washed with water and brine, dried over Na$_2$SO$_4$, filtered and concentrated. The residue was purified by column chromatography to give the title compound (166 mg, 61.2%) as a white foam solid. LCMS m/z=619.6 [M+H]$^+$; $^1$H NMR (400 MHz, CD$_3$OD) δ ppm 1.46 (s, 9H), 1.48-1.54 (m, 1H), 1.61-1.69 (m, 1H), 1.70-1.77 (m, 2H), 2.06-2.14 (m, 2H), 3.11 (s, 3H), 3.34-3.46 (m, 2H), 3.54-3.70 (m, 3H), 3.84 (dd, J=8.84, 7.07 Hz, 1H), 3.94-4.11 (m, 3H), 4.13-4.20 (m, 1H), 4.48-4.57 (m, 2H), 5.11 (s, 2H), 7.27-7.37 (m, 6H), 7.50 (t, J=1.26 Hz, 1H), 7.52-7.58 (m, 2H).

Step C: Preparation of tert-Butyl ((R)-2-Hydroxy-3-(3-(methylsulfonyl)phenoxy)propyl)((R)-1-oxa-8-azaspiro[4.5]decan-3-yl)carbamate To a solution of (R)-benzyl 3-((tert-butoxycarbonyl)((R)-2-hydroxy-3-(3-(methylsulfonyl)phenoxy)propyl)amino)-1-oxa-8-azaspiro[4.5]decane-8-carboxylate (187 mg, 0.30 mmol) in MeOH (10 mL) was added Palladium/C (32.16 mg, 30.22 µmol) under nitrogen. The reaction was placed under $H_2$ balloon and stirred at room temperature overnight. The mixture was filtered through a pad of Celite® then washed with MeOH. The filtrate was concentrated to give the title compound (137 mg, 93.5%) as a white foam. This material was used in the next step without further purification. LCMS m/z=485.4 [M+H]$^+$; $^1$H NMR (400 MHz, CD$_3$OD) δ ppm 1.47 (s, 9H), 1.49-1.84 (m, 4H), 2.08 (t, J=7.96 Hz, 2H), 2.37-2.66 (m, 2H), 2.67-2.78 (m, 1H), 2.87-3.00 (m, 1H), 3.12 (s, 3H), 3.25-3.34 (m, 1H), 3.57 (ddd, J=14.65, 4.80, 1.52 Hz, 1H), 3.78-3.85 (m, 1H), 3.95 (ddd, J=8.78, 7.64, 5.56 Hz, 1H), 3.99-4.06 (m, 1H), 4.06-4.11 (m, 1H), 4.13-4.21 (m, 1H), 4.46-4.57 (m, 1H), 7.30 (dt, J=7.01, 2.43 Hz, 1H), 7.50 (t, J=2.02 Hz, 1H), 7.52-7.58 (m, 2H).

Step D: Preparation of tert-Butyl ((R)-8-((1-Ethyl-4-oxo-1,4-dihydroquinolin-3-yl)sulfonyl)-1-oxa-8-azaspiro[4.5]decan-3-yl)((R)-2-hydroxy-3-(3-(methylsulfonyl)phenoxy)propyl)carbamate To a solution of tert-butyl ((R)-2-hydroxy-3-(3-(methylsulfonyl)phenoxy)propyl)((R)-1-oxa-8-azaspiro[4.5]decan-3-yl)carbamate (137 mg, 0.28 mmol) in CH$_2$Cl$_2$ (3 mL) was added DIEA (0.17 mL, 0.96 mmol) and 1-ethyl-4-oxo-1,4-dihydroquinoline-3-sulfonyl chloride (0.13 g, 0.28 mmol). The reaction was stirred at room temperature overnight then quenched with water and extracted with IPA/DCM (10%, 2×100 mL). The combined organic layers were washed with brine, and dried over Na$_2$SO$_4$ then filtered. The filtrate was concentrated and purified by silica gel column chromatography to give the title compound as white foam solid (116 mg, 57.0%). LCMS m/z=720.6 [M+H]$^+$; $^1$H NMR (400 MHz, DMSO-d$_6$) δ ppm 1.32-1.37 (m, 13H), 1.45-1.54 (m, 1H), 1.56-1.64 (m, 1H), 1.67-1.73 (m, 1H), 1.92-1.98 (m, 1H), 3.04-3.22 (m, 7H), 3.33-3.44 (m, 2H), 3.63 (t, J=7.96 Hz, 1H), 3.79 (t, J=8.21 Hz, 1H), 3.90-4.01 (m, 3H), 4.34-4.50 (m, 3H), 5.20 (d, J=4.55 Hz, 1H), 7.25 (dd, J=8.08, 2.27 Hz, 1H), 7.39 (s, 1H), 7.44-7.49 (m, 1H), 7.50-7.57 (m, 2H), 7.82-7.90 (m, 2H), 8.26 (d, J=8.59 Hz, 1H), 8.61 (s, 1H).

Step E: Preparation of 1-Ethyl-3-((R)-3-((R)-2-hydroxy-3-(3-(methylsulfonyl)phenoxy) propylamino)-1-oxa-8-azaspiro[4.5]decan-8-ylsulfonyl)quinolin-4(1H)-one (Compound 337)

A solution of tert-butyl ((R)-8-((1-ethyl-4-oxo-1,4-dihydroquinolin-3-yl)sulfonyl)-1-oxa-8-azaspiro[4.5]decan-3-yl)((R)-2-hydroxy-3-(3-(methylsulfonyl)phenoxy)propyl) carbamate (116 mg, 0.16 mmol) in TFA (0.5 mL, 6.529 mmol) and CH$_2$Cl$_2$ (1.50 mL) was stirred at room temperature for 2 h then concentrated. The residue was purified by prep-HPLC to give the title compound (74.3 mg, 70.3%). LCMS m/z=620.4 [M+H]$^+$; $^1$H NMR (400 MHz, D20) δ ppm 1.54 (t, J=7.20 Hz, 3H), 1.66-1.76 (m, 1H), 1.78-1.93 (m, 4H), 2.39 (dd, J=13.39, 7.58 Hz, 1H), 3.08-3.20 (m, 1H), 3.20-3.24 (m, 1H), 3.24 (s, 3H), 3.25-3.33 (m, 2H), 3.40-3.49 (m, 2H), 3.87-4.02 (m, 2H), 4.09-4.15 (m, 1H), 4.16-4.25 (m, 2H), 4.27-4.33 (m, 1H), 4.52 (q, J=7.24 Hz, 2H), 7.37 (dt, J=8.08, 1.26 Hz, 1H), 7.51 (s, 1H), 7.54-7.64 (m, 2H), 7.67 (t, J=7.33 Hz, 1H), 7.91-8.01 (m, 2H), 8.36 (d, J=8.08 Hz, 1H), 8.77 (s, 1H).

Example 1.68: Preparation of Additional Compounds of the Present Invention

The following compounds were prepared using similar methods to the ones described in the above examples from proper intermediate(s) obtained through commercial sources or synthesized as describe above or according to literature preparation. The specific method(s) used to prepare the compounds and the LCMS [M+H]$^+$ for each compound are provided below:

Compound 2, Intermediates used: (R)-2-(chloromethyl)oxirane, 3-(methylsulfonyl)phenol, naphthalene-2-sulfonyl chloride, Method C, LCMS m/z=575.4 [M+H]$^+$; Compound 5, Intermediates used: 3-(methylsulfonyl)phenol, 3-((2-hydroxyethyl)sulfonyl)phenol, Method C, LCMS m/z=605.4 [M+H]$^+$; Compound 6, Intermediates used: 8-(naphthalen-2-ylsulfonyl)-1-oxa-8-azaspiro[4.5]decan-3-amine, C1, Method D, LCMS m/z=603.4 [M+H]$^+$; Compound 7, Intermediates used: 8-(naphthalen-2-ylsulfonyl)-1-oxa-8-azaspiro[4.5]decan-3-amine, C2, Method D, LCMS m/z=615 [M+H]$^+$; Compound 8, Intermediates used: 8-(naphthalen-2-ylsulfonyl)-1-oxa-8-azaspiro[4.5]decan-3-amine, C3, Method D, LCMS m/z=603.4 [M+H]$^+$; Compound 9, Intermediates used: 8-(naphthalen-2-ylsulfonyl)-1-oxa-8-azaspiro[4.5]decan-3-amine, C4, Method D, LCMS m/z=657.4 [M+H]$^+$; Compound 10, Intermediates used: 8-(naphthalen-2-ylsulfonyl)-1-oxa-8-azaspiro[4.5]decan-3-amine, C5, Method D, LCMS m/z=617.4 [M+H]$^+$; Compound 11, Intermediates used: 8-(naphthalen-2-ylsulfonyl)-1-oxa-8-azaspiro[4.5]decan-3-amine, C6, Method D, LCMS m/z=631.6 [M+H]$^+$; Compound 12, Intermediates used: benzyl 3-((tert-butoxycarbonyl)amino)-1-oxa-8-azaspiro[4.5]decane-8-carboxylate, naphthalene-2-sulfonyl chloride, C7, Method C, LCMS m/z=600.4 [M+H]$^+$; Compound 13, Intermediates used: benzyl 3-((tert-butoxycarbonyl)amino)-1-oxa-8-azaspiro[4.5]decane-8-carboxylate, naphthalene-2-sulfonyl chloride, C8, Method C, LCMS m/z=629.4 [M+H]$^+$; Compound 14, Intermediates used: benzyl 3-((tert-butoxycarbonyl)amino)-1-oxa-8-azaspiro[4.5]decane-8-carboxylate, naphthalene-2-sulfonyl chloride, C9, Method C, LCMS m/z=671.4 [M+H]$^+$; Compound 16, Intermediates used: tert-butyl (8-(naphthalen-2-ylsulfonyl)-1-oxa-8-azaspiro[4.5]decan-3-yl)((S)-oxiran-2-ylmethyl)carbamate, C11, Method C, LCMS m/z=657.6 [M+H]$^+$; Compound 17, Intermediates used: 8-(naphthalen-2-ylsulfonyl)-1-oxa-8-azaspiro[4.5]decan-3-amine, C12, Method D, LCMS m/z=651.6 [M+H]$^+$; Compound 18, Intermediates used: benzyl 3-((tert-butoxycarbonyl)amino)-1-oxa-8-azaspiro[4.5]decane-8-carboxylate, naphthalene-2-sulfonyl chloride, C62, Method C, LCMS m/z=615.4 [M+H]$^+$; Compound 19, Intermediates used: benzyl 3-((tert-butoxycarbonyl)amino)-1-oxa-8-azaspiro[4.5]decane-8-carboxylate, naphthalene-2-sulfonyl chloride, C14, Method C, LCMS m/z=629.6 [M+H]$^+$; Compound 20, Intermediates used: benzyl 3-((tert-butoxycarbonyl)amino)-1-oxa-8-azaspiro[4.5]decane-8-carboxylate, naphthalene-2-sulfonyl chloride, C15, Method C, LCMS m/z=651.2 [M+H]$^+$; Compound 21, Intermediates used: benzyl 3-((tert-butoxycarbonyl)amino)-1-oxa-8- azaspiro[4.5]decane-8-carboxylate, naphthalene-2-sulfonyl chloride, C16, Method C, LCMS m/z=616.2 [M+H]+; Compound 22, Intermediates used: benzyl 3-((tert-butoxycarbonyl)amino)-1-oxa-8-azaspiro[4.5]decane-8-carboxylate, naphthalene-2-sulfonyl chloride, C17, Method C, LCMS m/z=604 [M+H]+; Compound 23, Intermediates used: (R)-8-(naphthalen-2-ylsulfonyl)-1-oxa-8-azaspiro[4.5]decan-3-amine, (R)-2-((3-(methylsulfonyl)phenoxy)methyl)oxirane, Method D, LCMS m/z=575.4 [M+H]+; Compound 24, Intermediates used: 8-(naphthalen-2-ylsulfonyl)-1-oxa-8-azaspiro[4.5]decan-3-amine, (S)-2-((3-iodophenoxy)methyl)oxirane, sodium oxetane-3-sulfinate, Methods B: Step D and I: Step B, LCMS m/z=617.4 [M+H]+; Compound 25, Intermediates used: 8-(naphthalen-2-ylsulfonyl)-1-oxa-8-azaspiro[4.5]decan-3-amine, C19, Method D, LCMS m/z=617.4 [M+H]+; Compound 26, Intermediates used: (S)-8-(naphthalen-2-ylsulfonyl)-1-oxa-8-azaspiro[4.5]decan-3-amine, C10, Method D, LCMS m/z=589.4 [M+H]+; Compound 27, Intermediates used: (R)-8-(naphthalen-2-ylsulfonyl)-1-oxa-8-azaspiro[4.5]decan-3-amine, C10, Method D, LCMS m/z=589.2 [M+H]+; Compound 29, Intermediates used: (2S)-1-(1-oxa-8-azaspiro[4.5]decan-3-ylamino)-3-(3-(methylsulfonyl)phenoxy)propan-2-ol, 5,6,7,8-tetrahydronaphthalene-2-sulfonyl chloride, Method J, LCMS m/z=579.8 [M+H]+; Compound 30, Intermediates used: (2S)-1-(1-oxa-8-azaspiro[4.5]decan-3-ylamino)-3-(3-(methylsulfonyl)phenoxy)propan-2-ol, 7-chlorobenzo[c][1,2,5]oxadiazole-4-sulfonyl chloride, Method J, LCMS m/z=601.4 [M+H]+; Compound 31, Intermediates used: tert-butyl ((S)-2-hydroxy-3-(3-(methylsulfonyl)phenoxy)propyl)(1-oxa-8-azaspiro[4.5]decan-3-yl)carbamate, 3-chlorobenzene-1-sulfonyl chloride, Method E: (Step C, D), LCMS m/z=559 [M+H]+; Compound 32, Intermediates used: (2S)-1-(1-oxa-8-azaspiro[4.5]decan-3-ylamino)-3-(3-(methylsulfonyl)phenoxy)propan-2-ol, 4-methyl-3,4-dihydro-2H-benzo[b][1,4]oxazine-6-sulfonyl chloride, Method J, LCMS m/z=556.4 [M+H]+; Compound 33, Intermediates used: (S)-8-(naphthalen-2-ylsulfonyl)-1-oxa-8-azaspiro[4.5]decan-3-amine, (R)-2-((3-(methylsulfonyl)phenoxy)methyl)oxirane, Method D, LCMS m/z=575.4 [M+H]+; Compound 34, Intermediates used: (S)-8-(naphthalen-2-ylsulfonyl)-1-oxa-8-azaspiro[4.5]decan-3-amine, (S)-2-((3-(oxiran-2-ylmethoxy)phenyl)sulfonyl)ethanol, Method B: Step D, LCMS m/z=606.4 [M+H]+; Compound 35, Intermediates used: (R)-8-(naphthalen-2-ylsulfonyl)-1-oxa-8-azaspiro[4.5]decan-3-amine, (S)-2-((3-(oxiran-2-ylmethoxy)phenyl)sulfonyl)ethanol, Method B: Step D, LCMS m/z=605.6 [M+H]+; Compound 36, Intermediates used: tert-butyl (84(3-bromophenyl)sulfonyl)-1-oxa-8-azaspiro[4.5]decan-3-yl)((S)-2-hydroxy-3-(3-(methylsulfonyl)phenoxy)propyl)carbamate, (1-ethyl-1H-pyrazol-4-yl)boronic acid, Method H: (Step C, E), LCMS m/z=619.4 [M+H]+; Compound 37, Intermediates used: tert-butyl (84(3-bromophenyl)sulfonyl)-1-oxa-8-azaspiro[4.5]decan-3-yl)((S)-2-hydroxy-3-(3-(methylsulfonyl)phenoxy)propyl)carbamate, tert-butyl 4-(4,4,5,5-tetramethyl-1,3,2-dioxaborolan-2-yl)-1H-pyrazole-1-carboxylate, Method H: (Step C, E), LCMS m/z=591.2 [M+H]+; Compound 38, Intermediates used: tert-butyl (84(3-bromophenyl)sulfonyl)-1-oxa-8-azaspiro[4.5]decan-3-yl)((S)-2-hydroxy-3-(3-(methylsulfonyl)phenoxy)propyl)carbamate, 1-propyl-4-(4,4,5,5-tetramethyl-1,3,2-dioxaborolan-2-yl)-1H-pyrazole, Method H: (Step C, E), LCMS m/z=633.6 [M+H]+; Compound 39, Intermediates used: tert-butyl (84(3-bromophenyl)sulfonyl)-1-oxa-8-azaspiro[4.5]decan-3-yl)((S)-2-hydroxy-3-(3-(methylsulfonyl)phenoxy)propyl)carbamate, 1-cyclopropyl-4-(4,4,5,5-tetramethyl-1,3,2-dioxaborolan-2-yl)-1H-pyrazole, Method H: (Step C, E), LCMS m/z=631.4 [M+H]+; Compound 40, Intermediates used: tert-butyl (8-((3-bromophenyl)sulfonyl)-1-oxa-8-azaspiro[4.5]decan-3-yl)((S)-2-hydroxy-3-(3-(methylsulfonyl)phenoxy)propyl)carbamate, (1-methyl-1H-pyrazol-4-yl)boronic acid, Method H: (Step C, E), LCMS m/z=605.6 [M+H]+; Compound 41, Intermediates used: tert-butyl (84(3-bromophenyl)sulfonyl)-1-oxa-8-azaspiro[4.5]decan-3-yl)((S)-2-hydroxy-3-(3-(methylsulfonyl)phenoxy)propyl)carbamate, (4-(((tert-butoxycarbonyl)amino)methyl)phenyl)boronic acid, Method H: (Step C, E), LCMS m/z=630 [M+H]+; Compound 42, Intermediates used: tert-butyl (84(3-bromophenyl)sulfonyl)-1-oxa-8-azaspiro[4.5]decan-3-yl)((S)-2-hydroxy-3-(3-(methylsulfonyl)phenoxy)propyl)carbamate, (4-sulfamoylphenyl)boronic acid, Method H: (Step C, E), LCMS m/z=680.4 [M+H]+; Compound 43, Intermediates used: tert-butyl (8-((3-bromophenyl)sulfonyl)-1-oxa-8-azaspiro[4.5]decan-3-yl)((S)-2-hydroxy-3-(3-(methylsulfonyl)phenoxy)propyl)carbamate, pyridin-4-ylboronic acid, Method H: (Step C, E), LCMS m/z=602.2 [M+H]+; Compound 44, Intermediates used: tert-butyl (84(3-bromophenyl)sulfonyl)-1-oxa-8-azaspiro[4.5]decan-3-yl)((S)-2-hydroxy-3-(3-(methylsulfonyl)phenoxy)propyl)carbamate, (2-methylpyridin-4-yl)boronic acid, Method H: Step, C, E, LCMS m/z=617.4 [M+H]+; Compound 45, Intermediates used: tert-butyl (84(3-bromophenyl)sulfonyl)-1-oxa-8-azaspiro[4.5]decan-3-yl)((S)-2-hydroxy-3-(3-(methylsulfonyl)phenoxy)propyl)carbamate, 2-(4,4,5,5-tetramethyl-1,3,2-dioxaborolan-2-yl)pyridine, Method H: (Step C, E), LCMS m/z=602.4 [M+H]+; Compound 46, Intermediates used: tert-butyl ((S)-2-hydroxy-3-(3-(methylsulfonyl)phenoxy)propyl)(1-oxa-8-azaspiro[4.5]decan-3-yl)carbamate, pyridine-3-sulfonyl chloride, Method H: (Step B, E), LCMS m/z=526.6 [M+H]+; Compound 47, Intermediates used: tert-butyl ((S)-2-hydroxy-3-(3-(methylsulfonyl)phenoxy)propyl)(1-oxa-8-azaspiro[4.5]decan-3-yl)carbamate, benzenesulfonyl chloride, Method H: (Step B, E), LCMS m/z=525.6 [M+H]+; Compound 48, Intermediates used: tert-butyl ((S)-2-hydroxy-3-(3-(methylsulfonyl)phenoxy)propyl)(1-oxa-8-azaspiro[4.5]decan-3-yl)carbamate, 3-methylbenzene-1-sulfonyl chloride, Method H: (Step B, E), LCMS m/z=539.4 [M+H]+; Compound 49, Intermediates used: tert-butyl ((S)-2-hydroxy-3-(3-(methylsulfonyl)phenoxy)propyl)(1-oxa-8-azaspiro[4.5]decan-3-yl)carbamate, 3-methoxybenzene-1-sulfonyl chloride, Method H: (Step B, E), LCMS m/z=555.6 [M+H]+; Compound 50, Intermediates used: tert-butyl ((S)-2-hydroxy-3-(3-(methylsulfonyl)phenoxy)propyl)(1-oxa-8-azaspiro[4.5]decan-3-yl)carbamate, 3-(trifluoromethyl)benzene-1-sulfonyl chloride, Method H: (Step B, E), LCMS m/z=593.4 [M+H]+; Compound 51, Intermediates used: tert-butyl ((S)-2-hydroxy-3-(3-(methylsulfonyl)phenoxy)propyl)(1-oxa-8-azaspiro[4.5]decan-3-yl)carbamate, 5-phenylthiophene-2-sulfonyl chloride, Method H: (Step B, E), LCMS m/z=607.6 [M+H]+; Compound 52, Intermediates used: tert-butyl ((S)-2-hydroxy-3-(3-(methylsulfonyl)phenoxy)propyl)(1-oxa-8-azaspiro[4.5]decan-3-yl)carbamate, 3,5-dimethylisoxazole-4-sulfonyl chloride, Method H: (Step B, E), LCMS m/z=544.4 [M+H]+; Compound 53, Intermediates used: tert-butyl ((S)-2-hydroxy-3-(3-(methylsulfonyl)phenoxy)propyl)(1-oxa-8-azaspiro[4.5]decan-3-yl)carbamate, 3-oxo-3,4-dihydro-2H-benzo[b][1,4]oxazine-6-sulfonyl chloride, Method H: (Step B, E), LCMS m/z=596.4 [M+H]+; Compound 54, Intermediates used: tert-butyl ((S)-2-hydroxy-3-(3-(methylsulfonyl)phenoxy)propyl)(1-oxa-8-azaspiro[4.5]decan-3-yl)carbamate, 3-fluorobenzene-1-sulfonyl chloride, Method H: (Step B, E), LCMS m/z=543.4 [M+H]+; Compound 55, Intermediates used: tert-butyl ((S)-2-hydroxy-3-(3-(methylsulfonyl)phenoxy)propyl)(1-oxa-8-azaspiro[4.5]decan-3-yl)carbamate, 3-cyanobenzene-1-sulfonyl chloride, Method H: (Step B, E), LCMS m/z=550.4 [M+H]+; Compound 56, Intermediates used: tert-butyl ((S)-2-hydroxy-3-(3-(methylsulfonyl)phenoxy)propyl)(1-oxa-8-azaspiro[4.5]decan-3-yl)carbamate, 2-(2-aminothiazol-4-yl)acetic acid, Method K, LCMS m/z=525.6 [M+H]+; Compound 57, Intermediates used: tert-butyl ((S)-2-hydroxy-3-(3-(methylsulfonyl)phenoxy)propyl)(1-oxa-8-azaspiro[4.5]decan-3-yl)carbamate, 2-naphthoic acid, Method K, LCMS m/z=539.4 [M+H]+; Compound 58, Intermediates used: tert-butyl ((S)-2-hydroxy-3-(3-(methylsulfonyl)phenoxy)propyl)(1-oxa-8-azaspiro[4.5]decan-3-yl)carbamate, 1-ethyl-5-methyl-1H-pyrazole-4-sulfonyl chloride, Method H: (Step B, E), LCMS m/z=557.4 [M+H]+; Compound 59, Intermediates used: tert-butyl ((S)-2-hydroxy-3-(3-(methylsulfonyl)phenoxy)propyl)(1-oxa-8-azaspiro[4.5]decan-3-yl)carbamate, 5-chloronaphthalene-2-sulfonyl chloride, Method H: (Step B, E), LCMS m/z=609.5 [M+H]+; Compound 60, Intermediates used: tert-butyl ((S)-2-hydroxy-3-(3-(methylsulfonyl)phenoxy)propyl)(1-oxa-8-azaspiro[4.5]decan-3-yl)carbamate, benzofuran-2-sulfonyl chloride, Method H: (Step B, E), LCMS m/z=565.4 [M+H]+; Compound 61, Intermediates used: tert-butyl ((S)-2-hydroxy-3-(3-(methylsulfonyl)phenoxy)propyl)(1-oxa-8-azaspiro[4.5]decan-3-yl)carbamate, benzofuran-5-sulfonyl chloride, Method H: (Step B, E), LCMS m/z=565.4 [M+H]+; Compound 62, Intermediates used: tert-butyl ((S)-2-hydroxy-3-(3-(methylsulfonyl)phenoxy)propyl)(1-oxa-8-azaspiro[4.5]decan-3-yl)carbamate, 1H-indole-5-sulfonyl chloride, Method H: (Step B, E), LCMS m/z=565.2 [M+H]+; Compound 63, Intermediates used: tert-butyl (84(3-bromophenyl)sulfonyl)-1-oxa-8-azaspiro[4.5]decan-3-yl)((S)-2-hydroxy-3-(3-(methylsulfonyl)phenoxy)propyl)carbamate, pyridin-3-ylboronic acid, Method H: (Step C, E), LCMS m/z=602.4 [M+H]+; Compound 65, Intermediates used: tert-butyl ((S)-2-hydroxy-3-(3-(methylsulfonyl)phenoxy)propyl)(1-oxa-8-azaspiro[4.5]decan-3-yl)carbamate, 1H-indole-2-carboxylic acid, Method K, LCMS m/z=528.6 [M+H]+; Compound 66, Intermediates used: tert-butyl ((S)-2-hydroxy-3-(3-(methylsulfonyl)phenoxy)propyl)(1-oxa-8-azaspiro[4.5]decan-3-yl)carbamate, 1H-indole-3-carboxylic acid, Method K, LCMS m/z=528.4 [M+H]+; Compound 67, Intermediates used: tert-butyl ((S)-2-hydroxy-3-(3-(methylsulfonyl)phenoxy)propyl)(1-oxa-8-azaspiro[4.5]decan-3-yl)carbamate, 1H-indole-5-carboxylic acid, Method K, LCMS m/z=528.5 [M+H]+; Compound 68, Intermediates used: tert-butyl ((S)-2-hydroxy-3-(3-(methylsulfonyl)phenoxy)propyl)(1-oxa-8-azaspiro[4.5]decan-3-yl)carbamate, 1H-indole-6-carboxylic acid, Method K, LCMS m/z=528.4 [M+H]+; Compound 69, Intermediates used: tert-butyl (84(3-bromophenyl)sulfonyl)-1-oxa-8-azaspiro[4.5]decan-3-yl)((S)-2-hydroxy-3-(3-(methylsulfonyl)phenoxy)propyl)carbamate, Method H: Step E, LCMS m/z=603.2 [M+H]+; Compound 70, Intermediates used: tert-butyl (8-((3-bromophenyl)sulfonyl)-1-oxa-8-azaspiro[4.5]decan-3-yl)((S)-2-hydroxy-3-(3-(methylsulfonyl)phenoxy)propyl)carbamate, 5-(4,4,5,5-tetramethyl-1,3,2-dioxaborolan-2-yl)pyridin-2-amine, Method H: (Step C, E), LCMS m/z=617.3 [M+H]+; Compound 71, Intermediates used: tert-butyl (84(3-bromophenyl)sulfonyl)-1-oxa-8-azaspiro[4.5]decan-3-yl)((S)-2-hydroxy-3-(3-(methylsulfonyl)phenoxy)propyl)carbamate, pyrimidin-5-ylboronic acid, Method H: (Step C, E), LCMS m/z=603.4 [M+H]+; Compound 72, Intermediates used: tert-butyl ((S)-2-hydroxy-3-(3-(methylsulfonyl)phenoxy)propyl)(1-oxa-8-azaspiro[4.5]decan-3-yl)carbamate, pyridine-2-sulfonyl chloride, Method H: (Step B, E), LCMS m/z=526.6 [M+H]+; Compound 73, Intermediates used: tert-butyl ((S)-2-hydroxy-3-(3-(methylsulfonyl)phenoxy)propyl)(1-oxa-8-azaspiro[4.5]decan-3-yl)carbamate, 6-chloronaphthalene-2-sulfonyl chloride, Method H: (Step B, E), LCMS m/z=609.6 [M+H]+; Compound 74, Intermediates used: tert-butyl ((S)-2-hydroxy-3-(3-(methylsulfonyl)phenoxy)propyl)(1-oxa-8-azaspiro[4.5]decan-3-yl)carbamate, 2,3-dihydrobenzofuran-5-sulfonyl chloride, Method H: (Step B, E), LCMS m/z=567.4 [M+H]+; Compound 75, Intermediates used: tert-butyl ((S)-2-hydroxy-3-(3-(methylsulfonyl)phenoxy)propyl)(1-oxa-8-azaspiro[4.5]decan-3-yl)carbamate, quinoline-6-sulfonyl chloride, Method H: (Step B, E), LCMS m/z=576.2 [M+H]+; Compound 76, Intermediates used: tert-butyl ((S)-2-hydroxy-3-(3-(methylsulfonyl)phenoxy)propyl)(1-oxa-8-azaspiro[4.5]decan-3-yl)carbamate, C35, Method H: (Step B, E), LCMS m/z=565.4 [M+H]+; Compound 77, Intermediates used: tert-butyl ((S)-2-hydroxy-3-(3-(methylsulfonyl)phenoxy)propyl)(1-oxa-8-azaspiro[4.5]decan-3-yl)carbamate, 1H-indazole-5-sulfonyl chloride, Method H: (Step B, E), LCMS m/z=565.5 [M+H]+; Compound 79, Intermediates used: tert-butyl ((S)-2-hydroxy-3-(3-(methylsulfonyl)phenoxy)propyl)(8-((4'-(hydroxymethyl)-[1,1'-biphenyl]-3-yl)sulfonyl)-1-oxa-8-azaspiro[4.5]decan-3-yl)carbamate, ethanamine, Method H: Step D, E, LCMS m/z=658.4 [M+H]+; Compound 80, Intermediates used: tert-butyl ((S)-2-hydroxy-3-(3-(methylsulfonyl)phenoxy)propyl)(8-((4'-(hydroxymethyl)-[1,1'-biphenyl]-3-yl)sulfonyl)-1-oxa-8-azaspiro[4.5]decan-3-yl) carbamate, propan-2-amine, Method H: Step D, E, LCMS m/z=672.4 [M+H]+; Compound 81, Intermediates used: tert-butyl ((S)-2-hydroxy-3-(3-(methylsulfonyl)phenoxy)propyl)(8-((4'-(hydroxymethyl)-[1,1'-biphenyl]-3-yl)sulfonyl)-1-oxa-8-azaspiro[4.5]decan-3-yl)carbamate, 2-methylpropan-1-amine, Method H: Step D, E, LCMS m/z=686.6 [M+H]+; Compound 82, Intermediates used: tert-butyl ((S)-2-hydroxy-3-(3-(methylsulfonyl)phenoxy)propyl)(8-((4'-(hydroxymethyl)-[1,1'-biphenyl]-3-yl)sulfonyl)-1-oxa-8-azaspiro[4.5]decan-3-yl)carbamate, 2,2,2-trifluoroethanamine, Method H: Step D, E, LCMS m/z=712.4 [M+H]+; Compound 83, Intermediates used: (R)-benzyl 3-amino-1-oxa-8-azaspiro[4.5]decane-8-carboxylate, (S)-2-((3-(oxiran-2-ylmethoxy)phenyl)sulfonyl)ethanol, chroman-6-sulfonyl chloride, Method E, LCMS m/z=611.6 [M+H]+; Compound 84, Intermediates used: (R)-benzyl 3-amino-1-oxa-8-azaspiro[4.5]decane-8-carboxylate, (S)-2-((3-(oxiran-2-ylmethoxy)phenyl)sulfonyl)ethanol, 4-methyl-3,4-dihydro-2H-benzo[b][1,4]oxazine-6-sulfonyl chloride, Method E, LCMS m/z=626.4 [M+H]+; Compound 85, Intermediates used: tert-butyl ((S)-2-hydroxy-3-(3-(methylsulfonyl)phenoxy)propyl)((S)-1-oxa-8-azaspiro[4.5]decan-3-yl)carbamate, quinoline-3-sulfonyl chloride, Method H: (Step B, E), LCMS m/z=576.4 [M+H]+; Compound 87, Intermediates used: (R)-benzyl 3-amino-1-oxa-8-azaspiro[4.5]decane-8-carboxylate, (S)-2-((3-(oxiran-2-ylmethoxy)phenyl)sulfonyl)ethanol, chroman-7-sulfonyl chloride, Method E, LCMS m/z=611.4 [M+H]+; Compound 89, Intermediates used: (R)-benzyl 3-amino-1-oxa-8-azaspiro[4.5]decane-8-carboxylate, (S)-2-((3-(oxiran-2-ylmethoxy)phenyl)sulfonyl)ethanol, 5-bromopyridine-3-sulfonyl chloride, (4-(((tert-butoxycarbonyl)amino)methyl)phenyl)boronic acid, Methods A: (Step A, B, C) and M: (Step B, C, D), LCMS m/z=661.6 [M+H]+; Compound 90, Intermediates used: (R)-benzyl 3-amino-1-oxa-8-azaspiro[4.5]decane-8-carboxylate, (S)-2-((3-(oxiran-2-ylmethoxy)phenyl)sulfonyl)ethanol, 5-bromopyridine-3-sulfonyl chloride, 1-methyl-4-(4,4,5,5-tetramethyl-1,3,2-dioxaborolan-2- yl)-1H-pyrazole, Methods A: (Step A, B, C) and M: (Step B, C, D), LCMS m/z=636.7 [M+H]⁺; Compound 91, Intermediates used: (R)-benzyl 3-amino-1-oxa-8-azaspiro[4.5]decane-8-carboxylate, (S)-2-((3-(oxiran-2-ylmethoxy)phenyl)sulfonyl)ethanol, 3-bromobenzene-1-sulfonyl chloride, (4-(((tert-butoxycarbonyl)amino)methyl)phenyl)boronic acid, Method A: (Step A, B, C) and M: (Step B, C, D), LCMS m/z=660.7 [M+H]⁺; Compound 92, Intermediates used: (R)-benzyl 3-amino-1-oxa-8-azaspiro[4.5]decane-8-carboxylate, (S)-2-((3-(oxiran-2-ylmethoxy)phenyl)sulfonyl)ethanol, quinoline-3-sulfonyl chloride, Method E, LCMS m/z=588.5 [M+H]⁺; Compound 93, Intermediates used: (R)-benzyl 3-amino-1-oxa-8-azaspiro[4.5]decane-8-carboxylate, (S)-2-((3-(oxiran-2-ylmethoxy)phenyl)sulfonyl)ethanol, quinoline-6-sulfonyl chloride, Method E, LCMS m/z=606.8 [M+H]⁺; Compound 94, Intermediates used: (R)-2-(chloromethyl)oxirane, 3-((methylsulfonyl)methyl)phenol, Method C, LCMS m/z=589.4 [M+H]⁺; Compound 95, Intermediates used: (R)-8-(quinolin-3-ylsulfonyl)-1-oxa-8-azaspiro[4.5]decan-3-amine, C21, Method B: Step D, LCMS m/z=590.4 [M+H]⁺; Compound 96, Intermediates used: (R)-benzyl 3-amino-1-oxa-8-azaspiro[4.5]decane-8-carboxylate, (S)-2-((3-(oxiran-2-ylmethoxy)phenyl)sulfonyl)ethanol, 3-bromobenzene-1-sulfonyl chloride, pyridin-4-ylboronic acid, Methods A: (Step A, B, C) and M: (Step B, C, D), LCMS m/z=632.6 [M+H]⁺; Compound 97, Intermediates used: (R)-benzyl 3-amino-1-oxa-8-azaspiro[4.5]decane-8-carboxylate, (S)-2-((3-(oxiran-2-ylmethoxy)phenyl)sulfonyl)ethanol, 3-bromobenzene-1-sulfonyl chloride, pyridin-3-ylboronic acid, Methods A: (Step A, B, C) and M: (Step B, C, D), LCMS m/z=632.6 [M+H]⁺; Compound 98, Intermediates used: (R)-benzyl 3-amino-1-oxa-8-azaspiro[4.5]decane-8-carboxylate, (S)-2-((3-(oxiran-2-ylmethoxy)phenyl)sulfonyl)ethanol, quinoline-7-sulfonyl chloride, Method E, LCMS m/z=606.7 [M+H]⁺; Compound 99, Intermediates used: (R)-benzyl 3-amino-1-oxa-8-azaspiro[4.5]decane-8-carboxylate, (S)-2-((3-(oxiran-2-ylmethoxy)phenyl)sulfonyl)ethanol, 4-bromobenzene-1-sulfonyl chloride, pyridin-3-ylboronic acid, Methods A: (Step A, B, C) and M: (Step B, C, D), LCMS m/z=632.7 [M+H]⁺; Compound 100, Intermediates used: (R)-benzyl 3-amino-1-oxa-8-azaspiro[4.5]decane-8-carboxylate, (S)-2-((3-(oxiran-2-ylmethoxy)phenyl)sulfonyl)ethanol, 3-bromobenzene-1-sulfonyl chloride, 2-(4,4,5,5-tetramethyl-1,3,2-dioxaborolan-2-yl)pyridine, Methods A: (Step A, B, C) and M: (Step B, C, D), LCMS m/z=632.6 [M+H]⁺; Compound 101, Intermediates used: (R)-benzyl 3-amino-1-oxa-8-azaspiro[4.5]decane-8-carboxylate, (S)-2-((3-(oxiran-2-ylmethoxy)phenyl)sulfonyl)ethanol, 4-bromobenzene-1-sulfonyl chloride, pyridin-4-ylboronic acid, Methods A: (Step A, B, C) and M: (Step B, C, D), LCMS m/z=632.7 [M+H]⁺; Compound 102, Intermediates used: (R)-benzyl 3-amino-1-oxa-8-azaspiro[4.5]decane-8-carboxylate, (S)-2-((3-(oxiran-2-ylmethoxy)phenyl)sulfonyl)ethanol, 4-bromobenzene-1-sulfonyl chloride, diisopropyl pyridin-2-ylboronate compound with 2-(4,4,5,5-tetramethyl-1,3,2-dioxaborolan-2-yl)pyridine (1:1), Methods A: (Step A, B, C) and M: (Step B, C, D), LCMS m/z=632.6 [M+H]⁺; Compound 103, Intermediates used: (R)-benzyl 3-amino-1-oxa-8-azaspiro[4.5]decane-8-carboxylate, (S)-2-((3-(oxiran-2-ylmethoxy)phenyl)sulfonyl)ethanol, 4-bromobenzene-1-sulfonyl chloride, (4-(((tert-butoxycarbonyl)amino)methyl)phenyl)boronic acid, Methods A: (Step A, B, C) and M: (Step B, C, D), LCMS m/z=660.8 [M+H]⁺; Compound 104, Intermediates used: (R)-8-((1-methyl-2,3-dihydro-1H-pyrido[2,3-b][1,4]oxazin-7-yl)sulfonyl)-1-oxa-8-azaspiro[4.5]decan-3-amine, C21, Method B: Step D, LCMS m/z=611.6 [M+H]⁺; Compound 105, Intermediates used: (R)-benzyl 3-amino-1-oxa-8-azaspiro[4.5]decane-8-carboxylate, (S)-2-((3-(oxiran-2-ylmethoxy)phenyl)sulfonyl)ethanol, isoquinoline-5-sulfonyl chloride, Method E, LCMS m/z=606.8 [M+H]⁺; Compound 106, Intermediates used: (R)-8-(quinolin-3-ylsulfonyl)-1-oxa-8-azaspiro[4.5]decan-3-amine, C22, Method B: Step D, LCMS m/z=634.8 [M+H]⁺; Compound 107, Intermediates used: (R)-8-(quinolin-3-ylsulfonyl)-1-oxa-8-azaspiro[4.5]decan-3-amine, C23, Method B: Step D, LCMS m/z=646.2 [M+H]⁺; Compound 108, Intermediates used: (R)-8-(quinolin-3-ylsulfonyl)-1-oxa-8-azaspiro[4.5]decan-3-amine, C24, Method B: Step D, LCMS m/z=647.6 [M+H]⁺; Compound 109, Intermediates used: (R)-8-(quinolin-6-ylsulfonyl)-1-oxa-8-azaspiro[4.5]decan-3-amine, C22, Method B: Step D, LCMS m/z=634.6 [M+H]⁺; Compound 110, Intermediates used: (R)-8-(quinolin-6-ylsulfonyl)-1-oxa-8-azaspiro[4.5]decan-3-amine, C23, Method B: Step D, LCMS m/z=646.4 [M+H]⁺; Compound 111, Intermediates used: (R)-8-(quinolin-6-ylsulfonyl)-1-oxa-8-azaspiro[4.5]decan-3-amine, (S)-2-((3-(methylsulfonyl)phenoxy)methyl)oxirane, Method B: Step D, LCMS m/z=576.6 [M+H]⁺; Compound 112, Intermediates used: (R)-8-(quinolin-6-ylsulfonyl)-1-oxa-8-azaspiro[4.5]decan-3-amine, C10, Method B: Step D, LCMS m/z=590.2 [M+H]⁺; Compound 113, Intermediates used: (R)-8-(quinolin-6-ylsulfonyl)-1-oxa-8-azaspiro[4.5]decan-3-amine, C3, Method B: Step D, LCMS m/z=604.6 [M+H]⁺; Compound 114, Intermediates used: (R)-8-(quinolin-6-ylsulfonyl)-1-oxa-8-azaspiro[4.5]decan-3-amine, C13, Method B: Step D, LCMS m/z=616.4 [M+H]⁺; Compound 115, Intermediates used: (R)-8-(quinolin-6-ylsulfonyl)-1-oxa-8-azaspiro[4.5]decan-3-amine, C1, Method B: Step D, LCMS m/z=604.4 [M+H]⁺; Compound 116, Intermediates used: (R)-8-(quinolin-6-ylsulfonyl)-1-oxa-8-azaspiro[4.5]decan-3-amine, C5, Method B: Step D, LCMS m/z=618.4 [M+H]⁺; Compound 117, Intermediates used: (R)-8-(quinolin-6-ylsulfonyl)-1-oxa-8-azaspiro[4.5]decan-3-amine, C2, Method B: Step D, LCMS m/z=616.2 [M+H]⁺; Compound 118, Intermediates used: (R)-8-(quinolin-3-ylsulfonyl)-1-oxa-8-azaspiro[4.5]decan-3-amine, (S)-2-((3-(methylsulfonyl)phenoxy)methyl)oxirane, Method B: Step D, LCMS m/z=576.4 [M+H]⁺; Compound 119, Intermediates used: (R)-8-(quinolin-3-ylsulfonyl)-1-oxa-8-azaspiro[4.5]decan-3-amine, C3, Method B: Step D, LCMS m/z=604.4 [M+H]⁺; Compound 120, Intermediates used: (S)-benzyl 3-amino-1-oxa-8-azaspiro[4.5]decane-8-carboxylate, (S)-2-((3-(oxiran-2-ylmethoxy)phenyl)sulfonyl)ethanol, 3-bromobenzene-1-sulfonyl chloride, (3-methylpyridin-2-yl)boronic acid, Methods A: (Step A, B, C) and M: (Step B, C, D), LCMS m/z=646.2 [M+H]⁺; Compound 121, Intermediates used: (R)-8-(quinolin-6-ylsulfonyl)-1-oxa-8-azaspiro[4.5]decan-3-amine, C25, Method B: Step D, LCMS m/z=620.4 [M+H]⁺; Compound 122, Intermediates used: (R)-8-(quinolin-3-ylsulfonyl)-1-oxa-8-azaspiro[4.5]decan-3-amine, C10, Method B: Step D, LCMS m/z=[M+H]⁺; Compound 124, Intermediates used: (R)-8-(quinolin-3-ylsulfonyl)-1-oxa-8-azaspiro[4.5]decan-3-amine, C5, Method B: Step D, LCMS m/z=618.4 [M+H]⁺; Compound 125, Intermediates used: (R)-benzyl 3-amino-1-oxa-8-azaspiro[4.5]decane-8-carboxylate, (S)-2-((3-(oxiran-2-ylmethoxy)phenyl)sulfonyl)ethanol, 3-bromobenzene-1-sulfonyl chloride, (6-(trifluoromethyl)pyridin-2-yl)boronic acid, Methods A: (Step A, B, C) and M: (Step B, C, D), LCMS m/z=700.6 [M+H]⁺; Compound 126, Intermediates used: (R)-benzyl 3-amino-1-oxa-8-azaspiro[4.5]decane-8-carboxylate, (S)-2-((3-(oxiran-2-ylmethoxy)phenyl)sulfonyl)ethanol, 3-bromobenzene-1-sulfonyl chloride, (3-fluoropyridin-2-yl)boronic acid, Methods A: (Step A, B, C) and M, LCMS m/z=650.6

[M+H]⁺; Compound 127, Intermediates used: (R)-benzyl 3-amino-1-oxa-8-azaspiro[4.5]decane-8-carboxylate, (S)-2-((3-(oxiran-2-ylmethoxy)phenyl)sulfonyl)ethanol, 3-bromobenzene-1-sulfonyl chloride, (5-methylpyridin-2-yl)boronic acid, Methods A: (Step A, B, C) and M: (Step B, C, D), LCMS m/z=646.2 [M+H]⁺; Compound 128, Intermediates used: (R)-benzyl 3-amino-1-oxa-8-azaspiro[4.5]decane-8-carboxylate, (S)-2-((3-(oxiran-2-ylmethoxy)phenyl)sulfonyl)ethanol, 3-bromobenzene-1-sulfonyl chloride, (6-methylpyridin-2-yl)boronic acid, Methods A: (Step A, B, C) and M: (Step B, C, D), LCMS m/z=646.4 [M+H]⁺; Compound 129, Intermediates used: (R)-benzyl 3-amino-1-oxa-8-azaspiro[4.5]decane-8-carboxylate, (S)-2-((3-(oxiran-2-ylmethoxy)phenyl)sulfonyl)ethanol, 3-bromobenzene-1-sulfonyl chloride, (4-methylpyridin-2-yl)boronic acid, Methods A: (Step A, B, C) and M: (Step B, C, D), LCMS m/z=646.4 [M+H]⁺; Compound 131, Intermediates used: (R)-8-(quinolin-6-ylsulfonyl)-1-oxa-8-azaspiro[4.5]decan-3-amine, C26, Method B: Step D, LCMS m/z=606.6 [M+H]⁺; Compound 132, Intermediates used: (R)-8-(quinolin-6-ylsulfonyl)-1-oxa-8-azaspiro[4.5]decan-3-amine, C27, Method B: Step D, LCMS m/z=634.6 [M+H]⁺; Compound 133, Intermediates used: (R)-8-(quinolin-6-ylsulfonyl)-1-oxa-8-azaspiro[4.5]decan-3-amine, C28, Method B: Step D, LCMS m/z=633.6 [M+H]⁺; Compound 134, Intermediates used: (R)-benzyl 3-amino-1-oxa-8-azaspiro[4.5]decane-8-carboxylate, (S)-2-((3-(oxiran-2-ylmethoxy)phenyl)sulfonyl)ethanol, 3-bromobenzene-1-sulfonyl chloride, (6-fluoropyridin-2-yl)boronic acid, Methods A: (Step A, B, C) and M: (Step B, C, D), LCMS m/z=650.6 [M+H]⁺; Compound 135, Intermediates used: (R)-8-(quinolin-3-ylsulfonyl)-1-oxa-8-azaspiro[4.5]decan-3-amine, C26, Method B: Step D, LCMS m/z=620.2 [M+H]⁺; Compound 136, Intermediates used: (R)-8-(quinolin-3-ylsulfonyl)-1-oxa-8-azaspiro[4.5]decan-3-amine, (S)-(1-((3-(oxiran-2-ylmethoxy)phenyl)sulfonyl)cyclopropyl)methanol, Method B: Step D, LCMS m/z=632.8 [M+H]⁺; Compound 137, Intermediates used: (R)-8-(quinolin-6-ylsulfonyl)-1-oxa-8-azaspiro[4.5]decan-3-amine, (S)-2-((3-(oxiran-2-ylmethoxy)phenyl)sulfonyl)acetamide, Method B: Step D, LCMS m/z=619.4 [M+H]⁺; Compound 138, Intermediates used: (R)-8-(quinolin-3-ylsulfonyl)-1-oxa-8-azaspiro[4.5]decan-3-amine, C13, Method B: Step D, LCMS m/z=616.4 [M+H]⁺; Compound 139, Intermediates used: (R)-8-(quinolin-3-ylsulfonyl)-1-oxa-8-azaspiro[4.5]decan-3-amine, C1, Method B: Step D, LCMS m/z=604.6 [M+H]⁺; Compound 140, Intermediates used: (R)-8-(quinolin-3-ylsulfonyl)-1-oxa-8-azaspiro[4.5]decan-3-amine, C2, Method B: Step D, LCMS m/z=616.4 [M+H]⁺; Compound 141, Intermediates used: (R)-8-(quinolin-3-ylsulfonyl)-1-oxa-8-azaspiro[4.5]decan-3-amine, C26, Method B: Step D, LCMS m/z=606.6 [M+H]⁺; Compound 142, Intermediates used: (R)-8-(quinolin-3-ylsulfonyl)-1-oxa-8-azaspiro[4.5]decan-3-amine, C28, Method B: Step D, LCMS m/z=633.6 [M+H]⁺; Compound 143, Intermediates used: (R)-8-(quinolin-6-ylsulfonyl)-1-oxa-8-azaspiro[4.5]decan-3-amine, (S)-2-((3-(cyclopropylsulfonyl)phenoxy)methyl)oxirane, Method B: Step D, LCMS m/z=602.6 [M+H]⁺; Compound 144, Intermediates used: (R)-8-(quinolin-3-ylsulfonyl)-1-oxa-8-azaspiro[4.5]decan-3-amine, (S)-2-((3-(cyclopropylsulfonyl)phenoxy)methyl)oxirane, Method B: Step D, LCMS m/z=602.4 [M+H]⁺; Compound 145, Intermediates used: (R)-8-(quinolin-3-ylsulfonyl)-1-oxa-8-azaspiro[4.5]decan-3-amine, C29, Method B: Step D, LCMS m/z=676.6 [M+H]⁺; Compound 146, Intermediates used: (R)-8-(quinolin-3-ylsulfonyl)-1-oxa-8-azaspiro[4.5]decan-3-amine, C30, Method B: Step D, LCMS m/z=632.4 [M+H]⁺; Compound 147, Intermediates used: (R)-8-(quinolin-6-ylsulfonyl)-1-oxa-8-azaspiro[4.5]decan-3-amine, (S)-(1-((3-(oxiran-2-ylmethoxy)phenyl)sulfonyl)cyclopropyl)methanol, Method B: Step D, LCMS m/z=632.4 [M+H]⁺; Compound 148, Intermediates used: (R)-8-(quinolin-6-ylsulfonyl)-1-oxa-8-azaspiro[4.5]decan-3-amine, (S)-2,2-difluoro-2-((3-(oxiran-2-ylmethoxy)phenyl)sulfonyl)ethanol, Method B: Step D, LCMS m/z=642.4 [M+H]⁺; Compound 149, Intermediates used: (R)-8-(quinolin-3-ylsulfonyl)-1-oxa-8-azaspiro[4.5]decan-3-amine, C27, Method B: Step D, LCMS m/z=634.6 [M+H]⁺; Compound 150, Intermediates used: (R)-8-((1-methyl-2,3-dihydro-1H-pyrido[2,3-b][1,4]oxazin-7-yl)sulfonyl)-1-oxa-8-azaspiro[4.5]decan-3-amine, C25, Method B: Step D, LCMS m/z=641.4 [M+H]⁺; Compound 151, Intermediates used: (R)-8-((1-methyl-2,3-dihydro-1H-pyrido[2,3-b][1,4]oxazin-7-yl)sulfonyl)-1-oxa-8-azaspiro[4.5]decan-3-amine, (S)-2-((3-(oxiran-2-ylmethoxy)phenyl)sulfonyl)ethanol, Method B: Step D, LCMS m/z=627.6 [M+H]⁺; Compound 152, Intermediates used: (R)-8-((1-methyl-2,3-dihydro-1H-pyrido[2,3-b][1,4]oxazin-7-yl)sulfonyl)-1-oxa-8-azaspiro[4.5]decan-3-amine, (S)-2-((3-(methylsulfonyl)phenoxy)methyl)oxirane, Method B: Step D, LCMS m/z=597.4 [M+H]⁺; Compound 153, Intermediates used: (R)-8-((1-methyl-2,3-dihydro-1H-pyrido[2,3-b][1,4]oxazin-7-yl)sulfonyl)-1-oxa-8-azaspiro[4.5]decan-3-amine, C3, Method B: Step D, LCMS m/z=625.4 [M+H]⁺; Compound 155, Intermediates used: (R)-8-((1-methyl-2,3-dihydro-1H-pyrido[2,3-b][1,4]oxazin-7-yl)sulfonyl)-1-oxa-8-azaspiro[4.5]decan-3-amine, (S)-(1-((3-(oxiran-2-ylmethoxy)phenyl)sulfonyl)cyclopropyl)methanol, Method B: Step D, LCMS m/z=653.6 [M+H]⁺; Compound 156, Intermediates used: (R)-8-((1-methyl-2,3-dihydro-1H-pyrido[2,3-b][1,4]oxazin-7-yl)sulfonyl)-1-oxa-8-azaspiro[4.5]decan-3-amine, (S)-2,2-difluoro-2-((3-(oxiran-2-ylmethoxy)phenyl)sulfonyl)ethanol, Method B: Step D, LCMS m/z=663.4 [M+H]⁺; Compound 157, Intermediates used: (R)-benzyl 3-amino-1-oxa-8-azaspiro[4.5]decane-8-carboxylate, 3-bromobenzene-1-sulfonyl chloride, (4-(((tert-butoxycarbonyl)amino)methyl)phenyl)boronic acid, Method F, LCMS m/z=686.4 [M+H]⁺; Compound 158, Intermediates used: (R)-8-((5-bromo-2-ethoxyphenyl)sulfonyl)-1-oxa-8-azaspiro[4.5]decan-3-amine, (S)-(1-((3-(oxiran-2-ylmethoxy)phenyl)sulfonyl)cyclopropyl)methanol, (4-(((tert-butoxycarbonyl)amino)methyl)phenyl)boronic acid, Method M, LCMS m/z=730.6 [M+H]⁺; Compound 159, Intermediates used: (R)-8-((1-methyl-2,3-dihydro-1H-pyrido[2,3-b][1,4]oxazin-7-yl)sulfonyl)-1-oxa-8-azaspiro[4.5]decan-3-amine, (S)-2-((3-(oxiran-2-ylmethoxy)phenyl)sulfonyl)acetamide, Method B: Step D, LCMS m/z=640.4 [M+H]⁺; Compound 161, Intermediates used: (S)-2,2-difluoro-2-((3-(oxiran-2-ylmethoxy)phenyl)sulfonyl)ethanol, (R)-8-((5-bromo-2-ethoxyphenyl)sulfonyl)-1-oxa-8-azaspiro[4.5]decan-3-amine, 5-bromo-2-ethoxybenzene-1-sulfonyl chloride, (4-((((benzyloxy)carbonyl)amino)methyl)phenyl)boronic acid, Methods B: (Step A, B, C) and F: (Step A, B, E, F), LCMS m/z=740.4 [M+H]⁺; Compound 162, Intermediates used: tert-butyl ((S)-2-hydroxy-3-(3-((1-(hydroxymethyl)cyclopropyl)sulfonyl)phenoxy)propyl)((S)-1-oxa-8-azaspiro[4.5]decan-3-yl)carbamate, 5-bromo-2-fluorobenzene-1-sulfonyl chloride, (4-(((tert-butoxycarbonyl)amino)methyl)phenyl)boronic acid, Method M: (Step B, C, D), LCMS m/z=704.4 [M+H]⁺; Compound 164, Intermediates used: tert-butyl ((S)-2-hydroxy-3-(3-((1-(hydroxymethyl)cyclopropyl)sulfonyl)phenoxy)propyl)((S)-1-oxa-8-azaspiro[4.5]decan-3-yl)carbamate, 3-bromobenzene-1-sulfonyl chloride, (4-(((tert-butoxycarbonyl)amino)methyl)phenyl)boronic acid, Method M: (Step B, C, D), LCMS m/z=686.2 [M+H]⁺; Compound 166, Intermediates used:

tert-butyl ((S)-2-hydroxy-3-(3-((1-(hydroxymethyl)cyclopropyl)sulfonyl)phenoxy)propyl)((S)-1-oxa-8-azaspiro[4.5]decan-3-yl)carbamate, 5-bromo-2-isopropoxybenzene-1-sulfonyl chloride, (4-(((tert-butoxycarbonyl)amino)methyl)phenyl)boronic acid, Method M: (Step B, C, D), LCMS m/z=714.6 [M+H]$^+$; Compound 167, Intermediates used: tert-butyl ((S)-2-hydroxy-3-(3-((1-(hydroxymethyl)cyclopropyl)sulfonyl)phenoxy)propyl)((S)-1-oxa-8-azaspiro[4.5]decan-3-yl)carbamate, 5-bromo-2-ethoxybenzene-1-sulfonyl chloride, (4-(((tert-butoxycarbonyl)amino)methyl)phenyl)boronic acid, Method M: (Step B, C, D), LCMS m/z=700.6 [M+H]$^+$; Compound 168, Intermediates used: (S)-2,2-difluoro-2-((3-(oxiran-2-ylmethoxy)phenyl)sulfonyl)ethanol, 5-bromo-2-ethoxybenzene-1-sulfonyl chloride, (4-(((tert-butoxycarbonyl)amino)methyl)phenyl)boronic acid, Method F, LCMS m/z=740.4 [M+H]$^+$; Compound 169, Intermediates used: (R)-(1-((3-(oxiran-2-ylmethoxy)phenyl)sulfonyl)cyclopropyl)methanol, 5-bromo-2-fluorobenzene-1-sulfonyl chloride, (4-(((tert-butoxycarbonyl)amino)methyl)phenyl)boronic acid, Method F, LCMS m/z=704.4 [M+H]$^+$; Compound 170, Intermediates used: (R)-tert-butyl 1-oxa-8-azaspiro[4.5]decan-3-ylcarbamate, 3-bromobenzene-1-sulfonyl chloride, (4-((((benzyloxy)carbonyl)amino)methyl)phenyl)boronic acid, (S)-(1-((3-(oxiran-2-ylmethoxy)phenyl)sulfonyl)cyclopropyl)methanol, Methods B: (Step A, B), M: (Step C, D), E: (Step A, B), and F: Step F, LCMS m/z=671.6 [M+H]$^+$; Compound 171, Intermediates used: tert-butyl ((S)-3-(3-(cyclopropylsulfonyl)phenoxy)-2-hydroxypropyl)((R)-1-oxa-8-azaspiro[4.5]decan-3-yl)carbamate, 5-bromo-2-isopropoxybezene-1-sulfonyl chloride, (4-(((tert-butoxycarbonyl)amino)methyl)phenyl)boronic acid, Method M: (Step B, C, D), LCMS m/z=714.8 [M+H]$^+$; Compound 172, Intermediates used: (R)-benzyl 3-amino-1-oxa-8-azaspiro[4.5]decane-8-carboxylate, (S)-(1-((3-(oxiran-2-ylmethoxy)phenyl)sulfonyl)cyclopropyl)methanol, 5-bromo-2-ethoxybezene-1-sulfonyl chloride, (4-(1-((tert-butoxycarbonyl)amino)cyclopropyl)phenyl)boronic acid, Method F, LCMS m/z=756.6 [M+H]$^+$; Compound 173, Intermediates used: (R)-benzyl 3-amino-1-oxa-8-azaspiro[4.5]decane-8-carboxylate, (S)-(1-((3-(oxiran-2-ylmethoxy)phenyl)sulfonyl)cyclopropyl)methanol, 3-bromobenzene-1-sulfonyl chloride, (4-(1-((tert-butoxycarbonyl)amino)cyclopropyl)phenyl)boronic acid, Method F, LCMS m/z=712.4 [M+H]$^+$; Compound 174, Intermediates used: (R)-benzyl 3-amino-1-oxa-8-azaspiro[4.5]decane-8-carboxylate, (S)-(1-((3-(oxiran-2-ylmethoxy)phenyl)sulfonyl)cyclopropyl)methanol, 3-bromobenzene-1-sulfonyl chloride, (4-(1-amino-2-methylpropan-2-yl)phenyl)boronic acid, Method F, LCMS m/z=772.6 [M+H]$^+$; Compound 175, Intermediates used: (R)-benzyl 3-amino-1-oxa-8-azaspiro[4.5]decane-8-carboxylate, (S)-(1-((3-(oxiran-2-ylmethoxy)phenyl)sulfonyl)cyclopropyl)methanol, 5-bromo-2-ethoxybezene-1-sulfonyl chloride, (4-(2-acetamidoethyl)phenyl)boronic acid, Method F, LCMS m/z=786.8 [M+H]$^+$; Compound 176, Intermediates used: (S)-benzyl 3-amino-1-oxa-8-azaspiro[4.5]decane-8-carboxylate, (S)-(1-((3-(oxiran-2-ylmethoxy)phenyl)sulfonyl)cyclopropyl)methanol, 5-bromo-2-ethoxybezene-1-sulfonyl chloride, (4-(1-amino-2-methylpropan-2-yl)phenyl)boronic acid, Method F, LCMS m/z=772.6 [M+H]$^+$; Compound 177, Intermediates used: (S)-benzyl 3-amino-1-oxa-8-azaspiro[4.5]decane-8-carboxylate, (S)-(1-((3-(oxiran-2-ylmethoxy)phenyl)sulfonyl)cyclopropyl)methanol, 5-bromo-2-ethoxybezene-1-sulfonyl chloride, (4-(2-acetamidoethyl)phenyl)boronic acid, Method F, LCMS m/z=786.6 [M+H]$^+$; Compound 178, Intermediates used: tert-butyl ((S)-3-(3-((2-amino-2-oxoethyl)sulfonyl)phenoxy)-2-hydroxypropyl)((R)-1-oxa-8-azaspiro[4.5]decan-3-yl)carbamate, 5-bromo-2-ethoxybenzene-1-sulfonyl chloride, (4-(((tert-butoxycarbonyl)amino)methyl)phenyl)boronic acid, Method M: (Step B, C, D), LCMS m/z=673.4 [M+H]$^+$; Compound 179, Intermediates used: tert-butyl ((S)-3-(3-((2-amino-2-oxoethyl)sulfonyl)phenoxy)-2-hydroxypropyl)((R)-1-oxa-8-azaspiro[4.5]decan-3-yl)carbamate, 5-bromo-2-ethoxybenzene-1-sulfonyl chloride, (4-(((tert-butoxycarbonyl)amino)methyl)phenyl)boronic acid, Method M: (Step B, C, D), LCMS m/z=717.6 [M+H]$^+$; Compound 180, Intermediates used: (S)-benzyl 3-((tert-butoxycarbonyl)amino)-1-oxa-8-azaspiro[4.5]decane-8-carboxylate, 3-bromobenzene-1-sulfonyl chloride, (S)-(1-((3-(oxiran-2-ylmethoxy)phenyl)sulfonyl)cyclopropyl)methanol, (4-(1-amino-2-methylpropan-2-yl)phenyl)boronic acid, Method B: (Step A, B, C) and F: (Step A, B, E, F), LCMS m/z=728.6 [M+H]$^+$; Compound 181, Intermediates used: (R)-benzyl 3-((tert-butoxycarbonyl)amino)-1-oxa-8-azaspiro[4.5]decane-8-carboxylate, 3-bromobenzene-1-sulfonyl chloride, (S)-(1-((3-(oxiran-2-ylmethoxy)phenyl)sulfonyl)cyclopropyl)methanol, (4-(1-amino-2-methylpropan-2-yl)phenyl)boronic acid, Method B: (Step A, B, C) and F: (Step A, B, E, F), LCMS m/z=728.6 [M+H]$^+$; Compound 182, Intermediates used: (S)-benzyl 3-((tert-butoxycarbonyl)amino)-1-oxa-8-azaspiro[4.5]decane-8-carboxylate, 3-bromobenzene-1-sulfonyl chloride, (S)-(1-((3-(oxiran-2-ylmethoxy)phenyl)sulfonyl)cyclopropyl)methanol, (4-(aminomethyl)-3-fluorophenyl)boronic acid, Method B: (Step A, B, C) and F: (Step A, B, E, F), LCMS m/z=704.6 [M+H]$^+$; Compound 183, Intermediates used: (R)-8-(quinolin-3-ylsulfonyl)-1-oxa-8-azaspiro[4.5]decan-3-amine, (S)-2-((3-(oxiran-2-ylmethoxy)phenyl)sulfonyl)acetamide, Method B: Step D, LCMS m/z=620.2 [M+H]$^+$; Compound 184, Intermediates used: (S)-benzyl 3-((tert-butoxycarbonyl)amino)-1-oxa-8-azaspiro[4.5]decane-8-carboxylate, 3-bromobenzene-1-sulfonyl chloride, (S)-(1-((3-(oxiran-2-ylmethoxy)phenyl)sulfonyl)cyclopropyl)methanol, (4-(1-((tert-butoxycarbonyl)amino)cyclopropyl)phenyl)boronic acid, Method B: (Step A, B, C) and F: (Step A, B, E, F), LCMS m/z=712.6 [M+H]$^+$; Compound 185, Intermediates used: (S)-(1-((3-(oxiran-2-ylmethoxy)phenyl)sulfonyl)cyclopropyl)methanol, (R)-benzyl 3-amino-1-oxa-8-azaspiro[4.5]decane-8-carboxylate, 5-bromopyridine-3-sulfonyl chloride, Method E, LCMS m/z=662.6 [M+H]$^+$; Compound 186, Intermediates used: (S)-(1-((3-(oxiran-2-ylmethoxy)phenyl)sulfonyl)cyclopropyl)methanol, (S)-benzyl 3-amino-1-oxa-8-azaspiro[4.5]decane-8-carboxylate, 5-bromopyridine-3-sulfonyl chloride, Method E, LCMS m/z=660.6 [M+H]$^+$; Compound 187, Intermediates used: (S)-benzyl 3-((tert-butoxycarbonyl)amino)-1-oxa-8-azaspiro[4.5]decane-8-carboxylate, 5-bromo-2-ethoxybenzene-1-sulfonyl chloride, (S)-2-methyl-24(3-(oxiran-2-ylmethoxy)phenyl)sulfonyl)propan-1-ol, (4-(((tert-butoxycarbonyl)amino)methyl)phenyl)boronic acid, Method B: (Step A, B, C) and F: (Step A, B, E, F), LCMS m/z=732.8 [M+H]$^+$; Compound 188, Intermediates used: (S)-benzyl 3-((tert-butoxycarbonyl)amino)-1-oxa-8-azaspiro[4.5]decane-8-carboxylate, 5-bromo-2-ethoxybenzene-1-sulfonyl chloride, (S)-(1-((3-(oxiran-2-ylmethoxy)phenyl)sulfonyl)cyclopropyl)methanol, (4-(1-((tert-butoxycarbonyl)amino)cyclopropyl)phenyl)boronic acid, Method B: (Step A, B, C) and F: (Step A, B, E, F), LCMS m/z=756.6 [M+H]$^+$; Compound 190, Intermediates used: (S)-benzyl 3-((tert-butoxycarbonyl)amino)-1-oxa-8-azaspiro[4.5]decane-8-carboxylate, 3-bromobenzene-1-sulfonyl chloride, (S)-(1-((3-(oxiran-2-ylmethoxy)phenyl)sulfonyl)cyclopropyl)methanol, (4-(2-acetamidoethyl)phenyl)

boronic acid, Method B: (Step A, B, C) and F: (Step A, B, E, F), LCMS m/z=742.6 [M+H]+; Compound 191, Intermediates used: (R)-benzyl 3-((tert-butoxycarbonyl)amino)-1-oxa-8-azaspiro[4.5]decane-8-carboxylate, 3-bromobenzene-1-sulfonyl chloride, (S)-(1-((3-(oxiran-2-ylmethoxy)phenyl)sulfonyl)cyclopropyl)methanol, (4-(2-acetamidoethyl)phenyl)boronic acid, Method B: (Step A, B, C) and F: (Step A, B, E, F), LCMS m/z=742.4 [M+H]+; Compound 192, Intermediates used: (S)-(1-((3-(oxiran-2-ylmethoxy)phenyl)sulfonyl)cyclopropyl)methanol, (R)-benzyl 3-amino-1-oxa-8-azaspiro[4.5]decane-8-carboxylate, 3-bromo-2-methylbenzene-1-sulfonyl chloride, Method E, LCMS m/z=673.2 [M+H]+; Compound 193, Intermediates used: (S)-(1-((3-(oxiran-2-ylmethoxy)phenyl)sulfonyl)cyclopropyl)methanol, (R)-benzyl 3-amino-1-oxa-8-azaspiro[4.5]decane-8-carboxylate, 3-bromo-4-methoxybenzene-1-sulfonyl chloride, Method E, LCMS m/z=691.4 [M+H]+; Compound 194, Intermediates used: (S)-(1-((3-(oxiran-2-ylmethoxy)phenyl)sulfonyl)cyclopropyl)methanol, (R)-benzyl 3-amino-1-oxa-8-azaspiro[4.5]decane-8-carboxylate, 4-bromo-3-methylbenzene-1-sulfonyl chloride, Method E, LCMS m/z=675.4 [M+H]+; Compound 195, Intermediates used: (S)-(1-((3-(oxiran-2-ylmethoxy)phenyl)sulfonyl)cyclopropyl)methanol, (R)-benzyl 3-amino-1-oxa-8-azaspiro[4.5]decane-8-carboxylate, pyridine-3-sulfonyl chloride, Method E, LCMS m/z=582.6 [M+H]+; Compound 196, Intermediates used: (S)-(1-((3-(oxiran-2-ylmethoxy)phenyl)sulfonyl)cyclopropyl)methanol, (S)-benzyl 3-amino-1-oxa-8-azaspiro[4.5]decane-8-carboxylate, 4-bromo-3-methylbenzene-1-sulfonyl chloride, Method E, LCMS m/z=675.4 [M+H]+; Compound 197, Intermediates used: (S)-(1-((3-(oxiran-2-ylmethoxy)phenyl)sulfonyl)cyclopropyl)methanol, (S)-benzyl 3-amino-1-oxa-8-azaspiro[4.5]decane-8-carboxylate, 3-bromo-2-methylbenzene-1-sulfonyl chloride, (4-(((tert-butoxycarbonyl)amino)methyl)phenyl)boronic acid, Method F, LCMS m/z=700.6 [M+H]+; Compound 198, Intermediates used: (S)-(1-((3-(oxiran-2-ylmethoxy)phenyl)sulfonyl)cyclopropyl)methanol, (S)-benzyl 3-amino-1-oxa-8-azaspiro[4.5]decane-8-carboxylate, 3-bromo-2-methylbenzene-1-sulfonyl chloride, (4-(1-((tert-butoxycarbonyl)amino)cyclopropyl)phenyl)boronic acid, Method F, LCMS m/z=726.4 [M+H]+; Compound 200, Intermediates used: (S)-(1-((3-(oxiran-2-ylmethoxy)phenyl)sulfonyl)cyclopropyl)methanol, (S)-benzyl 3-amino-1-oxa-8-azaspiro[4.5]decane-8-carboxylate, 3-bromo-2-methylbenzene-1-sulfonyl chloride, Method E, LCMS m/z=675.2 [M+H]+; Compound 201, Intermediates used: (S)-(1-((3-(oxiran-2-ylmethoxy)phenyl)sulfonyl)cyclopropyl)methanol, (S)-benzyl 3-amino-1-oxa-8-azaspiro[4.5]decane-8-carboxylate, 3-bromo-4-methoxybenzene-1-sulfonyl chloride, Method E, LCMS m/z=691.4 [M+H]+; Compound 202, Intermediates used: (S)-(1-((3-(oxiran-2-ylmethoxy)phenyl)sulfonyl)cyclopropyl)methanol, (S)-benzyl 3-amino-1-oxa-8-azaspiro[4.5]decane-8-carboxylate, pyridine-3-sulfonyl chloride, Method E, LCMS m/z=582.4 [M+H]+; Compound 203, Intermediates used: (S)-(1-((3-(oxiran-2-ylmethoxy)phenyl)sulfonyl)cyclopropyl)methanol, (R)-benzyl 3-amino-1-oxa-8-azaspiro[4.5]decane-8-carboxylate, 3-bromo-2-methylbenzene-1-sulfonyl chloride, (4-(((tert-butoxycarbonyl)amino)methyl)phenyl)boronic acid, Method F, LCMS m/z=700.4 [M+H]+; Compound 204, Intermediates used: (S)-(1-((3-(oxiran-2-ylmethoxy)phenyl)sulfonyl)cyclopropyl)methanol, (R)-benzyl 3-amino-1-oxa-8-azaspiro[4.5]decane-8-carboxylate, 3-bromo-2-methylbenzene-1-sulfonyl chloride, (4-(1-((tert-butoxycarbonyl)amino)cyclopropyl)phenyl)boronic acid, Method F, LCMS m/z=726.6 [M+H]+; Compound 205, Intermediates used: (S)-2-((3-(oxiran-2-ylmethoxy)phenyl)sulfonyl)acetamide, (S)-benzyl 3-amino-1-oxa-8-azaspiro[4.5]decane-8-carboxylate, 5-bromo-2-ethoxybenzene-1-sulfonyl chloride, (4-(((tert-butoxycarbonyl)amino)methyl)phenyl)boronic acid, Methods E: (Step A, B) and M: (Step B, C, D), LCMS m/z=717.4 [M+H]+; Compound 206, Intermediates used: (S)-2-((3-(oxiran-2-ylmethoxy)phenyl)sulfonyl)acetamide, (S)-benzyl 3-amino-1-oxa-8-azaspiro[4.5]decane-8-carboxylate, 3-bromo-2-methoxybenzene-1-sulfonyl chloride, (4-(((tert-butoxycarbonyl)amino)methyl)phenyl)boronic acid, Methods E: (Step A, B) and M: (Step B, C, D), LCMS m/z=703.2 [M+H]+; Compound 207, Intermediates used: (S)-(1-((3-(oxiran-2-ylmethoxy)phenyl)sulfonyl)cyclopropyl)methanol, (R)-benzyl 3-amino-1-oxa-8-azaspiro[4.5]decane-8-carboxylate, 3-bromo-4-methoxybenzene-1-sulfonyl chloride, (4-(((tert-butoxycarbonyl)amino)methyl)phenyl)boronic acid, Method F, LCMS m/z=716.6 [M+H]+; Compound 208, Intermediates used: (S)-(1-((3-(oxiran-2-ylmethoxy)phenyl)sulfonyl)cyclopropyl)methanol, (S)-benzyl 3-amino-1-oxa-8-azaspiro[4.5]decane-8-carboxylate, 3-bromo-4-methoxybenzene-1-sulfonyl chloride, (4-(((tert-butoxycarbonyl)amino)methyl)phenyl)boronic acid, Method F, LCMS m/z=716.8 [M+H]+; Compound 210, Intermediates used: (S)-benzyl 3-((tert-butoxycarbonyl)amino)-1-oxa-8-azaspiro[4.5]decane-8-carboxylate, 3-bromobenzene-1-sulfonyl chloride, (S)-2,2-difluoro-2-((3-(oxiran-2-ylmethoxy)phenyl)sulfonyl)ethanol, (4-(aminomethyl)-3-fluorophenyl)boronic acid, Methods B: (Step A, B, C) and F: (Step A, B, E, F), LCMS m/z=710.4 [M+H]+; Compound 211, Intermediates used: (S)-benzyl 3-((tert-butoxycarbonyl)amino)-1-oxa-8-azaspiro[4.5]decane-8-carboxylate, 3-bromobenzene-1-sulfonyl chloride, (S)-(1-((3-(oxiran-2-ylmethoxy)phenyl)sulfonyl)cyclopropyl)methanol, (4-(aminomethyl)-3-fluorophenyl)boronic acid, Methods B: (Step A, B, C) and F: (Step A, B, E, F), LCMS m/z=700.6 [M+H]+; Compound 212, Intermediates used: (R)-benzyl 3-((tert-butoxycarbonyl)amino)-1-oxa-8-azaspiro[4.5]decane-8-carboxylate, 3-bromobenzene-1-sulfonyl chloride, (S)-(1-((3-(oxiran-2-ylmethoxy)phenyl)sulfonyl)cyclopropyl)methanol, (4-(aminomethyl)-3-fluorophenyl)boronic acid, Methods B: (Step A, B, C) and F: (Step A, B, E, F), LCMS m/z=700.4 [M+H]+; Compound 213, Intermediates used: (R)-benzyl 3-((tert-butoxycarbonyl)amino)-1-oxa-8-azaspiro[4.5]decane-8-carboxylate, 3-bromobenzene-1-sulfonyl chloride, (S)-2,2-difluoro-2-((3-(oxiran-2-ylmethoxy)phenyl)sulfonyl)ethanol, (4-(aminomethyl)-3-fluorophenyl)boronic acid, Methods B: (Step A, B, C) and F: (Step A, B, E, F), LCMS m/z=710.4 [M+H]+; Compound 214, Intermediates used: (S)-(1-((3-(oxiran-2-ylmethoxy)phenyl)sulfonyl)cyclopropyl)methanol, (S)-benzyl 3-amino-1-oxa-8-azaspiro[4.5]decane-8-carboxylate, 5-bromo-2-ethoxybenzene-1-sulfonyl chloride, (4-(2-((tert-butoxycarbonyl)amino)ethyl)phenyl)boronic acid, Method F, LCMS m/z=744.8 [M+H]+; Compound 215, Intermediates used: (S)-(1-((3-(oxiran-2-ylmethoxy)phenyl)sulfonyl)cyclopropyl)methanol, (S)-benzyl 3-amino-1-oxa-8-azaspiro[4.5]decane-8-carboxylate, 3-bromo-4-methoxybenzene-1-sulfonyl chloride, (4-(2-((tert-butoxycarbonyl)amino)ethyl)phenyl)boronic acid, Method F, LCMS m/z=730.6 [M+–H]+; Compound 216, Intermediates used: (S)-(1-((3-(oxiran-2-ylmethoxy)phenyl)sulfonyl)cyclopropyl)methanol, (R)-benzyl 3-amino-1-oxa-8-azaspiro[4.5]decane-8-carboxylate, 3-bromo-4-fluorobenzene-1-sulfonyl chloride, (4-(((tert-butoxycarbonyl)amino)methyl)phenyl)boronic acid, Method F, LCMS m/z=704.6 [M+H]+; Compound 217, Intermediates used: (S)-(1-((3-(oxiran-2-ylmethoxy)phenyl)sulfonyl)cyclopropyl)methanol, (R)- benzyl 3-amino-1-oxa-8-azaspiro[4.5]decane-8-carboxylate, 3-bromo-4-fluorobenzene-1-sulfonyl chloride, (4-(1-((tert-butoxycarbonyl)amino)cyclopropyl)phenyl)boronic acid, Method F, LCMS m/z=730.6 [M+H]+; Compound 218, Intermediates used: (S)-(1-((3-(oxiran-2-ylmethoxy)phenyl)sulfonyl)cyclopropyl)methanol, (S)-benzyl 3-amino-1-oxa-8-azaspiro[4.5]decane-8-carboxylate, 3-bromo-4-fluorobenzene-1-sulfonyl chloride, (4-(((tert-butoxycarbonyl)amino)methyl)phenyl)boronic acid, Method F, LCMS m/z=704.4 [M+H]+; Compound 219, Intermediates used: (S)-(1-((3-(oxiran-2-ylmethoxy)phenyl)sulfonyl)cyclopropyl)methanol, (S)-benzyl 3-amino-1-oxa-8-azaspiro[4.5]decane-8-carboxylate, 3-bromo-4-fluorobenzene-1-sulfonyl chloride, (4-(1-((tert-butoxycarbonyl)amino)cyclopropyl)phenyl)boronic acid, Method F, LCMS m/z=730.6 [M+H]+; Compound 220, Intermediates used: (S)-(1-((3-(oxiran-2-ylmethoxy)phenyl)sulfonyl)cyclopropyl)methanol, (S)-tert-butyl 1-oxa-8-azaspiro[4.5]decan-3-ylcarbamate, 5-bromo-2-ethoxybenzene-1-sulfonyl chloride, (4-(aminomethyl)-3-fluorophenyl)boronic acid, Methods B: (Step A, B, C) and F: (Step A, B, E, F), LCMS m/z=748.6 [M+H]+; Compound 221, Intermediates used: (S)-(1-((3-(oxiran-2-ylmethoxy)phenyl)sulfonyl)cyclopropyl)methanol, (R)-benzyl 3-amino-1-oxa-8-azaspiro[4.5]decane-8-carboxylate, 5-bromo-6-chloropyridine-3-sulfonyl chloride Method E, LCMS m/z=696.4 [M+H]+; Compound 223, Intermediates used: (S)-2-methyl-2-((3-(oxiran-2-ylmethoxy)phenyl)sulfonyl)propan-1-ol, (S)-tert-butyl 1-oxa-8-azaspiro[4.5]decan-3-ylcarbamate, 3-bromo-4-methoxybenzene-1-sulfonyl chloride, (4-(((tert-butoxycarbonyl)amino)methyl)phenyl)boronic acid, Methods B: (Step A, B, C) and F: (Step A, B, E, F), LCMS m/z=718.6 [M+H]+; Compound 224, Intermediates used: (S)-2-methyl-24(3-(oxiran-2-ylmethoxy)phenyl)sulfonyl)propan-1-ol, (S)-tert-butyl 1-oxa-8-azaspiro[4.5]decan-3-ylcarbamate, 3-bromo-4-methoxybenzene-1-sulfonyl chloride, (4-(1-((tert-butoxycarbonyl)amino)cyclopropyl)phenyl)boronic acid, Methods B: (Step A, B, C) and F: (Step A, B, E, F), LCMS m/z=744.8 [M+H]+; Compound 225, Intermediates used: (S)-(1-((3-(oxiran-2-ylmethoxy)phenyl)sulfonyl)cyclopropyl)methanol, (S)-benzyl 3-amino-1-oxa-8-azaspiro[4.5]decane-8-carboxylate, 3-bromo-4-methoxybenzene-1-sulfonyl chloride, (4-(1-((tert-butoxycarbonyl)amino)cyclopropyl)phenyl)boronic acid, Method F, LCMS m/z=742.8 [M+H]+; Compound 226, Intermediates used: C10(S)-benzyl 3-amino-1-oxa-8-azaspiro[4.5]decane-8-carboxylate, 5-bromo-2-ethoxybenzene-1-sulfonyl chloride, (4-(((tert-butoxycarbonyl)amino)methyl)phenyl)boronic acid, Method F, LCMS m/z=688.6 [M+H]+; Compound 227, Intermediates used: tert-butyl ((S)-3-(3-(cyclopropylsulfonyl)phenoxy)-2-hydroxypropyl)((S)-1-oxa-8-azaspiro[4.5]decan-3-yl)carbamate, 3-bromo-4-methoxybenzene-1-sulfonyl chloride, (4-(((tert-butoxycarbonyl)amino)methyl)phenyl)boronic acid, Method M: (Step B, C, D), LCMS m/z=686.6 [M+H]+; Compound 228, Intermediates used: tert-butyl ((S)-3-(3-(cyclopropylsulfonyl)phenoxy)-2-hydroxypropyl)((S)-1-oxa-8-azaspiro[4.5]decan-3-yl)carbamate, 3-bromo-2-methoxybenzene-1-sulfonyl chloride, (4-(((tert-butoxycarbonyl)amino)methyl)phenyl)boronic acid, Method M: (Step B, C, D), LCMS m/z=686.4 [M+H]+; Compound 229, Intermediates used: tert-butyl ((S)-3-(3-(cyclopropylsulfonyl)phenoxy)-2-hydroxypropyl)((S)-1-oxa-8-azaspiro[4.5]decan-3-yl)carbamate, 3-bromo-5-methoxybenzene-1-sulfonyl chloride, (4-(((tert-butoxycarbonyl)amino)methyl)phenyl)boronic acid, Method M: (Step B, C, D), LCMS m/z=686.6 [M+H]+; Compound 230, Intermediates used: C26, (S)-benzyl 3-amino-1-oxa-8-azaspiro[4.5]decane-8-carboxylate, 5-bromo-2-ethoxybenzene-1-sulfonyl chloride, (4-(((tert-butoxycarbonyl)amino)methyl)phenyl)boronic acid, Method M: (Step B, C, D), LCMS m/z=704.4 [M+H]+; Compound 231, Intermediates used: (S)-2-((3-(methylsulfonyl)phenoxy)methyl)oxirane, (S)-benzyl 3-amino-1-oxa-8-azaspiro[4.5]decane-8-carboxylate, 5-bromo-2-ethoxybenzene-1-sulfonyl chloride, (4-(((tert-butoxycarbonyl)amino)methyl)phenyl)boronic acid, Method F, LCMS m/z=674.4 [M+H]+; Compound 232, Intermediates used: C3, (S)-benzyl 3-amino-1-oxa-8-azaspiro[4.5]decane-8-carboxylate, 5-bromo-2-ethoxybenzene-1-sulfonyl chloride, (4-(((tert-butoxy carbonyl)amino)methyl)phenyl)boronic acid, Method M: (Step B, C, D), LCMS m/z=702.4 [M+H]+; Compound 233, Intermediates used: C33, (R)-8-(quinolin-3-ylsulfonyl)-1-oxa-8-azaspiro[4.5]decan-3-amine, Method B: Step D, LCMS m/z=608.6 [M+H]+; Compound 234, Intermediates used: C33, (R)-8-(quinolin-6-ylsulfonyl)-1-oxa-8-azaspiro[4.5]decan-3-amine, Method B: Step D, LCMS m/z=608.6 [M+H]+; Compound 235, Intermediates used: C33(R)-8-((1-methyl-2,3-dihydro-1H-pyrido[2,3-b][1,4]oxazin-7-yl)sulfonyl)-1-oxa-8-azaspiro[4.5]decan-3-amine, Method B: Step D, LCMS m/z=629.4 [M+H]+; Compound 236, Intermediates used: (S)-(1-((3-(oxiran-2-ylmethoxy)phenyl)sulfonyl)cyclopropyl)methanol, (R)-benzyl 3-amino-1-oxa-8-azaspiro[4.5]decane-8-carboxylate, 4-methyl-2-oxo-1,2-dihydroquinoline-6-sulfonyl chloride, Method E, LCMS m/z=662.6 [M+H]+; Compound 237, Intermediates used: (S)-(1-((3-(oxiran-2-ylmethoxy)phenyl)sulfonyl)cyclopropyl)methanol, (S)-benzyl 3-amino-1-oxa-8-azaspiro[4.5]decane-8-carboxylate, 3-bromo-4-ethoxybenzene-1-sulfonyl chloride, (4-(((tert-butoxycarbonyl)amino)methyl)phenyl)boronic acid, Method F, LCMS m/z=730.6 [M+H]+; Compound 238, Intermediates used: (S)-2,2-difluoro-2-((3-(oxiran-2-ylmethoxy)phenyl)sulfonyl)ethanol, (S)-tert-butyl 1-oxa-8-azaspiro[4.5]decan-3-ylcarbamate, 3-bromo-4-methoxybenzene-1-sulfonyl chloride, (4-(((tert-butoxycarbonyl)amino)methyl)phenyl)boronic acid, Methods B: (Step A, B, C) and F: (Step A, B, E, F), LCMS m/z=726.4 [M+H]+; Compound 239, Intermediates used: (S)-2,2-difluoro-2-((3-(oxiran-2-ylmethoxy)phenyl)sulfonyl)ethanol, (S)-tert-butyl 1-oxa-8-azaspiro[4.5]decan-3-ylcarbamate, 3-bromo-4-methoxybenzene-1-sulfonyl chloride, (4-(1-((tert-butoxycarbonyl)amino)cyclopropyl)phenyl)boronic acid, Methods B: (Step A, B, C) and F: (Step A, B, E, F), LCMS m/z=752.2 [M+H]+; Compound 240, Intermediates used: (S)-(1-((3-(oxiran-2-ylmethoxy)phenyl)sulfonyl)cyclopropyl)methanol, (S)-tert-butyl 1-oxa-8-azaspiro[4.5]decan-3-ylcarbamate, 3-bromobenzene-1-sulfonyl chloride, (4-formylphenyl)boronic acid, 2-methylpropan-2-amine, Methods B and L, LCMS m/z=742.8 [M+H]+; Compound 241, Intermediates used: (S)-(1-((3-(oxiran-2-ylmethoxy)phenyl)sulfonyl)cyclopropyl)methanol, (S)-tert-butyl 1-oxa-8-azaspiro[4.5]decan-3-ylcarbamate, 3-bromobenzene-1-sulfonyl chloride, (4-formylphenyl)boronic acid, 2-methylbutan-2-amine, Methods B and L, LCMS m/z=756.6 [M+H]+; Compound 242, Intermediates used: (S)-(1-((3-(oxiran-2-ylmethoxy)phenyl)sulfonyl)cyclopropyl)methanol, (S)-tert-butyl 1-oxa-8-azaspiro[4.5]decan-3-ylcarbamate, 3-bromobenzene-1-sulfonyl chloride, (4-formylphenyl)boronic acid, 2,2,2-trifluoroethanamine, Methods B and L, LCMS m/z=768.6 [M+H]+; Compound 243, Intermediates used: (S)-(1-((3-(oxiran-2-ylmethoxy)phenyl)sulfonyl)cyclopropyl)methanol, (S)-tert-butyl 1-oxa-8-azaspiro[4.5]decan-3-ylcarbamate, 3-bromobenzene-1-sulfonyl chloride, (4-formylphenyl)boronic acid, azetidine, Methods B and L, LCMS m/z=726.2

[M+H]⁺; Compound 244, Intermediates used: (S)-(1-((3-(oxiran-2-ylmethoxy)phenyl)sulfonyl)cyclopropyl)methanol, (S)-tert-butyl 1-oxa-8-azaspiro[4.5]decan-3-ylcarbamate, 3-bromobenzene-1-sulfonyl chloride, (4-formylphenyl)boronic acid, propan-1-amine, Methods B and L, LCMS m/z=728.6 [M+H]⁺; Compound 245, Intermediates used: (S)-(1-((3-(oxiran-2-ylmethoxy)phenyl)sulfonyl)cyclopropyl)methanol, (S)-tert-butyl 1-oxa-8-azaspiro[4.5]decan-3-ylcarbamate, 3-bromobenzene-1-sulfonyl chloride, (4-formylphenyl)boronic acid, butan-1-amine, Methods B and L, LCMS m/z=742.8 [M+H]⁺; Compound 246, Intermediates used: (S)-(1-((3-(oxiran-2-ylmethoxy)phenyl)sulfonyl)cyclopropyl)methanol, (S)-tert-butyl 1-oxa-8-azaspiro[4.5]decan-3-ylcarbamate, 3-bromobenzene-1-sulfonyl chloride, (4-formylphenyl)boronic acid, morpholine, Methods B and L, LCMS m/z=756.6 [M+H]⁺; Compound 247, Intermediates used: (S)-(1-((3-(oxiran-2-ylmethoxy)phenyl)sulfonyl)cyclopropyl)methanol, (S)-tert-butyl 1-oxa-8-azaspiro[4.5]decan-3-ylcarbamate, 3-bromobenzene-1-sulfonyl chloride, (4-formylphenyl)boronic acid, 2-methoxyethanamine, Methods B and L, LCMS m/z=744.6 [M+H]⁺; Compound 248, Intermediates used: (R)-8-(quinolin-3-ylsulfonyl)-1-oxa-8-azaspiro[4.5]decan-3-amine, C34, Method B: Step D, LCMS m/z=624.4 [M+H]⁺; Compound 249, Intermediates used: (R)-8-(quinolin-6-ylsulfonyl)-1-oxa-8-azaspiro[4.5]decan-3-amine, C34, Method B: Step D, LCMS m/z=624.4 [M+H]⁺; Compound 250, Intermediates used: (S)-(1-((3-(oxiran-2-ylmethoxy)phenyl)sulfonyl)cyclopropyl)methanol, (S)-benzyl 3-amino-1-oxa-8-azaspiro[4.5]decane-8-carboxylate, C36, Method E, LCMS m/z=667.2 [M+H]⁺; Compound 251, Intermediates used: (S)-(1-((3-(oxiran-2-ylmethoxy)phenyl)sulfonyl)cyclopropyl)methanol, (S)-benzyl 3-amino-1-oxa-8-azaspiro[4.5]decane-8-carboxylate, 5-bromo-2-ethoxybenzene-1-sulfonyl chloride, (4-(2-((tert-butoxycarbonyl)amino)propan-2-yl)phenyl)boronic acid, Method F, LCMS m/z=758.4 [M+H]⁺; Compound 252, Intermediates used: (S)-2-((3-(cyclopropylsulfonyl)phenoxy)methyl)oxirane, (S)-benzyl 3-amino-1-oxa-8-azaspiro[4.5]decane-8-carboxylate, 5-bromo-2-ethoxybenzene-1-sulfonyl chloride, (4-(1-((tert-butoxycarbonyl)amino)cyclopropyl)phenyl)boronic acid, Method F, LCMS m/z=726.4 [M+H]⁺; Compound 253, Intermediates used: (S)-2-((3-(cyclopropylsulfonyl)phenoxy)methyl)oxirane, (S)-benzyl 3-amino-1-oxa-8-azaspiro[4.5]decane-8-carboxylate, 3-bromo-4-methoxybenzene-1-sulfonyl chloride, (4-(1-((tert-butoxycarbonyl)amino)cyclopropyl)phenyl)boronic acid, Method F, LCMS m/z=712.6 [M+H]⁺; Compound 254, Intermediates used: (S)-2-((3-(cyclopropylsulfonyl)phenoxy)methyl)oxirane, (R)-benzyl 3-amino-1-oxa-8-azaspiro[4.5]decane-8-carboxylate, 5-bromo-2-ethoxybenzene-1-sulfonyl chloride, (4-(1-((tert-butoxycarbonyl)amino)cyclopropyl)phenyl)boronic acid, Method F, LCMS m/z=726.4 [M+H]⁺; Compound 255, Intermediates used: (S)-2-((3-(cyclopropylsulfonyl)phenoxy)methyl)oxirane, (R)-benzyl 3-amino-1-oxa-8-azaspiro[4.5]decane-8-carboxylate, 3-bromo-4-methoxybenzene-1-sulfonyl chloride, (4-(1-((tert-butoxycarbonyl)amino)cyclopropyl)phenyl)boronic acid, Method F, LCMS m/z=712.6 [M+H]⁺; Compound 256, Intermediates used: C10, (S)-benzyl 3-amino-1-oxa-8-azaspiro[4.5]decane-8-carboxylate, 5-bromo-2-ethoxybenzene-1-sulfonyl chloride, (4-(1-((tert-butoxycarbonyl)amino)cyclopropyl)phenyl)boronic acid, Method F, LCMS m/z=714.6 [M+H]⁺; Compound 257, Intermediates used: C10, (R)-benzyl 3-amino-1-oxa-8-azaspiro[4.5]decane-8-carboxylate, 5-bromo-2-ethoxybenzene-1-sulfonyl chloride, (4-(1-((tert-butoxycarbonyl)amino)cyclopropyl)phenyl)boronic acid, Method F, LCMS m/z=714.6 [M+H]⁺; Compound 258, Intermediates used: C10, (R)-benzyl 3-amino-1-oxa-8-azaspiro[4.5]decane-8-carboxylate, 3-bromo-4-methoxybenzene-1-sulfonyl chloride, (4-(1-((tert-butoxycarbonyl)amino)cyclopropyl)phenyl)boronic acid, Method F, LCMS m/z=700.4 [M+H]⁺; Compound 259, Intermediates used: tert-butyl ((S)-3-(3-(cyclopropylsulfonyl)phenoxy)-2-hydroxypropyl)((R)-1-oxa-8-azaspiro[4.5]decan-3-yl)carbamate, C37, Method E, LCMS m/z=637.6 [M+H]⁺; Compound 260, Intermediates used: (S)-(1-((3-(oxiran-2-ylmethoxy)phenyl)sulfonyl)cyclopropyl)methanol, (R)-benzyl 3-amino-1-oxa-8-azaspiro[4.5]decane-8-carboxylate, C36, Method E, LCMS m/z=667.4 [M+H]⁺; Compound 261, Intermediates used: C10, (S)-benzyl 3-amino-1-oxa-8-azaspiro[4.5]decane-8-carboxylate, 3-bromo-4-methoxybenzene-1-sulfonyl chloride, (4-(1-((tert-butoxycarbonyl)amino)cyclopropyl)phenyl)boronic acid, Method F, LCMS m/z=700.6 [M+H]⁺; Compound 262, Intermediates used: (S)-(1-((3-(oxiran-2-ylmethoxy)phenyl)sulfonyl)cyclopropyl)methanol, (R)-tert-butyl 1-oxa-8-azaspiro[4.5]decan-3-ylcarbamate, 3-bromobenzene-1-sulfonyl chloride, (4-formylphenyl)boronic acid, 2-methylpropan-2-amine, Methods B and L, LCMS m/z=742.8 [M+H]⁺; Compound 263, Intermediates used: (S)-(1-((3-(oxiran-2-ylmethoxy)phenyl)sulfonyl)cyclopropyl)methanol, (R)-tert-butyl 1-oxa-8-azaspiro[4.5]decan-3-ylcarbamate, 3-bromobenzene-1-sulfonyl chloride, (4-formylphenyl)boronic acid, 2-methylbutan-2-amine, Methods B and L, LCMS m/z=756.6 [M+H]⁺; Compound 264, Intermediates used: (S)-(1-((3-(oxiran-2-ylmethoxy)phenyl)sulfonyl)cyclopropyl)methanol, (R)-tert-butyl 1-oxa-8-azaspiro[4.5]decan-3-ylcarbamate, 3-bromobenzene-1-sulfonyl chloride, (4-formylphenyl)boronic acid, 2,2,2-trifluoroethanamine, Methods B and L, LCMS m/z=768.6 [M+H]⁺; Compound 265, Intermediates used: (S)-(1-((3-(oxiran-2-ylmethoxy)phenyl)sulfonyl)cyclopropyl)methanol, (R)-tert-butyl 1-oxa-8-azaspiro[4.5]decan-3-ylcarbamate, 3-bromobenzene-1-sulfonyl chloride, (4-formylphenyl)boronic acid, azetidine, Methods B and L, LCMS m/z=726.4 [M+H]⁺; Compound 266, Intermediates used: (S)-(1-((3-(oxiran-2-ylmethoxy)phenyl)sulfonyl)cyclopropyl)methanol, (R)-tert-butyl 1-oxa-8-azaspiro[4.5]decan-3-ylcarbamate, 3-bromobenzene-1-sulfonyl chloride, (4-formylphenyl)boronic acid, morpholine, Methods B and L, LCMS m/z=756.6 [M+H]⁺; Compound 267, Intermediates used: (S)-(1-((3-(oxiran-2-ylmethoxy)phenyl)sulfonyl)cyclopropyl)methanol, (R)-tert-butyl 1-oxa-8-azaspiro[4.5]decan-3-ylcarbamate, 3-bromobenzene-1-sulfonyl chloride, (4-formylphenyl)boronic acid, 2-methoxyethanamine, Methods B and L, LCMS m/z=744.8 [M+H]⁺; Compound 268, Intermediates used: (S)-(1-((3-(oxiran-2-ylmethoxy)phenyl)sulfonyl)cyclopropyl)methanol, (R)-tert-butyl 1-oxa-8-azaspiro[4.5]decan-3-ylcarbamate, 3-bromobenzene-1-sulfonyl chloride, (4-formylphenyl)boronic acid, ethanamine, Methods B and L, LCMS m/z=714.6 [M+H]⁺; Compound 269, Intermediates used: (S)-(1-((3-(oxiran-2-ylmethoxy)phenyl)sulfonyl)cyclopropyl)methanol, (R)-tert-butyl 1-oxa-8-azaspiro[4.5]decan-3-ylcarbamate, 3-bromobenzene-1-sulfonyl chloride, (4-formylphenyl)boronic acid, cyclobutanamine, Methods B and L, LCMS m/z=740.6 [M+1-1]+; Compound 270, Intermediates used: (S)-(1-((3-(oxiran-2-ylmethoxy)phenyl)sulfonyl)cyclopropyl)methanol, (R)-tert-butyl 1-oxa-8-azaspiro[4.5]decan-3-ylcarbamate, 3-bromobenzene-1-sulfonyl chloride, (4-formylphenyl)boronic acid, tert-butyl (2-aminoethyl)carbamate, Methods B and L, LCMS m/z=729.6 [M+H]⁺; Compound 271, Intermediates used: (S)-(1-((3-(oxiran-2-ylmethoxy)phenyl)sulfonyl)cyclopropyl)methanol, (R)-tert-butyl 1-oxa-8-azaspiro[4.5]decan-3-ylcarbamate, 3-bromobenzene-1-sulfonyl chloride, (4-formylphenyl)boronic acid, tert-butyl (3-aminopropyl)carbamate, Methods B and L, LCMS m/z=743.8 [M+1-1]±; Compound 272, Intermediates used: (S)-(1-((3-(oxiran-2-ylmethoxy)phenyl)sulfonyl)cyclopropyl)methanol, (R)-tert-butyl 1-oxa-8-azaspiro[4.5]decan-3-ylcarbamate, 3-bromobenzene-1-sulfonyl chloride, (4-formylphenyl)boronic acid, 2-methylpropan-1-amine, Methods B and L, LCMS m/z=742.6 [M+H]$^+$; Compound 273, Intermediates used: tert-butyl ((S)-3-(3-(cyclopropylsulfonyl)phenoxy)-2-hydroxypropyl)((R)-1-oxa-8-azaspiro[4.5]decan-3-yl)carbamate, C38, Method E, LCMS m/z=651.6 [M+H]$^+$; Compound 274, Intermediates used: tert-butyl ((S)-3-(3-(cyclopropylsulfonyl)phenoxy)-2-hydroxypropyl)((R)-1-oxa-8-azaspiro[4.5]decan-3-yl)carbamate, C48, Method E, LCMS m/z=637.6 [M+H]$^+$; Compound 275, Intermediates used: tert-butyl ((S)-3-(3-(cyclopropylsulfonyl)phenoxy)-2-hydroxypropyl)((R)-1-oxa-8-azaspiro[4.5]decan-3-yl)carbamate, C36, Method E, LCMS m/z=637.6 [M+H]$^+$; Compound 276, Intermediates used: tert-butyl ((S)-3-(3-((2-amino-2-oxoethyl)sulfonyl)phenoxy)-2-hydroxypropyl)((R)-1-oxa-8-azaspiro[4.5]decan-3-yl)carbamate, C36, Method E2, LCMS m/z=654.6 [M+H]$^+$; Compound 277, Intermediates used: (S)-2-((3-(cyclopropylsulfonyl)phenoxy)methyl)oxirane, (S)-benzyl 3-amino-1-oxa-8-azaspiro[4.5]decane-8-carboxylate, C48, Method E, LCMS m/z=637.6 [M+H]$^+$; Compound 278, Intermediates used: tert-butyl ((S)-3-(34(2-amino-2-oxoethyl)sulfonyl)phenoxy)-2-hydroxypropyl) ((R)-1-oxa-8-azaspiro[4.5]decan-3-yl)carbamate, C48, Method E2, LCMS m/z=654.6 [M+H]$^+$; Compound 280, Intermediates used: tert-butyl ((S)-3-(3-(cyclopropylsulfonyl)phenoxy)-2-hydroxypropyl)((R)-1-oxa-8-azaspiro[4.5]decan-3-yl)carbamate, 5-oxo-6,7-dihydro-5H-pyrrolo[3,4-b]pyridine-3-sulfonyl chloride, Method N, LCMS m/z=607.6 [M+H]$^+$; Compound 281, Intermediates used: tert-butyl ((S)-3-(3-(cyclopropylsulfonyl)phenoxy)-2-hydroxypropyl)((R)-1-oxa-8-azaspiro[4.5]decan-3-yl)carbamate, 2-oxo-2,3-dihydro-1H-imidazo[4,5-b]pyridine-6-sulfonyl chloride, Method N, LCMS m/z=608.4 [M+H]$^+$; Compound 282, Intermediates used: tert-butyl ((S)-3-(3-(cyclopropylsulfonyl)phenoxy)-2-hydroxypropyl)((R)-1-oxa-8-azaspiro[4.5]decan-3-yl)carbamate, 5,6,7,8-tetrahydroquinoline-3-sulfonyl chloride, Method N, LCMS m/z=606.6 [M+H]$^+$; Compound 283, Intermediates used: (S)-(1-((3-(oxiran-2-ylmethoxy)phenyl)sulfonyl)cyclopropyl)methanol, (R)-benzyl 3-amino-1-oxa-8-azaspiro[4.5]decane-8-carboxylate, C48, Method E, LCMS m/z=667.2 [M+H]$^+$; Compound 284, Intermediates used: (S)-(1-((3-(oxiran-2-ylmethoxy)phenyl)sulfonyl)cyclopropyl)methanol, (R)-benzyl 3-amino-1-oxa-8-azaspiro[4.5]decane-8-carboxylate, C43, Method E, LCMS m/z=638.6 [M+H]$^+$; Compound 285, Intermediates used: (S)-(1-((3-(oxiran-2-ylmethoxy)phenyl)sulfonyl)cyclopropyl)methanol, (R)-benzyl 3-amino-1-oxa-8-azaspiro[4.5]decane-8-carboxylate, C44, Method E, LCMS m/z=640.2 [M+H]$^+$; Compound 286, Intermediates used: (S)-(1-((3-(oxiran-2-ylmethoxy)phenyl)sulfonyl)cyclopropyl)methanol, (R)-benzyl 3-amino-1-oxa-8-azaspiro[4.5]decane-8-carboxylate, C45, Method E, LCMS m/z=653.4 [M+H]$^+$; Compound 287, Intermediates used: (S)-(1-((3-(oxiran-2-ylmethoxy)phenyl)sulfonyl)cyclopropyl)methanol, (R)-benzyl 3-amino-1-oxa-8-azaspiro[4.5]decane-8-carboxylate, 3-methyl-3H-imidazo[4,5-b]pyridine-5-sulfonyl chloride, Method E, LCMS m/z=636.6 [M+H]$^+$; Compound 288, Intermediates used: (S)-(1-((3-(oxiran-2-ylmethoxy)phenyl)sulfonyl)cyclopropyl)methanol, (R)-benzyl 3-amino-1-oxa-8-azaspiro[4.5]decane-8-carboxylate, C46, Method E, LCMS m/z=681.4 [M+H]$^+$; Compound 289, Intermediates used: tert-butyl ((S)-3-(3-(cyclopropylsulfonyl)phenoxy)-2-hydroxypropyl)((R)-1-oxa-8-azaspiro[4.5]decan-3-yl)carbamate, 2,3-dihydro-[1,4]dioxino[2,3-b]pyridine-7-sulfonyl chloride, Method N, LCMS m/z=610.6 [M+H]$^+$; Compound 290, Intermediates used: tert-butyl ((S)-3-(3-(cyclopropylsulfonyl)phenoxy)-2-hydroxypropyl)((R)-1-oxa-8-azaspiro[4.5]decan-3-yl)carbamate, 4-methyl-3,4-dihydro-2H-pyrido[3,2-b][1,4]oxazine-7-sulfonyl chloride, Method N, LCMS m/z=623.6 [M+H]$^+$; Compound 291, Intermediates used: tert-butyl ((S)-3-(3-(cyclopropylsulfonyl)phenoxy)-2-hydroxypropyl)((R)-1-oxa-8-azaspiro[4.5]decan-3-yl)carbamate, 3,4-dihydro-2H-pyrano[2,3-b]pyridine-6-sulfonyl chloride, Method N, LCMS m/z=608.8 [M+H]$^+$; Compound 292, Intermediates used: (S)-(1-((3-(oxiran-2-ylmethoxy)phenyl)sulfonyl)cyclopropyl)methanol, (R)-benzyl 3-amino-1-oxa-8-azaspiro[4.5]decane-8-carboxylate, 1-ethyl-4-oxo-1,4-dihydroquinoline-3-sulfonyl chloride, Method E, LCMS m/z=676.4 [M+H]$^+$; Compound 293, Intermediates used: (S)-(1-((3-(oxiran-2-ylmethoxy)phenyl)sulfonyl)cyclopropyl)methanol, (S)-benzyl 3-amino-1-oxa-8-azaspiro[4.5]decane-8-carboxylate, 1-ethyl-4-oxo-1,4-dihydroquinoline-3-sulfonyl chloride, Method E, LCMS m/z=676.4 [M+H]$^+$; Compound 294, Intermediates used: (S)-2-methyl-2-((3-(oxiran-2-ylmethoxy)phenyl)sulfonyl) propan-1-ol, (R)-benzyl 3-amino-1-oxa-8-azaspiro[4.5]decane-8-carboxylate, 1-ethyl-4-oxo-1,4-dihydroquinoline-3-sulfonyl chloride, Method E, LCMS m/z=678.4 [M+−H]$^+$; Compound 295, Intermediates used: (S)-(1-((3-(oxiran-2-ylmethoxy)phenyl)sulfonyl)cyclopropyl)methanol, (R)-benzyl 3-amino-1-oxa-8-azaspiro[4.5]decane-8-carboxylate, C63, Method E, LCMS m/z=662.6 [M+H]$^+$; Compound 296, Intermediates used: (S)-(1-((3-(oxiran-2-ylmethoxy)phenyl)sulfonyl)cyclopropyl)methanol, (S)-benzyl 3-amino-1-oxa-8-azaspiro[4.5]decane-8-carboxylate, C63, Method E, LCMS m/z=662.6 [M+H]$^+$; Compound 298, Intermediates used: (S)-2,2-difluoro-2-((3-(oxiran-2-ylmethoxy)phenyl)sulfonyl)ethanol, (R)-benzyl 3-((tert-butoxycarbonyl)amino)-1-oxa-8-azaspiro[4.5]decane-8-carboxylate, 1-ethyl-4-oxo-1,4-dihydroquinoline-3-sulfonyl chloride, Method B, LCMS m/z=686.4 [M+H]$^+$; Compound 299, Intermediates used: C33, (R)-benzyl 3-((tert-butoxycarbonyl)amino)-1-oxa-8-azaspiro[4.5]decane-8-carboxylate, 1-ethyl-4-oxo-1,4-dihydroquinoline-3-sulfonyl chloride, Method B, LCMS m/z=652.6 [M+H]$^+$; Compound 300, Intermediates used: (S)-(1-((3-(oxiran-2-ylmethoxy)phenyl)sulfonyl)cyclopropyl)methanol, (R)-benzyl 3-amino-1-oxa-8-azaspiro[4.5]decane-8-carboxylate, naphthalene-2-sulfonyl chloride, Method E, LCMS m/z=631.6 [M+H]$^+$; Compound 301, Intermediates used: (S)-(1-((3-(oxiran-2-ylmethoxy)phenyl)sulfonyl)cyclopropyl)methanol, (R)-benzyl 3-amino-1-oxa-8-azaspiro[4.5]decane-8-carboxylate, C56, Method E, LCMS m/z=675.4 [M+H]$^+$; Compound 302, Intermediates used: (S)-(1-((3-(oxiran-2-ylmethoxy)phenyl)sulfonyl)cyclopropyl)methanol, (R)-benzyl 3-amino-1-oxa-8-azaspiro[4.5]decane-8-carboxylate, C57, Method E, LCMS m/z=621.6 [M+H]$^+$; Compound 303, Intermediates used: (S)-2-((3-(cyclopropylsulfonyl)phenoxy)methyl)oxirane, (R)-benzyl 3-amino-1-oxa-8-azaspiro[4.5]decane-8-carboxylate, C47, Method E, LCMS m/z=609.6 [M+H]$^+$; Compound 304, Intermediates used: (S)-2-((3-(cyclopropylsulfonyl)phenoxy)methyl)oxirane, (R)-benzyl 3-amino-1-oxa-8-azaspiro[4.5]decane-8-carboxylate, 1-(2-methoxyethyl)-2,3-dihydro-1H-pyrido[2,3-b][1,4]oxazine-7-sulfonyl chloride, Method E, LCMS m/z=667.4 [M+H]$^+$; Compound 305, Intermediates used:

(S)-2-((3-(cyclopropylsulfonyl)phenoxy)methyl)oxirane, (R)-benzyl 3-amino-1-oxa-8-azaspiro[4.5]decane-8-carboxylate, C42, Method E, LCMS m/z=637.6 [M+H]⁺; Compound 306, Intermediates used: C26, (R)-benzyl 3-amino-1-oxa-8-azaspiro[4.5]decane-8-carboxylate, 1-ethyl-4-oxo-1,4-dihydroquinoline-3-sulfonyl chloride, Method E, LCMS m/z=650.6 [M+H]⁺; Compound 307, Intermediates used: (S)-2-((3-(cyclopropylsulfonyl)phenoxy)methyl)oxirane, (R)-benzyl 3-amino-1-oxa-8-azaspiro[4.5]decane-8-carboxylate, C49, Method E, LCMS m/z=591.4 [M+H]⁺; Compound 308, Intermediates used: (S)-2-((3-(cyclopropylsulfonyl)phenoxy)methyl)oxirane, (R)-benzyl 3-amino-1-oxa-8-azaspiro[4.5]decane-8-carboxylate, 1H-indole-3-sulfonyl chloride, Method E, LCMS m/z=590.6 [M+H]⁺; Compound 309, Intermediates used: (S)-2-((3-(cyclopropylsulfonyl)phenoxy)methyl)oxirane, (R)-benzyl 3-amino-1-oxa-8-azaspiro[4.5]decane-8-carboxylate, C31, Method E, LCMS m/z=591.4 [M+H]⁺; Compound 311, Intermediates used: tert-butyl ((S)-2-hydroxy-3-(3-(methylsulfonyl)phenoxy)propyl)((R)-1-oxa-8-azaspiro[4.5]decan-3-yl)carbamate, 1H-indole-3-sulfonyl chloride, Method A: Step F, G, LCMS m/z=564.4 [M+H]⁺; Compound 312, Intermediates used: C26, (R)-benzyl 3-amino-1-oxa-8-azaspiro[4.5]decane-8-carboxylate, 1H-indole-3-sulfonyl chloride, Method E, LCMS m/z=594.6 [M+H]⁺; Compound 313, Intermediates used: (S)-2-((3-(cyclopropylsulfonyl)phenoxy)methyl)oxirane, (R)-benzyl 3-amino-1-oxa-8-azaspiro[4.5]decane-8-carboxylate, C50, Method E, LCMS m/z=607.6 [M+H]⁺; Compound 314, Intermediates used: tert-butyl ((S)-3-(3-(cyclopropylsulfonyl)phenoxy)-2-hydroxypropyl) ((R)-1-oxa-8-azaspiro[4.5]decan-3-yl)carbamate, C61, bromoethane, Method G, LCMS m/z=664.6 [M+H]⁺; Compound 315, Intermediates used: tert-butyl ((S)-3-(3-(cyclopropylsulfonyl)phenoxy)-2-hydroxypropyl)((R)-1-oxa-8-azaspiro[4.5]decan-3-yl)carbamate, C53, iodoethane, Method G, LCMS m/z=660.6 [M+H]⁺; Compound 316, Intermediates used: tert-butyl ((S)-3-(3-(cyclopropylsulfonyl)phenoxy)-2-hydroxypropyl)((R)-1-oxa-8-azaspiro[4.5]decan-3-yl)carbamate, 7-fluoro-4-hydroxyquinoline-3-sulfonyl chlorideiodoethane, Method G, LCMS m/z=664.6 [M+H]⁺; Compound 317, Intermediates used: tert-butyl ((S)-3-(3-(cyclopropylsulfonyl)phenoxy)-2-hydroxypropyl)((R)-1-oxa-8-azaspiro[4.5]decan-3-yl)carbamate, C60, iodoethane, Method G, LCMS m/z=660.6 [M+H]⁺; Compound 318, Intermediates used: tert-butyl ((S)-3-(3-(cyclopropylsulfonyl)phenoxy)-2-hydroxypropyl)((R)-1-oxa-8-azaspiro[4.5]decan-3-yl)carbamate, 4-hydroxy-7-methylquinoline-3-sulfonyl chloride, iodoethane, Method G, LCMS m/z=660.6 [M+H]⁺; Compound 319, Intermediates used: (S)-2-((3-(cyclopropylsulfonyl)phenoxy)methyl)oxirane, (R)-benzyl 3-amino-1-oxa-8-azaspiro[4.5]decane-8-carboxylate, C51, Method E, LCMS m/z=592.4 [M+H]⁺; Compound 323, Intermediates used: C3, C52, (R)-benzyl 3-amino-1-oxa-8-azaspiro[4.5]decane-8-carboxylate, Method E3, LCMS m/z=638.6 [M+H]⁺; Compound 324, Intermediates used: (S)-2-((3-(cyclopropylsulfonyl)phenoxy)methyl)oxirane, (R)-benzyl 3-amino-1-oxa-8-azaspiro[4.5]decane-8-carboxylate, C60, Method E3, LCMS m/z=632.6 [M+H]⁺; Compound 325, Intermediates used: (S)-2-((3-(cyclopropylsulfonyl)phenoxy)methyl)oxirane, (R)-benzyl 3-amino-1-oxa-8-azaspiro[4.5]decane-8-carboxylate, C61, Method E3, LCMS m/z=636.6 [M+H]⁺; Compound 328, Intermediates used: (S)-2-((3-(cyclopropylsulfonyl)phenoxy)methyl)oxirane, (R)-benzyl 3-amino-1-oxa-8-azaspiro[4.5]decane-8-carboxylate, C52, Method E3, LCMS m/z=636.6 [M+H]⁺; Compound 330, Intermediates used: (S)-2-((3-(cyclopropylsulfonyl)phenoxy)methyl)oxirane, (R)-benzyl 3-amino-1-oxa-8-azaspiro[4.5]decane-8-carboxylate, 4-hydroxy-7-methylquinoline-3-sulfonyl chloride, Method E3, LCMS m/z=632.6 [M+H]⁺; Compound 335, Intermediates used: naphthalene-2-sulfonyl chloride, 3-((methylsulfonyl)methyl)phenol, Method C, LCMS m/z=589.2 [M+H]⁺; and Compound 336, Intermediates used: (R)-8-(quinolin-6-ylsulfonyl)-1-oxa-8-azaspiro[4.5]decan-3-amine, C21, Method B: Step D, LCMS m/z=590.4 [M+H]⁺.

The following NMR data are for selected compounds from above:

Compound 2, ¹H NMR (400 MHz, DMSO-d₆) δ ppm 1.37 (s, 9H), 1.47-1.81 (m, 5H), 1.84-2.01 (m, 1H), 2.42-2.48 (m, 1H), 2.57-2.76 (m, 3H), 2.92-3.01 (m, 1H), 3.27-3.39 (m, 3H), 3.43-3.50 (m, 1H), 3.51-3.59 (m, 1H), 3.63-3.74 (m, 1H), 4.32-4.54 (m, 1H), 7.66-7.80 (m, 3H), 8.08 (d, J=7.9 Hz, 1H), 8.17 (d, J=8.8 Hz, 1H), 8.21 (d, J=8.0 Hz, 1H), 8.43 (s, 1H).

Compound 6, ¹H NMR (400 MHz, CD₃OD) δ ppm 0.98 (t, J=7.33 Hz, 3H), 1.59-1.72 (m, 3H), 1.76-1.95 (m, 4H), 2.28 (dd, J=12.63, 7.33 Hz, 1H), 2.71-2.89 (m, 2H), 3.06-3.19 (m, 3H), 3.26 (t, J=9.98 Hz, 1H), 3.42-3.55 (m, 2H), 3.79-3.89 (m, 1H), 3.92-4.02 (m, 2H), 4.03-4.12 (m, 2H), 4.23 (d, J=4.80 Hz, 1H), 7.29 (d, J=7.83 Hz, 1H), 7.44 (s, 1H), 7.48-7.60 (m, 2H), 7.62-7.74 (m, 2H), 7.77 (d, J=8.59 Hz, 1H), 8.01 (d, J=7.83 Hz, 1H), 8.08 (d, J=6.57 Hz, 2H), 8.37 (s, 1H).

Compound 7, ¹H NMR (400 MHz, CD₃OD) δ ppm 0.09-0.17 (m, 2H), 0.46-0.55 (m, 2H), 0.86-0.99 (m, 1H), 1.60-1.71 (m, 1H), 1.75-1.94 (m, 4H), 2.28 (dd, J=13.77, 7.96 Hz, 1H), 2.73-2.90 (m, 2H), 3.06-3.18 (m, 3H), 3.22-3.30 (m, 1H), 3.49 (t, J=11.49 Hz, 2H), 3.78-3.88 (m, 1H), 3.92-4.03 (m, 2H), 4.08 (d, J=4.29 Hz, 2H), 4.22 (dd, J=8.46, 3.41 Hz, 1H), 7.30 (t, J=3.16 Hz, 1H), 7.46 (s, 1H), 7.51-7.57 (m, 2H), 7.61-7.74 (m, 2H), 7.77 (dd, J=8.59, 1.77 Hz, 1H), 8.01 (d, J=7.83 Hz, 1H), 8.08 (d, J=7.33 Hz, 2H), 8.38 (s, 1H).

Compound 8, ¹H NMR (400 MHz, CD₃OD) δ ppm 1.23 (d, J=6.57 Hz, 6H), 1.66 (m, 1H), 1.75-1.95 (m, 4H), 2.28 (dd, J=12.76, 7.71 Hz, 1H), 2.72-2.90 (m, 2H), 3.05-3.18 (m, 1H), 3.21-3.29 (m, 1H), 3.34 (m, 1H), 3.48 (t, J=12.38 Hz, 2H), 3.78-3.88 (m, 1H), 3.92-4.02 (m, 2H), 4.08 (d, J=4.80 Hz, 2H), 4.23 (dd, J=8.97, 3.66 Hz, 1H), 7.30 (d, J=7.58 Hz, 1H), 7.40 (s, 1H), 7.45-7.50 (m, 1H), 7.56 (t, J=7.96 Hz, 1H), 7.61-7.73 (m, 2H), 7.77 (d, J=8.59 Hz, 1H), 8.00 (d, J=8.08 Hz, 1H), 8.07 (d, J=8.34 Hz, 2H), 8.37 (s, 1H).

Compound 9, ¹H NMR (400 MHz, CD₃OD) δ ppm 1.67 (td, J=10.74, 4.17 Hz, 1H), 1.76-1.92 (m, 4H), 2.28 (ddd, J=13.58, 8.15, 2.53 Hz, 1H), 2.49-2.64 (m, 2H), 2.73-2.90 (m, 2H), 3.12 (dt, J=12.82, 9.51 Hz, 1H), 3.22-3.30 (m, 1H), 3.42-3.54 (m, 4H), 3.80-3.88 (m, 1H), 3.92-4.03 (m, 2H), 4.10 (d, J=4.80 Hz, 2H), 4.19-4.27 (m, 1H), 7.33 (ddd, J=7.39, 2.34, 2.15 Hz, 1H), 7.50 (d, J=2.02 Hz, 1H), 7.53-7.62 (m, 2H), 7.63-7.73 (m, 2H), 7.77 (dd, J=8.59, 1.77 Hz, 1H), 8.00 (d, J=7.83 Hz, 1H), 8.08 (d, J=8.59 Hz, 2H), 8.38 (d, J=1.52 Hz, 1H).

Compound 11, ¹H NMR (400 MHz, CD₃OD) δ ppm 0.86 (dd, J=6.57, 1.01 Hz, 6H), 1.46-1.55 (m, 2H), 1.56-1.70 (m, 2H), 1.76-1.92 (m, 4H), 2.28 (ddd, J=13.64, 8.08, 2.53 Hz, 1H), 2.73-2.89 (m, 2H), 3.07-3.15 (m, 1H), 3.15-3.22 (m, 2H), 3.25 (dt, J=12.82, 2.81 Hz, 1H), 3.49 (t, J=12.76 Hz, 2H), 3.80-3.88 (m, 1H), 3.92-4.02 (m, 2H), 4.04-4.12 (m, 2H), 4.19-4.27 (m, 1H), 7.29 (ddd, J=8.08, 2.53, 1.26 Hz, 1H), 7.42-7.48 (m, 1H), 7.54 (dd, J=15.28, 7.83, 7.71 Hz, 2H), 7.63-7.73 (m, 2H), 7.77 (dd, J=8.59, 1.77 Hz, 1H), 8.01 (d, J=8.08 Hz, 1H), 8.08 (d, J=8.84 Hz, 2H), 8.38 (d, J=1.52 Hz, 1H).

Compound 12, $^1$H NMR (400 MHz, CD$_3$OD) δ ppm 1.59-1.70 (m, 1H), 1.71-1.93 (m, 4H), 2.14-2.32 (m, 1H), 2.32-2.53 (m, 1H), 2.73-2.88 (m, 2H), 2.88-3.03 (m, 1H), 3.08-3.26 (m, 1H), 3.33-3.42 (m, 1H), 3.43-3.55 (m, 2H), 3.75-3.85 (m, 1H), 3.87-4.04 (m, 2H), 7.14-7.57 (m, 4H), 7.63-7.73 (m, 2H), 7.77 (dd, J=8.72, 1.89 Hz, 1H), 8.01 (d, J=8.08 Hz, 1H), 8.08 (d, J=8.59 Hz, 2H), 8.38 (s, 1H).

Compound 13, $^1$H NMR (400 MHz, CD$_3$OD) δ ppm 1.61-1.74 (m, 1H), 1.74-1.95 (m, 8H), 1.96-2.06 (m, 2H), 2.29 (dd, J=13.64, 8.08 Hz, 1H), 2.56-2.68 (m, 1H), 2.74-2.89 (m, 2H), 3.07-3.18 (m, 1H), 3.25 (dd, J=12.88, 3.03 Hz, 1H), 3.43-3.54 (m, 2H), 3.79-3.88 (m, 1H), 3.93-4.02 (m, 2H), 4.08 (dd, J=4.93, 2.40 Hz, 2H), 4.18-4.27 (m, 1H), 7.29 (ddd, J=8.08, 2.53, 1.01 Hz, 1H), 7.42 (t, J=2.52 Hz, 1H), 7.47-7.51 (m, 1H), 7.54 (t, J=8.08 Hz, 1H), 7.68 (qd, J=7.96, 7.71 Hz, 2H), 7.77 (dd, J=8.59, 1.77 Hz, 1H), 8.01 (d, J=8.08 Hz, 1H), 8.08 (d, J=8.84 Hz, 2H), 8.38 (d, J=1.26 Hz, 1H).

Compound 14, $^1$H NMR (400 MHz, CD$_3$OD) δ ppm 1.68 (td, J=10.99, 4.17 Hz, 1H), 1.76-1.95 (m, 6H), 2.23-2.38 (m, 3H), 2.74-2.89 (m, 2H), 3.07-3.17 (m, 1H), 3.21-3.30 (m, 2H), 3.49 (t, J=12.88 Hz, 2H), 3.79-3.88 (m, 1H), 3.92-4.02 (m, 2H), 4.04-4.12 (m, 2H), 4.19-4.27 (m, 1H), 7.32 (ddd, J=8.08, 2.53, 1.26 Hz, 1H), 7.46 (t, J=2.27 Hz, 1H), 7.56 (dt, J=15.66, 7.83 Hz, 2H), 7.68 (qd, J=8.25, 8.08 Hz, 2H), 7.77 (dd, J=8.72, 1.89 Hz, 1H), 8.01 (d, J=8.08 Hz, 1H), 8.08 (d, J=8.59 Hz, 2H), 8.38 (d, J=1.52 Hz, 1H).

Compound 16, $^1$H NMR (400 MHz, CD$_3$OD) δ ppm 1.08 (q, J=12.29 Hz, 2H), 1.14-1.31 (m, 3H), 1.57-1.72 (m, 4H), 1.75-1.93 (m, 7H), 2.29 (ddd, J=13.77, 7.96, 2.02 Hz, 1H), 2.73-2.90 (m, 2H), 3.09 (dd, J=5.94, 1.89 Hz, 2H), 3.14 (t, J=9.22 Hz, 1H), 3.22-3.30 (m, 1H), 3.42-3.57 (m, 2H), 3.78-3.88 (m, 1H), 3.93-4.02 (m, 2H), 4.04-4.12 (m, 2H), 4.18-4.27 (m, 1H), 7.29 (ddd, J=7.89, 2.59, 1.39 Hz, 1H), 7.45 (t, J=2.27 Hz, 1H), 7.49-7.53 (m, 1H), 7.55 (t, J=7.56 Hz, 1H), 7.63-7.73 (m, 2H), 7.77 (dd, J=8.72, 1.89 Hz, 1H), 8.01 (d, J=8.08 Hz, 1H), 8.09 (d, J=8.84 Hz, 2H), 8.38 (d, J=1.52 Hz, 1H).

Compound 17, $^1$H NMR (400 MHz, CD$_3$OD) δ ppm 1.16 (dddd, J=11.81, 7.83, 7.64, 3.79 Hz, 1H), 1.52-1.70 (m, 2H), 1.77-1.95 (m, 5H), 2.28 (ddd, J=13.64, 8.21, 2.40 Hz, 1H), 2.73-2.89 (m, 2H), 3.12 (dt, J=12.82, 9.51 Hz, 1H), 3.21-3.29 (m, 1H), 3.33-3.43 (m, 2H), 3.49 (t, J=12.63 Hz, 2H), 3.79-3.88 (m, 1H), 3.92-4.02 (m, 2H), 4.04-4.13 (m, 2H), 4.19-4.27 (m, 1H), 7.32 (dt, J=7.33, 2.27 Hz, 1H), 7.47 (d, J=2.02 Hz, 1H), 7.52-7.60 (m, 2H), 7.68 (qd, J=8.25, 8.08 Hz, 2H), 7.77 (dd, J=8.59, 1.77 Hz, 1H), 8.01 (d, J=8.08 Hz, 1H), 8.08 (d, J=8.59 Hz, 2H), 8.38 (d, J=1.26 Hz, 1H).

Compound 18, $^1$H NMR (400 MHz, CD$_3$OD) δ ppm 1.68 (td, J=10.99, 4.17 Hz, 1H), 1.76-2.08 (m, 6H), 2.11-2.22 (m, 2H), 2.29 (ddd, J=13.77, 8.08, 2.15 Hz, 1H), 2.40-2.53 (m, 2H), 2.73-2.89 (m, 2H), 3.06-3.17 (m, 1H), 3.26 (ddd, J=12.82, 9.66, 3.03 Hz, 1H), 3.44-3.56 (m, 2H), 3.79-3.88 (m, 1H), 3.92-4.03 (m, 3H), 4.03-4.11 (m, 2H), 4.17-4.27 (m, 1H), 7.28 (dd, J=6.57, 1.77 Hz, 1H), 7.40 (t, J=2.77 Hz, 1H), 7.47 (ddd, J=7.71, 1.26, 1.14 Hz, 1H), 7.54 (t, J=7.96 Hz, 1H), 7.63-7.73 (m, 2H), 7.77 (dd, J=8.72, 1.89 Hz, 1H), 8.01 (d, J=8.08 Hz, 1H), 8.09 (d, J=8.59 Hz, 2H), 8.38 (d, J=1.52 Hz, 1H).

Compound 19, $^1$H NMR (400 MHz, CD$_3$OD) δ ppm 1.56-1.76 (m, 5H), 1.76-1.92 (m, 6H), 1.92-2.03 (m, 2H), 2.28 (ddd, J=13.58, 8.15, 2.27 Hz, 1H), 2.74-2.89 (m, 2H), 3.07-3.17 (m, 1H), 3.22-3.29 (m, 1H), 3.43-3.56 (m, 2H), 3.67 (dq, J=8.65, 7.14 Hz, 1H), 3.80-3.88 (m, 1H), 3.92-4.02 (m, 2H), 4.04-4.12 (m, 2H), 4.22 (sxt, J=3.79 Hz, 1H) 7.29 (ddd, J=8.02, 2.59, 1.01 Hz, 1H), 7.44 (dd, J=2.53 Hz, 1H), 7.53 (ddd, J=16.42, 8.08, 7.83 Hz, 2H), 7.63-7.74 (m, 2H), 7.77 (dd, J=8.59, 1.77 Hz, 1H), 8.01 (d, J=7.83 Hz, 1H), 8.08 (d, J=8.84 Hz, 2H), 8.38 (d, J=1.52 Hz, 1H).

Compound 20, $^1$H NMR (400 MHz, CD$_3$OD) δ ppm 1.66 (dd, J=10.86, 4.29 Hz, 1H), 1.75-1.92 (m, 4H), 2.28 (ddd, J=13.83, 8.15, 1.77 Hz, 1H), 2.74-2.89 (m, 2H), 3.02-3.12 (m, 1H), 3.22 (ddd, J=12.69, 9.54, 3.03 Hz, 1H), 3.45-3.56 (m, 2H), 3.82 (td, J=8.97, 3.03 Hz, 1H), 3.90-4.02 (m, 4H), 4.17 (td, J=9.09, 5.56 Hz, 1H), 4.48 (d, J=1.26 Hz, 2H), 7.09-7.15 (m, 3H), 7.24 (t, J=7.45 Hz, 3H), 7.27-7.33 (m, 2H), 7.45 (t, J=8.08 Hz, 1H), 7.63-7.74 (m, 2H), 7.77 (dd, J=8.72, 1.89 Hz, 1H), 8.01 (d, J=7.83 Hz, 1H), 8.09 (d, J=8.84 Hz, 2H), 8.38 (d, J=1.52 Hz, 1H).

Compound 21, $^1$H NMR (400 MHz, CD$_3$OD) δ ppm 1.68 (td, J=10.74, 3.92 Hz, 1H), 1.75-1.92 (m, 4H), 2.24-2.34 (m, 1H), 2.73-2.88 (m, 2H), 3.06-3.16 (m, 1H), 3.21-3.29 (m, 1H), 3.44-3.56 (m, 2H), 3.84 (dd, J=8.21, 6.19 Hz, 1H) 3.93-4.03 (m, 2H), 4.09 (d, J=5.05 Hz, 2H), 4.23 (dd, J=8.72, 3.92 Hz, 1H), 4.37 (d, J=7.58 Hz, 4H), 4.53 (q, J=7.24 Hz, 1H), 7.37 (d, J=7.07 Hz, 1H), 7.49 (s, 1H), 7.59 (dt, J=15.16, 7.58 Hz, 2H), 7.64-7.74 (m, 2H), 7.77 (dd, J=8.59, 1.77 Hz, 1H), 8.01 (d, J=8.08 Hz, 1H), 8.09 (d, J=8.84 Hz, 2H), 8.38 (s, 1H).

Compound 22, $^1$H NMR (400 MHz, CD$_3$OD) δ ppm 1.68 (td, J=11.12, 4.29 Hz, 1H), 1.76-1.93 (m, 4H), 2.25-2.33 (m, 1H), 2.73-2.87 (m, 2H), 3.08-3.17 (m, 1H), 3.22-3.28 (m, 1H), 3.35-3.43 (m, 3H), 3.46-3.53 (m, 3H), 3.58 (td, J=6.76, 1.64 Hz, 2H), 3.79-3.88 (m, 1H), 3.94-4.02 (m, 2H), 4.10 (d, J=5.05 Hz, 2H), 4.19-4.27 (m, 1H), 7.37 (d, J=9.35 Hz, 1H), 7.52 (d, J=1.77 Hz, 1H), 7.58-7.64 (m, 2H), 7.64-7.74 (m, 2H), 7.77 (dd, J=8.59, 1.77 Hz, 1H), 8.01 (d, J=7.83 Hz, 1H), 8.09 (d, J=9.09 Hz, 2H), 8.38 (d, J=1.01 Hz, 1H).

Compound 23, $^1$H NMR (400 MHz, CD$_3$OD) δ ppm 1.67 (td, J=10.74, 4.17 Hz, 1H), 1.76-1.92 (m, 4H), 2.28 (dd, J=13.89, 8.34 Hz, 1H), 2.72-2.89 (m, 2H), 3.05-3.14 (m, 4H), 3.28 (dd, J=12.76, 3.16 Hz, 1H), 3.43-3.55 (m, 2H), 3.77-3.88 (m, 1H), 3.92-4.02 (m, 2H), 4.08 (dd, J=4.93, 1.64 Hz, 2H), 4.23 (dddd, J=9.60, 4.99, 4.86, 3.03 Hz, 1H), 7.28 (dd, J=6.57, 2.78 Hz, 1H), 7.49 (d, J=1.52 Hz, 1H), 7.52-7.58 (m, 2H), 7.62-7.73 (m, 2H), 7.77 (dd, J=8.59, 2.02 Hz, 1H), 8.00 (d, J=8.08 Hz, 1H), 8.08 (d, J=9.09 Hz, 2H), 8.37 (d, J=1.26 Hz, 1H).

Compound 24, $^1$H NMR (400 MHz, CD$_3$OD) δ ppm 1.68 (td, J=10.86, 4.29 Hz, 1H), 1.76-1.95 (m, 4H), 2.28 (ddd, J=13.71, 8.15, 2.40 Hz, 1H), 2.74-2.90 (m, 2H), 3.12 (dt, J=12.63, 9.60 Hz, 1H), 3.26 (ddd, J=12.88, 9.98, 3.16 Hz, 1H), 3.49 (t, J=12.51 Hz, 2H), 3.79-3.88 (m, 1H), 3.92-4.02 (m, 2H), 4.08 (d, J=5.05 Hz, 2H), 4.19-4.26 (m, 1H), 4.66-4.75 (m, 1H), 4.76-4.89 (m, 4H), 7.32 (ddd, J=8.08, 2.65, 1.14 Hz, 1H), 7.46 (t, J=2.27 Hz, 1H), 7.51 (dt, J=8, 1.26 Hz, 1H), 7.56 (t, J=2.83 Hz, 1H), 7.68 (qd, J=8.25, 8.08 Hz, 2H), 7.77 (dd, J=8.59, 1.77 Hz, 1H), 8.01 (d, J=8.08 Hz, 1H), 8.08 (d, J=8.59 Hz, 2H), 8.38 (d, J=1.26 Hz, 1H).

Compound 25, $^1$H NMR (400 MHz, CD$_3$OD) δ ppm 0.97 (t, J=7.45 Hz, 3H), 1.22 (d, J=6.82 Hz, 3H), 1.35-1.48 (m, 1H), 1.67 (td, J=10.86, 3.79 Hz, 1H), 1.76-1.98 (m, 5H), 2.22-2.33 (m, 1H), 2.72-2.89 (m, 2H), 3.12 (ddd, J=12.51, 9.60, 9.47 Hz, 2H), 3.22-3.29 (m, 1H), 3.49 (t, J=12.76 Hz, 1H), 3.78-3.89 (m, 1H), 3.92-4.02 (m, 2H), 4.08 (d, J=4.29 Hz, 2H), 4.18-4.27 (m, 1H), 7.30 (dd, J=8.21, 1.64 Hz, 1H), 7.41 (s, 1H), 7.47 (d, J=8.21 Hz, 1H), 7.55 (t, J=7.96 Hz, 1H), 7.63-7.73 (m, 2H), 7.77 (dd, J=8.59, 1.52 Hz, 1H), 8.01 (d, J=8.08 Hz, 1H), 8.08 (d, J=8.84 Hz, 2H), 8.37 (s, 1H).

Compound 26, $^1$H NMR (400 MHz, CD$_3$OD) δ ppm 1.20 (t, J=7.33 Hz, 3H), 1.68 (dt, J=10.99, 4.42 Hz, 1H), 1.75-1.97 (m, 4H), 2.28 (ddd, J=13.77, 8.21 Hz, 1H), 2.73-2.89 (m, 2H), 3.06-3.15 (m, 1H), 3.20 (q, J=7.33 Hz, 2H), 3.24-3.29 (m, 2H), 3.34-3.37 (m, 1H), 3.44-3.56 (m, 2H), 3.79-3.85

(m, 1H), 3.92-4.02 (m, 2H), 4.08 (dd, J=5.05, 1.52 Hz, 2H), 4.18-4.26 (m, 1H), 7.30 (ddd, J=8.08, 2.53, 1.01 Hz, 1H), 7.44 (t, J=J=2.27 Hz, 1H), 7.50 (dt, J=8.21, 1.39 Hz, 1H), 7.55 (t, J=8.08 Hz, 1H), 7.64-7.74 (m, 2H), 7.78 (dd, J=8.59, 1.77 Hz, 1H), 8.01 (d, J=8.08 Hz, 1H), 8.09 (d, J=8.84 Hz, 2H), 8.38 (d, J=1.52 Hz, 1H).

Compound 27, $^1$H NMR (400 MHz, CD$_3$OD) δ ppm 1.20 (t, J=7.45 Hz, 3H), 1.68 (td, J=10.99, 4.17 Hz, 1H), 1.75-1.97 (m, 4H), 2.29 (dd, J=13.64, 8.08 Hz, 1H), 2.81 (dq, J=14.43, 11.27 Hz, 2H), 3.07-3.16 (m, 1H), 3.16-3.28 (m, 3H), 3.44-3.54 (m, 2H), 3.56-3.77 (m, 1H), 3.80-3.88 (m, 1H), 3.91-4.02 (m, 2H), 4.08 (dd, J=5.18, 1.64 Hz, 2H), 4.17-4.26 (m, 1H), 7.30 (ddd, J=8.08, 2.65, 1.14 Hz, 1H), 7.44 (t, J=2.53 Hz, 1H), 7.50 (dt, J=8.08, 1.39 Hz, 1H), 7.56 (t, J=7.83 Hz, 1H), 7.63-7.74 (m, 2H), 7.77 (dd, J=8.72, 1.89 Hz, 1H), 8.01 (d, J=7.83 Hz, 1H), 8.06-8.11 (m, 2H), 8.38 (d, J=1.52 Hz, 1H).

Compound 29, $^1$H NMR (400 MHz, CD$_3$OD) δ ppm 1.60-1.69 (m, 1H), 1.77-1.91 (m, 8H), 2.31 (ddd, J=13.71, 8.27, 2.27 Hz, 1H), 2.63-2.77 (m, 2H), 2.85 (bs, 4H), 3.11 (s, 3H), 3.12-3.19 (m, 1H), 3.25-3.30 (m, 1H), 3.33-3.44 (m, 2H), 3.88 (td, J=8.72, 3.03 Hz, 1H), 3.95-4.07 (m, 2H), 4.07-4.17 (m, 2H), 4.25 (td, J=9.22, 3.41 Hz, 1H), 7.25-7.33 (m, 1H), 7.42-7.46 (m, 2H), 7.51 (t, J=1.77 Hz, 1H), 7.53-7.60 (m, 2H).

Compound 30, $^1$H NMR (400 MHz, CD$_3$OD) δ ppm 1.59-1.71 (m, 1H), 1.77-1.91 (m, 4H), 2.33 (ddd, J=7.83, 6.06 2.27 Hz, 1H), 3.01-3.20 (m, 6H), 3.28 (dd, J=9.22, 3.16 Hz, 1H), 3.67 (t, J=13.52 Hz, 2H), 3.89 (td, J=8.08, 6.06 Hz, 1H), 3.96-4.15 (m, 4H), 4.25 (dt, J=9.09, 3.79 Hz, 1H), 7.30 (td, J=4.67, 2.53 Hz, 1H), 7.50 (d, J=1.26 Hz, 1H), 7.53-7.59 (m, 2H), 7.77 (d, J=7.33 Hz, 1H), 8.04 (d, J=7.58 Hz, 1H).

Compound 31, $^1$H NMR (400 MHz, CD$_3$OD) δ ppm 1.68 (td, J=12.63, 4.80 Hz, 1H), 1.79-1.98 (m, 5H), 2.26-2.37 (m, 1H), 2.66-2.83 (m, 2H), 3.09-3.20 (m, 4H), 3.27 (bs, 1H), 3.40-3.52 (m, 2H), 3.89 (td, J=8.65, 2.40 Hz, 1H), 3.97-4.08 (m, 2H), 4.08-4.15 (m, 2H), 4.25 (bs, 1H), 7.26-7.35 (m, 1H), 7.50 (s, 1H), 7.57 (d, J=5.05 Hz, 2H), 7.61 (t, J=7.83 Hz, 1H), 7.67-7.74 (m, 2H), 7.77 (t, J=1.77 Hz, 1H).

Compound 32, $^1$H NMR (400 MHz, CD$_3$OD) δ ppm 1.65 (td, J=10.74, 3.92 Hz, 1H), 1.76-1.90 (m, 4H), 2.30 (ddd, J=13.52, 8.21, 2.27 Hz, 1H), 2.66-2.83 (m, 2H), 2.92 (s, 3H), 3.11 (s, 3H), 3.12-3.20 (m, 1H), 3.25-3.30 (m, 1H), 3.34-3.40 (m, 2H), 3.90 (td, J=9.22, 3.79 Hz, 1H), 3.96-4.08 (m, 2H), 4.08-4.15 (m, 2H), 4.26 (dt, J=9.35, 3.28 Hz, 1H), 4.32 (t, J=4.55 Hz, 2H), 6.84 (d, J=8.34 Hz, 1H), 6.96 (d, J=2.27 Hz, 1H), 6.97-7.01 (m, 1H), 7.27-7.34 (m, 1H), 7.50 (t, J=1.26 Hz, 1H), 7.56 (d, J=5.05 Hz, 2H).

Compound 33, $^1$H NMR (400 MHz, CD$_3$OD) δ ppm 1.60-1.71 (m, 1H), 1.75-1.92 (m, 4H), 2.29 (dd, J=13.77, 8.21 Hz, 1H), 2.74-2.89 (m, 2H), 3.10 (s, 3H), 3.15 (d, J=9.85 Hz, 1H), 3.25 (dd, J=12.76, 3.16 Hz, 1H), 3.42-3.56 (m, 2H), 3.79-3.88 (m, 1H), 3.93-4.01 (m, 2H), 4.04-4.13 (m, 2H), 4.18-4.26 (m, 1H), 7.24-7.31 (m, 1H), 7.49 (d, J=1.52 Hz, 1H), 7.51-7.58 (m, 2H), 7.63-7.73 (m, 2H), 7.77 (dd, J=8.72, 1.89 Hz, 1H), 8.01 (d, J=8.08 Hz, 1H), 8.08 (d, J=8.59 Hz, 1H), 8.38 (d, J=1.52 Hz, 1H).

Compound 34, $^1$H NMR (400 MHz, CD$_3$OD) δ ppm 1.61-1.71 (m, 1H), 1.78-1.96 (m, 4H), 2.29 (dd, J=13.77, 8.21 Hz, 1H), 2.81 (qt, J=12.25, 3.03 Hz, 2H), 3.05-3.15 (m, 1H), 3.24-3.27 (m, 1H), 3.34-3.37 (m, 1H), 3.40 (t, J=6.32 Hz, 2H), 3.45-3.55 (m, 2H), 3.85 (t, J=6.19 Hz, 3H), 3.93-4.03 (m, 2H), 4.09 (dd, J=4.93, 2.40 Hz, 2H), 4.18-4.26 (m, 1H), 7.29 (ddd, J=6.25, 2.97, 2.65 Hz, 1H), 7.47 (t, J=1.26 Hz, 1H), 7.51-7.57 (m, 2H), 7.62-7.74 (m, 2H), 7.78 (dd, J=8.59, 1.77 Hz, 1H), 8.01 (d, J=7.83 Hz, 1H), 8.09 (d, J=8.84 Hz, 2H), 8.38 (s, 1H).

Compound 36, $^1$H NMR (400 MHz, CD$_3$OD) δ ppm 1.50 (t, J=7.33 Hz, 3H), 1.68 (dd, J=11.24, 4.17 Hz, 1H), 1.77-1.95 (m, 4H), 2.31 (ddd, J=7.96, 6.32, 5.94 Hz, 1H), 2.69-2.86 (m, 2H), 3.08-3.19 (m, 4H), 3.23-3.29 (m, 1H), 3.40-3.53 (m, 2H), 3.87 (td, J=8.46, 5.94 Hz, 1H), 3.95-4.06 (m, 2H), 4.10 (dd, J=4.93, 2.40 Hz, 2H), 4.24 (q, J=7.33 Hz, 3H), 7.30 (td, J=4.61, 2.65 Hz, 1H), 7.50 (d, J=1.52 Hz, 1H), 7.56 (d, J=5.05 Hz, 2H), 7.58-7.63 (m, 2H), 7.83-7.94 (m, 3H), 8.14 (s, 1H).

Compound 37, $^1$H NMR (400 MHz, CD$_3$OD) δ ppm 1.68 (td, J=10.99, 4.17 Hz, 1H), 1.78-1.95 (m, 4H), 2.31 (ddd, J=13.77, 8.21, 1.77 Hz, 1H), 2.70-2.87 (m, 2H), 3.08-3.19 (m, 4H), 3.27 (ddd, J=9.98, 3.03, 2.91 Hz, 1H), 3.40-3.53 (m, 2H), 3.87 (td, J=8.46, 5.94 Hz, 1H), 3.94-4.05 (m, 2H), 4.10 (dd, J=5.05, 2.27 Hz, 2H), 4.20-4.29 (m, 1H), 7.25-7.33 (m, 1H), 7.50 (d, J=1.52 Hz, 1H), 7.56 (d, J=5.05 Hz, 2H), 7.61 (d, J=5.31 Hz, 2H), 7.86-7.94 (m, 2H), 8.07 (s, 2H).

Compound 38, $^1$H NMR (400 MHz, CD$_3$OD) δ ppm 0.94 (t, J=7.33 Hz, 3H), 1.68 (td, J=10.99, 4.17 Hz, 1H), 1.78-1.97 (m, 6H), 2.31 (ddd, J=13.77, 8.21, 1.77 Hz, 1H), 2.70-2.86 (m, 2H), 3.08-3.18 (m, 4H), 3.24-3.29 (m, 1H), 3.38-3.53 (m, 2H), 3.87 (td, J=8.46, 5.94 Hz, 1H), 3.94-4.06 (m, 2H), 4.08-4.12 (m, 2H), 4.15 (t, J=6.95 Hz, 2H), 4.24 (dt, J=9.09, 3.54 Hz, 1H), 7.25-7.33 (m, 1H), 7.50 (t, J=1.52 Hz, 1H), 7.56 (d, J=5.31 Hz, 2H), 7.59-7.62 (m, 2H), 7.84-7.93 (m, 3H), 8.14 (s, 1H).

Compound 39, $^1$H NMR (400 MHz, CD$_3$OD) δ ppm 1.05-1.11 (m, 2H), 1.11-1.18 (m, 2H), 1.68 (td, J=10.99, 4.42 Hz, 1H), 1.77-1.96 (m, 4H), 2.31 (dd, J=13.52, 7.96 Hz, 1H), 2.69-2.86 (m, 2H), 3.08-3.19 (m, 4H), 3.24-3.29 (m, 2H), 3.39-3.52 (m, 2H), 3.66-3.76 (m, 1H), 3.83-3.92 (m, 1H), 3.94-4.05 (m, 2H), 4.10 (dd, J=4.80, 2.53 Hz, 2H), 4.19-4.27 (m, 1H), 4.54 (bs, 1H), 7.26-7.36 (m, 1H), 7.50 (d, J=1.52 Hz, 1H), 7.56 (d, J=5.05 Hz, 2H), 7.58-7.63 (m, 2H), 7.84-7.94 (m, 3H), 8.18 (s, 1H).

Compound 40, $^1$H NMR (400 MHz, CD$_3$OD) δ ppm 1.68 (td, J=10.86, 4.04 Hz, 1H), 1.78-1.95 (m, 4H), 2.31 (ddd, J=13.77, 8.21, 1.77 Hz, 1H), 2.70-2.85 (m, 2H), 3.09-3.18 (m, 4H), 3.24-3.29 (m, 1H), 3.46 (t, J=12.76 Hz, 2H), 3.87 (td, J=8.72, 3.03 Hz, 1H), 3.95 (s, 3H), 3.97-4.05 (m, 2H), 4.06-4.14 (m, 2H), 4.24 (dt, J=9.09, 3.54 Hz, 1H), 7.26-7.33 (m, 1H), 7.50 (d, J=1.52 Hz, 1H), 7.56 (d, J=5.31 Hz, 2H), 7.58-7.62 (m, 2H), 7.82-7.91 (m, 3H), 8.09 (s, 1H).

Compound 41, $^1$H NMR (400 MHz, CD$_3$OD) δ ppm 1.69 (td, J=11.12, 4.04 Hz, 1H), 1.77-1.97 (m, 4H), 2.32 (ddd, J=13.71, 8.27, 2.27 Hz, 1H), 2.78 (qd, J=11.94, 2.91 Hz, 2H), 3.09-3.19 (m, 4H), 3.25-3.29 (m, 1H), 3.43-3.55 (m, 2H), 3.88 (td, J=8.59, 5.81 Hz, 1H), 3.96-4.06 (m, 2H), 4.10 (dd, J=4.93, 2.40 Hz, 2H), 4.19 (s, 2H), 4.22-4.29 (m, 1H), 7.26-7.34 (m, 1H), 7.49 (t, J=1.26 Hz, 1H), 7.56 (d, J=5.05 Hz, 2H), 7.60 (d, J=8.34 Hz, 2H), 7.69-7.82 (m, 4H), 7.93-8.01 (m, 2H).

Compound 42, $^1$H NMR (400 MHz, CD$_3$OD) δ ppm 1.69 (td, J=11.24, 4.42 Hz, 1H), 1.79-1.98 (m, 4H), 2.32 (ddd, J=13.77, 8.21, 1.77 Hz, 1H), 2.70-2.85 (m, 2H), 3.09-3.19 (m, 4H), 3.24-3.29 (m, 1H), 3.44-3.56 (m, 2H), 3.87 (td, J=8.46, 5.94 Hz, 1H), 3.95-4.05 (m, 2H), 4.10 (dd, J=4.93, 2.40 Hz, 2H), 4.19-4.28 (m, 1H), 7.26-7.33 (m, 1H), 7.50 (d, J=1.52 Hz, 1H), 7.56 (d, J=5.05 Hz, 2H), 7.75 (t, J=7.96 Hz, 1H), 7.81-7.89 (m, 3H), 7.98-8.06 (m, 4H).

Compound 44, $^1$H NMR (400 MHz, CD$_3$OD) δ ppm 1.63-1.74 (m, 1H), 1.80-1.99 (m, 4H), 2.33 (ddd, J=7.26, 5.46, 1.77 Hz, 5H), 2.70-2.85 (m, 4H), 3.08-3.20 (m, 2H), 3.24-3.30 (m, 2H), 3.50-3.61 (m, 1H), 3.82-3.91 (m, 1H), 3.96-4.06 (m, 2H), 4.06-4.15 (m, 2H), 4.19-4.28 (m, 1H), 7.26-7.33 (m, 1H), 7.49 (t, J=1.01 Hz, 1H), 7.56 (d, J=5.31 Hz, 2H), 7.86 (t, J=7.83 Hz, 1H), 7.99 (dt, J=8.08, 1.26, 1.01

Hz, 1H), 8.04 (d, J=5.81 Hz, 1H), 8.12 (s, 1H), 8.19 (d, J=7.83 Hz, 1H), 8.22 (t, J=1.64 Hz, 1H), 8.69 (d, J=6.06 Hz, 1H).

Compound 45, $^1$H NMR (400 MHz, CD$_3$OD) δ ppm 1.62-1.73 (m, 1H), 1.78-1.97 (m, 4H), 2.31 (ddd, J=13.77, 8.21, 2.02 Hz, 1H), 2.73-2.89 (m, 2H), 3.11 (s, 3H), 3.12-3.18 (m, 1H), 3.24-3.29 (m, 1H), 3.42-3.58 (m, 2H), 3.83-3.90 (m, 1H), 3.95-4.05 (m, 2H), 4.06-4.13 (m, 2H), 4.19-4.27 (m, 1H), 7.25-7.33 (m, 1H), 7.46-7.51 (m, 2H), 7.54-7.58 (m, 2H), 7.76 (t, J=7.83 Hz, 1H), 7.87 (dt, J=7.83, 1.39 Hz, 1H), 7.96-8.04 (m, 2H), 8.27 (dt, J=7.83, 1.39 Hz, 1H), 8.39 (t, J=1.64 Hz, 1H), 8.70 (dt, J=4.86, 1.36 Hz, 1H).

Compound 46, $^1$H NMR (400 MHz, CD$_3$OD) δ ppm 1.61-1.72 (m, 1H), 1.79-1.96 (m, 4H), 2.33 (ddd, J=13.89, 8.34, 2.02 Hz, 1H), 2.69-2.84 (m, 2H), 3.09-3.20 (m, 4H), 3.24-3.30 (m, 1H), 3.44-3.60 (m, 2H), 3.84-3.94 (m, 1H), 3.98-4.08 (m, 2H), 4.11 (dd, J=4.93, 2.40 Hz, 2H), 4.21-4.29 (m, 1H), 7.25-7.34 (m, 1H), 7.50 (t, J=1.26 Hz, 1H), 7.57 (d, J=5.05 Hz, 2H), 7.68 (dd, J=8.08, 4.80 Hz, 1H), 8.21 (dd, J=8.21, 1.89 Hz, 1H), 8.85 (bs, 1H), 8.94 (bs, 1H).

Compound 47, $^1$H NMR (400 MHz, CD$_3$OD) δ ppm 1.59-1.70 (m, 1H), 1.77-1.94 (m, 4H), 2.30 (ddd, J=13.77, 8.21, 2.27 Hz, 1H), 2.66-2.81 (m, 2H), 3.11 (s, 3H), 3.16 (t, J=9.47 Hz, 1H), 3.28 (dd, J=9.47, 3.16 Hz, 1H), 3.43 (t, J=12.63 Hz, 2H), 3.88 (td, J=8.72, 5.94 Hz, 1H), 3.95-4.06 (m, 2H), 4.10 (dd, J=4.93, 1.89 Hz, 2H), 4.25 (dt, J=9.09, 3.54 Hz, 1H), 7.25-7.34 (m, 1H), 7.50 (t, J=1.26 Hz, 1H), 7.56 (d, J=5.05 Hz, 2H), 7.59-7.64 (m, 2H), 7.65-7.71 (m, 1H), 7.74-7.81 (m, 2H).

Compound 48, $^1$H NMR (400 MHz, CD$_3$OD) δ ppm 1.58-1.70 (m, 1H), 1.77-1.94 (m, 4H), 2.31 (ddd, J=13.83, 8.27, 2.15 Hz, 1H), 2.45 (s, 3H), 2.67-2.79 (m, 2H), 3.11 (s, 3H), 3.16 (t, J=9.47 Hz, 1H), 3.25-3.30 (m, 1H), 3.42 (t, J=12.76 Hz, 2H), 3.88 (td, J=8.59, 6.06 Hz, 1H), 3.94-4.07 (m, 2H), 4.11 (dd, J=4.93, 2.15 Hz, 2H), 4.25 (dt, J=9.22, 3.41 Hz, 1H), 7.26-7.34 (m, 1H), 7.45-7.52 (m, 3H), 7.53-7.63 (m, 4H).

Compound 49, $^1$H NMR (400 MHz, CD$_3$OD) δ ppm 1.59-1.71 (m, 1H), 1.78-1.94 (m, 4H), 2.31 (ddd, J=13.83, 8.27, 2.15 Hz, 1H), 2.68-2.84 (m, 2H), 3.11 (s, 3H), 3.16 (t, J=9.47 Hz, 1H), 3.25-3.30 (m, 1H), 3.43 (t, J=13.01 Hz, 2H), 3.84-3.93 (m, 4H), 3.96-4.07 (m, 2H), 4.11 (dd, J=4.93, 2.15 Hz, 2H), 4.21-4.29 (m, 1H), 7.21-7.36 (m, 4H), 7.49-7.60 (m, 4H).

Compound 50, $^1$H NMR (400 MHz, CD$_3$OD) δ ppm 1.62-1.71 (m, 1H), 1.78-1.96 (m, 4H), 2.32 (ddd, J=13.83, 8.27, 1.89 Hz, 1H), 2.67-2.82 (m, 2H), 3.11 (s, 3H), 3.16 (t, J=9.22 Hz, 1H), 3.24-3.30 (m, 1H), 3.44-3.58 (m, 2H), 3.84-3.92 (m, 1H), 3.96-4.07 (m, 2H), 4.11 (dd, J=4.93, 2.40 Hz, 2H), 4.25 (dt, J=8.84, 3.54 Hz, 1H), 7.27-7.33 (m, 1H), 7.50 (t, J=1.77 Hz, 1H), 7.54-7.61 (m, 2H), 7.85 (t, J=7.96 Hz, 1H), 7.98-8.04 (m, 2H), 8.06 (d, J=7.83 Hz, 1H).

Compound 51, $^1$H NMR (400 MHz, CD$_3$OD) δ ppm 1.65-1.76 (m, 1H), 1.82-2.00 (m, 4H), 2.34 (ddd, J=13.64, 8.21, 2.15 Hz, 1H), 2.81-2.97 (m, 2H), 3.11 (s, 3H), 3.17 (t, J=9.60 Hz, 1H), 3.26-3.30 (m, 1H), 3.47 (t, J=12.63 Hz, 2H), 3.91 (td, J=9.16, 3.92 Hz, 1H), 3.98-4.14 (m, 4H), 4.25 (dt, J=9.22, 3.41 Hz, 1H), 7.27-7.33 (m, 1H), 7.37-7.52 (m, 5H), 7.54-7.56 (m, 2H), 7.56 (s, 1H), 7.65-7.72 (m, 2H).

Compound 52, $^1$H NMR (400 MHz, CD$_3$OD) δ ppm 1.62-1.72 (m, 1H), 1.82-1.94 (m, 4H), 2.31-2.41 (m, 4H), 2.63 (s, 3H), 2.87-3.03 (m, 2H), 3.12 (s, 3H), 3.18 (ddd, J=12.38, 9.35, 9.09 Hz, 1H), 3.32-3.37 (m, 1H), 3.41-3.52 (m, 2H), 3.91-3.99 (m, 1H), 4.00-4.17 (m, 4H), 4.23-4.32 (m, 1H), 7.26-7.36 (m, 1H), 7.51 (t, J=1.26 Hz, 1H), 7.54-7.60 (m, 2H).

Compound 53, $^1$H NMR (400 MHz, CD$_3$OD) δ ppm 1.61-1.71 (m, 1H), 1.78-1.95 (m, 4H), 2.32 (ddd, J=13.83, 8.27, 2.15 Hz, 1H), 2.66-2.81 (m, 2H), 3.11 (s, 3H), 3.17 (t, J=9.60 Hz, 1H), 3.26-3.30 (m, 1H), 3.41 (t, J=12.76 Hz, 2H), 3.89 (td, J=8.34, 5.81 Hz, 1H), 3.97-4.08 (m, 2H), 4.11 (dd, J=4.93, 2.40 Hz, 2H), 4.20-4.31 (m, 1H), 4.70 (s, 2H), 7.13 (d, J=8.59 Hz, 1H), 7.27-7.33 (m, 2H), 7.37 (dd, J=8.46, 2.15 Hz, 1H), 7.50 (t, J=1.26 Hz, 1H), 7.53-7.60 (m, 2H).

Compound 54, $^1$H NMR (400 MHz, CD$_3$OD) δ ppm 1.58-1.71 (m, 1H), 1.77-1.95 (m, 4H), 2.32 (ddd, J=13.77, 8.34, 2.15 Hz, 1H), 2.69-2.84 (m, 2H), 3.11 (s, 3H), 3.17 (t, J=9.35 Hz, 1H), 3.25-3.30 (m, 1H), 3.39-3.53 (m, 2H), 3.89 (td, J=8.46, 5.94 Hz, 1H), 3.96-4.08 (m, 2H), 4.11 (dd, J=4.93, 2.15 Hz, 2H), 4.25 (dt, J=9.09, 3.28 Hz, 1H), 7.26-7.34 (m, 1H), 7.40-7.48 (m, 1H), 7.49-7.54 (m, 2H), 7.57 (d, J=5.05 Hz, 2H), 7.59-7.69 (m, 2H).

Compound 55, $^1$H NMR (400 MHz, CD$_3$OD) δ ppm 1.60-1.72 (m, 1H), 1.79-1.95 (m, 4H), 2.32 (ddd, J=13.77, 8.34, 2.15 Hz, 1H), 2.69-2.85 (m, 2H), 3.12 (s, 3H), 3.17 (t, J=9.47 Hz, 1H), 3.26-3.30 (m, 1H), 3.43-3.54 (m, 2H), 3.89 (td, J=8.46, 5.94 Hz, 1H), 3.96-4.07 (m, 2H), 4.11 (dd, J=5.05, 2.27 Hz, 2H), 4.26 (dt, J=9.09, 3.54 Hz, 1H), 7.25-7.34 (m, 1H), 7.50 (t, J=1.26 Hz, 1H), 7.56 (d, J=5.05 Hz, 2H), 7.81 (t, J=7.71 Hz, 1H), 8.05 (dddd, J=11.05, 7.96, 1.33, 1.14 Hz, 2H), 8.15 (t, J=1.52 Hz, 1H).

Compound 63, $^1$H NMR (400 MHz, CD$_3$OD) δ ppm 1.71 (td, J=11.24, 4.17 Hz, 1H), 1.80-2.00 (m, 4H), 2.34 (ddd, J=13.39, 7.96, 1.64 Hz, 1H), 2.70-2.89 (m, 2H), 3.07-3.20 (m, 4H), 3.24-3.29 (m, 1H), 3.50-3.61 (m, 2H), 3.83-3.93 (m, 1H), 3.98-4.08 (m, 2H), 4.11 (dd, J=4.93, 1.89 Hz, 2H), 4.26 (bs, 1H), 7.23-7.37 (m, 1H), 7.50 (d, J=1.26 Hz, 1H), 7.53-7.60 (m, 2H), 7.87 (t, J=7.83 Hz, 1H), 7.98 (d, J=8.08 Hz, 1H), 8.14 (d, J=7.83 Hz, 1H), 8.18-8.28 (m, 2H), 8.92 (bs, 1H), 8.98 (d, J=8.34 Hz, 1H), 9.29 (bs, 1H).

Compound 106, $^1$H NMR (400 MHz, CDCl$_3$) δ ppm 1.30 (s, 6H), 1.56 (dd, J=13.01, 5.18 Hz, 1H), 1.72 (dd, J=7.58, 4.04 Hz, 2H), 1.81-1.89 (m, 2H), 2.00 (dd, J=13.14, 7.33 Hz, 1H), 2.67-2.75 (m, 1H), 2.76-2.88 (m, 3H), 3.40 (dd, J=7.07, 5.56 Hz, 2H), 3.52 (dd, J=9.22, 4.93 Hz, 1H), 3.56-3.65 (m, 2H), 3.73 (s, 2H), 3.82 (dd, J=9.22, 5.68 Hz, 1H), 3.97-4.04 (m, 3H), 5.30 (s, 2H), 7.16-7.23 (m, 1H), 7.34-7.38 (m, 1H), 7.43-7.52 (m, 2H), 7.66-7.73 (m, 1H), 7.90 (ddd, J=8.53, 7.01, 1.39 Hz, 1H), 7.96 (d, J=8.08 Hz, 1H), 8.20 (d, J=8.59 Hz, 1H), 8.60 (d, J=1.77 Hz, 1H), 9.17 (d, J=2.27 Hz, 1H).

Compound 107, $^1$H NMR (400 MHz, CDCl$_3$) δ ppm 1.56 (dd, J=13.01, 5.18 Hz, 1H), 1.69-1.76 (m, 2H), 1.81-1.89 (m, 2H), 1.94-2.07 (m, 6H), 2.64-2.76 (m, 3H), 2.76-2.87 (m, 3H), 3.35-3.44 (m, 1H), 3.52 (dd, J=9.09, 4.80 Hz, 1H), 3.57-3.65 (m, 2H), 3.78-3.86 (m, 3H), 3.96-4.04 (m, 3H), 7.15-7.22 (m, 1H), 7.34-7.39 (m, 1H), 7.43-7.51 (m, 2H), 7.65-7.73 (m, 1H), 7.90 (ddd, J=8.53, 7.01, 1.39 Hz, 1H), 7.96 (d, J=8.34 Hz, 1H), 8.21 (d, J=8.34 Hz, 1H), 8.60 (d, J=1.77 Hz, 1H), 9.17 (d, J=2.27 Hz, 1H).

Compound 108, $^1$H NMR (400 MHz, CD$_3$OD) δ ppm 1.29 (s, 6H), 1.31-1.37 (m, 1H), 1.55-1.64 (m, 2H), 1.68-1.76 (m, 2H), 1.76-1.81 (m, 2H), 1.90 (dd, J=12.88, 7.58 Hz, 1H), 2.61-2.69 (m, 2H), 2.70-2.78 (m, 2H), 2.82-2.96 (m, 2H), 3.33-3.43 (m, 1H), 3.60-3.70 (m, 2H), 3.75-3.83 (m, 1H), 3.99 (bs, 4H), 4.55 (s, 1H), 7.25 (ddd, J=8.08, 2.53, 1.26 Hz, 1H), 7.34-7.38 (m, 1H), 7.40-7.45 (m, 1H), 7.45-7.51 (m, 1H), 7.74-7.82 (m, 1H), 7.98 (ddd, J=8.53, 7.01, 1.39 Hz, 1H), 8.17 (d, J=9.60 Hz, 2H), 8.82 (d, J=2.27 Hz, 1H), 9.12 (d, J=2.27 Hz, 1H).

Compound 109, $^1$H NMR (400 MHz, CD$_3$OD) δ ppm 1.28 (s, 6H), 1.61-1.71 (m, 1H), 1.77-1.95 (m, 4H), 2.30 (dd, J=13.77, 7.96 Hz, 1H), 2.75-2.90 (m, 2H), 3.14 (dd, J=12.63, 9.60 Hz, 1H), 3.22-3.29 (m, 1H), 3.46-3.58 (m, 2H), 3.65 (s, 2H), 3.81-3.90 (m, 1H), 3.92-4.02 (m, 2H), 4.04-4.12 (m, 2H), 4.20-4.28 (m, 1H), 7.27-7.33 (m, 1H), 7.38-7.42 (m, 1H), 7.44-7.50 (m, 1H), 7.54 (t, J=7.96 Hz, 1H), 7.74 (dd, J=8.34, 4.29 Hz, 1H), 8.09 (dd, J=8.84, 2.02 Hz, 1H), 8.25 (d, J=9.09 Hz, 1H), 8.51 (d, J=2.02 Hz, 1H), 8.64 (d, J=7.33 Hz, 1H), 9.07 (bs, 1H).

Compound 110, $^1$H NMR (400 MHz, CD$_3$OD) δ ppm 1.61-1.71 (m, 1H), 1.77-1.91 (m, 4H), 1.92-2.02 (m, 2H), 2.05-2.15 (m, 2H), 2.30 (dd, J=13.77, 7.96 Hz, 1H), 2.60-2.74 (m, 2H), 2.76-2.91 (m, 2H), 3.14 (dd, J=12.76, 9.73 Hz, 1H), 3.23-3.29 (m, 1H), 3.46-3.60 (m, 2H), 3.71 (s, 2H), 3.82-3.90 (m, 1H), 3.94-4.02 (m, 2H), 4.03-4.11 (m, 2H), 4.19-4.28 (m, 1H), 7.23-7.31 (m, 1H), 7.39-7.43 (m, 1H), 7.45-7.49 (m, 1H), 7.50-7.56 (m, 1H), 7.74 (dd, J=8.34, 4.29 Hz, 1H), 8.10 (dd, J=8.84, 2.02 Hz, 1H), 8.25 (d, J=8.84 Hz, 1H), 8.52 (d, J=1.77 Hz, 1H), 8.65 (d, J=7.58 Hz, 1H), 9.07 (dd, J=4.29, 1.26 Hz, 1H).

Compound 120, $^1$H NMR (400 MHz, CD$_3$OD) δ ppm 1.62-1.73 (m, 1H), 1.81-1.97 (m, 4H), 2.32 (dd, J=13.64, 8.08 Hz, 1H), 2.38 (s, 3H), 2.73-2.88 (m, 2H), 3.14 (dd, J=12.76, 9.47 Hz, 1H), 3.41 (t, J=6.19 Hz, 2H), 3.45-3.55 (m, 2H), 3.82-3.90 (m, 3H), 3.96-4.06 (m, 2H), 4.07-4.15 (m, 2H), 4.21-4.30 (m, 1H), 7.27-7.34 (m, 1H), 7.47-7.50 (m, 1H), 7.52-7.61 (m, 3H), 7.78-7.83 (m, 1H), 7.83-7.88 (m, 1H), 7.90-7.96 (m, 2H), 8.04 (d, J=7.07 Hz, 1H), 8.54 (d, J=4.29 Hz, 1H).

Compound 125, $^1$H NMR (400 MHz, CD$_3$OD) δ ppm 1.69 (dd, J=11.12, 4.29 Hz, 1H), 1.79-1.95 (m, 4H), 2.29 (dd, J=13.64, 8.34 Hz, 1H), 2.73-2.89 (m, 2H), 3.09 (dd, J=12.63, 9.60 Hz, 1H), 3.26 (dd, J=12.76, 2.91 Hz, 1H), 3.40 (t, J=6.19 Hz, 2H), 3.45-3.56 (m, 2H), 3.84 (t, J=6.32 Hz, 3H), 3.92-3.99 (m, 1H), 3.99-4.04 (m, 1H), 4.06-4.12 (m, 2H), 4.18-4.26 (m, 1H), 7.26-7.33 (m, 1H), 7.45-7.49 (m, 1H), 7.51-7.56 (m, 2H), 7.78 (t, J=7.83 Hz, 1H), 7.81 (d, J=7.07 Hz, 1H), 7.87-7.91 (m, 1H), 8.15 (t, J=7.96 Hz, 1H), 8.21-8.26 (m, 1H), 8.39-8.44 (m, 1H), 8.49-8.52 (m, 1H).

Compound 126, $^1$H NMR (400 MHz, CD$_3$OD) δ ppm 1.58-1.70 (m, 2H), 1.72-1.78 (m, 2H), 1.80-1.86 (m, 2H), 2.09 (dd, J=13.14, 7.83 Hz, 1H), 2.72-2.91 (m, 4H), 3.37-3.46 (m, 4H), 3.53 (quin, J=5.81 Hz, 1H), 3.60 (dd, J=9.22, 5.43 Hz, 1H), 3.85 (t, J=6.19 Hz, 2H), 3.91 (dd, J=9.35, 6.06 Hz, 1H), 3.98-4.12 (m, 3H), 7.28 (ddd, J=5.18, 2.53, 2.40 Hz, 1H), 7.45-7.50 (m, 1H), 7.50-7.56 (m, 2H), 7.67 (dd, J=6.82, 5.05 Hz, 1H), 7.79 (t, J=7.71 Hz, 1H), 7.88-7.92 (m, 1H), 7.95-8.00 (m, 1H), 8.04 (d, J=1.77 Hz, 1H), 8.51 (d, J=5.05 Hz, 1H), 8.59 (d, J=2.78 Hz, 1H).

Compound 127, $^1$H NMR (400 MHz, CD$_3$OD) δ ppm 1.61-1.69 (m, 2H), 1.72-1.79 (m, 1H), 1.81-1.86 (m, 2H), 2.12 (dd, J=13.26, 7.71 Hz, 1H), 2.61 (s, 3H), 2.77-2.88 (m, 3H), 2.92-2.96 (m, 1H), 3.40 (t, J=6.19 Hz, 2H), 3.39-3.44 (m, 2H), 3.56-3.66 (m, 2H), 3.84 (t, J=6.32 Hz, 2H), 3.89-3.94 (m, 1H), 4.01-4.12 (m, 3H), 7.25-7.31 (m, 2H), 7.44-7.47 (m, 1H), 7.48-7.55 (m, 2H), 7.72 (t, J=7.71 Hz, 1H), 7.70 (d, J=7.58 Hz, 1H), 7.77-7.84 (m, 2H), 8.24 (ddd, J=7.71, 1.52, 1.39 Hz, 1H), 8.35 (t, J=1.64 Hz, 1H).

Compound 128, $^1$H NMR (400 MHz, CD$_3$OD) δ ppm 1.61 (dd, J=13.01, 5.94 Hz, 1H), 1.67 (dd, J=10.48, 4.17 Hz, 1H), 1.72-1.77 (m, 1H), 1.80-1.84 (m, 2H), 2.09 (dd, J=13.14, 7.58 Hz, 1H), 2.41 (s, 3H), 2.72-2.91 (m, 4H), 3.37-3.43 (m, 2H), 3.40 (t, J=6.19 Hz, 2H), 3.51-3.63 (m, 2H), 3.84 (t, J=6.32 Hz, 2H), 3.90 (dd, J=9.22, 5.94 Hz, 1H), 4.00-4.10 (m, 3H), 7.27 (dt, J=7.14, 2.37 Hz, 1H), 7.45-7.47 (m, 1H), 7.48-7.55 (m, 2H), 7.72 (t, J=7.71 Hz, 1H), 7.75-7.79 (m, 1H), 7.79-7.82 (m, 1H), 7.82-7.85 (m, 1H), 8.23 (dt, J=7.77, 1.42 Hz, 1H), 8.34 (t, J=1.52 Hz, 1H), 8.51 (d, J=2.27 Hz, 1H).

Compound 129, $^1$H NMR (400 MHz, CD$_3$OD) δ ppm 1.61-1.70 (m, 2H), 1.73-1.79 (m, 1H), 1.80-1.85 (m, 2H), 2.12 (dd, J=13.26, 7.45 Hz, 1H), 2.47 (s, 3H), 2.76-2.88 (m, 3H), 2.92-2.97 (m, 1H), 3.40 (t, J=6.19 Hz, 2H), 3.41-3.45 (m, 2H), 3.58-3.66 (m, 2H), 3.84 (t, J=6.32 Hz, 2H), 3.88-3.95 (m, 1H), 4.01-4.12 (m, 3H), 7.26-7.30 (m, 2H), 7.46 (d, J=2.02 Hz, 1H), 7.48-7.56 (m, 2H), 7.73 (t, J=7.83 Hz, 1H), 7.78 (bs, 1H), 7.82-7.85 (m, 1H), 8.24 (dt, J=7.83, 1.39 Hz, 1H), 8.34 (t, J=1.64 Hz, 1H), 8.51 (d, J=5.05 Hz, 1H).

Compound 134, $^1$H NMR (400 MHz, CD$_3$OD) δ ppm 1.58 (dd, J=13.01, 6.19 Hz, 1H), 1.63-1.70 (m, 1H), 1.70-1.77 (m, 1H), 1.78-1.86 (m, 2H), 2.07 (dd, J=13.01, 7.71 Hz, 1H), 2.71 (dd, J=12.13, 7.33 Hz, 1H), 2.76-2.88 (m, 3H), 3.36-3.43 (m, 2H), 3.40 (t, J=6.19 Hz, 2H), 3.45-3.53 (m, 1H), 3.57 (t, J=4.55 Hz, 1H), 3.84 (t, J=6.32 Hz, 2H), 3.89 (dd, J=9.22, 5.94 Hz, 1H), 3.98-4.08 (m, 3H), 7.06 (dd, J=8.08, 2.53 Hz, 1H), 7.27 (ddd, J=7.39, 2.34, 2.15 Hz, 1H), 7.44-7.47 (m, 1H), 7.48-7.56 (m, 2H), 7.73 (t, J=7.83 Hz, 1H), 7.84 (ddd, J=8.08, 1.39, 1.14 Hz, 1H), 7.89 (dd, J=7.58, 2.27 Hz, 1H), 8.04 (q, J=8.08 Hz, 1H), 8.32 (dt, J=7.83, 1.39 Hz, 1H), 8.41 (t, J=1.64 Hz, 1H).

Compound 136, $^1$H NMR (400 MHz, CDCl$_3$) δ ppm 1.03-1.08 (m, 2H), 1.55-1.63 (m, 3H), 1.69-1.74 (m, 2H), 1.82-1.89 (m, 2H), 2.01 (dd, J=13.01, 7.45 Hz, 1H), 2.69-2.76 (m, 1H), 2.77-2.87 (m, 3H), 3.37-3.45 (m, 1H), 3.53 (dd, J=9.22, 4.93 Hz, 1H), 3.57-3.63 (m, 2H), 3.65 (s, 2H), 3.82 (dd, J=9.09, 5.81 Hz, 1H), 4.02 (s, 3H), 7.14-7.20 (m, 1H), 7.39-7.42 (m, 1H), 7.43-7.49 (m, 2H), 7.66-7.74 (m, 1H), 7.90 (ddd, J=8.46, 6.95, 1.26 Hz, 1H), 7.96 (d, J=8.08 Hz, 1H), 8.20 (d, J=8.34 Hz, 1H), 8.60 (d, J=2.02 Hz, 1H), 9.17 (d, J=2.27 Hz, 1H).

Compound 146, $^1$H NMR (400 MHz, CD$_3$OD) δ ppm 1.68-1.78 (m, 1H), 1.82-2.01 (m, 2H), 2.24-2.47 (m, 5H), 2.89-3.06 (m, 2H), 3.11-3.19 (m, 1H), 3.24-3.28 (m, 1H), 3.45-3.55 (m, 1H), 3.63 (t, J=12.63 Hz, 2H), 3.87-3.94 (m, 1H), 3.99-4.06 (m, 2H), 4.07-4.16 (m, 3H), 4.22-4.31 (m, 1H), 7.30 (dd, J=8.21, 1.64 Hz, 1H), 7.40 (s, 1H), 7.46 (d, J=7.83 Hz, 1H), 7.55 (t, J=7.96 Hz, 1H), 8.00 (t, J=7.45 Hz, 1H), 8.22 (t, J=7.58 Hz, 1H), 8.28-8.35 (m, 1H), 8.41 (d, J=8.08 Hz, 1H), 9.35 (d, J=1.01 Hz, 1H), 9.44 (d, J=1.77 Hz, 1H).

Compound 147, $^1$H NMR (400 MHz, CD$_3$OD) δ ppm 1.05-1.12 (m, 2H), 1.46-1.51 (m, 2H), 1.64-1.75 (m, 1H), 1.79-1.98 (m, 4H), 2.33 (dd, J=13.89, 7.83 Hz, 1H), 2.77-2.92 (m, 2H), 3.16 (d, J=9.60 Hz, 1H), 3.24-3.29 (m, 1H), 3.53-3.65 (m, 2H), 3.71 (s, 2H), 3.83-3.89 (m, 1H), 3.97-4.03 (m, 2H), 4.05-4.14 (m, 2H), 4.18-4.28 (m, 1H), 7.28 (ddd, J=7.77, 2.59, 1.52 Hz, 1H), 7.46 (d, J=2.27 Hz, 1H), 7.47-7.57 (m, 2H), 8.03 (dd, J=8.46, 4.93 Hz, 1H), 8.27-8.33 (m, 1H), 8.34-8.40 (m, 1H), 8.72 (d, J=1.77 Hz, 1H), 9.07 (d, J=8.59 Hz, 1H), 9.25 (d, J=1.01 Hz, 1H).

Compound 148, $^1$H NMR (400 MHz, CD$_3$OD) δ ppm 1.64-1.74 (m, 1H), 1.80-1.98 (m, 4H), 2.33 (dd, J=13.89, 7.83 Hz, 1H), 2.77-2.92 (m, 2H), 3.15 (dd, J=13.01, 9.73 Hz, 1H), 3.24-3.29 (m, 1H), 3.55-3.67 (m, 2H), 3.82-3.90 (m, 1H), 3.96-4.04 (m, 2H), 4.06-4.11 (m, 2H), 4.11-4.19 (m, 2H), 4.25 (dd, J=9.47, 3.16 Hz, 1H), 7.43 (dt, J=7.77, 2.05 Hz, 1H), 7.49-7.52 (m, 1H), 7.57-7.66 (m, 2H), 8.12 (dd, J=8.46, 5.18 Hz, 1H), 8.33-8.43 (m, 2H), 8.78 (d, J=1.52 Hz, 1H), 9.20 (d, J=8.59 Hz, 1H), 9.31 (dd, J=5.05, 1.52 Hz, 1H).

Compound 155, $^1$H NMR (400 MHz, CD$_3$OD) δ ppm 1.05-1.13 (m, 2H), 1.46-1.52 (m, 2H), 1.62-1.73 (m, 1H), 1.82-1.94 (m, 4H), 2.32-2.41 (m, 1H), 2.76-2.92 (m, 2H), 3.04 (s, 3H), 3.14-3.22 (m, 1H), 3.49 (bs, 4H), 3.59 (d, J=5.31 Hz, 1H), 3.63-3.69 (m, 2H), 3.72 (s, 2H), 3.75 (d, J=1.01 Hz, 1H), 3.94 (d, J=7.58 Hz, 1H), 4.00-4.17 (m, 4H), 4.28 (bs, 1H), 4.63 (bs, 2H), 7.26 (s, 1H), 7.30 (d, J=7.58 Hz, 1H), 7.48-7.51 (m, 2H), 7.49-7.57 (m, 1H), 7.83 (bs, 1H).

Compound 156, $^1$H NMR (400 MHz, CD$_3$OD) δ ppm 1.63-1.73 (m, 1H), 1.83-1.96 (m, 4H), 2.35 (dd, J=13.52, 8.21 Hz, 1H), 2.75-2.84 (m, 1H), 2.84-2.91 (m, 1H), 3.02 (s, 3H), 3.18 (dd, J=12.63, 9.60 Hz, 1H), 3.41-3.53 (m, 2H), 3.56-3.61 (m, 2H), 3.63-3.69 (m, 3H), 3.71-3.76 (m, 2H), 3.90-3.95 (m, 1H), 3.98-4.10 (m, 2H), 4.10-4.19 (m, 3H), 4.28 (td, J=4.74, 3.16 Hz, 1H), 4.60 (d, J=4.55 Hz, 2H), 7.24 (d, J=2.02 Hz, 1H), 7.42-7.47 (m, 1H), 7.53 (s, 1H), 7.58-7.67 (m, 2H), 7.81 (bs, 1H).

Compound 157, $^1$H NMR (400 MHz, CD$_3$OD) δ ppm 1.06-1.11 (m, 2H), 1.47-1.51 (m, 2H), 1.63-1.73 (m, 1H), 1.81-1.96 (m, 3H), 2.33 (dd, J=13.64, 8.08 Hz, 1H), 2.71-2.85 (m, 2H), 3.16 (dd, J=12.63, 9.60 Hz, 1H), 3.24-3.28 (m, 1H), 3.43-3.54 (m, 2H), 3.56-3.60 (m, 2H), 3.64-3.68 (m, 3H), 3.71-3.76 (m, 3H), 3.88-3.94 (m, 1H), 3.98-4.06 (m, 2H), 4.10 (dd, J=4.93, 2.15 Hz, 2H), 4.19 (s, 2H), 4.23-4.30 (m, 1H), 7.29 (dt, J=8.53, 1.55 Hz, 1H), 7.44-7.50 (m, 1H), 7.50-7.56 (m, 2H), 7.61 (d, J=8.08 Hz, 2H), 7.69-7.82 (m, 4H), 7.94-7.99 (m, 2H).

Compound 158, $^1$H NMR (400 MHz, CD$_3$OD) δ ppm 1.06-1.11 (m, 2H), 1.49 (t, J=6.95 Hz, 3H), 1.48-1.52 (m, 2H), 1.60-1.68 (m, 1H), 1.78-1.80 (m, 1H), 1.81-1.91 (m, 3H), 2.37 (dd, J=13.77, 8.21 Hz, 1H), 3.07-3.22 (m, 2H), 3.51-3.62 (m, 3H), 3.63-3.69 (m, 2H), 3.72 (s, 2H), 3.74-3.76 (m, 1H), 3.94-3.99 (m, 1H), 4.01-4.07 (m, 1H), 4.08-4.14 (m, 2H), 4.16 (s, 2H), 4.23-4.28 (m, 2H), 4.26-4.31 (m, 1H), 7.30 (d, J=8.59 Hz, 2H), 7.47-7.50 (m, 1H), 7.51-7.57 (m, 4H), 7.69 (d, J=8.34 Hz, 2H), 7.87 (dd, J=8.72, 2.40 Hz, 1H), 8.08 (d, J=2.53 Hz, 1H).

Compound 161, $^1$H NMR (400 MHz, CD$_3$OD) δ ppm 1.48 (t, J=6.82 Hz, 3H), 1.59-1.68 (m, 1H), 1.77-1.91 (m, 3H), 2.37 (dd, J=13.26, 7.71 Hz, 1H), 3.08-3.23 (m, 2H), 3.51-3.56 (m, 1H), 3.56-3.60 (m, 2H), 3.63-3.69 (m, 4H), 3.72-3.76 (m, 2H), 3.95-4.01 (m, 1H), 4.03-4.08 (m, 1H), 4.08-4.12 (m, 1H), 4.12-4.15 (m, 2H), 4.17 (s, 2H), 4.25 (q, J=6.99 Hz, 2H), 4.29-4.35 (m, 1H), 7.29 (d, J=8.59 Hz, 1H), 7.46 (d, J=7.83 Hz, 1H), 7.53 (s, 1H), 7.56 (d, J=8.08 Hz, 2H), 7.59-7.66 (m, 2H), 7.69 (d, J=8.34 Hz, 2H), 7.87 (dd, J=8.59, 2.27 Hz, 1H), 8.07 (d, J=2.27 Hz, 1H).

Compound 162, $^1$H NMR (400 MHz, CD$_3$OD) δ ppm 1.07-1.11 (m, 2H), 1.47-1.51 (m, 2H), 1.67 (t, J=10.23 Hz, 1H), 1.84 (d, J=13.89 Hz, 1H), 1.89-1.95 (m, 3H), 2.36 (dd, J=13.77, 7.96 Hz, 1H), 2.95-3.09 (m, 2H), 3.16 (dd, J=12.38, 9.85 Hz, 1H), 3.56-3.61 (m, 2H), 3.63-3.69 (m, 2H), 3.71-3.75 (m, 4H), 3.91-3.96 (m, 1H), 4.00-4.11 (m, 2H), 4.12 (d, J=5.05 Hz, 2H), 4.19 (s, 2H), 4.27-4.33 (m, 1H), 7.27-7.32 (m, 1H), 7.42-7.51 (m, 3H), 7.52-7.56 (m, 1H), 7.60 (d, J=8.34 Hz, 2H), 7.73 (d, J=8.08 Hz, 2H), 7.97 (ddd, J=8.46, 4.42, 2.27 Hz, 1H), 8.02 (dd, J=6.32, 2.27 Hz, 1H).

Compound 164, $^1$H NMR (400 MHz, CD$_3$OD) δ ppm 1.06-1.10 (m, 2H), 1.46-1.52 (m, 2H), 1.64-1.73 (m, 1H), 1.80-1.98 (m, 3H), 2.31 (dd, J=13.89, 7.83 Hz, 1H), 2.69-2.85 (m, 2H), 3.13 (dd, J=12.13, 10.36 Hz, 1H), 3.44-3.55 (m, 2H), 3.72 (s, 2H), 3.87 (d, J=6.06 Hz, 1H), 3.97-4.06 (m, 2H), 4.07-4.14 (m, 2H), 4.19 (s, 2H), 4.23-4.30 (m, 1H), 7.29 (d, J=7.83 Hz, 1H), 7.45-7.56 (m, 3H), 7.60 (d, J=8.08 Hz, 2H), 7.73 (t, J=7.58 Hz, 1H), 7.75-7.80 (m, 1H), 7.77 (d, J=8.34 Hz, 2H), 7.95-7.99 (m, 2H).

Compound 168, $^1$H NMR (400 MHz, DMSO-d$_6$) δ ppm 1.39 (t, J=6.95 Hz, 3H), 1.56 (ddd, J=13.83, 10.29, 3.92 Hz, 1H), 1.64-1.71 (m, 1H), 1.74-1.82 (m, 4H), 1.87 (dd, J=12.76, 6.95 Hz, 1H), 2.19 (dd, J=13.01, 8.21 Hz, 1H), 2.92-3.10 (m, 3H), 3.12-3.22 (m, 1H), 3.35-3.43 (m, 1H), 3.44-3.53 (m, 2H), 3.63-3.73 (m, 2H), 3.80-3.86 (m, 1H), 3.87-3.94 (m, 1H), 3.95-4.00 (m, 1H), 4.01-4.14 (m, 3H), 4.17-4.28 (m, 1H), 4.23 (q, J=6.82 Hz, 2H), 4.61 (bs, 1H), 5.95 (d, J=4.80 Hz, 1H), 6.11 (t, J=6.57 Hz, 1H), 7.35 (d, J=8.84 Hz, 1H), 7.43 (d, J=1.77 Hz, 1H), 7.51 (dd, J=8.21, 1.89 Hz, 1H), 7.54-7.61 (m, 1H), 7.57 (d, J=8.08 Hz, 2H), 7.67-7.73 (m, 1H), 7.71 (d, J=8.34 Hz, 2H), 7.94 (dd, J=8.59, 2.27 Hz, 1H), 7.98 (d, J=2.53 Hz, 1H), 8.36 (bs, 2H), 8.98 (bs, 1H), 9.34 (bs, 1H).

Compound 169, $^1$H NMR (400 MHz, DMSO-d$_6$) δ ppm 1.04-1.10 (m, 2H), 1.33-1.38 (m, 2H), 1.57-1.74 (m, 2H), 1.77-1.90 (m, 2H), 2.21 (dd, J=13.39, 7.83 Hz, 1H), 2.82-3.04 (m, 2H), 3.07-3.18 (m, 1H), 3.44-3.53 (m, 3H), 3.62 (s, 2H), 3.65-3.73 (m, 3H), 3.82-3.99 (m, 3H), 4.03-4.11 (m, 1H), 4.08 (t, J=5.05 Hz, 2H), 4.23 (dd, J=8.72, 3.66 Hz, 1H), 7.30 (dd, J=8.21, 1.89 Hz, 1H), 7.35-7.36 (m, 1H), 7.45 (d, J=8.34 Hz, 1H), 7.56 (t, J=7.96 Hz, 1H), 7.59-7.65 (m, 3H), 7.77 (d, J=8.34 Hz, 2H), 7.95 (dd, J=6.57, 2.27 Hz, 1H), 8.08 (ddd, J=8.59, 4.55, 2.53 Hz, 1H), 8.47 (bs, 2H), 9.15 (bs, 1H), 9.40 (bs, 1H).

Compound 170, $^1$H NMR (400 MHz, DMSO-d$_6$) δ ppm 1.03-1.09 (m, 2H), 1.33-1.37 (m, 2H), 1.56-1.65 (m, 1H), 1.66-1.74 (m, 1H), 1.77-1.86 (m, 3H), 2.16 (dd, J=13.26, 7.96 Hz, 1H), 2.37 (s, 3H), 2.57-2.71 (m, 2H), 2.92-3.02 (m, 1H), 3.04-3.17 (m, 1H), 3.44-3.53 (m, 3H), 3.62 (d, J=2.78 Hz, 2H), 3.65-3.73 (m, 3H), 3.75-3.82 (m, 1H), 3.85-3.93 (m, 2H), 4.05 (d, J=5.05 Hz, 2H), 4.15-4.22 (m, 1H), 4.84-4.96 (m, 1H), 5.91 (d, J=4.80 Hz, 1H), 7.26-7.36 (m, 4H), 7.42-7.47 (m, 1H), 7.55 (t, J=7.96 Hz, 1H), 7.64 (d, J=8.34 Hz, 2H), 7.68-7.77 (m, 2H), 7.87-7.91 (m, 1H), 8.01 (dt, J=7.01, 1.80 Hz, 1H), 9.02 (bs, 1H), 9.19 (bs, 1H).

Compound 172, $^1$H NMR (400 MHz, CD$_3$OD) δ ppm 1.05-1.12 (m, 2H), 1.31-1.36 (m, 2H), 1.41-1.45 (m, 2H), 1.46-1.52 (m, 3H), 1.58-1.72 (m, 1H), 1.77-1.93 (m, 3H), 2.36 (bs, 1H), 3.08-3.23 (m, 2H), 3.50-3.60 (m, 1H), 3.59 (q, J=4.72 Hz, 2H), 3.65 (s, 3H), 3.70-3.76 (m, 3H), 3.98 (d, J=9.09 Hz, 1H), 4.03-4.18 (m, 4H), 4.22-4.29 (m, 2H), 4.30 (bs, 1H), 7.27-7.34 (m, 2H), 7.44-7.55 (m, 3H), 7.57 (d, J=8.08 Hz, 2H), 7.68 (d, J=8.08 Hz, 2H), 7.87 (d, J=7.33 Hz, 1H), 8.07 (d, J=1.52 Hz, 1H).

Compound 174, $^1$H NMR (400 MHz, CD$_3$OD) δ ppm 1.06-1.12 (m, 2H), 1.45-1.52 (m, 5H), 1.64 (t, J=10.36 Hz, 1H), 1.81 (d, J=13.64 Hz, 1H), 1.85-1.92 (m, 3H), 2.37 (dd, J=13.64, 7.83 Hz, 1H), 3.07-3.20 (m, 2H), 3.48-3.55 (m, 3H), 3.56-3.60 (m, 3H), 3.63-3.69 (m, 7H), 3.71-3.77 (m, 3H), 3.95-4.00 (m, 1H), 4.06 (bs, 1H), 4.08-4.16 (m, 3H), 4.25 (q, J=6.82 Hz, 2H), 4.28-4.33 (m, 1H), 7.29 (t, J=8.59 Hz, 1H), 7.28-7.33 (m, 1H), 7.46-7.52 (m, 3H), 7.55 (d, J=8.34 Hz, 2H), 7.65 (d, J=8.34 Hz, 2H), 7.86 (dd, J=8.59, 2.27 Hz, 1H), 8.07 (d, J=2.27 Hz, 1H).

Compound 175, $^1$H NMR (400 MHz, CD$_3$OD) δ ppm 1.05-1.12 (m, 2H), 1.48 (d, J=6.57 Hz, 5H), 1.58-1.67 (m, 1H), 1.77-1.92 (m, 3H), 2.05 (s, 3H), 2.36 (dd, J=13.77, 7.96 Hz, 1H), 2.88 (t, J=7.33 Hz, 2H), 3.06-3.22 (m, 3H), 3.51 (t, J=7.33 Hz, 2H), 3.48-3.55 (m, 1H), 3.56-3.60 (m, 2H), 3.63-3.69 (m, 3H), 3.71-3.76 (m, 3H), 3.94-4.00 (m, 1H), 4.01-4.06 (m, 1H), 4.07-4.16 (m, 2H), 4.23 (q, J=6.91 Hz, 2H), 4.27-4.33 (m, 1H), 7.24-7.31 (m, 2H), 7.32 (d, J=8.08 Hz, 2H), 7.46-7.50 (m, 1H), 7.50-7.56 (m, 4H), 7.82 (dd, J=8.72, 2.40 Hz, 1H), 8.03 (d, J=2.27 Hz, 1H).

Compound 176, $^1$H NMR (400 MHz, CD$_3$OD) δ ppm 1.06-1.11 (m, 2H), 1.46-1.52 (m, 9H), 1.60-1.69 (m, 1H), 1.77-1.95 (m, 3H), 2.36 (dd, J=13.64, 8.34 Hz, 1H), 3.06-3.20 (m, 3H), 3.55-3.60 (m, 2H), 3.63-3.69 (m, 3H), 3.71-3.76 (m, 4H), 3.94 (dd, J=10.11, 4.29 Hz, 1H), 4.01-4.08 (m, 3H), 4.09-4.14 (m, 3H), 4.22-4.28 (m, 2H), 4.26-4.32 (m, 1H), 7.29-7.33 (m, 1H), 7.46-7.50 (m, 1H), 7.50-7.54 (m, 2H), 7.55 (d, J=7.07 Hz, 2H), 7.64-7.67 (m, 2H), 7.86 (dd, J=8.59, 2.27 Hz, 1H), 8.07 (d, J=2.27 Hz, 1H).

Compound 177, $^1$H NMR (400 MHz, CD$_3$OD) δ ppm 1.06-1.11 (m, 2H), 1.45-1.52 (m, 5H), 1.59-1.68 (m, 1H), 1.80 (d, J=13.89 Hz, 1H), 1.84-1.92 (m, 3H), 1.99 (s, 3H), 2.36 (dd, J=13.52, 8.21 Hz, 1H), 2.86 (t, J=7.33 Hz, 2H), 3.06-3.21 (m, 3H), 3.47 (t, J=7.33 Hz, 2H), 3.59 (d, J=5.05 Hz, 2H), 3.63-3.69 (m, 2H), 3.71-3.76 (m, 3H), 3.94 (dd, J=10.11, 4.29 Hz, 1H), 4.00-4.07 (m, 1H), 4.07-4.15 (m, 2H), 4.23 (q, J=6.99 Hz, 2H), 4.26-4.31 (m, 1H), 7.26 (d, J=8.84 Hz, 1H), 7.28-7.32 (m, 1H), 7.32 (d, J=8.34 Hz, 2H), 7.46-7.50 (m, 1H), 7.50-7.56 (m, 2H), 7.53 (d, J=8.08 Hz, 2H), 7.82 (dd, J=8.59, 2.27 Hz, 1H), 8.03 (d, J=2.53 Hz, 1H).

Compound 180, $^1$H NMR (400 MHz, CD$_3$OD) δ ppm 1.04-1.12 (m, 2H), 1.49 (s, 6H), 1.62-1.73 (m, 1H), 1.79-1.97 (m, 4H), 2.32 (dd, J=13.26, 7.71 Hz, 1H), 2.70-2.85 (m, 2H), 3.09-3.19 (m, 1H), 3.24 (s, 2H), 3.41-3.53 (m, 2H), 3.59 (d, J=5.31 Hz, 1H), 3.63-3.69 (m, 2H), 3.70-3.76 (m, 2H), 3.85-3.91 (m, 1H), 3.98-4.07 (m, 2H), 4.08-4.14 (m, 2H), 4.23-4.30 (m, 1H), 7.26-7.32 (m, 1H), 7.41-7.56 (m, 3H), 7.60 (d, J=8.08 Hz, 2H), 7.69-7.79 (m, 4H), 7.93-7.99 (m, 2H).

Compound 181, $^1$H NMR (400 MHz, CD$_3$OD) δ ppm 1.05-1.12 (m, 2H), 1.49-1.50 (m, 6H), 1.68 (t, J=11.12 Hz, 1H), 1.80-1.96 (m, 4H), 2.27-2.38 (m, 1H), 2.69-2.85 (m, 2H), 3.10-3.19 (m, 1H), 3.25 (s, 2H), 3.42-3.53 (m, 2H), 3.56-3.59 (m, 1H), 3.63-3.69 (m, 2H), 3.71-3.77 (m, 2H), 3.90 (d, J=6.57 Hz, 1H), 3.97-4.06 (m, 2H), 4.07-4.14 (m, 2H), 4.27 (bs, 1H), 7.29 (d, J=7.58 Hz, 1H), 7.44-7.56 (m, 3H), 7.60 (d, J=8.08 Hz, 2H), 7.68-7.78 (m, 4H), 7.94-7.98 (m, 2H).

Compound 182, $^1$H NMR (400 MHz, CD$_3$OD) δ ppm 1.06-1.11 (m, 2H), 1.47-1.51 (m, 2H), 1.61-1.73 (m, 1H), 1.80-1.98 (m, 4H), 2.33 (dd, J=13.39, 7.83 Hz, 1H), 2.71-2.85 (m, 2H), 3.10-3.17 (m, 1H), 3.44-3.55 (m, 2H), 3.64-3.76 (m, 1H), 3.72 (s, 2H), 3.85-3.91 (m, 1H), 3.97-4.07 (m, 2H), 4.08-4.14 (m, 2H), 4.26 (s, 2H), 4.25-4.30 (m, 1H), 7.26-7.31 (m, 1H), 7.44-7.56 (m, 3H), 7.57-7.68 (m, 3H), 7.74 (t, J=7.96 Hz, 1H), 7.83 (d, J=7.83 Hz, 1H), 7.96-8.01 (m, 2H).

Compound 184, $^1$H NMR (400 MHz, CD$_3$OD) δ ppm 1.05-1.11 (m, 2H), 1.34-1.39 (m, 2H), 1.40-1.44 (m, 2H), 1.46-1.52 (m, 2H), 1.62-1.73 (m, 1H), 1.79-1.97 (m, 4H), 2.32 (dd, J=13.64, 8.08 Hz, 1H), 2.69-2.84 (m, 2H), 3.13 (dd, J=12.63, 9.60 Hz, 1H), 3.42-3.55 (m, 2H), 3.63-3.76 (m, 1H), 3.72 (s, 2H), 3.85-3.90 (m, 1H), 3.96-4.07 (m, 1H), 4.08-4.14 (m, 2H), 4.21-4.29 (m, 1H), 7.29 (ddd, J=7.71, 2.53, 1.64 Hz, 1H), 7.45-7.56 (m, 3H), 7.58-7.63 (m, 2H), 7.69-7.81 (m, 4H), 7.94-7.98 (m, 2H).

Compound 185, $^1$H NMR (400 MHz, CD$_3$OD) δ ppm 1.09 (dd, J=12.13, 1.01 Hz, 1H), 1.47-1.53 (m, 2H), 1.63-1.73 (m, 1H), 1.79-1.97 (m, 3H), 2.34 (dd, J=13.77, 8.21 Hz, 1H), 2.72-2.90 (m, 2H), 3.17 (dd, J=12.88, 9.60 Hz, 1H), 3.46-3.60 (m, 3H), 3.62-3.76 (m, 1H), 3.72 (s, 2H), 3.86-3.95 (m, 1H), 3.98-4.14 (m, 4H), 4.21-4.29 (m, 1H), 7.29 (dt, J=8.59, 1.64 Hz, 1H), 7.45-7.58 (m, 3H), 8.37 (t, J=2.02 Hz, 1H), 8.89 (bs, 1H), 8.96 (bs, 1H).

Compound 186, $^1$H NMR (400 MHz, CD$_3$OD) δ ppm 1.06-1.12 (m, 2H), 1.47-1.52 (m, 2H), 1.67 (ddd, J=13.89, 10.99, 4.17 Hz, 1H), 1.79-1.95 (m, 4H), 2.34 (dd, J=13.52, 8.21 Hz, 1H), 2.73-2.89 (m, 2H), 3.15 (dd, J=12.76, 9.47 Hz, 1H), 3.29-3.35 (m, 1H), 3.44-3.56 (m, 2H), 3.56-3.60 (m, 2H), 3.66 (d, J=5.31 Hz, 3H), 3.70-3.77 (m, 4H), 3.86-3.92 (m, 1H), 3.98-4.14 (m, 4H), 4.21-4.29 (m, 1H), 7.30 (dt, J=7.64, 2.12 Hz, 3H), 7.45-7.58 (m, 3H), 8.37 (t, J=2.02 Hz, 1H), 8.89 (s, 1H), 8.96 (s, 1H).

Compound 187, $^1$H NMR (400 MHz, CD$_3$OD) δ ppm 1.29 (s, 6H), 1.49 (t, J=6.95 Hz, 3H), 1.60-1.69 (m, 1H), 1.78-1.84 (m, 1H), 1.85-1.92 (m, 3H), 2.36 (dd, J=13.64, 8.34 Hz, 1H), 3.06-3.22 (m, 2H), 3.30-3.37 (m, 1H), 3.50-3.62 (m, 3H), 3.65-3.76 (m, 2H), 3.94 (dd, J=10.23, 4.42 Hz, 1H), 4.00-4.07 (m, 1H), 4.08-4.15 (m, 3H), 4.16 (s, 2H), 4.22-4.31 (m, 3H), 7.29 (d, J=8.59 Hz, 1H), 7.34 (dd, J=6.95, 1.39 Hz, 1H), 7.41-7.45 (m, 1H), 7.47-7.50 (m, 1H), 7.53-7.59 (m, 3H), 7.69 (d, J=8.08 Hz, 2H), 7.87 (dd, J=8.59, 2.53 Hz, 1H), 8.08 (d, J=2.53 Hz, 1H).

Compound 188, $^1$H NMR (400 MHz, CD$_3$OD) δ ppm 1.05-1.11 (m, 2H), 1.30-1.37 (m, 2H), 1.39-1.43 (m, 2H), 1.45-1.53 (m, 2H), 1.48 (t, J=6.06 Hz, 3H), 1.59-1.69 (m, 1H), 1.78-1.93 (m, 4H), 2.36 (dd, J=13.64, 8.34 Hz, 1H), 3.05-3.22 (m, 3H), 3.50-3.62 (m, 3H), 3.63-3.69 (m, 3H), 3.71-3.77 (m, 4H), 3.94 (dd, J=9.98, 4.17 Hz, 1H), 4.00-4.07 (m, 1H), 4.08-4.16 (m, 3H), 4.20-4.31 (m, 1H), 4.25 (q, J=6.82 Hz, 2H), 7.26-7.33 (m, 3H), 7.46-7.56 (m, 3H), 7.56 (d, J=8.34 Hz, 2H), 7.69 (d, J=8.34 Hz, 2H), 7.87 (dd, J=8.59, 2.27 Hz, 1H), 8.07 (d, J=2.27 Hz, 1H).

Compound 190, $^1$H NMR (400 MHz, CD$_3$OD) δ ppm 1.08 (d, J=2.02 Hz, 2H), 1.47-1.52 (m, 2H), 1.62-1.76 (m, 2H), 1.79-1.91 (m, 3H), 1.92 (s, 3H), 2.30 (dd, J=13.64, 8.34 Hz, 1H), 2.70-2.83 (m, 2H), 2.85 (t, J=7.33 Hz, 2H), 3.12 (dd, J=12.00, 10.48 Hz, 1H), 3.28 (d, J=3.03 Hz, 1H), 3.44 (t, J=7.45 Hz, 2H), 3.43-3.52 (m, 3H), 3.71 (s, 2H), 3.83-3.88 (m, 1H), 3.95-4.05 (m, 2H), 4.06-4.13 (m, 2H), 4.20-4.27 (m, 1H), 7.25-7.31 (m, 1H), 7.36 (d, J=8.34 Hz, 2H), 7.43-7.47 (m, 1H), 7.48-7.56 (m, 2H), 7.60 (d, J=8.34 Hz, 2H), 7.69 (d, J=7.83 Hz, 1H), 7.73 (dt, J=7.83, 1.52 Hz, 1H), 7.90-7.95 (m, 2H).

Compound 191, $^1$H NMR (400 MHz, CD$_3$OD) δ ppm 1.05-1.10 (m, 2H), 1.47-1.52 (m, 2H), 1.61-1.74 (m, 2H), 1.79-1.90 (m, 4H), 1.92 (s, 3H), 2.31 (dd, J=13.89, 8.08 Hz, 1H), 2.70-2.83 (m, 2H), 2.85 (t, J=7.45 Hz, 2H), 3.15 (dd, J=12.63, 9.60 Hz, 1H), 3.27 (dd, J=12.76, 3.16 Hz, 1H), 3.44 (t, J=7.33 Hz, 2H), 3.42-3.52 (m, 2H), 3.71 (s, 2H), 3.85-3.90 (m, 1H), 3.95-4.04 (m, 2H), 4.06-4.12 (m, 2H), 4.18-4.26 (m, 1H), 7.28 (ddd, J=5.31, 2.53, 2.27 Hz, 1H), 7.36 (d, J=8.34 Hz, 2H), 7.42-7.47 (m, 1H), 7.48-7.56 (m, 2H), 7.60 (d, J=8.34 Hz, 2H), 7.69 (d, J=8.08 Hz, 1H), 7.73 (dt, J=7.83, 1.52 Hz, 1H), 7.89-7.96 (m, 2H).

Compound 192, $^1$H NMR (400 MHz, CD$_3$OD) δ ppm 1.06-1.12 (m, 2H), 1.48-1.52 (m, 2H), 1.60-1.69 (m, 1H), 1.78-1.93 (m, 4H), 2.37 (dd, J=13.77, 8.21 Hz, 1H), 2.70 (s, 3H), 3.03-3.23 (m, 3H), 3.39-3.51 (m, 2H), 3.63-3.69 (m, 1H), 3.72 (s, 2H), 3.73-3.76 (m, 1H), 3.94-3.99 (m, 1H), 4.01-4.07 (m, 1H), 4.08-4.16 (m, 3H), 4.23-4.30 (m, 1H), 7.25-7.33 (m, 2H), 7.46-7.58 (m, 3H), 7.87 (d, J=8.08 Hz, 1H), 7.92 (d, J=7.83 Hz, 1H).

Compound 193, $^1$H NMR (400 MHz, CD$_3$OD) δ ppm 1.06-1.11 (m, 2H), 1.48-1.52 (m, 2H), 1.61-1.70 (m, 1H), 1.79-1.94 (m, 3H), 2.32 (dd, J=13.77, 8.21 Hz, 1H), 2.64-2.80 (m, 2H), 3.11-3.20 (m, 1H), 3.27 (d, J=3.03 Hz, 1H), 3.36-3.46 (m, 2H), 3.55-3.61 (m, 1H), 3.63-3.69 (m, 1H), 3.72 (s, 2H), 3.73-3.76 (m, 1H), 3.87-3.93 (m, 1H), 3.96-4.05 (m, 1H), 3.98 (s, 3H), 4.07-4.14 (m, 2H), 4.22-4.28 (m, 1H), 7.24 (d, J=8.59 Hz, 1H), 7.29 (dt, J=7.64, 2.12 Hz, 1H), 7.45-7.57 (m, 3H), 7.75 (dd, J=8.84, 2.27 Hz, 1H), 7.90 (d, J=2.27 Hz, 1H).

Compound 194, $^1$H NMR (400 MHz, CD$_3$OD) δ ppm 1.07-1.11 (m, 2H), 1.48-1.52 (m, 2H), 1.60-1.70 (m, 1H), 1.77-1.94 (m, 3H), 2.32 (dd, J=13.89, 8.08 Hz, 1H), 2.49 (s, 3H), 2.66-2.81 (m, 2H), 3.13-3.20 (m, 1H), 3.27 (d, J=3.03 Hz, 1H), 3.38-3.49 (m, 2H), 3.56-3.60 (m, 1H), 3.63-3.68 (m, 1H), 3.72 (s, 2H), 3.73-3.76 (m, 1H), 3.87-3.92 (m, 1H), 3.96-4.06 (m, 1H), 4.06-4.14 (m, 2H), 4.20-4.27 (m, 1H), 7.29 (dt, J=7.52, 2.05 Hz, 1H), 7.44-7.57 (m, 4H), 7.68 (d, J=2.02 Hz, 1H), 7.80 (d, J=8.34 Hz, 1H).

Compound 195, $^1$H NMR (400 MHz, CD$_3$OD) δ ppm 1.06-1.11 (m, 2H), 1.46-1.52 (m, 2H), 1.65-1.75 (m, 1H), 1.81-1.96 (m, 3H), 2.36 (dd, J=13.64, 7.83 Hz, 1H), 2.85-2.99 (m, 2H), 3.14-3.22 (m, 1H), 3.53-3.62 (m, 3H), 3.64-3.68 (m, 1H), 3.72 (s, 2H), 3.73-3.77 (m, 1H), 3.89-3.96 (m, 1H), 4.01-4.09 (m, 1H), 4.08-4.16 (m, 2H), 4.28 (dd, J=8.72, 2.91 Hz, 1H), 7.30 (d, J=7.83 Hz, 1H), 7.44-7.58 (m, 3H), 8.06 (dd, J=7.58, 5.56 Hz, 1H), 8.66 (d, J=8.08 Hz, 1H), 9.02 (bs, 1H), 9.18 (bs, 1H).

Compound 196, $^1$H NMR (400 MHz, CD$_3$OD) δ ppm 1.06-1.11 (m, 2H), 1.48-1.52 (m, 2H), 1.61-1.70 (m, 1H), 1.79-1.95 (m, 4H), 2.32 (dd, J=13.64, 8.08 Hz, 1H), 2.49 (s, 3H), 2.67-2.80 (m, 2H), 3.14 (dd, J=12.76, 9.47 Hz, 1H), 3.37-3.50 (m, 2H), 3.56-3.60 (m, 1H), 3.63-3.69 (m, 1H), 3.72 (s, 2H), 3.73-3.76 (m, 1H), 3.85-3.90 (m, 1H), 3.98-4.07 (m, 1H), 4.09-4.14 (m, 2H), 4.21-4.29 (m, 1H), 7.29 (dt, J=8.59, 1.64 Hz, 1H), 7.45-7.57 (m, 4H), 7.68 (d, J=1.77 Hz, 1H), 7.80 (d, J=8.34 Hz, 1H).

Compound 197, $^1$H NMR (400 MHz, CD$_3$OD) δ ppm 1.07-1.12 (m, 2H), 1.49-1.52 (m, 2H), 1.63-1.73 (m, 1H), 1.78-1.97 (m, 4H), 2.39 (dd, J=13.52, 8.21 Hz, 1H), 2.44 (s, 3H), 3.09-3.25 (m, 3H), 3.32-3.38 (m, 1H), 3.44-3.56 (m, 2H), 3.63-3.69 (m, 1H), 3.73 (s, 2H), 3.73-3.76 (m, 1H), 3.93-4.00 (m, 1H), 4.02-4.09 (m, 1H), 4.10-4.17 (m, 3H), 4.20 (s, 2H), 4.24-4.31 (m, 1H), 7.31 (ddd, J=7.71, 2.53, 1.39 Hz, 1H), 7.39 (d, J=8.08 Hz, 2H), 7.43-7.47 (m, 2H), 7.47-7.54 (m, 2H), 7.56 (d, J=8.34 Hz, 2H), 7.92-7.97 (m, 1H).

Compound 198, $^1$H NMR (400 MHz, CD$_3$OD) δ ppm 1.07-1.11 (m, 2H), 1.33-1.39 (m, 2H), 1.41-1.46 (m, 2H), 1.47-1.52 (m, 2H), 1.67 (t, J=10.23 Hz, 1H), 1.79-1.97 (m, 4H), 2.35-2.43 (m, 1H), 2.44 (s, 3H), 3.10-3.24 (m, 3H), 3.33-3.38 (m, 1H), 3.48 (t, J=13.39 Hz, 2H), 3.56-3.60 (m, 2H), 3.63-3.68 (m, 2H), 3.73 (s, 2H), 3.73-3.76 (m, 2H), 3.98 (dd, J=9.98, 3.92 Hz, 1H), 4.07 (bs, 1H), 4.10-4.18 (m, 2H), 4.27-4.34 (m, 1H), 7.31 (d, J=7.33 Hz, 1H), 7.38 (d, J=8.08 Hz, 2H), 7.43-7.46 (m, 2H), 7.47-7.55 (m, 3H), 7.59 (d, J=8.08 Hz, 2H), 7.92-7.99 (m, 1H).

Compound 200, $^1$H NMR (400 MHz, CD$_3$OD) δ ppm 1.07-1.11 (m, 2H), 1.48-1.53 (m, 2H), 1.60-1.68 (m, 1H), 1.79-1.91 (m, 4H), 2.37 (dd, J=13.64, 8.34 Hz, 1H), 2.70 (s, 3H), 3.04-3.20 (m, 3H), 3.32-3.37 (m, 1H), 3.40-3.51 (m, 2H), 3.56-3.60 (m, 1H), 3.63-3.69 (m, 1H), 3.72 (s, 2H), 3.72-3.76 (m, 1H), 3.92-3.97 (m, 1H), 4.00-4.08 (m, 1H), 4.09-4.16 (m, 2H), 4.24-4.30 (m, 1H), 7.26-7.33 (m, 2H), 7.47-7.58 (m, 3H), 7.87 (dd, J=8.08, 1.01 Hz, 1H), 7.91 (d, J=8.08 Hz, 1H).

Compound 201, $^1$H NMR (400 MHz, CD$_3$OD) δ ppm 1.07-1.11 (m, 2H), 1.48-1.52 (m, 2H), 1.65 (dd, J=13.64, 6.82 Hz, 1H), 1.78-1.93 (m, 4H), 2.32 (dd, J=13.64, 8.08 Hz, 1H), 2.65-2.79 (m, 2H), 3.14 (dd, J=12.63, 9.60 Hz, 1H), 3.35-3.46 (m, 2H), 3.56-3.59 (m, 1H), 3.63-3.68 (m, 1H), 3.72 (s, 2H), 3.73-3.76 (m, 1H), 3.86-3.90 (m, 1H), 3.98 (s, 3H), 4.01-4.07 (m, 1H), 4.08-4.14 (m, 2H), 4.22-4.29 (m, Hz, 1H), 7.24 (d, J=8.84 Hz, 1H), 7.27-7.31 (m, 1H), 7.46-7.50 (m, 1H), 7.51-7.57 (m, 2H), 7.75 (dd, J=8.84, 2.27 Hz, 1H), 7.90 (d, J=2.27 Hz, 1H).

Compound 202, $^1$H NMR (400 MHz, CD$_3$OD) δ ppm 1.07-1.11 (m, 2H), 1.47-1.51 (m, 2H), 1.65-1.76 (m, 1H), 1.83-1.97 (m, 4H), 2.36 (bs, 1H), 2.84-2.99 (m, 2H), 3.12-3.20 (m, 1H), 3.52-3.61 (m, 2H), 3.63-3.69 (m, 2H), 3.72 (s, 2H), 3.72-3.77 (m, 1H), 3.92 (d, J=8.34 Hz, 1H), 4.01-4.17 (m, 3H), 4.29 (bs, 1H), 7.31 (d, J=7.33 Hz, 1H), 7.44-7.57 (m, 3H), 8.10 (bs, 1H), 8.69 (d, J=7.58 Hz, 1H), 9.06 (bs, 1H), 9.22 (bs, 1H).

Compound 203, $^1$H NMR (400 MHz, CD$_3$OD) δ ppm 1.07-1.12 (m, 2H), 1.48-1.52 (m, 2H), 1.63-1.72 (m, 1H), 1.79-1.95 (m, 3H), 2.40 (dd, J=13.77, 8.21 Hz, 1H), 2.44 (s, 3H), 3.10-3.25 (m, 4H), 3.32-3.35 (m, 1H), 3.43-3.54 (m, 2H), 3.56-3.60 (m, 1H), 3.63-3.69 (m, 2H), 3.73 (s, 2H), 3.72-3.76 (m, 1H), 3.96-4.01 (m, 1H), 4.02-4.09 (m, 1H), 4.09-4.16 (m, 3H), 4.20 (s, 2H), 4.25-4.32 (m, 1H), 7.31 (dt, J=7.83, 2.02 Hz, 1H), 7.39 (d, J=8.34 Hz, 2H), 7.43-7.47 (m, 2H), 7.48-7.51 (m, 1H), 7.51-7.59 (m, 4H), 7.92-7.98 (m, 1H).

Compound 204, $^1$H NMR (400 MHz, CD$_3$OD) δ ppm 1.07-1.11 (m, 2H), 1.34-1.39 (m, 2H), 1.40-1.45 (m, 2H), 1.48-1.53 (m, 2H), 1.63-1.72 (m, 1H), 1.79-1.95 (m, 3H), 2.40 (dd, J=13.89, 8.34 Hz, 1H), 2.44 (s, 3H), 3.10-3.24 (m, 3H), 3.44-3.55 (m, 2H), 3.56-3.59 (m, 1H), 3.63-3.69 (m, 2H), 3.73 (s, 2H), 3.72-3.76 (m, 1H), 3.96-4.01 (m, 1H), 4.02-4.09 (m, 1H), 4.09-4.16 (m, 3H), 4.25-4.31 (m, 1H), 7.31 (ddd, J=7.77, 2.59, 1.52 Hz, 1H), 7.39 (d, J=8.34 Hz, 2H), 7.43-7.46 (m, 2H), 7.47-7.51 (m, 1H), 7.51-7.56 (m, 2H), 7.58 (d, J=8.34 Hz, 2H), 7.94 (d, J=4.29 Hz, 1H).

Compound 207, $^1$H NMR (400 MHz, CD$_3$OD) δ ppm 1.06-1.11 (m, 2H), 1.48-1.51 (m, 2H), 1.63-1.71 (m, 1H), 1.79-1.96 (m, 3H), 2.33 (dd, J=13.52, 8.21 Hz, 1H), 2.68-2.81 (m, 2H), 3.14 (dd, J=12.63, 9.60 Hz, 1H), 3.32-3.34 (m, 1H), 3.38-3.49 (m, 2H), 3.56-3.60 (m, 1H), 3.64-3.68 (m, 2H), 3.70-3.76 (m, 1H), 3.72 (s, 2H), 3.88 (t, J=3.03 Hz, 1H), 3.90 (s, 3H), 3.97-4.07 (m, 1H), 4.08-4.15 (m, 2H), 4.17 (s, 2H), 4.24-4.30 (m, 1H), 7.27-7.31 (m, 1H), 7.32 (d, J=8.84 Hz, 1H), 7.46-7.48 (m, 1H), 7.49-7.55 (m, 4H), 7.57-7.61 (m, 2H), 7.64 (d, J=2.27 Hz, 1H), 7.79 (dd, J=8.72, 2.40 Hz, 1H).

Compound 208, $^1$H NMR (400 MHz, CD$_3$OD) δ ppm 1.06-1.11 (m, 2H), 1.47-1.51 (m, 2H), 1.63-1.72 (m, 1H), 1.80-1.96 (m, 3H), 2.33 (dd, J=13.77, 8.21 Hz, 1H), 2.67-2.83 (m, 2H), 3.16 (dd, J=12.63, 9.60 Hz, 1H), 3.26-3.33 (m, 1H), 3.39-3.48 (m, 2H), 3.56-3.60 (m, 1H), 3.63-3.69 (m, 2H), 3.72 (s, 2H), 3.73-3.76 (m, 1H), 3.88-3.93 (m, 1H), 3.90 (s, 2H), 3.97-4.06 (m, 2H), 4.08-4.14 (m, 2H), 4.17 (s, 3H), 4.22-4.29 (m, 1H), 7.27-7.31 (m, 1H), 7.32 (d, J=0.84 Hz, 1H), 7.45-7.48 (m, 1H), 7.49-7.55 (m, 4H), 7.56-7.61 (m, 2H), 7.64 (d, J=2.27 Hz, 1H), 7.79 (dd, J=8.72, 2.40 Hz, 1H).

Compound 210, $^1$H NMR (400 MHz, CD$_3$OD) δ ppm 1.63-1.72 (m, 1H), 1.79-1.98 (m, 4H), 2.32 (dd, J=13.64, 8.08 Hz, 1H), 2.70-2.86 (m, 2H), 3.03 (t, J=7.71 Hz, 2H), 3.13 (dd, J=12.76, 9.47 Hz, 1H), 3.23 (t, J=7.83 Hz, 2H), 3.28-3.30 (m, 1H), 3.42-3.54 (m, 2H), 3.85-3.89 (m, 1H), 3.95-4.06 (m, 2H), 4.14 (t, J=14.40 Hz, 2H), 4.11 (d, J=5.56 Hz, 2H), 7.43 (d, J=8.08 Hz, 2H), 7.43-7.46 (m, 1H), 7.50-7.53 (m, 1H), 7.58-7.66 (m, 2H), 7.68 (d, J=8.08 Hz, 2H), 7.71 (d, J=7.83 Hz, 1H), 7.75 (dt, J=7.83, 1.39 Hz, 1H), 7.91-7.98 (m, 2H).

Compound 211, $^1$H NMR (400 MHz, CD$_3$OD) δ ppm 1.06-1.11 (m, 2H), 1.46-1.51 (m, 2H), 1.63-1.72 (m, 1H), 1.79-1.97 (m, 4H), 2.32 (dd, J=13.77, 8.21 Hz, 1H), 2.69-2.85 (m, 2H), 3.03 (t, J=7.71 Hz, 2H), 3.13 (dd, J=12.63, 9.60 Hz, 1H), 3.23 (t, J=7.83 Hz, 2H), 3.43-3.54 (m, 2H), 3.63-3.76 (m, 1H), 3.72 (s, 2H), 3.84-3.91 (m, 1H), 3.95-4.06 (m, 2H), 4.07-4.15 (m, 2H), 4.23-4.29 (m, 1H), 7.29 (dt, J=8.59, 1.64 Hz, 1H), 7.43 (d, J=8.34 Hz, 2H), 7.45-7.47 (m, 1H), 7.48-7.51 (m, 1H), 7.51-7.56 (m, 1H), 7.68 (d, J=8.34 Hz, 2H), 7.71 (d, J=7.83 Hz, 1H), 7.75 (dt, J=7.83, 1.52 Hz, 1H), 7.92-7.97 (m, 2H).

Compound 212, $^1$H NMR (400 MHz, CD$_3$OD) δ ppm 1.06-1.11 (m, 2H), 1.47-1.51 (m, 2H), 1.63-1.72 (m, 1H), 1.78-1.96 (m, 4H), 2.32 (dd, J=13.77, 8.21 Hz, 1H), 2.71-2.84 (m, 2H), 3.03 (t, J=7.83 Hz, 2H), 3.15 (dd, J=12.76, 9.73 Hz, 1H), 3.23 (t, J=7.71 Hz, 2H), 3.27 (d, J=3.03 Hz, 1H), 3.42-3.53 (m, 2H), 3.72 (s, 2H), 3.86-3.94 (m, 1H), 3.97-4.05 (m, 2H), 4.06-4.15 (m, 2H), 4.22-4.29 (m, 1H), 7.29 (dt, J=6.88, 1.74 Hz, 1H), 7.44 (d, J=8.34 Hz, 2H), 7.45-7.48 (m, 1H), 7.48-7.51 (m, 1H), 7.52 (d, J=7.83 Hz, 1H), 7.67 (d, J=8.08 Hz, 2H), 7.71 (d, J=7.83 Hz, 1H), 7.74-7.79 (m, 1H), 7.91-7.98 (m, 2H).

Compound 213, $^1$H NMR (400 MHz, CD$_3$OD) δ ppm 1.63-1.72 (m, 1H), 1.79-1.96 (m, 4H), 2.32 (dd, J=13.89, 8.08 Hz, 1H), 2.70-2.84 (m, 2H), 3.03 (t, J=7.71 Hz, 2H), 3.16 (dd, J=12.63, 9.60 Hz, 1H), 3.23 (t, J=7.71 Hz, 2H), 3.26 (d, J=3.03 Hz, 1H), 3.43-3.53 (m, 2H), 3.87-3.92 (m, 1H), 3.97-4.06 (m, 2H), 4.09-4.13 (m, 2H), 4.14 (t, J=14.40 Hz, 2H), 4.22-4.30 (m, 1H), 7.42-7.46 (m, 1H), 7.43 (d, J=8.08 Hz, 2H), 7.51-7.52 (m, 1H), 7.58-7.61 (m, 1H), 7.62 (d, J=7.83 Hz, 1H), 7.68 (d, J=8.08 Hz, 2H), 7.71 (d, 1H), 7.75 (dt, J=8.08, 1.39 Hz, 1H), 7.92-7.96 (m, 2H).

Compound 214, $^1$H NMR (400 MHz, CD$_3$OD) δ ppm 1.06-1.11 (m, 2H), 1.44-1.53 (m, 2H), 1.48 (t, J=6.95 Hz, 3H), 1.60-1.69 (m, 1H), 1.79-1.92 (m, 4H), 2.36 (dd, J=13.64, 8.34 Hz, 1H), 3.01 (t, J=7.71 Hz, 2H), 3.07-3.24 (m, 5H), 3.35 (d, J=2.78 Hz, 1H), 3.50-3.61 (m, 2H), 3.72 (s, 2H), 3.94 (dd, J=10.23, 4.17 Hz, 1H), 4.00-4.07 (m, 1H), 4.08-4.15 (m, 2H), 4.25 (q, J=6.99 Hz, 2H), 4.25-4.31 (m, 1H), 7.28 (d, J=8.84 Hz, 1H), 7.29-7.33 (m, 2H), 7.38 (d, J=8.08 Hz, 2H), 7.46-7.49 (m, 1H), 7.49-7.52 (m, 1H), 7.53 (d, J=7.83 Hz, 1H), 7.60 (d, J=8.34 Hz, 2H), 7.84 (dd, J=8.72, 2.40 Hz, 1H), 8.05 (d, J=2.27 Hz, 1H).

Compound 215, $^1$H NMR (400 MHz, CD$_3$OD) δ ppm 1.07-1.10 (m, 2H), 1.47-1.52 (m, 2H), 1.68 (dd, J=11.12, 4.04 Hz, 1H), 1.79-1.96 (m, 4H), 2.32 (d, J=5.56 Hz, 1H), 2.67-2.82 (m, 2H), 3.02 (t, J=7.71 Hz, 2H), 3.14 (dd, J=12.63, 9.60 Hz, 1H), 3.23 (t, J=7.71 Hz, 2H), 3.33 (d, J=3.03 Hz, 1H), 3.37-3.50 (m, 2H), 3.72 (s, 2H), 3.86-3.90 (m, 1H), 3.90 (s, 3H), 3.98-4.07 (m, 2H), 4.08-4.15 (m, 2H), 4.23-4.30 (m, 1H), 7.29 (d, J=8.84 Hz, 2H), 7.36 (d, J=8.08 Hz, 2H), 7.46-7.57 (m, 5H), 7.62 (d, J=2.27 Hz, 1H), 7.76 (dd, J=8.72, 2.40 Hz, 1H).

Compound 216, $^1$H NMR (400 MHz, CD$_3$OD) δ ppm 1.06-1.10 (m, 2H), 1.47-1.51 (m, 2H), 1.64-1.72 (m, 1H), 1.80-1.97 (m, 4H), 2.34 (dd, J=13.52, 7.96 Hz, 1H), 2.71-2.87 (m, 2H), 3.17 (dd, J=12.51, 9.73 Hz, 1H), 3.28 (d, J=2.53 Hz, 1H), 3.43-3.54 (m, 2H), 3.72 (s, 2H), 3.92 (d, J=6.06 Hz, 1H), 3.99-4.07 (m, 2H), 4.08-4.14 (m, 2H), 4.21 (s, 2H), 4.27 (dd, J=8.84, 2.78 Hz, 1H), 7.27-7.33 (m, 1H), 7.44-7.50 (m, 2H), 7.51 (s, 1H), 7.53 (d, J=7.83 Hz, 1H), 7.59-7.63 (m, 2H), 7.65-7.70 (m, 2H), 7.82-7.90 (m, 2H).

Compound 217, $^1$H NMR (400 MHz, CD$_3$OD) δ ppm 1.06-1.11 (m, 2H), 1.35-1.40 (m, 2H), 1.41-1.46 (m, 2H), 1.47-1.52 (m, 2H), 1.61-1.73 (m, 1H), 1.79-1.97 (m, 4H), 2.34 (dd, J=13.64, 7.58 Hz, 1H), 2.65-2.85 (m, 2H), 3.17 (dd, J=12.51, 9.73 Hz, 1H), 3.28 (d, J=2.53 Hz, 1H), 3.39-3.54 (m, 2H), 3.72 (s, 2H), 3.88-3.96 (m, 1H), 3.98-4.07 (m, 2H), 4.08-4.15 (m, 2H), 4.22-4.31 (m, 1H), 7.30 (dt, J=7.77, 1.93 Hz, 1H), 7.45-7.50 (m, 2H), 7.50-7.52 (m, 1H), 7.53 (d, J=7.58 Hz, 1H), 7.60-7.63 (m, 2H), 7.65-7.70 (m, 2H), 7.80-7.90 (m, 2H).

Compound 218, $^1$H NMR (400 MHz, CD$_3$OD) δ ppm 1.06-1.11 (m, 2H), 1.46-1.52 (m, 2H), 1.61-1.73 (m, 1H), 1.81-1.98 (m, 4H), 2.34 (dd, J=13.39, 8.08 Hz, 1H), 2.70-2.85 (m, 2H), 3.14 (dd, J=12.76, 9.47 Hz, 1H), 3.32-3.35 (m, 1H), 3.43-3.55 (m, 2H), 3.72 (s, 2H), 3.86-3.92 (m, 1H), 3.97-4.09 (m, 2H), 4.08-4.14 (m, 2H), 4.20 (s, 2H), 4.23-4.31 (m, 1H), 7.30 (td, J=7.77, 2.59, 1.52 Hz, 1H), 7.45-7.50 (m, 2H), 7.50-7.52 (m, 1H), 7.52-7.57 (m, 1H), 7.59-7.63 (m, 2H), 7.65-7.69 (m, 2H), 7.81-7.90 (m, 2H).

Compound 219, $^1$H NMR (400 MHz, CD$_3$OD) δ ppm 1.06-1.11 (m, 2H), 1.35-1.40 (m, 2H), 1.42-1.47 (m, 2H), 1.47-1.52 (m, 2H), 1.61-1.72 (m, 1H), 1.79-1.97 (m, 4H), 2.33 (dd, J=13.77, 6.69 Hz, 1H), 2.66-2.86 (m, 2H), 3.08-3.20 (m, 1H), 3.32-3.35 (m, 1H), 3.42-3.53 (m, 2H), 3.72 (s, 2H), 3.86-3.93 (m, 1H), 3.98-4.07 (m, 2H), 4.09-4.16 (m, 2H), 4.23-4.31 (m, 1H), 7.27-7.32 (m, 1H), 7.44-7.49 (m, 2H), 7.50-7.56 (m, 2H), 7.60-7.63 (m, 2H), 7.65-7.69 (m, 2H), 7.80-7.90 (m, 2H).

Compound 220, $^1$H NMR (400 MHz, CD$_3$OD) δ ppm 1.06-1.11 (m, 2H), 1.46-1.53 (m, 5H), 1.59-1.71 (m, 1H), 1.82 (d, J=14.15 Hz, 1H), 1.85-1.93 (m, 3H), 2.37 (dd, J=13.52, 8.21 Hz, 1H), 3.07-3.22 (m, 3H), 3.56-3.60 (m, 2H), 3.63-3.68 (m, 2H), 3.72 (s, 2H), 3.72-3.76 (m, 1H), 3.91-3.97 (m, 1H), 4.01-4.07 (m, 1H), 4.09-4.16 (m, 3H), 4.21-4.32 (m, 5H), 7.31 (d, J=8.59 Hz, 2H), 7.46-7.62 (m, 6H), 7.90 (dd, J=8.72, 2.40 Hz, 1H), 8.09 (d, J=2.53 Hz, 1H).

Compound 221, $^1$H NMR (400 MHz, CD$_3$OD) δ ppm 1.07-1.12 (m, 2H), 1.48-1.52 (m, 2H), 1.63-1.73 (m, 1H), 1.80-1.98 (m, 4H), 2.35 (d, J=5.56 Hz, 1H), 2.77-2.85 (m, 1H), 2.85-2.92 (m, 1H), 3.14-3.22 (m, 1H), 3.28 (d, J=3.03 Hz, 1H), 3.47-3.60 (m, 2H), 3.73 (s, 2H), 3.90-3.95 (m, 1H), 3.98-4.08 (m, 2H), 4.08-4.15 (m, 2H), 4.22-4.30 (m, 1H), 7.30 (ddd, J=7.64, 2.59, 1.64 Hz, 1H), 7.45-7.49 (m, 1H), 7.49-7.53 (m, 1H), 7.54 (d, J=7.83 Hz, 1H), 8.47 (d, J=2.27 Hz, 1H), 8.72 (d, J=2.27 Hz, 1H).

Compound 223, $^1$H NMR (400 MHz, CD$_3$OD) δ ppm 1.31 (s, 6H), 1.64-1.74 (m, 1H), 1.81-1.99 (m, 4H), 2.33 (d, J=13.39 Hz, 1H), 2.69-2.83 (m, 2H), 3.16 (dd, J=12.38, 9.60 Hz, 1H), 3.34-3.36 (m, 1H), 3.41-3.51 (m, 3H), 3.68-3.70 (m, 1H), 3.87-3.92 (m, 1H), 3.92 (s, 3H), 3.99-4.10 (m, 2H), 4.09-4.16 (m, 2H), 4.19 (s, 2H), 4.25-4.33 (m, 1H), 7.30-7.37 (m, 2H), 7.43-7.46 (m, 1H), 7.48-7.52 (m, 1H), 7.52-7.63 (m, 5H), 7.65 (d, J=2.27 Hz, 1H), 7.81 (dd, J=8.72, 2.15 Hz, 1H).

Compound 224, $^1$H NMR (400 MHz, CD$_3$OD) δ ppm 1.31 (s, 6H), 1.34-1.40 (m, 2H), 1.40-1.47 (m, 2H), 1.63-1.72 (m, 1H), 1.81-1.98 (m, 4H), 2.34 (dd, J=13.39, 8.08 Hz, 1H), 2.68-2.84 (m, 2H), 3.16 (dd, J=12.63, 9.60 Hz, 1H), 3.35 (d, J=3.03 Hz, 1H), 3.39-3.50 (m, 2H), 3.68-3.71 (m, 1H), 3.87-3.91 (m, 2H), 3.92 (s, 3H), 3.99-4.10 (m, 2H), 4.10-4.16 (m, 2H), 4.26-4.33 (m, 1H), 7.33 (d, J=8.84 Hz, 1H), 7.33-7.37 (m, 1H), 7.43-7.46 (m, 1H), 7.49-7.52 (m, 1H), 7.54-7.61 (m, 5H), 7.65 (d, J=2.27 Hz, 1H), 7.80 (dd, J=8.72, 2.40 Hz, 1H).

Compound 225, $^1$H NMR (400 MHz, CD$_3$OD) δ ppm 1.06-1.12 (m, 2H), 1.33-1.38 (m, 2H), 1.39-1.45 (m, 2H), 1.47-1.52 (m, 2H), 1.62-1.72 (m, 1H), 1.79-1.96 (m, 4H), 2.33 (dd, J=13.52, 8.21 Hz, 1H), 2.68-2.82 (m, 2H), 3.14 (dd, J=12.63, 9.60 Hz, 1H), 3.32-3.35 (m, 1H), 3.38-3.50 (m, 2H), 3.72 (s, 2H), 3.86-3.89 (m, 1H), 3.91 (s, 3H), 3.98-4.07 (m, 2H), 4.07-4.15 (m, 2H), 4.23-4.32 (m, 1H), 7.27-7.34 (m, 2H), 7.46-7.48 (m, 1H), 7.49-7.60 (m, 6H), 7.63 (d, J=2.53 Hz, 1H), 7.79 (dd, J=8.72, 2.40 Hz, 1H).

Compound 233, $^1$H NMR (400 MHz, CD$_3$OD) δ ppm 1.58-1.67 (m, 3H), 1.68-1.76 (m, 1H), 1.82-2.00 (m, 4H), 2.34 (dd, J=13.77, 7.96 Hz, 1H), 2.88-3.01 (m, 2H), 3.15 (dd, J=12.88, 9.60 Hz, 1H), 3.24-3.30 (m, 1H), 3.56-3.67 (m, 2H), 3.85-3.92 (m, 1H), 3.97-4.05 (m, 2H), 4.06-4.14 (m, 2H), 4.22-4.30 (m, 1H), 5.45-5.62 (m, 1H), 7.37 (ddd, J=8.08, 2.53, 1.01 Hz, 1H), 7.46 (t, J=2.02 Hz, 1H), 7.51-7.56 (m, 1H), 7.59 (d, J=8.08 Hz, 1H), 7.93-8.00 (m, 1H), 8.18 (ddd, J=8.59, 7.07, 1.52 Hz, 1H), 8.28 (d, J=8.59 Hz, 1H), 8.36 (d, J=8.08 Hz, 1H), 9.25 (d, J=1.77 Hz, 1H), 9.38 (d, J=2.02 Hz, 1H).

Compound 234, $^1$H NMR (400 MHz, CD$_3$OD) δ ppm 1.58-1.67 (m, 3H), 1.68-1.76 (m, 1H), 1.82-2.00 (m, 4H), 2.34 (dd, J=13.77, 7.96 Hz, 1H), 2.88-3.01 (m, 2H), 3.15 (dd, J=12.88, 9.60 Hz, 1H), 3.24-3.30 (m, 1H), 3.56-3.67 (m, 2H), 3.85-3.92 (m, 1H), 3.97-4.05 (m, 2H), 4.06-4.14 (m, 2H), 4.22-4.30 (m, 1H), 5.45-5.62 (m, 1H), 7.37 (ddd, J=8.08, 2.53, 1.01 Hz, 1H), 7.46 (t, J=2.02 Hz, 1H), 7.51-7.56 (m, 1H), 7.59 (d, J=8.08 Hz, 1H), 7.93-8.00 (m, 1H), 8.18 (ddd, J=8.59, 7.07, 1.52 Hz, 1H), 8.28 (d, J=8.59 Hz, 1H), 8.36 (d, J=8.08 Hz, 1H), 9.25 (d, J=1.77 Hz, 1H), 9.38 (d, J=2.02 Hz, 1H).

Compound 235, $^1$H NMR (400 MHz, CD$_3$OD) δ ppm 1.64 (dd, J=23.75, 6.57 Hz, 3H), 1.68-1.74 (m, 1H), 1.82-1.96 (m, 4H), 2.38 (dd, J=13.52, 7.96 Hz, 1H), 2.84-2.99 (m, 2H), 3.10 (s, 3H), 3.15-3.23 (m, 1H), 3.32-3.35 (m, 1H), 3.44-3.54 (m, 2H), 3.59 (t, J=4.42 Hz, 2H), 3.91-3.97 (m, 1H), 4.01-4.10 (m, 2H), 4.10-4.17 (m, 2H), 4.26-4.34 (m, 1H), 4.75 (t, J=4.42 Hz, 2H), 5.49 (dq, J=47.49, 6.32 Hz, 1H), 7.37-7.42 (m, 2H), 7.47-7.51 (m, 1H), 7.54-7.56 (m, 1H), 7.61 (t, J=7.96 Hz, 1H), 7.87 (d, J=1.52 Hz, 1H).

Example 2: IC50 Determinations in Homogeneous Time-Resolved Fluorescence (HTRF®) cAMP Antagonist Assays HTRF cAMP assays were performed according to manufacturer's instructions (Cisbio, cAMP Dynamic 2 Assay Kit; #62AM4PEJ). CHO-K1 cells stably expressing recombinant receptor were harvested and suspended in warm PBS to make a 300,000 cells/mL stock. This cell suspension was dispensed into 384 well assay plates (PerkinElmer Proxi-Plate #6008280) at 5 µL per well (1500 cells/well) along with a cAMP standard curve.

Compounds were dissolved and serially diluted (5-fold) in DMSO to generate a 10-point dose response stock. The stock was then diluted 100-fold in assay buffer (PBS containing 1 mM IBMX) before a volume of 2.5 µL was added to the cells (the final, top concentration of compound in the dose-response is typically 10 or 100 µM). After a brief incubation, 2.5 µL of isoproterenol stock, prepared at a concentration 4 times its EC$_{90}$ at the receptor of interest, was added to the wells. The EC$_{90}$ for isoproterenol, a beta-adrenergic agonist, was determined in separate experiments using standard methods to measure agonist potencies.

Following a 1-hour incubation at room temperature, 5 µL of cAMP-D2 Reagent diluted in Lysis Buffer was added to each well followed by 5 µL of Cryptate Reagent. Plates were further incubated at room temperature for 1 hour prior to reading. Time resolved fluorescence measurements were collected on a suitable, HTRF-capable plate reader.

Counts from the plate reader were fit to the cAMP standard curve on the assay plate in order to determine cAMP concentrations in each well, and these values were used to construct dose-response curves to obtain IC$_{50}$ values.

TABLE B

Beta-3 Adrenergic Receptor IC$_{50}$ Values

| Cmpd No. | IC$_{50}$ |
|---|---|
| 5 | 33.31 nM |
| 88 | 25.12 nM |
| 123 | 53.17 nM |
| 136 | 18.83 nM |
| 154 | 17.5 nM |
| 161 | 21.14 nM |

TABLE B-continued

Beta-3 Adrenergic Receptor IC$_{50}$ Values

| Cmpd No. | IC$_{50}$ |
|---|---|
| 163 | 17.31 nM |
| 169 | 17.47 nM |
| 199 | 25.01 nM |
| 210 | 22.43 nM |
| 211 | 26.18 nM |
| 217 | 28.43 nM |
| 225 | 33.1 nM |
| 227 | 17.9 nM |
| 229 | 11.58 nM |
| 230 | 14.99 nM |
| 232 | 16.63 nM |
| 234 | 10.19 nM |
| 240 | 31.69 nM |
| 241 | 21.06 nM |
| 243 | 35.01 nM |
| 244 | 27.83 nM |
| 245 | 18.38 nM |
| 247 | 33.47 nM |
| 296 | 107.3 nM |
| 297 | 26.5 nM |
| 300 | 20.39 nM |
| 309 | 7.003 nM |
| 310 | 37.65 nM |
| 320 | 11.18 nM |
| 321 | 17.83 nM |
| 322 | 21.77 nM |
| 326 | 17.26 nM |
| 327 | 28.92 nM |
| 329 | 29.49 nM |
| 331 | 30.04 nM |

Each of the compounds specifically described herein was observed to have a beta-3 adrenergic receptor IC$_{50}$ value in the range of about 3.0 nM to about 2.0 µM.

Specific IC$_{50}$ values for certain compounds are provided below, where the number directly preceding the IC$_{50}$ value refers to the compound number (e.g., 1: 4.42 nM refers to Compound 1 with an IC$_{50}$ value of 4.42 nM):

1: 4.42 nM; 2: 44.79 nM; 3: 5.47 nM; 4: 4.45 nM; 6: 16.46 nM; 7: 34.24 nM; 8: 12.08 nM; 9: 24.25 nM; 10: 25.05 nM; 11: 35.52 nM; 12: 130.50 nM; 13: 97.85 nM; 14: 56.71 nM; 15: 5.70 nM; 16: 132.70 nM; 17: 38.76 nM; 18: 48.93 nM; 19: 66.74 nM; 20: 76.21 nM; 21: 252.30 nM; 22: 302.00 nM; 23: 242.00 nM; 24: 23.63 nM; 25: 54.56 nM; 26: 5.25 nM; 27: 19.33 nM; 28: 18.52 nM; 29: 16.09 nM; 30: 34.28 nM; 31: 49.26 nM; 32: 21.06 nM; 33: 189.20 nM; 34: 31.24 nM; 35: 20.26 nM; 36: 21.51 nM; 37: 9.37 nM; 38: 3.99 nM; 39: 70.81 nM; 40: 20.33 nM; 41: 13.68 nM; 42: 18.68 nM; 43: 32.42 nM; 44: 21.51 nM; 45: 23.64 nM; 46: 87.03 nM; 47: 82.09 nM; 48: 46.11 nM; 49: 33.13 nM; 50: 42.23 nM; 51: 17.36 nM; 52: 61.20 nM; 53: 23.93 nM; 54: 45.94 nM; 55: 30.55 nM; 56: 1988.00 nM; 57: 486.90 nM; 58: 109.30 nM; 59: 12.30 nM; 60: 17.37 nM; 61: 29.81 nM; 62: 24.46 nM; 63: 17.20 nM; 64: 921.70 nM; 65: 710.50 nM; 66: 981.60 nM; 67: 821.90 nM; 68: 493.60 nM; 69: 21.25 nM; 70: 24.43 nM; 71: 38.95 nM; 72: 328.70 nM; 73: 23.95 nM; 74: 37.97 nM; 75: 26.70 nM; 76: 35.91 nM; 77: 35.08 nM; 78: 41.93 nM; 79: 42.20 nM; 80: 38.10 nM; 81: 27.79 nM; 82: 43.23 nM; 83: 53.47 nM; 84: 54.69 nM; 85: 17.84 nM; 86: 9.10 nM; 87: 41.12 nM; 89: 110.10 nM; 90: 354.30 nM; 91: 37.14 nM; 92: 26.93 nM; 93: 75.04 nM; 94: 113.50 nM; 95: 21.09 nM; 96: 410.60 nM; 97: 212.10 nM; 98: 89.00 nM; 99: 287.30 nM; 100: 92.16 nM; 101: 466.20 nM; 102: 113.80 nM; 103: 1195.00 nM; 104: 36.50 nM; 105: 277.40 nM; 106: 36.24 nM; 107: 25.73 nM; 108: 325.30 nM; 109: 144.60 nM; 110: 68.65 nM; 111: 31.07 nM; 112: 39.47 nM; 113: 26.79 nM; 114: 51.96 nM; 115: 120.50 nM; 116: 319.70 nM; 117: 171.60 nM; 118: 10.44 nM; 119: 11.64 nM; 120: 177.30 nM; 121: 562.40 nM; 122: 7.81 nM; 124: 78.20 nM; 125: 48.81 nM; 126: 126.50 nM; 127: 156.60 nM; 128: 108.50 nM; 129: 485.00 nM; 130: 12.00 nM; 131: 23.72 nM; 132: 739.30 nM; 133: 443.00 nM; 134: 55.13 nM; 135: 88.77 nM; 137: 349.50 nM; 138: 20.41 nM; 139: 36.18 nM; 140: 45.89 nM; 141: 11.63 nM; 142: 106.00 nM; 143: 13.23 nM; 144: 7.77 nM; 145: 81.89 nM; 146: 103.60 nM; 147: 53.32 nM; 148: 21.76 nM; 149: 97.26 nM; 150: 226.60 nM; 151: 40.85 nM; 152: 24.68 nM; 153: 18.80 nM; 155: 48.24 nM; 156: 24.78 nM; 157: 25.73 nM; 158: 27.29 nM; 159: 177.90 nM; 160: 11.58 nM; 162: 29.51 nM; 164: 27.73 nM; 165: 64.38 nM; 166: 51.18 nM; 167: 15.79 nM; 168: 15.38 nM; 170: 416.40 nM; 171: 25.03 nM; 172: 50.34 nM; 173: 31.25 nM; 174: 699.30 nM; 175: 715.60 nM; 176: 58.42 nM; 177: 50.59 nM; 178: 84.61 nM; 179: 49.11 nM; 180: 30.67 nM; 181: 179.70 nM; 182: 24.74 nM; 183: 1600.00 nM; 184: 26.72 nM; 185: 257.80 nM; 186: 78.60 nM; 187: 33.40 nM; 188: 35.02 nM; 189: 10.31 nM; 190: 31.27 nM; 191: 439.90 nM; 192: 298.30 nM; 193: 26.90 nM; 194: 13.65 nM; 195: 1530.00 nM; 196: 34.61 nM; 197: 84.99 nM; 198: 62.23 nM; 200: 72.38 nM; 201: 41.80 nM; 202: 345.90 nM; 203: 1111.00 nM; 204: 503.80 nM; 205: 92.19 nM; 206: 402.80 nM; 207: 51.11 nM; 208: 34.76 nM; 209: 8.79 nM; 212: 25.96 nM; 213: 18.62 nM; 214: 36.66 nM; 215: 38.42 nM; 216: 26.42 nM; 218: 29.32 nM; 219: 21.59 nM; 220: 27.50 nM; 221: 20.57 nM; 222: 47.57 nM; 223: 83.59 nM; 224: 73.16 nM; 226: 12.46 nM; 228: 29.07 nM; 231: 19.61 nM; 233: 9.72 nM; 235: 14.97 nM; 236: 368.60 nM; 237: 81.97 nM; 238: 22.84 nM; 239: 30.94 nM; 242: 35.50 nM; 246: 48.29 nM; 248: 72.39 nM; 249: 224.40 nM; 250: 335.70 nM; 251: 51.62 nM; 252: 29.26 nM; 253: 29.15 nM; 254: 41.77 nM; 255: 27.94 nM; 256: 32.64 nM; 257: 37.84 nM; 258: 27.73 nM; 259: 158.30 nM; 260: 177.90 nM; 261: 38.77 nM; 262: 981.90 nM; 263: 754.60 nM; 264: 979.70 nM; 265: 374.30 nM; 266: 1291.00 nM; 267: 442.30 nM; 268: 138.30 nM; 269: 399.70 nM; 270: 92.31 nM; 271: 205.50 nM; 272: 566.10 nM; 273: 29.35 nM; 274: 38.43 nM; 275: 62.29 nM; 276: 1808.00 nM; 277: 16.46 nM; 278: 585.90 nM; 279: 39.75 nM; 280: 96.39 nM; 281: 57.87 nM; 282: 23.74 nM; 283: 68.93 nM; 284: 106.40 nM; 285: 303.30 nM; 286: 56.94 nM; 287: 150.50 nM; 288: 176.50 nM; 289: 65.82 nM; 290: 34.18 nM; 291: 69.80 nM; 292: 90.25 nM; 293: 130.20 nM; 294: 109.80 nM; 295: 143.20 nM; 298: 82.52 nM; 299: 44.31 nM; 301: 357.00 nM; 302: 696.00 nM; 303: 17.11 nM; 304: 69.02 nM; 305: 17.11 nM; 306: 62.90 nM; 307: 59.18 nM; 308: 34.50 nM; 311: 43.50 nM; 312: 31.55 nM; 313: 141.50 nM; 314: 269.70 nM; 315: 23.94 nM; 316: 63.76 nM; 317: 104.00 nM; 318: 95.17 nM; 319: 16.51 nM; 323: 49.56 nM; 324: 22.46 nM; 325: 34.05 nM; 328: 35.37 nM; 330: 70.08 nM; 332: 42.26 nM; 333: 16.28 nM; 334: 79.94 nM; 335: 14.45 nM; 336: 101.70 nM; 337: 1689.00 nM; and 338: 32.15 nM.

Example 3: Ki Determination By Radioligand Binding

Radioligand binding assays are performed using the commercially available adrenergic receptor agonist [$^{125}$I]Cyanopindolol as the radioligand and non-specific binding is determined in the presence of unlabeled L-748,337 at a saturating concentration of 10 μM. For the beta-3 adrenergic receptor, the radioligand is used in the assay at a final concentration of 0.4 nM. Membrane pellets prepared from CHO-K1 cells stably expressing recombinant beta-3 adrenergic receptors are prepared using standard methods and stored at −80° C. Membranes are thawed on ice and resuspended in Assay Buffer (20 mM HEPES, pH 7.4, 10 mM MgCl$_2$) by dounce homogenization. Competition experiments consist of addition of 145 μL of membranes, 50 μL of radioligand stock, and 5 μL of test compound diluted in DMSO to 96-well microtiter plates. Plates are incubated for one hour at room temperature and the assay terminated by rapid filtration through Perkin Elmer GF/C filtration, plates pretreated with 0.5% PEI, under vacuum pressure using a 96-well Packard filtration apparatus. Plates are rapidly washed several times with ice-cold Assay Buffer and then dried overnight at 45° C. Finally, 25 μL of BetaScint scintillation cocktail is added to each well and plates counted in a Packard TopCount scintillation counter. In each competition study, test compounds are dosed at eight to ten concentrations with triplicate determinations at each test concentration. A reference compound, typically isoproterenol, is included in every experiment for quality control purposes.

Raw counts from scintillation counters are fit to a non-linear least squares curve fitting program to obtain IC$_{50}$ values. Ki values are determined from IC$_{50}$ values using the Cheng-Prusoff equation and the radioligand Kd. Mean Ki values and 95% confidence intervals are calculated from the mean log(Ki) value.

Example 4: Beta-3 Adrenergic Receptor Antagonists in Normal and Chronic Heart Failure Models Beta-3 adrenergic receptor antagonists were evaluated for effects on cardiac contractility in normal and chronic heart failure (CHF) rats. Because beta-3 adrenergic receptor expression is weak in the normal rat heart, compounds were evaluated for the ability to attenuate the negative contractile effects of the beta-3 adrenergic receptor agonist BRL 37344 (Tocris Bioscience, Bristol, UK) in the normal rats. Because beta-3 adrenergic receptor expression is higher in the rat heart with CHF, a compound was evaluated for the ability to improve contractility compared to baseline in this CHF rat model.

Myocardial infarction was induced in male Sprague-Dawley rats by performing left coronary descending artery ligation. The rats were anesthetized using an isoflurane vaporizer (Summit Medical; 5% induction and 2-3% during the surgery), intubated, and placed on a ventilator (Cat. #55-0000, Harvard Apparatus, Holliston, Mass.) supplying 2-3% isoflurane in oxygen at a tidal volume of 2.5 mL/stroke at a rate of 70 strokes per minute. A 2-cm incision was made to open the chest with a hemostat. The left coronary descending artery was ligated with a 7-0 Prolene suture 3 mm from origin of the left coronary descending artery. The chest was then closed using 4-0 silk suture (Cat #1677G, Ethicon, Somerville, N.J.), and the rats were taken off the ventilator and placed in a home cage following spontaneous breathing.

Heart failure was evaluated weekly following surgery by testing impaired left ventricular function by echocardiography. Left ventricle end-diastolic volume (LVEDV) and left ventricle end-systolic volume (LVESV) were measured for at least three consecutive cardiac cycles in long-axis view images. Ejection Fraction (EF %) was calculated using the following formula: EF %=(LVEDV−LVESV)/LVEDV. An ejection fraction <30% was used at the cutoff for heart failure.

A direct determination of left ventricular function was used for all rats to evaluate the effects of compounds on left ventricular contractility. Right carotid artery catheterization was used for contractility measurements. The rats were anesthetized with an intraperitoneal injection of INACTIN® (Cat # T-133, Sigma, St. Louis, Mo.) (100 mg/kg body weight), and a Millar MIKRO-TIP® pressure catheter (Cat # SPR-320NR, Millar, Inc., Houston, Tex.) was passed through the carotid artery into left ventricle. Left ventricular pressure (LVP) was monitored by LabChart with POWER-LAB® Data Acquisition System (ADInstruments, Sydney, Australia).

Jugular vein catheterization was used for compound administration. A silastic catheter (Cat #427411, BD, Franklin Lakes, N.J.) was introduced into the jugular vein, and a right venous catheter was connected to an automated drug delivery system (11 Plus Syringe Pump, Harvard Apparatus, Holliston, Mass.).

Figure 25:
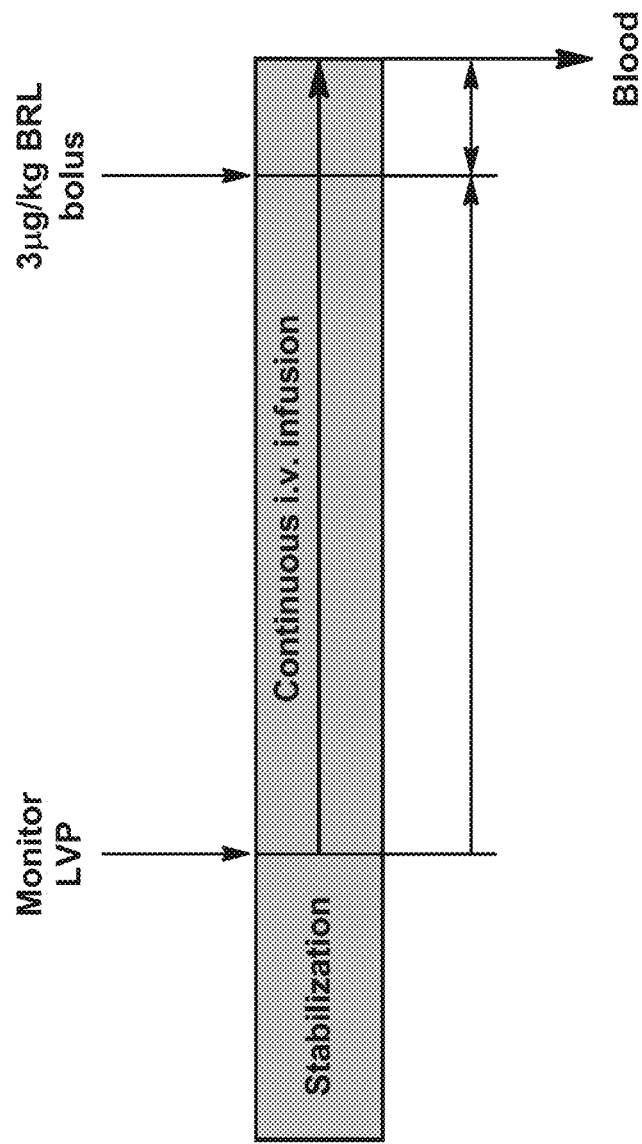
FIG. 25 shows the scheme for administration of compounds of the present invention in normal rats in Example 4.

In the normal rats, 3 mg/kg, 10 mg/kg, 30 mg/kg, or 60 mg/kg of test compounds were administered starting 30-45 minutes after catheter implantation. A bolus injection of BRL 37344 (3 µg/kg) was administered via the left jugular vein 15-20 minutes after test compound infusion was started, and five minutes before compound infusion was stopped. A blood sample (800 µl) was then taken from the left venous catheter five minutes after the bolus injection of BRL 37344 (FIG. 25).

Figure 26:
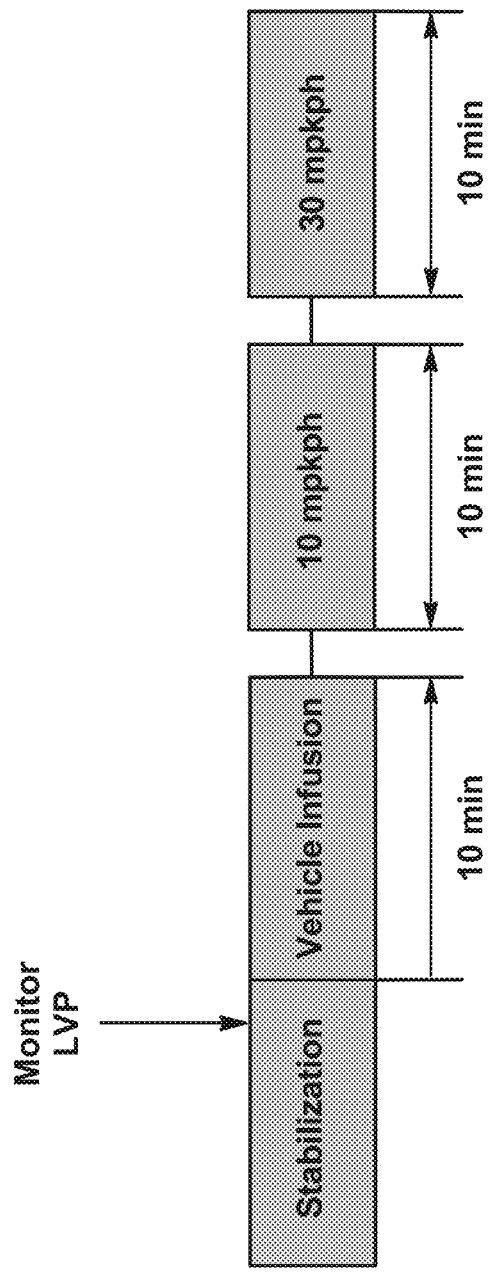
FIG. 26 shows the scheme for administration of compounds of the present invention in heart failure rats in Example 4.

Development of CHF was monitored by echocardiography in rats after the surgically-induced myocardial infarction. When the EF % fell below 30% (typically 3-5 months following artery ligation), each animal was prepared for drug testing. Vehicle was administered for 10 minutes following stabilization. Test compound was then administered for 10 minutes at 10 mg/kg, followed by 10 minutes at 30 mg/kg. A blood sample (800 microliters whole blood) was then taken from the left venous catheter immediately following each 10-minute drug infusion to monitor plasma concentrations of test compound (FIG. 26).

Figure 27:
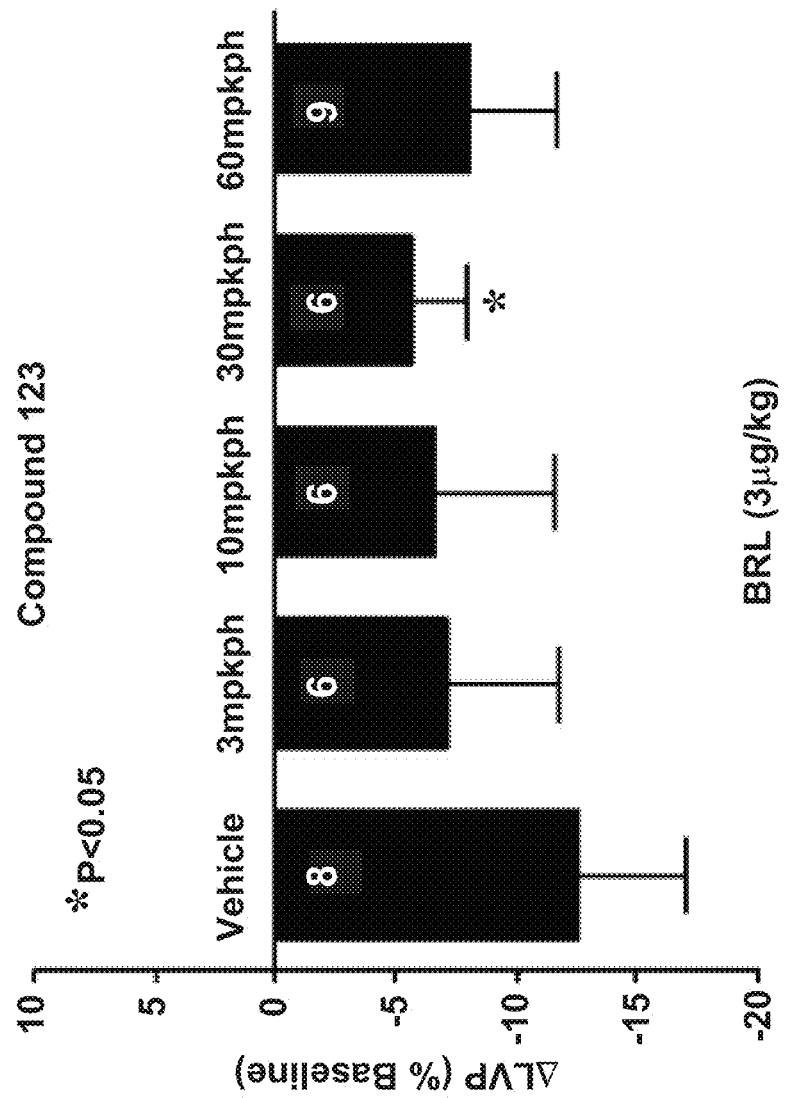
FIG. 27 shows the inhibition of negative effects of BRL on LVP in normal rats following the administration of Compound 123 (Example 4).
Figure 28:
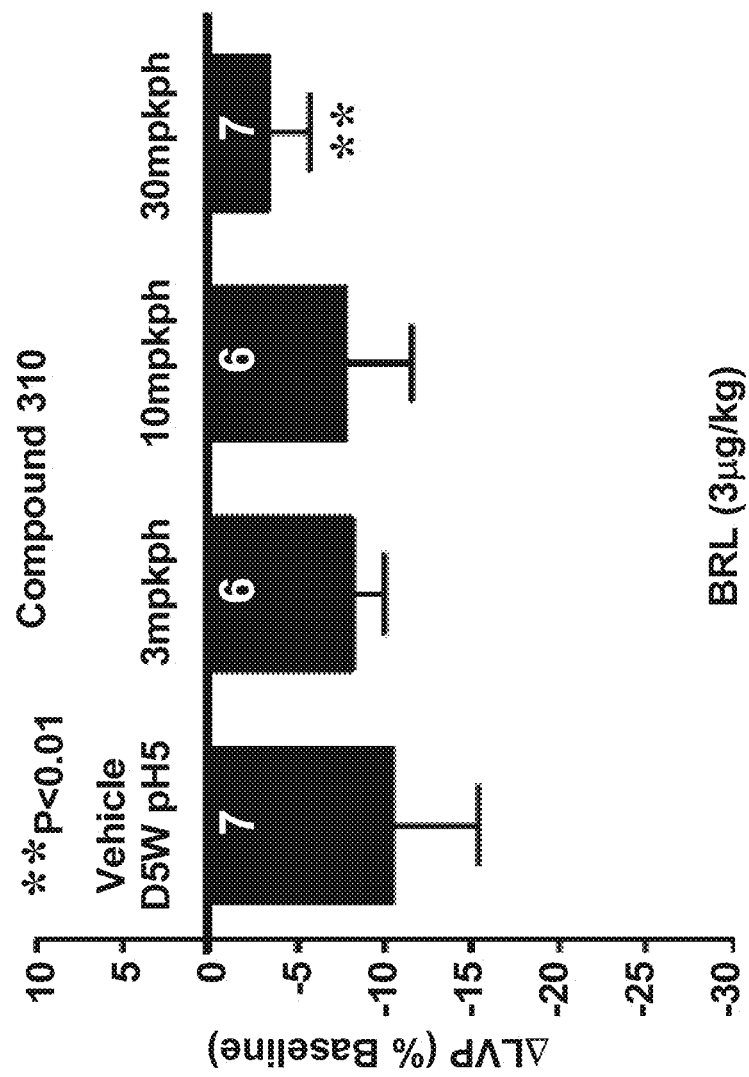
FIG. 28 shows the inhibition of negative effects of BRL on LVP in normal rats following the administration of Compound 310 (Example 4).
Figure 29:
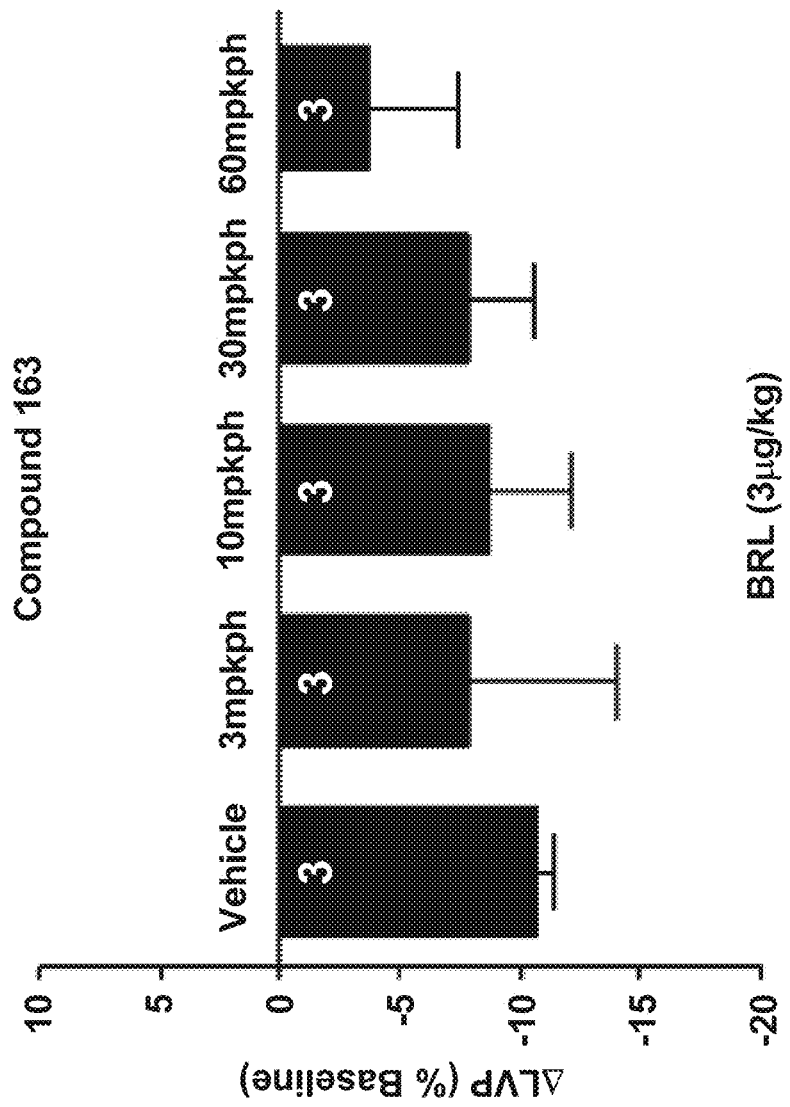
FIG. 29 shows the inhibition of negative effects of BRL on LVP in normal rats following the administration of Compound 163 (Example 4).
Figure 30:
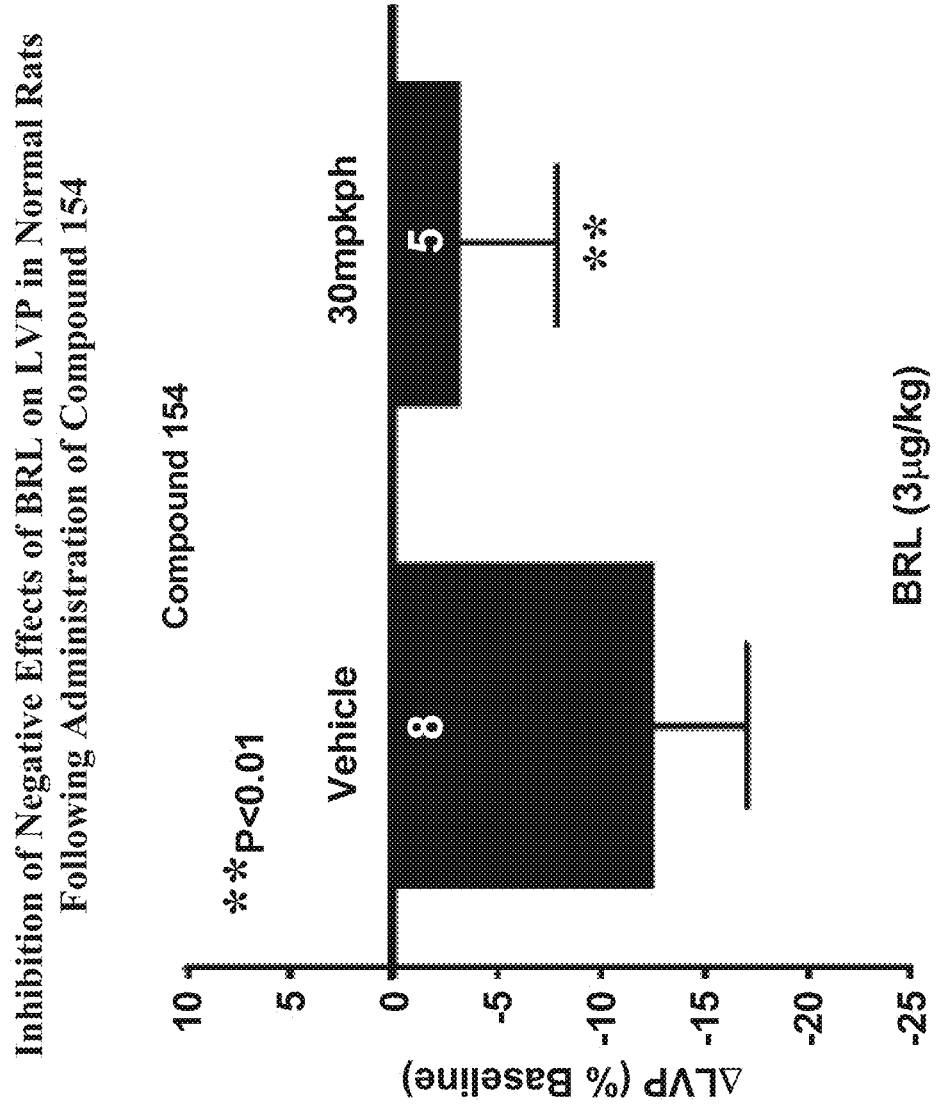
FIG. 30 shows the inhibition of negative effects of BRL on LVP in normal rats following the administration of Compound 154 (Example 4).
Figure 31:
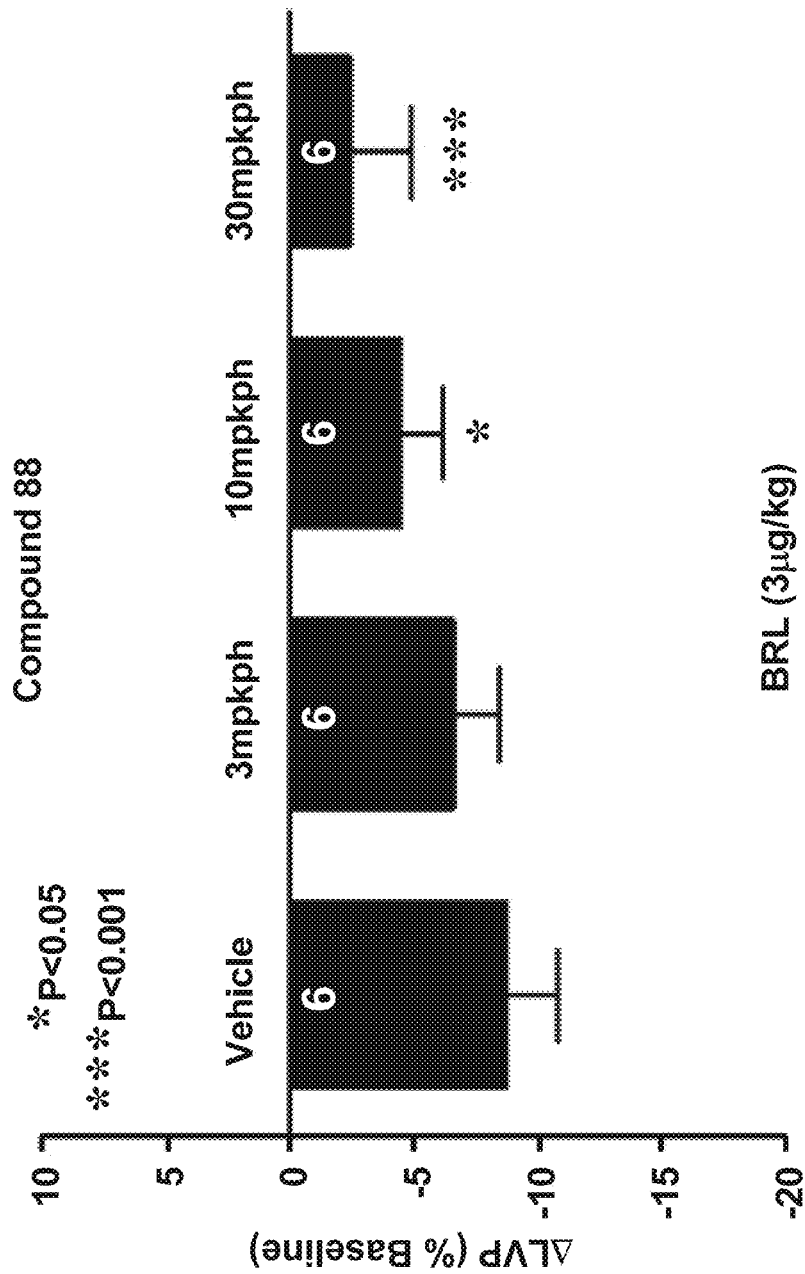
FIG. 31 shows the inhibition of negative effects of BRL on LVP in normal rats following the administration of Compound 88 (Example 4).
Figure 32:
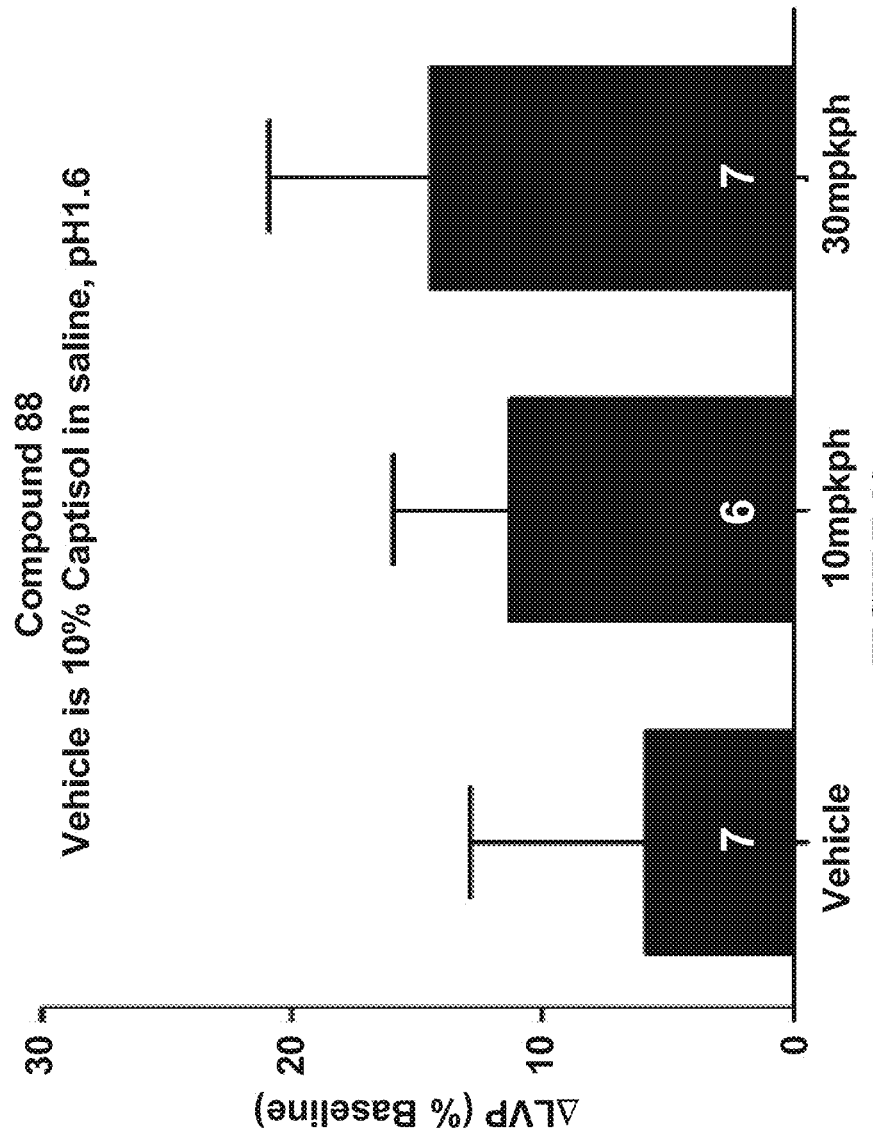
FIG. 32 shows the inhibition of negative effects of BRL on LVP in a rat with heart failure following the administration of Compound 88 (Example 4).
Figure 33A:
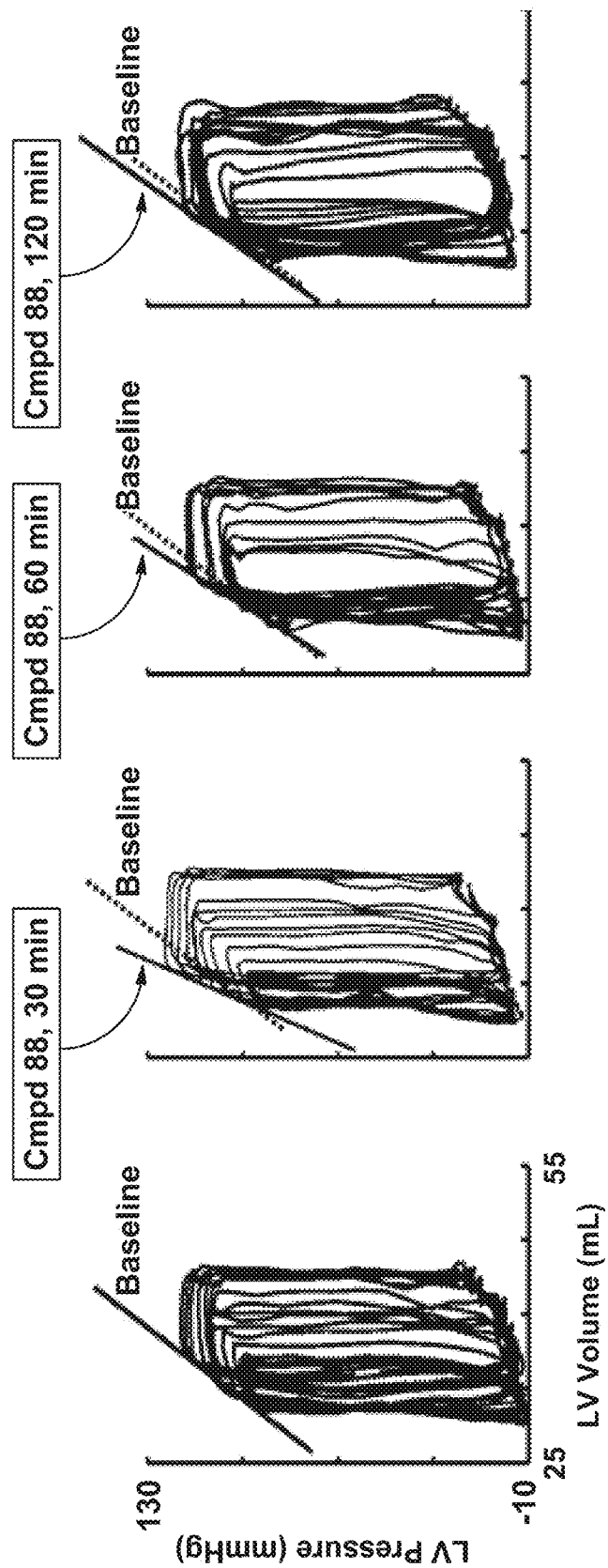
FIG. 33A show an example of the effect of Compound 88 in a dog prior to heart failure.
Figure 33B:
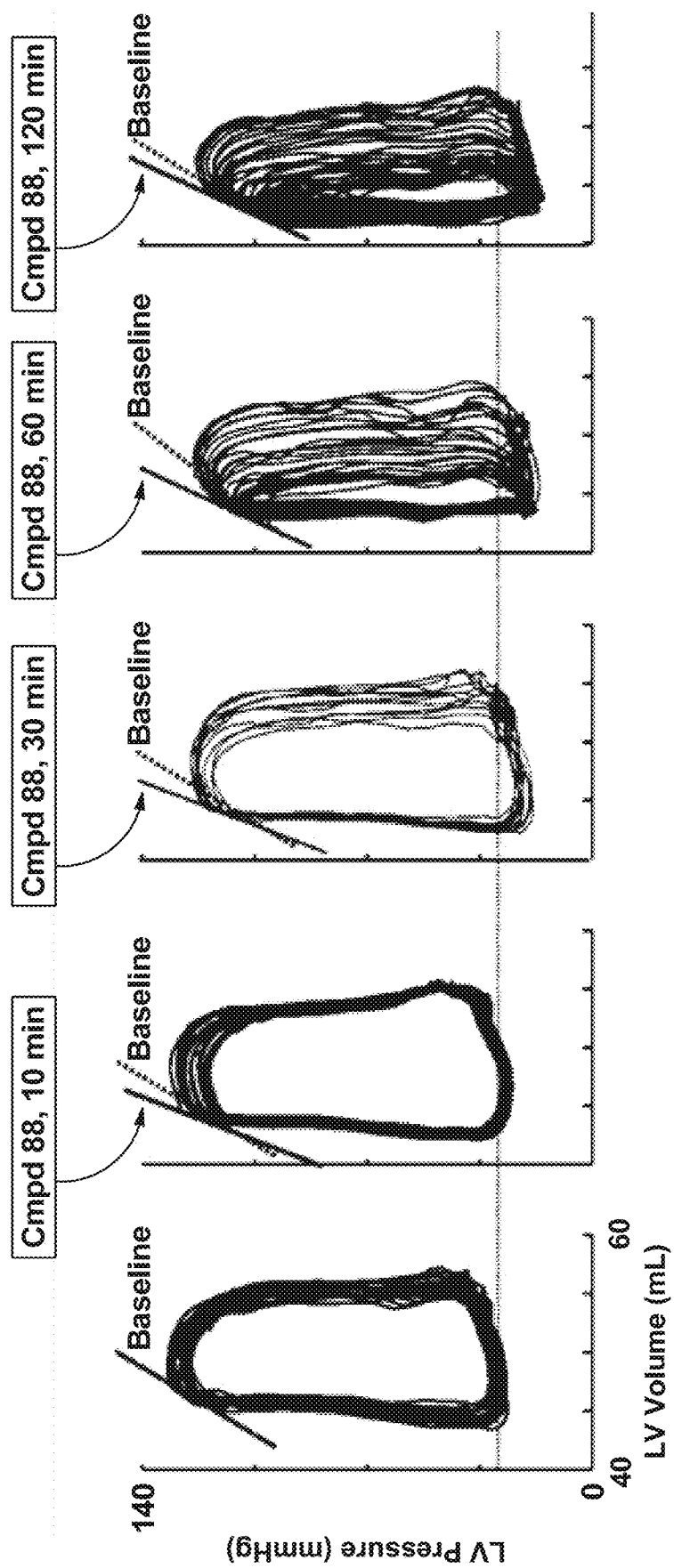
FIG. 33B show an example of the effect of Compound 88 in a dog following heart failure. The horizontal dashed line in the graphs is the baseline LV pressure indicating the presence of heart failure (compare the lower LV pressures in FIG. 33A and the baseline LV pressure in FIG. 33B).

Compound 123 (FIG. 27), Compound 310 (FIG. 28), Compound 163 (FIG. 29), Compound 154 (FIG. 30), and Compound 88 (FIG. 31) dose-dependently inhibited the negative effect of beta-3 adrenergic receptor agonist BRL on LVP in normal rats. In addition, Compound 88 demonstrated a trend toward improved contractility with increased dosage in a rat with CHF (FIG. 32).

Those skilled in the art will recognize that various modifications, additions, substitutions, and variations to the illustrative examples set forth herein can be made without departing from the spirit of the invention and are, therefore, considered within the scope of the invention.

The invention claimed is:

1. A compound selected from compounds of Formula (Ii) and pharmaceutically acceptable salts, solvates, and hydrates thereof:

wherein:
$R^2$ is selected from: $C_1$-$C_6$ alkyl, $C_3$-$C_7$ cycloalkyl, and $C_1$-$C_6$ haloalkyl; each optionally substituted with one or more substituents selected from: $C_1$-$C_6$ alkoxy, $C_1$-$C_6$ alkylenehydroxyl, and hydroxyl;
$R^{3a}$, $R^{3b}$, $R^{3c}$, and $R^{3d}$ are each independently H or halogen;
$R^4$ is H or $C_1$-$C_6$ alkyl; and
$R^{5a}$, $R^{5b}$, $R^{5c}$, and $R^{5d}$ are independently H, $C_1$-$C_6$ alkyl, and halogen.

2. The compound according to claim 1, wherein the carbon designated as C(3) of the oxa-azaspiro[4.5]decanyl group bonded to the nitrogen has the (R) stereochemistry and the carbon designated as C(2) of the propyl group bonded to the hydroxyl group has the (S) stereochemistry.

3. The compound according to claim 1, wherein:
$R^2$ is selected from: 1-(hydroxymethyl)cyclopropyl, 1,1-difluoro-2-hydroxyethyl, 1-fluoroethyl, 1-hydroxy-2-methylpropan-2-yl, cyclopropyl, isopropyl, methoxymethyl, and methyl;
$R^{3a}$, $R^{3b}$, $R^{3c}$, and $R^{3d}$ are each H;
$R^4$ is selected from: H, methyl, and ethyl;
$R^{5a}$, $R^{5b}$, and $R^{5c}$ are independently H, methyl, and fluoro; and
$R^{5d}$ is H.

4. The compound according to claim 2, wherein:
$R^2$ is selected from: 1-(hydroxymethyl)cyclopropyl, 1,1-difluoro-2-hydroxyethyl, 1-fluoroethyl, 1-hydroxy-2-methylpropan-2-yl, cyclopropyl, isopropyl, methoxymethyl, and methyl;
$R^{3a}$, $R^{3b}$, $R^{3c}$, and $R^{3d}$ are each H;
$R^4$ is selected from: H, methyl, and ethyl;
$R^{5a}$, $R^{5b}$, and $R^{5c}$ are independently H, methyl, and fluoro; and
$R^{5d}$ is H.

5. The compound according to claim 1 that is 1-ethyl-8-fluoro-3-((R)-3-((S)-2-hydroxy-3-(3-(methylsulfonyl)phenoxy)propylamino)-1-oxa-8-azaspiro[4.5]decan-8-ylsulfonyl)quinolin-4(1H)-one (Compound 322).

6. The compound according to claim 1 that is the hydrochloric acid salt of 1-ethyl-8-fluoro-3-((R)-3-((S)-2-hydroxy-3-(3-(methylsulfonyl)phenoxy)propylamino)-1-oxa-8-azaspiro[4.5]decan-8-ylsulfonyl)quinolin-4(1H)-one (Compound 322).

7. The compound according to claim 1 that is the methanesulfonic acid salt of 1-ethyl-3-((R)-3-((S)-2-hydroxy-3-(3-(methylsulfonyl)phenoxy)propylamino)-1-oxa-8-azaspiro[4.5]decan-8-ylsulfonyl)quinolin-4(1H)-one (Compound 310).

8. The compound according to claim 1 that is the hydrochloric acid salt of 3-((R)-3-((S)-3-(3-(cyclopropylsulfonyl)phenoxy)-2-hydroxypropylamino)-1-oxa-8-azaspiro[4.5]decan-8-ylsulfonyl)quinolin-4(1H)-one (Compound 326).

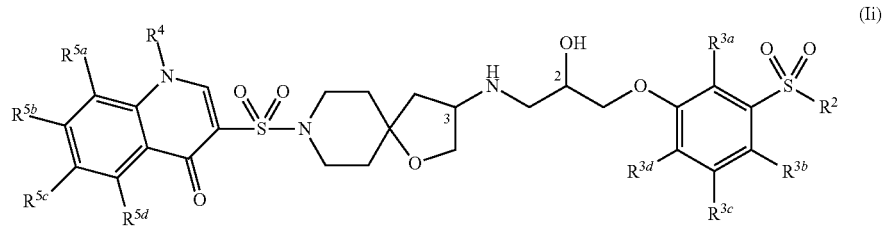

9. The compound according to claim 1 that is the hydrochloric acid salt of 3-((R)-3-((S)-3-(3-(Cyclopropylsulfonyl)phenoxy)-2-hydroxypropylamino)-1-oxa-8-azaspiro[4.5]decan-8-ylsulfonyl)-1-ethyl-8-fluoroquinolin-4(1H)-one (Compound 333).

10. A pharmaceutical composition comprising a compound according to claim 1, and a pharmaceutically acceptable carrier.

11. The pharmaceutical composition according to claim 10, wherein the compound is 1-ethyl-8-fluoro-3-((R)-3-((S)-2-hydroxy-3-(3-(methylsulfonyl)phenoxy)propylamino)-1-oxa-8-azaspiro[4.5]decan-8-ylsulfonyl)quinolin-4(1H)-one (Compound 322).

12. The pharmaceutical composition according to claim 10, wherein the compound is 1-ethyl-3-((R)-3-((S)-2-hydroxy-3-(3-(methylsulfonyl)phenoxy)propylamino)-1-oxa-8-azaspiro[4.5]decan-8-ylsulfonyl)quinolin-4(1H)-one (Compound 310).

13. The pharmaceutical composition according to claim 10, wherein the compound is 3-((R)-3-((S)-3-(3-(cyclopropylsulfonyl)phenoxy)-2-hydroxypropylamino)-1-oxa-8-azaspiro[4.5]decan-8-ylsulfonyl)quinolin-4(1H)-one (Compound 326).

14. The pharmaceutical composition according to claim 10, wherein the compound is 3-((R)-3-((S)-3-(3-(cyclopropylsulfonyl)phenoxy)-2-hydroxypropylamino)-1-oxa-8-azaspiro[4.5]decan-8-ylsulfonyl)-1-ethyl-8-fluoroquinolin-4(1H)-one (Compound 333).

15. The pharmaceutical composition according to claim 10, wherein the compound is the hydrochloric acid salt of 1-ethyl-8-fluoro-3-((R)-3-((S)-2-hydroxy-3-(3-(methylsulfonyl)phenoxy)propylamino)-1-oxa-8-azaspiro[4.5]decan-8-ylsulfonyl)quinolin-4(1H)-one (Compound 322).

16. The pharmaceutical composition according to claim 10, wherein the compound is the methanesulfonic acid salt of 1-ethyl-3-((R)-3-((S)-2-hydroxy-3-(3-(methylsulfonyl)phenoxy)propyl amino)-1-oxa-8-azaspiro[4.5]decan-8-ylsulfonyl)quinolin-4(1H)-one (Compound 310).

17. The pharmaceutical composition according to claim 10, wherein the compound is the hydrochloric acid salt of 3-((R)-3-((S)-3-(3-(cyclopropylsulfonyl)phenoxy)-2-hydroxypropylamino)-1-oxa-8-azaspiro[4.5]decan-8-ylsulfonyl)quinolin-4(1H)-one (Compound 326).

18. The pharmaceutical composition according to claim 10, wherein the compound is the hydrochloric acid salt of 3-((R)-3-((S)-3-(3-(Cyclopropylsulfonyl)phenoxy)-2-hydroxypropylamino)-1-oxa-8-azaspiro[4.5]decan-8-ylsulfonyl)-1-ethyl-8-fluoroquinolin-4(1H)-one (Compound 333).

19. A method for treating heart failure in an individual, comprising administering to said individual in need thereof, a therapeutically effective amount of a compound according to claim 1.

20. The method according to claim 19, wherein the compound is 1-ethyl-8-fluoro-3-((R)-3-((S)-2-hydroxy-3-(3-(methylsulfonyl)phenoxy)propylamino)-1-oxa-8-azaspiro[4.5]decan-8-ylsulfonyl)quinolin-4(1H)-one (Compound 322).

21. The method according to claim 19, wherein the compound is the hydrochloric acid salt of 1-ethyl-8-fluoro-3-((R)-3-((S)-2-hydroxy-3-(3-(methylsulfonyl)phenoxy)propylamino)-1-oxa-8-azaspiro[4.5]decan-8-ylsulfonyl)quinolin-4(1H)-one (Compound 322).

22. The method according to claim 19, wherein the compound is the methanesulfonic acid salt of 1-ethyl-3-((R)-3-((S)-2-hydroxy-3-(3-(methylsulfonyl)phenoxy)propylamino)-1-oxa-8-azaspiro[4.5]decan-8-ylsulfonyl)quinolin-4(1H)-one (Compound 310).

23. The method according to claim 19, wherein the compound is the hydrochloric acid salt of 3-((R)-3-((S)-3-(3-(cyclopropylsulfonyl)phenoxy)-2-hydroxypropylamino)-1-oxa-8-azaspiro[4.5]decan-8-ylsulfonyl)quinolin-4(1H)-one (Compound 326).

24. The method according to claim 19, wherein the compound is the hydrochloric acid salt of 3-((R)-3-((S)-3-(3-(Cyclopropylsulfonyl)phenoxy)-2-hydroxypropylamino)-1-oxa-8-azaspiro[4.5]decan-8-ylsulfonyl)-1-ethyl-8-fluoroquinolin-4(1H)-one (Compound 333).

\* \* \* \* \*

UNITED STATES PATENT AND TRADEMARK OFFICE
CERTIFICATE OF CORRECTION

PATENT NO. : 10,662,200 B2
APPLICATION NO. : 16/563353
DATED : May 26, 2020
INVENTOR(S) : Thuy-Anh Tran et al.

Page 1 of 1

It is certified that error appears in the above-identified patent and that said Letters Patent is hereby corrected as shown below:

In the Claims

Column 217, Line 37, Claim 16, delete "propyl amino)" and insert -- propylamino) --.

Signed and Sealed this
Seventh Day of July, 2020

Andrei Iancu
*Director of the United States Patent and Trademark Office*